US012391679B2

(12) United States Patent
Alvey et al.

(10) Patent No.: US 12,391,679 B2
(45) Date of Patent: Aug. 19, 2025

(54) BENZAMIDE-SUBSTITUTED BICYCLIC IMIDAZO- AND PYRAZOLO-FUSED -PYRIDINE, -PYRIMIDE, AND -PYRIDAZINE COMPOUNDS FOR TREATMENT OF INFLAMMATORY DISEASES

(71) Applicant: ONCO3R Therapeutics BV, Brussels (BE)

(72) Inventors: Luke Jonathan Alvey, Romainville (FR); Denis Bucher, Rheinfelden (CH); Nicolas Desroy, Romainville (FR); Hélène Marie Jary, Romainville (FR); Christophe Peixoto, Romainville (FR); Taoues Temal-Laïb, Romainville (FR); Amynata Tirera, Romainville (FR); Florence Marie-Emilie Bonnaterre, Romainville (FR); Béranger Duthion, Romainville (FR)

(73) Assignee: ONCO3R Therapeutics BV, Brussels (BE)

( * ) Notice: Subject to any disclaimer, the term of this patent is extended or adjusted under 35 U.S.C. 154(b) by 751 days.

(21) Appl. No.: 17/614,854

(22) PCT Filed: May 25, 2020

(86) PCT No.: PCT/EP2020/064368

§ 371 (c)(1),
(2) Date: Nov. 29, 2021

(87) PCT Pub. No.: WO2020/239658

PCT Pub. Date: Dec. 3, 2020

(65) Prior Publication Data

US 2022/0340548 A1 Oct. 27, 2022

(30) Foreign Application Priority Data

May 29, 2019 (GB) ..................................... 1907616

(51) Int. Cl.

| | |
|---|---|
| ***C07D 405/10*** | (2006.01) |
| ***A61P 1/00*** | (2006.01) |
| ***A61P 9/00*** | (2006.01) |
| ***A61P 11/00*** | (2006.01) |
| ***A61P 19/02*** | (2006.01) |

(Continued)

(52) U.S. Cl.

CPC .............. *C07D 405/10* (2013.01); *A61P 1/00* (2018.01); *A61P 9/00* (2018.01); *A61P 11/00* (2018.01); *A61P 19/02* (2018.01); *A61P 37/00* (2018.01); *C07D 235/16* (2013.01); (Continued)

(58) Field of Classification Search

None

See application file for complete search history.

(56) References Cited

FOREIGN PATENT DOCUMENTS

| | | |
|---|---|---|
| CN | 104284896 A | 9/2013 |
| CN | 118684661 A | 9/2024 |

(Continued)

OTHER PUBLICATIONS

Argilés JM et al, "Catabolic proinflammatory cytokines", Curr. Opin. Clin. Nutr. Metab. Care, 1998, vol. 1, No. 3, pp. 245-251.

(Continued)

*Primary Examiner* — Kortney L. Klinkel
*Assistant Examiner* — Sophia Reilly
(74) *Attorney, Agent, or Firm* — ArentFox Schiff LLP

(57) ABSTRACT

The present invention discloses compounds according to Formula I:

I

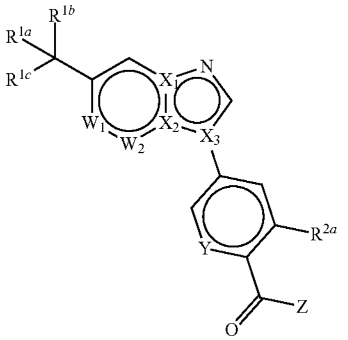

wherein $R^{1a}$, $R^{1b}$, $R^{1c}$, $R^{2a}$, $W_1$, $W_2$, $X_1$, $X_2$, $X_3$, Y, and Z are as defined herein.

The present invention relates to compounds, methods for their production, pharmaceutical compositions comprising the same, and methods of treatment using the same, for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases by administering the compound of the invention.

15 Claims, No Drawings

(51) Int. Cl.
*A61P 37/00* (2006.01)
*C07D 235/16* (2006.01)
*C07D 401/10* (2006.01)
*C07D 471/04* (2006.01)
*C07D 519/00* (2006.01)

(52) U.S. Cl.
CPC ......... *C07D 401/10* (2013.01); *C07D 471/04* (2013.01); *C07D 519/00* (2013.01)

(56) References Cited

FOREIGN PATENT DOCUMENTS

| | | | | |
|---|---|---|---|---|
| WO | WO-2009014620 A1 * | 1/2009 | | C07D 487/04 |
| WO | 2013135612 A1 | 9/2013 | | |
| WO | 2014/093383 A1 | 6/2014 | | |
| WO | 2012/068406 A2 | 5/2015 | | |
| WO | 2019/105886 A1 | 6/2019 | | |

OTHER PUBLICATIONS

Ashcroft T. et al., "Simple method of estimating severity of pulmonary fibrosis on a numerical scale.," J. Clin. Pathol., 1988, vol. 41, No. 4, pp. 467-470.

Ashour Ahmed A et al., "SIK2 is a centrosome kinase required for bipolar mitotic spindle formation that provides a potential target for therapy in ovarian cancer", Cancer Cell, 2001, vol. 18, No. 2, pp. 109-121.

Bush KA et al., "Reduction of joint inflammation and bone erosion in rat adjuvant arthritis by treatment with Interleukin-17 receptor IgG1 Fc fusion protein", Arthritis Rheum., 2002, vol. 46, No. 3, pp. 802-805.

Charoenfuprasert S et al., "Identification of salt-inducible kinase 3 as a novel tumor antigen associated with tumorigenesis of ovarian cancer", Oncogene, 2011, vol. 30, No. 33, pp. 3570-3584.

Clark K et al., "Phosphorylation of CRTC3 by the salt-inducible kinases controls the interconversion of classically activated and regulatory macrophages", Proc. Natl. Acad. Sci. U. S. A., 2012, vol. 109 no. 42, pp. 16986-16991.

Darling NJ et al., Inhibition of SIK2 and SIK3 during differentiation enhances the anti-inflammatory phenotype of macrophages. Biochem. J., 2017, vol. 474, No. 4, pp. 521-537.

Dempster DW et al., "Standardized nomenclature, symbols, and units for bone histomorphometry: a 2012 update of the report of the ASBMR Histomorphometry Nomenclature Committee", J. Bone Miner. Res. Off. J. Am. Soc. Bone Miner. Res., vol. 28, No. 1, pp. 2-17.

Devos FC et al., "Forced expiration measurements in mouse models of obstructive and restrictive lung diseases", Respir. Res., 2017, vol. 18, No. 1, p. 123.

Favaudon V et al., "Ultrahigh dose-rate FLASH irradiation increases the differential response between normal and tumor tissue in mice", Sci. Transl. Med., vol. 6, No. 245, p. 245ra93.

Van der Fits L et al., "Imiquimod-induced psoriasis-like skin inflammation in mice is mediated via the IL-23/IL-17 axis", J. Immunol., 2009, vol. 182, No. 9, pp. 5836-5845.

Glasson SS et al., The surgical destabilization of the medial meniscus (DMM) model of osteoarthritis in the 129/SvEv mouse, Osteoarthritis Cartilage, 2007, vol. 15, No. 9, pp. 1061-1069.

Jou I-M et al., "Thrombospondin 1 as an effective gene therapeutic strategy in collagen-induced arthritis", Arthritis Rheum., 2005, vol. 52, No. 1, pp. 339-344.

Katoh Y et al., "Salt-inducible kinase (SIK) isoforms: their involvement in steroidogenesis and adipogenesis", Mol. Cell. Endocrinol, 2004, vol. 217, No. 1-2, pp. 109-112.

Khachigian LM., "Collagen antibody-induced arthritis", Nat. Protoc., 2006, vol. 1, No. 5, pp. 2512-2516.

Kumagai A et al., A Potent Inhibitor of SIK2, 3, 3', 7-Trihydroxy-4'-Methoxyflavon (4'-O-Methylfisetin), Promotes Melanogenesis in B16F10 Melanoma Cells, PLoS One, 2011, vol. 6, No. 10, pp. e26148.

Li M et al., "Topical vitamin D3 and low-calcemic analogs induce thymic stromal lymphopoietin in mouse keratinocytes and trigger an atopic dermatitis", Proc. Natl. Acad. Sci. U. S. A., 2006, vol. 103, No. 31, pp. 11736-11741.

Lin H-S et al., "Anti-rheumatic activities of histone deacetylase (HDAC) inhibitors in vivo in collagen-induced arthritis in rodents", Br. J. Pharmacol., 2007, vol. 150, No. 7, pp. 862-872.

Lindebo Holm T et al., "Pharmacological Evaluation of the SCID T Cell Transfer Model of Colitis: As a Model of Crohn's Disease", Int. J. Inflamm., 2012, vol. 1, 412178.

Liu JZ et al., "Dense genotyping of immune-related disease regions identifies nine new risk loci for primary sclerosing cholangitis", Nat. Genet., 2013, vol. 45, No. 6, pp. 670-675.

Matsuse T et al., "ICAM-1 mediates lung leukocyte recruitment but not pulmonary fibrosis in a murine model of oleomycin-induced lung injury", Eur. Respir. J., 1999, vol. 13, No. 1, pp. 71-77.

Maxwell JR et al., "Differential Roles for Interleukin-23 and Interleukin-17 in Intestinal Immunoregulation", Immunity, 2015, vol. 43, No. 4, pp. 739-750.

MD Biosciences Inc., "Monoclonal Antibody Induced Arthritis: a shorter, more synchronized alternative to the classic CIA model", 2008, BioTechniques vol. 44, No. 2, pp. 279-280.

Miller RE et al., "Therapeutic effects of an anti-ADAMTS-5 antibody on joint damage and mechanical allodynia in a murine model of osteoarthritis", 2016, Osteoarthritis Cartilage, vol. 24, No. 2, pp. 299-306.

Nandakumar KS et al., "Collagen Type II-Specific Monoclonal Antibody-Induced Arthritis in Mice", Am. J. Pathol., 2003. vol. 163, No. 5, pp. 1827-1837.

Nishida K et al., "Histone deacetylase inhibitor suppression of autoantibody-mediated arthritis in mice via regulation of p16INK4a and p21WAF1/Cip1 expression", Arthritis Rheum., 2004, vol. 50, No. 10, pp. 3365-3376.

Nixon M et al., "Skeletal muscle salt inducible kinase 1 promotes insulin resistance in obesity", Mol. Metab., 2015, vol. 5, No. 1, pp. 34-46.

Ozanne J, "The clinically approved drugs dasatinib and bosutinib induce anti-inflammatory macrophages by inhibiting the salt-inducible kinases", Biochem. J., 2015, vol. 465, No. 2, pp. 271-279.

Rall LC et al., "Rheumatoid cachexia: metabolic abnormalities, mechanisms and interventions", Rheumatology, 2004, vol. 43, No. 10, pp. 1219-1223.

Rizzo HL et al., "IL-23-Mediated Psoriasis-Like Epidermal Hyperplasia Is Dependent on IL-17A", J. Immunol., 2011, vol. 186, No. 3, pp. 1495-1502.

Salvemini D et al., "Amelioration of joint disease in a rat model of collagen-induced arthritis by M40403, a superoxide dismutase mimetic", Arthritis Rheum., 2001, vol. 44, No. 12, pp. 2909-2921.

Sasaki T et al., "SIK2 Is a Key Regulator for Neuronal Survival after Ischemia via TORC1-CREB", Neuron, 2011, vol. 69, No. 1, pp. 106-119.

Shelton DL et al., "Nerve growth factor mediates hyperalgesia and cachexia in auto-immune arthritis", Pain, 2005, vol. 116, No. 1-2, pp. 8-16.

Sherlock JP et al. "IL-23 induces spondyloarthropathy by acting on ROR-yt+ CD3+CD4-CD8-entheseal resident T cells", Nat. Med., 2012, vol. 18, No. 7, pp. 1069-1076.

Sims NA et al., "Targeting osteoclasts with zoledronic acid prevents bone destruction in collagen-induced arthritis", Arthritis Rheum., 2004, vol. 50, No. 7, pp. 2338-2346.

Sina C et al., "G Protein-Coupled Receptor 43 Is Essential for Neutrophil Recruitment during Intestinal Inflammation", J. Immunol., 2009, vol. 183, No. 11, pp. 7514-7522.

Sundberg TB et al., "Small-molecule screening identifies inhibition of salt-inducible kinases as a therapeutic strategy to enhance immunoregulatory functions of dendritic cells", Proc. Natl. Acad. Sci. U. S. A, 2014, vol. 111, No. 34, pp. 12468-12473.

Walsmith J et al., "Tumor necrosis factor-alpha production is associated with less body cell mass in women with rheumatoid arthritis". J. Rheumatol., 2004, vol. 31, No. 1, pp. 23-29.

Wein MN et al., "SIKs control osteocyte responses to parathyroid hormone", Nat. Commun., vol. 7, Art No. 13176.

(56) References Cited

OTHER PUBLICATIONS

Wirtz S et al. "Chemically induced mouse models of intestinal inflammation", Nat. Protoc., 2007, vol. 2, No. 3, pp. 541-546.
Yao C et al. "Prostaglandin E promotes Th1 differentiation via synergistic amplification of IL-12 signalling by cAMP and PI3-kinase", Nat. Commun., 2013, vol. 4, p. 1685.
Yokogawa M et al., "Epicutaneous Application of Toll-like Receptor 7 Agonists Leads to Systemic Autoimmunity in Wild-Type Mice: A New Model of Systemic Lupus Erythematosus", Arthritis Rheumatol., 2014, vol. 66, No. 3, pp. 694-706.
Yu J et al., Salt-inducible kinase 1 is involved in high glucose-induced mesangial cell proliferation mediated by the ALK5 signaling pathway, Int. J. Mol. Med., 2013, vol. 32, No. 1, pp. 151-157.
International Search Report and Written Opinion Issued Jul. 20, 2020 in PCT/EP2020/064368.
Desroy, N., et al., "Salt-inducible kinases: an emerging target class with broad therapeutic potential", Medicinal Chemistry Reviews (2023) 58:209-231, https://pubs.acs.org/doi/10.1021/mc-2023-vol58.ch09.
Öster Linda., et al., "The structures of salt inducible kinase 3 in complex with pharmacological inhibitors reveal determinants for binding and selectivity", J. Biol. Chem. (2024) 300(5):1-18, https://doi.org/10.1016/j.jbc.2024.107201.

* cited by examiner

BENZAMIDE-SUBSTITUTED BICYCLIC IMIDAZO- AND PYRAZOLO-FUSED -PYRIDINE, -PYRIMIDE, AND -PYRIDAZINE COMPOUNDS FOR TREATMENT OF INFLAMMATORY DISEASES

CROSS-REFERENCE TO RELATED APPLICATIONS

This application is a National Stage Entry of PCT/EP2020/064368, filed May 25, 2020, which claims priority to GB application No. 1907616.5, filed May 29, 2019, the disclosures of each of which are hereby incorporated by reference in their entirety.

FIELD OF THE INVENTION

The present invention relates to compounds, methods for the production of the compounds of the invention, pharmaceutical compositions comprising the compounds of the invention, uses and methods for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases by administering the compounds of the invention. In particular, the compounds of the invention may inhibit Salt-Inducible Kinases ("SIK" kinases).

BACKGROUND OF THE INVENTION

Protein kinases belong to a large family of structurally related enzymes which are responsible for the control of a wide variety of cellular signal transduction processes. In particular, they have been shown to be key regulators in cellular functions including for example proliferation, metabolism, and apoptosis. Consequently, defective control of protein phosphorylation which leads to uncontrolled signaling is involved in a number of diseases, including for example, inflammation, allergies, cancer, autoimmune diseases, CNS disorders, and angiogenesis.

In healthy individuals inflammation is self-limiting, and resolution is controlled by the release of anti-inflammatory mediators and cytokines, such as interleukin-10 (IL-10), produced by "suppressive" or "regulatory" cells, which are produced as part of a negative feedback loop.

Indeed, in the normal process of inflammation in the body, an initial pro-inflammatory response is followed by a pro-resolution response which turns the inflammation off after the insult has been resolved, leading to the reduction of pro-inflammatory cytokines such as TNFα and IL-12, coupled with increased levels of anti-inflammatory cytokines such as IL-10 and TGF-β, resulting in the generation of a so-called tolerogenic environment.

Adenosine Monophosphate-activated Protein Kinases (AMPK) belong to the protein kinase family, which comprises Salt-Inducible Kinases (SIKs), a family of serine/threonine kinases widely expressed in the body, and involved in particular in cellular energy homeostasis. Three SIK isoforms have been identified, named SIK1 (also referred as SNFI-Like Kinase (SNF1LK) or Myocardial Snfl-like Kinase (MSK)), SIK2 (SNF1LK2 or KIAA0781) and SIK3 (KIAA0999) (Katoh et al. 2004).

The SIKs play a number of roles in different cell types. They have been found to phosphorylate a number of substrates including CREB-responsive transcriptional co-activator (CRTC) proteins and Histone de-acetylase (HDAC) proteins, thereby regulating the transcription of a number of different genes. One of the roles of CRTC signalling relates to control the phenotype of macrophages, in particular polarisation of macrophages through phosphorylation of CRTC3 as measured by decreased proinflammatory cytokine IL-12 secretion and concomitant increased pro-resolution cytokine IL-10 secretion (Clark et al. 2012; Ozanne et al. 2015).

SIK1 has recently been shown to be involved in skeletal muscle sensitivity in obese mice, and may be an interesting target to prevent type II diabetes (Nixon et al. 2016), and diabetic nephropathy (Yu et al. 2013).

The regulation of ALK5 by SIK1 (Yu et al. 2013) and the identification of the SIK2 gene as a risk locus for primary sclerosing cholangitis (Liu et al. 2013) suggest a role for SIK proteins in fibrotic diseases.

SIK2 and SIK3 have recently been identified to play a role in inflammation through the secretion of high levels of anti-inflammatory cytokines, in particular Interleukin-10 (IL-10) and very low levels of pro-inflammatory cytokines such as TNFα (Darling et al. 2017).

A role for SIK2 in T helper (Th)1 cell differentiation has recently been described through the regulation of IFNγ and IL-12 signaling, suggesting SIK2 may be an interesting target for inflammatory diseases (Yao et al. 2013).

Recently, it has also been shown that like PTH, small molecule SIK inhibitors cause decreased phosphorylation and increased nuclear translocation of HDAC4/5 and CRTC2. Treatment with the small molecule SIK inhibitor YKL-05-099 increased bone formation and bone mass in mice (Wein et al. 2016), confirming the relevance of SIK inhibition in the treatment of bone turnover diseases.

Furthermore, it was shown that inhibition of SIK2 after oxygen-glucose deprivation enhances neuron survival (Sasaki et al. 2011) or promotes melanogenesis in melanoma cells (Kumagai et al. 2011). In this context, since therapeutic strategies are needed to modulate the stress cellular response, such as during ischaemia and post reperfusion of tissue, in the chronic phase of cardiac remodelling, in diabetes and neurodegenerative conditions, the rapid activation or degradation of the SIK proteins, following multiple kinds of stresses, makes them interesting targets in inflammatory, cardiac or metabolic diseases and neurodegenerative disorders. SIK inhibition might also have application in cosmetology or pigmentation-related diseases to induce melanogenesis.

The regulation of ALK5 by SIK1 (Yu et al. 2013) and the identification of the SIK2 gene as a risk locus for primary sclerosing cholangitis (Liu et al. 2013) suggest a role for SIK proteins in fibrotic diseases.

Besides the pivotal function in cellular energy homeostasis, the SIK proteins have also been involved in the regulation of the cell cycle. Higher expression of SIK2 significantly correlated with poor survival in patients with high-grade serous ovarian cancers (Ashour Ahmed et al. 2010), moreover, expression of SIK3 was elevated in ovarian cancers, particularly in the serous subtype and at later stages (Charoenfuprasert et al. 2011). Therefore SIK inhibition may be useful in the treatment of cancer.

Despite great advances over the past two decades in the treatments of patients affected by autoimmune disorders, based on antibodies targeting pro-inflammatory cytokines such as anti-TNFα, a significant proportion of patients do not respond to these therapies or experience serious adverse events such as opportunistic infections. Therefore a large unmet medical need still exists for the treatment of these diseases, and new agents for the prophylaxis and/or treatment of the above mentioned diseases are required.

SUMMARY OF THE INVENTION

The present invention is based on the identification of novel compounds, and their use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases. In particular, the compounds of the invention may be SIK inhibitors, and more particularly SIK1, SIK2 and/or SIK3 inhibitors. The present invention also provides methods for the production of these compounds, pharmaceutical compositions comprising these compounds and methods for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases by administering the compounds of the invention.

Accordingly, in a first aspect of the invention, the compounds of the invention are provided having a Formula I:

I

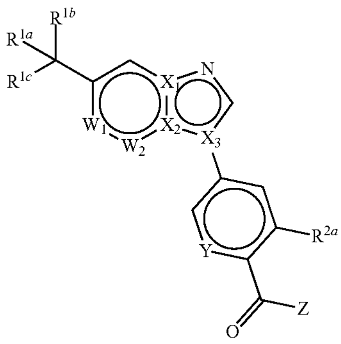

wherein, $W_1$ is N or $CR^3$ and $W_2$ is N or CH, with the proviso that $W_1$ and $W_2$ cannot both be N;

one of $X_1$, $X_2$ and $X_3$ is N and the other two are C;

Y is N or $CR^2$b;

Z is

—$NR^{4a}R^{4b}$,

—$NR^{4c}$—, wherein the N atom and $R^{2a}$ together with the atoms onto which they are attached form a fused 5-6 membered heterocycloalkenyl comprising one double bond, or N-linked 4-7 membered monocyclic or spirocyclic heterocycloalkyl further comprising zero, one, or two additional heteroatoms independently selected from N, O, and S, optionally substituted with one or more independently selected $R^5$ groups;

$R^{1a}$ is selected from

H, halo,

—OH,

—CN, $C_{1-6}$ alkyl optionally substituted with one or more independently selected $R^6$, $C_{1-4}$ alkoxy optionally substituted with one or more —OH or 5-6 membered monocyclic heterocycloalkyl comprising one, two or three heteroatoms independently selected from N, O, and S,

—C(═O)—$R^7$,

—$NR^{8a}R^{8b}$,

—$S(═O)_2$—$C_{1-4}$ alkyl, 5-6 membered monocyclic heteroaryl comprising one, two or three heteroatoms independently selected from N, O, and S, which heteroaryl is optionally substituted with one or more independently selected $C_{1-4}$ alkyl, and 4-6 membered monocyclic heterocycloalkyl comprising one, two or three heteroatoms independently selected from N, O, and S;

$R^{1b}$ and $R^{1c}$ are independently selected from halo,

—OH,

—CN, $C_{1-4}$ alkyl optionally substituted with one or more independently selected —OH, —CN, or $C_{2-4}$ alkenyl, $C_{3-7}$ cycloalkyl, 4-8 membered monocyclic or spirocyclic heterocycloalkyl comprising one, two or three heteroatoms independently selected from N, O, and S, which heterocycloalkyl is optionally substituted with one or more independently selected $R^9$ groups, and —$NR^{10a}R^{10b}$, or $R^{1b}$ and $R^{1c}$ together with the atom onto which they are attached form a $C_{3-6}$ cycloalkyl, or $R^{1b}$ and $R^{1c}$ together with the atom onto which they are attached form a 4-6 membered monocyclic heterocycloalkyl comprising one, two, or three heteroatoms independently selected from N, O, and S, which heterocycloalkyl is optionally substituted with one or more independently selected $R^{11}$ groups;

$R^{2a}$ and $R^{2b}$ are independently selected from halo, $C_{1-4}$ alkyl, $C_{1-4}$ alkoxy optionally substituted with one or more independently selected halo, —OH, or $C_{1-4}$ alkoxy, —$NR^{12a}R^{12b}$, and

—OH;

$R^3$ is H, halo, or $C_{1-4}$ alkoxy optionally substituted with one or more independently selected —OH or $C_{1-4}$ alkoxy;

$R^{4a}$ is H or $C_{1-4}$ alkyl;

$R^{4b}$ is selected from $C_{1-6}$ alkyl optionally substituted with one or more independently selected $R^{13}$, $C_{3-7}$ cycloalkyl optionally substituted with one or more independently selected $R^{14a}$, 4-7 membered monocyclic heterocycloalkyl comprising one, two or three heteroatoms independently selected from N, O, and S, which heterocycloalkyl is optionally substituted with one or more independently selected $R^{14b}$, and 5-6 membered monocyclic heteroaryl comprising one, two or three heteroatoms independently selected from N, O, and S, which heteroaryl is optionally substituted with one or more independently selected $C_{1-4}$ alkyl;

$R^{4c}$ is H, $C_{3-7}$ cycloalkyl, or $C_{1-6}$ alkyl optionally substituted with one or more independently selected halo or —CN;

each $R^5$ is independently selected from:

oxo, halo,

—CN,

—OH,

—$NR^{15a}R^{15b}$, phenyl, $C_{3-7}$ cycloalkyl, $C_{2-4}$ alkynyl,

—C(═O)—$C_{1-4}$ alkoxy, $C_{1-4}$ alkoxy optionally substituted with one or more independently selected halo or phenyl, $C_{1-4}$ alkyl optionally substituted with one or more independently selected halo, —OH, or $C_{1-4}$ alkoxy, and 4-7 membered monocyclic heterocycloalkyl comprising one, two or three heteroatoms independently selected from N, O, and S;

each $R^6$ is independently selected from halo,

—O—$R^{16}$,

—$NR^{17a}R^{17b}$, 5-6 membered monocyclic heteroaryl comprising one, two or three heteroatoms independently selected from N, O, and S, and 4-6 membered monocyclic heterocycloalkyl comprising one, two or three heteroatoms independently selected from N, O, and S, which heterocycloalkyl is optionally substituted with one or more independently selected halo;

$R^7$ is —OH, $C_{1-4}$ alkyl, $C_{1-4}$ alkoxy, —$NR^{18a}R^{18b}$, or 4-6 membered monocyclic heterocycloalkyl comprising one, two or three heteroatoms independently selected from N, O, and S, which heterocycloalkyl is optionally substituted with one or more —OH;

$R^{8a}$ and $R^{8b}$ are independently H, —C(═O)—$C_{1-4}$ alkoxy, or $C_{1-4}$ alkyl optionally substituted with one or more independently selected halo, —CN or —OH;

each $R^9$ is independently halo, —OH, or $C_{1-4}$ alkyl optionally substituted with one or more —OH;

each $R^{10a}$ and $R^{10b}$ is independently H or $C_{1-4}$ alkyl optionally substituted with one or more —OH;

each $R^{11}$ is independently selected from $C_{1-4}$ alkyl optionally substituted with one or more independently selected —CN or $C_{1-4}$ alkoxy, —C(═O)—$C_{1-6}$ alkyl, and —C(═O)—$C_{1-6}$ alkoxy;

each $R^{12a}$ and $R^{12b}$ is independently H or $C_{1-4}$ alkyl optionally substituted with one —OH or $C_{1-4}$ alkoxy;

each $R^{13}$ is independently selected from halo,

—CN,

—$NR^{19a}R^{19b}$,

—OH, $C_{1-4}$ alkoxy, $C_{3-7}$ cycloalkyl,

—S(═O)$_2$—$C_{1-4}$ alkyl, 4-7 membered monocyclic heterocycloalkyl comprising one, two or three heteroatoms independently selected from N, O, and S, and 5-6 membered monocyclic heteroaryl comprising one, two or three heteroatoms independently selected from N, O, and S, which heteroaryl is optionally substituted with one or more independently selected $C_{1-4}$ alkyl;

each $R^{14a}$ and $R^{14b}$ is independently selected from halo, oxo, $C_{1-4}$ alkyl optionally substituted with one or more independently selected halo, —OH, or $C_{1-4}$ alkoxy,

—OH, $C_{1-4}$ alkoxy, and

—$NR^{20a}R^{20b}$.

each $R^{15a}$ and $R^{15b}$ is independently H, $C_{1-4}$ alkyl, or —C(═O)—$C_{1-4}$ alkoxy;

each $R^{16}$ is independently selected from

H,

—S(═O)$_2$—$C_{1-4}$alkyl, $C_{1-4}$ alkyl optionally substituted with one or more —C(═O)—$NR^{21a}R^{21b}$ or 4-6 membered monocyclic heterocycloalkyl comprising one, two or three heteroatoms independently selected from N, O, and S, and 4-6 membered monocyclic heterocycloalkyl comprising one, two or three heteroatoms independently selected from N, O, and S;

each $R^{17a}$ and $R^{17b}$ is independently H or $C_{1-4}$ alkyl optionally substituted with one or more independently selected —OH or $C_{1-4}$ alkoxy;

$R^{18a}$ and $R^{18b}$ are independently H or $C_{1-4}$ alkyl optionally substituted with one or more independently selected —OH or $C_{1-4}$ alkoxy;

each $R^{19a}$, $R^{19b}$, $R^{20a}$, $R^{20b}$, $R^{21a}$, and $R^{21b}$ is independently H or $C_{1-4}$ alkyl.

In a particular aspect, the compounds of the invention are provided for use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases.

Furthermore, it has also been unexpectedly demonstrated that the compounds of the invention exhibit potency against SIK, particularly SIK1, SIK2 and/or SIK3, more particularly SIK3, which may result in a tolerogenic therapy (i.e. reduction of pro-inflammatory cytokines such as TNFα and IL-12, coupled with increased levels of anti-inflammatory cytokines such as IL-10 and TGF-β).

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the treatment of inflammatory diseases, autoinflammatory diseases, autoimmune diseases, proliferative diseases, fibrotic diseases, transplantation rejection, diseases involving impairment of cartilage turnover, congenital cartilage malformation, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon having the specified number of carbon atoms. Particular alkyl groups have 1 to 6 carbon atoms or 1 to 4 carbon atoms. Branched means that one or more alkyl groups such as methyl, ethyl or propyl is attached to a linear alkyl chain. Particular alkyl groups are methyl ($—CH_3$), ethyl ($—CH_2—CH_3$), n-propyl ($—CH_2—CH_2—CH_3$), isopropyl ($—CH(CH_3)_2$), n-butyl ($—CH_2—CH_2—CH_2—CH_3$), tert-butyl ($—C(CH_3)_3$), sec-butyl ($—CH(CH_3)—CH_2CH_3$), isobutyl ($—CH_2—CH(CH_3)_2$), n-pentyl ($—CH_2—CH_2—CH_2—CH_2—CH_3$), n-hexyl ($—CH_2—CH_2—CH_2—CH_2—CH_2—CH_3$), and 1,2- dimethylbutyl ($—CHCH_3)—C(CH_3)H_2—CH_2—CH_3$). Particular alkyl groups have between 1 and 4 carbon atoms.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl ($—CH{=}CH_2$), n-propenyl ($—CH_2CH{=}CH_2$), isopropenyl ($—C(CH_3){=}CH_2$) and the like.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene ($—CH_2—$), ethylene ($—CH_2—CH_2—$), or $—CH(CH_3)—$ and the like.

'Alkynylene' refers to divalent alkyne radical groups having the number of carbon atoms and the number of triple bonds specified, in particular 2 to 6 carbon atoms and more particularly 2 to 4 carbon atoms which can be straight-chained or branched. This term is exemplified by groups such as $—C{\equiv}C—$, $—CH_2—C{\equiv}C—$, and $—C(CH_3)H—C{\equiv}CH—$.

'Alkoxy' refers to the group O-alkyl, where the alkyl group has the number of carbon atoms specified. In particular the term refers to the group $—O—C_{1-6}$ alkyl. Particular alkoxy groups are methoxy, ethoxy, n-propoxy, isopropoxy, n-butoxy, tert-butoxy, isobutoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Amino' refers to the radical $—NH_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or fused polycyclic, with the number of ring atoms specified. Specifically, the term includes groups that include from 6 to 10 ring members. Particular aryl groups include phenyl, and naphthyl.

'Cycloalkyl' refers to a non-aromatic hydrocarbyl ring structure, monocyclic, fused polycyclic, bridged polycyclic, or spirocyclic, with the number of ring atoms specified. A cycloalkyl may have from 3 to 12 carbon atoms, in particular from 3 to 10, and more particularly from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

As used herein, term 'polycyclic' refers to chemical groups featuring several closed rings of atoms. In particular it refers to groups featuring two, three or four rings of atoms, more particularly two or three rings of atoms, most particularly two rings of atoms.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or fused polycyclic, that includes one or more heteroatoms independently selected from O, N and S and the number of ring atoms specified. In particular, the aromatic ring structure may have from 5 to 9 ring members. The heteroaryl group can be, for example, a five membered or six membered monocyclic ring or a fused bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In particular, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered monocyclic heteroaryl groups include but are not limited to pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered monocyclic heteroaryl groups include but are not limited to pyridinyl, pyrazinyl, pyridazinyl, pyrimidinyl and triazinyl.

Particular examples of bicyclic heteroaryl groups containing a five membered ring fused to another five-membered ring include but are not limited to imidazothiazolyl and imidazoimidazolyl.

Particular examples of bicyclic heteroaryl groups containing a six membered ring fused to a five membered ring include but are not limited to benzofuranyl, benzothiophenyl, benzoimidazolyl, benzoxazolyl, benzisoxazolyl, benzothiazolyl, benzisothiazolyl, isobenzofuranyl, indolyl, isoindolyl, indolizinyl, purinyl (e.g. adenine, guanine), indazolyl, pyrazolopyrimidinyl, triazolopyrimidinyl, and pyrazolopyridinyl groups.

Particular examples of bicyclic heteroaryl groups containing two fused six membered rings include but are not limited to quinolinyl, isoquinolinyl, pyridopyridinyl, quinoxalinyl, quinazolinyl, cinnolinyl, phthalazinyl, naphthyridinyl, and pteridinyl groups. Particular heteroaryl groups are those derived from thiophenyl, pyrrolyl, benzothiophenyl, benzofuranyl, indolyl, pyridinyl, quinolinyl, imidazolyl, oxazolyl and pyrazinyl.

Examples of representative heteroaryls include the following:

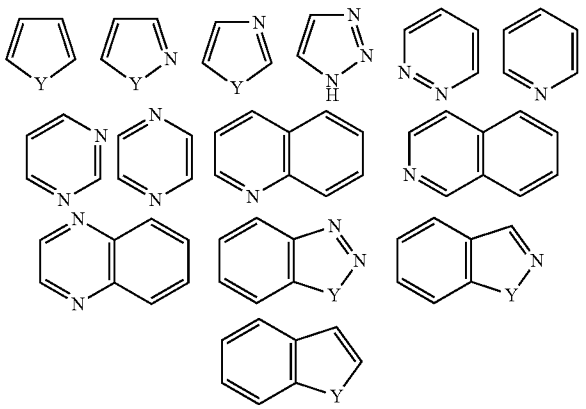

wherein each Y is selected from >C═O, NH, O and S.

'Heterocycloalkyl' means a non-aromatic fully saturated ring structure, monocyclic, fused polycyclic, spirocyclic, or bridged polycyclic, that includes one or more heteroatoms independently selected from O, N and S and the number of ring atoms specified. The heterocycloalkyl ring structure may have from 4 to 12 ring members, in particular from 4 to 10 ring members and more particularly from 4 to 7 ring members. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. Examples of heterocyclic rings include, but are not limited to azetidinyl, oxetanyl, thietanyl, pyrrolidinyl (e.g. 1-pyrrolidinyl, 2-pyrrolidinyl and 3-pyrrolidinyl), tetrahydrofuranyl (e.g. 1-tetrahydrofuranyl, 2-tetrahydrofuranyl and 3-tetrahydrofuranyl), tetrahydrothiophenyl (e.g. 1-tetrahydrothiophenyl, 2-tetrahydrothiophenyl and 3-tetrahydrothiophenyl), piperidinyl (e.g. 1-piperidinyl, 2-piperidinyl, 3-piperidinyl and 4-piperidinyl), tetrahydropyranyl (e.g. 4-tetrahydropyranyl), tetrahydrothiopyranyl (e.g. 4-tetrahydrothiopyranyl), morpholinyl, thiomorpholinyl, dioxanyl, or piperazinyl.

As used herein, the term 'heterocycloalkenyl' means a 'heterocycloalkyl', which comprises at least one double bond. Particular examples of heterocycloalkenyl groups are shown in the following illustrative examples:

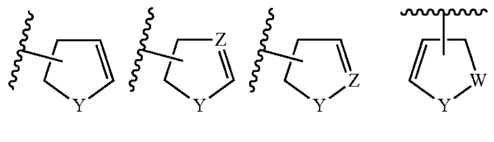

-continued

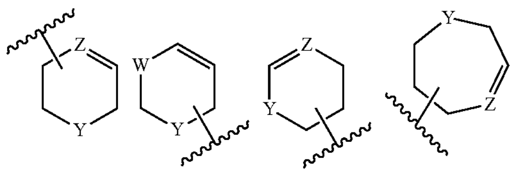

wherein each W is selected from $CH_2$, NH, O and S; each Y is selected from NH, O, C(=O), $SO_2$, and S; and each Z is selected from N or CH.

Particular examples of monocyclic rings are shown in the following illustrative examples:

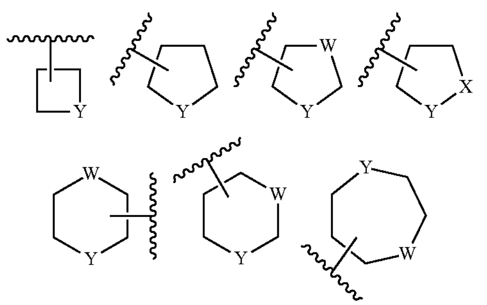

wherein each W and Y is independently selected from $-CH_2-$, —NH—, —O— and —S—.

Particular examples of fused bicyclic rings are shown in the following illustrative examples:

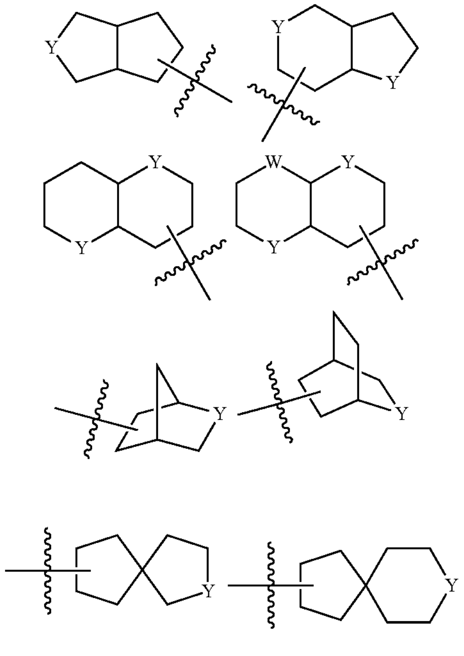

wherein each W and Y is independently selected from $-CH_2-$, —NH—, —O— and —S—.

Particular examples of bridged bicyclic rings are shown in the following illustrative examples:

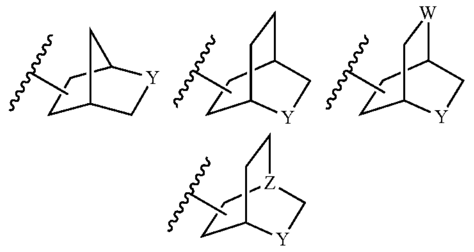

wherein each W and Y is independently selected from $-CH_2-$, —NH—, —O— and —S—.

Particular examples of spirocyclic rings are shown in the following illustrative examples:

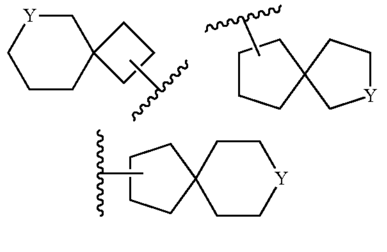

wherein each Y is selected from $-CH_2-$, —NH—, —O— and —S—.

'Hydroxyl' refers to the radical —OH.

'Oxo' refers to the radical =O.

'Substituted' refers to a group in which one or more hydrogen atoms are each independently replaced with the same or different substituent(s).

'Sulfo' or 'sulfonic acid' refers to a radical such as $-SO_3H$.

'Thiol' refers to the group —SH.

As used herein, term 'substituted with one or more' refers to one to four substituents. In particular, it refers to one to three substituents. More particularly, it refers to one or two substituents. Most particularly, it refers to one substituent.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzene-sulfonic acid, 4-chlorobenzenesulfonic acid, 2-naphthalene-sulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'inflammatory disease(s)' refers to the group of conditions including, rheumatoid arthritis, osteoarthritis, juvenile idiopathic arthritis, psoriasis, psoriatic arthritis, ankylosing spondylitis, allergic airway disease (e.g. asthma, rhinitis), chronic obstructive pulmonary disease (COPD), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, chronic obstructive pulmonary disease (COPD) and inflammatory bowel diseases.

As used herein the term 'autoinflammatory diseases(s)' refers to the group of diseases including Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease.

As used herein the term 'autoimmune disease(s)' refers to the group of diseases including obstructive airways disease, including conditions such as COPD, asthma (e.g intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, autoimmune liver diseases (e.g. autoimmune hepatitis, primary sclerosing cholangitis, and primary biliary cirrhosis), Sjögren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly the term refers to COPD, asthma, systemic lupus erythematosis, type I diabetes mellitus and inflammatory bowel disease.

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukemia, acute and chronic lymphoblastic leukemia), multiple myeloma, psoriasis, restenosis, scleroderma or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasize) to distant organs, for example to bone, liver, lung or the brain. As used herein the term cancer includes both metastatic tumour cell types (such as but not limited to, melanoma, lymphoma, leukemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, and uterine leiomyosarcoma). In particular, the term 'cancer' refers to acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-cell lymphoma, embryonal tumors, endometrial cancer, ependymoblastoma, ependymoma, esophageal cancer, Ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hypopharyngeal cancer, intraocular melanoma, islet cell tumors (endocrine pancreas), Kaposi sarcoma, kidney cancer, Langerhans cell histiocytosis, laryngeal cancer, leukemia, hairy cell leukemia, liver cancer, non-small cell lung cancer, small cell lung cancer, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, myeloid leukemia, multiple myeloma, nasopharyngeal cancer, neuroblastoma, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, Sezary syndrome, skin cancer, small cell lung cancer, small intestine cancer, soft tissue sarcoma, squamous cell carcinoma, stomach (gastric) cancer, supratentorial primitive neuroectodermal tumors, testicular cancer, throat cancer, thymoma and thymic carcinoma, thyroid cancer, urethral cancer, uterine cancer, uterine sarcoma, vaginal cancer, vulvar cancer, and Wilms tumor.

As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukemia (AML), and acute lymphoblastic leukemia (ALL) and chronic lymphoblastic leukemia (CLL).

As used herein the term 'fibrotic disease(s)' refers to diseases characterized by excessive scarring due to excessive production, deposition, and contraction of extracellular matrix, and that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular, the term fibrotic diseases refers to idiopathic pulmonary fibrosis (IPF); cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak syndrome, tuberous sclerosis, neurofibromatosis, metabolic storage diseases, familial interstitial lung disease); radiation induced fibrosis; chronic obstructive pulmonary disease; scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; diabetic nephropathy, focal segmental glomerular sclerosis; IgA nephropathy; hypertension; Alport syndrome; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Dupuytren disease, keloids, cutaneous fibrosis; cutaneous scleroderma; systemic sclerosis, spinal cord injury/fibrosis; myelofibrosis; Duchenne muscular dystrophy (DMD) associated musculoskeletal fibrosis, vascular restenosis; atherosclerosis; arteriosclerosis; Wegener's granulomatosis; Peyronie's disease, or chronic lymphocytic. More particularly, the term 'fibrotic diseases' refers to idiopathic pulmonary fibrosis (IPF), Dupuytren disease, nonalcoholic steatohepatitis (NASH), systemic sclerosis, renal fibrosis, and cutaneous fibrosis.

As used herein the term 'transplantation rejection' refers to the acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases.

As used herein the term 'diseases involving impairment of cartilage turnover' includes conditions such as osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis.

As used herein the term 'congenital cartilage malformation(s)' includes conditions such as hereditary chondrolysis, chondrodysplasias and pseudochondrodysplasias, in particular, but without limitation, microtia, anotia, metaphyseal chondrodysplasia, and related disorders.

As used herein the term 'diseases involving impairment of bone turnover' includes conditions such as osteoporosis (including postmenopausal osteoporosis, male osteoporosis, glucocorticosteroid induced osteoporosis and juvenile osteoporosis), osteoporosis caused through neoplastic bone marrow disorders, osteopenia, hormone deficiency (vitamin D deficiency, male and female hypogonadism), hormone excess (hyperprolactinemia, excess glucocorticoid, hyperthyroidism, hyperparathyroidism), Paget's disease, osteoarthritis, renal bone disease, osteogenesis imperfecta, hypophosphatasia.

As used herein the term 'disease(s) associated with hypersecretion of IL-6' includes conditions such as Castleman's disease, multiple myeloma, psoriasis, Kaposi's sarcoma and/or mesangial proliferative glomerulonephritis.

As used herein the term 'disease(s) associated with hypersecretion of TNFα, interferons, IL-12 and/or IL-23' includes conditions such as systemic and cutaneous lupus erythematosis, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease.

As used herein, the term 'respiratory disease(s)' refers to diseases affecting the organs that are involved in breathing, such as the nose, throat, larynx, eustachian tubes, trachea, bronchi, lungs, related muscles (e.g., diaphragm and intercostals), and nerves. In particular, examples of respiratory diseases include asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation, cystic fibrosis, and hypoxia.

As used herein the term 'endocrine and/or metabolic disease(s)' refers to the group of conditions involving the body's over- or under-production of certain hormones, while metabolic disorders affect the body's ability to process certain nutrients and vitamins. Endocrine disorders include hypothyroidism, congenital adrenal hyperplasia, diseases of the parathyroid gland, diabetes mellitus, diseases of the adrenal glands (including Cushing's syndrome and Addison's disease), and ovarian dysfunction (including polycystic ovary syndrome), among others. Some examples of metabolic disorders include cystic fibrosis, phenylketonuria (PKU), diabetes, hyperlipidemia, gout, and rickets. A particular example of metabolic disorders is obesity and/or type II diabetes.

As used herein the term 'cardiovascular disease(s)' refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis (e.g., giant cell arteritis (GCA), retinal vasculitis, rheumatoid vasculitis), stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, cardiovascular disease refers to atherosclerosis or giant cell arteritis.

As used herein the term 'dermatological disease(s)' refers to a skin disorder. In particular, dermatological disorders include proliferative or inflammatory disorders of the skin such as atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria. More particularly, the term dermatological disorders refers to vitiligo.

As used herein the term 'abnormal angiogenesis associated disease(s)' refers to diseases caused by the dysregulation of the processes mediating angiogenesis. In particular, abnormal angiogenesis associated disease refers to atherosclerosis, hypertension, tumor growth, inflammation, rheumatoid arthritis, wet-form macular degeneration, choroidal neovascularization, retinal neovascularization, and diabetic retinopathy.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgaard 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

The present disclosure includes all isotopic forms of the compounds of the invention provided herein, whether in a form (i) wherein all atoms of a given atomic number have a mass number (or mixture of mass numbers) which predominates in nature (referred to herein as the "natural isotopic form") or (ii) wherein one or more atoms are replaced by atoms having the same atomic number, but a mass number different from the mass number of atoms which predominates in nature (referred to herein as an "unnatural variant isotopic form"). It is understood that an atom may naturally exists as a mixture of mass numbers. The term "unnatural variant isotopic form" also includes embodiments in which the proportion of an atom of given atomic number having a mass number found less commonly in nature (referred to herein as an "uncommon isotope") has been increased relative to that which is naturally occurring e.g. to the level of >20%, >50%, >75%, >90%, >95% or >99% by number of the atoms of that atomic number (the latter embodiment referred to as an "isotopically enriched variant form"). The term "unnatural variant isotopic form" also includes embodiments in which the proportion of an uncommon isotope has been reduced relative to that which is naturally occurring. Isotopic forms may include radioactive forms (i.e. they incorporate radioisotopes) and non-radioactive forms. Radioactive forms will typically be isotopically enriched variant forms.

An unnatural variant isotopic form of a compound may thus contain one or more artificial or uncommon isotopes such as deuterium ($^2$H or D), carbon-11 ($^{11}$C), carbon-13 ($^{13}$C), carbon-14 ($^{14}$C), nitrogen-13 ($^{13}$N), nitrogen-15 ($^{15}$N), oxygen-15 ($^{15}$O), oxygen-17 ($^{17}$O), oxygen-18 ($^{18}$O), phosphorus-32 ($^{32}$P), sulphur-35 ($^{35}$S), chlorine-36 ($^{36}$Cl), chlorine-37 ($^{37}$Cl), fluorine-18 ($^{18}$F) iodine-123 ($^{123}$I), iodine-125 ($^{125}$I) in one or more atoms or may contain an increased proportion of said isotopes as compared with the proportion that predominates in nature in one or more atoms.

Unnatural variant isotopic forms comprising radioisotopes may, for example, be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Unnatural variant isotopic forms which incorporate deuterium i.e $^2$H or D may afford certain therapeutic advantages resulting from greater metabolic stability, for example, increased in vivo half-life or reduced dosage requirements, and hence may be preferred in some circumstances. Further, unnatural variant isotopic forms may be prepared which incorporate positron emitting isotopes, such as $^{11}$C, $^{18}$F, $^{15}$O and $^{13}$N, and would be useful in Positron Emission Topography (PET) studies for examining substrate receptor occupancy.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

The Invention

The present invention is based on the identification of novel compounds, and their use in the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases. In particular, the compounds of the invention may be SIK inhibitors, more particularly SIK1, SIK2 and/or SIK3 inhibitors.

The present invention also provides methods for the production of these compounds, pharmaceutical compositions comprising these compounds and methods for the prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases by administering the compounds of the invention.

Accordingly, in a first aspect of the invention, the compounds of the invention are provided having Formula I:

I

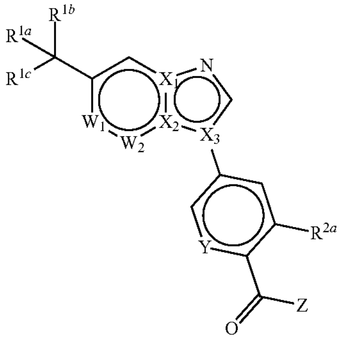

wherein, $W_1$ is N or $CR^3$ and $W_2$ is N or CH, with the proviso that $W_1$ and $W_2$ cannot both be N;

one of $X_1$, $X_2$ and $X_3$ is N and the other two are C;
Y is N or $CR^2b$;
Z is
—$NR^{4a}R^{4b}$,
—$NR^{4c}$—, wherein the N atom and $R^{2a}$ together with the atoms onto which they are attached form a fused 5-6 membered heterocycloalkenyl comprising one double bond, or
N-linked 4-7 membered monocyclic or spirocyclic heterocycloalkyl further comprising zero, one, or two additional heteroatoms independently selected from N, O, and S, optionally substituted with one or more independently selected $R^5$ groups;
$R^{1a}$ is selected from
H,
halo,
—OH,
CN,
$C_{1-6}$ alkyl optionally substituted with one or more independently selected $R^6$,
$C_{1-4}$ alkoxy optionally substituted with one or more —OH or 5-6 membered monocyclic heterocycloalkyl comprising one, two or three heteroatoms independently selected from N, O, and S,
—C(═O)—$R^7$,
—$NR^{8a}R^{8b}$,
—$S(═O)_2$—$C_{1-4}$ alkyl,
5-6 membered monocyclic heteroaryl comprising one, two or three heteroatoms independently selected from N, O, and S, which heteroaryl is optionally substituted with one or more independently selected $C_{1-4}$ alkyl, and
4-6 membered monocyclic heterocycloalkyl comprising one, two or three heteroatoms independently selected from N, O, and S;
$R^{1b}$ and $R^{1c}$ are independently selected from
halo,
—OH,
—CN,
$C_{1-4}$ alkyl optionally substituted with one or more independently selected —OH, —CN, or $C_{2-4}$ alkenyl,
$C_{3-7}$ cycloalkyl,
4-8 membered monocyclic or spirocyclic heterocycloalkyl comprising one, two or three heteroatoms independently selected from N, O, and S, which heterocycloalkyl is optionally substituted with one or more independently selected $R^9$ groups, and
—$NR^{10a}R^{10b}$,
or $R^{1b}$ and $R^{1c}$ together with the atom onto which they are attached form a $C_{3-6}$ cycloalkyl,
or $R^{1b}$ and $R^{1c}$ together with the atom onto which they are attached form a 4-6 membered monocyclic heterocycloalkyl comprising one, two, or three heteroatoms independently selected from N, O, and S, which heterocycloalkyl is optionally substituted with one or more independently selected $R^{11}$ groups;
$R^{2a}$ and $R^{2b}$ are independently selected from
halo,
$C_{1-4}$ alkyl,
$C_{1-4}$ alkoxy optionally substituted with one or more independently selected halo, —OH, or $C_{1-4}$ alkoxy,
—$NR^{12a}R^{12b}$, and
—OH;
$R^3$ is H, halo, or $C_{1-4}$ alkoxy optionally substituted with one or more independently selected —OH or $C_{1-4}$ alkoxy;
$R^{4a}$ is H or $C_{1-4}$ alkyl;
$R^{4b}$ is selected from
$C_{1-6}$ alkyl optionally substituted with one or more independently selected $R^{13}$,
$C_{3-7}$ cycloalkyl optionally substituted with one or more independently selected $R^{14a}$,
4-7 membered monocyclic heterocycloalkyl comprising one, two or three heteroatoms independently selected from N, O, and S, which heterocycloalkyl is optionally substituted with one or more independently selected $R^{14b}$, and
5-6 membered monocyclic heteroaryl comprising one, two or three heteroatoms independently selected from N, O, and S, which heteroaryl is optionally substituted with one or more independently selected $C_{1-4}$ alkyl;
$R^{4c}$ is H, $C_{3-7}$ cycloalkyl, or $C_{1-6}$ alkyl optionally substituted with one or more independently selected halo or —CN;
each $R^5$ is independently selected from
oxo,
halo,
—CN,
—OH,
—$NR^{15a}R^{15b}$,
phenyl,
$C_{3-7}$ cycloalkyl,
$C_{2-4}$ alkynyl,
—C(═O)—$C_{1-4}$ alkoxy,
$C_{1-4}$ alkoxy optionally substituted with one or more independently selected halo or phenyl,
$C_{1-4}$ alkyl optionally substituted with one or more independently selected halo, —OH, or $C_{1-4}$ alkoxy, and
4-7 membered monocyclic heterocycloalkyl comprising one, two or three heteroatoms independently selected from N, O, and S;
each $R^6$ is independently selected from
halo,
—O—$R^{16}$,
—$NR^{17a}R^{17b}$,
5-6 membered monocyclic heteroaryl comprising one, two or three heteroatoms independently selected from N, O, and S, and
4-6 membered monocyclic heterocycloalkyl comprising one, two or three heteroatoms independently selected from N, O, and S, which heterocycloalkyl is optionally substituted with one or more independently selected halo;
$R^7$ is —OH, $C_{1-4}$ alkyl, $C_{1-4}$ alkoxy, —$NR^{18a}R^{18b}$, or 4-6 membered monocyclic heterocycloalkyl comprising one, two or three heteroatoms independently selected from N, O, and S, which heterocycloalkyl is optionally substituted with one or more —OH;
$R^{8a}$ and $R^{8b}$ are independently H, —C(═O)—$C_{1-4}$ alkoxy, or $C_{1-4}$ alkyl optionally substituted with one or more independently selected halo, —CN or —OH;
each $R^9$ is independently halo, —OH, or $C_{1-4}$ alkyl optionally substituted with one or more —OH;
each $R^{10a}$ and $R^{10b}$ is independently H or $C_{1-4}$ alkyl optionally substituted with one or more —OH;
each $R^{11}$ is independently selected from
$C_{1-4}$ alkyl optionally substituted with one or more independently selected —CN or $C_{1-4}$ alkoxy,
—C(═O)—$C_{1-6}$ alkyl, and
—C(═O)—$C_{1-6}$ alkoxy;

each $R^{12a}$ and $R^{12b}$ is independently H or $C_{1-4}$ alkyl optionally substituted with one —OH or $C_{1-4}$ alkoxy;

each $R^{13}$ is independently selected from
- halo,
- —CN,
- $—NR^{19a}R^{19b}$,
- —OH,
- $C_{1-4}$ alkoxy,
- $C_{3-7}$ cycloalkyl,
- $—S(=O)_2—C_{1-4}$ alkyl,
- 4-7 membered monocyclic heterocycloalkyl comprising one, two or three heteroatoms independently selected from N, O, and S, and
- 5-6 membered monocyclic heteroaryl comprising one, two or three heteroatoms independently selected from N, O, and S, which heteroaryl is optionally substituted with one or more independently selected $C_{1-4}$ alkyl;

each $R^{14a}$ and $R^{14b}$ is independently selected from
- halo,
- oxo,
- $C_{1-4}$ alkyl optionally substituted with one or more independently selected halo, —OH, or $C_{1-4}$ alkoxy,
- —OH,
- $C_{1-4}$ alkoxy, and
- $—NR^{20a}R^{20b}$.

each $R^{15a}$ and $R^{15b}$ is independently H, $C_{1-4}$ alkyl, or $—C(=O)—C_{1-4}$ alkoxy;

each $R^{16}$ is independently selected from
- H,
- $—S(=O)_2—C_{1-4}$alkyl,
- $C_{1-4}$ alkyl optionally substituted with one or more $—C(=O)—NR^{21a}R^{21b}$ or 4-6 membered monocyclic heterocycloalkyl comprising one, two or three heteroatoms independently selected from N, O, and S, and
- 4-6 membered monocyclic heterocycloalkyl comprising one, two or three heteroatoms independently selected from N, O, and S;

each $R^{17a}$ and $R^{17b}$ is independently H or $C_{1-4}$ alkyl optionally substituted with one or more independently selected —OH or $C_{1-4}$ alkoxy;

$R^{18a}$ and $R^{18b}$ are independently H or $C_{1-4}$ alkyl optionally substituted with one or more independently selected —OH or $C_{1-4}$ alkoxy;

each $R^{19a}$, $R^{19b}$, $R^{20a}$, $R^{20b}$, $R^{21a}$, and $R^{21b}$ is independently H or $C_{1-4}$ alkyl.

In one embodiment, the compound of the invention is according to Formula I, wherein $W_2$ is N.

In one embodiment, the compound of the invention is according to Formula I, wherein $W_2$ is CH.

In one embodiment, the compound of the invention is according to Formula I, wherein $W_1$ is N.

In one embodiment, the compound of the invention is according to Formula I, wherein $W_1$ is $CR^3$, and $R^3$ is H.

In one embodiment, the compound of the invention is according to Formula I, wherein $W_1$ is $CR^3$, and $R^3$ is halo. In a particular embodiment, $R^3$ is F, Cl, or Br. In a more particular embodiment, $R^3$ is F.

In one embodiment, the compound of the invention is according to Formula I, wherein $W_1$ is $CR^3$, and $R^3$ is $C_{1-4}$ alkoxy. In a particular embodiment, $R^3$ is $—O—CH_3$, $—O—CH_2CH_3$, or $—O—CH(CH_3)_2$. In a more particular embodiment, $R^3$ is $—O—CH_3$ or $—O—CH_2CH_3$. In a most particular embodiment, $R^3$ is $—O—CH_3$.

In one embodiment, the compound of the invention is according to Formula I, wherein $W_1$ is $CR^3$, and $R^3$ is $C_{1-4}$ alkoxy substituted with one or more independently selected —OH or $C_{1-4}$ alkoxy. In a particular embodiment, $R^3$ is $—O—CH_2CH_3$, or $—O—CH(CH_3)_2$, each of which is substituted with one or more independently selected —OH or $C_{1-4}$ alkoxy. In another particular embodiment, $R^3$ is $C_{1-4}$ alkoxy substituted with one, two, or three independently selected —OH or $C_{1-4}$ alkoxy. In yet another particular embodiment, $R^3$ is $C_{1-4}$ alkoxy substituted with one or more independently selected —OH, $—O—CH_3$, $—O—CH_2CH_3$, or $—O—CH(CH_3)_2$. In a more particular embodiment, $R^3$ is $—O—CH_2CH_3$, or $—O—CH(CH_3)_2$, each of which is substituted with one, two, or three independently selected —OH or $C_{1-4}$ alkoxy. In another more particular embodiment, $R^3$ is $C_{1-4}$ alkoxy substituted with one, two, or three independently selected —OH, $—O—CH_3$, $—O—CH_2CH_3$, or $—O—CH(CH_3)_2$. In a further more particular embodiment, $R^3$ is $—O—CH_2CH_3$, substituted with one, two, or three independently selected —OH or $C_{1-4}$ alkoxy. In a most particular embodiment, $R^3$ is $—O—CH_2CH_2—OH$.

In one embodiment, the compound of the invention is according to Formula I, wherein $R^{2a}$ is halo or —OH. In a particular embodiment, $R^{2a}$ is F, Cl, or —OH. In a more particular embodiment, $R^{2a}$ is F.

In one embodiment, the compound of the invention is according to Formula I, wherein $R^{2a}$ is $C_{1-4}$ alkyl. In a particular embodiment, $R^{2a}$ is $—CH_3$, $—CH_2CH_3$, or $—CH(CH_3)_2$. In a more particular embodiment, $R^{2a}$ is $—CH_3$.

In one embodiment, the compound of the invention is according to Formula I, wherein $R^{2a}$ is $C_{1-4}$ alkoxy. In a particular embodiment, $R^{2a}$ is $—O—CH_3$, $—O—CH_2CH_3$, or $—O—CH(CH_3)_2$. In a more particular embodiment, $R^{2a}$ is $—O—CH_3$ or $—O—CH_2CH_3$. In a most particular embodiment, $R^{2a}$ is $—O—CH_3$.

In one embodiment, the compound of the invention is according to Formula I, wherein $R^{2a}$ is $C_{1-4}$ alkoxy substituted with one or more independently selected halo, —OH, or $C_{1-4}$ alkoxy. In a particular embodiment, $R^{2a}$ is $—O—CH_3$, $—O—CH_2CH_3$, or $—O—CH(CH_3)_2$, each of which is substituted with one or more independently selected halo, —OH, or $C_{1-4}$ alkoxy. In another particular embodiment, $R^{2a}$ is $C_{1-4}$ alkoxy substituted with one, two, or three independently selected halo, —OH, or $C_{1-4}$ alkoxy. In yet another particular embodiment, $R^{2a}$ is $C_{1-4}$ alkoxy substituted with one or more independently selected F, Cl, Br, —OH, $—O—CH_3$, $—O—CH_2CH_3$, or $—O—CH(CH_3)_2$. In a more particular embodiment, $R^{2a}$ is $—O—CH_3$, $—O—CH_2CH_3$, or $—O—CH(CH_3)_2$, each of which is substituted with one, two, or three independently selected halo, —OH, or $C_{1-4}$ alkoxy. In another more particular embodiment, $R^{2a}$ is $C_{1-4}$ alkoxy substituted with one, two, or three independently selected F, Cl, Br, —OH, $—O—CH_3$, $—O—CH_2CH_3$, or $—O—CH(CH_3)_2$. In a further more particular embodiment, $R^{2a}$ is $—O—CH_3$, substituted with one, two, or three independently selected halo. In another further more particular embodiment, $R^{2a}$ is $—O—CH_2CH_3$, substituted with one, two, or three independently selected halo, —OH, or $C_{1-4}$ alkoxy. In a most particular embodiment, $R^{2a}$ is $—O—CHF_2$, $—O—CH_2CH_2—OH$, or $—O—CH_2CH_2—O—CH_3$.

In one embodiment, the compound of the invention is according to Formula I, wherein $R^{2a}$ is $—NR^{12a}R^{6b}$, and $R^{12a}$ and $R^{12b}$ are independently H or $C_{1-4}$ alkyl optionally substituted with one —OH or $C_{1-4}$ alkoxy. In a particular embodiment, $R^{12a}$ and $R^{12b}$ are both H. In another particular embodiment, one of $R^{12a}$ and $R^{12b}$ is H, and the other is $C_{1-4}$ alkyl optionally substituted with one —OH or $C_{1-4}$ alkoxy. In yet another particular embodiment, $R^{12a}$ and $R^{12b}$ are both $C_{1-4}$ alkyl optionally substituted with one —OH or $C_{1-4}$ alkoxy. In a more particular embodiment, one of $R^{12a}$ and $R^{12b}$ is H, and the other is —$CH_3$, —$CH_2CH_3$, or —CH$(CH_3)_2$. In another more particular embodiment, one of $R^{12a}$ and $R^{12b}$ is H, and the other is —$CH_3$, —$CH_2CH_3$, or —$CH(CH_3)_2$, each of which is substituted with one —OH, —O—$CH_3$, —O—$CH_2CH_3$, or —O—$CH(CH_3)_2$. In a most particular embodiment, $R^{2a}$ is —NH—$CH_3$, —NH—CH$(CH_3)_2$, or —NH—$CH_2CH_2$—OH.

In one embodiment, the compound of the invention is according to Formula I, wherein Z is —$NR^{4c}$, wherein the N atom and $R^{2a}$ together with the atoms onto which they are attached form a fused 5-6 membered heterocycloalkenyl comprising one double bond, and $R^{4c}$ is as previously described. In a particular embodiment, Z is —$NR^{4c}$—, wherein the N atom and $R^{2a}$ together with the atoms onto which they are attached form a fused 3-pyrroline or 1,2,3,6-tetrahydropyridine. In a more particular embodiment, Z is —$NR^{4c}$—, wherein the N atom and $R^{2a}$ together with the atoms onto which they are attached form a fused 1,2,3,6-tetrahydropyridine.

In one embodiment, the compound of the invention is according to Formula IIa, IIb, IIc, IId, IIe, IIf, IIg, or IIh:

IIa

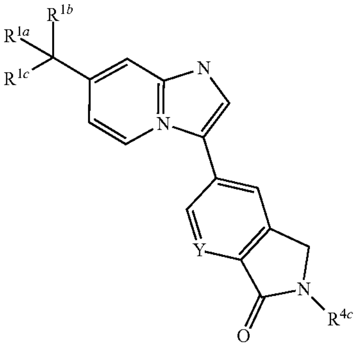

IIb

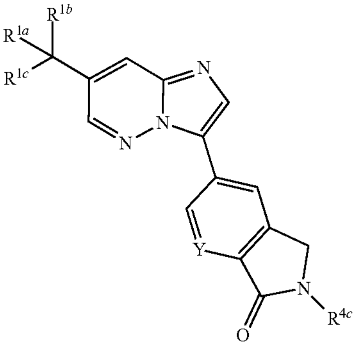

IIc

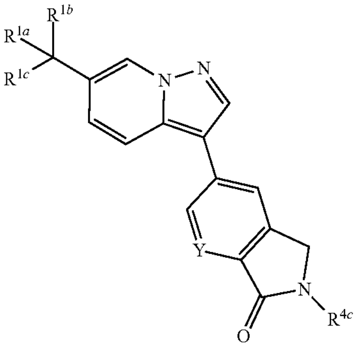

-continued

IId

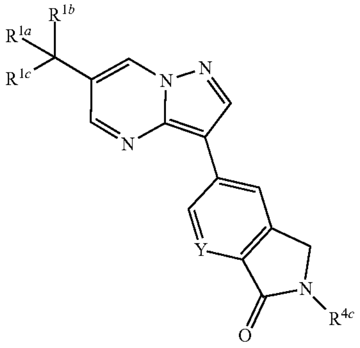

IIe

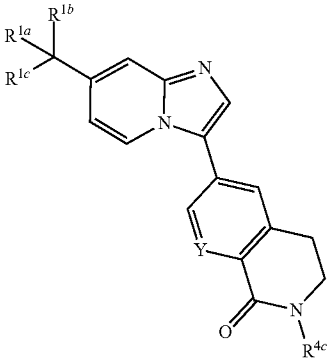

IIf

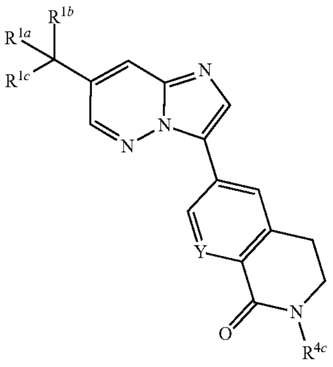

IIg

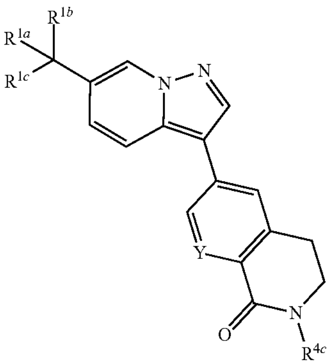

-continued

IIh

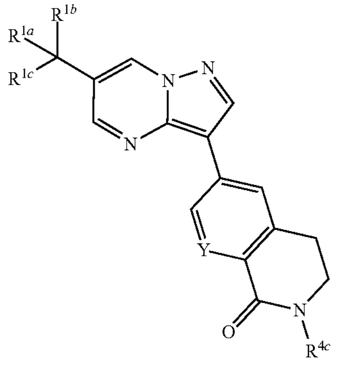

wherein $R^{1a}$, $R^{1b}$, $R^{1c}$, $R^{4c}$, and Y are as described above.

In one embodiment, the compound of the invention is according to any one of Formulae I-IIh, wherein $R^{4c}$ is H.

In one embodiment, the compound of the invention is according to any one of Formulae I-IIh, wherein $R^{4c}$ is $C_{3-7}$ cycloalkyl. In a particular embodiment, $R^{4c}$ is cyclopropyl, cyclobutyl, or cyclopentyl. In a more particular embodiment, $R^{4c}$ is cyclopropyl.

In one embodiment, the compound of the invention is according to any one of Formulae I-IIh, wherein $R^{4c}$ is $C_{1-6}$ alkyl. In a particular embodiment, $R^{4c}$ is —$CH_3$, —$CH_2CH_3$, —$CH_2CH_2CH_3$, —$CH(CH_3)_2$, or —$C(CH_3)_3$. In a more particular embodiment, $R^{4c}$ is —$CH_2CH_3$.

In one embodiment, the compound of the invention is according to any one of Formulae I-IIh, wherein $R^{4c}$ is $C_{1-6}$ alkyl substituted with one or more independently selected halo or —CN. In a particular embodiment, $R^{4c}$ is —$CH_3$, —$CH_2CH_3$, —$CH_2CH_2CH_3$, —$CH(CH_3)_2$, or —$C(CH_3)_3$, each of which is substituted with one or more independently selected halo or —CN. In another particular embodiment, $R^{4c}$ is $C_{1-6}$ alkyl substituted with one, two, or three independently selected halo or —CN. In yet another particular embodiment, $R^{4c}$ is $C_{1-6}$ alkyl substituted with one or more independently selected F, Cl, or —CN. In a more particular embodiment, $R^{4c}$ is —$CH_3$, —$CH_2CH_3$, —$CH_2CH_2CH_3$, —$CH(CH_3)_2$, or —$C(CH_3)_3$, each of which is substituted with one, two, or three independently selected halo or —CN. In another more particular embodiment, $R^{4c}$ is $C_{1-6}$ alkyl substituted with one, two, or three independently selected F, Cl, or —CN. In yet another more particular embodiment, $R^{4c}$ is —$CH_3$, —$CH_2CH_3$, —$CH_2CH_2CH_3$, —$CH(CH_3)_2$, or —$C(CH_3)_3$, each of which is substituted with one or more independently selected F, Cl, or —CN. In a further more particular embodiment, $R^{4c}$ is —$CH_3$, —$CH_2CH_3$, —$CH_2CH_2CH_3$, —$CH(CH_3)_2$, or —$C(CH_3)_3$, each of which is substituted with one, two, or three independently selected F, Cl, or —CN. In another further more particular embodiment, $R^{4c}$ is —$CH_3$, —$CH_2CH_3$, —$CH_2CH_2CH_3$, —$CH(CH_3)_2$, or —$C(CH_3)_3$, each of which is substituted with one or more F or —CN. In yet another further more particular embodiment, $R^{4c}$ is $C_{1-6}$ alkyl substituted with one, two, or three independently selected F or —CN. In a most particular embodiment, $R^{4c}$ is —$CH_2CH_3$ substituted with one, two, or three F. In another most particular embodiment, $R^{4c}$ is —$CH_2$—CN. In a further most particular embodiment, $R^{4c}$ is —$CH_2CF_3$.

In one embodiment, the compound of the invention is according to Formula I, wherein Z is monocyclic or spirocyclic N-linked 4-7 membered heterocycloalkyl further comprising zero, one, or two additional heteroatoms independently selected from N, O, and S. In a particular embodiment, Z is azetidinyl, pyrrolidinyl, piperidinyl, morpholinyl, thiomorpholinyl, piperazinyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl. In a more particular embodiment, Z is azetidinyl, pyrrolidinyl, piperidinyl, piperazinyl, morpholinyl, thiomorpholinyl, 2-oxa-6-azaspiro[3.3]heptanyl, or 2-thia-6-azaspiro[3.3]heptanyl.

In one embodiment, the compound of the invention is according to Formula I, wherein Z is monocyclic or spirocyclic N-linked 4-7 membered heterocycloalkyl further comprising zero, one, or two additional heteroatoms independently selected from N, O, and S, substituted with one or more independently selected $R^5$ groups. In a particular embodiment, Z is azetidinyl, pyrrolidinyl, piperidinyl, morpholinyl, thiomorpholinyl, piperazinyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl, each of which is substituted with one, two or three independently selected $R^5$ groups. In a more particular embodiment, Z is azetidinyl, pyrrolidinyl, piperidinyl, piperazinyl, thiomorpholinyl, or 2-thia-6-azaspiro[3.3]heptanyl, each of which is substituted with one, two or three independently selected $R^5$ groups.

In one embodiment, the compound of the invention is according to Formula I, wherein Z is N-linked 4-7 membered monocyclic or spirocyclic heterocycloalkyl further comprising zero, one, or two additional heteroatoms independently selected from N, O, and S, substituted with one or more independently selected $R^5$ groups, and $R^5$ is oxo, halo, —CN, —OH, phenyl, $C_{3-7}$ cycloalkyl, $C_{2-4}$ alkynyl, or —C(═O)—$C_{1-4}$ alkoxy. In a particular embodiment, $R^5$ is oxo, F, Cl, —CN, —OH, phenyl, cyclopropyl, cyclobutyl, cyclopentyl, —C≡CH, —C(═O)—O—$CH_3$, —C(═O)—O—$CH_2CH_3$, or —C(═O)—O—$CH(CH_3)_2$. In a more particular embodiment, $R^5$ is oxo, F, —CN, —OH, phenyl, cyclopropyl, or —C≡CH.

In one embodiment, the compound of the invention is according to Formula I, wherein Z is N-linked monocyclic or spirocyclic 4-7 membered heterocycloalkyl further comprising zero, one, or two additional heteroatoms independently selected from N, O, and S, substituted with one or more independently selected $R^5$ groups, and $R^5$ is —$NR^{15a}R^{15b}$, and each $R^{15a}$ and $R^{15b}$ is as previously described. In a particular embodiment, $R^{15a}$ and $R^{15b}$ are both H. In another particular embodiment, one of $R^{15a}$ and $R^{15b}$ is H, and the other is $C_{1-4}$ alkyl or —C(═O)—$C_{1-4}$ alkoxy. In yet another particular embodiment, $R^{15a}$ and $R^{15b}$ are both $C_{1-4}$ alkyl. In a more particular embodiment, one of $R^{15a}$ and $R^{15b}$ is H, and the other is —$CH_3$, —$CH_2CH_3$, —$CH(CH_3)_2$, —C(═O)—O—$CH_3$, —C(═O)—O—$CH_2CH_3$, —C(═O)—O—$CH(CH_3)_2$, or —C(═O)—O—$C(CH_3)_3$. In another more particular embodiment, $R^{15a}$ and $R^{15b}$ are —$CH_3$, —$CH_2CH_3$, or —$CH(CH_3)_2$. In a most particular embodiment, one of $R^{15a}$ and $R^{15b}$ is H, and the other is —C(═O)—O—$C(CH_3)_3$.

In one embodiment, the compound of the invention is according to Formula I, wherein Z is N-linked 4-7 membered monocyclic or spirocyclic heterocycloalkyl further comprising zero, one, or two additional heteroatoms independently selected from N, O, and S, substituted with one or more independently selected $R^5$ groups, and $R^5$ is $C_{1-4}$ alkoxy. In a particular embodiment, $R^5$ is —O—$CH_3$, —O—$CH_2CH_3$, or —O—$CH(CH_3)_2$. In a more particular embodiment, $R^5$ is —O—$CH_3$.

In one embodiment, the compound of the invention is according to Formula I, wherein Z is N-linked 4-7 membered monocyclic or spirocyclic heterocycloalkyl further comprising zero, one, or two additional heteroatoms independently selected from N, O, and S, substituted with one or more independently selected $R^5$ groups, and $R^5$ is $C_{1-4}$ alkoxy substituted with one or more halo or phenyl. In a particular embodiment, $R^5$ is —O—$CH_3$, —O—$CH_2CH_3$, or —O—$CH(CH_3)_2$, each of which is substituted with one or more halo or phenyl. In another particular embodiment, $R^5$ is $C_{1-4}$ alkoxy substituted with one, two, or three halo or phenyl. In yet another particular embodiment, $R^5$ is $C_{1-4}$ alkoxy substituted with one or more F, Cl or phenyl. In a more particular embodiment, $R^5$ is —O—$CH_3$, —O—$CH_2CH_3$, or —O—$CH(CH_3)_2$, each of which is substituted with one or more F, Cl, or phenyl. In another more particular embodiment, $R^5$ is $C_{1-4}$ alkoxy substituted with one, two, or three F, Cl, or phenyl. In yet another more particular embodiment, $R^5$ is —O—$CH_3$ substituted with one, two, or three halo or phenyl. In a most particular embodiment, $R^5$ is —O—$CH_3$ substituted with one, two, or three F. In another most particular embodiment, $R^5$ is —O—$CH_3$ substituted with one phenyl.

In one embodiment, the compound of the invention is according to Formula I, wherein Z is N-linked 4-7 membered monocyclic or spirocyclic heterocycloalkyl further comprising zero, one, or two additional heteroatoms independently selected from N, O, and S, substituted with one or more independently selected $R^5$ groups, and $R^5$ is $C_{1-4}$ alkyl. In a particular embodiment, $R^5$ is —$CH_3$, —$CH_2CH_3$, or —$CH(CH_3)_2$. In a more particular embodiment, $R^5$ is —$CH_3$.

In one embodiment, the compound of the invention is according to Formula I, wherein Z is N-linked 4-7 membered monocyclic or spirocyclic heterocycloalkyl further comprising zero, one, or two additional heteroatoms independently selected from N, O, and S, substituted with one or more independently selected $R^5$ groups, and $R^5$ is $C_{1-4}$ alkyl substituted with one or more halo, —OH, or $C_{1-4}$ alkoxy. In a particular embodiment, R is —$CH_3$, —$CH_2CH_3$, or —$CH(CH_3)_2$ substituted with one or more halo, —OH, or $C_{1-4}$ alkoxy. In another particular embodiment, $R^5$ is $C_{1-4}$ alkyl substituted with one, two, or three halo, —OH, or $C_{1-4}$ alkoxy. In yet another particular embodiment, $R^5$ is $C_{1-4}$ alkyl substituted with one or more F, Cl, —OH, —O—$CH_3$, —O—$CH_2CH_3$, or —O—$CH(CH_3)_2$. In a more particular embodiment, $R^5$ is —$CH_3$ substituted with one, two, or three halo, —OH, or $C_{1-4}$ alkoxy. In another more particular embodiment, $R^5$ is $C_{1-4}$ alkyl substituted with one, two, or three F, Cl, —OH, —O—$CH_3$, —O—$CH_2CH_3$, or —O—$CH(CH_3)_2$. In a further more particular embodiment, $R^5$ is —$CH_3$, —$CH_2CH_3$, or —$CH(CH_3)_2$, each of which is substituted with one, two, or three F, Cl, —OH, —O—$CH_3$, —O—$CH_2CH_3$, or —O—$CH(CH_3)_2$. In a most particular embodiment, $R^5$ is —$CH_3$ substituted with one, two, or three F, or —OH.

In one embodiment, the compound of the invention is according to Formula I, wherein Z is N-linked 4-7 membered monocyclic or spirocyclic heterocycloalkyl further comprising zero, one, or two additional heteroatoms independently selected from N, O, and S, substituted with one or more independently selected $R^5$ groups, and $R^5$ is 4-7 membered monocyclic heterocycloalkyl comprising one, two or three heteroatoms independently selected from N, O, and S. In a particular embodiment, $R^5$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl.

In one embodiment, the compound of the invention is according to any one of Formulae I-IIh, wherein Y is N.

In one embodiment, the compound of the invention is according to any one of Formulae I-IIh, wherein Y is $CR^{2b}$ and $R^{2b}$ is halo or —OH. In a particular embodiment, $R^{2b}$ is F, Cl, or —OH. In a more particular embodiment, $R^{2b}$ is F.

In one embodiment, the compound of the invention is according to any one of Formulae I-IIh, wherein Y is $CR^{2b}$ and $R^{2b}$ is $C_{1-4}$ alkyl. In a particular embodiment, $R^{2b}$ is —$CH_3$, —$CH_2CH_3$, or —$CH(CH_3)_2$. In a more particular embodiment, $R^{2b}$ is —$CH_3$.

In one embodiment, the compound of the invention is according to any one of Formulae I-IIh, wherein Y is $CR^{2b}$ and $R^{2b}$ is $C_{1-4}$ alkoxy. In a particular embodiment, $R^{2b}$ is —O—$CH_3$, —O—$CH_2CH_3$, or —O—$CH(CH_3)_2$. In a more particular embodiment, $R^{2b}$ is —O—$CH_3$ or —O—$CH_2CH_3$. In a most particular embodiment, $R^{2b}$ is —O—$CH_3$.

In one embodiment, the compound of the invention is according to any one of Formulae I-IIh, wherein Y is $CR^{2b}$ and $R^{2b}$ is $C_{1-4}$ alkoxy substituted with one or more independently selected halo, —OH, or $C_{1-4}$ alkoxy. In a particular embodiment, $R^{2b}$ is —O—$CH_3$, —O—$CH_2CH_3$, or —O—$CH(CH_3)_2$, each of which is substituted with one or more independently selected halo, —OH, or $C_{1-4}$ alkoxy. In another particular embodiment, $R^{2b}$ is $C_{1-4}$ alkoxy substituted with one, two, or three independently selected halo, —OH, or $C_{1-4}$ alkoxy. In yet another particular embodiment, $R^{2b}$ is $C_{1-4}$ alkoxy substituted with one or more independently selected F, Cl, Br, —OH, —O—$CH_3$, —O—$CH_2CH_3$, or —O—$CH(CH_3)_2$. In a more particular embodiment, $R^{2b}$ is —O—$CH_3$, —O—$CH_2CH_3$, or —O—$CH(CH_3)_2$, each of which is substituted with one, two, or three independently selected halo, —OH, or $C_{1-4}$ alkoxy. In another more particular embodiment, $R^{2b}$ is $C_{1-4}$ alkoxy substituted with one, two, or three independently selected F, Cl, Br, —OH, —O—$CH_3$, —O—$CH_2CH_3$, or —O—$CH(CH_3)_2$. In a further more particular embodiment, $R^{2b}$ is —O—$CH_3$, substituted with one, two, or three independently selected halo. In another further more particular embodiment, $R^{2b}$ is —O—$CH_2CH_3$, substituted with one, two, or three independently selected halo, —OH, or $C_{1-4}$ alkoxy. In a most particular embodiment, $R^{2b}$ is —O—$CHF_2$, —O—$CH_2CH_2$—OH, or —O—$CH_2CH_2$—O—$CH_2CH_3$.

In one embodiment, the compound of the invention is according to any one of Formulae I-IIh, wherein Y is $CR^{2b}$, $R^{2b}$ is —$NR^{12a}R^{12b}$, and $R^{12a}$ and $R^{12b}$ are independently H or $C_{1-4}$ alkyl optionally substituted with one —OH or $C_{1-4}$ alkoxy. In a particular embodiment, $R^{12a}$ and $R^{12b}$ are both H. In another particular embodiment, one of $R^{12a}$ and $R^{12b}$ is H, and the other is $C_{1-4}$ alkyl optionally substituted with one —OH or $C_{1-4}$ alkoxy. In yet another particular embodiment, $R^{12a}$ and $R^{12b}$ are both $C_{1-4}$ alkyl optionally substituted with one —OH or $C_{1-4}$ alkoxy. In a more particular embodiment, one of $R^{12a}$ and $R^{12b}$ is H, and the other is —$CH_3$, —$CH_2CH_3$, or —$CH(CH_3)_2$. In another more particular embodiment, one of $R^{12a}$ and $R^{12b}$ is H, and the other is —$CH_3$, —$CH_2CH_3$, or —$CH(CH_3)_2$, each of which is substituted with one —OH, —O—$CH_3$, —O—$CH_2CH_3$, or —O—$CH(CH_3)_2$. In a most particular embodiment, $R^{2b}$ is —NH—$CH_3$, —NH—$CH(CH_3)_2$, or —NH—$CH_2CH_2$—OH.

In one embodiment, the compound of the invention is according to Formula I, wherein Z is —$NR^{4a}R^{4b}$, and $R^{4a}$ and $R^{4b}$ are as previously described. In a particular embodiment, $R^{4a}$ is H. In another particular embodiment, $R^{4a}$ is $C_{1-4}$ alkyl. In a more particular embodiment, $R^{4a}$ is —$CH_3$, —$CH_2CH_3$, or —$CH(CH_3)_2$. In a most particular embodiment, $R^{4a}$ is —$CH_3$.

In one embodiment, the compound of the invention is according to Formula IIIa, IIIb, IIIc, or IIId:

IIIa

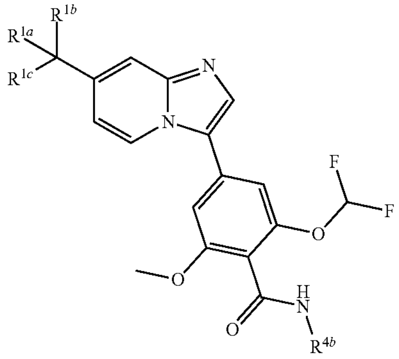

IIIb

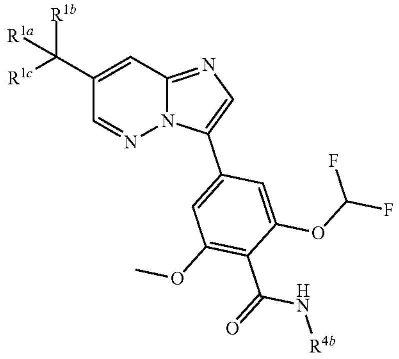

IIIc

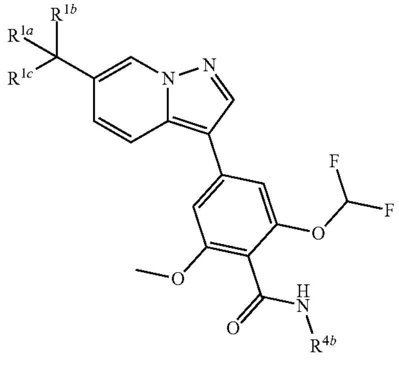

-continued

IIId

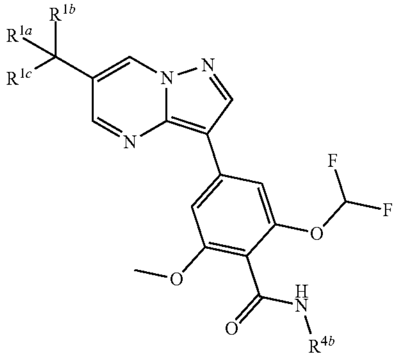

wherein $R^{1a}$, $R^{1b}$, $R^{1c}$, and $R^{4b}$ are as described above.

In one embodiment, the compound of the invention is according to any one of Formulae I-IIId, wherein $R^{1b}$ is halo, —OH, —CN, or $C_{3-7}$ cycloalkyl. In a particular embodiment, $R^{1b}$ is F, Cl, —OH, —CN, cyclopropyl, cyclobutyl, cyclopentyl, or cyclohexyl. In a more particular embodiment, $R^{1b}$ is F, —OH, —CN, cyclopropyl, or cyclobutyl.

In one embodiment, the compound of the invention is according to any one of Formulae I-IIId, wherein $R^{1b}$ is $C_{1-4}$ alkyl. In a particular embodiment, $R^{1b}$ is —$CH_3$, —$CH_2CH_3$, or —$CH(CH_3)_2$.

In one embodiment, the compound of the invention is according to any one of Formulae I-IIId, wherein $R^{1b}$ is $C_{1-4}$ alkyl substituted with one or more independently selected —OH, —CN, or $C_{2-4}$ alkenyl. In a particular embodiment, $R^{1b}$ is —$CH_3$, —$CH_2CH_3$, or —$CH(CH_3)_2$, each of which is substituted with one, two, or three independently selected —OH, —CN, —$CH{=}CH_2$, —$CH_2CH{=}CH_2$, —$C(CH_3){=}CH_2$, or —$CH_2C(CH_3){=}CH_2$. In a more particular embodiment, $R^{1b}$ is —$CH_2$—OH, —$CH_2$—CN, or —$CH_2$—$CH{=}CH_2$.

In one embodiment, the compound of the invention is according to any one of Formulae I-IIId, wherein $R^{1b}$ is 4-8 membered monocyclic or spirocyclic heterocycloalkyl comprising one, two or three heteroatoms independently selected from N, O, and S. In a particular embodiment, $R^{1b}$ is azetidinyl, oxetanyl, pyrrolidinyl, tetrahydrofuranyl, piperidinyl, tetrahydropyranyl, tetrahydrothiopyranyl, morpholinyl, thiomorpholinyl, piperazinyl, dioxanyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl. In a more particular embodiment, $R^{1b}$ is azetidinyl, oxetanyl, pyrrolidinyl, piperidinyl, tetrahydropyranyl, morpholinyl, or 2-oxa-6-azaspiro[3.3]heptanyl.

In one embodiment, the compound of the invention is according to any one of Formulae I-IIId, wherein $R^{1b}$ is 4-8 membered monocyclic or spirocyclic heterocycloalkyl comprising one, two or three heteroatoms independently selected from N, O, and S, which heterocycloalkyl is substituted with one or more independently selected $R^9$ groups. In a particular embodiment, $R^{1b}$ is azetidinyl, oxetanyl, pyrrolidinyl, tetrahydrofuranyl, piperidinyl, tetrahydropyranyl, tetrahydrothiopyranyl, morpholinyl, thiomorpholinyl, piperazinyl, dioxanyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl, each of which is substituted with one, two, or three independently selected $R^9$ groups. In a more particular embodiment, $R^{1b}$ is azetidinyl, oxetanyl, or morpholinyl, each of which is substituted with one, two, or three independently selected $R^9$ groups.

In one embodiment, the compound of the invention is according to any one of Formulae I-IIId, wherein $R^{1b}$ is 4-8 membered monocyclic or spirocyclic heterocycloalkyl comprising one, two or three heteroatoms independently selected from N, O, and S, which heterocycloalkyl is substituted with one or more independently selected $R^9$ groups, and $R^9$ is halo or —OH. In a particular embodiment, $R^9$ is F, Cl, or —OH. In a more particular embodiment, $R^9$ is F or —OH.

In one embodiment, the compound of the invention is according to any one of Formulae I-IIId, wherein $R^{1b}$ is 4-8 membered monocyclic or spirocyclic heterocycloalkyl comprising one, two or three heteroatoms independently selected from N, O, and S, which heterocycloalkyl is substituted with one or more independently selected $R^9$ groups, and $R^9$ is $C_{1-4}$ alkyl. In a particular embodiment, $R^9$ is $—CH_3$, $—CH_2CH_3$, or $—CH(CH_3)_2$. In a more particular embodiment, $R^9$ is $—CH_3$.

In one embodiment, the compound of the invention is according to any one of Formulae I-IIId, wherein $R^{1b}$ is 4-8 membered monocyclic or spirocyclic heterocycloalkyl comprising one, two or three heteroatoms independently selected from N, O, and S, which heterocycloalkyl is substituted with one or more independently selected $R^9$ groups, and $R^9$ is $C_{1-4}$ alkyl substituted with one or more —OH. In a particular embodiment, $R^9$ is $—CH_3$, $—CH_2CH_3$, or $—CH(CH_3)_2$, each of which is substituted with one, two, or three —OH. In a more particular embodiment, $R^9$ is $—CH_2—OH$.

In one embodiment, the compound of the invention is according to any one of Formulae I-IIId, wherein $R^{1b}$ is $—NR^{10a}R^{10b}$, and each $R^{10a}$ and $R^{10b}$ are as previously described. In a particular embodiment, $R^{10a}$ and $R^{10b}$ are both H. In another particular embodiment, one of $R^{10a}$ and $R^{10b}$ is H, and the other is $C_{1-4}$ alkyl optionally substituted with one or more —OH. In yet another particular embodiment, $R^{10a}$ and $R^{10b}$ are both $C_{1-4}$ alkyl optionally substituted with one or more —OH. In a more particular embodiment, one of $R^{10a}$ and $R^{10b}$ is H, and the other is $—CH_3$, $—CH_2CH_3$, or $—CH(CH_3)_2$. In another more particular embodiment, one of $R^{10a}$ and $R^{10b}$ is H, and the other is $—CH_3$, $—CH_2CH_3$, or $—CH(CH_3)_2$, each of which is substituted with one or more —OH. In yet another more particular embodiment, $R^{10a}$ and $R^{10b}$ are both $—CH_3$, $—CH_2CH_3$, or $—CH(CH_3)_2$, each of which is optionally substituted with one or more —OH. In a most particular embodiment, $R^{10b}$ is $—NH—CH(CH_3)_2$, $—NH—CH_2CH_2—OH$, $—N(CH_2CH_3)_2$ or $—N(CH_3)—CH_2CH_2—OH$.

In one embodiment, the compound of the invention is according to any one of Formulae I-IIId, wherein $R^{1c}$ is halo, —OH, —CN, or $C_{3-7}$ cycloalkyl. In a particular embodiment, $R^{1c}$ is F, Cl, —OH, —CN, cyclopropyl, cyclobutyl, cyclopentyl, or cyclohexyl. In a more particular embodiment, $R^{1c}$ is F, —OH, —CN, cyclopropyl, or cyclobutyl.

In one embodiment, the compound of the invention is according to any one of Formulae I-IIId, wherein $R^{1c}$ is $C_{1-4}$ alkyl. In a particular embodiment, $R^{1c}$ is $—CH_3$, $—CH_2CH_3$, or $—CH(CH_3)_2$.

In one embodiment, the compound of the invention is according to any one of Formulae I-IIId, wherein $R^{1c}$ is $C_{1-4}$ alkyl substituted with one or more independently selected —OH, —CN, or $C_{2-4}$ alkenyl. In a particular embodiment, $R^{1c}$ is $—CH_3$, $—CH_2CH_3$, or $—CH(CH_3)_2$, each of which is substituted with one, two, or three independently selected —OH, —CN, $—CH{=}CH_2$, $—CH_2CH{=}CH_2$, $—C(CH_3){=}CH_2$, or $—CH_2C(CH_3){=}CH_2$. In a more particular embodiment, $R^{1c}$ is $—CH_2—OH$, $—CH_2—CN$, or $—CH_2—CH{=}CH_2$.

In one embodiment, the compound of the invention is according to any one of Formulae I-IIId, wherein $R^{1c}$ is 4-8 membered monocyclic or spirocyclic heterocycloalkyl comprising one, two or three heteroatoms independently selected from N, O, and S. In a particular embodiment, $R^{1c}$ is azetidinyl, oxetanyl, pyrrolidinyl, tetrahydrofuranyl, piperidinyl, tetrahydropyranyl, tetrahydrothiopyranyl, morpholinyl, thiomorpholinyl, piperazinyl, dioxanyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl. In a more particular embodiment, $R^{1c}$ is azetidinyl, oxetanyl, pyrrolidinyl, piperidinyl, tetrahydropyranyl, morpholinyl, or 2-oxa-6-azaspiro[3.3]heptanyl.

In one embodiment, the compound of the invention is according to any one of Formulae I-IIId, wherein $R^{1c}$ is 4-8 membered monocyclic or spirocyclic heterocycloalkyl comprising one, two or three heteroatoms independently selected from N, O, and S, which heterocycloalkyl is substituted with one or more independently selected $R^9$ groups. In a particular embodiment, $R^{1c}$ is azetidinyl, oxetanyl, pyrrolidinyl, tetrahydrofuranyl, piperidinyl, tetrahydropyranyl, tetrahydrothiopyranyl, morpholinyl, thiomorpholinyl, piperazinyl, dioxanyl, 2-azaspiro[3.3]heptanyl, 1,6-diazaspiro[3.3]heptanyl, 2,6-diazaspiro[3.3]heptanyl, 1-oxa-6-azaspiro[3.3]heptanyl, 2-oxa-6-azaspiro[3.3]heptanyl, 1-thia-6-azaspiro[3.3]heptanyl, or 2-thia-6-azaspiro[3.3]heptanyl, each of which is substituted with one, two, or three independently selected $R^9$ groups. In a more particular embodiment, $R^{1c}$ is azetidinyl, oxetanyl, or morpholinyl, each of which is substituted with one, two, or three independently selected $R^9$ groups.

In one embodiment, the compound of the invention is according to any one of Formulae I-IIId, wherein $R^{1c}$ is 4-8 membered monocyclic or spirocyclic heterocycloalkyl comprising one, two or three heteroatoms independently selected from N, O, and S, which heterocycloalkyl is substituted with one or more independently selected $R^9$ groups, and $R^9$ is halo or —OH. In a particular embodiment, $R^9$ is F, Cl, or —OH. In a more particular embodiment, $R^9$ is F or —OH.

In one embodiment, the compound of the invention is according to any one of Formulae I-IIId, wherein $R^{1c}$ is 4-8 membered monocyclic or spirocyclic heterocycloalkyl comprising one, two or three heteroatoms independently selected from N, O, and S, which heterocycloalkyl is substituted with one or more independently selected $R^9$ groups, and $R^9$ is $C_{1-4}$ alkyl. In a particular embodiment, $R^9$ is $—CH_3$, $—CH_2CH_3$, or $—CH(CH_3)_2$. In a more particular embodiment, $R^9$ is $—CH_3$.

In one embodiment, the compound of the invention is according to any one of Formulae I-IIId, wherein $R^{1c}$ is 4-8 membered monocyclic or spirocyclic heterocycloalkyl comprising one, two or three heteroatoms independently selected from N, O, and S, which heterocycloalkyl is substituted with one or more independently selected $R^9$ groups, and $R^9$ is $C_{1-4}$ alkyl substituted with one or more —OH. In a particular embodiment, $R^9$ is $—CH_3$, $—CH_2CH_3$, or $—CH(CH_3)_2$, each of which is substituted with one, two, or three —OH. In a more particular embodiment, $R^9$ is $—CH_2—OH$.

In one embodiment, the compound of the invention is according to any one of Formulae I-IIId, wherein $R^{1c}$ is $—NR^{10a}R^{10b}$, and each $R^{10a}$ and $R^{10b}$ is independently H or $C_{1-4}$ alkyl optionally substituted with one or more —OH. In a particular embodiment, $R^{10a}$ and $R^{10b}$ are both H. In another particular embodiment, one of $R^{10a}$ and $R^{10b}$ is H, and the other is $C_{1-4}$ alkyl optionally substituted with one or more —OH. In yet another particular embodiment, $R^{10a}$ and $R^{10b}$ are both $C_{1-4}$ alkyl optionally substituted with one or more —OH. In a more particular embodiment, one of $R^{10a}$ and $R^{10b}$ is H, and the other is —$CH_3$, —$CH_2CH_3$, or —$CH(CH_3)_2$. In another more particular embodiment, one of $R^{10a}$ and $R^{10b}$ is H, and the other is —$CH_3$, —$CH_2CH_3$, or —$CH(CH_3)_2$, each of which is substituted with one or more —OH. In yet another more particular embodiment, $R^{10a}$ and $R^{10b}$ are both —$CH_3$, —$CH_2CH_3$, or —$CH(CH_3)_2$, each of which is optionally substituted with one or more —OH. In a most particular embodiment, $R^{1c}$ is —NH—CH$(CH_3)_2$, —NH—$CH_2CH_2$—OH, —$N(CH_2CH_3)_2$ or —$N(CH_3)$—$CH_2CH_2$—OH.

In one embodiment, the compound of the invention is according to any one of Formulae I-IIId, wherein $R^{1b}$ and $R^{1c}$ together with the atom onto which they are attached form a $C_{3-6}$ cycloalkyl. In a particular embodiment, $R^{1b}$ and $R^{1c}$ together with the atom onto which they are attached form a cyclopropyl, cyclobutyl, or cyclopentyl. In a more particular embodiment, $R^{1b}$ and $R^{1c}$ together with the atom onto which they are attached form a cyclobutyl.

In one embodiment, the compound of the invention is according to any one of Formulae I-IIId, wherein $R^{1b}$ and $R^{1c}$ together with the atom onto which they are attached form a 4-6 membered monocyclic heterocycloalkyl comprising one, two, or three heteroatoms independently selected from N, O, and S. In a particular embodiment, $R^{1b}$ and $R^{1c}$ together with the atom onto which they are attached form an azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^{1b}$ and $R^{1c}$ together with the atom onto which they are attached form an azetidinyl, oxetanyl, pyrrolidinyl, tetrahydrofuranyl, piperidinyl, tetrahydropyranyl, morpholinyl, or 1,4-dioxanyl.

In one embodiment, the compound of the invention is according to any one of Formulae I-IIId, wherein $R^{1b}$ and $R^{1c}$ together with the atom onto which they are attached form a 4-6 membered monocyclic heterocycloalkyl comprising one, two, or three heteroatoms independently selected from N, O, and S, which heterocycloalkyl is substituted with one or more independently selected $R^{11}$ groups. In a particular embodiment, $R^{1b}$ and $R^{1c}$ together with the atom onto which they are attached form an azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl, each of which is substituted with one, two or three independently selected $R^{11}$ groups. In a more particular embodiment, $R^{1b}$ and $R^{1c}$ together with the atom onto which they are attached form an azetidinyl, oxetanyl, pyrrolidinyl, tetrahydrofuranyl, piperidinyl, tetrahydropyranyl, morpholinyl, or 1,4-dioxanyl, each of which is substituted with one, two or three independently selected $R^{11}$ groups.

In one embodiment, the compound of the invention is according to any one of Formulae I-IIId, wherein $R^{1b}$ and $R^{1c}$ together with the atom onto which they are attached form a 4-6 membered monocyclic heterocycloalkyl comprising one, two, or three heteroatoms independently selected from N, O, and S, which heterocycloalkyl is substituted with one or more independently selected $R^{11}$ groups, and $R^{11}$ is $C_{1-4}$ alkyl. In a particular embodiment, $R^{11}$ is —$CH_3$, —$CH_2CH_3$, or —$CH(CH_3)_2$. In a more particular embodiment, $R^{11}$ is —$CH_3$ or —$CH(CH_3)_2$.

In one embodiment, the compound of the invention is according to any one of Formulae I-IIId, wherein $R^{1b}$ and $R^{1c}$ together with the atom onto which they are attached form a 4-6 membered monocyclic heterocycloalkyl comprising one, two, or three heteroatoms independently selected from N, O, and S, which heterocycloalkyl is substituted with one or more independently selected $R^{11}$ groups, and $R^{11}$ is $C_{1-4}$ alkyl substituted with one or more independently selected —CN or $C_{1-4}$ alkoxy. In a particular embodiment, $R^{11}$ is —$CH_3$, —$CH_2CH_3$, or —$CH(CH_3)_2$, each of which is substituted with one, two, or three independently selected —CN, —O—$CH_3$, —O—$CH_2CH_3$, or —O—CH$(CH_3)_2$. In a more particular embodiment, $R^{11}$ is —$CH_2$—CN or —$CH_2CH_2$—O—$CH_3$.

In one embodiment, the compound of the invention is according to any one of Formulae I-IIId, wherein $R^{1b}$ and $R^{1c}$ together with the atom onto which they are attached form a 4-6 membered monocyclic heterocycloalkyl comprising one, two, or three heteroatoms independently selected from N, O, and S, which heterocycloalkyl is substituted with one or more independently selected $R^{11}$ groups, and $R^{11}$ is —C(═O)—$C_{1-6}$ alkyl. In a particular embodiment, $R^{11}$ is —C(═O)—$CH_3$, —C(═O)—$CH_2CH_3$, —C(═O)—$CH_2CH_2CH_3$, —C(═O)—$CH(CH_3)_2$, —C(═O)—$C(CH_3)_3$, —C(═O)—$CH_2CH(CH_3)_2$, —C(═O)—$CH_2C(CH_3)_3$, —C(═O)—$CH(CH_3)CH_2CH_3$, —C(═O)—$CH(CH_3)CH(CH_3)_2$, —C(═O)—$C(CH_3)_2$—$CH_2CH_3$, —C(═O)—$CH(CH_3)C(CH_3)_3$, or —C(═O)—$CH_2C(CH_3)_3$. In a more particular embodiment, $R^{11}$ is —C(═O)—$CH_3$.

In one embodiment, the compound of the invention is according to any one of Formulae I-IIId, wherein $R^{1b}$ and $R^{1c}$ together with the atom onto which they are attached form a 4-6 membered monocyclic heterocycloalkyl comprising one, two, or three heteroatoms independently selected from N, O, and S, which heterocycloalkyl is substituted with one or more independently selected $R^{11}$ groups, and $R^{11}$ is —C(═O)—$C_{1-6}$ alkoxy. In a particular embodiment, $R^{11}$ is —C(═O)—O—$CH_3$, —C(═O)—O—$CH_2CH_3$, —C(═O)—O—$CH_2CH_2CH_3$, —C(═O)—O—$CH(CH_3)_2$, —C(═O)—O—$C(CH_3)_3$, —C(═O)—O—$CH_2CH(CH_3)_2$, —C(═O)—O—$CH_2C(CH_3)_3$, —C(═O)—O—$CH(CH_3)CH_2CH_3$, —C(═O)—O—CH$(CH_3)$C H$(CH_3)_2$, —C(═O)—O—$C(CH_3)_2$—$CH_2CH_3$, —C(═O)—O—$CH(CH_3)C(CH_3)_3$, or —C(═O)—O—$CH_2C(CH_3)_3$. In a more particular embodiment, $R^{11}$ is —C(═O)—O—$C(CH_3)_3$.

In one embodiment, the compound of the invention is according to Formula IVa, IVb, IVc, IVd, IVe, IVf, IVg, IVh, IVi, IVj, IVk, IVl, IVm, IVn, IVo, or IVp:

IVa

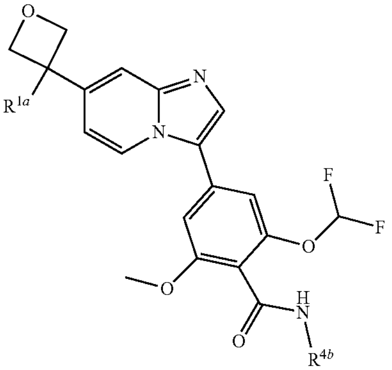

-continued
IVb
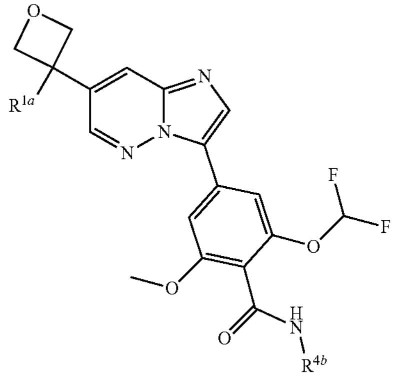
IVc
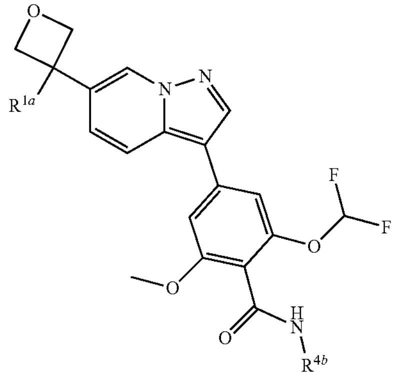
IVd
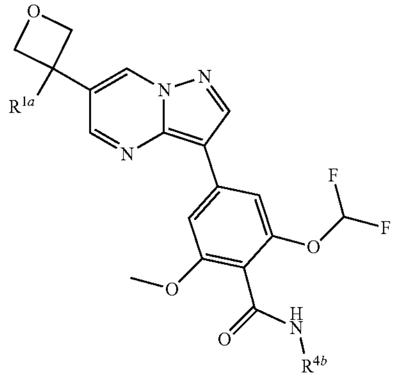
IVe
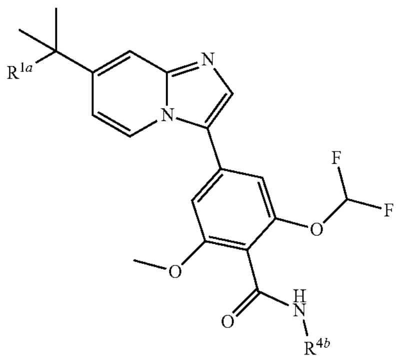
-continued
IVf
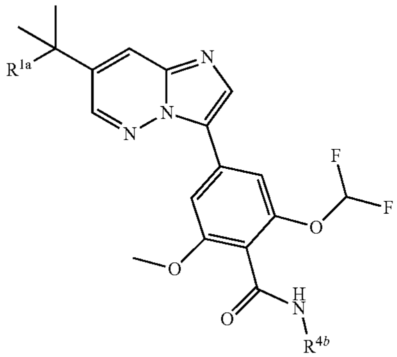
IVg
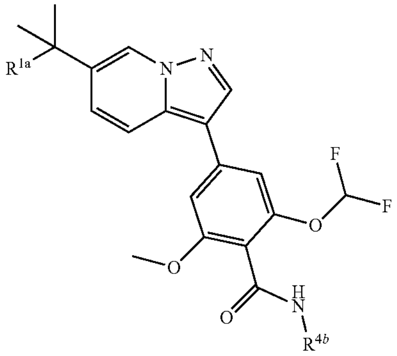
IVh
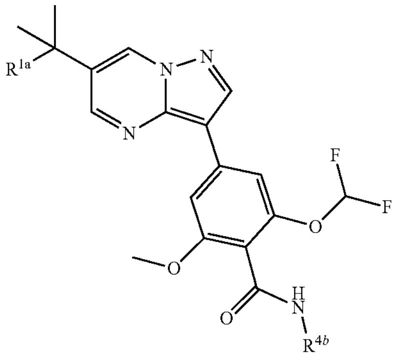
IVi
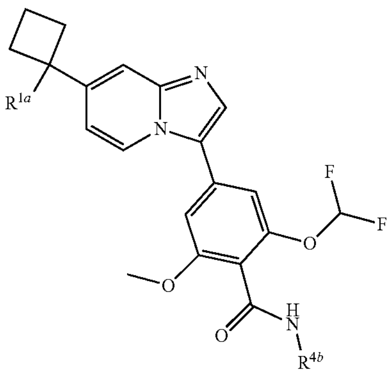

-continued

IVj

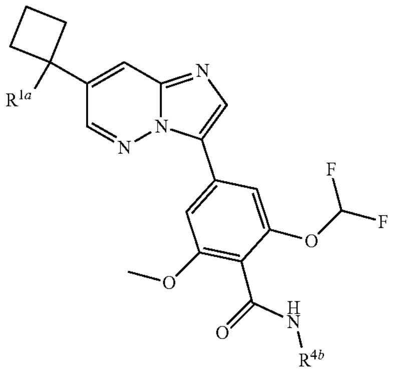

IVk

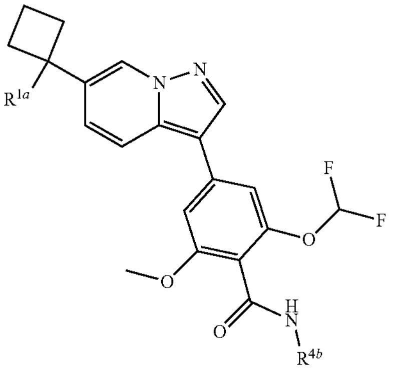

IVl

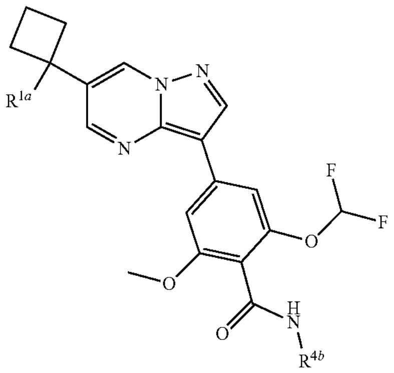

IVm

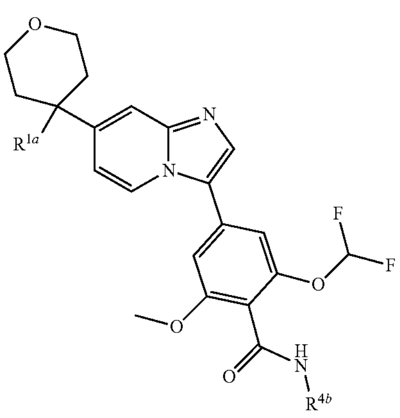

-continued

IVn

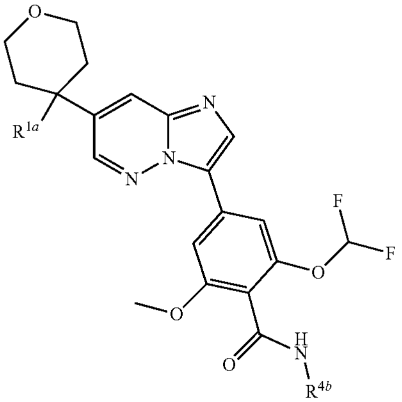

IVo

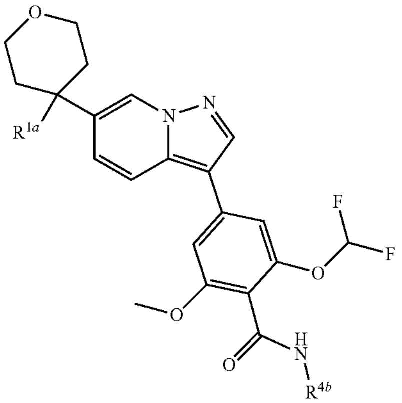

IVp

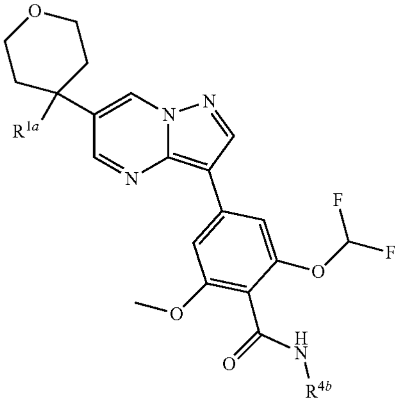

wherein $R^{1a}$ and $R^{4b}$ are as described above.

In one embodiment, the compound of the invention is according to Formula I wherein Z is $—NR^{4a}R^{4b}$ and $R^{4a}$ is as previously described, or any one of Formulae IIIa-IVp, wherein $R^{4b}$ is $C_{1-6}$ alkyl. In a particular embodiment, $R^{4b}$ is $—CH_3$, $—CH_2CH_3$, $—CH_2CH_2CH_3$, $—CH(CH_3)_2$, $—CH_2CH(CH_3)_2$, $—C(CH_3)_3$, $—CH(CH_3)CH_2CH_3$, or $—CH(CH_3)CH(CH_3)_2$. In a more particular embodiment, $R^{4b}$ is $—CH_3$, $—CH_2CH_3$, $—CH_2CH_2CH_3$, $—CH(CH_3)_2$, or $—CH_2CH(CH_3)_2$. In a most particular embodiment, $R^{4b}$ is $—CH_2CH_3$, $—CH(CH_3)_2$, or $—CH_2CH(CH_3)_2$.

In one embodiment, the compound of the invention is according to Formula I wherein Z is $—NR^{4a}R^{4b}$ and $R^{4a}$ is as previously described, or any one of Formulae IIIa-IVp, wherein $R^{4b}$ is $C_{1-6}$ alkyl substituted with one or more independently selected $R^{13}$. In a particular embodiment, $R^{4b}$ is $—CH_3$, $—CH_2CH_3$, $—CH_2CH_2CH_3$, $—CH(CH_3)_2$, —$CH_2CH(CH_3)_2$, —$C(CH_3)_3$, —$CH(CH_3)CH_2CH_3$, or —$CH(CH_3)CH(CH_3)_2$, each of which is substituted with one or more independently selected $R^{13}$. In another particular embodiment, $R^{4b}$ is $C_{1-6}$ alkyl substituted with one, two, or three independently selected $R^{13}$. In a more particular embodiment, $R^{4b}$ is —$CH_3$, —$CH_2CH_3$, —$CH_2CH_2CH_3$, —$CH(CH_3)_2$, —$C(CH_3)_3$, or —$CH(CH_3)CH(CH_3)_2$, each of which is substituted with one or more independently selected $R^{13}$. In another more particular embodiment, $R^{4b}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$, each of which is substituted with one, two, or three independently selected $R^{13}$. In yet another more particular embodiment, $R^{4b}$ is $C_{1-6}$ alkyl substituted with one $R^{13}$. In an even more particular embodiment, $R^{4b}$ is —$CH_3$, —$CH_2CH_3$, —$CH_2CH_2CH_3$, —$CH(CH_3)_2$, —$C(CH_3)_3$, or —$CH(CH_3)CH(CH_3)_2$, each of which is substituted with one, two, or three independently selected $R^{13}$. In another even more particular embodiment, $R^{4b}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, or —$CH(CH_3)CH(CH_3)_2$, each of which is substituted with one $R^{13}$. In a most particular embodiment, $R^{4b}$ is —$CH_3$, —$CH_2CH_3$, —$CH_2CH_2CH_3$, —$CH(CH_3)_2$, —$C(CH_3)_3$, or —$CH(CH_3)CH(CH_3)_2$, each of which is substituted with one $R^{13}$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{1-6}$ alkyl substituted with one or more independently selected $R^{13}$, and $R^{13}$ is halo, —CN, —OH, $C_{1-4}$ alkoxy, $C_{3-7}$ cycloalkyl, or —$S(=O)_2$—$C_{1-4}$ alkyl. In a particular embodiment, each $R^{13}$ is independently F, Cl, —CN, —OH, —O—$CH_3$, —O—$CH_2CH_3$, —O—$CH(CH_3)_2$, cyclopropyl, cyclobutyl, cyclopentyl, cyclohexyl, —$S(=O)_2$—$CH_3$, —$S(=O)_2$—$CH_2CH_3$, or —$S(=O)_2$—$CH(CH_3)_2$. In a more particular embodiment, each $R^{13}$ is independently F, —CN, —OH, —O—$CH_3$, cyclopropyl, cyclobutyl, or —$S(=O)_2$—$CH_3$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{1-6}$ alkyl substituted with one or more independently selected $R^{13}$, and $R^{13}$ is —$NR^{19a}R^{19b}$, and each $R^{19a}$ and $R^{19b}$ is as previously described. In a particular embodiment, $R^{19a}$ and $R^{19b}$ are both H. In another particular embodiment, one of $R^{19a}$ and $R^{19b}$ is H, and the other is $C_{1-4}$ alkyl. In yet another particular embodiment, $R^{19a}$ and $R^{19b}$ are both $C_{1-4}$ alkyl. In a more particular embodiment, one of $R^{19a}$ and $R^{19b}$ is H, and the other is —$CH_3$, —$CH_2CH_3$, or —$CH(CH_3)_2$. In another more particular embodiment, $R^{19a}$ and $R^{19b}$ are —$CH_3$, —$CH_2CH_3$, or —$CH(CH_3)_2$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{1-6}$ alkyl substituted with one or more independently selected $R^{13}$, and $R^{13}$ is 4-7 membered monocyclic heterocycloalkyl comprising one, two or three heteroatoms independently selected from N, O, and S. In a particular embodiment, $R^{13}$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^{13}$ is oxetanyl, tetrahydrofuranyl, or morpholinyl.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{1-6}$ alkyl substituted with one or more independently selected $R^{13}$, and $R^{13}$ is 5-6 membered monocyclic heteroaryl comprising one, two or three heteroatoms independently selected from N, O, and S. In a particular embodiment, $R^{13}$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl. In a more particular embodiment, $R^{13}$ is imidazolyl, pyrazolyl, or pyridinyl.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{1-6}$ alkyl substituted with one or more independently selected $R^{13}$, and $R^{13}$ is 5-6 membered monocyclic heteroaryl comprising one, two or three heteroatoms independently selected from N, O, and S, which heteroaryl is substituted with one or more independently selected $C_{1-4}$ alkyl. In a particular embodiment, $R^{13}$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more independently selected $C_{1-4}$ alkyl. In another particular embodiment, $R^{13}$ is 5-6 membered monocyclic heteroaryl comprising one, two or three heteroatoms independently selected from N, O, and S, which heteroaryl is substituted with one $C_{1-4}$ alkyl. In yet another particular embodiment, $R^{13}$ is 5-6 membered monocyclic heteroaryl comprising one, two or three heteroatoms independently selected from N, O, and S, which heteroaryl is substituted with one or more independently selected —$CH_3$, —$CH_2CH_3$, or —$CH(CH_3)_2$. In a more particular embodiment, $R^{13}$ is imidazolyl or pyrazolyl, each of which is substituted with one or more independently selected $C_{1-4}$ alkyl. In another more particular embodiment, $R^{13}$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one $C_{1-4}$ alkyl. In yet another more particular embodiment, $R^{13}$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more independently selected —$CH_3$, —$CH_2CH_3$, or —$CH(CH_3)_2$. In a further more particular embodiment, $R^{13}$ is 5-6 membered monocyclic heteroaryl comprising one, two or three heteroatoms independently selected from N, O, and S, which heteroaryl is substituted with one —$CH_3$, —$CH_2CH_3$, or —$CH(CH_3)_2$. In yet a further more particular embodiment, $R^{13}$ is 5-6 membered monocyclic heteroaryl comprising one, two or three heteroatoms independently selected from N, O, and S, which heteroaryl is substituted with one or more —$CH_3$. In an even more particular embodiment, $R^{13}$ is imidazolyl or pyrazolyl, each of which is substituted with one $C_{1-4}$ alkyl. In another even more particular embodiment, $R^{13}$ is pyrrolyl, furanyl, thiophenyl, imidazolyl, furazanyl, oxazolyl, oxadiazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one —$CH_3$, —$CH_2CH_3$, or —$CH(CH_3)_2$. In yet another even more particular embodiment, $R^{13}$ is 5-6 membered monocyclic heteroaryl comprising one, two or three heteroatoms independently selected from N, O, and S, which heteroaryl is substituted with one —$CH_3$. In a most particular embodiment, $R^{13}$ is

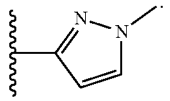 [SMILES: *c1ccn(C)n1]

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{3-7}$ cycloalkyl. In a particular embodiment, $R^{4b}$ is cyclopropyl, cyclobutyl, cyclopentyl, or cyclohexyl. In a more particular embodiment, $R^{4b}$ is cyclopropyl, cyclobutyl, cyclopentyl. In a most particular embodiment, $R^{4b}$ is cyclopropyl.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{3-7}$ cycloalkyl substituted with one or more independently selected $R^{14a}$. In a particular embodiment, $R^{4b}$ is cyclopropyl, cyclobutyl, cyclopentyl, or cyclohexyl, each of which is substituted with one or more independently selected $R^{14a}$. In another particular embodiment, $R^{4b}$ is $C_{3-7}$ cycloalkyl substituted with one, two, or three independently selected $R^{14a}$. In a more particular embodiment, $R^{4b}$ is cyclopropyl, cyclobutyl, cyclopentyl, or cyclohexyl, each of which is substituted with one, two, or three independently selected $R^{14a}$. In another more particular embodiment, $R^{4b}$ is $C_{3-7}$ cycloalkyl substituted with one $R^{14a}$ In a most particular embodiment, $R^{4b}$ is cyclopropyl, cyclobutyl, cyclopentyl, or cyclohexyl, each of which is substituted with one $R^{14a}$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{3-7}$ cycloalkyl substituted with one or more independently selected $R^{14a}$, and $R^{14a}$ is halo, —OH, or $C_{1-4}$ alkoxy. In a particular embodiment, $R^{14a}$ is F, Cl, —OH, —O—$CH_3$, —O—$CH_2CH_3$, or —O—$CH(CH_3)_2$. In a more particular embodiment, $R^{14a}$ is F, —OH, or —O—$CH_3$. In a further more particular embodiment, $R^{4b}$ is

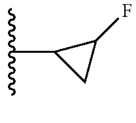

or

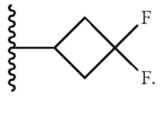

In a most particular embodiment, $R^{4b}$ is

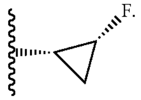 [SMILES: *[C@H]1C[C@H]1F]

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{3-7}$ cycloalkyl substituted with one or more independently selected $R^{14a}$, and $R^{14a}$ is $C_{1-4}$ alkyl. In a particular embodiment, $R^{14a}$ is —$CH_3$, —$CH_2CH_3$, or —$CH(CH_3)_2$. In a more particular embodiment, $R^{14a}$ is —$CH_2CH_3$ or —$CH(CH_3)_2$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{3-7}$ cycloalkyl substituted with one or more independently selected $R^{14a}$, and $R^{14a}$ is $C_{1-4}$ alkyl substituted with one or more independently selected halo, —OH, or $C_{1-4}$ alkoxy. In a particular embodiment, $R^{14a}$ is —$CH_3$, —$CH_2CH_3$, or —$CH(CH_3)_2$, each of which is substituted with one or more independently selected halo, —OH, or $C_{1-4}$ alkoxy. In another particular embodiment, $R^{14a}$ is $C_{1-4}$ alkyl substituted with one, two, or three independently selected halo, —OH, or $C_{1-4}$ alkoxy. In yet another particular embodiment, $R^{14a}$ is $C_{1-4}$ alkyl substituted with one or more F, Cl, —OH, —O—$CH_3$, —O—$CH_2CH_3$, or —O—$CH(CH_3)_2$. In a more particular embodiment, $R^{14a}$ is —$CH_3$ substituted with one or more independently selected halo, —OH, or $C_{1-4}$ alkoxy. In another more particular embodiment, $R^{14a}$ is $C_{1-4}$ alkyl substituted with one halo, —OH, or $C_{1-4}$ alkoxy. In yet another more particular embodiment, $R^{14a}$ is $C_{1-4}$ alkyl substituted with one or more independently selected F or —OH. In a further more particular embodiment, $R^{14a}$ is —$CH_3$, —$CH_2CH_3$, or —$CH(CH_3)_2$, each of which is substituted with one, two, or three independently selected halo, —OH, or $C_{1-4}$ alkoxy. In yet a further more particular embodiment, $R^{14a}$ is $C_{1-4}$ alkyl substituted with one, two, or three independently selected F, Cl, —OH, —O—$CH_3$, —O—$CH_2CH_3$, or —O—$CH(CH_3)_2$. In a most particular embodiment, $R^{14a}$ is —$CH_2$—O—$CH_3$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is $C_{3-7}$ cycloalkyl substituted with one or more independently selected $R^{14a}$, and $R^{14a}$ is —$NR^{20a}R^{20b}$, and each $R^{20a}$ and $R^{20b}$ is as previously described. In a particular embodiment, $R^{20a}$ and $R^{20b}$ are both H. In another particular embodiment, one of $R^{20a}$ and $R^{20b}$ is H, and the other is $C_{1-4}$ alkyl. In yet another particular embodiment, $R^{20a}$ and $R^{20b}$ are both $C_{1-4}$ alkyl. In a more particular embodiment, one of $R^{20a}$ and $R^{20b}$ is H, and the other is —$CH_3$, —$CH_2CH_3$, or —$CH(CH_3)_2$. In another more particular embodiment, $R^{20a}$ and $R^{20b}$ are —$CH_3$, —$CH_2CH_3$, or —$CH(CH_3)_2$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is 4-7 membered monocyclic heterocycloalkyl comprising one, two or three heteroatoms independently selected from N, O, and S. In a particular embodiment, $R^{4b}$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl. In a more particular embodiment, $R^{4b}$ is oxetanyl, thietanyl, or tetrahydrofuranyl. In a most particular embodiment, $R^{4b}$ is oxetanyl or tetrahydrofuranyl.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is 4-7 membered monocyclic heterocycloalkyl comprising one, two or three heteroatoms independently selected from N, O, and S, which heterocycloalkyl is substituted with one or more independently selected $R^{14b}$. In a particular embodiment, $R^{4b}$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl, each of which is substituted with one or more independently selected $R^{14b}$. In another particular embodiment, $R^{4b}$ is 4-7 membered monocyclic heterocycloalkyl comprising one, two or three heteroatoms independently selected from N, O, and S, which heterocycloalkyl is substituted with one, two, or three independently selected $R^{14b}$. In a more particular embodiment, $R^{4b}$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl, each of which is substituted with one, two, or three independently selected $R^{14b}$. In another more particular embodiment, $R^{4b}$ is 4-7 membered monocyclic heterocycloalkyl comprising one, two or three heteroatoms independently selected from N, O, and S, which heterocycloalkyl is substituted with one $R^{14b}$. In a most particular embodiment, $R^{4b}$ is thietanyl substituted with two $R^{14b}$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is 4-7 membered monocyclic heterocycloalkyl comprising one, two or three heteroatoms independently selected from N, O, and S, which heterocycloalkyl is substituted with one or more independently selected $R^{14b}$, and $R^{14b}$ is halo, oxo, —OH, or $C_{1-4}$ alkoxy. In a particular embodiment, $R^{14b}$ is F, Cl, oxo, —OH, —O—$CH_3$, —O—$CH_2CH_3$, or —O—$CH(CH_3)_2$. In a more particular embodiment, $R^{14b}$ is F, oxo, —OH, or —O—$CH_3$. In a most particular embodiment, $R^{14b}$ is oxo.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is 4-7 membered monocyclic heterocycloalkyl comprising one, two or three heteroatoms independently selected from N, O, and S, which heterocycloalkyl is substituted with one or more independently selected $R^{14b}$, and $R^{14b}$ is $C_{1-4}$ alkyl. In a particular embodiment, $R^{14b}$ is —$CH_3$, —$CH_2CH_3$, or —$CH(CH_3)_2$. In a more particular embodiment, $R^{14b}$ is —$CH_3$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is 4-7 membered monocyclic heterocycloalkyl comprising one, two or three heteroatoms independently selected from N, O, and S, which heterocycloalkyl is substituted with one or more independently selected $R^{14b}$, and $R^{14b}$ is $C_{1-4}$ alkyl substituted with one or more independently selected halo, —OH, or $C_{1-4}$ alkoxy. In a particular embodiment, $R^{14b}$ is —$CH_3$, —$CH_2CH_3$, or —$CH(CH_3)_2$, each of which is substituted with one or more independently selected halo, —OH, or $C_{1-4}$ alkoxy. In another particular embodiment, $R^{14b}$ is $C_{1-4}$ alkyl substituted with one, two, or three independently selected halo, —OH, or $C_{1-4}$ alkoxy. In yet another particular embodiment, $R^{14b}$ is $C_{1-4}$ alkyl substituted with one or more F, Cl, —OH, —O—$CH_3$, —O—$CH_2CH_3$, or —O—$CH(CH_3)_2$. In a more particular embodiment, $R^{14b}$ is —$CH_3$ substituted with one or more independently selected halo, —OH, or $C_{1-4}$ alkoxy. In another more particular embodiment, $R^{14b}$ is $C_{1-4}$ alkyl substituted with one halo, —OH, or $C_{1-4}$ alkoxy. In yet another more particular embodiment, $R^{14b}$ is $C_{1-4}$ alkyl substituted with one or more independently selected F or —OH. In a further more particular embodiment, $R^{14b}$ is —$CH_3$, —$CH_2CH_3$, or —$CH(CH_3)_2$, each of which is substituted with one, two, or three independently selected halo, —OH, or $C_{1-4}$ alkoxy. In yet a further more particular embodiment, $R^{14b}$ is $C_{1-4}$ alkyl substituted with one, two, or three independently selected F, Cl, —OH, —O—$CH_3$, —O—$CH_2CH_3$, or —O—$CH(CH_3)_2$. In a most particular embodiment, $R^{14b}$ is —$CH_2F$, —$CHF_2$, —$CF_3$, or —$CH_2$—OH.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is 4-7 membered monocyclic heterocycloalkyl comprising one, two or three heteroatoms independently selected from N, O, and S, which heterocycloalkyl is substituted with one or more independently selected $R^{14b}$, $R^{14b}$ is —$NR^{20a}R^{20b}$, and each $R^{20a}$ and $R^{20b}$ is as previously described. In a particular embodiment, $R^{20a}$ and $R^{20b}$ are both H. In another particular embodiment, one of $R^{20a}$ and $R^{20b}$ is H, and the other is $C_{1-4}$ alkyl. In yet another particular embodiment, $R^{20a}$ and $R^{20b}$ are both $C_{1-4}$ alkyl. In a more particular embodiment, one of $R^{20a}$ and $R^{20b}$ is H, and the other is —$CH_3$, —$CH_2CH_3$, or —$CH(CH_3)_2$. In another more particular embodiment, $R^{20a}$ and $R^{20b}$ are —$CH_3$, —$CH_2CH_3$, or —$CH(CH_3)_2$. In a most particular embodiment, $R^{20a}$ and $R^{20b}$ are —$CH_3$.

In one embodiment, the compound of the invention is according to any one of Formulae I and IIIa-IVp, wherein Z is —$NR^{4a}R^{4b}$, $R^{4a}$ is as previously described, and $R^{4b}$ is 5-6 membered monocyclic heteroaryl comprising one, two or three heteroatoms independently selected from N, O, and S. In a particular embodiment, $R^{4b}$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl. In a more particular embodiment, $R^{4b}$ is imidazolyl, pyrazolyl, isoxazolyl, or pyrimidinyl. In a most particular embodiment, $R^{4b}$ is isoxazolyl.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is 5-6 membered monocyclic heteroaryl comprising one, two or three heteroatoms independently selected from N, O, and S, which heteroaryl is substituted with one or more independently selected $C_{1-4}$ alkyl. In a particular embodiment, $R^{4b}$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more independently selected $C_{1-4}$ alkyl. In another particular embodiment, $R^{4b}$ is 5-6 membered monocyclic heteroaryl comprising one, two or three heteroatoms independently selected from N, O, and S, which heteroaryl is substituted with one $C_{1-4}$ alkyl. In yet another particular embodiment, $R^{4b}$ is 5-6 membered monocyclic heteroaryl comprising one, two or three heteroatoms independently selected from N, O, and S, which heteroaryl is substituted with one or more independently selected —$CH_3$, —$CH_2CH_3$, or —$CH(CH_3)_2$. In a more particular embodiment, $R^{4b}$ is imidazolyl, pyrazolyl, or pyrimidinyl, each of which is substituted with one or more independently selected $C_{1-4}$ alkyl. In another more particular embodiment, $R^{4b}$ is 5-6 membered monocyclic heteroaryl comprising one, two or three heteroatoms independently selected from N, O, and S, which heteroaryl is substituted with one —$CH_3$. In yet another more particular embodiment, $R^{4b}$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one $C_{1-4}$ alkyl. In a further more particular embodiment, $R^{4b}$ is 5-6 membered monocyclic heteroaryl comprising one, two or three heteroatoms independently selected from N, O, and S, which heteroaryl is substituted with one —$CH_3$, —$CH_2CH_3$, or —$CH(CH_3)_2$. In an even more particular embodiment, $R^{4b}$ is imidazolyl, pyrazolyl, or pyrimidinyl, each of which is substituted with one $C_{1-4}$ alkyl. In another even more particular embodiment, $R^{4b}$ is $R^{4b}$ is imidazolyl, pyrazolyl, or pyrimidinyl, each of which is substituted with one or more —$CH_3$, —$CH_2CH_3$, or —$CH(CH_3)_2$. In yet another even more particular embodiment, $R^{4b}$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one or more —$CH_3$. In a further even more particular embodiment, $R^{4b}$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one —$CH_3$, —$CH_2CH_3$, or —$CH(CH_3)_2$. In yet a further even more particular embodiment, $R^{4b}$ is 5-6 membered monocyclic heteroaryl comprising one, two or three heteroatoms independently selected from N, O, and S, which heteroaryl is substituted with one —$CH_3$. In a most particular embodiment, $R^{4b}$ is imidazolyl, pyrazolyl, or pyrimidinyl, each of which is substituted with one —$CH_3$.

In one embodiment, the compound of the invention is according to Formula I wherein Z is —$NR^{4a}R^{4b}$ and $R^{4a}$ is as previously described, or any one of Formulae IIIa-IVp, wherein $R^{4b}$ is cyclopropyl or 2-fluorocyclopropyl. In a particular embodiment, Z is —$NR^{4a}R^{4b}$, $R^{4a}$ is H, and $R^{4b}$ is cyclopropyl or (1R,2S)-2-fluorocyclopropyl.

In one embodiment, the compound of the invention is according to any one of Formulae I-IVp, wherein $R^{1a}$ is H.

In one embodiment, the compound of the invention is according to any one of Formulae I-IVp, wherein $R^{1a}$ is halo, —OH, —CN, or —$S(=O)_2$—$C_{1-4}$ alkyl. In a particular embodiment, $R^{1a}$ is F, Cl, Br, —OH, —CN, —$S(=O)_2$—$CH_3$, —$S(=O)_2$—$CH_2CH_3$, or —$S(=O)_2$—$CH(CH_3)_2$. In a more particular embodiment, $R^{1a}$ is F, Cl, —OH, —CN, or —$S(=O)_2$—$CH_3$. In a most particular embodiment, $R^{1a}$ is —CN.

In one embodiment, the compound of the invention is according to any one of Formulae I-IVp, wherein $R^{1a}$ is $C_{1-6}$ alkyl. In a particular embodiment, Ria is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, —$CH(CH_3)CH(CH_3)_2$, —$CH_2CH(CH_3)CH_2CH_3$, or —$CH_2CH_2CH(CH_3)_2$. In a more particular embodiment, Ria is —$CH_3$, —$CH_2CH_3$, or —$CH(CH_3)_2$.

In one embodiment, the compound of the invention is according to any one of Formulae I-IVp, wherein $R^{1a}$ is $C_{1-6}$ alkyl substituted with one or more independently selected $R^6$. In a particular embodiment, $R^{1a}$ is —$CH_3$, —$CH_2CH_3$, —$CH_2CH_2CH_3$, —$CH(CH_3)_2$, —$CH_2CH(CH_3)_2$, —$C(CH_3)_3$, —$CH(CH_3)CH_2CH_3$, —$CH(CH_3)CH(CH_3)_2$, —$CH_2CH(CH_3)CH_2CH_3$, or —$CH_2CH_2CH(CH_3)_2$, each of which is substituted with one, two, or three independently selected $R^6$. In a more particular embodiment, Ria is —$CH_3$, —$CH_2CH_3$, —$CH_2CH_2CH_3$, or —$CH_2CH(CH_3)_2$, each of which is substituted with one, two, or three independently selected $R^6$.

In one embodiment, the compound of the invention is according to any one of Formulae I-IVp, wherein $R^{1a}$ is $C_{1-6}$ alkyl substituted with one or more independently selected $R^6$, and $R^6$ is halo. In a particular embodiment, $R^6$ is F or Cl. In a more particular embodiment, $R^{1a}$ is —$CHF_2$ or —$CF_3$. In a most particular embodiment, $R^{1a}$ is —$CF_3$.

In one embodiment, the compound of the invention is according to any one of Formulae I-IVp, wherein $R^{1a}$ is $C_{1-6}$ alkyl substituted with one or more independently selected $R^6$, $R^6$ is —O—$R^{16}$, and $R^{16}$ is as previously described. In a particular embodiment, $R^{16}$ is H or —$S(=O)_2$—$C_{1-4}$alkyl. In a more particular embodiment, $R^{16}$ is H, —$S(=O)_2$—$CH_3$, —$S(=O)_2$—$CH_2CH_3$, or —$S(=O)_2$—$CH(CH_3)_2$. In a further more particular embodiment, $R^{16}$ is H or —$S(=O)_2$ —$CH_3$. In a most particular embodiment, $R^{1a}$ is —$CH_2$—OH or —$CH_2$—O—$S(=O)_2$—$CH_3$.

In one embodiment, the compound of the invention is according to any one of Formulae I-IVp, wherein $R^{1a}$ is $C_{1-6}$ alkyl substituted with one or more independently selected $R^6$, $R^6$ is —O—$R^{16}$, and $R^{16}$ is $C_{1-4}$ alkyl. In a particular embodiment, $R^{16}$ is —$CH_3$, —$CH_2CH_3$, or —$CH(CH_3)_2$. In a more particular embodiment, $R^{16}$ is —$CH_3$.

In one embodiment, the compound of the invention is according to any one of Formulae I-IVp, wherein $R^{1a}$ is $C_{1-6}$ alkyl substituted with one or more independently selected $R^6$, $R^6$ is —O—$R^{16}$, and $R^{16}$ is $C_{1-4}$ alkyl substituted with one or more —C(=O)—$NR^{21a}R^{21b}$ or 4-6 membered monocyclic heterocycloalkyl comprising one, two or three heteroatoms independently selected from N, O, and S, and $R^{21a}$ and $R^{21b}$ are as previously described. In a particular embodiment, $R^{16}$ is —$CH_3$, —$CH_2CH_3$, or —$CH(CH_3)_2$, each of which is substituted with one —C(=O)—$NH_2$, —C(=O)—NH—$CH_3$, —C(=O)—NH—$CH_2CH_3$, —C(=O)—NH—$CH(CH_3)_2$, —C(=O)—$N(CH_3)_2$, —C(=O)—$N(CH_2CH_3)_2$, —C(=O)—$N(CH(CH_3)_2)_2$, azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^{16}$ is —$CH_3$ substituted with one —C(=O)—NH—$CH_3$, —C(=O)—$N(CH_3)_2$, or oxetanyl.

In one embodiment, the compound of the invention is according to any one of Formulae I-IVp, wherein $R^{1a}$ is $C_{1-6}$ alkyl substituted with one or more independently selected $R^6$, $R^6$ is —O—$R^{16}$, and $R^{16}$ is 4-6 membered monocyclic heterocycloalkyl comprising one, two or three heteroatoms independently selected from N, O, and S. In a particular embodiment, $R^{16}$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^{16}$ is oxetanyl.

In one embodiment, the compound of the invention is according to any one of Formulae I-IVp, wherein $R^{1a}$ is $C_{1-6}$ alkyl substituted with one or more independently selected $R^6$, $R^6$ is —$NR^{17a}R^{17b}$, and $R^{17a}$ and $R^{17b}$ are as previously described. In a particular embodiment, $R^{17a}$ and $R^{17b}$ are both H. In another particular embodiment, one of $R^{17a}$ and $R^{17b}$ is H, and the other is $C_{1-4}$ alkyl optionally substituted with one —OH or $C_{1-4}$ alkoxy. In yet another particular embodiment, $R^{17a}$ and $R^{17b}$ are both $C_{1-4}$ alkyl optionally substituted with one —OH or $C_{1-4}$ alkoxy. In a more particular embodiment, one of $R^{17a}$ and $R^{17b}$ is H, and the other is —$CH_3$, —$CH_2CH_3$, or —$CH(CH_3)_2$. In another more particular embodiment, one of $R^{17a}$ and $R^{17b}$ is H, and the other is —$CH_3$, —$CH_2CH_3$, or —$CH(CH_3)_2$, each of which is substituted with one —OH, —O—$CH_3$, —O—$CH_2CH_3$, or —O—$CH(CH_3)_2$. In a most particular embodiment, $R^6$ is —$NH_2$, —NH—$CH(CH_3)_2$, or —$N(CH_3)$—$CH_2CH_2$—OH.

In one embodiment, the compound of the invention is according to any one of Formulae I-IVp, wherein $R^{1a}$ is $C_{1-6}$ alkyl substituted with one or more independently selected $R^6$, and $R^6$ is 5-6 membered monocyclic heteroaryl comprising one, two or three heteroatoms independently selected from N, O, and S. In a particular embodiment, $R^6$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl. In a more particular embodiment, $R^6$ is imidazolyl, pyrazolyl, or 1,2,4-triazolyl.

In one embodiment, the compound of the invention is according to any one of Formulae I-IVp, wherein $R^{1a}$ is $C_{1-6}$ alkyl substituted with one or more independently selected $R^6$, and $R^6$ is 4-6 membered monocyclic heterocycloalkyl comprising one, two or three heteroatoms independently selected from N, O, and S. In a particular embodiment, $R^6$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^6$ is pyrrolidinyl, piperidinyl, or morpholinyl.

In one embodiment, the compound of the invention is according to any one of Formulae I-IVp, wherein $R^{1a}$ is $C_{1-6}$ alkyl substituted with one or more independently selected $R^6$, and $R^6$ is 4-6 membered monocyclic heterocycloalkyl comprising one, two or three heteroatoms independently selected from N, O, and S, which heterocycloalkyl is substituted with one or more independently selected halo. In a particular embodiment, $R^6$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl, each of which is substituted with one, two, or three F or Cl. In a more particular embodiment, $R^6$ is azetidinyl substituted with one, two, or three F. In a most particular embodiment, $R^6$ is

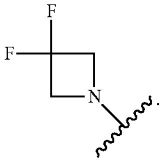

In one embodiment, the compound of the invention is according to any one of Formulae I-IVp, wherein $R^{1a}$ is $C_{1-4}$ alkoxy. In a particular embodiment, $R^{1a}$ is —O—$CH_3$, —O—$CH_2CH_3$, or —O—$CH(CH_3)_2$. In a more particular embodiment, $R^{1a}$ is —O—$CH_3$ or —O—$CH_2CH_3$.

In one embodiment, the compound of the invention is according to any one of Formulae I-IVp, wherein $R^{1a}$ is $C_{1-4}$ alkoxy substituted with one or more —OH or 5-6 membered monocyclic heterocycloalkyl comprising one, two or three heteroatoms independently selected from N, O, and S. In a particular embodiment, $R^{1a}$ is —O—$CH_3$, —O—$CH_2CH_3$, or —O—$CH(CH_3)_2$, each of which is substituted with one —OH, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^{1a}$ is —O—$CH_2CH_3$ substituted with one —OH or morpholinyl.

In one embodiment, the compound of the invention is according to any one of Formulae I-IVp, wherein $R^{1a}$ is —C(═O)—$R^7$, and $R^7$ is as previously defined. In a particular embodiment, $R^7$ is —OH, $C_{1-4}$ alkyl, or $C_{1-4}$ alkoxy. In a more particular embodiment, $R^7$ is —OH, —$CH_3$, —$CH_2CH_3$, —$CH(CH_3)_2$, —O—$CH_3$, —O—$CH_2CH_3$, or —O—$CH(CH_3)_2$. In a further more particular embodiment, $R^7$ is —OH, —$CH_3$, or —O—$CH_3$.

In one embodiment, the compound of the invention is according to any one of Formulae I-IVp, wherein $R^{1a}$ is —C(═O)—$R^7$, $R^7$ is —$NR^{18a}R^{18b}$, and $R^{18a}$ and $R^{18b}$ are as previously described. In a particular embodiment, $R^{18a}$ and $R^{18b}$ are both H. In another particular embodiment, one of $R^{18a}$ and $R^{18b}$ is H, and the other is $C_{1-4}$ alkyl optionally substituted with one —OH or $C_{1-4}$ alkoxy. In yet another particular embodiment, $R^{18a}$ and $R^{18b}$ are both $C_{1-4}$ alkyl optionally substituted with one —OH or $C_{1-4}$ alkoxy. In a more particular embodiment, one of $R^{18a}$ and $R^{18b}$ is H, and the other is —$CH_3$, —$CH_2CH_3$, or —$CH(CH_3)_2$. In another more particular embodiment, one of $R^{17a}$ and $R^{17b}$ is H, and the other is —$CH_3$, —$CH_2CH_3$, or —$CH(CH_3)_2$, each of which is substituted with one —OH, —O—$CH_3$, —O—$CH_2CH_3$, or —O—$CH(CH_3)_2$. In a most particular embodiment, $R^7$ is —$NH_2$, —NH—$CH_3$, —NH—$CH_2CH_3$, —$N(CH_2CH_3)_2$, —NH—$CH_2CH_2$—OH, or —NH—$CH_2CH_2$—O—$CH_3$.

In one embodiment, the compound of the invention is according to any one of Formulae I-IVp, wherein $R^{1a}$ is —C(═O)—$R^7$, and $R^7$ is 4-6 membered monocyclic heterocycloalkyl comprising one, two or three heteroatoms independently selected from N, O, and S. In a particular embodiment, $R^7$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl. In a more particular embodiment, $R^7$ is morpholinyl.

In one embodiment, the compound of the invention is according to any one of Formulae I-IVp, wherein $R^{1a}$ is —C(═O)—$R^7$, and $R^7$ is 4-6 membered monocyclic heterocycloalkyl comprising one, two or three heteroatoms independently selected from N, O, and S, which heterocycloalkyl is substituted with one or more —OH. In a particular embodiment, $R^7$ is azetidinyl, oxetanyl, pyrrolidinyl, tetrahydrofuranyl, piperidinyl, tetrahydropyranyl, tetrahydrothiopyranyl, morpholinyl, thiomorpholinyl, dioxanyl, or piperazinyl, each of which is substituted with one, two, or three —OH. In a more particular embodiment, $R^7$ is azetidinyl substituted with one —OH. In a most particular embodiment, $R^7$ is

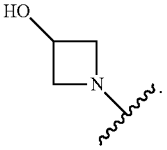 [SMILES: *N1CC(O)C1]

In one embodiment, the compound of the invention is according to any one of Formulae I-IVp, wherein $R^{1a}$ is —$NR^{8a}R^{8b}$, and each $R^{8a}$ and $R^{8b}$ are as previously described. In a particular embodiment, $R^{8a}$ and $R^{8b}$ are both H. In another particular embodiment, one of $R^{8a}$ and $R^{8b}$ is H, and the other is —C(═O)—$C_{1-4}$ alkoxy or $C_{1-4}$ alkyl optionally substituted with one or more halo, —CN or —OH. In yet another particular embodiment, $R^{8a}$ and $R^{8b}$ are both —C(═O)—$C_{1-4}$ alkoxy or $C_{1-4}$ alkyl optionally substituted with one or more halo, —CN or —OH. In a more particular embodiment, one of $R^{8a}$ and $R^{8b}$ is H, and the other is —C(═O)—O—$CH_3$, —C(═O)—O—$CH_2CH_3$, —C(═O)—O—$CH(CH_3)_2$, —C(═O)—O—$CH_2CH_2CH_3$, —C(═O)—O—$CH_2CH_2CH_2CH_3$, —$CH_3$, —$CH_2CH_3$, or —$CH(CH_3)_2$. In another more particular embodiment, one of $R^{8a}$ and $R^{8b}$ is H, and the other is —$CH_3$, —$CH_2CH_3$, or —$CH(CH_3)_2$, each of which is substituted with one, two, or three F, Cl, —CN, or —OH. In a most particular embodiment, $R^7$ is —$NH_2$, —NH—C(═O)—O—$CH_3$, —NH—C(═O)—O—$CH_2CH_2CH_2CH_3$, —NH—$CH_2CHF_2$, —NH—$CH_2CN$, or —NH—$CH_2CH_2$—OH.

In one embodiment, the compound of the invention is according to any one of Formulae I-IVp, wherein $R^{1a}$ is 5-6 membered monocyclic heteroaryl comprising one, two or three heteroatoms independently selected from N, O, and S. In a particular embodiment, $R^{1a}$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl. In a more particular embodiment, Ria is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, or tetrazolyl.

In one embodiment, the compound of the invention is according to any one of Formulae I-IVp, wherein $R^{1a}$ is 5-6 membered monocyclic heteroaryl comprising one, two or three heteroatoms independently selected from N, O, and S, which heteroaryl is substituted with one or more independently selected $C_{1-4}$ alkyl. In a particular embodiment, $R^{1a}$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, tetrazolyl, pyridinyl, pyrazinyl, pyridazinyl, or pyrimidinyl, each of which is substituted with one, two, or three independently selected $—CH_3$, $—CH_2CH_3$, or $—CH(CH_3)_2$. In a more particular embodiment, $R^{1a}$ is pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl, or tetrazolyl, each of which is substituted with one $—CH_3$. In a most particular embodiment, $R^{1a}$ is

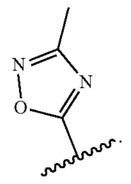 [SMILES: *c1nc(C)no1]

In one embodiment, the compound of the invention is according to any one of Formulae I-IVp, wherein $R^{1a}$ is 4-6 membered monocyclic heterocycloalkyl comprising one, two or three heteroatoms independently selected from N, O, and S. In a particular embodiment, $R^{1a}$ is azetidinyl, oxetanyl, thietanyl, pyrrolidinyl, tetrahydrofuranyl, tetrahydrothiophenyl, piperidinyl, tetrahydropyranyl, tetrahydrothiopyranyl, morpholinyl, thiomorpholinyl, dioxanyl, or piperazinyl. In a more particular embodiment, $R^{1a}$ is oxetanyl, tetrahydropyranyl, or morpholinyl.

In one embodiment, the compound of the invention is according to Formula I, wherein the compound is selected from:

2,6-dimethoxy-4-[5-(1-methyl-4-piperidyl)benzimidazol-1-yl]-N-(2,2,2-trifluoroethyl)benzamide, tert-butyl 4-[1-[3,5-dimethoxy-4-(2,2,2-trifluoroethylcarbamoyl)phenyl]benzimidazol-5-yl]piperidine-1-carboxylate, 2,6-dimethoxy-4-[5-(4-piperidyl)benzimidazol-1-yl]-N-(2,2,2-trifluoroethyl)benzamide, 4-[5-[1-(cyanomethyl)-4-piperidyl]benzimidazol-1-yl]-2,6-dimethoxy-N-(2,2,2-trifluoroethyl)benzamide, 2,6-dimethoxy-4-(5-tetrahydropyran-4-ylbenzimidazol-1-yl)-N-(2,2,2-trifluoroethyl)benzamide, 2,6-dimethoxy-4-[5-(1-methyl-3-piperidyl)benzimidazol-1-yl]-N-(2,2,2-trifluoroethyl)benzamide, tert-butyl 3-[1-[3,5-dimethoxy-4-(2,2,2-trifluoroethylcarbamoyl)phenyl]benzimidazol-5-yl]piperidine-1-carboxylate, 2,6-dimethoxy-4-[5-(3-piperidyl)benzimidazol-1-yl]-N-(2,2,2-trifluoroethyl)benzamide, 4-[5-[1-(cyanomethyl)-3-piperidyl]benzimidazol-1-yl]-2,6-dimethoxy-N-(2,2,2-trifluoroethyl)benzamide, 4-[5-(1-cyano-1-methyl-ethyl)benzimidazol-1-yl]-2,6-dimethoxy-N-(2,2,2-trifluoroethyl)benzamide, 4-[5-(1-cyano-1-methyl-ethyl)benzimidazol-1-yl]-N-cyclopropyl-2,6-dimethoxy-benzamide, 4-[5-(1-cyano-1-methyl-ethyl)benzimidazol-1-yl]-N-cyclopropyl-2-(difluoromethoxy)-6-methoxy-benzamide, 4-[5-(1-cyanocyclobutyl)benzimidazol-1-yl]-2,6-dimethoxy-N-(2,2,2-trifluoroethyl)benzamide, 4-[5-(1-cyanocyclobutyl)benzimidazol-1-yl]-N-cyclopropyl-2,6-dimethoxy-benzamide, 4-[5-(1-cyanoethyl)benzimidazol-1-yl]-2,6-dimethoxy-N-(2,2,2-trifluoroethyl)benzamide, tert-butyl 4-[3-[3,5-dimethoxy-4-(2,2,2-trifluoroethylcarbamoyl)phenyl]imidazo[1,2-a]pyridin-7-yl]piperidine-1-carboxylate, 4-[7-(1-cyano-1-methyl-ethyl)imidazo[1,2-a]pyridin-3-yl]-2,6-dimethoxy-N-(2,2,2-trifluoroethyl)benzamide, 2-[3-[4-(3,3-difluoroazetidine-1-carbonyl)-3,5-dimethoxyphenyl]imidazo[1,2-a]pyridin-7-yl]-2-methyl-propanenitrile, 4-[7-(1-cyano-1-methyl-ethyl)imidazo[1,2-a]pyridin-3-yl]-N-cyclopropyl-2-(difluoromethoxy)-6-methoxy-benzamide, 2-[3-(8-methoxy-1-oxo-3,4-dihydro-2H-isoquinolin-6-yl)imidazo[1,2-a]pyridin-7-yl]-2-methyl-propanenitrile, tert-butyl 3-[3-[3,5-dimethoxy-4-(2,2,2-trifluoroethylcarbamoyl)phenyl]imidazo[1,2-a]pyridin-7-yl]piperidine-1-carboxylate, 2,6-dimethoxy-4-[7-(1-methyl-4-piperidyl)imidazo[1,2-a]pyridin-3-yl]-N-(2,2,2-trifluoroethyl)benzamide, 2,6-dimethoxy-4-[7-(3-piperidyl)imidazo[1,2-a]pyridin-3-yl]-N-(2,2,2-trifluoroethyl)benzamide, 2,6-dimethoxy-4-[7-(1-methyl-3-piperidyl)imidazo[1,2-a]pyridin-3-yl]-N-(2,2,2-trifluoroethyl)benzamide, 2-[3-[8-methoxy-1-oxo-2-(2,2,2-trifluoroethyl)-3,4-dihydroisoquinolin-6-yl]imidazo[1,2-a]pyridin-7-yl]-2-methyl-propanenitrile, 4-[7-(1-cyanoethyl)imidazo[1,2-a]pyridin-3-yl]-N-cyclopropyl-2-(difluoromethoxy)-6-methoxy-benzamide, 4-[7-(1-cyano-1-methyl-propyl)imidazo[1,2-a]pyridin-3-yl]-N-cyclopropyl-2-(difluoromethoxy)-6-methoxy-benzamide, 4-[7-(1-cyano-1-methyl-ethyl)imidazo[1,2-a]pyridin-3-yl]-N-cyclopropyl-2,6-dimethoxy-benzamide, 4-[7-(2-amino-1,1-dimethyl-2-oxo-ethyl)imidazo[1,2-a]pyridin-3-yl]-N-cyclopropyl-2,6-dimethoxy-benzamide, 4-[7-(1-cyano-1-methyl-ethyl)imidazo[1,2-a]pyridin-3-yl]-N-ethyl-2,6-dimethoxy-benzamide, 4-[7-(2-amino-1,1-dimethyl-2-oxo-ethyl)imidazo[1,2-a]pyridin-3-yl]-N-ethyl-2,6-dimethoxy-benzamide, N-(cyanomethyl)-4-[7-(1-cyano-1-methyl-ethyl)imidazo[1,2-a]pyridin-3-yl]-2,6-dimethoxy-benzamide, 4-[7-(1-cyanocyclopropyl)imidazo[1,2-a]pyridin-3-yl]-N-cyclopropyl-2-(difluoromethoxy)-6-methoxy-benzamide, 4-[7-(1-cyanocyclobutyl)imidazo[1,2-a]pyridin-3-yl]-N-cyclopropyl-2-(difluoromethoxy)-6-methoxy-benzamide, N-cyclopropyl-2-(difluoromethoxy)-4-[7-(1-hydroxy-1-methyl-ethyl)imidazo[1,2-a]pyridin-3-yl]-6-methoxy-benzamide, 4-[7-(1-allyl-1-cyano-but-3-enyl)imidazo[1,2-a]pyridin-3-yl]-N-cyclopropyl-2-(difluoromethoxy)-6-methoxy-benzamide, 2,6-dimethoxy-4-(7-tetrahydropyran-4-ylimidazo[1,2-a]pyridin-3-yl)-N-(2,2,2-trifluoroethyl)benzamide, 2-[3-[3-(difluoromethoxy)-4-(1,1-dioxo-1,4-thiazinane-4-carbonyl)-5-methoxy-phenyl]imidazo[1,2-a]pyridin-7-yl]-2-methyl-propanenitrile, 4-[7-(1-cyano-1-methyl-ethyl)imidazo[1,2-a]pyridin-3-yl]-N-(cyclopropylmethyl)-2-(difluoromethoxy)-6-methoxy-benzamide, 4-[7-(1-cyano-1-methyl-ethyl)imidazo[1,2-a]pyridin-3-yl]-2-(difluoromethoxy)-N-ethyl-6-methoxy-N-methyl-benzamide, 2-[3-[3-(difluoromethoxy)-4-(4-hydroxypiperidine-1-carbonyl)-5-methoxy-phenyl]imidazo[1,2-a]pyridin-7-yl]-2-methyl-propanenitrile, 4-[7-(1-cyano-1-methyl-ethyl)imidazo[1,2-a]pyridin-3-yl]-2-(difluoromethoxy)-6-methoxy-N-(2-morpholinoethyl)benzamide, 4-[7-(1-cyano-1-methyl-ethyl)imidazo[1,2-a]pyridin-3-yl]-2-(difluoromethoxy)-6-methoxy-N-(oxetan-3-yl)benzamide, 4-[7-(1-cyano-1-methyl-ethyl)imidazo[1,2-a]pyridin-3-yl]-2-(difluoromethoxy)-N-(3-hydroxypropyl)-6-methoxy-benzamide, 4-[7-(1-cyano-1-methyl-ethyl)imidazo[1,2-a]pyridin-3-yl]-2-(difluoromethoxy)-6-methoxy-N-(3-methoxypropyl)benzamide, 2-[3-[3-(difluoromethoxy)-5-methoxy-4-(4-methoxypiperidine-1-carbonyl)phenyl]imidazo[1,2-a]pyridin-7-yl]-2-methyl-propanenitrile, 2-[3-[3-(difluoromethoxy)-4-(3,3-difluoropyrrolidine-1-carbonyl)-5-methoxy-phenyl]imidazo[1,2-a]pyridin-7-yl]-2-methyl-propanenitrile, 2-[3-[3-(difluoromethoxy)-5-methoxy-4-(morpholine-4-carbonyl)phenyl]imidazo[1,2-a]pyridin-7-yl]-2-methyl-propanenitrile, 2-[3-[3-(difluoromethoxy)-5-methoxy-4-(4-methylpiperazine-1-carbonyl)phenyl]imidazo[1,2-a]pyridin-7-yl]-2-methyl-propanenitrile, 2-[3-[3-(difluoromethoxy)-4-(3-hydroxyazetidine-1-carbonyl)-5-methoxy-phenyl]imidazo[1,2-a]pyridin-7-yl]-2-methyl-propanenitrile, 2-[3-[3-(difluoromethoxy)-5-methoxy-4-(2-oxa-6-azaspiro[3.3]heptane-6-carbonyl)phenyl]imidazo[1,2-a]pyridin-7-yl]-2-methyl-propanenitrile, 4-[7-(1-cyano-1-methyl-ethyl)imidazo[1,2-a]pyridin-3-yl]-2-(difluoromethoxy)-6-methoxy-N-[(1-methylpyrazol-3-yl)methyl]benzamide, 4-[7-(1-cyanocyclopentyl)imidazo[1,2-a]pyridin-3-yl]-N-cyclopropyl-2-(difluoromethoxy)-6-methoxy-benzamide, 4-[7-(1-hydroxyethyl)imidazo[1,2-a]pyridin-3-yl]-2,6-dimethoxy-N-(2,2,2-trifluoroethyl)benzamide, 4-[7-(1-amino-1-methyl-ethyl)imidazo[1,2-a]pyridin-3-yl]-2,6-dimethoxy-N-(2,2,2-trifluoroethyl)benzamide, 4-[7-(1,1-dimethyl-2-oxo-propyl)imidazo[1,2-a]pyridin-3-yl]-2,6-dimethoxy-N-(2,2,2-trifluoroethyl)benzamide, 4-[7-(1-hydroxy-1-methyl-ethyl)imidazo[1,2-a]pyridin-3-yl]-2,6-dimethoxy-N-(2,2,2-trifluoroethyl)benzamide, tert-butyl 3-[3-[3,5-dimethoxy-4-(2,2,2-trifluoroethylcarbamoyl)phenyl]imidazo[1,2-a]pyridin-7-yl]azetidine-1-carboxylate, tert-butyl 3-[3-[4-(cyclopropylcarbamoyl)-3-(difluoromethoxy)-5-methoxy-phenyl]imidazo[1,2-a]pyridin-7-yl]azetidine-1-carboxylate, tert-butyl 4-[3-[4-(cyclopropylcarbamoyl)-3-(difluoromethoxy)-5-methoxy-phenyl]imidazo[1,2-a]pyridin-7-yl]piperidine-1-carboxylate, N-cyclopropyl-2-(difluoromethoxy)-6-methoxy-4-[7-[1-methyl-1-(5-methyl-1,2,4-oxadiazol-3-yl)ethyl]imidazo[1,2-a]pyridin-3-yl]benzamide, 4-[7-(2-hydroxy-1,1-dimethyl-propyl)imidazo[1,2-a]pyridin-3-yl]-2,6-dimethoxy-N-(2,2,2-trifluoroethyl)benzamide, 4-[7-(1-acetylazetidin-3-yl)imidazo[1,2-a]pyridin-3-yl]-N-cyclopropyl-2-(difluoromethoxy)-6-methoxy-benzamide, tert-butyl 3-[3-[4-(cyclopropylcarbamoyl)-3-(difluoromethoxy)-5-methoxy-phenyl]imidazo[1,2-a]pyridin-7-yl]piperidine-1-carboxylate, N-cyclopropyl-2-(difluoromethoxy)-6-methoxy-4-[7-(3-piperidyl)imidazo[1,2-a]pyridin-3-yl]benzamide, N-cyclopropyl-2-(difluoromethoxy)-6-methoxy-4-[7-(4-piperidyl)imidazo[1,2-a]pyridin-3-yl]benzamide, N-cyclopropyl-2-(difluoromethoxy)-6-methoxy-4-[7-(1-methyl-3-piperidyl)imidazo[1,2-a]pyridin-3-yl]benzamide, N-cyclopropyl-2-(difluoromethoxy)-6-methoxy-4-[7-(1-methyl-4-piperidyl)imidazo[1,2-a]pyridin-3-yl]benzamide, 2-[3-[4-(3,3-difluoroazetidine-1-carbonyl)-3-(difluoromethoxy)-5-methoxy-phenyl]imidazo[1,2-a]pyridin-7-yl]-2-methyl-propanenitrile, 4-[7-(1-cyano-1-methyl-ethyl)imidazo[1,2-a]pyridin-3-yl]-N-(2,2-difluoroethyl)-2-(difluoromethoxy)-6-methoxy-benzamide, 4-[7-(1-cyano-1-methyl-ethyl)imidazo[1,2-a]pyridin-3-yl]-2-(difluoromethoxy)-N-(2,2-difluoro-1-methyl-ethyl)-6-methoxy-benzamide, 4-[7-(1-cyano-1-methyl-ethyl)imidazo[1,2-a]pyridin-3-yl]-2-(difluoromethoxy)-N-isobutyl-6-methoxy-benzamide, 4-[7-(1-cyano-1-methyl-ethyl)imidazo[1,2-a]pyridin-3-yl]-2-(difluoromethoxy)-N-(1,1-dioxothietan-3-yl)-6-methoxy-benzamide, 2-[3-[4-(3-cyclopropyl-3-hydroxy-azetidine-1-carbonyl)-3-(difluoromethoxy)-5-methoxy-phenyl]imidazo[1,2-a]pyridin-7-yl]-2-methyl-propanenitrile, 2-[3-[3-(difluoromethoxy)-4-[3-hydroxy-3-(trifluoromethyl)azetidine-1-carbonyl]-5-methoxy-phenyl]imidazo[1,2-a]pyridin-7-yl]-2-methyl-propanenitrile, 2-[3-[3-(difluoromethoxy)-5-methoxy-4-[3-(trifluoromethyl)azetidine-1-carbonyl]phenyl]imidazo[1,2-a]pyridin-7-yl]-2-methyl-propanenitrile, 1-[4-[7-(1-cyano-1-methyl-ethyl)imidazo[1,2-a]pyridin-3-yl]-2-(difluoromethoxy)-6-methoxy-benzoyl]azetidine-3-carbonitrile, 4-[7-(1-cyano-1-methyl-ethyl)imidazo[1,2-a]pyridin-3-yl]-2-(difluoromethoxy)-N-isopropyl-6-methoxy-benzamide, 4-[7-(1-cyano-1-methyl-ethyl)imidazo[1,2-a]pyridin-3-yl]-2-(difluoromethoxy)-N-[(1R,2S)-2-fluorocyclopropyl]-6-methoxy-benzamide, 4-[7-(1-cyano-1-methyl-ethyl)imidazo[1,2-a]pyridin-3-yl]-2-(difluoromethoxy)-N-(1-isopropylcyclopropyl)-6-methoxy-benzamide, 4-[7-(1-cyano-1-methyl-ethyl)imidazo[1,2-a]pyridin-3-yl]-2-(difluoromethoxy)-6-methoxy-N-[1-(methoxymethyl)cyclopropyl]benzamide, 4-[7-(1-cyano-1-methyl-ethyl)imidazo[1,2-a]pyridin-3-yl]-N-(cyclopropylmethyl)-2-(difluoromethoxy)-6-methoxy-N-methyl-benzamide, 4-[7-(1-cyano-1-methyl-ethyl)imidazo[1,2-a]pyridin-3-yl]-2-(difluoromethoxy)-N-(1-ethylcyclopropyl)-6-methoxy-benzamide, 4-[7-(1-cyano-1-methyl-ethyl)imidazo[1,2-a]pyridin-3-yl]-N-cyclopropyl-2-(difluoromethoxy)-6-methoxy-N-methyl-benzamide, 4-[7-(1-cyano-1-methyl-ethyl)imidazo[1,2-a]pyridin-3-yl]-2-(difluoromethoxy)-6-methoxy-N-(tetrahydrofuran-3-ylmethyl)benzamide, 4-[7-(1-cyano-1-methyl-ethyl)imidazo[1,2-a]pyridin-3-yl]-2-(difluoromethoxy)-6-methoxy-N-tetrahydrofuran-3-yl-benzamide, 4-[7-(1-cyano-1-methyl-ethyl)imidazo[1,2-a]pyridin-3-yl]-N-(1-cyclopropyl-2-hydroxy-ethyl)-2-(difluoromethoxy)-6-methoxy-benzamide, 4-[7-(1-cyano-1-methyl-ethyl)imidazo[1,2-a]pyridin-3-yl]-N-(3,3-difluorocyclobutyl)-2-(difluoromethoxy)-6-methoxy-benzamide, 2-[3-[3-(difluoromethoxy)-4-(3-ethynyl-3-hydroxy-azetidine-1-carbonyl)-5-methoxy-phenyl]imidazo[1,2-a]pyridin-7-yl]-2-methyl-propanenitrile, 4-[7-(1-cyano-1-methyl-ethyl)imidazo[1,2-a]pyridin-3-yl]-N-(cyclobutylmethyl)-2-(difluoromethoxy)-6-methoxy-benzamide, N-cyclopropyl-2-(difluoromethoxy)-6-methoxy-4-[7-(1-methylazetidin-3-yl)imidazo[1,2-a]pyridin-3-yl]benzamide, N-[(1S,2S)-2-aminocyclohexyl]-4-[7-(1-cyano-1-methyl-ethyl)imidazo[1,2-a]pyridin-3-yl]-2-(difluoromethoxy)-6-methoxy-benzamide, 4-[7-(2-amino-1,1-dimethyl-ethyl)imidazo[1,2-a]pyridin-3-yl]-N-cyclopropyl-2-(difluoromethoxy)-6-methoxy-benzamide, tert-butyl N-[1-[4-[7-(1-cyano-1-methyl-ethyl)imidazo[1,2-a]pyridin-3-yl]-2-(difluoromethoxy)-6-methoxy-benzoyl]azetidin-3-yl]carbamate, N-cyclopropyl-2-(difluoromethoxy)-6-methoxy-4-(6-tetrahydropyran-4-ylpyrazolo[1,5-a]pyrimidin-3-yl)benzamide, 2-[3-[3-(difluoromethoxy)-4-(3-fluoroazetidine-1-carbonyl)-5-methoxy-phenyl]imidazo[1,2-a]pyridin-7-yl]-2-methyl-propanenitrile, 2-[3-[3-(difluoromethoxy)-4-[3-(hydroxymethyl)azetidine-1-carbonyl]-5-methoxy-phenyl]imidazo[1,2-a]pyridin-7-yl]-2-methyl-propanenitrile, 2-[3-[3-(difluoromethoxy)-5-methoxy-4-(3-methoxyazetidine-1-carbonyl)phenyl]imidazo[1,2-a]pyridin-7-yl]-2-methyl-propanenitrile, 2-[3-[3-(difluoromethoxy)-5-methoxy-4-(6-methyl-2,6-diazaspiro[3.3]heptane-2-carbonyl)phenyl]imidazo[1,2-a]pyridin-7-yl]-2-methyl-propanenitrile, 4-[7-(1-cyano-1-methyl-ethyl)imidazo[1,2-a]pyridin-3-yl]-N-(1-cyclopropyl-2,2,2-trifluoro-ethyl)-2-(difluoromethoxy)-6-methoxy-benzamide, 4-[7-(1-cyano-1-methyl-ethyl)imidazo[1,2-a]pyridin-3-yl]-N-(1-cyclopropylethyl)-2-(difluoromethoxy)-6-methoxy-benzamide, 4-[7-(1-cyano-1-methyl-ethyl)imidazo[1,2-a]pyridin-3-yl]-2-(difluoromethoxy)-6-methoxy-N-(oxetan-3-ylmethyl)benzamide, 2-[3-[4-(3-aminoazetidine-1-carbonyl)-3-(difluoromethoxy)-5-methoxy-phenyl]imidazo[1,2-a]pyridin-7-yl]-2-methyl-propanenitrile, 2-[3-[3-(difluoromethoxy)-5-methoxy-4-(2-methylazetidine-1-carbonyl)phenyl]imidazo[1,2-a]pyridin-7-yl]-2-methyl-propanenitrile, 2-[3-[3-(difluoromethoxy)-4-[2-(hydroxymethyl)azetidine-1-carbonyl]-5-methoxy-phenyl]imidazo[1,2-a]pyridin-7-yl]-2-methyl-propanenitrile, 4-[7-(1-amino-1-methyl-ethyl)imidazo[1,2-a]pyridin-3-yl]-N-cyclopropyl-2-(difluoromethoxy)-6-methoxy-benzamide, 4-[7-(4-cyanotetrahydropyran-4-yl)imidazo[1,2-a]pyridin-3-yl]-2,6-dimethoxy-N-(2,2,2-trifluoroethyl)benzamide, N-cyclopropyl-2-(difluoromethoxy)-6-methoxy-4-(7-tetrahydropyran-4-ylimidazo[1,2-a]pyridin-3-yl)benzamide, N-cyclopropyl-2-(difluoromethoxy)-6-methoxy-4-(7-tetrahydropyran-4-ylimidazo[1,2-c]pyrimidin-3-yl)benzamide, 4-[7-(3-cyanoazetidin-3-yl)imidazo[1,2-a]pyridin-3-yl]-N-cyclopropyl-2-(difluoromethoxy)-6-methoxy-benzamide, 2-[3-(7-methoxy-1-oxo-isoindolin-5-yl)imidazo[1,2-a]pyridin-7-yl]-2-methyl-propanenitrile, N-cyclopropyl-2-(difluoromethoxy)-6-methoxy-4-(6-tetrahydropyran-4-ylpyrazolo[1,5-a]pyridin-3-yl)benzamide, methyl 1-[3-[4-(cyclopropylcarbamoyl)-3-(difluoromethoxy)-5-methoxy-phenyl]imidazo[1,2-a]pyridin-7-yl]cyclopropanecarboxylate, 1-[3-[4-(cyclopropylcarbamoyl)-3-(difluoromethoxy)-5-methoxy-phenyl]imidazo[1,2-a]pyridin-7-yl]cyclopropanecarboxylic acid, N-cyclopropyl-2-(difluoromethoxy)-4-[7-[1-(hydroxymethyl)cyclopropyl]imidazo[1,2-a]pyridin-3-yl]-6-methoxy-benzamide, 4-[7-(4-cyanotetrahydropyran-4-yl)imidazo[1,2-a]pyridin-3-yl]-N-cyclopropyl-2-(difluoromethoxy)-6-methoxy-benzamide, 4-[7-(3-cyanooxetan-3-yl)imidazo[1,2-a]pyridin-3-yl]-N-cyclopropyl-2-(difluoromethoxy)-6-methoxy-benzamide, N-cyclopropyl-2-(difluoromethoxy)-6-methoxy-4-[7-(1-methoxy-1-methyl-ethyl)imidazo[1,2-c]pyrimidin-3-yl]benzamide, N-cyclopropyl-2-(difluoromethoxy)-4-[7-(1-hydroxy-1-methyl-ethyl)imidazo[1,2-c]pyrimidin-3-yl]-6-methoxy-benzamide, N-cyclopropyl-2-(difluoromethoxy)-6-methoxy-4-[7-(1-methoxy-1-methyl-ethyl)imidazo[1,2-a]pyridin-3-yl]benzamide, 4-[7-(3-cyano-1-methyl-azetidin-3-yl)imidazo[1,2-a]pyridin-3-yl]-N-cyclopropyl-2-(difluoromethoxy)-6-methoxy-benzamide, 4-[7-(1-acetyl-3-cyano-azetidin-3-yl)imidazo[1,2-a]pyridin-3-yl]-N-cyclopropyl-2-(difluoromethoxy)-6-methoxy-benzamide, 4-[7-(3-cyanotetrahydrofuran-3-yl)imidazo[1,2-a]pyridin-3-yl]-N-cyclopropyl-2-(difluoromethoxy)-6-methoxy-benzamide, N-cyclopropyl-2-(difluoromethoxy)-4-[7-(1-ethyl-1-hydroxy-propyl)imidazo[1,2-a]pyridin-3-yl]-6-methoxy-benzamide, 5-[7-(3-cyanooxetan-3-yl)imidazo[1,2-a]pyridin-3-yl]-3-methoxy-N-(2,2,2-trifluoroethyl)pyridine-2-carboxamide, N-cyclopropyl-2-(difluoromethoxy)-4-[7-(1-ethyl-1-methoxy-propyl)imidazo[1,2-a]pyridin-3-yl]-6-methoxy-benzamide, 5-[7-(1-cyano-1-methyl-ethyl)imidazo[1,2-a]pyridin-3-yl]-3-methoxy-N-(2,2,2-trifluoroethyl)pyridine-2-carboxamide, N-cyclopropyl-2-(difluoromethoxy)-4-[7-(1-ethoxy-1-methyl-ethyl)imidazo[1,2-a]pyridin-3-yl]-6-methoxy-benzamide, N-cyclopropyl-2-(difluoromethoxy)-6-methoxy-4-[7-(2,2,2-trifluoro-1-hydroxy-1-methyl-ethyl)imidazo[1,2-a]pyridin-3-yl]benzamide, 4-[7-(3-cyanooxetan-3-yl)imidazo[1,2-a]pyridin-3-yl]-2-(difluoromethoxy)-N-[(1R,2S)-2-fluorocyclopropyl]-6-methoxy-benzamide, methyl 2-[3-[4-(cyclopropylcarbamoyl)-3-(difluoromethoxy)-5-methoxy-phenyl]imidazo[1,2-a]pyridin-7-yl]-2,2-difluoro-acetate, 2-[3-[4-(cyclopropylcarbamoyl)-3-(difluoromethoxy)-5-methoxy-phenyl]imidazo[1,2-a]pyridin-7-yl]-2,2-difluoro-acetic acid, N-cyclopropyl-2-(difluoromethoxy)-4-[7-(1-fluoro-1-methyl-ethyl)imidazo[1,2-a]pyridin-3-yl]-6-methoxy-benzamide, N-cyclopropyl-2-(difluoromethoxy)-4-[7-(1-hydroxy-1-tetrahydropyran-4-yl-ethyl)imidazo[1,2-a]pyridin-3-yl]-6-methoxy-benzamide, N-cyclopropyl-2-(difluoromethoxy)-4-[7-(1-hydroxy-1,2-dimethyl-propyl)imidazo[1,2-a]pyridin-3-yl]-6-methoxy-benzamide, N-cyclopropyl-4-[7-(1,1-difluoro-2-hydroxy-ethyl)imidazo[1,2-a]pyridin-3-yl]-2-(difluoromethoxy)-6-methoxy-benzamide, N-cyclopropyl-2-(difluoromethoxy)-4-[7-(1-hydroxy-1-methyl-propyl)imidazo[1,2-a]pyridin-3-yl]-6-methoxy-benzamide, N-cyclopropyl-4-[7-(1-cyclopropyl-1-hydroxy-ethyl)imidazo[1,2-a]pyridin-3-yl]-2-(difluoromethoxy)-6-methoxy-benzamide, N-cyclopropyl-2-(difluoromethoxy)-6-methoxy-4-[7-(1-morpholinoethyl)imidazo[1,2-a]pyridin-3-yl]benzamide, N-cyclopropyl-2-(difluoromethoxy)-4-[7-(1-hydroxyethyl)imidazo[1,2-a]pyridin-3-yl]-6-methoxy-benzamide, N-cyclopropyl-2-(difluoromethoxy)-6-methoxy-4-[7-[1-(morpholine-4-carbonyl)cyclopropyl]imidazo[1,2-a]pyridin-3-yl]benzamide, N-cyclopropyl-2-(difluoromethoxy)-6-methoxy-4-[7-[1-(2-methoxyethylcarbamoyl)cyclopropyl]imidazo[1,2-a]pyridin-3-yl]benzamide, N-cyclopropyl-4-[7-[1-(diethylcarbamoyl)cyclopropyl]imidazo[1,2-a]pyridin-3-yl]-2-(difluoromethoxy)-6-methoxy-benzamide, N-cyclopropyl-2-(difluoromethoxy)-4-[7-[1-(3-hydroxyazetidine-1-carbonyl)cyclopropyl]imidazo[1,2-a]pyridin-3-yl]-6-methoxy-benzamide, N-cyclopropyl-2-(difluoromethoxy)-6-methoxy-4-[7-[1-(morpholinomethyl)cyclopropyl]imidazo[1,2-a]pyridin-3-yl]benzamide, N-cyclopropyl-2-(difluoromethoxy)-6-methoxy-4-[7-[1-(1-piperidyl)ethyl]imidazo[1,2-a]pyridin-3-yl]benzamide, N-cyclopropyl-2-(difluoromethoxy)-4-[7-[1-(2-hydroxyethylcarbamoyl)cyclopropyl]imidazo[1,2-a]pyridin-3-yl]-6-methoxy-benzamide, N-cyclopropyl-4-[7-[1-(diethylamino)ethyl]imidazo[1,2-a]pyridin-3-yl]-2-(difluoromethoxy)-6-methoxy-benzamide, N-cyclopropyl-2-(difluoromethoxy)-4-[7-[1-(isopropylamino)ethyl]imidazo[1,2-a]pyridin-3-yl]-6-methoxy-benzamide, N-cyclopropyl-2-(difluoromethoxy)-4-[7-(2-hydroxy-1,1-dimethyl-ethyl)imidazo[1,2-a]pyridin-3-yl]-6-methoxy-benzamide, N-cyclopropyl-2-(difluoromethoxy)-4-[7-[1-[(isopropylamino)methyl]cyclopropyl]imidazo[1,2-a]pyridin-3-yl]-6-methoxy-benzamide, N-cyclopropyl-2-(difluoromethoxy)-6-methoxy-4-[7-[1-(2-oxa-6-azaspiro[3.3]heptan-6-yl)ethyl]imidazo[1,2-a]pyridin-3-yl]benzamide, N-cyclopropyl-2-(difluoromethoxy)-6-methoxy-4-[7-(1-pyrrolidin-1-ylethyl)imidazo[1,2-a]pyridin-3-yl]benzamide, N-cyclopropyl-2-(difluoromethoxy)-4-[7-[1-[2-hydroxyethyl(methyl)amino]ethyl]imidazo[1,2-a]pyridin-3-yl]-6-methoxy-benzamide, N-cyclopropyl-2-(difluoromethoxy)-4-[7-[1-(3-hydroxyazetidin-1-yl)ethyl]imidazo[1,2-a]pyridin-3-yl]-6-methoxy-benzamide, N-cyclopropyl-4-[7-[1-(3,3-difluoroazetidin-1-yl)ethyl]imidazo[1,2-a]pyridin-3-yl]-2-(difluoromethoxy)-6-methoxy-benzamide, N-cyclopropyl-2-(difluoromethoxy)-4-[7-[1-[(2S)-2-(hydroxymethyl)morpholin-4-yl]ethyl]imidazo[1,2-a]pyridin-3-yl]-6-methoxy-benzamide, tert-butyl 3-[3-[4-(cyclopropylcarbamoyl)-3-(difluoromethoxy)-5-methoxy-phenyl]-6-fluoro-imidazo[1,2-a]pyridin-7-yl]azetidine-1-carboxylate, 4-(7-cyclobutylimidazo[1,2-a]pyridin-3-yl)-N-cyclopropyl-2-(difluoromethoxy)-6-methoxy-benzamide, N-cyclopropyl-2-(difluoromethoxy)-4-[7-(1,1-dimethyl-2-morpholino-ethyl)imidazo[1,2-a]pyridin-3-yl]-6-methoxy-benzamide, N-cyclopropyl-2-(difluoromethoxy)-4-[7-(1,1-dimethyl-2-pyrrolidin-1-yl-ethyl)imidazo[1,2-a]pyridin-3-yl]-6-methoxy-benzamide, N-cyclopropyl-2-(difluoromethoxy)-4-(6-fluoro-7-tetrahydropyran-4-yl-imidazo[1,2-a]pyridin-3-yl)-6-methoxy-benzamide, N-cyclopropyl-2-(difluoromethoxy)-6-methoxy-4-(6-methoxy-7-tetrahydropyran-4-yl-imidazo[1,2-a]pyridin-3-yl)benzamide, 4-(7-cyclobutyl-6-fluoro-imidazo[1,2-a]pyridin-3-yl)-N-cyclopropyl-2-(difluoromethoxy)-6-methoxy-benzamide, 4-[7-(1-acetylazetidin-3-yl)-6-fluoro-imidazo[1,2-a]pyridin-3-yl]-N-cyclopropyl-2-(difluoromethoxy)-6-methoxy-benzamide, N-cyclopropyl-2-(difluoromethoxy)-4-[7-(4-hydroxytetrahydropyran-4-yl)imidazo[1,2-a]pyridin-3-yl]-6-methoxy-benzamide, N-cyclopropyl-2-(difluoromethoxy)-6-methoxy-4-[7-(1-methylpyrrolidin-2-yl)imidazo[1,2-a]pyridin-3-yl]benzamide, N-cyclopropyl-2-(difluoromethoxy)-4-[7-(2-hydroxy-1,1-dimethyl-propyl)imidazo[1,2-a]pyridin-3-yl]-6-methoxy-benzamide, N-cyclopropyl-2-(difluoromethoxy)-4-[7-(1-hydroxycyclobutyl)imidazo[1,2-a]pyridin-3-yl]-6-methoxy-benzamide, N-cyclopropyl-2-(difluoromethoxy)-6-methoxy-4-[7-(oxetan-3-yl)imidazo[1,2-a]pyridin-3-yl]benzamide, 4-[7-(2-cyano-1-hydroxy-ethyl)imidazo[1,2-a]pyridin-3-yl]-N-cyclopropyl-2-(difluoromethoxy)-6-methoxy-benzamide, 4-[7-(1-cyano-2-hydroxy-1-methyl-ethyl)imidazo[1,2-a]pyridin-3-yl]-N-cyclopropyl-2-(difluoromethoxy)-6-methoxy-benzamide, N-cyclopropyl-2-(difluoromethoxy)-4-[7-(3-hydroxyoxetan-3-yl)imidazo[1,2-a]pyridin-3-yl]-6-methoxy-benzamide, N-cyclopropyl-2-(difluoromethoxy)-4-[7-(1-hydroxy-1-methyl-2-morpholino-ethyl)imidazo[1,2-a]pyridin-3-yl]-6-methoxy-benzamide, 4-[7-(2-cyano-1-hydroxy-1-methyl-ethyl)imidazo[1,2-a]pyridin-3-yl]-N-cyclopropyl-2-(difluoromethoxy)-6-methoxy-benzamide, tert-butyl 2-[3-[4-(cyclopropylcarbamoyl)-3-(difluoromethoxy)-5-methoxy-phenyl]imidazo[1,2-a]pyridin-7-yl]pyrrolidine-1-carboxylate,
N-cyclopropyl-2-(difluoromethoxy)-4-[7-(1-hydroxy-2-imidazol-1-yl-1-methyl-ethyl)imidazo[1,2-a]pyridin-3-yl]-6-methoxy-benzamide,
N-cyclopropyl-2-(difluoromethoxy)-4-[7-(1-hydroxy-2-methoxy-1-methyl-ethyl)imidazo[1,2-a]pyridin-3-yl]-6-methoxy-benzamide,
N-cyclopropyl-2-(difluoromethoxy)-4-[6-(2-hydroxyethoxy)-7-tetrahydropyran-4-yl-imidazo[1,2-a]pyridin-3-yl]-6-methoxy-benzamide,
methyl 2-cyano-2-[3-[4-(cyclopropylcarbamoyl)-3-(difluoromethoxy)-5-methoxy-phenyl]imidazo[1,2-a]pyridin-7-yl]propanoate,
N-cyclopropyl-2-(difluoromethoxy)-4-[7-[1-hydroxy-1-methyl-2-(1-piperidyl)ethyl]imidazo[1,2-a]pyridin-3-yl]-6-methoxy-benzamide,
tert-butyl 3-[3-[4-(cyclopropylcarbamoyl)-3-(difluoromethoxy)-5-methoxy-phenyl]imidazo[1,2-a]pyridin-7-yl]morpholine-4-carboxylate,
N-cyclopropyl-2-(difluoromethoxy)-6-methoxy-4-(7-morpholin-3-ylimidazo[1,2-a]pyridin-3-yl)benzamide,
N-cyclopropyl-2-(difluoromethoxy)-6-methoxy-4-(7-pyrrolidin-2-ylimidazo[1,2-a]pyridin-3-yl)benzamide,
N-cyclopropyl-4-[7-[2-(3,3-difluoroazetidin-1-yl)-1-hydroxy-1-methyl-ethyl]imidazo[1,2-a]pyridin-3-yl]-2-(difluoromethoxy)-6-methoxy-benzamide,
N-cyclopropyl-2-(difluoromethoxy)-4-[7-(1-hydroxy-1-methyl-2-pyrazol-1-yl-ethyl)imidazo[1,2-a]pyridin-3-yl]-6-methoxy-benzamide,
N-cyclopropyl-2-(difluoromethoxy)-6-methoxy-4-[7-(4-methylmorpholin-3-yl)imidazo[1,2-a]pyridin-3-yl]benzamide,
N-cyclopropyl-2-(difluoromethoxy)-4-[7-[1-hydroxy-1-methyl-2-(1,2,4-triazol-1-yl)ethyl]imidazo[1,2-a]pyridin-3-yl]-6-methoxy-benzamide,
4-[7-(1-cyano-2-methoxy-1-methyl-ethyl)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-[1-(2-methoxyethyl)pyrrolidin-2-yl]imidazo[1,2-a]pyridin-3-yl]benzamide,
N-cyclopropyl-2-(difluoromethoxy)-4-[7-(1-isopropylpyrrolidin-2-yl)imidazo[1,2-a]pyridin-3-yl]-6-methoxy-benzamide,
4-[7-(1-acetylpyrrolidin-2-yl)imidazo[1,2-a]pyridin-3-yl]-N-cyclopropyl-2-(difluoromethoxy)-6-methoxy-benzamide,
4-[7-[cyclobutyl(hydroxy)methyl]imidazo[1,2-a]pyridin-3-yl]-N-cyclopropyl-2-(difluoromethoxy)-6-methoxy-benzamide,
4-[7-(1-cyano-1-methyl-ethyl)-6-methoxy-imidazo[1,2-a]pyridin-3-yl]-N-cyclopropyl-2-(difluoromethoxy)-6-methoxy-benzamide,
N-cyclopropyl-2-(difluoromethoxy)-4-[7-(2-hydroxy-1,1-dimethyl-butyl)imidazo[1,2-a]pyridin-3-yl]-6-methoxy-benzamide,
N-cyclopropyl-2-(difluoromethoxy)-4-[7-(2-hydroxy-1,1,3-trimethyl-butyl)imidazo[1,2-a]pyridin-3-yl]-6-methoxy-benzamide,
4-[7-(azetidin-2-yl)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(1-methylazetidin-2-yl)imidazo[1,2-a]pyridin-3-yl]benzamide,
2-(difluoromethoxy)-N-[(1R,2S)-2-fluorocyclopropyl]-4-[7-(1-hydroxycyclobutyl)imidazo[1,2-a]pyridin-3-yl]-6-methoxy-benzamide,
2-(difluoromethoxy)-N-[(1R,2S)-2-fluorocyclopropyl]-6-methoxy-4-[7-(oxetan-3-yl)imidazo[1,2-a]pyridin-3-yl]benzamide,
N-cyclopropyl-2-(difluoromethoxy)-4-[7-(3-fluorooxetan-3-yl)imidazo[1,2-a]pyridin-3-yl]-6-methoxy-benzamide,
4-[6-(1-cyano-1-methyl-ethyl)pyrazolo[1,5-a]pyridin-3-yl]-N-cyclopropyl-2-(difluoromethoxy)-6-methoxy-benzamide,
N-cyclopropyl-2-(difluoromethoxy)-4-[7-[1-hydroxy-2-[2-hydroxyethyl(methyl)amino]-1-methyl-ethyl]imidazo[1,2-a]pyridin-3-yl]-6-methoxy-benzamide,
N-cyclopropyl-2-(difluoromethoxy)-4-[7-(2,4-dimethylmorpholin-2-yl)imidazo[1,2-a]pyridin-3-yl]-6-methoxy-benzamide,
2-(difluoromethoxy)-N-[(1R,2S)-2-fluorocyclopropyl]-4-[7-(1-hydroxy-1-methyl-ethyl)imidazo[1,2-a]pyridin-3-yl]-6-methoxy-benzamide,
N-cyclopropyl-2-(difluoromethoxy)-6-methoxy-4-[7-(3-methoxyoxetan-3-yl)imidazo[1,2-a]pyridin-3-yl]benzamide,
N-cyclopropyl-2-(difluoromethoxy)-4-[7-(3-hydroxytetrahydrofuran-3-yl)imidazo[1,2-a]pyridin-3-yl]-6-methoxy-benzamide,
2-(difluoromethoxy)-4-[7-(2,4-dimethylmorpholin-2-yl)imidazo[1,2-a]pyridin-3-yl]-6-methoxy-N-(2,2,2-trifluoroethyl)benzamide,
N-cyclopropyl-2-(difluoromethoxy)-6-methoxy-4-[6-methoxy-7-(oxetan-3-yl)imidazo[1,2-a]pyridin-3-yl]benzamide,
N-cyclopropyl-2-(difluoromethoxy)-6-methoxy-4-[6-(oxetan-3-yl)pyrazolo[1,5-a]pyridin-3-yl]benzamide,
4-[7-(3-chlorooxetan-3-yl)imidazo[1,2-a]pyridin-3-yl]-N-cyclopropyl-2-(difluoromethoxy)-6-methoxy-benzamide,
2-(difluoromethoxy)-N-[(1R,2S)-2-fluorocyclopropyl]-6-methoxy-4-[6-(oxetan-3-yl)pyrazolo[1,5-a]pyridin-3-yl]benzamide,
4-[6-(1-cyano-1-methyl-ethyl)pyrazolo[1,5-a]pyridin-3-yl]-2-(difluoromethoxy)-N-[(1R,2S)-2-fluorocyclopropyl]-6-methoxy-benzamide,
N-cyclopropyl-2-(difluoromethoxy)-6-methoxy-4-[7-(2-methyl-1,4-dioxan-2-yl)imidazo[1,2-a]pyridin-3-yl]benzamide,
4-[7-(1-cyano-1-methyl-ethyl)-6-(2-hydroxyethoxy)imidazo[1,2-a]pyridin-3-yl]-N-cyclopropyl-2-(difluoromethoxy)-6-methoxy-benzamide,
N-cyclopropyl-2-(difluoromethoxy)-6-methoxy-4-[7-(3-morpholinooxetan-3-yl)imidazo[1,2-a]pyridin-3-yl]benzamide,
2-(difluoromethoxy)-N-[(1R,2S)-2-fluorocyclopropyl]-4-[7-(3-hydroxyoxetan-3-yl)imidazo[1,2-a]pyridin-3-yl]-6-methoxy-benzamide,
2-(difluoromethoxy)-N-[(1R,2S)-2-fluorocyclopropyl]-4-[7-(3-fluorooxetan-3-yl)imidazo[1,2-a]pyridin-3-yl]-6-methoxy-benzamide,
4-[7-(1-cyano-1-methyl-ethyl)imidazo[1,2-a]pyridin-3-yl]-2-(difluoromethoxy)-N-(2-fluorocyclopropyl)-6-methoxy-benzamide,
N-cyclopropyl-2-(difluoromethoxy)-6-methoxy-4-[7-(1-methyl-1-morpholino-ethyl)imidazo[1,2-a]pyridin-3-yl]benzamide,
2-(difluoromethoxy)-N-[(1R,2S)-2-fluorocyclopropyl]-4-[6-(1-hydroxy-1-methyl-ethyl)pyrazolo[1,5-a]pyridin-3-yl]-6-methoxy-benzamide, 4-[7-(1-cyano-1-methyl-ethyl)imidazo[1,2-b]pyridazin-3-yl]-2-(difluoromethoxy)-N-[(1R,2S)-2-fluorocyclopropyl]-6-methoxy-benzamide, N-cyclopropyl-2-(difluoromethoxy)-6-methoxy-4-[7-[1-methyl-1-(oxetan-2-yl)ethyl]imidazo[1,2-a]pyridin-3-yl]benzamide, 4-[7-[1-cyano-2,2,2-trideuterio-1-(trideuteriomethyl)ethyl]imidazo[1,2-a]pyridin-3-yl]-N-cyclopropyl-2-(difluoromethoxy)-6-methoxy-benzamide, 4-[6-(1-cyano-1-methyl-ethyl)pyrazolo[1,5-a]pyrimidin-3-yl]-2-(difluoromethoxy)-N-[(1R,2S)-2-fluorocyclopropyl]-6-methoxy-benzamide, N-cyclopropyl-2-(difluoromethoxy)-4-[6-(1,4-dioxan-2-yl)pyrazolo[1,5-a]pyridin-3-yl]-6-methoxy-benzamide, 4-[6-(1-cyano-1-methyl-ethyl)pyrazolo[1,5-a]pyridin-3-yl]-2-(difluoromethoxy)-N-(2-fluorocyclopropyl)-6-methoxy-benzamide, 4-[6-(1-cyano-1-methyl-ethyl)pyrazolo[1,5-a]pyridin-3-yl]-2-(difluoromethoxy)-N-[(1S,2R)-2-fluorocyclopropyl]-6-methoxy-benzamide, 4-[6-(1-cyanocyclopropyl)pyrazolo[1,5-a]pyridin-3-yl]-2-(difluoromethoxy)-N-[(1R,2S)-2-fluorocyclopropyl]-6-methoxy-benzamide, N-cyclopropyl-2-(difluoromethoxy)-4-[6-(2-hydroxy-1,1-dimethyl-ethyl)pyrazolo[1,5-a]pyridin-3-yl]-6-methoxy-benzamide, 4-[6-(4-cyanotetrahydropyran-4-yl)pyrazolo[1,5-a]pyridin-3-yl]-N-cyclopropyl-2-(difluoromethoxy)-6-methoxy-benzamide, N-cyclopropyl-2-(difluoromethoxy)-6-methoxy-4-[6-(2-methoxy-1,1-dimethyl-ethyl)pyrazolo[1,5-a]pyridin-3-yl]benzamide, N-cyclopropyl-2-(difluoromethoxy)-4-[6-[1-(2-hydroxyethoxy)-1-methyl-ethyl]pyrazolo[1,5-a]pyridin-3-yl]-6-methoxy-benzamide, 2-(difluoromethoxy)-4-[6-(1,4-dioxan-2-yl)pyrazolo[1,5-a]pyridin-3-yl]-N-[(1R,2S)-2-fluorocyclopropyl]-6-methoxy-benzamide, 2-(difluoromethoxy)-N-[(1R,2S)-2-fluorocyclopropyl]-4-[6-(2-hydroxy-1,1-dimethyl-ethyl)pyrazolo[1,5-a]pyridin-3-yl]-6-methoxy-benzamide, 4-[6-(4-cyanotetrahydropyran-4-yl)pyrazolo[1,5-a]pyridin-3-yl]-2-(difluoromethoxy)-N-[(1R,2S)-2-fluorocyclopropyl]-6-methoxy-benzamide, 4-[6-(2-amino-1,1-dimethyl-2-oxo-ethyl)pyrazolo[1,5-a]pyridin-3-yl]-N-cyclopropyl-2-(difluoromethoxy)-6-methoxy-benzamide, 4-[6-(1-cyano-1-methyl-ethyl)pyrazolo[1,5-a]pyridin-3-yl]-N-[(1R,2S)-2-fluorocyclopropyl]-2,6-dimethoxy-benzamide, 2-(difluoromethoxy)-N-[(1R,2S)-2-fluorocyclopropyl]-6-methoxy-4-[6-(1-methyl-1-methylsulfonyl-ethyl)pyrazolo[1,5-a]pyridin-3-yl]benzamide, N-cyclopropyl-2-(difluoromethoxy)-6-methoxy-4-[6-[1-methyl-1-(5-methyl-1,2,4-oxadiazol-3-yl)ethyl]pyrazolo[1,5-a]pyridin-3-yl]benzamide, N-cyclopropyl-2-(difluoromethoxy)-6-methoxy-4-[6-[1-methyl-1-(3-methyl-1,2,4-oxadiazol-5-yl)ethyl]pyrazolo[1,5-a]pyridin-3-yl]benzamide, N-cyclopropyl-2-(difluoromethoxy)-4-[6-[2-(ethylamino)-1,1-dimethyl-2-oxo-ethyl]pyrazolo[1,5-a]pyridin-3-yl]-6-methoxy-benzamide, and 4-[6-(1-cyanocyclobutyl)pyrazolo[1,5-a]pyridin-3-yl]-2-(difluoromethoxy)-N-[(1R,2S)-2-fluorocyclopropyl]-6-methoxy-benzamide, 2-(difluoromethoxy)-4-[6-[2-[2-(dimethylamino)-2-oxo-ethoxy]-1,1-dimethyl-ethyl]pyrazolo[1,5-a]pyridin-3-yl]-N-[(1R,2S)-2-fluorocyclopropyl]-6-methoxy-benzamide, 4-[6-(1-cyano-1-methyl-ethyl)pyrazolo[1,5-a]pyridin-3-yl]-N-cyclopropyl-2-fluoro-6-methoxy-benzamide, 2-(difluoromethoxy)-4-[6-[1,1-dimethyl-2-[2-(methylamino)-2-oxo-ethoxy]ethyl]pyrazolo[1,5-a]pyridin-3-yl]-N-[(1R,2S)-2-fluorocyclopropyl]-6-methoxy-benzamide, 4-[6-(1-carbamoylcyclobutyl)pyrazolo[1,5-a]pyridin-3-yl]-2-(difluoromethoxy)-N-[(1R,2S)-2-fluorocyclopropyl]-6-methoxy-benzamide, 2-(difluoromethoxy)-N-[(1R,2S)-2-fluorocyclopropyl]-6-methoxy-4-[6-[1-methyl-1-(2-morpholinoethoxy)ethyl]pyrazolo[1,5-a]pyridin-3-yl]benzamide, 4-[6-(1-amino-1-methyl-ethyl)pyrazolo[1,5-a]pyridin-3-yl]-2-(difluoromethoxy)-N-[(1R,2S)-2-fluorocyclopropyl]-6-methoxy-benzamide, 4-[6-(1-cyano-1-methyl-ethyl)pyrazolo[1,5-a]pyridin-3-yl]-N-cyclopropyl-2,6-dimethoxy-benzamide, 4-[6-(1-cyano-1-methyl-ethyl)pyrazolo[1,5-a]pyridin-3-yl]-N-cyclopropyl-2-methoxy-6-(2-methoxyethoxy)benzamide, 4-[6-(1-aminocyclobutyl)pyrazolo[1,5-a]pyridin-3-yl]-2-(difluoromethoxy)-N-[(1R,2S)-2-fluorocyclopropyl]-6-methoxy-benzamide, 2-(difluoromethoxy)-4-[6-[1,1-dimethyl-2-(oxetan-3-ylmethoxy)ethyl]pyrazolo[1,5-a]pyridin-3-yl]-N-[(1R,2S)-2-fluorocyclopropyl]-6-methoxy-benzamide, 4-[6-(1-cyano-1-methyl-ethyl)pyrazolo[1,5-a]pyridin-3-yl]-N-cyclopropyl-2-(2-hydroxyethoxy)-6-methoxy-benzamide, butyl N-[1-[3-[3-(difluoromethoxy)-4-[[(1R,2S)-2-fluorocyclopropyl]carbamoyl]-5-methoxy-phenyl]pyrazolo[1,5-a]pyridin-6-yl]-1-methyl-ethyl]carbamate, 2-(difluoromethoxy)-4-[6-[1,1-dimethyl-2-(oxetan-3-yloxy)ethyl]pyrazolo[1,5-a]pyridin-3-yl]-N-[(1R,2S)-2-fluorocyclopropyl]-6-methoxy-benzamide, 2-(difluoromethoxy)-N-[(1R,2S)-2-fluorocyclopropyl]-4-[6-(1-hydroxycyclobutyl)pyrazolo[1,5-a]pyridin-3-yl]-6-methoxy-benzamide,

[2-[3-[3-(difluoromethoxy)-4-[[(1R,2S)-2-fluorocyclopropyl]carbamoyl]-5-methoxy-phenyl]pyrazolo[1,5-a]pyridin-6-yl]-2-methyl-propyl]methanesulfonate, 2-(difluoromethoxy)-N-[(1R,2S)-2-fluorocyclopropyl]-4-[6-[1-(2-hydroxyethylamino)-1-methyl-ethyl]pyrazolo[1,5-a]pyridin-3-yl]-6-methoxy-benzamide, 2-(difluoromethoxy)-4-[6-(1,1-dimethyl-2-morpholino-ethyl)pyrazolo[1,5-a]pyridin-3-yl]-N-[(1R,2S)-2-fluorocyclopropyl]-6-methoxy-benzamide, 4-[6-[1-(cyanomethylamino)cyclobutyl]pyrazolo[1,5-a]pyridin-3-yl]-2-(difluoromethoxy)-N-[(1R,2S)-2-fluorocyclopropyl]-6-methoxy-benzamide, 4-[6-[1-(2,2-difluoroethylamino)cyclobutyl]pyrazolo[1,5-a]pyridin-3-yl]-2-(difluoromethoxy)-N-[(1R,2S)-2-fluorocyclopropyl]-6-methoxy-benzamide, methyl N-[1-[3-[3-(difluoromethoxy)-4-[[(1R,2S)-2-fluorocyclopropyl]carbamoyl]-5-methoxy-phenyl]pyrazolo[1,5-a]pyridin-6-yl]cyclobutyl]carbamate, 2-(difluoromethoxy)-N-[(1R,2S)-2-fluorocyclopropyl]-6-methoxy-4-[6-[1-(methylcarbamoyl)cyclobutyl]pyrazolo[1,5-a]pyridin-3-yl]benzamide, and 2-(difluoromethoxy)-N-[(1R,2S)-2-fluorocyclopropyl]-6-methoxy-4-[6-[1-(morpholine-4-carbonyl)cyclobutyl]pyrazolo[1,5-a]pyridin-3-yl]benzamide.

In one embodiment, the compound of the invention is according to Formula I, wherein the compound is selected from: 4-[6-[1-cyano-2,2,2-trideuterio-1-(trideuteriomethyl)

ethyl]pyrazolo[1,5-a]pyridin-3-yl]-2-(difluoromethoxy)-N-[(1R,2S)-2-fluorocyclopropyl]-6-methoxy-benzamide, and 4-[6-[2-(diethylamino)-1,1-dimethyl-ethyl]pyrazolo[1,5-a]pyridin-3-yl]-2-(difluoromethoxy)-N-[(1R,2S)-2-fluorocyclopropyl]-6-methoxy-benzamide.

In one embodiment, the compound of the invention is according to Formula I, wherein the compound is 4-[6-(1-cyano-1-methyl-ethyl)pyrazolo[1,5-a]pyridin-3-yl]-2-(difluoromethoxy)-N-[(1R,2S)-2-fluorocyclopropyl]-6-methoxy-benzamide.

In one embodiment, the compound of the invention is according to Formula I, wherein the compound is not 4-[6-(1-cyano-1-methyl-ethyl)pyrazolo[1,5-a]pyridin-3-yl]-2-(difluoromethoxy)-N-[(1R,2S)-2-fluorocyclopropyl]-6-methoxy-benzamide.

In one embodiment, the compound of the invention is according to Formula I, wherein the compound is 4-[7-(1-cyano-1-methyl-ethyl)imidazo[1,2-a]pyridin-3-yl]-N-cyclopropyl-2-(difluoromethoxy)-6-methoxy-benzamide.

In one embodiment, the compound of the invention is according to Formula I, wherein the compound is not 4-[7-(1-cyano-1-methyl-ethyl)imidazo[1,2-a]pyridin-3-yl]-N-cyclopropyl-2-(difluoromethoxy)-6-methoxy-benzamide.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the C1 to C8 alkyl, C2-C8 alkenyl, aryl, C7-C12 substituted aryl, and C7-C12 arylalkyl esters of the compounds of the invention.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration or stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pennsylvania, which is incorporated herein by reference.

A compound of the invention can also be administered in sustained release forms or from sustained release drug delivery systems. A description of representative sustained release materials can be found in Remington's Pharmaceutical Sciences. (Remington 1985)

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine.

In one embodiment, the present invention provides compounds of the invention or pharmaceutical compositions comprising a compound of the invention, for use in the prophylaxis and/or treatment of inflammatory diseases. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In another embodiment, the present invention provides the use of compounds of the invention or pharmaceutical compositions comprising a compound of the invention in the manufacture of a medicament for the prophylaxis and/or treatment of inflammatory diseases. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In additional method of treatment aspects, this invention provides methods of prophylaxis and/or treatment of a mammal afflicted with inflammatory diseases, which methods comprise the administration of an effective amount of a compound of the invention or one or more of the pharmaceutical compositions herein described for the treatment or prophylaxis of said condition. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In one embodiment, the present invention provides pharmaceutical compositions comprising a compound of the invention, and another therapeutic agent. In a particular embodiment, the other therapeutic agent is a inflammatory diseases treatment agent. In particular, the term inflammatory diseases refers to rheumatoid arthritis, osteoarthritis, allergic airway disease (e.g. asthma), chronic obstructive pulmonary disease (COPD) and inflammatory bowel diseases (e.g. Crohn's disease, ulcerative colitis). More particularly, the term refers to rheumatoid arthritis, chronic obstructive pulmonary disease (COPD) and inflammatory bowel diseases (e.g. Crohn's disease, ulcerative colitis).

In one embodiment, the present invention provides compounds of the invention or pharmaceutical compositions comprising a compound of the invention, for use in the prophylaxis and/or treatment of autoinflammatory diseases. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In another embodiment, the present invention provides the use of compounds of the invention or pharmaceutical compositions comprising a compound of the invention in the manufacture of a medicament for the prophylaxis and/or treatment of autoinflammatory diseases. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In additional method of treatment aspects, this invention provides methods of prophylaxis and/or treatment of a mammal afflicted with autoinflammatory diseases, which methods comprise the administration of an effective amount of a compound of the invention or one or more of the pharmaceutical compositions herein described for the treatment or prophylaxis of said condition. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In one embodiment, the present invention provides pharmaceutical compositions comprising a compound of the invention, and another therapeutic agent. In a particular embodiment, the other therapeutic agent is a autoinflammatory diseases treatment agent. In particular, the term autoinflammatory diseases refers to Cryopyrin-Associated Periodic Syndromes (CAPS), Familial Mediterranean Fever (FMF) and Tumor necrosis factor receptor-associated periodic syndrome (TRAPS), Behçets, Systemic-Onset Juvenile Idiopathic Arthritis (SJIA) or Still's disease. More particularly, the term refers to CAPS, FMF, TRAPS and Still's disease.

In one embodiment, the present invention provides compounds of the invention or pharmaceutical compositions comprising a compound of the invention, for use in the prophylaxis and/or treatment of autoimmune diseases. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosis, type I diabetes mellitus and inflammatory bowel disease.

In another embodiment, the present invention provides the use of compounds of the invention or pharmaceutical compositions comprising a compound of the invention in the manufacture of a medicament for the prophylaxis and/or treatment of autoimmune diseases. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosis, type I diabetes mellitus and inflammatory bowel disease.

In additional method of treatment aspects, this invention provides methods of prophylaxis and/or treatment of a mammal afflicted with autoimmune diseases, which methods comprise the administration of an effective amount of a compound of the invention or one or more of the pharmaceutical compositions herein described for the treatment or prophylaxis of said condition. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosis, type I diabetes mellitus and inflammatory bowel disease.

In one embodiment, the present invention provides pharmaceutical compositions comprising a compound of the invention, and another therapeutic agent. In a particular embodiment, the other therapeutic agent is an autoimmune diseases treatment agent. In particular, the term autoimmune diseases refers to COPD, asthma, bronchitis, systemic lupus erythematosus (SLE), cutaneous lupus erythrematosis (CLE), lupus nephritis, dermatomyositis, autoimmune hepatitis, primary sclerosing cholangitis, primary biliary cirrhosis, Sjögren's syndrome, multiple sclerosis, psoriasis, dry eye disease, type I diabetes mellitus, atopic dermatitis, thyroiditis, contact dermatitis, eczematous dermatitis, inflammatory bowel disease (e.g. Crohn's disease and ulcerative colitis), atherosclerosis and amyotrophic lateral sclerosis. More particularly, the term refers to COPD, asthma, systemic lupus erythematosis, type I diabetes mellitus and inflammatory bowel disease.

In one embodiment, the present invention provides compounds of the invention or pharmaceutical compositions comprising a compound of the invention, for use in the prophylaxis and/or treatment of proliferative diseases. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In another embodiment, the present invention provides the use of compounds of the invention or pharmaceutical compositions comprising a compound of the invention in the manufacture of a medicament for the prophylaxis and/or treatment of proliferative diseases. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In additional method of treatment aspects, this invention provides methods of prophylaxis and/or treatment of a mammal afflicted with proliferative diseases, which methods comprise the administration of an effective amount of a compound of the invention or one or more of the pharmaceutical compositions herein described for the treatment or prophylaxis of said condition. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In one embodiment, the present invention provides pharmaceutical compositions comprising a compound of the invention, and another therapeutic agent. In a particular embodiment, the other therapeutic agent is a proliferative diseases treatment agent. In particular, the term proliferative diseases refers to cancer, myeloproliferative disorders, leukemia, multiple myeloma, psoriasis, restenosis, scleroderma or fibrosis. More particularly, the term refers to cancer, leukemia, multiple myeloma and psoriasis.

In one embodiment, the present invention provides compounds of the invention or pharmaceutical compositions comprising a compound of the invention, for use in the prophylaxis and/or treatment of fibrotic diseases. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In another embodiment, the present invention provides the use of compounds of the invention or pharmaceutical compositions comprising a compound of the invention in the manufacture of a medicament for the prophylaxis and/or treatment of fibrotic diseases. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In additional method of treatment aspects, this invention provides methods of prophylaxis and/or treatment of a mammal afflicted with fibrotic diseases, which methods comprise the administration of an effective amount of a compound of the invention or one or more of the pharmaceutical compositions herein described for the treatment or prophylaxis of said condition. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In one embodiment, the present invention provides pharmaceutical compositions comprising a compound of the invention, and another therapeutic agent. In a particular embodiment, the other therapeutic agent is a fibrotic diseases treatment agent. In particular, the term fibrotic diseases refers to idiopathic pulmonary fibrosis (IPF), Dupuytren disease, nonalcoholic steatohepatitis (NASH), systemic sclerosis, renal fibrosis, and cutaneous fibrosis.

In one embodiment, the present invention provides compounds of the invention or pharmaceutical compositions comprising a compound of the invention, for use in the prophylaxis and/or treatment of transplantation rejection. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to graft-versus-host disease.

In another embodiment, the present invention provides the use of compounds of the invention or pharmaceutical compositions comprising a compound of the invention in the manufacture of a medicament for the prophylaxis and/or treatment of transplantation rejection. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to graft-versus-host disease.

In additional method of treatment aspects, this invention provides methods of prophylaxis and/or treatment of a mammal afflicted with transplantation rejection, which methods comprise the administration of an effective amount of a compound of the invention or one or more of the pharmaceutical compositions herein described for the treatment or prophylaxis of said condition. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to graft-versus-host disease.

In one embodiment, the present invention provides pharmaceutical compositions comprising a compound of the invention, and another therapeutic agent. In a particular embodiment, the other therapeutic agent is a transplantation rejection treatment agent. In particular, the term transplantation rejection refers to acute or chronic rejection of cells, tissue or solid organ allo- or xenografts of e.g. pancreatic islets, stem cells, bone marrow, skin, muscle, corneal tissue, neuronal tissue, heart, lung, combined heart-lung, kidney, liver, bowel, pancreas, trachea or oesophagus, or graft-versus-host diseases. More particularly, the term refers to graft-versus-host disease.

In one embodiment, the present invention provides compounds of the invention or pharmaceutical compositions comprising a compound of the invention, for use in the prophylaxis and/or treatment of diseases involving impairment of cartilage turnover. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In another embodiment, the present invention provides the use of compounds of the invention or pharmaceutical compositions comprising a compound of the invention in the manufacture of a medicament for the prophylaxis and/or treatment of diseases involving impairment of cartilage turnover. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In additional method of treatment aspects, this invention provides methods of prophylaxis and/or treatment of a mammal afflicted with diseases involving impairment of cartilage turnover, which methods comprise the administration of an effective amount of a compound of the invention or one or more of the pharmaceutical compositions herein described for the treatment or prophylaxis of said condition. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In one embodiment, the present invention provides pharmaceutical compositions comprising a compound of the invention, and another therapeutic agent. In a particular embodiment, the other therapeutic agent is a diseases involving impairment of cartilage turnover treatment agent. In particular, the term diseases involving impairment of cartilage turnover refers to osteoarthritis, psoriatic arthritis, juvenile rheumatoid arthritis, gouty arthritis, septic or infectious arthritis, reactive arthritis, reflex sympathetic dystrophy, algodystrophy, Tietze syndrome or costal chondritis, fibromyalgia, osteochondritis, neurogenic or neuropathic arthritis, arthropathy, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis, psoriatic arthritis, juvenile rheumatoid arthritis, systemic lupus erythematosus, scleroderma and ankylosing spondylitis.

In one embodiment, the present invention provides compounds of the invention or pharmaceutical compositions comprising a compound of the invention, for use in the prophylaxis and/or treatment of congenital cartilage malformation. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In another embodiment, the present invention provides the use of compounds of the invention or pharmaceutical compositions comprising a compound of the invention in the manufacture of a medicament for the prophylaxis and/or treatment of congenital cartilage malformation. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In additional method of treatment aspects, this invention provides methods of prophylaxis and/or treatment of a mammal afflicted with congenital cartilage malformation, which methods comprise the administration of an effective amount of a compound of the invention or one or more of the pharmaceutical compositions herein described for the treatment or prophylaxis of said condition. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In one embodiment, the present invention provides pharmaceutical compositions comprising a compound of the invention, and another therapeutic agent. In a particular embodiment, the other therapeutic agent is a congenital cartilage malformation treatment agent. In particular, the term congenital cartilage malformation refers to hereditary chondrolysis, chondrodysplasias and pseudochondrodysplasias, microtia, anotia, metaphyseal chondrodysplasia. More particularly, the term refers to microtia, anotia, metaphyseal chondrodysplasia.

In one embodiment, the present invention provides compounds of the invention or pharmaceutical compositions comprising a compound of the invention, for use in the prophylaxis and/or treatment of diseases involving impairment of bone turnover. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In another embodiment, the present invention provides the use of compounds of the invention or pharmaceutical compositions comprising a compound of the invention in the manufacture of a medicament for the prophylaxis and/or treatment of diseases involving impairment of bone turnover. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In additional method of treatment aspects, this invention provides methods of prophylaxis and/or treatment of a mammal afflicted with diseases involving impairment of bone turnover, which methods comprise the administration of an effective amount of a compound of the invention or one or more of the pharmaceutical compositions herein described for the treatment or prophylaxis of said condition. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In one embodiment, the present invention provides pharmaceutical compositions comprising a compound of the invention, and another therapeutic agent. In a particular embodiment, the other therapeutic agent is a diseases involving impairment of bone turnover treatment agent. In particular, the term diseases involving impairment of bone turnover refers to osteoporosis, osteopenia, hormone deficiency, hormone excess, Paget's disease, osteoarthritis, renal bone disease, osteogenesis imperfecta, and hypophosphatasia. More particularly, the term refers to osteoporosis.

In one embodiment, the present invention provides compounds of the invention or pharmaceutical compositions comprising a compound of the invention, for use in the prophylaxis and/or treatment of diseases associated with hypersecretion of IL-6. In particular, the term diseases associated with hypersecretion of IL-6 refers to Castleman's disease, multiple myeloma, psoriasis, Kaposi's sarcoma and/or mesangial proliferative glomerulonephritis.

In another embodiment, the present invention provides the use of compounds of the invention or pharmaceutical compositions comprising a compound of the invention in the manufacture of a medicament for the prophylaxis and/or treatment of diseases associated with hypersecretion of IL-6. In particular, the term diseases associated with hypersecretion of IL-6 refers to Castleman's disease, multiple myeloma, psoriasis, Kaposi's sarcoma and/or mesangial proliferative glomerulonephritis.

In additional method of treatment aspects, this invention provides methods of prophylaxis and/or treatment of a mammal afflicted with diseases associated with hypersecretion of IL-6, which methods comprise the administration of an effective amount of a compound of the invention or one or more of the pharmaceutical compositions herein described for the treatment or prophylaxis of said condition. In particular, the term diseases associated with hypersecretion of IL-6 refers to Castleman's disease, multiple myeloma, psoriasis, Kaposi's sarcoma and/or mesangial proliferative glomerulonephritis.

In one embodiment, the present invention provides pharmaceutical compositions comprising a compound of the invention, and another therapeutic agent. In a particular embodiment, the other therapeutic agent is a diseases associated with hypersecretion of IL-6 treatment agent. In particular, the term diseases associated with hypersecretion of IL-6 refers to Castleman's disease, multiple myeloma, psoriasis, Kaposi's sarcoma and/or mesangial proliferative glomerulonephritis.

In one embodiment, the present invention provides compounds of the invention or pharmaceutical compositions comprising a compound of the invention, for use in the prophylaxis and/or treatment of diseases associated with hypersecretion of TNFα, interferons, IL-12 and/or IL-23. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In another embodiment, the present invention provides the use of compounds of the invention or pharmaceutical compositions comprising a compound of the invention in the manufacture of a medicament for the prophylaxis and/or treatment of diseases associated with hypersecretion of TNFα, interferons, IL-12 and/or IL-23. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In additional method of treatment aspects, this invention provides methods of prophylaxis and/or treatment of a mammal afflicted with diseases associated with hypersecretion of TNFα, interferons, IL-12 and/or IL-23, which methods comprise the administration of an effective amount of a compound of the invention or one or more of the pharmaceutical compositions herein described for the treatment or prophylaxis of said condition. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In one embodiment, the present invention provides pharmaceutical compositions comprising a compound of the invention, and another therapeutic agent. In a particular embodiment, the other therapeutic agent is a diseases associated with hypersecretion of TNFα, interferons, IL-12 and/or IL-23 treatment agent. In particular, the term diseases associated with hypersecretion of TNFα, interferons, IL-12 and/or IL-23 refers to systemic and cutaneous lupus erythematosus, lupus nephritis, dermatomyositis, Sjögren's syndrome, psoriasis, rheumatoid arthritis, psoriatic arthritis, multiple sclerosis, trisomy 21, ulcerative colitis, and/or Crohn's disease. More particularly, the term refers to Sjögren's syndrome, psoriasis, rheumatoid arthritis, psoriatic arthritis, multiple sclerosis, trisomy 21, ulcerative colitis, and/or Crohn's disease.

In one embodiment, the present invention provides compounds of the invention or pharmaceutical compositions comprising a compound of the invention, for use in the prophylaxis and/or treatment of respiratory diseases. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In another embodiment, the present invention provides the use of compounds of the invention or pharmaceutical compositions comprising a compound of the invention in the manufacture of a medicament for the prophylaxis and/or treatment of respiratory diseases. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In additional method of treatment aspects, this invention provides methods of prophylaxis and/or treatment of a mammal afflicted with respiratory diseases, which methods comprise the administration of an effective amount of a compound of the invention or one or more of the pharmaceutical compositions herein described for the treatment or prophylaxis of said condition. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In one embodiment, the present invention provides pharmaceutical compositions comprising a compound of the invention, and another therapeutic agent. In a particular embodiment, the other therapeutic agent is a respiratory diseases treatment agent. In particular, the term respiratory diseases refers to asthma, adult respiratory distress syndrome, isocapnic hyperventilation, seasonal asthma, seasonal allergic rhinitis, perennial allergic rhinitis, chronic obstructive pulmonary disease, emphysema, pulmonary hypertension, interstitial lung fibrosis, cystic fibrosis, or hypoxia. More particularly, the term refers to pulmonary hypertension or interstitial lung fibrosis.

In one embodiment, the present invention provides compounds of the invention or pharmaceutical compositions comprising a compound of the invention, for use in the prophylaxis and/or treatment of endocrine and/or metabolic diseases. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or type II diabetes.

In another embodiment, the present invention provides the use of compounds of the invention or pharmaceutical compositions comprising a compound of the invention in the manufacture of a medicament for the prophylaxis and/or treatment of endocrine and/or metabolic diseases. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or type II diabetes.

In additional method of treatment aspects, this invention provides methods of prophylaxis and/or treatment of a mammal afflicted with endocrine and/or metabolic diseases, which methods comprise the administration of an effective amount of a compound of the invention or one or more of the pharmaceutical compositions herein described for the treatment or prophylaxis of said condition. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or type II diabetes.

In one embodiment, the present invention provides pharmaceutical compositions comprising a compound of the invention, and another therapeutic agent. In a particular embodiment, the other therapeutic agent is a endocrine and/or metabolic diseases treatment agent. In particular, the term endocrine and/or metabolic diseases refers to hypothyroidism, congenital adrenal hyperplasia, diseases of the parathyroid gland, diabetes mellitus, diseases of the adrenal glands, Cushing's syndrome and Addison's disease, and ovarian dysfunction polycystic ovary syndrome, cystic fibrosis, phenylketonuria (PKU), diabetes, hyperlipidemia, gout, and rickets. More particularly, the term refers to obesity and/or type II diabetes.

In one embodiment, the present invention provides compounds of the invention or pharmaceutical compositions comprising a compound of the invention, for use in the prophylaxis and/or treatment of cardiovascular diseases. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, the term refers to atherosclerosis or giant cell arteritis.

In another embodiment, the present invention provides the use of compounds of the invention or pharmaceutical compositions comprising a compound of the invention in the manufacture of a medicament for the prophylaxis and/or treatment of cardiovascular diseases. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, the term refers to atherosclerosis or giant cell arteritis.

In additional method of treatment aspects, this invention provides methods of prophylaxis and/or treatment of a mammal afflicted with cardiovascular diseases, which methods comprise the administration of an effective amount of a compound of the invention or one or more of the pharmaceutical compositions herein described for the treatment or prophylaxis of said condition. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, the term refers to atherosclerosis or giant cell arteritis.

In one embodiment, the present invention provides pharmaceutical compositions comprising a compound of the invention, and another therapeutic agent. In a particular embodiment, the other therapeutic agent is a cardiovascular diseases treatment agent. In particular, the term cardiovascular diseases refers to arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, or insufficiency limited to a single organ or tissue. More particularly, the term refers to atherosclerosis or giant cell arteritis.

In one embodiment, the present invention provides compounds of the invention or pharmaceutical compositions comprising a compound of the invention, for use in the prophylaxis and/or treatment of dermatological diseases. In particular, the term dermatological diseases refers to atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, vitiligo, or urticaria.

In another embodiment, the present invention provides the use of compounds of the invention or pharmaceutical compositions comprising a compound of the invention in the manufacture of a medicament for the prophylaxis and/or treatment of dermatological diseases. In particular, the term dermatological diseases refers to atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, vitiligo, or urticaria.

In additional method of treatment aspects, this invention provides methods of prophylaxis and/or treatment of a mammal afflicted with dermatological diseases, which methods comprise the administration of an effective amount of a compound of the invention or one or more of the pharmaceutical compositions herein described for the treatment or prophylaxis of said condition. In particular, the term dermatological diseases refers to atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, vitiligo, or urticaria.

In one embodiment, the present invention provides pharmaceutical compositions comprising a compound of the invention, and another therapeutic agent. In a particular embodiment, the other therapeutic agent is a dermatological diseases treatment agent. In particular, the term dermatological diseases refers to atopic dermatitis, bullous disorders, collagenoses, psoriasis, psoriatic lesions, dermatitis, contact dermatitis, eczema, vitiligo, pruritus, scleroderma, wound healing, scarring, hypertrophic scarring, keloids, Kawasaki disease, rosacea, Sjögren-Larsson syndrome, or urticaria. More particularly, the term refers to atopic dermatitis, scleroderma, Sjögren-Larsson syndrome, vitiligo, or urticaria.

In one embodiment, the present invention provides compounds of the invention or pharmaceutical compositions comprising a compound of the invention, for use in the prophylaxis and/or treatment of abnormal angiogenesis associated diseases. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

In another embodiment, the present invention provides the use of compounds of the invention or pharmaceutical compositions comprising a compound of the invention in the manufacture of a medicament for the prophylaxis and/or treatment of abnormal angiogenesis associated diseases. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

In additional method of treatment aspects, this invention provides methods of prophylaxis and/or treatment of a mammal afflicted with abnormal angiogenesis associated diseases, which methods comprise the administration of an effective amount of a compound of the invention or one or more of the pharmaceutical compositions herein described for the treatment or prophylaxis of said condition. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

In one embodiment, the present invention provides pharmaceutical compositions comprising a compound of the invention, and another therapeutic agent. In a particular embodiment, the other therapeutic agent is a abnormal angiogenesis associated diseases treatment agent. In particular, the term abnormal angiogenesis associated diseases refers to atherosclerosis, hypertension, tumor growth, inflammation, rheumatoid arthritis, wet-form macular degeneration, choroidal neovascularization, retinal neovascularization, and diabetic retinopathy. More particularly, the term refers to atherosclerosis, hypertension, or diabetic retinopathy.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of proliferative disorders, particular agents include but are not limited to: methotrexate, leucovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin®), capecitabine, raloxifene hydrochloride, EGFR inhibitors (e.g. Iressa®, Tarceva®, Erbitux®), VEGF inhibitors (e.g. Avastin®), proteasome inhibitors (e.g. Velcade®), Glivec® and hsp90 inhibitors (e.g. 17-AAG). Additionally, the compound of the invention according to Formula I may be administered in combination with other therapies including, but not limited to, radiotherapy or surgery. In a specific embodiment the proliferative disorder is selected from cancer, myeloproliferative disease or leukemia.

In one embodiment, a compound of the invention is co-administered with another therapeutic agent for the treatment and/or prophylaxis of autoimmune diseases, particular agents include but are not limited to: glucocorticoids, cytostatic agents (e.g. purine analogs), alkylating agents, (e.g nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-β), TNF binding proteins (e.g. infliximab, etanercept, or adalimumab), mycophenolate, fingolimod and myriocin.

In one embodiment, a compound of the invention is co-administered with another therapeutic agent for the treatment and/or prophylaxis of transplant rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, a compound of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled), long-acting β2-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. cetirizine, cinnarizine, fexofenadine) and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a compound of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort®), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive®, Enbrel®, Humira®, Remicade®, Raptiva® and ustekinumab (an IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

In one embodiment, a compound of the invention is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anti-cholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Wuts & Greene 2006).

The following methods are presented with details as to the preparation of a compound of the invention as defined hereinabove and the comparative examples. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica gel 60 (35-70 μm) or with Biotage® SNAP KP-NH, Biotage® SNAP Ultra, or Interchim© PuriFlash® Si HC flash chromatography cartridges. Thin layer chromatography is carried out using pre-coated silica gel F-254 plates (thickness 0.25 mm). Biotage® ISOLUTE® phase separators (e.g., Cat #120-1907-E) are used for aqueous phase separation. $^{1}H$ NMR spectra are recorded on a Bruker DPX 400 NMR spectrometer (400 MHz) or a Bruker Avance 300 NMR spectrometer (300 MHz). Chemical shifts (6) for $^{1}H$ NMR spectra are reported in parts per million (ppm) relative to tetramethylsilane (δ 0.00) or the appropriate residual solvent peak, i.e. $CHCl_3$ (δ 7.27), as internal reference. Multiplicities are given as singlet (s), doublet (d), triplet (t), quartet (q), quintet (quin), multiplet (m) and broad (br). Electrospray MS spectra are obtained on a Waters Acquity H-Class UPLC system coupled to a UV PDA detector and to a Waters SQD or SQD2 mass spectrometer. Columns used: Waters Acquity UPLC BEH C18 1.7 μm, 2.1 mm ID×30/50 mm L; Waters Acquity UPLC CSH C18 1.7 μm, 2.1 mm ID×50/100 mm L; Waters Acquity UPLC CSH PhenylHexyl 1.7 μm, 2.1 mm ID×100 mm L; Waters Acquity UPLC HSS PFP 1.8 μm, 2.1 mm ID×100 mm L. The methods are using ACN/$H_2O$ gradients with either 0.1% formic acid in both mobile phases, 0.05% $NH_3$ in both mobile phases, or 10 mM $NH_4HCO_3$ in $H_2O$ (adjusted to pH 10 with ammonia). Preparative HPLC is performed on a Waters AutoPurification system with UV and MS detection using Waters XBRIDGE BEH C18 OBD 30 mm ID×100/150 mm L columns and ACN/$H_2O$ gradients with either 0.1% formic acid in both mobile phases, 0.1% diethylamine in both mobile phases, 0.1% formic acid in $H_2O$, or 10 mM $NH_4HCO_3$ in $H_2O$ (adjusted to pH 10 with ammonia). Microwave heating is performed with a Biotage® Initiator.

TABLE I

List of abbreviations used in the experimental section:

| Abreviation | Definition |
|---|---|
| ACN | acetonitrile |
| AcOH | acetic acid |
| ANOVA | analysis of variance |
| aq. | aqueous |
| ATP | adenosine 5'-triphosphate |
| b.i.d. | bis in die (twice a day) |
| Boc | tert-butyloxy-carbonyl |
| $B_2pin_2$ | 4,4,5,5-tetramethyl-2-(4,4,5,5-tetramethyl-1,3,2-dioxaborolan-2-yl)-1,3,2-dioxaborolane |
| br s | broad singlet |
| calcd | calculated |
| d | doublet |
| DAST | diethylaminosulfur trifluoride |
| DCM | dichloromethane |
| dd | doublet of doublets |
| DIAD | diisopropyl azodicarboxylate |
| DIPEA | N,N-diisopropylethylamine |
| DMAC | dimethylacetamide |
| DMF | N,N-dimethylformamide |
| DMSO | Dimethylsulfoxide |
| dppf | 1,1'-bis(diphenylphosphino) ferrocene |
| dppp | 1,3-bis(diphenyl phosphino)propane |
| dtbpy | 4,4'-di-tert-butyl-2,2'-dipyridyl |
| $Et_3N$ | triethylamine |
| $Et_2O$ | diethyl ether |
| EtOAc | ethyl acetate |
| EtOH | ethanol |
| eq. | equivalent |
| h | hour |
| HATU | 1-[bis(dimethylamino) methylene]-1H-1,2,3-triazolo[4,5-b]pyridinium 3-oxid hexafluorophosphate (CAS# 148893-10-1) |
| HPLC | high-performance liquid chromatography |
| i.n. | intranasal |
| i.p. | intraperitoneal |
| i-PrOH | isopropanol |
| $[Ir(OCH_3)(COD)]_2$ | (1,5-cyclooctadiene) (methoxy)iridium(I) dimer (CAS# 12148-71-9) |
| $(Ir[dF(CF_3)ppy]_2(dtbpy))PF_6$ | 4,4'-bis(1,1-dimethylethyl)-2,2'-bipyridine-N1,N1']bis [3,5-difluoro-2-[5-(trifluoro methyl)-2-pyridinyl-N]phenyl-C]iridium(III) hexafluorophosphate (CAS# 870987-63-6) |
| i.v. | intravenous |
| KHMDS | potassium hexamethy Idisilazane |
| KOAc | potassium acetate |
| LCMS | liquid chromatography-mass spectrometry |
| LDA | lithium diisopropylamide |

TABLE I-continued

List of abbreviations used in the experimental section:

| Abreviation | Definition |
|---|---|
| LiHMDS | lithium hexamethyldisilazane |
| m | multiplet |
| MeOH | methanol |
| MeONa | sodium methoxide |
| mg | milligram |
| min | minute |
| mE | milliliter |
| mmol | millimole |
| MorDalphos | di(1-adamantyl)-2-morpholinophenylphosphine (CAS# 1237588-12-3) |
| MS | mass spectrometry |
| MTBE | methyl tert-butyl ether |
| MW | molecular weight |
| MW (calcd) | molecular weight calculated |
| MW (obsd) | molecular weight observed |
| NA | not available |
| $NaBH_3CN$ | sodium cyanoborohydride |
| n-BuOH | butan-1-ol |
| $NiCl_2 \cdot$ glyme | nickel(II) chloride ethylene glycol dimethyl ether complex (CAS# 29046-78-4) |
| NMP | N-methyl-2-pyrrolidone |
| obsd | observed |
| $Pd(dppf)Cl_2 \cdot$ DCM | 1,1'-bis(diphenylphosphino) ferrocene]dichloropalladium(II), complex with dichloromethane (CAS# 95464-05-4) |
| $Pd(PPh_3)_4$ | tetrakis(triphenylphosphine) palladium(0) |
| PIFA | [bis(trifluoroacetoxy)iodo] benzene (CAS# 2712-78-9) |
| p.o. | per os |
| ppm | parts-per-million |
| q | quartet |
| q.d. | quaque die (once a day) |
| RT | room temperature |
| s | singlet |
| sat. | saturated |
| sc | subcutaneous |
| SEM | standard error of the mean |
| SM | starting material |
| t | triplet |
| t-BuOK | potassium tert-butoxide |
| td | triplet of doublets |
| TFA | trifluoroacetic acid |
| THF | tetrahydrofuran |
| tt | triplet of triplets |

Synthetic Preparation of the Compounds of the Invention
Example 1. General Synthetic Methods
1.1. Synthetic Methods Overview
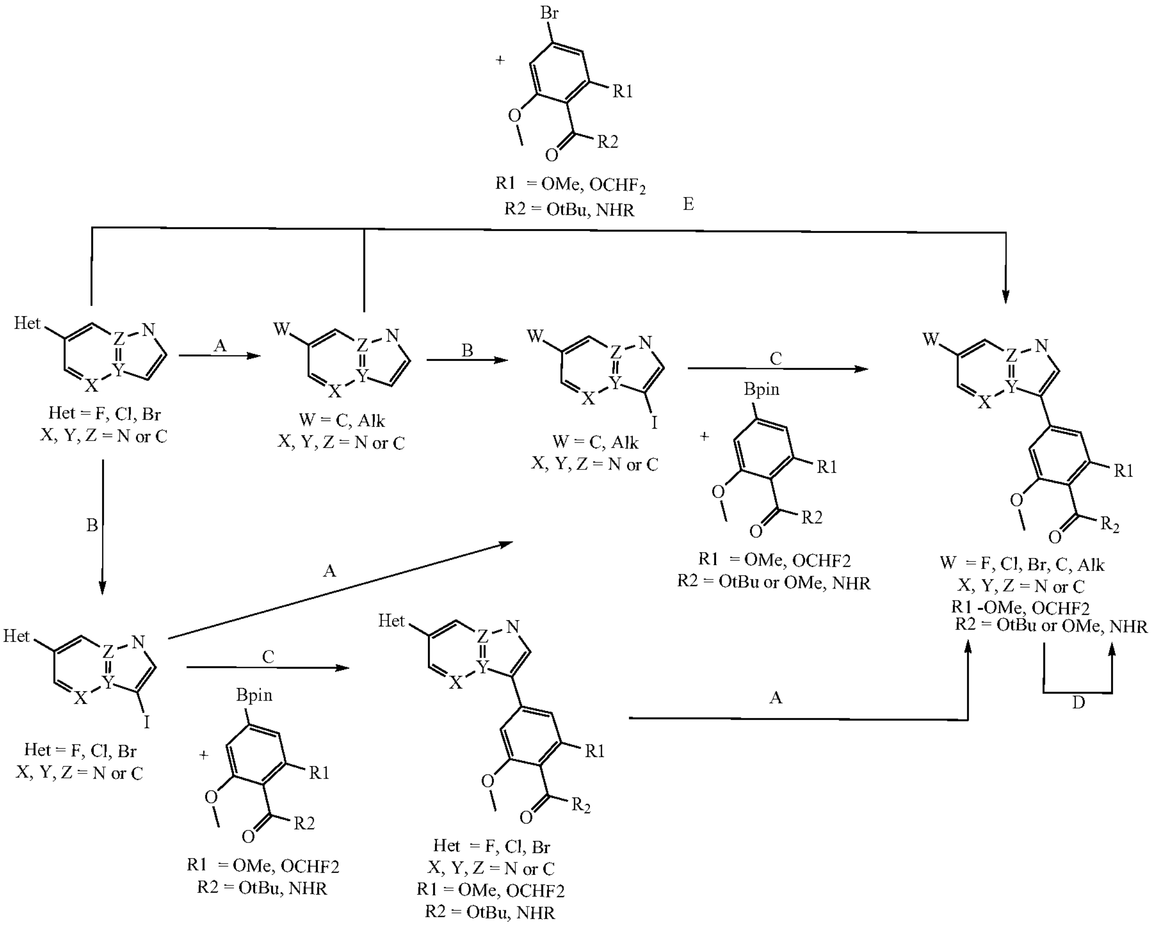
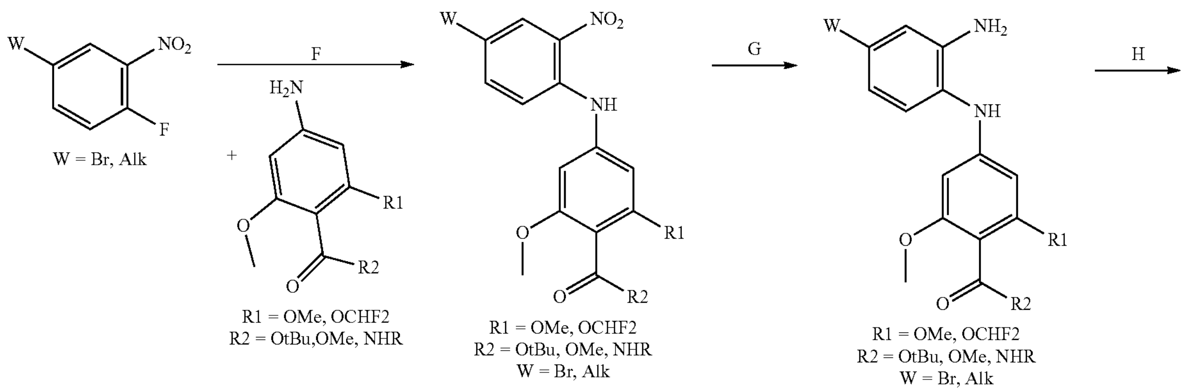

-continued

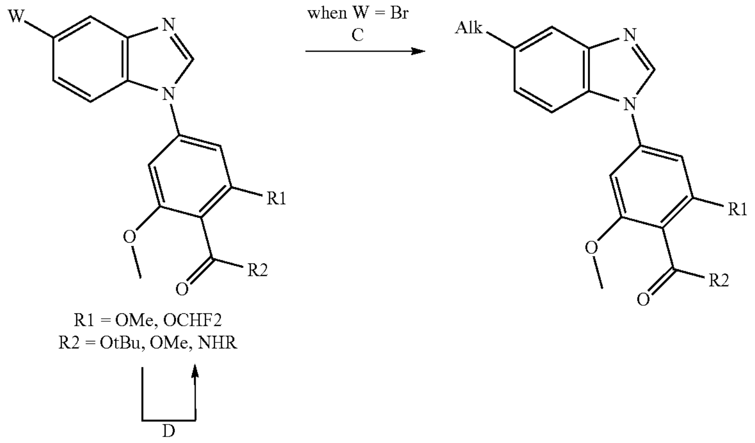

General Methods A: Functionalization of halogenated heteroaryl compound
- Method A1: Alkylation
- Method A2: Palladium-catalyzed decarboxylative coupling
- Method A3: Negishi coupling
- Method A4: Nickel coupling
- Method A5: Addition to keto derivative
- Method A6: Photochemical reaction
- Method A7: Functionalization of halogenated pyridine by metalation
- Method A8: Functionalization of halogenated heteroaryl compound by Suzuki coupling/degradation General method B: Iodination of heteroaryl compounds General method C: Suzuki coupling of heteroaryl compounds General methods D: Synthesis of amides from esters
- Method D1: Tert-butyl ester hydrolysis then peptide coupling
- Method D2: Methyl ester saponification then peptide coupling General method E: C—H activation of heteroaryl compounds General methods F: $S_NAr$ of di or trisubstituted aniline on halogeno nitro phenyl or pyridine derivatives
- Method F1: $S_NAr$ of disubstituted amino benzoates on halogeno nitro phenyl derivatives with LiHMDS
- Method F2: $S_NAr$ of disubstituted amino benzamides or benzoates on halogeno nitro phenyl derivatives with NaH General method G: Nitro reduction
- Method G1: Nitro reduction with $SnCl_2$, $2H_2O/SnCl_2$
- Method G2: Nitro reduction with Zn/AcOH General method H: Cyclization into benzimidazole General methods I: O-alkylation/N-Alkylation
- Method I1: O-alkylation
- Method I2: N-alkylation General method J: N-acylation General methods K: Reductive amination
- Method K1: Amine functionalization by reductive amination
- Method K2: Ketone functionalization by reductive amination
- Method K3: Aldehyde functionalization by reductive amination General method L: Reduction of olefins General methods M: Amine deprotection
- Method M1: Amine deprotection using TFA
- Method M2: Amine deprotection using HCl General methods N: Alcohol synthesis
- Method N1: Ketone or ester reduction
- Method N2: Addition of magnesium reagent on ketone
- Method N3: Epoxidation/epoxide opening sequence General method O: Aminopyridine cyclization into imidazopyridine General methods P: Synthesis of boronates
- Method P1: Bromides borylation
- Method P2: Borylation by C—H activation General method Q: Fluorine displacement with an alkoxide on a trisubstituted benzamide or benzoate General method R: Difluoromethylation of a phenol intermediate General method S: Nitration of halogenated benzylcyanides General method T: Fluoration of alcohol General method U: Alcohol oxidation into aldehyde General method V: Amine synthesis by Hofmann rearrangement General method W: Potassium carboxylate salts synthesis

1.2. General Methods

1.2.1. Method A1: Functionalization of Halogenated Heteroaryl Compound by Alkylation To a degassed solution of 7-fluoroimidazo[1,2-a]pyridine (CAS #1260903-17-0; 1 eq.) and alkylnitrile (1 to 1.5 eq.) in dry THF or toluene under inert atmosphere at −78° C. or 0° C. is added dropwise LiHMDS (1M in THF, CAS #4039-32-1; 1.3 to 1.45 eq.) or KHMDS (0.5 M in THF, CAS #40949-94-8; 1.3 to 1.45 eq.). The reaction mixture is stirred at 60° C. for 3 to 18 h, quenched with water and concentrated to dryness. The residue is triturated in pentane; the solid is filtered and dried in vacuo.

Alternative work-up: The reaction mixture is quenched with water and extracted with EtOAc followed by extraction with n-BuOH or not. The combined organic layers are washed with brine, dried over $Na_2SO_4$ or $MgSO_4$, filtered and concentrated in vacuo. The residue is purified by flash chromatography on silica gel.

Illustrative Synthesis of Int 96

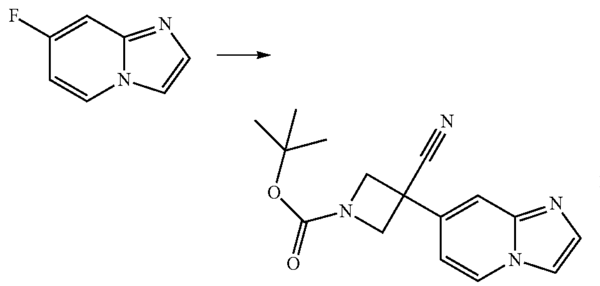

To a degassed solution of 7-fluoroimidazo[1,2-a]pyridine (150 mg, 1.10 mmol, 1 eq.) and 1-boc-3-cyanoazetidine (CAS #142253-54-1; 301 mg, 1.65 mmol, 1.5 eq.) in dry toluene (3 mL) under inert atmosphere at 0° C. is added dropwise KHMDS (0.5 M in THF, 2.9 mL, 1.43 mmol, 1.3 eq.). The reaction mixture is stirred at RT for 1.5 h then at 60° C. for 3 h, quenched with water and brine, and extracted with EtOAc then n-BuOH. The combined organic layers are dried over $MgSO_4$, filtered and concentrated in vacuo. The residue is purified by flash chromatography (eluting with heptane/EtOAc 100/0 to 0/100) to afford the desired intermediate.

1.2.2. Method A2: Functionalization of Halogenated Heteroaryl Compound by Palladium-Catalyzed Decarboxylative Coupling To a solution of heteroaryl halide (1 eq.) in 1,3,5-trimethylbenzene under inert atmosphere is added the corresponding potassium carboxylic acid salt (2 eq.), 4,5-bis(diphenylphosphino)-9,9-dimethylxanthene (CAS #161265-03-8; 0.06 eq.) and allylpalladium chloride dimer (CAS #12012-95-2; 0.02 eq.) or alternatively Xantphos Pd G4 (CAS #1621274-19-8; 0.05 eq.). The reaction mixture is stirred at 140° C. for 30 min to 6 h then cooled to RT and filtered on Dicalite™, rinsed with EtOAc and concentrated in vacuo. The residue is purified by flash chromatography on silica gel. Alternatively the reaction mixture is directly concentrated in vacuo and the residue is purified by flash chromatography on silica gel.

Illustrative Synthesis of Int 171

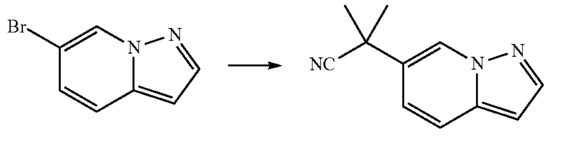

In a round bottom flask under $N_2$ atmosphere, to a solution of 6-bromopyrazolo[1,5-a]pyridine (CAS #1264193-11-4; 10 g, 50 mmol, 1 eq.) in 1,3,5-trimethylbenzene (74 mL) are added potassium 2-cyano-2-methyl-propanoic acid Int 170 (15 g, 99 mmol, 2 eq.), 4,5-bis(diphenylphosphino)-9,9-dimethylxanthene (1.8 g, 3.0 mmol, 0.06 eq.) and allylpalladium chloride dimer (370 mg, 0.99 mmol, 0.02 eq.). The reaction mixture is stirred at 140° C. for 30 min then cooled to RT and filtered on Dicalite™ rinsed with EtOAc and concentrated in vacuo. The residue is purified by flash chromatography on silica gel (eluting with heptane/EtOAc 100/0 to 50/50) to afford the desired intermediate.

1.2.3. Method A3: Functionalization of Halogenated Heteroaryl Compound by Negishi Coupling In a sealed vial under $N_2$ atmosphere are introduced the halogenated heteroaryl compound (1 eq.) and DMAC or THF. The resulting solution is degassed then Pd-PEPPSI™-IPent catalyst (CAS #1158652-41-5; 0.1 eq.) or alternatively copper iodide (CAS #7681-65-4; 0.1 eq.) and Pd(dppf) $Cl_2$·DCM (CAS #95464-05-4; 0.05 eq.) are added. The resulting solution is degassed before introduction of a solution of alkylzinc halide (0.94 to 3 eq.). The reaction mixture is heated to 80° C. for 2 to 18 h then filtered on Clarcel® and concentrated in vacuo. The residue is diluted with water and extracted with EtOAc. The combined organic layers are dried over $MgSO_4$, filtered or passed through a phase separator and concentrated. The residue is purified by flash chromatography.

Alternative work-up: The reaction mixture is diluted with EtOAc, stirred for 1 h, filtered over Clarcel® and quenched with a sat. $NH_4Cl$ solution. The solution is stirred for 30 min before addition of a 2N NaOH solution and extraction with EtOAc. The combined organic layers are washed with a 10% aq. $Na_2S_2O_3$ solution, brine, dried over $Na_2SO_4$, filtered and concentrated. The residue is purified by flash chromatography on silica gel.

Illustrative Synthesis of Int 127

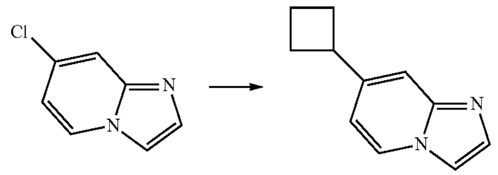 [SMILES: Clc1ccn2ccnc2c1 ; c1cn2ccc(C3CCC3)cc2n1]

In a sealed vial are 7-chloroimidazo[1,2-a]pyridine (100 mg, 0.65 mmol, 1 eq.) and THF (0.5 mL). The resulting solution is degassed then Pd-PEPPSI™-IPent catalyst (CAS #1158652-41-5; 52 mg, 0.065 mmol, 0.1 eq.) is added. The resulting solution is degassed before introduction of a solution of bromocyclobutyl zinc (0.5 M in THF, CAS #1019205-65-2; 4 mL, 1.96 mmol, 3 eq.). The reaction mixture is heated to 80° C. for 18 h then filtered on Clarcel® and concentrated in vacuo. The residue is diluted with water and extracted with EtOAc. The combined organic layers are dried over $MgSO_4$, filtered and concentrated. The residue is purified by flash chromatography on silica gel (eluting with DCM/MeOH 100/0 to 95/5) to afford the desired compound.

1.2.4. Method A4: Functionalization of Halogenated Heteroaryl Compound by Nickel Coupling In a sealed vial under $N_2$ atmosphere are introduced degassed DMAC, halogenated heteroaryl compound (1 eq.), the alkyl bromide (1.5 to 2 eq.), $NiCl_2$·glyme (CAS #29046-78-4; 0.05 to 0.1 eq.), Int 230 (0.05 to 0.1 eq.), sodium iodide (CAS #7681-82-5; 0.25 eq.), zinc powder (CAS #7440-66-6; 2 eq.) and TFA (CAS #76-05-1; 0.1 eq.). The resulting solution is heated to 60° C. for 1 to 18 h then filtered on Clarcel®, washed with EtOAc and concentrated in vacuo. The residue is purified by flash chromatography on silica gel.

Alternative work-up: The reaction mixture is filtered on Clarcel®. The filtrate is quenched with water or a 5% aq. ammonia solution, extracted with EtOAc. The combined organic layers are dried over $MgSO_4$, filtered or passed through a phase separator and concentrated to afford the desired compound.

Illustrative Synthesis of Int 142

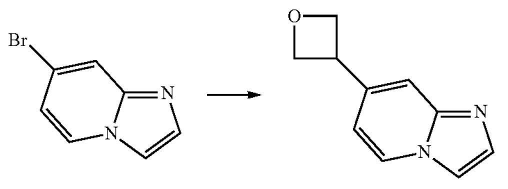 [SMILES: Brc1ccn2ccnc2c1 ; c1cn2ccc(C3COC3)cc2n1]

In a sealed vial under $N_2$ atmosphere are introduced degassed DMAc, 7-Bromoimidazo[1,2-a]pyridine (CAS #808744-34-5; 300 mg, 1.52 mmol, 1 eq.), 3-bromooxetane (CAS #39264-79-3; 253 μL, 3.05 mmol, 2 eq.), $NiCl_2$·glyme (34 mg, 0.15 mmol, 0.1 eq.), ligand Int 230 (36 mg, 0.15 mmol, 0.1 eq.), sodium iodide (57 mg, 0.38 mmol, 0.25 eq.), zinc powder (199 mg, 3.05 mmol, 2 eq.) and TFA (12 μL, 0.15 mmol, 0.1 eq.). The resulting solution is heated to 60° C. for 1 h then filtered on Clarcel® and washed with EtOAc. The filtrate is quenched with a 5% aq. ammonia solution, extracted with EtOAc. The combined organic layers are passed through a phase separator and concentrated in vacuo to afford the desired compound.

1.25. Method A5: Functionalization of Halogenated Heteroaryl Compound by Addition to Keto Derivative To a solution of 7-bromoimidazo[1,2-a]pyridine (CAS #808744-34-5; 1 eq.) in dry THF under inert atmosphere at 0° C. is added a iPrMgCl·LiCl solution (1.3 M in THF, CAS #745038-86-2; 3 eq.). The resulting solution is allowed to warm to RT, stirred at RT for 1.5 to 2 h, then cooled to 0° C. before adding dropwise the corresponding ketone or Weinreb amide (4 to 6 eq.) in solution in THF. The resulting solution is stirred at RT for 4 to 48 h then quenched with a sat. $NH_4Cl$ solution and concentrated. The residue is purified by reverse phase flash chromatography.

Alternative work-up: The solution is quenched with a sat. $NH_4Cl$ solution and extracted with EtOAc. The combined organic layers are washed with brine, dried over $MgSO_4$, filtered or passed through a phase separator and concentrated. The residue is purified by flash chromatography on silica gel.

Illustrative Synthesis of Int 141

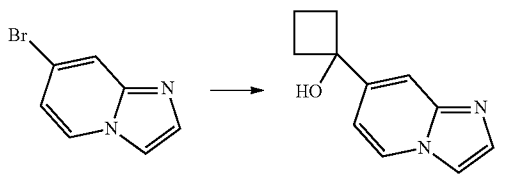 [SMILES: Brc1ccn2ccnc2c1 ; OC1(c2ccn3ccnc3c2)CCC1]

To a solution of 7-bromoimidazo[1,2-a]pyridine (1 g, 5.07 mmol, 1 eq.) in dry THF (3 mL) under $N_2$ atmosphere at 0° C. is added a iPrMgCl·LiCl solution (1.3 M in THF, 11.7 mL, 15.2 mmol, 3 eq.). The resulting solution is stirred at RT for 1.5 h, then cooled to 0° C. before adding dropwise cyclobutanone (CAS #1191-95-3; 1.9 mL, 25.4 mmol, 5 eq.) in solution in THF (10 mL). The resulting solution is stirred at RT for 4 h then quenched with a sat. $NH_4Cl$ solution and extracted with EtOAc. The combined organic layers are washed with brine, passed through a phase separator and concentrated. The residue is purified by flash chromatography on silica gel (eluting with DCM/MeOH 100/0 to 95/5) to afford the desired compound.

1.26. Method A6: Functionalization of Halogenated Heteroaryl Compound by Photochemical Reaction In a sealed vial containing a solution of 2-amino-4-bromopyridine (CAS #84249-14-9; 1 eq.), the corresponding carboxylic acid (2 eq.) and $Cs_2CO_3$ (CAS #534-17-8; 2 eq.) in dry DMF are added $NiCl_2$·glyme (CAS #29046-78-4; 0.2 eq.), dtbpy (CAS #72914-19-3; 0.15 eq.) and (Ir[dF($CF_3$)ppy]$_2$(dtbpy))$PF_6$ (CAS #870987-63-6; 0.01 eq.). The resulting mixture is degassed for 15 min then the vial is sealed and irradiated at 34 W for 48 to 72 h. The reaction mixture is then concentrated to dryness, the residue is diluted with a 2N NaOH solution or a sat. $NaHCO_3$ solution and extracted with EtOAc. The combined organic layers are dried over $Na_2SO_4$, filtered and concentrated. The residue is purified by flash chromatography on silica gel.

Illustrative Synthesis of Int 150

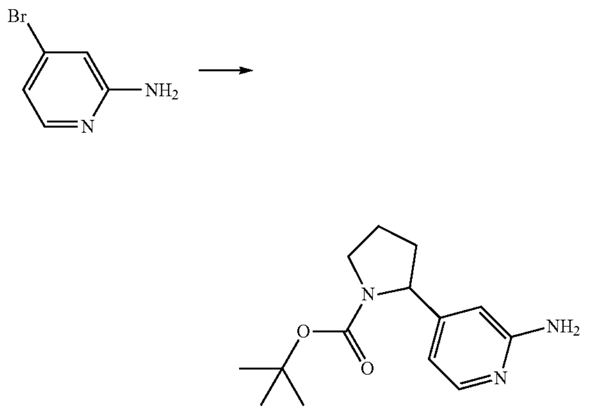

In a sealed vial containing a solution of 2-amino-4-bromopyridine (138 mg, 0.80 mmol, 1 eq.), N-(tert-butoxycarbonyl)-L-proline (CAS #15761-39-4; 345 mg, 1.6 mmol, 2 eq.) and $Cs_2CO_3$ (521 mg, 1.6 mmol, 2 eq.) in dry DMF (1 mL) are added $NiCl_2$·glyme (35 mg, 0.16 mmol, 0.2 eq.), dtbpy (32 mg, 0.12 mmol, 0.15 eq.) and (Ir[dF($CF_3$)ppy]$_2$(dtbpy))$PF_6$ (9 mg, 0.008 mmol, 0.01 eq.). The resulting mixture is degassed for 15 min then the vial is sealed and irradiated at 34 W for 48 h. The reaction mixture is then concentrated to dryness, the residue is diluted with a 2N NaOH solution and extracted with EtOAc. The combined organic layers are dried over $Na_2SO_4$, filtered and concentrated. The residue is purified by flash chromatography on silica gel (eluting with heptane/EtOAc 90/10 to 0/100) to afford the desired compound.

1.2.7. Method A7: Functionalization of Halogenated Pyridine by Metalation

To a solution of bromo pyridine derivative (1 eq.) in dry THF under inert atmosphere at −78° C. is added a methyllithium solution (1.6 M in $Et_2O$, CAS #917-54-4; 1.2 eq.). The resulting solution is stirred at −78° C. for 15 min, then a nBuLi solution is added (2.5 M in hexane, CAS #109-72-8; 1.2 eq.). Alternatively only nBuLi is added. After stirring at −78° C. for 15 min, a solution of the corresponding ketone (1.2 to 3 eq.) is introduced. The resulting solution is allowed to warm to RT for 10 min then is quenched with water and extracted with EtOAc. The combined organic layers are dried over $MgSO_4$, filtered and concentrated. The residue is purified by flash chromatography on silica gel.

Illustrative Synthesis of Int 178

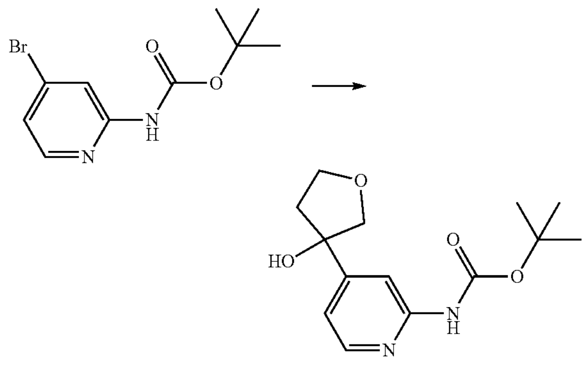

To a solution of 2-(Boc-amino)-4-bromopyridine (CAS #207799-10-8; 400 mg, 1.46 mmol, 1 eq.) in dry THF (4.5 mL) under inert atmosphere at −78° C. is added methyllithium (1.6 M in $Et_2O$, 1.1 mL, 1.76 mmol, 1.2 eq.). The resulting solution is stirred at −78° C. for 15 min, then a nBuLi solution is added (2.5 M in hexane, 0.7 mL, 1.76 mmol, 1.2 eq.). After stirring at −78° C. for 15 min, a solution of 4,5-(dihydro-3(2H)-furanone (CAS #22929-52-8; 378 mg, 4.39 mmol, 3 eq.) is introduced. The resulting solution is allowed to warm to RT for 10 min then is quenched with water and extracted with EtOAc. The combined organic layers are dried over $MgSO_4$, filtered and concentrated. The residue is purified by flash chromatography on silica gel (eluting with heptane/EtOAc 100/0 to 0/100) to afford the desired intermediate.

1.2.8. Method A8: Functionalization of Halogenated Heteroaryl Compound by Suzuki Coupling/Degradation To a solution of 7-bromoimidazo[1,2-a]pyridine (CAS #808744-34-5; 1 eq.) in DMSO and 4-(4,4,5,5-tetramethyl-1,3,2-dioxaborolan-2-yl)isoxazole (CAS #928664-98-6; 1.1 eq.), under $N_2$ atmosphere are added water and potassium fluoride (CAS #7789-23-3; 3 eq.). The resulting solution is degassed and Pd(dppf)$Cl_2$·DCM adduct (CAS #95464-05-4; 0.10 eq.) is added. The mixture is stirred at 90-135° C. for 3 to 18 h. The reaction mixture is cooled at RT and filtered over Dicalite™. The filtrate is diluted with brine and water, extracted with EtOAc. The combined organic layers are dried over $MgSO_4$ or $Na_2SO_4$, filtered and concentrated to dryness. The residue is purified by flash chromatography on silica gel.

Illustrative Synthesis of Int 62

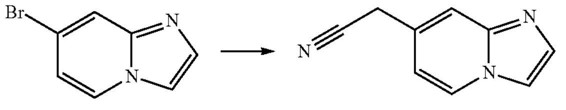 [SMILES: Brc1ccn2ccnc2c1 ; N#CCc1ccn2ccnc2c1]

To a solution of 7-bromoimidazo[1,2-a]pyridine (1.3 g, 6.6 mmol, 1 eq.) in DMSO (47 mL) and 4-(4,4,5,5-tetramethyl-1,3,2-dioxaborolan-2-yl)isoxazole (1.4 g, 7.3 mmol, 1.1 eq.), under $N_2$ atmosphere are added water (20 mL) and potassium fluoride (1.15 g, 19.8 mmol, 3 eq.). The resulting solution is degassed and Pd(dppf)$Cl_2$·DCM adduct (483 mg, 0.66 mmol, 0.10 eq.) is added. The mixture is stirred at 130° C. for 3.5 h, then at 90° C. for 18 h. The reaction mixture is cooled at RT and filtered over Dicalite™. The filtrate is diluted with brine and water, extracted with EtOAc. The combined organic layers are dried over $Na_2SO_4$, filtered and concentrated to dryness. The residue is purified by flash chromatography on silica gel (eluting with DCM/MeOH 100/0 to 98/2) to afford the desired intermediate.

Illustrative Synthesis of Int 207

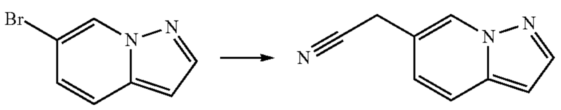 [SMILES: Brc1ccc2ccnn2c1 ; N#CCc1ccc2ccnn2c1]

To a solution of 6-bromopyrazolo[1,5-a]pyridine (600 mg, 3.0 mmol, 1 eq.) in DMSO (21 mL) under $N_2$ atmosphere are added 4-(4,4,5,5-tetramethyl-1,3,2-dioxaborolan-2-yl)isoxazole (650 mg, 3.3 mmol, 1.1 eq.), water (9 mL) and potassium fluoride (530 mg, 9.1 mmol, 3 eq.). The resulting solution is degassed and Pd(dppf)$Cl_2$·DCM adduct (230 mg, 0.30 mmol, 0.10 eq.) is added. The mixture is stirred at 135° C. for 18 h, then cooled at RT and filtered over Dicalite™. The filtrate is diluted with brine, extracted with EtOAc. The combined organic layers are dried over $MgSO_4$, filtered and concentrated to dryness. The residue is purified by flash chromatography on silica gel (eluting with heptane/EtOAc 100/0 to 50/50) to afford the desired intermediate.

1.2.9. Method A9: Functionalization of Halogenated Heteroaryl Compound by Coupling with Organolithium Derivative In a round-bottom flask previously degassed with $N_2$ containing BINAP (CAS #98327-87-8; 0.15 eq.) and $Pd_2dba_3$ (CAS #51364-51-3; 0.075 eq.) is added degassed THF (0.24 mL). The resulting suspension is stirred under $N_2$ for 20 min. In a separate flask bromide (1.0 eq.) and carbonitrile (2 to 3 eq.) are diluted with cyclopentylmethyl ether. The resulting solution is degassed by bubbling $N_2$ through the solution for 10 min. The previous suspension of catalyst is then added to the solution of reagents via syringe and LiHMDS is added dropwise (1M solution in THF, 2 to 3 eq.) at RT. The reaction mixture is heated to 80° C. for 3 h, then stirred at RT for 18 h. The reaction solution is quenched by addition of a sat. $NH_4Cl$ solution and extracted with EtOAc. The combined organic layers are washed with brine, dried over $MgSO_4$, filtered and concentrated in vacuo. The residue is purified either by flash chromatography on silica gel, or by preparative HPLC then recrystallized in hot ACN, filtered, washed with ACN and $Et_2O$ and dried to afford the desired compound.

Illustrative Synthesis of Cpd 107

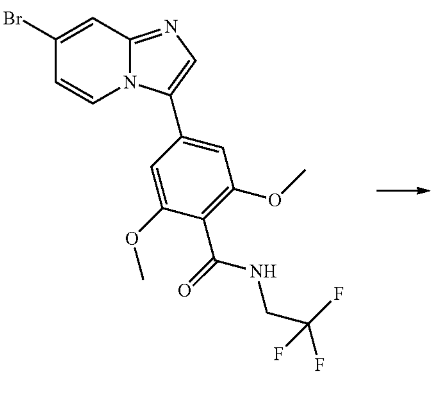

-continued

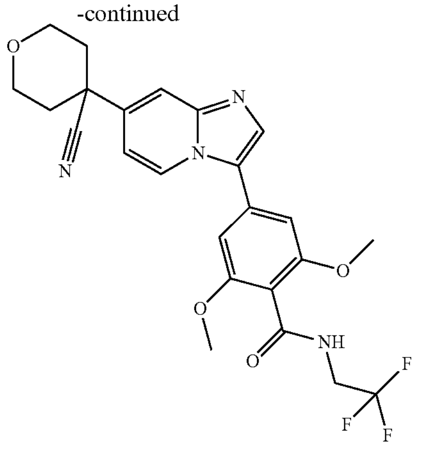

In a round-bottom flask previously degassed with $N_2$ containing BINAP (CAS #98327-87-8; 10 mg, 0.016 mmol, 0.15 eq.) and $Pd_2dba_3$ (CAS #51364-51-3; 7.4 mg, 0.008 mmol, 0.075 eq.) is added degassed THF (0.24 mL). The resulting suspension is stirred under $N_2$ for 20 min. In a separate flask bromide Int 36 (50 mg, 0.11 mmol, 1.0 eq.) and tetrahydropyran-4-carbonitrile (CAS #4295-99-2; 36 mg, 0.33 mmol, 3 eq.) are diluted with cyclopentylmethyl ether (0.63 mL). The solution is degassed by bubbling $N_2$ through the solution for 10 min. The previous suspension of catalyst is then added to the solution of reagents via syringe. To the resulting mixture is added dropwise LiHMDS (1M solution in THF, 0.33 mL, 0.33 mmol, 3 eq.) at RT. The reaction mixture is heated to 80° C. for 3 h, then stirred at RT for 18 h. The reaction solution is quenched by addition of a sat. $NH_4Cl$ solution and extracted with EtOAc. The combined organic layers are washed with brine, dried over $MgSO_4$, filtered and concentrated in vacuo. The residue is purified by preparative HPLC then recrystallized in hot ACN, filtered, washed with ACN and $Et_2O$ and dried to afford the desired compound.

1.2.10. Method B: Iodination of Heteroaryl Compound

To a solution of heteroaryl compound (1 eq.) in ACN or DMF under $N_2$ atmosphere is introduced N-iodosuccinimide (CAS #516-12-1; 1.1 to 1.2 eq.). The resulting solution is stirred either at RT for 18 h or at 60° C. for 1 to 18 h until total completion. The reaction mixture is quenched with a 10% $Na_2S_2O_3$ aq. solution and extracted with EtOAc or DCM. The combined organic layers are washed with brine, dried over $Na_2SO_4$ or $MgSO_4$, filtered or passed through a phase separator and concentrated. The residue is used directly in the next step without further purification or purified by flash chromatography on silica gel. Alternative work-up: when the reaction is performed in DMF, the reaction mixture is quenched by water, the precipitate formed is filtered and dried in vacuo to afford the desired iodo heteroaryl compound.

Illustrative Synthesis of Int 190

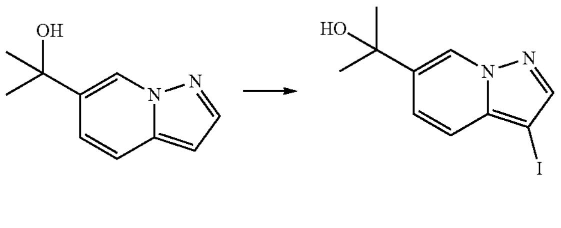

To a solution of Int 191 (80 mg, 0.45 mmol, 1 eq.) in ACN (2.3 mL) under $N_2$ atmosphere is introduced N-iodosuccinimide (118 mg, 0.50 mmol, 1.1 eq.). The resulting solution is stirred at RT for 18 h. The reaction mixture is quenched with a 10% $Na_2S_2O_3$ aq. solution and extracted with EtOAc. The combined organic layers are washed with brine, dried over $Na_2SO_4$ filtered or passed through a phase separator and concentrated. The residue is used directly in the next step without further purification.

Illustrative Synthesis of Int 169

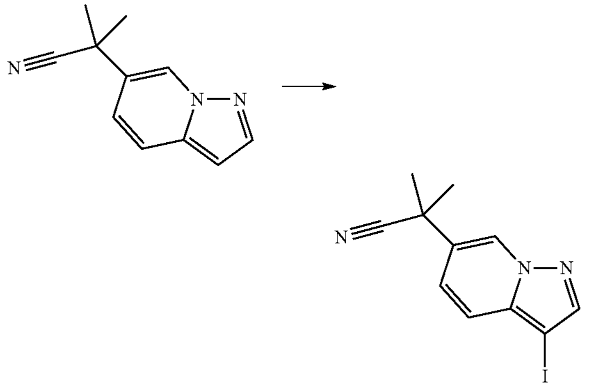

To a solution of Int 171 (5.0 g, 27.0 mmol, 1 eq.) in DMF (50 mL) under $N_2$ atmosphere is introduced N-iodosuccinimide (7.3 g, 32.4 mmol, 1.2 eq.). The resulting solution is stirred at RT for 18 h. The reaction mixture is quenched by water (150 mL), the precipitate formed is filtered and dried in vacuo to afford the desired iodo heteroaryl compound.

1.2.11. Method C: Suzuki Coupling of Heteroaryl Compound

A pressure reactor or an open round bottom flask equipped with a condenser is charged with heteroarylbromide or iodide derivative (1 eq.), boronic acid or boronic acid pinacol ester (1.2 to 1.5 eq.), a base ($Cs_2CO_3$, $K_2CO_3$, or KF, 1.3 to 3 eq.) and dioxane/water solvent mixture: 4/1 or 3/1 or DMF/water solvent mixture: 4/1. The mixture is either heated to 100° C., degassed with $N_2$ then Pd catalyst ($Pd(PPh_3)_4$ CAS #14221-01-3; $Pd(dppf)Cl_2 \cdot DCM$ adduct CAS #95464-05-4; or Xphos Pd G3 CAS #1445085-55-1; 0.07 to 0.2 eq.) is added, or degassed with $N_2$ or Ar at RT before addition of the Pd catalyst. The mixture is stirred at 90 to 100° C. for 5 min to 18 h. The reaction mixture is concentrated in vacuo or not, and diluted in EtOAc or DCM and water or a sat. $NaHCO_3$ solution. The resulting mixture is filtered over sand or Dicalite™ or not. The mixture is then extracted with EtOAc or DCM. The combined organic layers are optionally washed with brine, dried over anhydrous $Na_2SO_4$ or $MgSO_4$, filtered, or passed through a phase separator, and then concentrated in vacuo. The residue is purified by flash chromatography on silica gel to afford the expected compound.

Alternative work-up 1: The reaction mixture is filtered on celite or Dicalite™, washed with EtOAc and concentrated in vacuo. The residue is either directly purified by flash chromatography, or diluted with water and EtOAc or DCM. The combined organic layers are washed with brine, dried over anhydrous $Na_2SO_4$ or $MgSO_4$, filtered, or passed through a phase separator, and then concentrated in vacuo. The residue is purified by flash chromatography on silica gel to afford the desired compound.

Alternative work-up 2: The reaction mixture is concentrated in vacuo then extracted with DCM. The combined organic layers are washed with water, passed through a phase separator, and then concentrated in vacuo. The residue is taken up in hot ACN or DCM, the insoluble is filtered to afford the desired compound.

Alternative work-up 3: The reaction mixture is concentrated in vacuo then diluted in DMSO and purified by preparative HPLC.

Illustrative Synthesis of Cpd 219

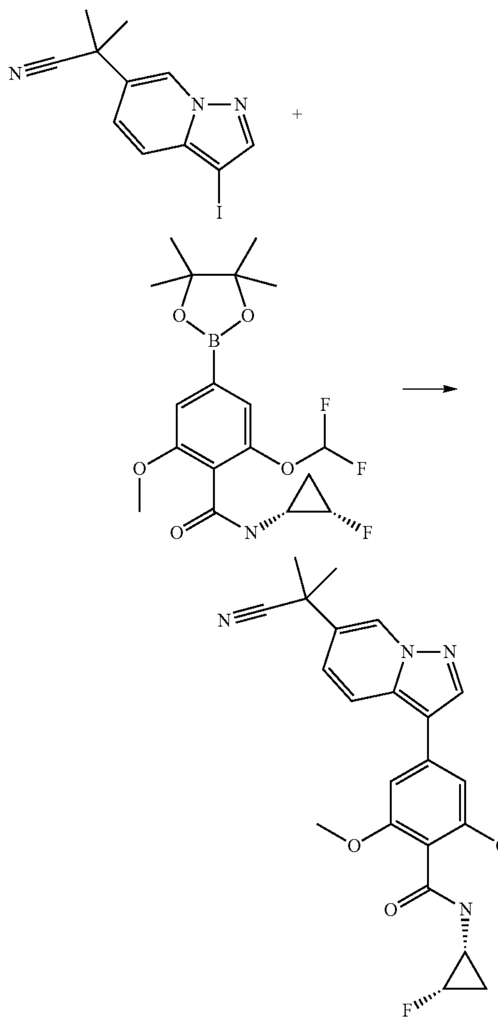

In a round bottom flask under $N_2$ atmosphere containing a solution of 2-(3-iodopyrazolo[1,5-a]pyridin-6-yl)-2-methyl-propanenitrile Int 169 (10 g, 32.1 mmol, 1 eq.) in a 4/1 degassed mixture of 1,4-dioxane (178 mL) and water (52 mL) are added Int 8 (14.2 g, 35.4 mmol, 1.1 eq.), $Cs_2CO_3$ (32 g, 96 mmol, 3 eq.) and Pd(dppf)$Cl_2$·DCM (2.8 g, 3.2 mmol, 0.1 eq.). The reaction mixture is stirred at 90° C. for 30 min. then is quenched with a sat. $NaHCO_3$ solution and extracted with EtOAc (×3). The combined organic layers are dried over $Na_2SO_4$, filtered on celite and concentrated under reduced pressure. The residue is purified by flash chromatography on silica gel (eluting with heptane/EtOAc 100/0 to 30/70) to afford Cpd 219.

Illustrative Synthesis of Int 59

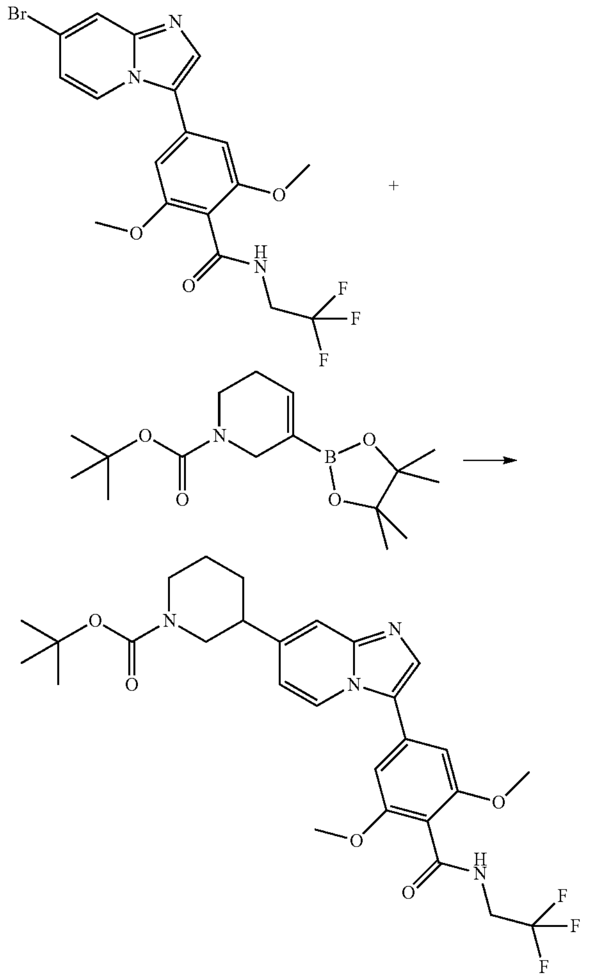

To a solution of bromide Int 36 (75 mg, 0.16 mmol, 1 eq.), boronate (CAS #885693-20-9; 43 mg, 0.19 mmol, 1.2 eq.), $Cs_2CO_3$ (156 mg, 0.48 mmol, 3 eq.) in a mixture dioxane/water 4/1 (2 mL) is added Pd(dppf)$Cl_2$·DCM (104 mg, 0.32 mmol, 2 eq.) The reaction mixture is stirred at 90° C. for 1 h. The reaction mixture is concentrated in vacuo, diluted in DCM and water. The combined organic layers are passed through a phase separator, and then concentrated in vacuo. The residue is purified by flash chromatography on silica gel (eluting with DCM/EtOAc 90/10 to 20/80) to afford the desired compound.

Illustrative Synthesis of Int 60

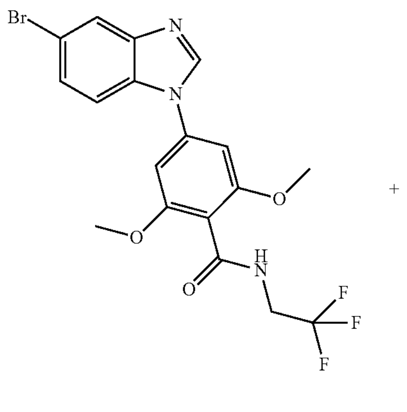

-continued

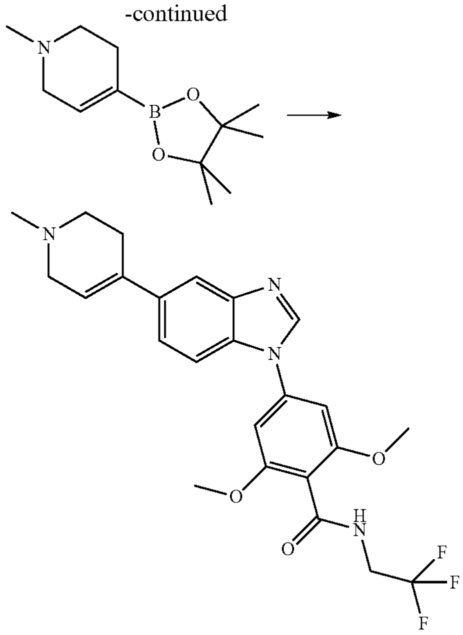

To a stirred solution of bromide Int 33 (75 mg, 0.16 mmol, 1 eq.) and corresponding boronate (CAS #454482-11-2; 43 mg, 0.19 mmol, 1.2 eq.) in degassed dioxane (2 mL) is added $Cs_2CO_3$ (104 mg, 0.32 mmol, 2 eq.) in $H_2O$ (0.5 mL). The mixture is degassed with argon for 10 min and $Pd(PPh_3)_4$ (19 mg, 0.016 mmol, 0.1 eq.) is added. The reaction mixture is stirred at 90° C. for 1 h. The reaction mixture is concentrated in vacuo, diluted in DCM and water. The combined organic layers are dried over anhydrous $MgSO_4$, filtered, and then concentrated in vacuo. The residue is purified by flash chromatography on silica gel (eluting with DCM/MeOH 100/0 to 90/10) to afford the desired compound.

1.2.12. Method D1: Synthesis of Amide Compound from Tert-Butylester Intermediate (Sequence: D1i then D1ii or D1iii)

1.2.12.1. D1i: Tert-Butylester Hydrolysis

A solution of tert-butyl ester (1 eq.) in a mixture DCM/TFA (4/1 to 9/1) is stirred at RT for 4 to 18 h. The reaction mixture is then diluted with toluene and concentrated in vacuo to afford the desired compound.

Illustrative Synthesis of Int 204

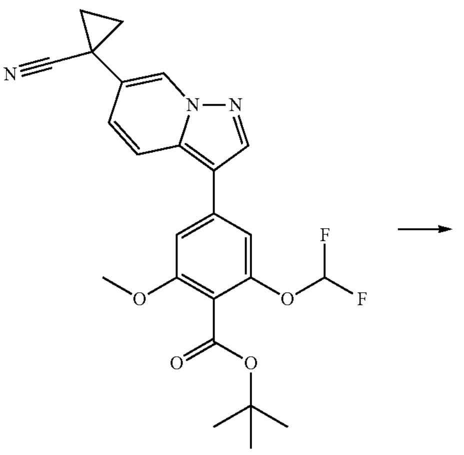

-continued

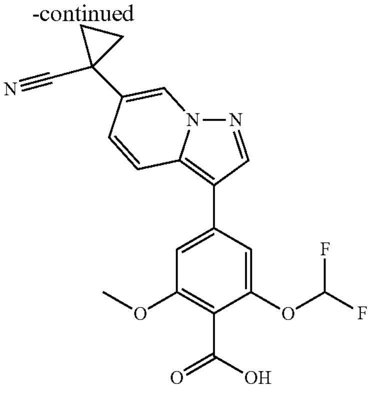

A solution of tert-butyl 4-[6-(1-cyanocyclopropyl)pyrazolo[1,5-a]pyridin-3-yl]-2-(difluoromethoxy)-6-methoxybenzoate Int 203 (115 mg, 0.25 mmol, 1 eq.) in a mixture 8/2 DCM/TFA (1.6 mL/0.4 mL) is stirred at RT for 3.5 h. The reaction mixture is concentrated, triturated with toluene and concentrated under reduced pressure to afford the desired acid intermediate.

1.2.12.2. D1ii: Peptidic Coupling

A flask is charged with the carboxylic acid derivative (1 eq.), anhydrous DMF or DMSO or DCM, HATU (1.2 to 2 eq.), DIPEA (3 to 10 eq.). The mixture is stirred for 5 to 15 min at RT then the amine or amine hydrochloride or sulfonate (1.1 to 4.8 eq.) is added. The mixture is stirred at RT for 1 to 72 h. The reaction mixture is concentrated in vacuo, then diluted with water or a sat. $NaHCO_3$ or $NH_4Cl$ solution and extracted with EtOAc. The combined organic layers are washed with brine or not, dried over anhydrous $Na_2SO_4$ or $MgSO_4$ and filtered, or passed through a phase separator, then concentrated in vacuo. The residue is purified by flash chromatography on silica gel or preparative HPLC.

Alternative work-up 1: the mixture is concentrated in vacuo, purified by flash chromatography on silica gel or C18 Biotage® reverse phase cartridge to afford the desired amide derivative.

Alternative work-up 2: when reaction performed in DMSO, the reaction mixture is directly purified by preparative HPLC.

Illustrative Synthesis of Int 5

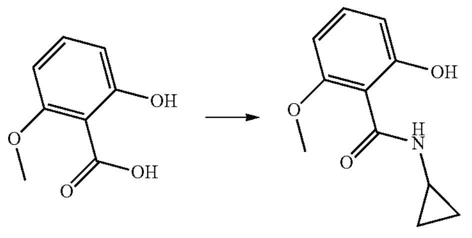

6-methoxysalicylic acid (CAS #3147-64-6; 10 g, 0.06 mmol, 1 eq.) is dissolved in DMF (50 mL), HATU (33.93 g, 0.09 mmol, 1.5 eq.) is added, followed 15 min later by cyclopropylamine (CAS #765-30-0; 10.18 g, 0.18 mmol, 3 eq.), and DIPEA (34.55 g, 0.26 mmol, 4.5 eq.). The reaction mixture is allowed to stir at RT for 18 h; then 1 eq. of HATU, 2 eq. of cyclopropylamine and 2 eq. of DIPEA are added. The reaction mixture is stirred at RT for 68 h. The reaction mixture is concentrated in vacuo and the residue is purified by flash chromatography on silica gel (eluting with heptane/

EtOAc 100/0 to 50/50). The collected fractions are concentrated in vacuo and triturated twice with $MeOH/Et_2O$. The filtrate is concentrated in vacuo to afford the desired compound.

Illustrative Synthesis of Int 33

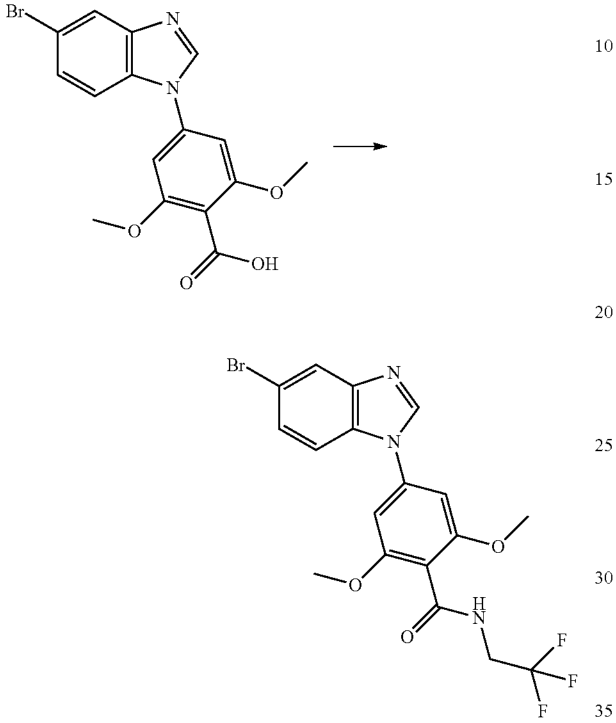

A flask is charged with Int 32 (0.3 g, 0.795 mmol, 1 eq.), HATU (332 mg, 0.874 mmol, 1.1 eq.), anhydrous DMF (9 mL) and DIPEA (0.4 mL, 2.39 mmol, 3 eq.). The mixture is stirred at RT for 10 min then 2,2,2-trifluoroethanamine hydrochloride (CAS #373-88-6; 216 mg, 1.6 mmol, 2 eq.) is added. The mixture is stirred at RT overnight. After evaporation of the DMF, the residue is partitioned between EtOAc and water. The aqueous layer is extracted with EtOAc. The combined organic layers are dried over anhydrous $Na_2SO_4$, filtered, concentrated in vacuo and purified by flash chromatography on silica gel (eluting with DCM/MeOH 100/0 to 95/5) to afford the desired intermediate.

Illustrative Synthesis of Cpd 235

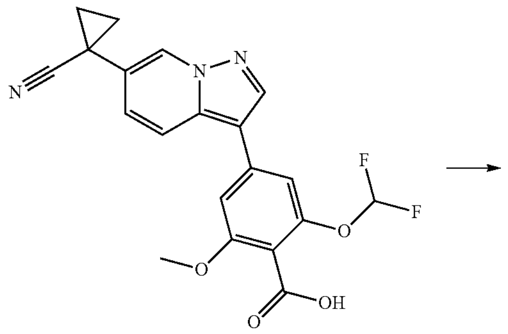

-continued

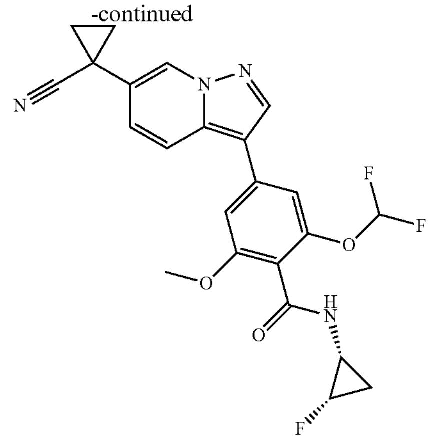

To a solution of 4-[6-(1-cyanocyclopropyl)pyrazolo[1,5-a]pyridin-3-yl]-2-(difluoromethoxy)-6-methoxy-benzoic acid Int 204 (95 mg, 0.23 mmol, 1 eq.) and HATU (105 mg, 0.28 mmol, 1.2 eq.) in anhydrous DCM (2 mL) is added DIPEA (121 μL, 0.69 mmol, 3 eq.). The reaction mixture is stirred at RT for 5 min and (1R,2S)-2-fluorocyclopropanamine 4-methylbenzenesulfonate (CAS #143062-84-4; 64 mg, 0.25 mmol, 1.1 eq.) is added. The reaction mixture is stirred at RT for 45 min then quenched with a sat. $NaHCO_3$ solution and the aqueous phase is extracted with EtOAc (*3). The combined organic layers are dried over $MgSO_4$, filtered and concentrated. The residue is purified by flash chromatography a on Biotage SNAP KP-NH column (eluting with heptane/EtOAc 90/10 to 20/80) to deliver the desired compound.

Illustrative Synthesis of Cpd 141

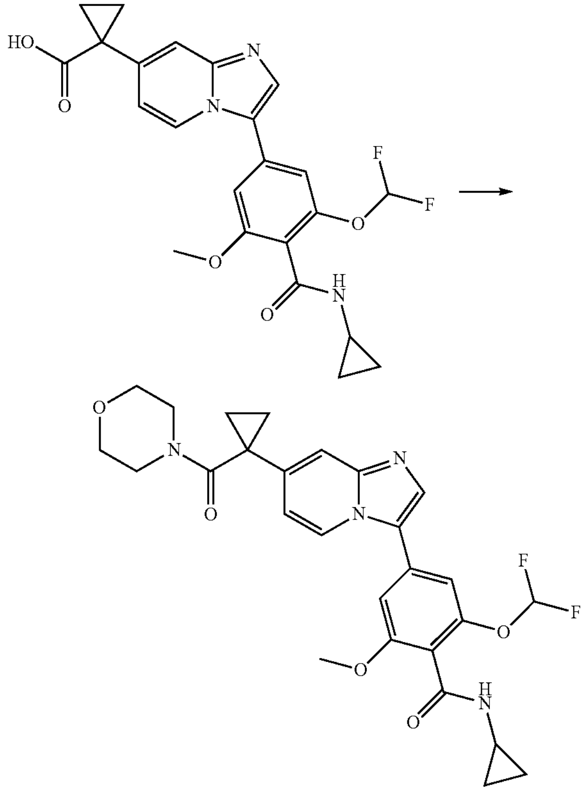

In a vial containing Cpd 114 (30 mg, 0.066 mmol, 1 eq.), are added HATU (50 mg, 0.13 mmol, 2 eq.), anhydrous DMSO (1 mL) and DIPEA (46 μL, 0.26 mmol, 4 eq.). The mixture is stirred at RT for 10 min then morpholine (CAS #110-91-8; 15 μL, 0.13 mmol, 2 eq.) is added. The mixture is stirred at RT for 1 h then directly purified by preparative HPLC to afford the desired compound.

1.2.12.3. D1iii: Amide Synthesis Via Acyl Chloride

To a solution of the carboxylic acid derivative (1 eq.) in DCM at 0° C. are added oxalyl chloride (1.2 eq.) and one drop of DMF. The resulting solution is stirred at 0° C. for 1 h then diluted with toluene and concentrated. The residue obtained is dissolved in DCM at 0° C. and DIPEA (6 eq.) and the corresponding amine (1.3 eq.) are added. The mixture is stirred at 0° C. for 1 h diluted with a sat. $NaHCO_3$ solution and extracted with DCM. The combined organic layers are passed through a phase separator, then concentrated in vacuo. The residue is purified by flash chromatography on silica gel or preparative HPLC.

Illustrative Synthesis of Cpd 243

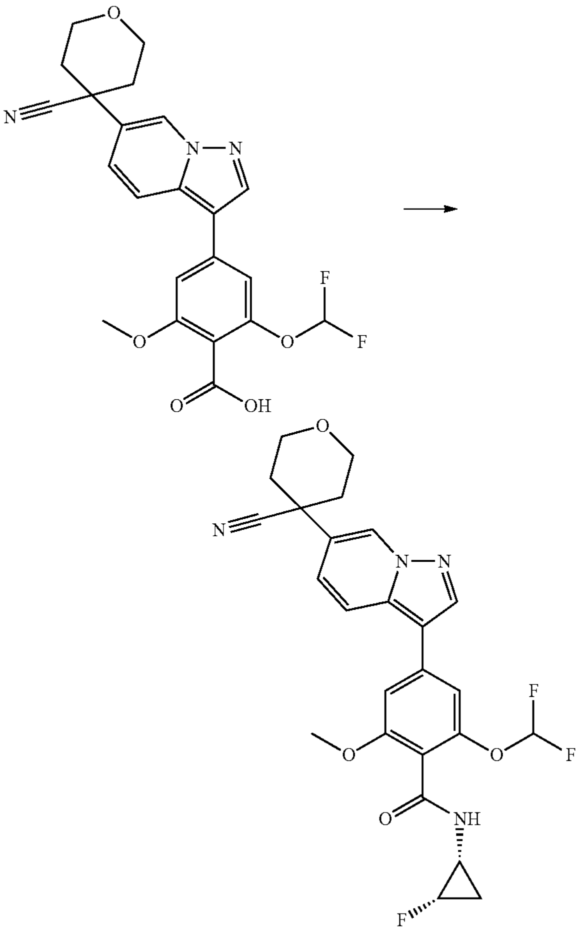

To a solution of 4-[6-(4-cyanotetrahydropyran-4-yl)pyrazolo[1,5-a]pyridin-3-yl]-2-(difluoromethoxy)-6-methoxy-benzoic acid Int 231 (180 mg, 0.40 mmol, 1.0 eq.) in DCM (2 mL) are added a drop of DMF and oxalyl chloride (0.24 mL, 0.48 mmol, 1.2 eq.) dropwise at 0° C. The resulting mixture is stirred at 0° C. for 1 h then concentrated and co-evaporated with toluene 2 times. The resulting beige solid is dissolved in DCM (2 mL) and DIPEA (0.420 mL, 2.41 mmol, 6 eq.) and (1R,2S)-2-fluorocyclopropanamine 4-methylbenzenesulfonate (0.523 mmol, 0.132 g, 1.3 eq.) are added dropwise. The reaction mixture is stirred at 0° C. for 1 h then quenched by a sat. $NaHCO_3$ solution and extracted with DCM. The combined organic layers are passed through a phase separator, concentrated in vacuo and the residue purified by flash chromatography on silica gel (eluting with DCM/MeOH 100/0 to 96/4). The resulting white solid is dissolved in $ACN/H_2O$, concentrated and finally dried in vacuo for 18 h to afford the desired compound.

1.2.13. Method D2: Synthesis of Amide Compound from Methyl Ester Intermediate (Sequence: D2i then D1ii Described Above)

1.2.13.1. D2i: Methyl Ester Saponification

To a solution of methyl ester derivative (1 eq.) in MeOH or a mixture MeOH/THF (1:1) is added a 2N NaOH solution (5 to 20 eq.) or NaOH in pellets (15 eq.) and water. The resulting solution is stirred at RT or 75° C. for 1 to 72 h. After cooling to RT the organic solvents are removed under reduced pressure. The residue is diluted with water, pH is adjusted until acidic pH with HCl (2N or 6N). The resulting suspension is filtered. The precipitate is washed with water and/or DCM and ACN and dried in vacuo to afford the desired compound.

Alternative work-up: The reaction mixture is quenched with a 1N HCl solution until pH is adjusted to 2 and is extracted with EtOAc. The combined organic layers are dried over $MgSO_4$ or passed through a phase separator, and concentrated in vacuo.

Illustrative Synthesis of Int 232

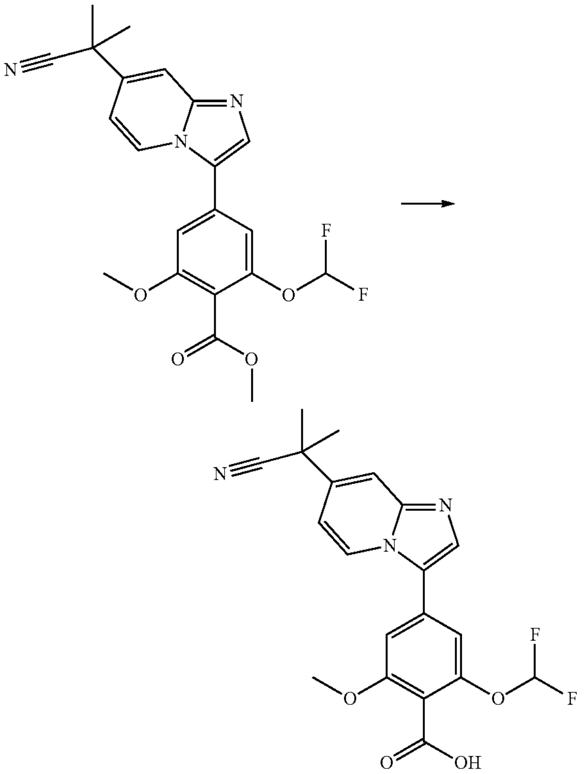

To a solution of methyl ester derivative Int 78 (855 mg, 2.06 mmol, 1 eq.) in a mixture MeOH/THF (1:1, 24 mL) is added NaOH in pellets (1.23 g, 30.9 mmol, 15 eq.) and water (5 mL). The resulting solution is heated at 75° C. for 1 h. After cooling to ambient temperature the organic solvents are removed under reduced pressure. The residue is diluted with water, pH is adjusted until acidic pH with HCl 2 N and the resulting suspension is stirred at RT for 10 min. The suspension is filtered, the precipitate is washed with water and DCM and ACN and dried in vacuo to afford the desired compound.

Illustrative Synthesis of Int 32

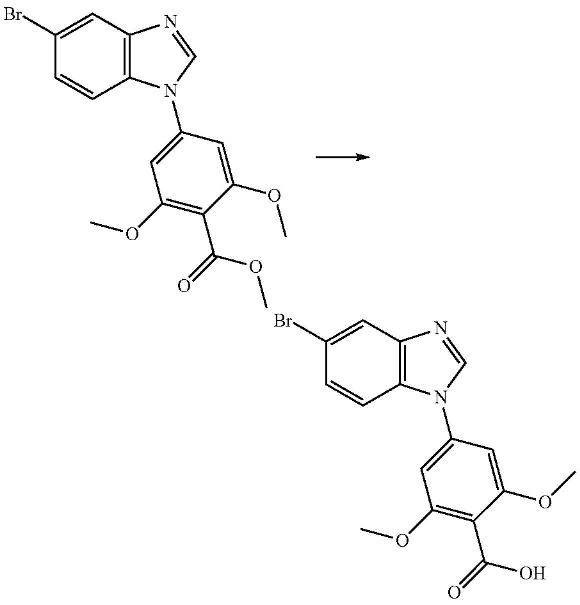

A mixture of methyl 4-(5-bromobenzimidazol-1-yl)-2,6-dimethoxy-benzoate Int 31 (82 g, 210 mmol, 1 eq.), MeOH (450 mL), THF (550 mL) and 2N NaOH (550 mL, 1100 mmol, 5.2 eq.) is stirred at 75° C. for 18 h. After cooling to RT the organic solvents are removed under reduced pressure. The residue is diluted with water (800 mL). pH is adjusted from 12.4 to 1.6 with a 6N HCl solution. The resulting suspension is stirred at 2° C. for 30 min and then filtered. The cake is washed with water (800 mL) and left on the funnel under suction for 20 min to give a dark red solid. The solid is dried in a vacuum oven at 45° C. for 2 h to afford the desired intermediate.

1.2.14. Method E: C—H Activation on Position 3 of an Imidazopyridine

The imidazopyridine derivative (1 eq.), the bromo derivative (0.6 to 1.5 eq.) and KOAc (2 to 3 eq.) are suspended in dry DMAC or DMSO, the mixture is degassed with $N_2$ before Pd(dppf)$Cl_2$·DCM adduct (CAS #95464-05-4, 0.03 to 0.1 eq.) is added. Alternatively all reagents are suspended in dry and degassed solvent, or all reagents are suspended in dry solvent. The mixture is stirred at 90-120° C. for 1 to 18 h. The reaction mixture is cooled to RT and directly purified by preparative HPLC to afford the desired compound.

Alternative work-up 1: The reaction mixture is concentrated in vacuo and purified by flash chromatography on silica gel to afford the desired compound.

Alternative work-up 2: The reaction mixture is diluted or not with EtOAc or DCM, water can be added also. The resulting suspension is filtered over Celite® or sand or passed through a phase separator and the filtrate concentrated in vacuo. The crude residue is then purified by flash chromatography on silica gel or preparative HPLC to afford the desired compound.

Alternative work-up 3: the reaction mixture is quenched with a sat. $NaHCO_3$ solution or water, extracted with EtOAc, the combined organic layers are or washed with water then brine and dried (over anhydrous $Na_2SO_4$ or $MgSO_4$), filtered and concentrated in vacuo. The residue obtained is purified by flash chromatography on silica gel to afford the desired compound.

Illustrative Synthesis of Cpd 213

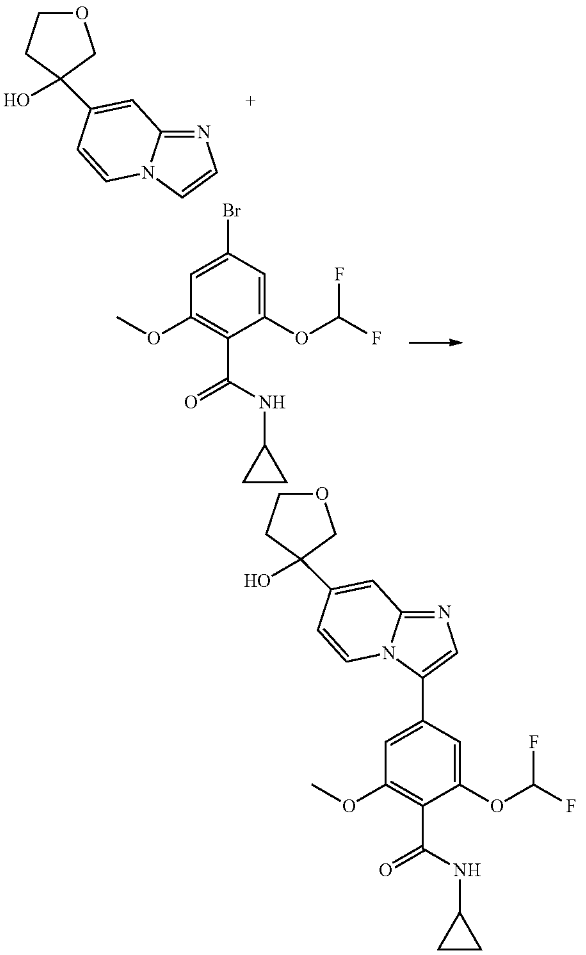

The imidazopyridine derivative Int 176 (40 mg, 0.20 mmol, 1 eq.), the bromo derivative Int 4 (99 mg, 0.30 mmol, 1.5 eq.), KOAc (38 mg, 0.39 mmol, 2 eq.) and Pd(dppf)$Cl_2$·DCM adduct (CAS #95464-05-4, 16 mg, 0.019 mmol, 0.1 eq.) are suspended in dry DMAC and the mixture is degassed with $N_2$. The mixture is stirred at 110° C. for 1 h. The reaction mixture is cooled to RT, concentrated in vacuo and purified by flash chromatography (eluting with DCM/MeOH 100/0 to 90/10) to afford Cpd 213.

1.2.15. Method F1: $S_NAr$ of Disubstituted Amino Benzoate on Halogeno Nitro Phenyl Derivative with LiHMDS A solution of methyl 4-amino-2,6-dimethoxy-benzoate (CAS #3956-34-1; 1 eq.) and 4-bromo-1-fluoro-2-nitro-benzene (CAS #364-73-8; 1 eq.) in THF is cooled at 0° C. under $N_2$. LiHMDS (1M solution in THF, CAS #4039-32-1; 2.3 eq.) is then added dropwise over 2 h. The reaction is quenched with water. THF is evaporated, and the rest of the reaction mixture is left stirring at 3° C. for 18 h. To the reaction mixture 2N HCl is added slowly while rapidly stirred and the mixture is stirred for 1 h at 3° C. The precipitate is filtered off then dried in a vacuum oven at 45° C. and 20 mbar for 5 h to afford the desired intermediate.

Illustrative Synthesis of Int 29

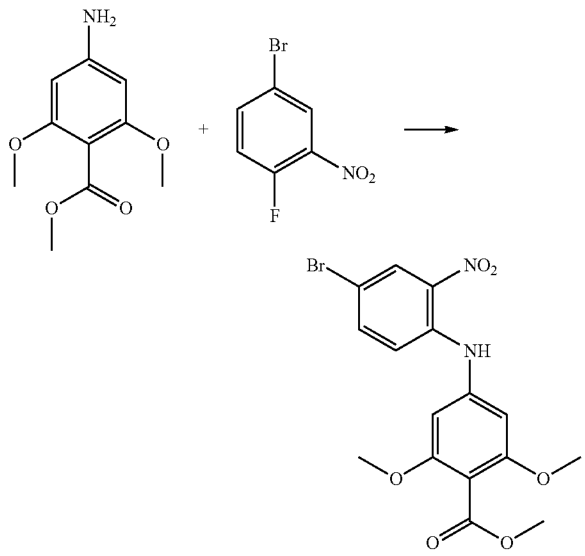

A solution of methyl 4-amino-2,6-dimethoxy-benzoate (40 g, 189.4 mmol, 1 eq.) and 4-bromo-1-fluoro-2-nitro-benzene (23.3 mL, 189.4 mmol, 1 eq.) in THF (1 L) is cooled at 0° C. under $N_2$. LiHMDS (1M solution in THF, 435.6 mL, 435.6 mmol, 2.3 eq.) is then added dropwise over 2 h. The reaction is quenched with water (800 mL). THF is evaporated, and the rest of the reaction mixture is left stirred at 3° C. for 18 h. To the reaction mixture 2 M HCl (600 mL) is added slowly while rapidly stirred and the mixture is stirred for 1 h at 3° C. The precipitate is filtered off then dried in a vacuum oven at 45° C. and 20 mbar for 5 h to afford the desired compound.

1.2.16. Method F2: $S_NAr$ of Disubstituted Amino Benzamide or Benzoate on Halogeno Nitro Phenyl Derivative with NaH

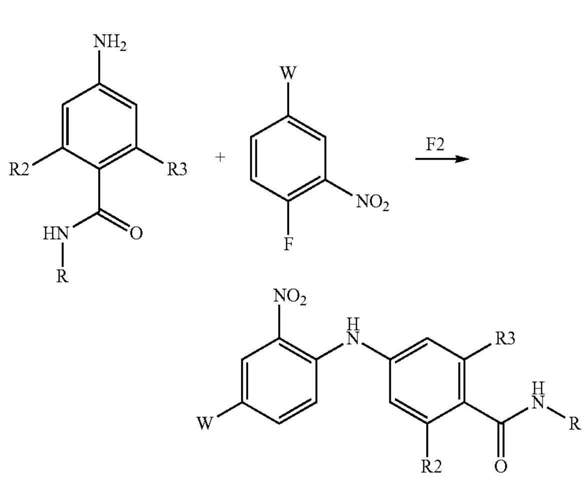

To a solution of disubstituted amino benzamide or methyl 4-amino-2,6-disubstituted-benzoate (1 to 1.1 eq.) in anhydrous THF, placed under argon atmosphere is added fluoro nitro derivative (1 to 1.7 eq.). The mixture is cooled at 0° C. and NaH (CAS #7646-69-7; 3 eq.) is added portionwise. The mixture is stirred at 0° C. for 10 min then at RT for 18 h. The mixture is cooled to 0° C., quenched with water or a sat. $NH_4Cl$ solution, diluted with EtOAc or DCM and water, a sat. $NH_4Cl$ solution or brine, extracted with EtOAc or DCM. The combined organic layers are dried or washed with brine then dried ($Na_2SO_4$ or $MgSO_4$), filtered and concentrated in vacuo. Purification by flash chromatography on silica gel affords the desired compound.

Illustrative Synthesis of Int 41

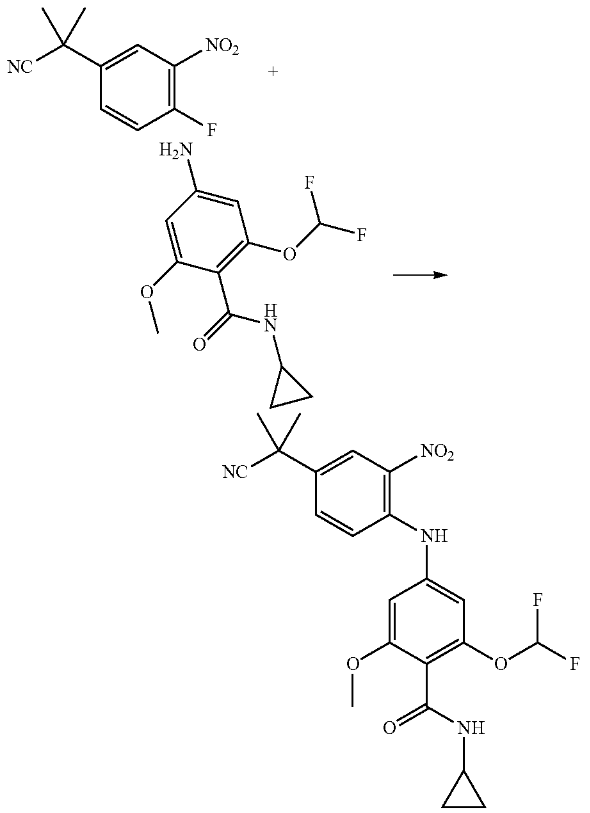

To a solution of Int 28 (82 mg, 0.30 mmol, 1 eq.) in anhydrous THF (2 mL), degassed with $N_2$ then placed under argon atmosphere is added Int 38 (69 mg, 0.33 mmol, 1.1 eq.). The mixture is cooled at 0° C. and NaH (36 mg, 0.90 mmol, 3 eq.) is added. The mixture is warmed to RT and stirred at RT for 18 h. The mixture is cooled to 0° C., quenched with a sat. $NH_4Cl$ solution, and extracted with EtOAc. The combined organic layers are dried over $MgSO_4$, filtered and concentrated in vacuo. The residue is purified by flash chromatography on silica gel (eluting with a gradient DCM/MeOH 100/0 to 99/1) to afford the desired compound.

1.2.17 Method G1: Nitro Reduction with $SnCl_2$, $2H_2O$/$SnCl_2$

A mixture of nitroaniline derivative (1 eq.), tin(II) chloride dihydrate (CAS #10025-69-1; 2.3 eq.) and tin(II) chloride (CAS #7772-99-8; 1.7 eq.) in EtOH is stirred at reflux for 2 h. After complete reduction to amine showed by UPLC monitoring, trimethyl orthoformate (CAS #149-73-5; 4 eq.) is added slowly to the mixture and the stirring continued at reflux for 2 h. The mixture is cooled to RT and concentrated to dryness. The residue is dissolved in EtOAc and washed with a 2N NaOH solution. The suspension formed (butter of tin) is filtered. The layers are separated. To the organic layer a sat. $NaHCO_3$ solution is added. Again the suspension forms. To the suspension 20% NaOH is added (exothermic). The layers are left to separate for 18 h. The organic layer is dried over $K_2CO_3$ and filtered. All filtration residues are washed with EtOAc, combined with aqueous layers and the layers are separated. The organic layers are combined and concentrated to dryness under reduced pressure. The residue is suspended in $Et_2O$, stirred for 30 min and filtered. The cake is left on the funnel under suction for 20 min to give the desired compound.

Illustrative Synthesis of Int 30

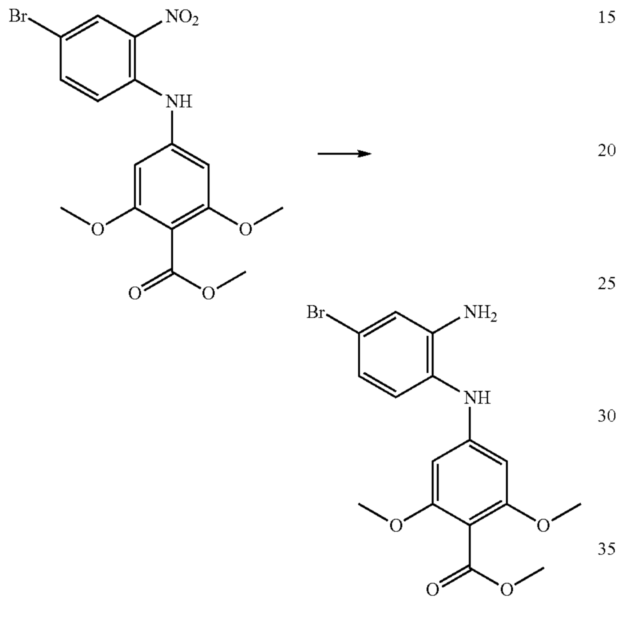

A mixture of Int 29 (148.2 g, 360.4 mmol, 1 eq.), tin(II) chloride dihydrate (188 g, 833.1 mmol, 2.3 eq.) and tin(II) chloride (116.2 g, 612.8 mmol, 1.7 eq.) in EtOH (1800 mL) is stirred at reflux for 2 h. After complete reduction to amine showed by UPLC monitoring, trimethyl orthoformate (157.7 mL, 1441.5 mmol, 4 eq.) is added slowly to the mixture and the stirring continued at reflux for 2 h. The mixture is cooled to RT and concentrated to dryness. The residue is dissolved in EtOAc (1400 mL) and washed with a 2N NaOH solution (600 mL). The suspension formed (butter of tin) is filtered (left filtering for 18 h). The layers are separated. To the organic layer sat. aq. $NaHCO_3$ (1000 mL) is added. Again the suspension forms. To the suspension 20% NaOH (2000 mL) is added. The layers are left to separate for 18 h. The organic layer is dried over $K_2CO_3$ and filtered. All filtration residues are washed with EtOAc, combined with aqueous layers and the layers are separated. The organic layers are combined and concentrated to dryness under reduced pressure. The residue is suspended in $Et_2O$ (500 mL), stirred for 30 min and filtered. The cake is left on the funnel under suction for 20 min to afford Int 30.

1.2.18. Method G2: Nitro Reduction with Zn/AcOH

To a solution of nitroamino derivative (1 eq.) in glacial AcOH stirred at RT or reflux is introduced by portions zinc dust (CAS #7440-66-6; 5 to 11.1 eq.). The resulting mixture is stirred (75° C. or reflux) for 10 min to 1 h. (completion of the reaction is monitored by TLC and/or UPLC-MS)). The reaction mixture is cooled to RT, filtered over Clarcel® after dilution in EtOAc or toluene or not diluted, rinsed with EtOAc or toluene or AcOH or EtOAc and toluene. The filtrate is evaporated to dryness and either the diamino derivative is used as such in the next step or the residue is purified by flash chromatography and used in the next step.

Illustrative Synthesis of Int 42

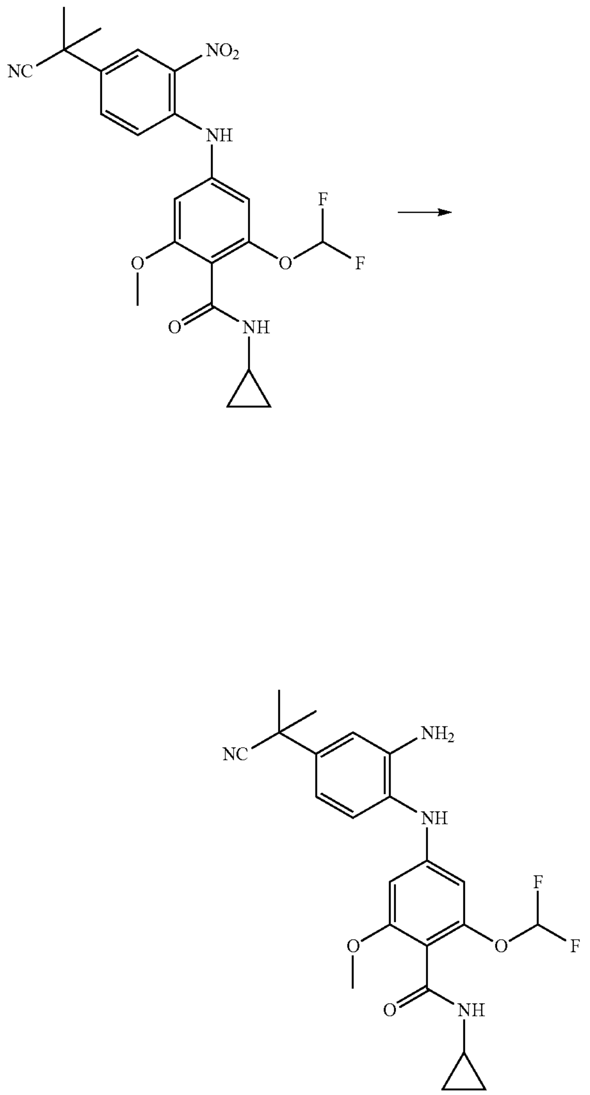

To a solution of Int 41 (75 mg, 0.16 mmol, 1 eq.) in glacial AcOH (1 mL) stirred at 75° C. is introduced zinc dust (105 mg, 1.6 mmol, 10 eq.). The resulting mixture is stirred at 75° C. for 1 h. The reaction mixture is cooled to RT, filtered over a pad of Dicalite™, rinsed with EtOAc. The filtrate is concentrated in vacuo to deliver the desired compound.

1.2.19. Method H: Cyclization into Benzimidazole

To a solution of diamino derivative (1 eq.) in MeOH is introduced p-Toluenesulfonic acid or p-Toluenesulfonic acid monohydrate (CAS #6192-52-5; 0.2 to 0.6 eq.) or AcOH (0.2 to 1 eq.) and trimethyl orthoformate (CAS #149-73-5; 3 to 5 eq.). The resulting mixture is stirred to 75° C.-reflux (30 min to for 18 h) and cooled to RT. The reaction mixture is concentrated in vacuo, purified by flash chromatography on silica gel or extracted with water/EtOAc and purified by flash chromatography on silica gel.

Illustrative Synthesis of Cpd 12

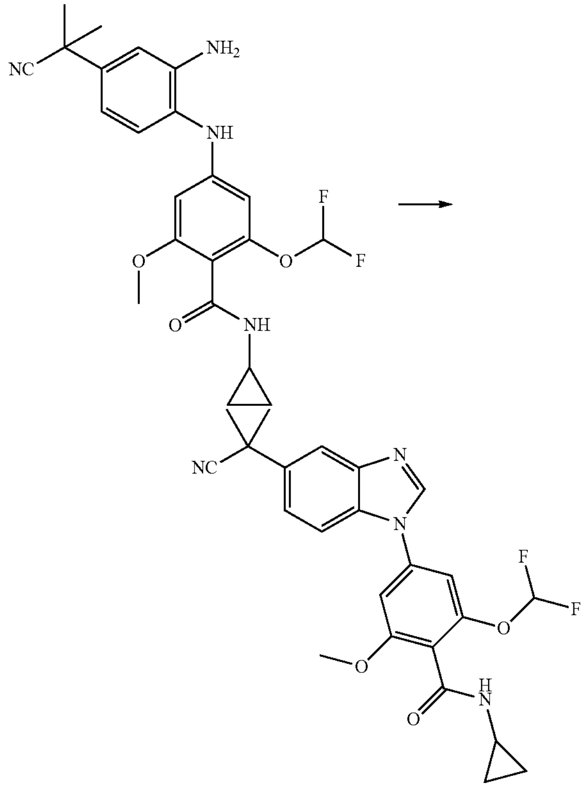

To a solution of intermediate Int 42 (69 mg, 0.16 mmol, 1 eq.) in MeOH (2 mL) is introduced AcOH (10 μL, 0.133 mmol, 0.2 eq.) and trimethyl orthoformate (88 μL, 0.80 mmol, 5 eq.). The resulting mixture is stirred to 75° C. for 18 h. The reaction mixture is concentrated in vacuo and purified by flash chromatography on silica gel (eluting with DCM/MeOH 100/0 to 98/2) to afford the desired compound.

1.2.20. Method I1: O-Alkylation

To a solution of alcohol (1 eq.) in THF or DMF or DMAc at 0° C. under inert atmosphere or not is added NaH (60% dispersion in mineral oil, CAS #7646-69-7; 1.2 to 1.3 eq.) and the mixture is stirred for 15 min. Then methyliodide (CAS #74-88-4; 1.2 to 2 eq.) or ethyl iodide (CAS #75-03-6; 2 eq.) is added and the reaction mixture is warmed to RT and stirred for 1 to 72 h. The reaction mixture is then concentrated to dryness, diluted with water and DCM. The aqueous phase is extracted with DCM and the combined organic layers are dried over $Na_2SO_4$, filtered and concentrated. The residue is purified by flash chromatography on silica gel.

Alternative work-up 1: the reaction mixture is quenched with a sat. $NH_4Cl$ solution and extracted with EtOAc. The combined organic layers are dried on a desiccant, filtered and concentrated. The residue is purified by flash chromatography on silica gel.

Alternative work-up 2: the reaction mixture is quenched with a sat. aq. $NH_4Cl$ solution and extracted with chloroform followed by EtOAc. The combined organic layers are dried on a desiccant, filtered and concentrated to afford the desired compound. The aqueous layer is then basified with a 2N NaOH solution and reextracted with chloroform. The combined organic layers are dried on a desiccant, filtered and concentrated to afford the desired compound.

Alternative work-up 3: the reaction mixture is quenched with water and then concentrated in vacuo. The residue is purified by flash chromatography on silica gel.

Illustrative Synthesis of Int 214

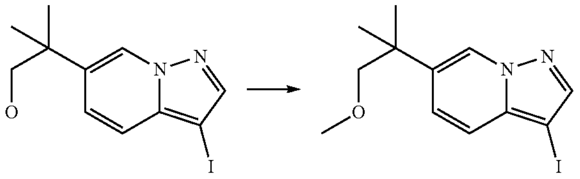 [SMILES: CC(C)(CO)c1ccc2c(I)cnn2c1 ; COCC(C)(C)c1ccc2c(I)cnn2c1]

To a solution of alcohol Int 208 (100 mg, 0.32 mmol, 1 eq.) in DMF (1.6 mL) at 0° C. is added NaH (60% dispersion in mineral oil, 16 mg, 0.40 mmol, 1.3 eq.) and the mixture is stirred for 15 min. Then methyliodide (29 μL, 0.48 mmol, 1.5 eq.) is added and the reaction mixture is warmed to RT and stirred for 1 h. The reaction mixture is then quenched with a sat. aq. $NH_4Cl$ solution and extracted with EtOAc. The combined organic layers are dried on a desiccant, filtered and concentrated. The residue is purified by flash chromatography on silica gel (eluting with heptane/EtOAc 100/0 to 60/40) to afford the desired intermediate.

1.2.21. Method 12: Amine Alkylation

To a stirred solution of amine derivative (1 eq.) in ACN or EtOH or DCM are added potassium carbonate (CAS #584-08-7; 2 to 3 eq.) and the corresponding halogeno derivative (1.1 to 3 eq.). The reaction mixture is stirred at RT or 90° C. for 18 to 72 h. Either the reaction mixture is concentrated in vacuo, diluted with DCM and water and the organic layer is separated, concentrated in vacuo or a sat. $NaHCO_3$ solution is added and the mixture is extracted with EtOAc, the combined organic layers are dried over anhydrous $Na_2SO_4$, filtered, concentrated in vacuo. The residue is purified by flash chromatography on silica gel to afford the desired compound.

Illustrative Synthesis of Cpd 4

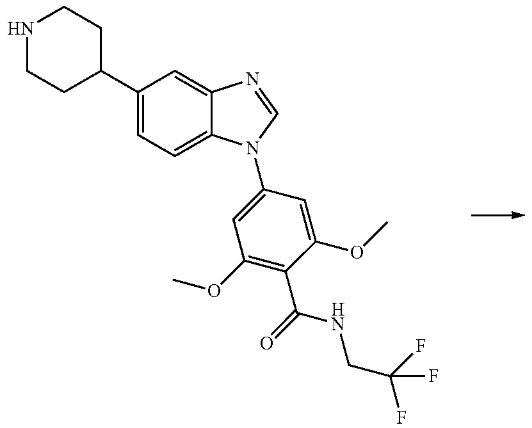

-continued

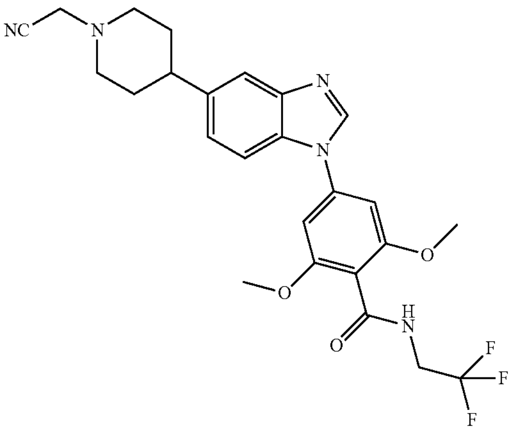

To a stirred solution of Cpd 3 (40 mg, 0.09 mmol, 1 eq.) in ACN (2 mL) are added potassium carbonate (25 mg, 0.16 mmol, 2 eq.) and 2-bromoacetonitrile (CAS #590-17-0; 8 μL, 0.09 mmol, 1.1 eq.). The reaction mixture is stirred at RT for 72 h. The reaction mixture is concentrated in vacuo, diluted with DCM and water. The organic layer is separated and concentrated in vacuo. The residue is purified by flash chromatography on silica gel (eluting with DCM/MeOH 100/0 to 96/4) to afford the desired compound.

1.2.22. Method J: N-Acylation

To a solution of amine derivative (1 eq.) in DCM at 0° C. or RT are added successively $Et_3N$ (1.5 to 3 eq.) and acetyl chloride (CAS #75-36-5; 1 eq. to 3 eq.) or acetic anhydride (CAS #108-24-7; 1.2 eq.). The resulting mixture is warmed to RT and stirred for 18 to 72 h. The reaction mixture is concentrated in vacuo and purified by preparative HPLC to afford the desired compound.

Alternative work-up 1: when a precipitate is formed, the solution is filtered and the resulting solid dried in vacuo to afford the desired compound.

Alternative work-up 2: The reaction mixture is concentrated in vacuo, diluted with DCM and a 2N NaOH solution. The organic layer is separated through a phase separator and concentrated in vacuo. The residue is purified by flash chromatography on silica gel to afford the desired compound.

Illustrative Synthesis of Cpd 169

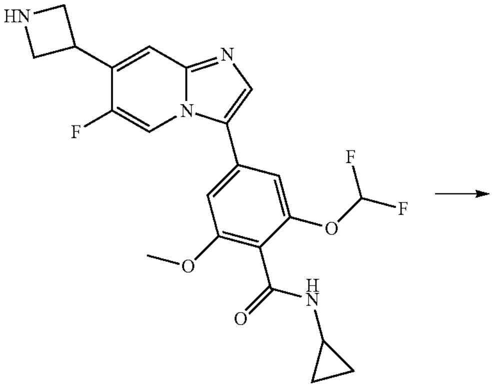

-continued

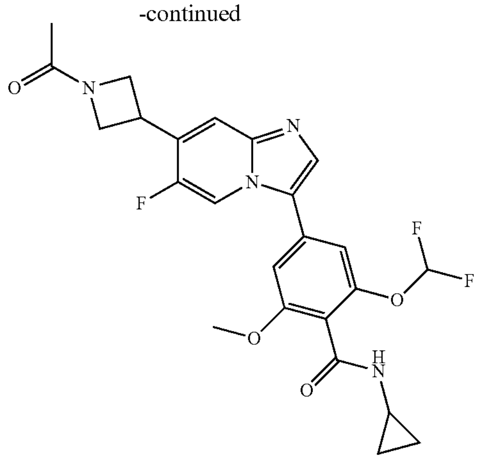

To a solution of Int 265 (44 mg, 0.08 mmol, 1 eq.) in DCM (1 mL) are added $Et_3N$ (40 μL, 0.24 mmol, 3 eq.) followed by acetyl chloride (6 μL, 0.08 mmol, 1 eq.). The reaction mixture is stirred at RT for 18 h. A precipitate is formed, is filtered and dried in vacuo to afford Cpd 169.

Illustrative Synthesis of Cpd 198

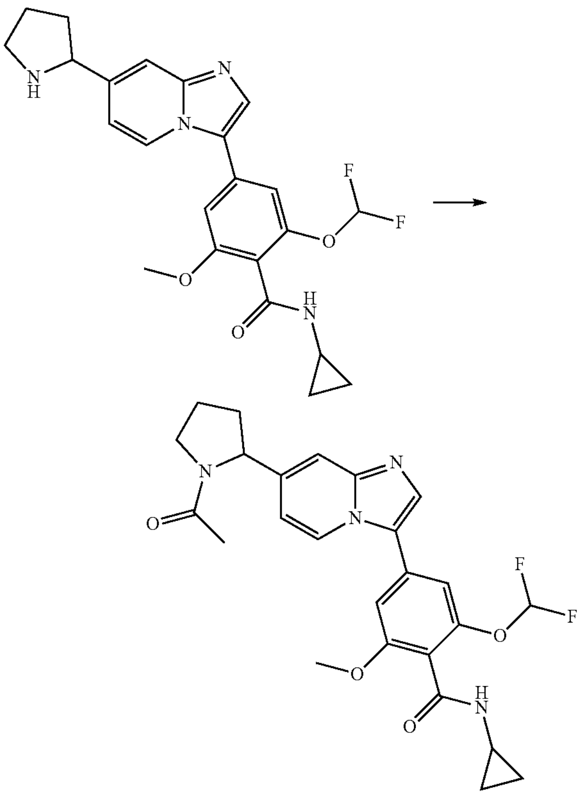

To a solution of Cpd 188 (50 mg, 0.11 mmol, 1 eq.) in DCM (1 mL) are added $Et_3N$ (24 μL, 0.17 mmol, 1.5 eq.) followed by acetic anhydride (13 μL, 0.13 mmol, 1.2 eq.). The reaction mixture is stirred at RT for 18 h. The reaction mixture is concentrated in vacuo, diluted with DCM and a 2N NaOH solution. The organic layer is separated through a phase separator and concentrated in vacuo. The residue is purified by flash chromatography on silica gel (eluting with DCM/MeOH 99/1 to 94/6) to afford the desired compound.

1.2.23. Method K1: Amine Functionalization by Reductive Amination

To a solution of the amine derivative (1 eq.) in MeOH or DCM are added formaldehyde (37% in water, CAS #50-00-0; 5 eq. to 5.5 eq.) and $NaBH_4$ (CAS #16940-66-2; 10 eq.) or $NaBH(OAc)_3$ (CAS #56553-60-7; 1.5 eq.). The mixture is stirred at RT for 1 to 18 h. The reaction mixture is quenched with water, the solvents are concentrated to dryness. The residue is purified by preparative HPLC to afford the desired compound.

Alternative work-up 1: The reaction mixture is quenched with a 2N NaOH solution and extracted with EtOAc. The combined organic layers are dried over $Na_2SO_4$, filtered, concentrated and the residue is purified by flash chromatography on silica gel to afford the desired compound.

Alternative work-up 2: The reaction mixture is diluted with water and extracted with DCM. The combined organic layers are passed through a phase separator, concentrated and the residue is recrystallized in hot ACN.

Alternative work-up 3: The reaction mixture is quenched with a sat. $NaHCO_3$ solution and extracted with EtOAc. The combined organic layers are dried over $Na_2SO_4$, filtered, concentrated and the residue is purified by flash chromatography on silica gel to afford the desired compound.

Illustrative Synthesis of Cpd 91

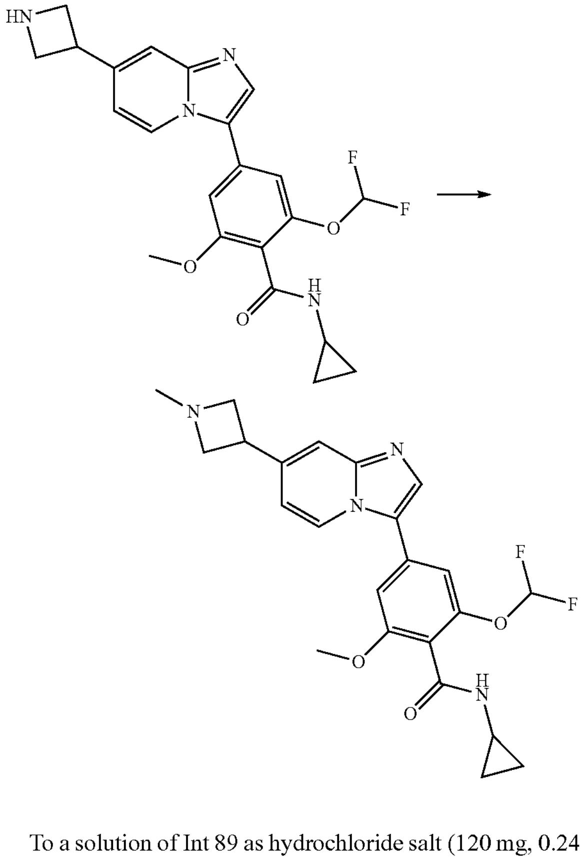

To a solution of Int 89 as hydrochloride salt (120 mg, 0.24 mmol, 1 eq.) in MeOH (2 mL) are added formaldehyde (37% in water, 100 µL, 1.31 mmol, 5.5 eq.) and $NaBH_4$ (90 mg, 2.39 mmol, 10 eq.). The mixture is stirred at RT for 1 h. The reaction mixture is quenched with water, concentrated and the residue is purified by preparative HPLC to afford the desired compound.

Illustrative Synthesis of Cpd 204

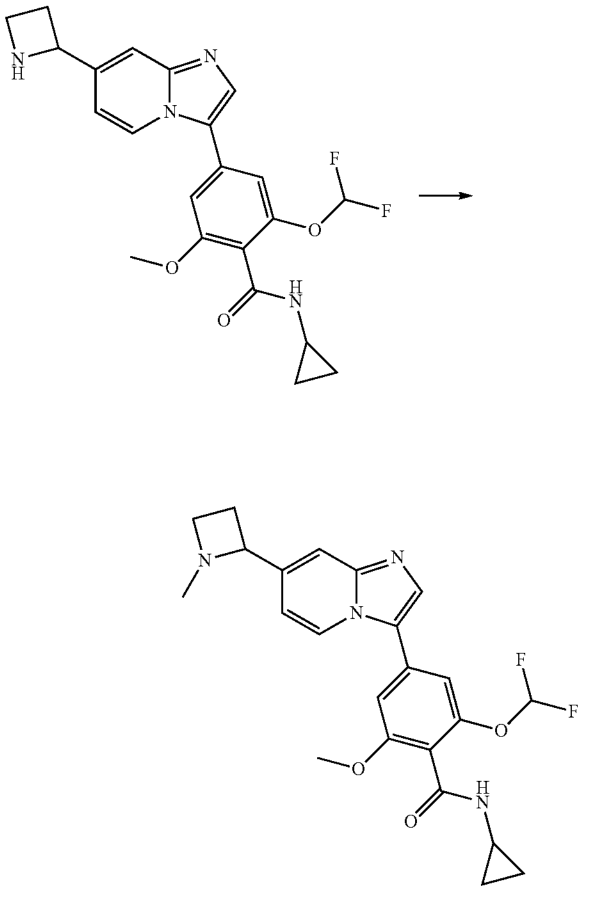

To a solution of Cpd 203 (36 mg, 0.08 mmol, 1 eq.) in DCM (2 mL) are added formaldehyde (37% in water, 32 µL, 0.42 mmol, 5 eq.) and $NaBH(OAc)_3$ (27 mg, 0.13 mmol, 1.5 eq.). The mixture is stirred at RT for 18 h. The reaction mixture is quenched with a sat. $NaHCO_3$ solution and extracted with EtOAc. The combined organic layers are dried over $Na_2SO_4$, filtered, concentrated and the residue is purified by flash chromatography on silica gel (eluting with DCM/MeOH 98/2 to 90/10 then EtOAc/MeOH 90/10) to afford the desired compound.

1.2.24. Method K2: Ketone Functionalization by Reductive Amination

To a solution of the amine derivative (1.5 eq.) in THF are added the ketone derivative (1 eq.) and $Ti(OEt)_4$ (CAS #3087-36-3; 1.5 eq.). When the amine derivative is hydrochloride salt, DIPEA (1.5 eq.) is added to the amine, the mixture is stirred for 15 min then the ketone and $Ti(OEt)_4$ are added. The resulting mixture is stirred at 65° C. for 18 h then cooled to RT and $NaBH_3CN$ (CAS #25895-60-7; 2.2 eq.) is added. The reaction mixture is stirred at 65° C. for 4 h then quenched with a sat. $NaHCO_3$ solution poured into water, stirred for 1 h at RT, filtered through a pad of Dicalite™ and the filtrate is extracted with DCM. The combined organic layers are washed with brine, filtered through a phase separator, concentrated. The residue is purified by preparative HPLC or by flash chromatography on silica gel to afford the desired compound.

Illustrative Synthesis of Cpd 153

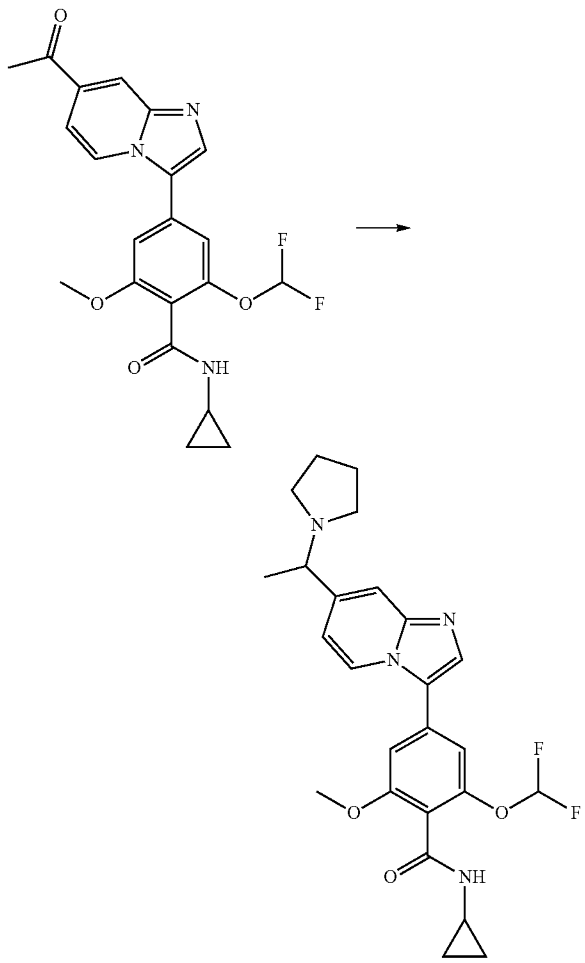

To a solution of pyrrolidine (CAS #123-75-1; 1.5 eq.) in THF (2 mL) are added the ketone Int 76 (60 mg, 0.14 mmol, 1 eq.) and $Ti(OEt)_4$ (CAS #3087-36-3; 45 μL, 0.22 mmol, 1.5 eq.). The resulting mixture is stirred at 65° C. for 18 h then cooled to RT and $NaBH_3CN$ (CAS #25895-60-7; 20 mg, 0.32 mmol, 2.2 eq.) is added. The reaction mixture is stirred at 65° C. for 4 h then quenched with a sat. $NaHCO_3$ solution poured into water, stirred for 1 h at RT, filtered through a pad of Dicalite™ and the filtrate is extracted with DCM. The combined organic layers are washed with brine, filtered through a phase separator, concentrated. The residue is purified by preparative HPLC to afford the desired compound.

1.2.25. Method K3: Aldehyde Functionalization by Reductive Amination

To a suspension of the aldehyde derivative (1 eq.) and few mg of $MgSO_4$ in MeOH with a drop of AcOH is added the amine (4 to 6 eq.). The reaction mixture is stirred at RT for 18 h or at 65° C. for 5 h-18 h. $NaBH_3CN$ (CAS #25895-60-7; 3 eq. to 6 eq.) is then added and the resulting suspension is stirred at 65° C. for 1 to 48 h. The reaction mixture is concentrated to dryness. The residue is purified by preparative HPLC.

Alternative work-up: The reaction mixture is quenched with water and a sat. $Na_2CO_3$ solution and extracted with EtOAc. The combined organic layers are dried over $Na_2SO_4$, filtered, concentrated and the residue is purified by flash chromatography on silica gel.

Illustrative Synthesis of Cpd 161

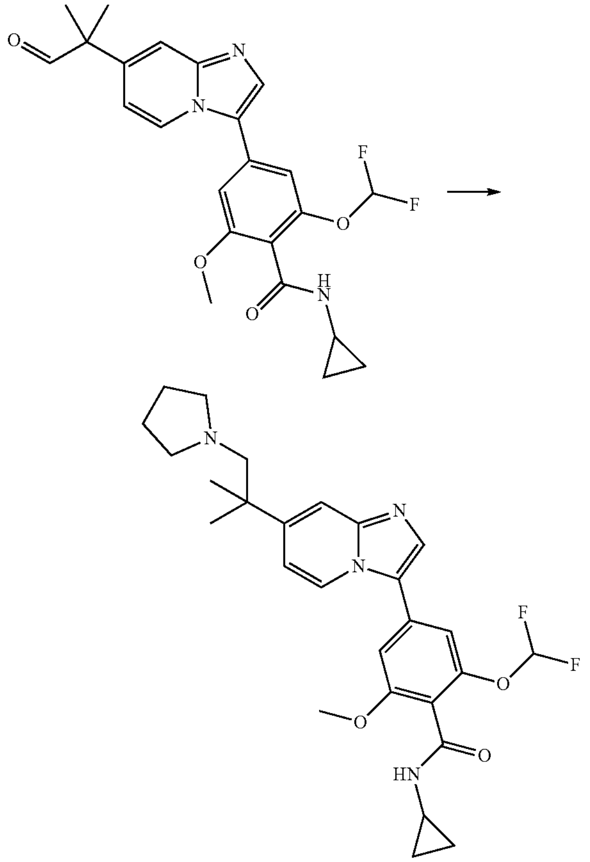

To a suspension of the aldehyde Int 130 (30 mg, 0.068 mmol, 1 eq.) and few mg of $MgSO_4$ in MeOH (2 mL) with a drop of AcOH is added pyrrolidine (CAS #123-75-1; 34 μL, 0.41 mmol, 6 eq.). The reaction mixture is stirred at 65° C. for 18 h. $NaBH_3CN$ (26 mg, 0.41 mmol, 6 eq.) is then added and the resulting suspension is stirred at 65° C. for 48 h. The reaction mixture is quenched with water and a sat. $Na_2CO_3$ solution and extracted with EtOAc. The combined organic layers are dried over $Na_2SO_4$, filtered, concentrated and the residue is purified by flash chromatography on silica gel (eluting with DCM/MeOH 100/0 to 90/10 then DCM/MeOH/$Et_3N$ 90/10/1) to afford the desired compound.

1.2.26. Method L: Reduction of Olefins

To a solution of unsaturated compound (1 eq.) in MeOH or a mixture MeOH: THF 1/1 under argon or $N_2$ is added either Pd/C 5% (0.1 eq.), Pd/C 10% (20% weight) or $Pd(OH)_2$ (0.2 eq.). The resulting suspension is degassed and filled with hydrogen. The reaction is stirred under a hydrogen atmosphere for 1 to 72 h. The reaction mixture is then filtered on a synthetic filter or over a pad of Dicalite™ or Clarcel®, and the filtrate is concentrated in vacuo. The residue is purified by flash chromatography on silica gel to afford the desired compound.

Alternative work-up: The reaction mixture is filtered over a pad of Dicalite™, and the filtrate is concentrated in vacuo. The residue is purified by flash chromatography on silica gel. The combined fractions are concentrated in vacuo then redissolved in DCM. Resin SPM 32 is added and the resulting suspension is stirred for 1 h. The resin is filtered and the filtrate concentrated in vacuo to deliver the desired compound.

Illustrative Synthesis of Cpd 1

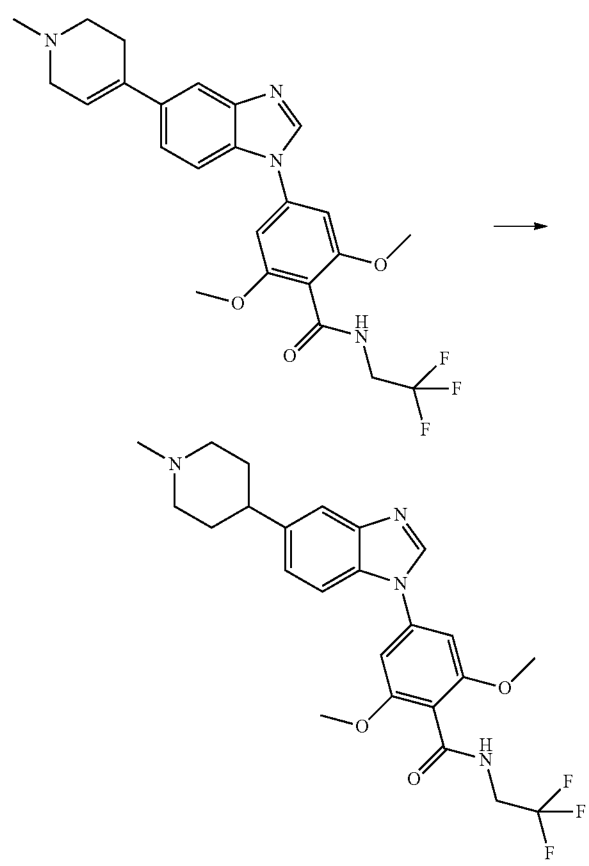

To a solution of Int 53 (56 mg, 0.12 mmol, 1 eq.) in MeOH (3 mL) under $N_2$ is added Pd/C 5% (26 mg, 0.012 mmol, 0.1 eq.). The resulting suspension is degassed and filled with hydrogen. The reaction is stirred under a hydrogen atmosphere for 18 h. The reaction mixture is then filtered on a synthetic filter, and the filtrate is concentrated in vacuo. The residue is purified by flash chromatography (eluting with DCM/MeOH 100/0 to 97/3) to afford the desired compound.

1.2.27. Method M1: Amine Deprotection Using TFA

To a stirred solution of N-Boc protected amine derivative (1 eq.) in DCM is added TFA (DCM/TFA mixture: 10/1 to 1/1). The reaction mixture is stirred at RT for 1 to 18 h until total completion. The reaction mixture is diluted in toluene, concentrated in vacuo, diluted with DCM or EtOAc and a sat. $Na_2CO_3$ solution or brine and the organic layer is separated, washed with brine, dried over anhydrous $Na_2SO_4$ or $MgSO_4$, filtered, concentrated in vacuo, purified by flash chromatography to afford the desired compound.

Alternative work-up 1: The reaction mixture is diluted in toluene, concentrated in vacuo and used directly in the next step without further purification.

Alternative work-up 2: The reaction mixture is concentrated in vacuo, diluted with EtOAc or DCM and water and the organic layer is separated, basified with a 2N NaOH solution (pH 10-11), and extracted with EtOAc or DCM. The combined organic layers are dried over anhydrous $Na_2SO_4$ or $MgSO_4$, filtered, concentrated in vacuo and used as such without further purification.

Illustrative Synthesis of Cpd 3

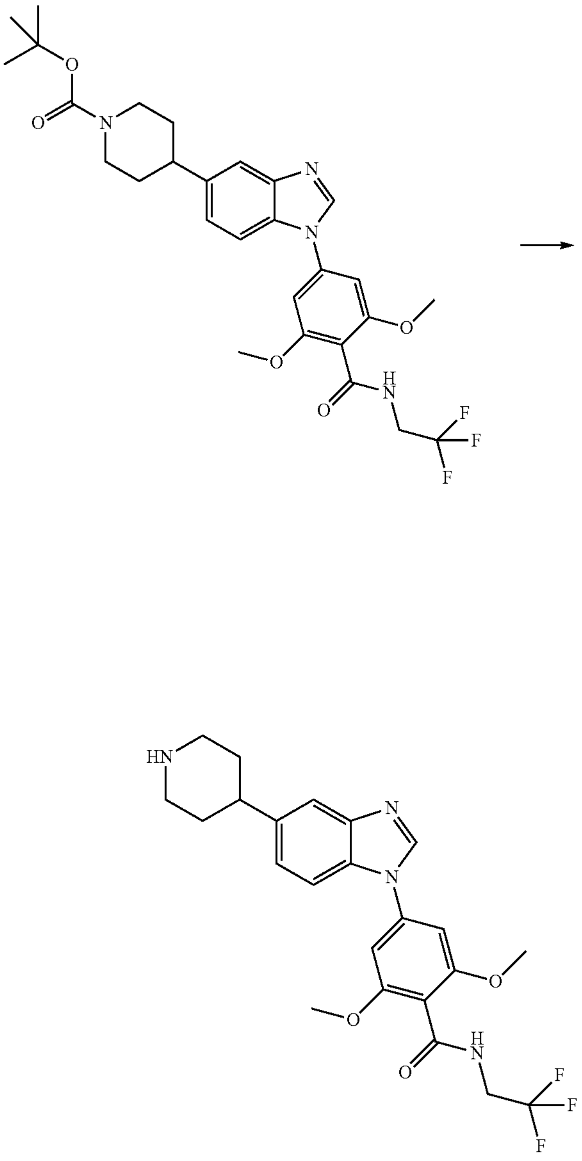

To a stirred solution of Cpd 2 (80 mg, 0.14 mmol, 1 eq.) in DCM (2 mL) is added TFA (0.2 mL). The reaction mixture is stirred at RT for 18 h. The reaction mixture is evaporated to dryness then diluted with DCM and a sat. $Na_2CO_3$ solution. The organic layer is separated and concentrated in vacuo. The residue is purified by flash chromatography (eluting with DCM/MeOH 100/0 to 95/5) to afford after concentration in vacuo the desired compound.

1.2.28. Method M2: Amine Deprotection Using HCl

To a stirred solution of N-Boc protected amine derivative (1 eq.) in DCM/MeOH (mixture 2/1 to 1/1) is added HCl 4N in dioxane (DCM/HCl mixture 50/50). The reaction mixture is stirred at RT for 3 h. The reaction mixture is concentrated in vacuo and either used as such without further purification or purified by flash chromatography to afford the expected compound.

Illustrative Synthesis of Cpd 66

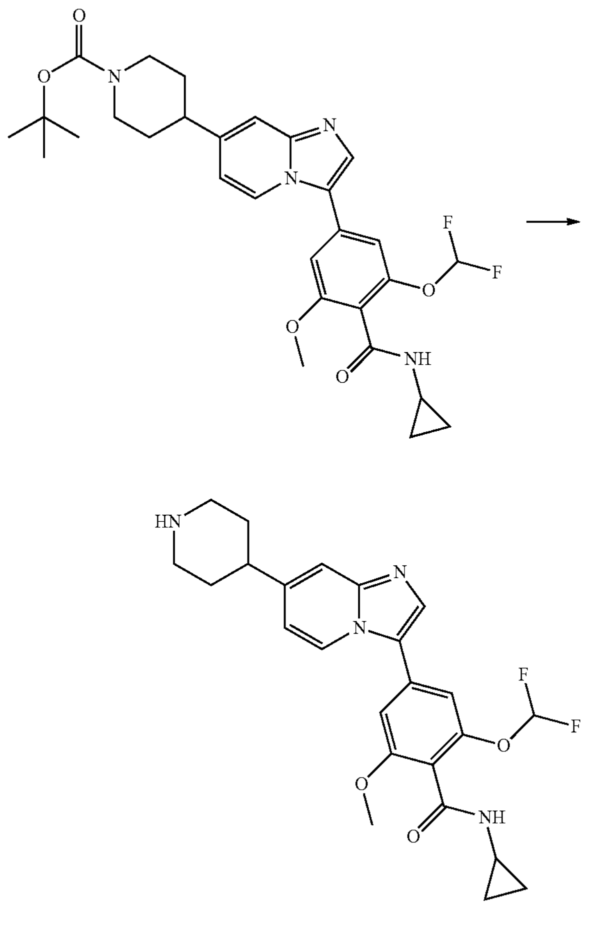

To a stirred solution of Cpd 60 (180 mg, 0.32 mmol, 1 eq.) in DCM (2 mL)/MeOH (1 mL) is added HCl 4N in dioxane (1.5 mL). The reaction mixture is stirred at RT for 3 h. The reaction mixture is concentrated in vacuo and purified by flash chromatography (eluting with DCM/MeOH 100/0 to 95/5) to afford the desired compound.

1.2.29. Method N1: Alcohol Synthesis by Ketone or Ester Reduction

To a solution of ketone or ester derivative (1 eq.) in MeOH or a mixture MeOH/EtOH 1/1 or MeOH/THF 1/1 at 0° C. or RT under inert atmosphere or not is added sodium borohydride (CAS #16940-66-2; 0.9 eq. to 10 eq.). The reaction mixture is stirred at RT for 30 min to 18 h. Then the mixture is quenched at 0° C. by addition of water or a sat. $NH_4Cl$ solution and optionally a 1N HCl solution and extracted with EtOAc. The combined organic layers are dried over $MgSO_4$, filtered or passed through a phase separator, and concentrated in vacuo. The residue is then delivered as such or purified by flash chromatography on silica gel or preparative HPLC.

Alternative work-up 1: the reaction mixture is directly concentrated in vacuo and purified by preparative HPLC.

Alternative work-up 2: the mixture is quenched at 0° C. by addition of water and a 1N HCl solution and concentrated. The residue is then triturated with a mixture pentane/$Et_2O$, the precipitate is filtered and dried.

Illustrative Synthesis of Cpd 140

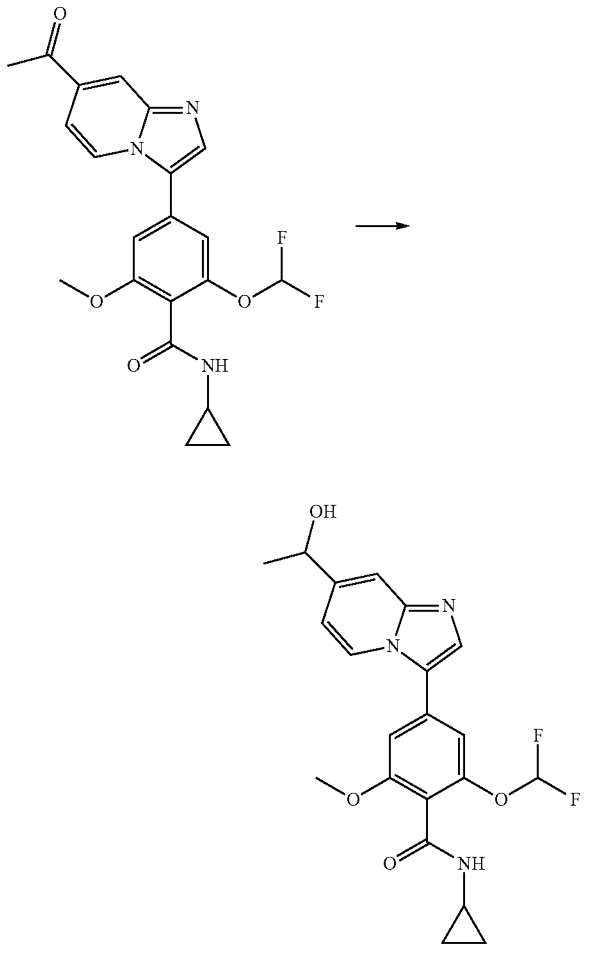

To a solution of ketone Int 76 (50 mg, 0.12 mmol, 1 eq.) in a mixture MeOH/EtOH 1/1 (6 mL) at RT is added sodium borohydride (9 mg, 0.24 mmol, 2 eq.). The reaction mixture is stirred at RT for 30 min. Then the mixture is quenched at 0° C. by addition of water and a 1N HCl solution and extracted with EtOAc. The combined organic layers are passed through a phase separator, and concentrated in vacuo to afford the desired compound.

Illustrative Synthesis of Int 143

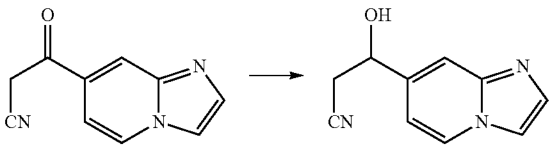 [SMILES: N#CCC(=O)c1ccn2ccnc2c1 ; N#CCC(O)c1ccn2ccnc2c1]

To a solution of ketone Int 144 (100 mg, 0.54 mmol, 1 eq.) in MeOH (6 mL) at 0° C. under inert atmosphere is added sodium borohydride (17 mg, 0.45 mmol, 0.9 eq.). The reaction mixture is stirred at RT for 3 h. Then the mixture is quenched at 0° C. by addition of water and a 1N HCl solution, and concentrated. The residue is triturated with a mixture pentane/$Et_2O$, the precipitate is filtered and dried to afford Int 143.

Illustrative Synthesis of Int 209

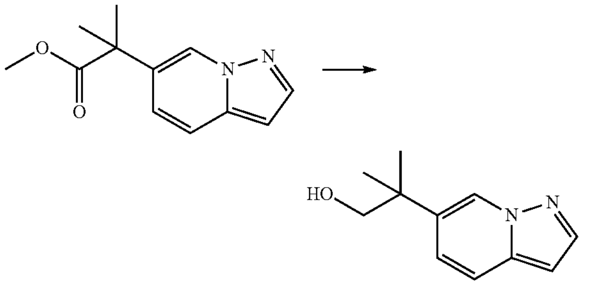

To a solution of ester Int 210 in a mixture MeOH/THF (3.2 mL/3.2 mL) under inert atmosphere is added carefully sodium borohydride (97 mg, 2.6 mmol, 2 eq.). The resulting white mixture is stirred at RT for 18 h, quenched at 0° C. with a sat. $NH_4Cl$ solution and extracted with EtOAc. The combined organic layers are passed through a phase separator, and concentrated in vacuo. The residue is then purified by flash chromatography on silica gel (eluting with heptane/EtOAc 100/0 to 0/100) to afford the desired compound.

1.2.30. Method N2: Alcohol Synthesis by Addition of Magnesium Reagent on Ketone

To a solution of ketone or ester derivative (1 eq.) in dry degassed (or not) THF at 0° C. or −78° C. under inert atmosphere is added the alkyl magnesium bromide or chloride (1 eq. to 10 eq.). The reaction mixture is stirred at RT for 2.5 to 20 h. Then the mixture is quenched at 0° C. by addition of a sat. $NH_4Cl$ solution and extracted with EtOAc. The combined organic layers are dried over $MgSO_4$, filtered and concentrated in vacuo. The residue is purified by flash chromatography on silica gel.

Alternative work-up: the reaction mixture is quenched at 0° C. by addition of a sat. $NH_4Cl$ solution and water and concentrated in vacuo. The residue is diluted in water and a pH 6.2 phosphate buffer and extracted with a mixture EtOAc/n-BuOH 8/2. The combined organic layers are dried over $MgSO_4$, filtered and concentrated in vacuo. The residue is purified by flash chromatography on silica gel.

Illustrative Synthesis of Int 106

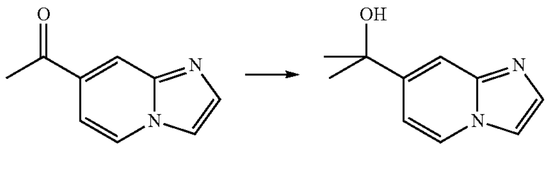

To a solution of 1-imidazo[1,2-a]pyridin-7-ylethanone (CAS #1036991-50-0; 500 mg, 3.12 mmol, 1 eq.) in dry THF (30 mL) at 0° C. under $N_2$ atmosphere is added dropwise methyl magnesium bromide (1M in THF, CAS #75-16-1; 9.4 mL, 9.37 mmol, 3 eq.). The reaction mixture is stirred at RT for 2.5 h. Then the mixture is quenched at 0° C. by addition of a sat. $NH_4Cl$ solution and extracted with EtOAc. The combined organic layers are dried over $MgSO_4$, filtered and concentrated in vacuo. The residue is purified by flash chromatography on silica gel (eluting with DCM/MeOH 100/0 to 90/10) to afford the desired compound.

Illustrative Synthesis of Cpd 57

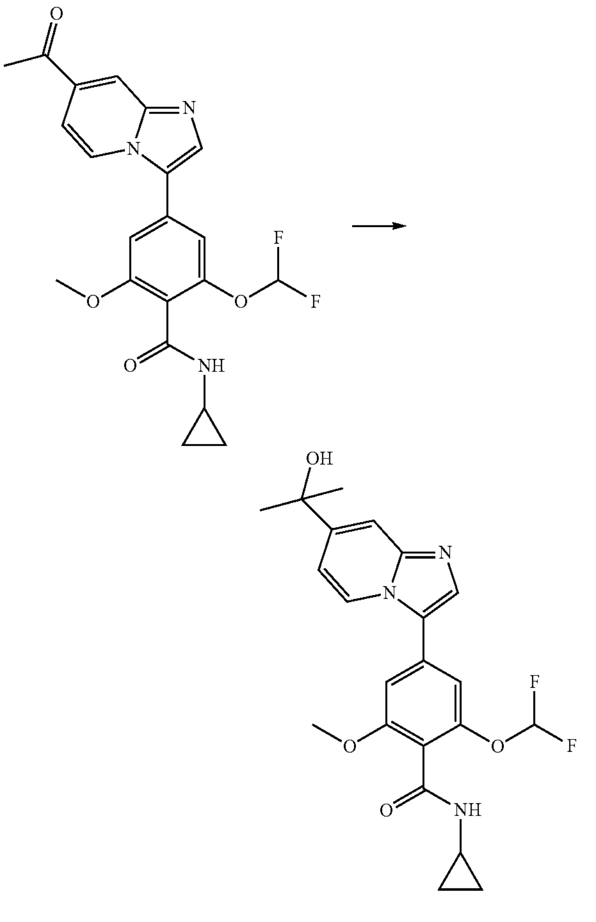

To a solution of ketone Int 76 (30 mg, 0.071 mmol, 1 eq.) in dry THF (2 mL) at −78° C. under $N_2$ atmosphere is added dropwise methyl magnesium bromide (3M in $Et_2O$, CAS #75-16-1; 119 μL, 0.36 mmol, 5 eq.). The reaction mixture is stirred at −78° C. for 1 h then the same amount of methyl magnesium bromide is added. After 1 h stirring at −78° C., the reaction mixture is allowed to warm to RT and stirred for 18 h. Then the mixture is quenched at 0° C. by addition of a sat. $NH_4Cl$ solution and extracted with EtOAc. The combined organic layers are washed with brine, passed through a phase separator and concentrated in vacuo. The residue is purified by flash chromatography on silica gel (eluting with DCM/MeOH 100/0 to 96/4) to afford the desired compound.

1.2.31. Method N3: Alcohol Synthesis by Epoxidation/Epoxide Opening Sequence (N3i+N3ii)

1.2.31.1. N3i: Epoxidation

To a solution of trimethylsulfonium iodide (CAS #2181-42-2; 2.5 eq.) in dry THF at 0° C. under inert atmosphere or not is added sodium hydride (60% dispersion in mineral oil, CAS #7646-69-7; 2.5 eq.). The resulting mixture is stirred at 0° C. for 5 min then a solution of ketone derivative (1 eq.) in a mixture DMSO/THF (6/1) is added dropwise. The reaction solution is stirred at RT for 15 min to 4 h. The reaction mixture is quenched by addition of a sat. $NH_4Cl$ solution and extracted with EtOAc. The combined organic layers are dried over $Na_2SO_4$ or $MgSO_4$, filtered or passed through a phase separator, and concentrated in vacuo.

Illustrative Synthesis of Int 233

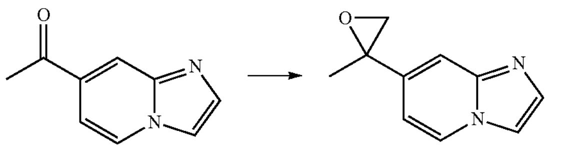

To a solution of trimethylsulfonium iodide (637 mg, 3.12 mmol, 2.5 eq.) in dry THF (2 mL) at 0° C. is added sodium hydride (60% dispersion in mineral oil, 75 mg, 3.12 mmol, 2.5 eq.). The resulting mixture is stirred at 0° C. for 5 min then a solution of 1-imidazo[1,2-a]pyridin-7-ylethanone (CAS #1036991-50-0; 200 mg, 1.25 mmol, 1 eq.) in a mixture DMSO/THF (12 mL/4 mL) is added dropwise. The reaction solution is stirred at RT for 4 h. The reaction mixture is quenched by addition of a sat. $NH_4Cl$ solution and extracted with EtOAc. The combined organic layers are dried over $Na_2SO_4$ or $MgSO_4$, filtered and concentrated in vacuo to afford the epoxide intermediate used directly in the next step.

Illustrative Synthesis of Int 234

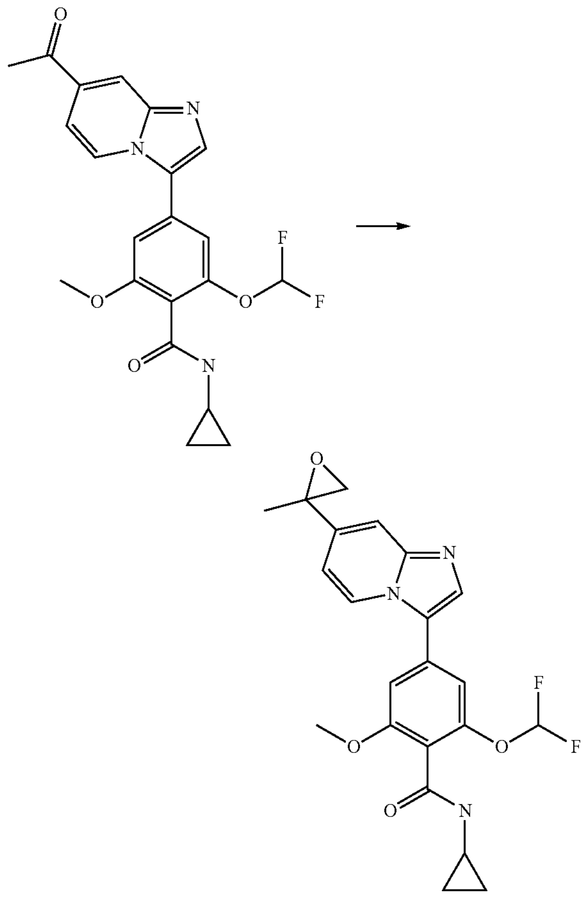

To a solution of trimethylsulfonium iodide (123 mg, 0.60 mmol, 2.5 eq.) in dry THF (0.4 mL) at 0° C. is added sodium hydride (60% dispersion in mineral oil, 24 mg, 0.60 mmol, 2.5 eq.). The resulting mixture is stirred at 0° C. for 5 min then a solution of ketone Int 76 (100 mg, 0.25 mmol, 1 eq.) in a mixture DMSO/THF (2.3 mL/0.37 mL) is added dropwise. The reaction solution is stirred at RT for 20 min. The reaction mixture is quenched by addition of a sat. $NH_4Cl$ solution and extracted with EtOAc. The combined organic layers are passed through a phase separator and concentrated in vacuo to afford the epoxide intermediate used directly in the next step.

1.2.31.2. N3ii: Epoxide Opening

To a solution of epoxide intermediate (1 eq.) in EtOH, MeOH or DMF under inert atmosphere or not is added the nucleophile (amine or MeONa in solution in MeOH) (0.8 eq. to 2 eq.). In case of amine nucleophile, a base can be added ($Et_3N$, AcONa or sodium hydride 60% dispersion in mineral oil, 0.85 eq. to 2 eq.). The reaction mixture is heated to 65 to 100° C. for 1.5 to 18 h. The reaction mixture is concentrated in vacuo and purified by flash chromatography on silica gel.

Illustrative Synthesis of Int 147

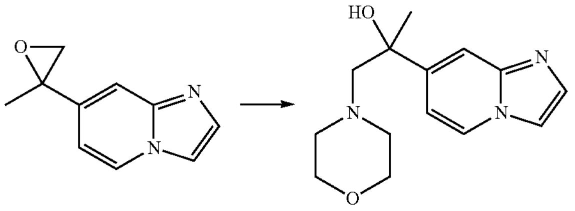 [SMILES: CC1(c2ccn3ccnc3c2)CO1 ; CC(O)(CN1CCOCC1)c1ccn2ccnc2c1]

To a solution of the above prepared epoxide intermediate Int 233 (50 mg, 0.29 mmol, 1 eq.) in EtOH (0.82 mL) is added morpholine (CAS #110-91-8; 50 µL, 0.57 mmol, 2 eq.). The reaction mixture is heated to 65° C. for 18 h. The reaction mixture is concentrated in vacuo and purified by flash chromatography on silica gel (eluting with DCM/MeOH 100/0 to 80/20) to afford the desired compound.

Illustrative Synthesis of Int 152

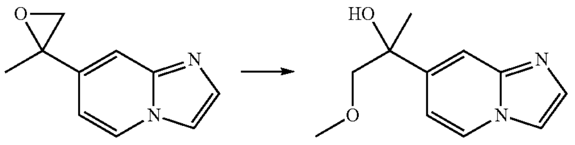

To a solution of the above prepared epoxide intermediate Int 233 (108 mg, 0.62 mmol, 1 eq.) in MeOH (1.5 mL) is added MeONa (0.5 M in MeOH solution, CAS #151-50-8; 1.36 mL, 0.68 mmol, 1.1 eq.). The reaction mixture is heated to 70° C. for 18 h. The reaction mixture is concentrated in vacuo and purified by flash chromatography on silica gel (eluting with DCM/MeOH 100/0 to 80/20) to afford the desired compound.

Illustrative Synthesis of Int 151

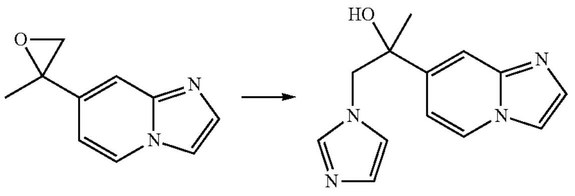 [SMILES: CC1(c2ccn3ccnc3c2)CO1 ; CC(O)(Cn1ccnc1)c1ccn2ccnc2c1]

To a solution of the above prepared epoxide intermediate Int 233 (108 mg, 0.62 mmol, 1 eq.) in EtOH (1.5 mL) under $N_2$ atmosphere are added imidazole (CAS #288-32-8; 32.5 mg, 0.48 mmol, 0.8 eq.) and sodium acetate (CAS #127-09-3; 43 mg, 0.52 mmol, 0.85 eq.). The reaction mixture is heated to 70° C. for 18 h. The reaction mixture is concentrated in vacuo and purified by flash chromatography on silica gel (eluting with DCM/MeOH 100/0 to 80/20) to afford the desired compound.

Illustrative Synthesis of Cpd 192

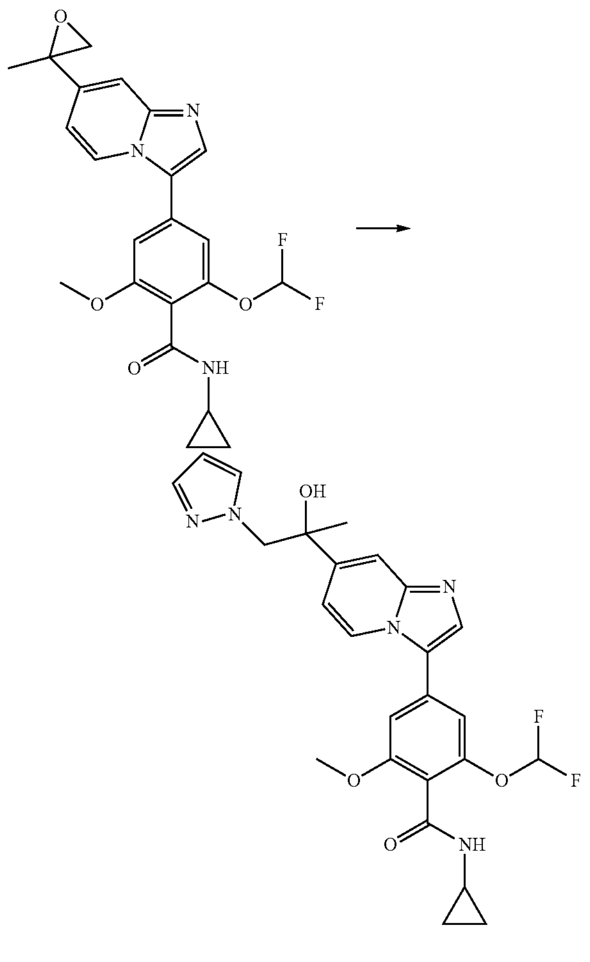

To a suspension of sodium hydride (60% dispersion in mineral oil, 9 mg, 0.23 mmol, 2 eq.) in dry DMF (0.25 mL) at 0° C. is added pyrazole (CAS #288-13-1; 16 mg, 0.23 mmol, 2 eq.). The resulting mixture is stirred at 0° C. for 10 min then a solution of epoxide above described Int 234 (50 mg, 0.12 mmol, 1 eq.) in DMF (0.5 mL) is added. The reaction solution is stirred at 100° C. for 1.5 h. The reaction mixture is quenched by addition of a sat. $NH_4Cl$ solution and extracted with EtOAc. The combined organic layers are passed through a phase separator and concentrated in vacuo. The residue is purified by flash chromatography on silica gel (eluting with DCM/MeOH 100/0 to 90/10) to afford the desired compound.

1.2.32. Method O: Cyclization of Aminopyridine into Imidazopyridine

To a solution of amine (1 eq.) in EtOH are added $NaHCO_3$ (CAS #144-55-8; 3 eq.) and chloroacetaldehyde (50% in water, CAS #107-20-0; 1.5 eq.). The reaction mixture is stirred at 80 to 90° C. for 1.5 h or 2 h. The reaction mixture is then concentrated and the crude residue is purified by flash chromatography on silica gel or C18 reverse phase Biotage® cartridge.

Alternative work-up 1: the crude residue is diluted in DCM, filtered and the filtrate is purified by flash chromatography on silica gel.

Alternative work-up 2: the crude residue is diluted in EtOAc, filtered and the filtrate is washed with water. The organic layer is dried over $MgSO_4$, filtered and concentrated in vacuo. The residue is purified by flash chromatography on silica gel.

Alternative work-up 3: the reaction mixture is purified on a Biotage® Isolute® SCX cartridge (eluting with DCM, MeOH then a 1N $NH_3$ solution in MeOH). The filtrate is concentrated in vacuo to afford the desired compound.

Illustrative Synthesis of Int 158

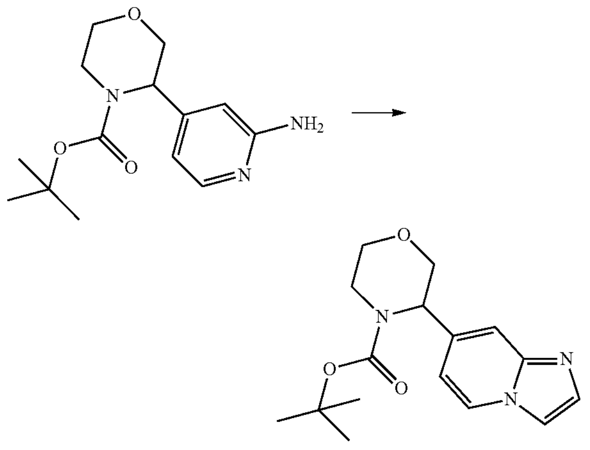

To a solution of amine Int 159 (68 mg, 0.24 mmol, 1 eq.) in EtOH (1 mL) are added $NaHCO_3$ (62 mg, 0.73 mmol, 3 eq.) and chloroacetaldehyde (50% in water, 57 µL, 0.36 mmol, 1.5 eq.). The reaction mixture is stirred at 80° C. for 1.5 h. The reaction mixture is then concentrated and the crude residue is purified on a C18 reverse phase Biotage® cartridge (eluting with water/ACN/$NH_3$ 1% in MeOH 98/2/1 to 50/50/1) to afford the desired intermediate.

1.2.33. Method P1: Borylation from Bromide

To a solution of bromide (1 eq.) in dioxane under inert atmosphere are added potassium acetate (CAS #127-08-2; 3 eq.) and $B_2pin_2$ (CAS #73183-34-3; 1.5 eq.). The resulting solution is degassed and heated to 110° C. before adding Pd(dppf)$Cl_2$·DCM adduct (CAS #95464-05-4; 0.1 eq.). The reaction mixture is stirred at 110° C. for 1 h, concentrated, diluted in DCM and filtered over Dicalite®. The filtrate is concentrated in vacuo and the residue purified by flash chromatography on silica gel.

Illustrative Synthesis of Int 20

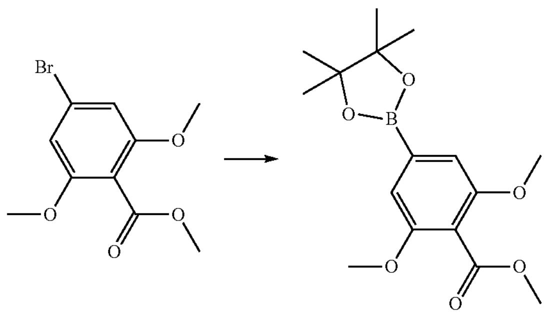

To a solution of bromide Int 21 (8.55 g, 30 mmol, 1 eq.) in dioxane (80 mL) under inert atmosphere are added potassium acetate (8.9 g, 90 mmol, 3 eq.) and $B_2pin_2$ (11.4 g, 45 mmol, 1.5 eq.). The resulting solution is degassed and heated to 110° C. before adding Pd(dppf)$Cl_2$·DCM adduct (2.45 g, 3.0 mmol, 0.1 eq.). The reaction mixture is stirred at 110° C. for 1 h, concentrated, diluted in DCM and filtered over Dicalite®. The filtrate is concentrated in vacuo and the residue purified by flash chromatography on silica gel (eluting with heptane/EtOAc 70/30) to afford the desired intermediate.

1.2.34. Method P2: Borylation by C—H Activation

To a degassed solution of heteroaryl compound (1 eq.) and $B_2pin_2$ (CAS #73183-34-3; 3 eq.) in THF under an inert atmosphere are added $[Ir(OCH_3)(COD)]_2$ (CAS #12148-71-9; 0.05 eq.) and 4,4'-di-tert-butyl-2,2'-bipyridine (CAS #72914-19-3; 0.04 eq.) The reaction mixture is stirred at 70° C. for 3 h then at RT for 18 h. The reaction solution is concentrated in vacuo and purified by flash chromatography on silica gel to afford the desired boronic ester.

Illustrative Synthesis of Int 7

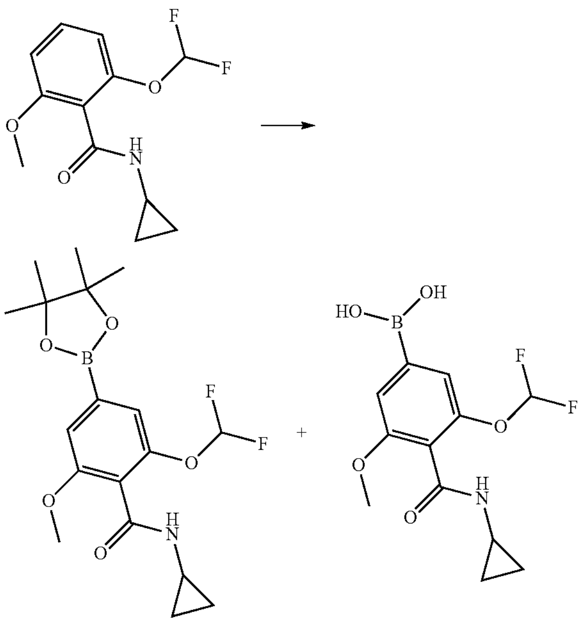

Under an inert atmosphere, N-cyclopropyl-2-(difluoromethoxy)-6-methoxy-benzamide Int 6 (2.80 g, 10.89 mmol, 1 eq.), $B_2pin_2$ (8.30 g, 32.68 mmol, 3 eq.), $[Ir(OCH_3)(COD)]_2$ (360 mg, 0.54 mmol, 0.05 eq.) and 4,4'-di-tert-butyl-2,2'-bipyridine (120 mg, 0.45 mmol, 0.04 eq.) are dissolved in degassed THF (70 mL). The reaction mixture is stirred at 70° C. under $N_2$ for 3 h then at RT for 18 h. The solution is concentrated, the residue is purified by flash chromatography on silica gel (eluting with heptane/EtOAc 100/0 to 30/70) to afford the desired product in mixture with the corresponding boronic acid.

1.2.35. Method Q: Fluorine Displacement with an Alkoxide on a Trisubstituted Benzamide or Benzoate To a solution of fluoro derivative (1 eq.) in THF or DMF or NMP is added dropwise MeONa (25% in MeOH or solid MeONa, CAS #124-41-4; 1.2 eq. to 4 eq.) or EtONa (25% in EtOH, CAS #141-52-6; 1.2 eq.) and the suspension is stirred for 1.5 to 20 h. More alkoxide solution (0 to 4.8 eq.) can be added to push the conversion further. The reaction is quenched with a sat. $NH_4Cl$ solution and the organic solvent is evaporated in vacuo. If a precipitate forms in the aqueous layer, it is filtered, washed with water and dried to afford the expected product. If no precipitation occurs, the aqueous phase is extracted with DCM or EtOAc, the organic layer is dried over $MgSO_4$, filtered and concentrated to give the desired compound.

Illustrative Synthesis of Int 13

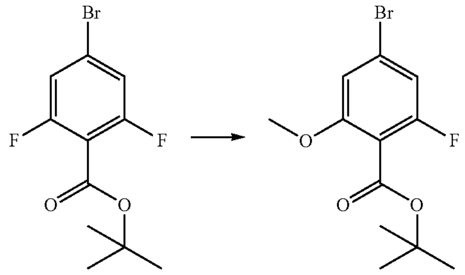 [SMILES: CC(C)(C)OC(=O)c1c(F)cc(Br)cc1F ; COc1cc(Br)cc(F)c1C(=O)OC(C)(C)C]

To a solution of tert-butyl 4-bromo-2,6-difluoro-benzoate Int 12 (19 g, 65 mmol, 1 eq.) in THF (320 mL) is added portionwise MeONa (15 g, 260 mmol, 4 eq.). The reaction mixture is stirred at RT for 18 h then quenched with a sat. $NH_4Cl$ solution, extracted with EtOAc (×3). The combined organic layers are dried over $MgSO_4$, filtered and concentrated under reduced pressure to afford the desired intermediate.

1.2.36. Method R: Difluoromethylation of a Phenol Intermediate

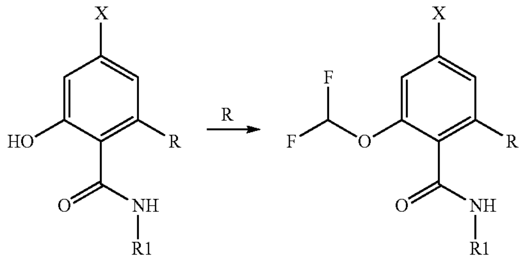

To a solution of phenol intermediate (1 eq.) in ACN at −35° C., −20° C. or 0° C. is added a cold solution of KOH (10 eq.) in water (water/ACN 1/1 final concentration). Diethyl (bromodifluoromethyl)phosphonate (CAS #65094-22-6; 1.4 to 3.1 eq.) is added dropwise while keeping the temperature below 20° C. The reaction is worked-up at the end of the addition or is stirred for 30 min at −20° C. or 0° C. Water is added and the aqueous layer is extracted with EtOAc. The combined organic layers are either dried over $MgSO_4$ and filtered, or are passed through a phase separator. The filtrate is concentrated to dryness and the residue is used as such or is purified by flash chromatography on silica gel to afford the expected product.

Illustrative Synthesis of Int 15

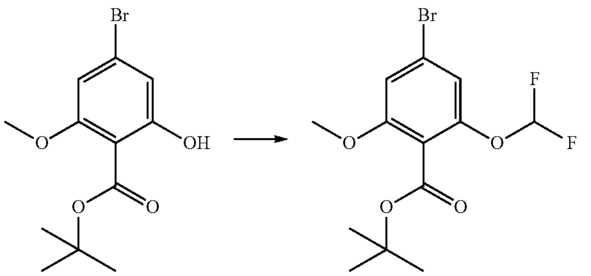 [SMILES: COc1cc(Br)cc(O)c1C(=O)OC(C)(C)C ; COc1cc(Br)cc(OC(F)F)c1C(=O)OC(C)(C)C]

To a solution of tert-butyl 4-bromo-2-(difluoromethoxy)-6-methoxy-benzoate Int 14 (19 g, 53.8 mmol, 0.65 eq.) in ACN (100 mL) at −35° C. under $N_2$ is added dropwise over 5 min a cold solution of KOH (46 g, 820 mmol, 10 eq.) in water (100 mL). The mixture is stirred at −35° C. for 15 min and then diethyl (bromodifluoromethyl)phosphonate (30 mL, 160 mmol, 2 eq.) is added dropwise keeping the temperature at −35° C. over 5 min. The mixture is allowed to warm to RT over 1.5 h. then quenched with water. The aqueous layer is extracted with EtOAc. The combined organic layers are washed with brine, dried over $MgSO_4$, filtered and concentrated in vacuo. The crude residue is purified by flash chromatography on silica gel (eluting with heptane/EtOAc 100/0 to 90/10) to afford the desired intermediate.

Illustrative Synthesis of Int 6

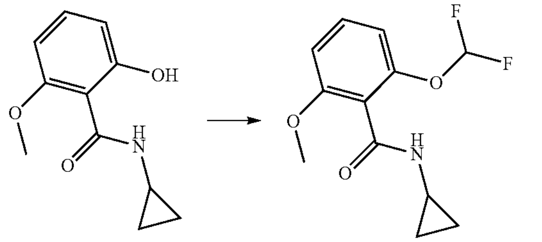 [SMILES: COc1cccc(O)c1C(=O)NC1CC1 ; COc1cccc(OC(F)F)c1C(=O)NC1CC1]

Under an inert atmosphere, N-cyclopropyl-2-hydroxy-6-methoxy-benzamide Int 5 (2.80 g, 0.013 mmol, 1 eq.) is dissolved in ACN (20 mL) and cooled to −20° C. A solution of KOH (7.57 g, 0.13 mmol, 10 eq.) in water (20 mL) is added and the mixture is stirred for 10 min, then diethyl (bromodifluoromethyl)phosphonate (10.9 g, 0.04 mmol, 3.1 eq.) is added slowly. The reaction mixture is stirred at −20° C. for 30 min then at RT for another 30 min. Water is added and three extractions with EtOAc are performed. The organic layers are dried on $Na_2SO_4$, filtered and concentrated in vacuo. The residue is purified by flash chromatography on silica gel (eluting with heptane/EtOAc 100/0 to 0/100) to afford the desired compound.

1.2.37 Method S: Nitration of Halogenated Benzylcyanides

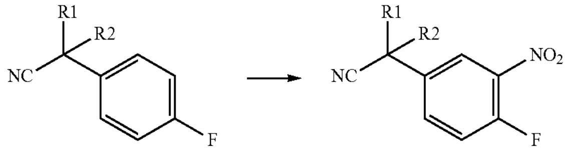

To neat 4-fluorobenzenacetonitrile derivative (1 eq.) at 0° C. is added dropwise fuming nitric acid (excess). The mixture is stirred 30 min at 0° C. until total completion. The reaction mixture is poured into to ice and then extracted with EtOAc. The combined organic layers are dried or washed with brine then dried over $MgSO_4$, filtered and concentrated in vacuo. Purification by flash chromatography on silica gel affords the desired compound.

Illustrative Synthesis of Int 38

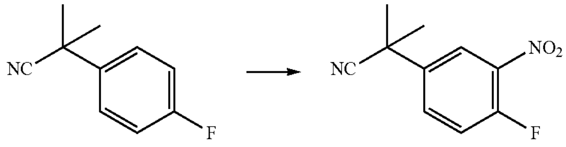

In a round bottom flask containing Int 37 (1.18 g, 7.23 mmol, 1 eq.) at 0° C. is added dropwise fuming nitric acid (5 mL). The mixture is stirred 30 min at 0° C. The reaction mixture is poured into to ice and then extracted with EtOAc. The combined organic layers are dried or washed with brine then dried over $MgSO_4$, filtered, concentrated in vacuo and purified by flash chromatography on silica gel (eluting with DCM/MeOH 100/0 to 96/4) to afford the desired intermediate.

1.2.38. Method T: Fluoration

To a solution of alcohol (1 eq.) in DCM at −78° C. or RT is added DAST (CAS #38078-09-0; 1.4-1.5 eq.). The resulting mixture is stirred at RT for 0.5 to 18 h then quenched with a sat. $NH_4Cl$ or $Na_2CO_3$ solution and concentrated in vacuo. The residue is purified by flash chromatography on silica gel or preparative HPLC.

Illustrative Synthesis of Cpd 224

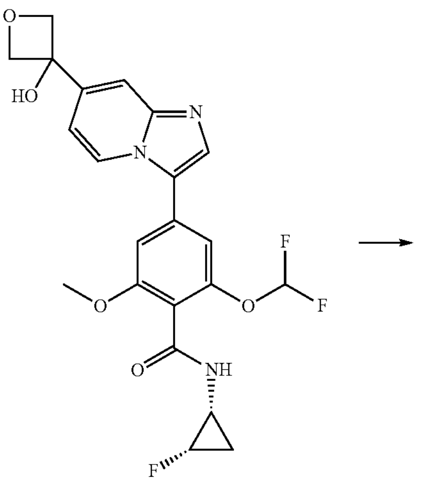

-continued

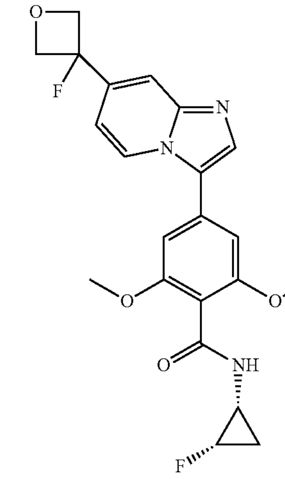

To a solution of Cpd 223 (74 mg, 0.16 mmol, 1 eq.) in DCM (1.9 mL) is added DAST (32 μL, 0.24 mmol, 1.5 eq.). The resulting mixture is stirred at RT for 30 min then quenched with a sat. $NH_4Cl$ solution and concentrated in vacuo. The residue is purified by flash chromatography on silica gel (eluting with DCM/MeOH 100/0 to 95/5) to afford the desired compound.

1.2.39. Method U: Alcohol Oxidation into Aldehyde

To a solution of alcohol (1 eq.) in DCM at 0° C. under inert atmosphere is added Dess-Martin periodinane (CAS #87413-09-0; 1 to 1.2 eq.). The reaction mixture is stirred at 0° C. for 20 min then at RT for 18 h, quenched with water and a sat. $NaHCO_3$ solution. The organic layer is separated, washed with brine, dried over $Na_2SO_4$, filtered and concentrated in vacuo. The residue is used directly in the next step or purified by flash chromatography on silica gel.

Illustrative Synthesis of Int 123

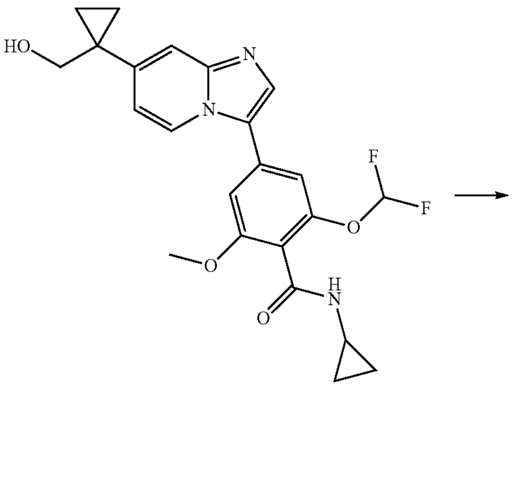

-continued

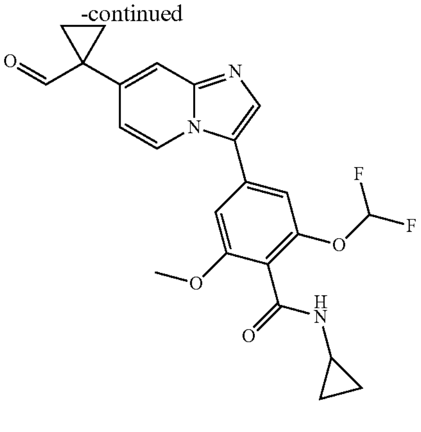

To a solution of Cpd 115 (25 mg, 0.06 mmol, 1 eq.) in DCM (3 mL) at 0° C. under inert atmosphere is added Dess-Martin periodinane (24 mg, 0.06 mmol, 1 eq.). The reaction mixture is stirred at 0° C. for 20 min then at RT for 18 h, quenched with water and a sat. $NaHCO_3$ solution. The organic layer is separated, washed with brine, dried over $Na_2SO_4$, filtered and concentrated in vacuo to afford the desired aldehyde.

1.2.40. Method V: Amine Synthesis by Hofmann Rearrangement (Sequence Vi then Vii)

1.2.40.1. Vi: Nitrile Hydrolysis

To a solution of nitrile (1 eq.) in a mixture of EtOH and a sat. $K_2CO_3$ solution (1/1) at 0° C. is added an aq. $H_2O_2$ solution (30% wt solution in water, CAS #7722-84-1; excess). The resulting solution is stirred at RT for 5 to 13 h. The reaction mixture is quenched with brine and extracted with DCM. The combined organic layers are dried over $Na_2SO_4$, filtered or passed through a phase separator and concentrated in vacuo.

1.2.40.2. Vii: Rearrangement

To a solution of the previous amide (1 eq.) in a mixture ACN/water (1/2) at 0° C. is added PIFA (CAS #2712-78-9; 1.1 eq.). The resulting solution is stirred at RT for 2 to 18 h then quenched with a sat. $Na_2CO_3$ solution or water or 1N NaOH solution, and extracted with DCM. The combined organic layers are passed through a phase separator, concentrated in vacuo and used without further purification or purified by preparative HPLC to afford the desired compound.

Illustrative Synthesis of Cpd 106

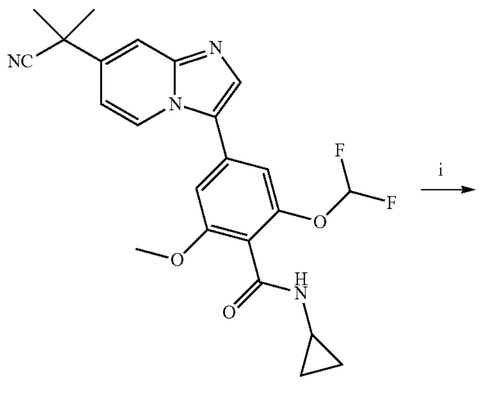

-continued

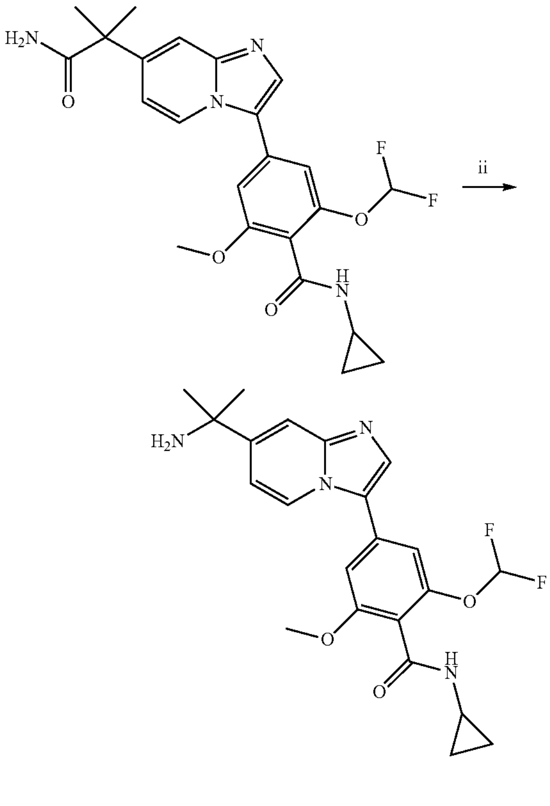

Step i: 4-[7-(2-amino-1,1-dimethyl-2-oxo-ethyl) imidazo[1,2-a]pyridin-3-yl]-N-cyclopropyl-2-(difluoromethoxy)-6-methoxy-benzamide To a solution of Cpd 19 (60 mg, 0.14 mmol, 1 eq.) in a mixture of EtOH (2 mL) and a sat. $K_2CO_3$ solution (2 mL) at 0° C. is added an aq. $H_2O_2$ solution (30% wt solution in water; 1 mL). The resulting solution is stirred at RT for 5 h before adding more $H_2O_2$ (1 mL). The reaction mixture is stirred at RT for 18 h then is quenched with brine and extracted with DCM. The combined organic layers are passed through a phase separator and concentrated in vacuo to afford 4-[7-(2-amino-1,1-dimethyl-2-oxo-ethyl)imidazo[1,2-a]pyridin-3-yl]-N-cyclopropyl-2-(difluoromethoxy)-6-methoxy-benzamide.

Step ii: Cpd 106

To a solution of the previous amide (1 eq.) in a mixture ACN/water (1/2 mL) at 0° C. is added PIFA (64 mg, 0.15 mmol, 1.1 eq.). The resulting solution is stirred at RT for 2 h then quenched with a sat. $Na_2CO_3$ solution and extracted with DCM. The combined organic layers are passed through a phase separator, concentrated in vacuo and purified by preparative HPLC to afford the desired compound.

1.2.41. Method W: Potassium Carboxylate Salts Synthesis

To a solution of ester derivative (1 eq.) in a mixture of EtOH and water is added t-BuOK (1 eq.). The reaction mixture is stirred at 60° C. for 1 to 3 h then concentrated under reduced pressure and the resulting solid is filtered and dried under vacuum to afford the desired intermediate.

Illustrative Synthesis of Int 170

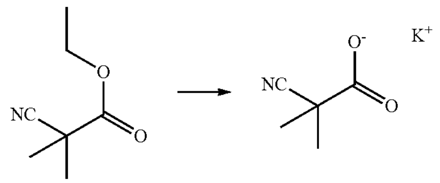

To a solution of ethyl 2-cyano-2-methyl-propanoate (CAS #1572-98-1; 25 g, 177 mmol, 1 eq.) in EtOH (354 mL) are added water (3.5 mL) and t-BuOK (CAS #865-47-4; 20 g, 177 mmol, 1 eq.). The reaction mixture is stirred at 60° C. for 3 h then concentrated under reduced pressure and the resulting solid is filtered and dried under vacuum for 18 h to afford the desired intermediate.

Example 2. Preparation of the Compounds of the Invention 2.1. Int 1

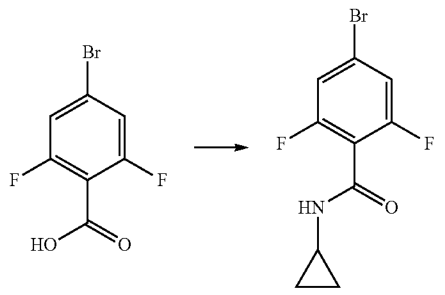 [SMILES: O=C(O)c1c(F)cc(Br)cc1F ; O=C(NC1CC1)c1c(F)cc(Br)cc1F]

In a 15 L jacketed reactor 4-bromo-2,6-difluorobenzoic acid (CAS #183065-68-1; 900 g, 3.80 mol, 1 eq.) is added to $SOCl_2$ (CAS #7719-09-7; 1.4 L, 19.1 mol, 5 eq.) in toluene (2 V, 1.8 mL) under $N_2$ flow at 20° C. (jacket temperature). The suspension is then heated to 80° C. for 17 h (jacket temperature set at 80° C.). The reaction mixture is cooled to 40° C. and concentrated (200 mL of toluene are used to wash the reactor). Toluene (1 V, 900 mL) is added to the residue and the solution is concentrated. The liquid residue (940 g) is dissolved in DCM (5 V, 4.5 L) under $N_2$ and placed into the 15 L reactor. The reaction mixture is cooled to 13° C. (jacket temperature: 5° C.) and a mixture of $Et_3N$ (582 mL, 4.18 mol, 1.1 eq.) and cyclopropylamine (276 mL, 4.0 mol, 1.1 eq.) is added over 1.3 h keeping the temperature below 25° C. (jacket temperature set at 5° C. during the addition). The reaction mixture is stirred under $N_2$ at 20° C. for 14 h. Water (2.2 V, 2 L) is added to the suspension. The biphasic solution is stirred (200 rpm) for 15 min. The organic phase is then successively washed with $NaHCO_3$ 5% (1.1 V, 1 L) and 20% NaCl solution (1.1 V, 1 L). The DCM layer is collected and put into a 15 L reactor. A solvent exchange is performed in the 15 L reactor: to the DCM layer is added 1 L of heptane. The mixture is heated progressively with the jacket temperature set at 65° C. and DCM is removed between 43° C. and 50° C. After removing 2 L of DCM, 1 L of heptane is added. After removing a total of 4 L of solvent, 1 L of heptane is added and the mixture is cooled to 20° C. in 20 min. Finally 1 L of heptane (a total of 4 L of heptane is added) is added and the mixture is stirred at 20° C. for 45 min. The suspension is filtered and the cake is washed with 1.5 L of heptane. The solid is dried at 50° C. under vacuum overnight to afford the desired intermediate.

2.2. Int 2

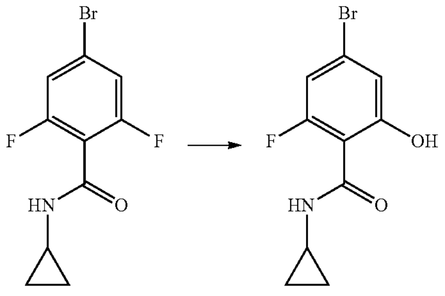 [SMILES: O=C(NC1CC1)c1c(F)cc(Br)cc1F ; O=C(NC1CC1)c1c(O)cc(Br)cc1F]

In a 15 L jacketed reactor, a 4N NaOH solution (2.1 L, 8.6 mol, 2.5 eq.) is added in one portion to a solution of Int 1 (952 g, 3.45 mol, 1 eq.) in DMSO (2 V, 1.9 L). The suspension is heated to 90° C. (jacket temperature from 50° C. to 90° C. over 20 min then hold at 90° C. for 2 h). The reaction mixture is then cooled to 25° C. (jacket temperature from 90° C. to 5° C. over 45 min) and HCl 2 N (2.7 L, 5.4 mol, 0.63 eq./NaOH) is added until pH 3 is reached. The temperature is kept below 30° C. during the addition of HCl (addition over 20 min and jacket temperature set at 5° C.). The suspension is stirred at 200 rpm for 2 h while the temperature decreases to 20° C. (jacket temperature set at 5° C.). The suspension is then filtered. The wet cake is washed with water (twice with 2 L, 2*2 V) and the solid is dried on a fritted funnel overnight. The solid is dried in a vacuum oven at 50° C. for 3 days to afford the desired intermediate.

2.3. Int 8

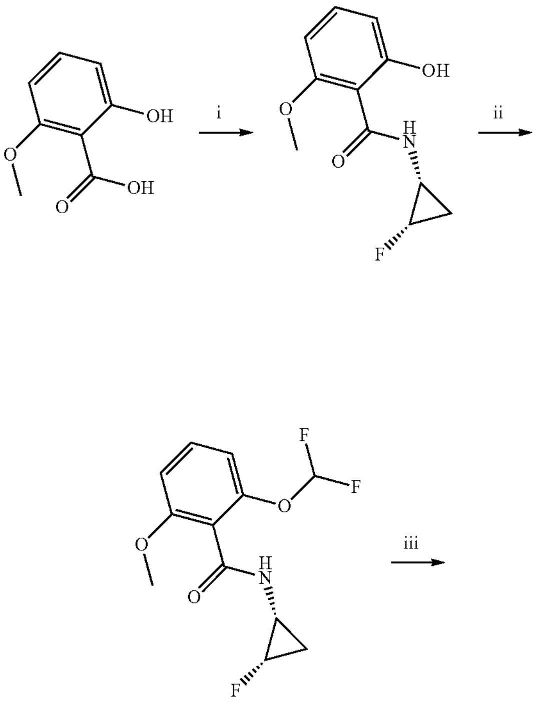

-continued

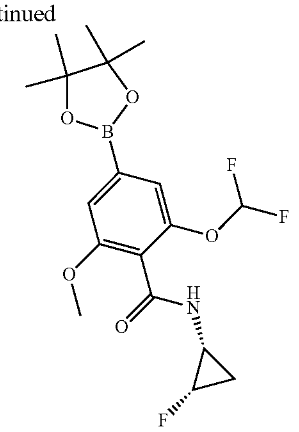

2.3.1. Step i: N-[(1R,2S)-2-fluorocyclopropyl]-2-hydroxy-6-methoxy-benzamide

To a solution of 2-hydroxy-6-methoxy-benzoic acid (CAS #3147-64-6; 50 g, 297 mmol, 1 eq.) in DCM (300 mL) is added 1,1'-carbonyldiimidazole (CAS #530-62-1; 49 g, 297 mmol, 1 eq.) portionwise causing release of $CO_2$. Then (1R,2S)-2-fluorocyclopropanamine 4-methylbenzenesulfonate (CAS #143062-84-4; 80 g, 312 mmol, 1.05 eq.) and $Et_3N$ (50 mL, 359 mmol, 1.21 eq.) are added to the mixture. The resulting solution is stirred at RT for 2.5 h. Water is added and the pH is adjusted to 2 using a 12N HCl solution (60 mL). The organic layer is separated and the aqueous layer is extracted twice with DCM. The combined organic layers are washed three times with a sat. $NaHCO_3$ solution, and dried over $Na_2SO_4$, filtered and concentrated in vacuo. The residue is purified by flash chromatography on silica gel (eluting with DCM/EtOAc 100/0 to 90/10) to afford the desired intermediate.

2.3.2. Step ii: 2-(difluoromethoxy)-N-[(1R,2S)-2-fluorocyclopropyl]-6-methoxy-benzamide In a 3-necked round-bottom flask equipped with a temperature probe and a funnel, containing a solution of the above prepared N-[(1R,2S)-2-fluorocyclopropyl]-2-hydroxy-6-methoxy-benzamide (29 g, 130 mmol, 1 eq.) in a mixture ACN/water (146 mL/146 mL) at 5° C. is added potassium hydroxide (73 g, 1298 mmol, 10 eq.) over 1 h. Then bromodifluoromethyl diethylphosphonate (CAS #65094-22-6; 46 mL, 260 mmol, 2 eq.) is added neat dropwise over 40 min while keeping the reaction temperature below 12° C. The reaction mixture is allowed to warm to RT and stirred at RT for 40 min. The reaction solution is then extracted twice with EtOAc. The combined organic layers are washed with brine, dried over $MgSO_4$, filtered and concentrated in vacuo. The residue is re-slurried in MTBE (80 mL). The suspension is filtered, the solid washed with MTBE (20 mL) and dried to afford the desired intermediate.

2.3.3. Step iii: Int 8

To a solution of the above prepared 2-(difluoromethoxy)-N-[(1R,2S)-2-fluorocyclopropyl]-6-methoxy-benzamide (22 g, 76 mmol, 1 eq.) in THF (217 mL) under inert atmosphere at RT is added $B_2pin_2$ (CAS #73183-34-3; 25 g, 98 mmol, 1.3 eq.), 4,4'-di-tert-butyl-2,2'-bipyridine (CAS #72914-19-3; 829 mg, 3.0 mmol, 0.04 eq.) and $[Ir(OCH_3)$ $(COD)]_2$ (CAS #12148-71-9; 1 g, 1.5 mmol, 0.02 eq.). The resulting mixture is heated to 70° C. for 2 h then concentrated in vacuo. This residue is purified by flash chromatography on silica gel (eluting with DCM/EtOAC 90/10). The collected fractions are concentrated and the obtained solid is then dissolved in a mixture DCM/heptane (100 mL/330 mL) and stirred for 15 min. The suspension is filtered; the solid is washed twice with heptane, dried in vacuo to afford the desired compound.

2.4. Int 12

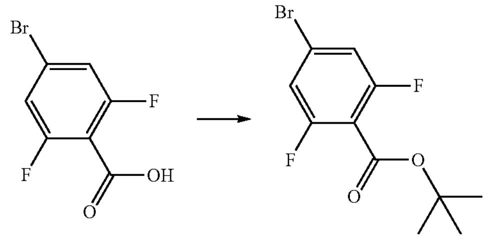 [SMILES: O=C(O)c1c(F)cc(Br)cc1F ; CC(C)(C)OC(=O)c1c(F)cc(Br)cc1F]

To a solution of 4-bromo-2,6-difluoro-benzoic acid (CAS #183065-68-1; 15 g, 63 mmol, 1 eq.) in THF (210 mL) are added tert-butanol (31 mL.), di-tert-butyl dicarbonate (CAS #183065-68-1; 28 g, 130 mmol, 2 eq.) and 4-dimethylaminopyridine (CAS #1122-58-3; 1.6 g, 13 mmol, 0.2 eq.). The resulting mixture is stirred at RT for 18 h. Imidazole (CAS #288-32-4; 5.7 g, 82 mmol, 1.3 eq.) is added and the reaction mixture id stirred at RT for 1 h, then concentrated, diluted with EtOAc and washed successively with a HCl 1N solution, a 0.2M $NaH_2PO_4$ solution, water and brine. The organic layer is separated, dried over $MgSO_4$, filtered and concentrated to afford the desired intermediate.

2.5. Int 14

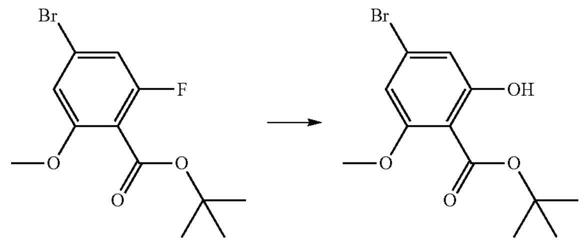 [SMILES: COc1cc(Br)cc(F)c1C(=O)OC(C)(C)C ; COc1cc(Br)cc(O)c1C(=O)OC(C)(C)C]

To a solution of 2-(methylsulfonyl)ethanol (CAS #15205-66-0; 16 g, 120 mmol, 1.5 eq.) in DMF (100 mL) at 0° C. under $N_2$ atmosphere is added NaH (60% suspension in oil, CAS #7646-69-7; 9 g, 230 mmol, 2.7 eq.). The reaction mixture is stirred at 0° C. for 10 min and a solution of tert-butyl 4-bromo-2-fluoro-6-methoxy-benzoate Int 13 (25 g, 82 mmol, 1 eq.) in DMF (60 mL) is added. The resulting solution is stirred at RT for 18 h, then quenched by the addition of a HCl 2N solution (170 mL, 4.0 eq.) and extracted with EtOAc. The combined organic layers are washed with water, brine, dried over $MgSO_4$, filtered and concentrated to dryness to afford the desired intermediate.

2.6. Int 17

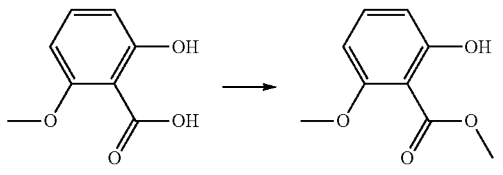

To a solution of acid (CAS #3147-64-6; 5.56 g, 33 mmol, 1 eq.) in MeOH (60 mL) is added dropwise sulfuric acid (CAS #7664-93-9; 3.5 mL, 66 mmol, 2 eq.). The resulting solution is heated to 70° C. for 18 h. Then thionyl chloride (CAS #7719-09-7; 1 mL, 13.2 mmol, 0.4 eq;) is added and the resulting mixture is stirred at 55° C. for 72 h. The solution is concentrated in vacuo, quenched with water and extracted with DCM. The combined organic layers are passed through a phase separator, concentrated. The residue is purified by flash chromatography on silica gel (eluting with heptane/EtOAc 100/0 to 93/7) to afford the desired intermediate.

2.7 Int 21

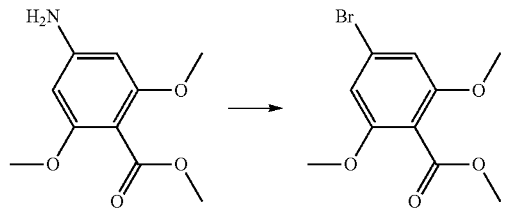

To a solution of methyl 4-amino-2,6-dimethoxybenzoate (CAS #3956-34-1; 8 g, 38 mmol, 1 eq.) in ACN (160 mL) at 0° C. is added carefully $H_2SO_4$ (8 mL, 151 mmol, 4 eq.) in water (17 mL). Then a solution of sodium nitrite (CAS #7632-00-0; 2.7 g, 39 mmol, 1.02 eq.) in water (16 mL) is added dropwise. A precipitate is formed. The resulting mixture is stirred at 0° C. for 30 min. Then CuBr (CAS #7789-45-9; 20.4 g, 142 mmol, 3.75 eq.) is introduced by portions. The resulting suspension is stirred at RT for 18 h, filtered on celite. The solid is washed with DCM (300 mL). The filtrate is washed with water and brine. The combined organic layers are dried over MgSO4, filtered and concentrated in vacuo. The residue is purified by flash chromatography on silica gel (eluting with heptane/EtOAc 98/2 to 70/30) to afford the desired intermediate.

2.8. Int 23

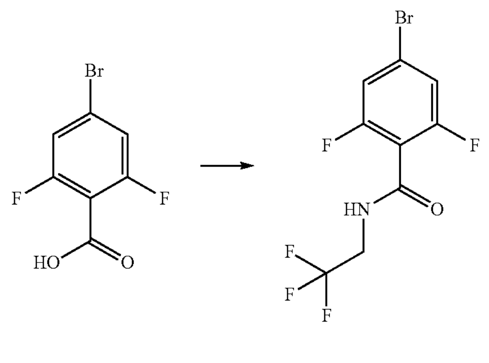 [SMILES: O=C(O)c1c(F)cc(Br)cc1F ; O=C(NCC(F)(F)F)c1c(F)cc(Br)cc1F]

4-bromo-2,6-difluorobenzoic acid (CAS #183065-68-1; 90.5 g, 381.9 mmol, 1 eq.) is added to $SOCl_2$ (CAS #7719-

09-7; 181 mL, 6.5 eq.). The reaction mixture is stirred at reflux. After 6 h of reflux, the heating is stopped and the reaction mixture is cooled down to RT and then concentrated in vacuo. The residue is diluted with toluene (181 mL, 2 volumes) and concentrated to eliminate residual thionyl chloride. The liquid residue is diluted with DCM (453 mL, 5 volumes). Trifluoro ethylamine hydrochloride (CAS #373-88-6; 54.3 g, 401 mmol, 1.05 eq.) is added to the reaction mixture under $N_2$ atmosphere and the latter is cooled to 5° C. $Et_3N$ (117 mL, 840 mmol, 2.2 eq.) is then added dropwise keeping the temperature of the reaction mixture under 27° C. The reaction mixture is then stirred under $N_2$ at RT for 14 h. The suspension is diluted with DCM (1000 mL, 10 volumes). The organic phase is washed with water (500 mL, 5 volumes) and a sat. $NaHCO_3$ solution (500 mL, 5 volumes). The organic phase is dried on $Na_2SO_4$ (100 g), filtered, concentrated and triturated with heptane (500 mL, 6 volumes). The suspension is filtered and washed with heptane (500 mL, 6 volumes) and the solid is dried under reduced pressure to give the desired compound.

2.9. Int 25

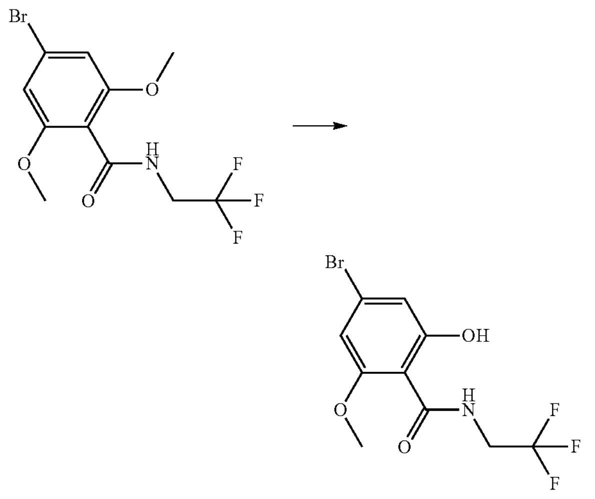

To a solution of Int 24 (700 mg, 2.05 mmol, 1.0 eq.) in DCM (28 mL) at 0° C. is added dropwise $BCl_3$ (1M in DCM, CAS #10294-34-5; 4.5 mL, 4.50 mmol, 2.2 eq.). The reaction mixture is stirred at 0° C. for 2 h then quenched with a 0.1N HCl solution HCl and ice. The resulting solution is extracted with DCM with several drops of MeOH. The combined organic layers are passed through a phase separator and concentrated in vacuo to afford the desired intermediate.

2.10. Int 28

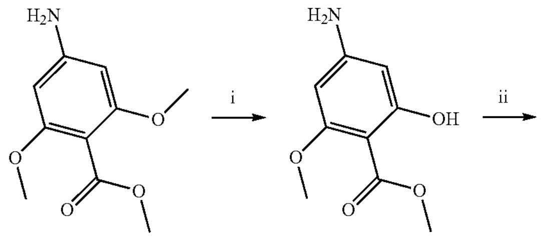

-continued

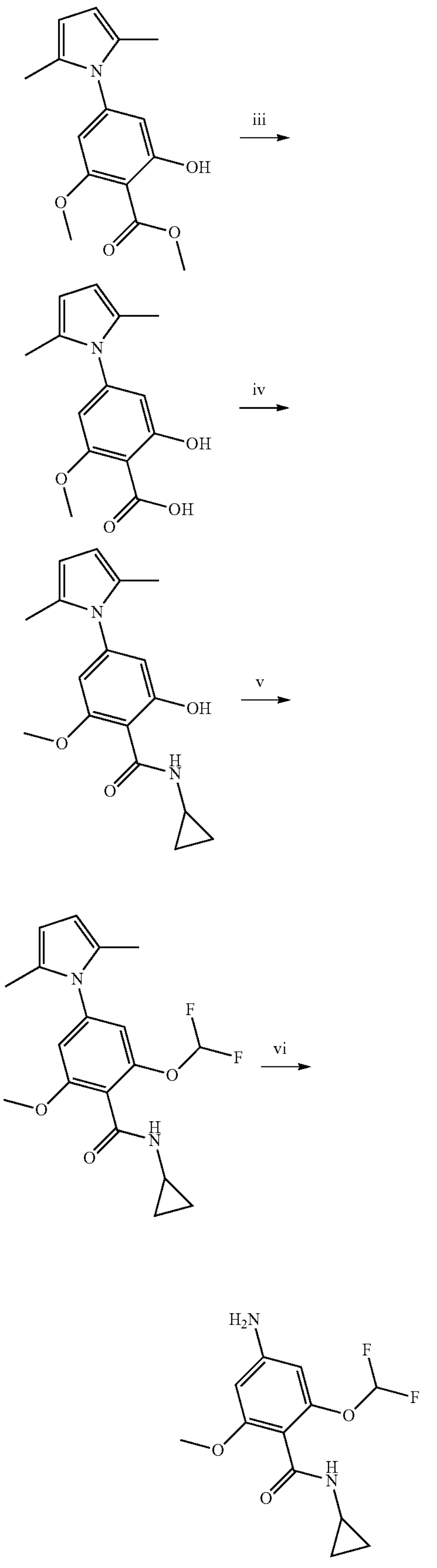

2.10.1. Step i: methyl 4-amino-2-hydroxy-6-methoxy-benzoate

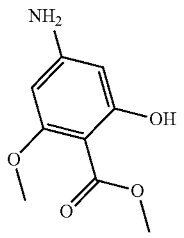

To a solution of methyl 4-amino-2,6-dimethoxy-benzoate (CAS #3956-34-1; 8.75 g, 41 mmol, 1 eq.) in dry DCM (230 mL) under $N_2$ atmosphere is added $BCl_3$ (1 M in DCM, CAS #10294-34-5; 91 mL, 91 mmol, 2.2 eq.) dropwise at 0° C. The resulting solution is stirred for 45 min and at RT for 18 h. HCl 2 N and ice-water is added and the mixture is extracted twice with DCM. The combined organic layers are washed with water, brine, dried over anhydrous $Na_2SO_4$, and concentrated in vacuo to afford the desired intermediate.

LCMS: MW (calcd): 197.1; m/z MW (obsd): 198.2 (M+H)

2.10.2. Step ii: methyl 4-(2,5-dimethylpyrrol-1-yl)-2-hydroxy-6-methoxy-benzoate

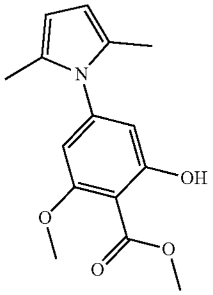 [SMILES: COC(=O)c1c(O)cc(-n2c(C)ccc2C)cc1OC]

To a solution of methyl 4-amino-2-hydroxy-6-methoxy-benzoate (4.72 g, 24 mmol, 1 eq.) in AcOH (100 mL) is added 2.5-hexanedione (CAS #110-13-4; 5.62 mL, 48 mmol, 2 eq.) and is stirred at 110° C. for 15 min then at RT for 1.5 h. The mixture is concentrated in vacuo and is purified by flash chromatography on silica gel (eluting with heptane/EtOAc 50/50) to afford the desired intermediate.

LCMS: MW (calcd): 275.3; m/z MW (obsd): 276.3 (M+H)

2.10.3. Step iii: 4-(2,5-dimethylpyrrol-1-yl)-2-hydroxy-6-methoxy-benzoic Acid

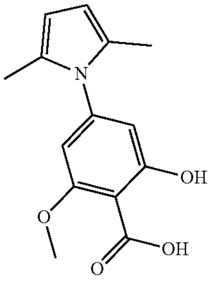 [SMILES: COc1cc(-n2c(C)ccc2C)cc(O)c1C(=O)O]

To a solution of the above prepared methyl 4-(2,5-dimethylpyrrol-1-yl)-2-hydroxy-6-methoxy-benzoate (6.10 g, 22 mmol) in MeOH (100 mL) is added a solution of NaOH 2 N (133 mL, 266 mmol, 12 eq.). The reaction mixture is stirred at 100° C. for 18 h, concentrated in vacuo then the aqueous layer is acidified with HCl 2 N (140 mL) and extracted with DCM three times. The combined organic layers are dried over $Na_2SO_4$, filtered and concentrated in vacuo to afford the desired intermediate.

LCMS: MW (calcd): 261.2; m/z MW (obsd): 262.2 (M+H)

2.10.4. Step iv: N-cyclopropyl-4-(2,5-dimethylpyrrol-1-yl)-2-hydroxy-6-methoxy-benzamide

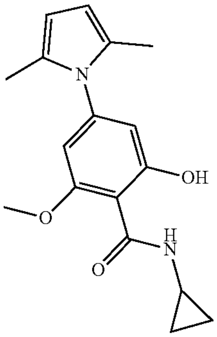 [SMILES: COc1cc(-n2c(C)ccc2C)cc(O)c1C(=O)NC1CC1]

To a stirred solution of the above prepared 4-(2,5-dimethylpyrrol-1-yl)-2-hydroxy-6-methoxy-benzoic acid (10 g, 38.3 mmol, 1 eq.) and HATU (CAS #14893-10-1; 16.01 g, 42.1 mmol, 1.1 eq.) in anhydrous DMF (200 mL) is added DIPEA (13.3 mL, 76.5 mmol, 2 eq.). The mixture is stirred at RT for 10 min and cyclopropylamine (CAS #765-30-0; 3.2 mL, 45.9 mmol, 1.2 eq.) is added. The resulting mixture is stirred at RT for 2 h, concentrated and then diluted with EtOAc and water. The organic layer is separated, dried over $Na_2SO_4$, filtered and concentrated under reduced pressure. The residue is purified by flash chromatography on silica gel (eluting with heptane/EtOAc 100/0 to 70/30) to afford the desired compound.

LCMS: MW (calcd): 300.3; m/z MW (obsd): 301.3 (M+H)

2.10.5. Step v: N-cyclopropyl-2-(difluoromethoxy)-4-(2,5-dimethylpyrrol-1-yl)-6-methoxy-benzamide

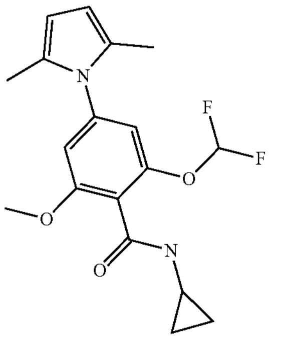 [SMILES: COc1cc(-n2c(C)ccc2C)cc(OC(F)F)c1C(=O)NC1CC1]

To a stirred solution of N-cyclopropyl-4-(2,5-dimethylpyrrol-1-yl)-2-hydroxy-6-methoxy-benzamide (6.3 g, 21.1 mmol, 1 eq.) in ACN (100 mL) at −10° C. is added dropwise KOH (23.6 g, 421 mmol, 20 eq.) in $H_2O$ (100 mL). The resulting mixture is stirred at −10° C. for 25 min and diethyl (bromodifluoromethyl)phosphonate (7.49 mL, 44.14 mmol, 2 eq.) in ACN (15 mL) is added dropwise. The mixture is quenched with ice/$H_2O$ and extracted twice with DCM. The organic layers are dried over $Na_2SO_4$, filtered and concentrated under reduced pressure. The residue is purified by flash chromatography on silica gel (eluting with DCM/MeOH 100/0 to 98/2) to afford the desired compound.

LCMS: MW (calcd): 350.3; m/z MW (obsd): 351.5 (M+H)

2.10.6. Step vi: Int 28

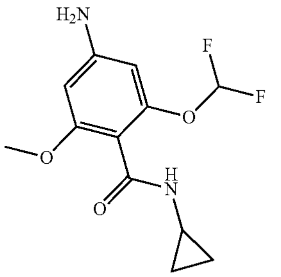 [SMILES: COc1cc(N)cc(OC(F)F)c1C(=O)NC1CC1]

To a stirred solution of N-cyclopropyl-2-(difluoromethoxy)-4-(2,5-dimethylpyrrol-1-yl)-6-methoxy-benzamide (6.8 g, 19.3 mmol, 1 eq.) in EtOH (100 mL) at RT is added hydroxylamine hydrochloride (CAS #5470-11-1; 13.4 g, 193 mmol, 10 eq.) in $H_2O$ (50 mL). The resulting mixture is stirred at 110° C. for 18 h. Hydroxylamine hydrochloride (5 eq.) and $Et_3N$ (2 eq.) are added. The resulting mixture is stirred at 110° C. for 3.5 h. EtOH is concentrated in vacuo. The pH of the aqueous layer is adjusted to pH 9 with a 2N NaOH solution, and the resulting solution is extracted twice with EtOAc. The combined organic layers are dried over $Na_2SO_4$, filtered and concentrated in vacuo. The residue is purified by chromatography on silica gel eluting with 0-5% MeOH in DCM. The residue is purified by flash chromatography on silica gel (eluting with DCM/MeOH 100/0 to 95/5). The product fractions are combined and concentrated in vacuo. The solid is triturated with $Et_2O$ and filtered to afford the desired intermediate.

2.11. Int 37

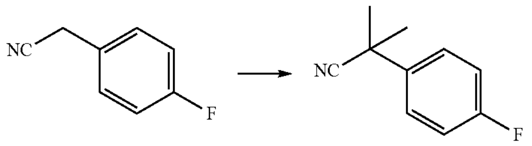

To a solution of 4-fluorobenzeneacetonitrile (CAS #459-22-3, 1 g, 7.4 mmol, 1 eq.) in THF at 0° C. is added methyl iodide (CAS #74-88-4, 1.38 mL, 22.2 mmol, 3.0 eq.) followed by addition of t-BuOK portionwise over 10 min (CAS #865-47-4, 2.49 g, 22.2 mmol, 3 eq.). The reaction mixture is stirred at RT for 2 h until total completion. The reaction is quenched with brine and extracted twice with EtOAc. The combined organic layers are dried over $MgSO_4$, filtered and concentrated to give the desired compound.

2.12. Int 39

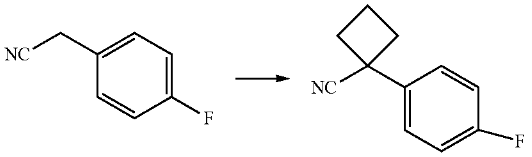 [SMILES: N#CCc1ccc(F)cc1 ; N#CC1(c2ccc(F)cc2)CCC1]

To a solution KOH (CAS #1310-58-3, 314 mg, 5.6 mmol, 2.8 eq.) in DMSO (4 mL) is added dropwise a solution of 4-fluorobenzeneacetonitrile (CAS #459-22-3, 270 mg, 2.0 mmol, 1 eq.) and 1,3-dibromopropane (CAS #109-64-8, 213 μL, 2.10 mmol, 1.05 eq.) in $Et_2O$ (0.4 mL). The reaction mixture is stirred vigorously at RT for 2 h until total completion. The reaction is quenched with water (0.5 mL), filtered through a pad of celite and washed with $Et_2O$. The aqueous layer is extracted twice with EtOAc. The combined organic layers are washed with water, dried over $Na_2SO_4$, filtered and concentrated. The residue is purified by flash chromatography on silica gel (eluting with heptane/EtOAc 100/0 to 90/10) to afford the desired intermediate.

2.13. Int 58

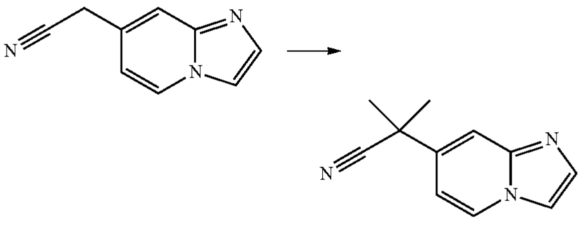

To a solution of nitrile Int 62 (2.8 g, 17.8 mmol, 1 eq.) in dry THF (50 mL) at −35° C. under inert atmosphere are added t-BuOK (CAS #865-47-4; 5 g, 44.5 mmol, 2.5 eq.) followed by methyl iodide (CAS #74-88-4; 3.1 mL, 44.5 mmol, 2.5 eq.). The resulting solution is then allowed to warm to RT and stirred for 1 h. The reaction mixture is quenched with a sat. $Na_2S_2O_3$ solution and extracted with EtOAc. The combined organic layers are dried over $MgSO_4$, filtered and concentrated in vacuo. The residue is purified by flash chromatography on silica gel (eluting with DCM/MeOH 100/0 to 98/2) to afford the desired compound.

2.14. Int 64

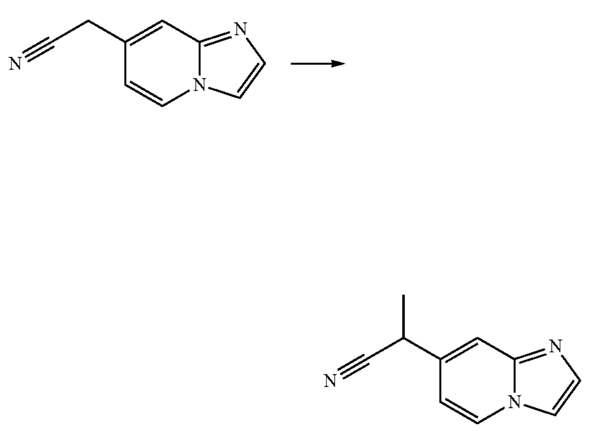

To a solution of nitrile Int 62 (100 mg, 0.64 mmol, 1 eq.) in dry THF (3 mL) under inert atmosphere are added t-BuOK (CAS #865-47-4; 71 mg, 0.64 mmol, 1 eq.) followed by methyl iodide (CAS #74-88-4; 40 µL, 0.64 mmol, 1 eq.). The resulting solution is stirred at RT for 1.5 h. The reaction mixture is quenched with a sat. $NH_4Cl$ solution and extracted with EtOAc. The combined organic layers are dried over $Na_2SO_4$, filtered and concentrated in vacuo. The residue is purified by flash chromatography on silica gel (eluting with DCM/MeOH 100/0 to 98/2) to afford the desired compound.

2.15. Int 65

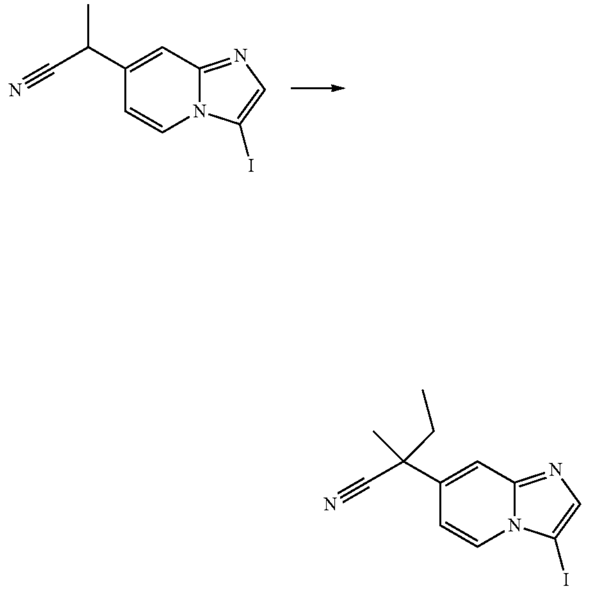

To a solution of Int 63 (20 mg, 0.13 mmol, 1 eq.) in dry THF (2 mL) at 0° C. is added t-BuOK (CAS #865-47-4, 17 mg, 0.15 mmol, 1.2 eq.) and iodoethane (CAS #75-03-6, 12 µL, 0.15 mmol, 1.2 eq.). The reaction mixture is stirred at RT for 20 min then quenched with a sat. aq. solution of $Na_2S_2O_3$ and extracted with DCM (twice). The combined organic layers are passed through a phase separator, concentrated to dryness to give the desired intermediate.

2.16. Int 66

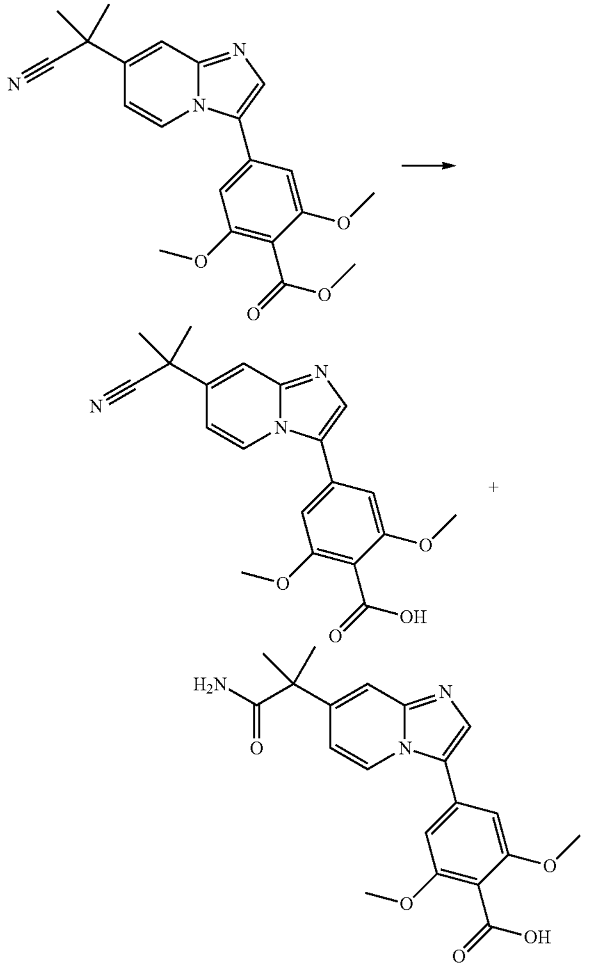

To a solution of methyl ester derivative Int 56 (609 mg, 1.60 mmol, 1 eq.) in a mixture MeOH/THF (1:1, 14 mL) is added a 2N NaOH solution (4.8 mL, 9.63 mmol, 6 eq.). The resulting solution is heated at 70° C. for 26 h then stirred at RT for 18 h. The organic solvents are removed under reduced pressure. The residue is diluted with water, pH is adjusted until acidic pH with HCl 2 N, ACN is added and the resulting solution is concentrated in vacuo. The residue is triturated in ACN, the solid is filtered, washed with ACN, MeOH and DCM and dried in vacuo to afford a mixture of 2 compounds cyano and primary amide Int 66.

2.17. Int 67

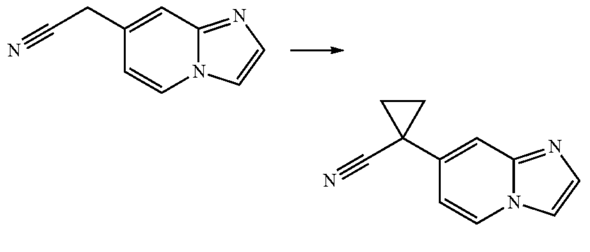

To a solution of nitrile Int 62 (200 mg, 1.27 mmol, 1 eq.) in dry ACN (10 mL) at 0° C. are added $Cs_2CO_3$ (CAS

#7646-69-7; 1.03 g, 3.18 mmol, 2.5 eq.) followed by 1.2-dibromoethane (CAS #110-52-1; 241 μL, 2.80 mmol, 2.2 eq.). The resulting solution is stirred at RT for 2 h then at 65-70° C. for 18 h. The reaction mixture is quenched with water, a sat. $Na_2S_2O_3$ solution and extracted with EtOAc. The combined organic layers are passed through a phase separator and concentrated. The residue is purified by flash chromatography on silica gel (eluting with DCM/MeOH 100/0 to 97.5/2.5) to afford the desired intermediate.

2.18. Int 69

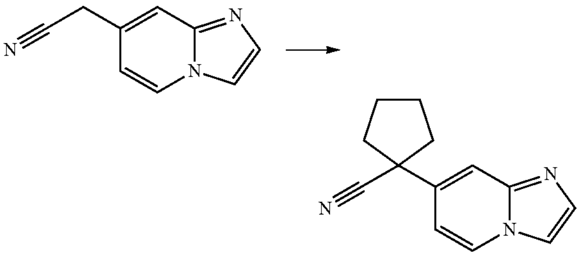

To a degassed solution of nitrile Int 62 (100 mg, 0.63 mmol, 1 eq.) in dry DMF (6 mL) under inert atmosphere at 0° C. are added sodium hydride (60% dispersion in mineral oil, CAS #7646-69-7; 76 mg, 1.91 mmol, 3 eq.) followed by 1.4-dibromobutane (CAS #110-52-1; 91 μL, 0.76 mmol, 1.2 eq.). The reaction mixture is stirred at 0° C. for 15 min then quenched with water, a sat. $NH_4Cl$ solution and extracted with DCM. The combined organic layers are washed with brine, passed through a phase separator and concentrated. The residue is purified by flash chromatography on silica gel (eluting with DCM/MeOH 100/0 to 98.5/1.5) to afford the desired compound.

2.19. Int 71 & Int 73

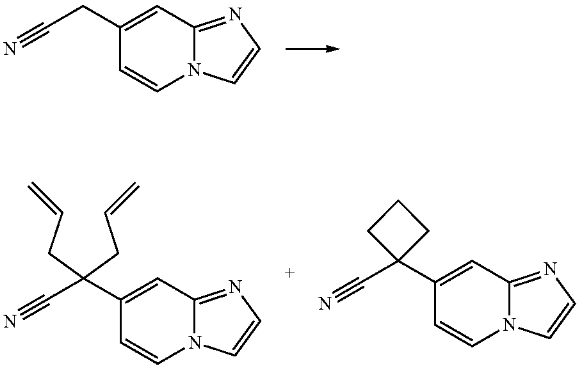 [SMILES: N#CCc1ccn2ccnc2c1 ; C=CCC(C#N)(CC=C)c1ccn2ccnc2c1 ; N#CC1(c2ccn3ccnc3c2)CCC1]

To a solution of Int 62 (150 mg, 0.95 mmol, 1 eq.) in dry THF (4 mL) at 0° C. are added t-BuOK (CAS #865-47-4; 321 mg, 2.86 mmol, 3 eq.) followed by 1.3-dibromobutane (242 μL, 2.39 mmol, 2.5 eq.). The reaction mixture is stirred at RT for 20 h, and at 70° C. for 4 h, then quenched with a sat. $Na_2S_2O_3$ solution and extracted with DCM. The combined organic layers are washed with brine, dried over $Na_2SO_4$, filtered and concentrated in vacuo. The residue is purified by flash chromatography on silica gel (eluting with DCM/MeOH 100/0 to 97.5/2.5) to afford two intermediates Int 71 and Int 73.

2.20. Int 75

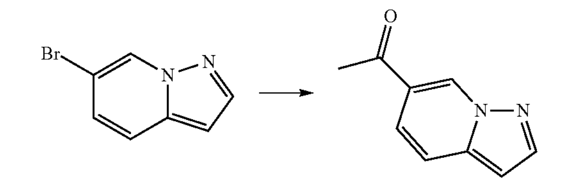

To a degassed solution of 6-bromopyrazolo[1,5-a]pyridine (CAS #1264193-11-4; 1 g, 5.07 mmol, 1 eq.) in dioxane (34 mL) under inert atmosphere are added tributyl(1-ethoxyvinyl)stannane (CAS #97674-02-7; 2.2 g, 6.09 mmol, 1.2 eq.) and $Pd(PPh_3)_4$ (CAS #14221-01-3; 587 mg, 0.51 mmol, 0.1 eq.). The mixture is stirred at 100° C. for 2 h, cooled to RT and then a 2N HCl solution (5.2 mL, 10.1 mmol, 2 eq.) is added and the resulting solution is stirred for 1 h at RT. The mixture is quenched with a sat. $NaHCO_3$ solution and extracted with EtOAc. The combined layers are dried over $Na_2SO_4$, filtered and concentrated in vacuo. The residue is purified by flash chromatography on silica gel (eluting with heptane/EtOAc 100/0 to 75/35) to afford the desired compound.

2.21. Int 80

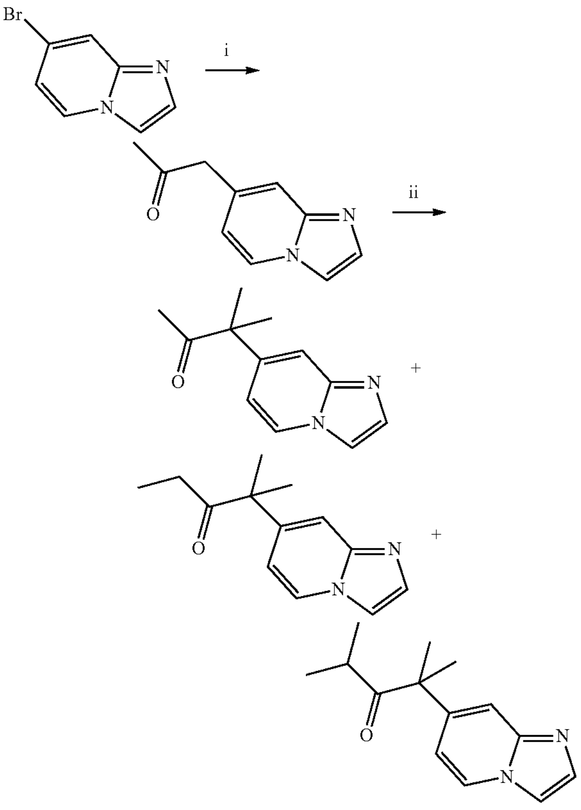

2.21.1. Step i: 1-imidazo[1,2-a]pyridin-7-ylpropan-2-one

To a solution of 7-bromoimidazo[1,2-a]pyridine (CAS #808744-34-5; 1 g, 5.07 mmol, 1 eq.) in dry dioxane under $N_2$ atmosphere are added $Cs_2CO_3$ (CAS #534-17-8; 3.3 g, 10.1 mmol, 2 eq.), acetone (CAS #67-64-1; 5.6 mL, 76.1 mmol, 15 eq.) MorDalphos (CAS #1237588-12-3; 94 mg, 0.20 mmol, 0.04 eq.) and bis[cinnamyl palladium(II) chloride (CAS #12131-44-1-; 52 mg, 0.10 mmol, 0.02 eq.). The resulting mixture is stirred at 90° C. for 18 h. Then more MorDalphos (47 mg, 0.10 mmol, 0.02 eq.), bis[cinnamyl palladium(II) chloride (CAS #12131-44-1-; 26 mg, 0.05 mmol, 0.01 eq.) and acetone (5.6 mL, 76.1 mmol, 15 eq.) are introduced. The reaction mixture is degassed and heated to 90° C. for 18 h. After cooling to RT, the precipitate formed is filtered, the filtrate is concentrated in vacuo and purified by flash chromatography on silica gel (eluting with DCM/MeOH 99/1 to 98/2) to afford 1-imidazo[1,2-a]pyridin-7-ylpropan-2-one.

2.21.2. Step ii: Int 80

To a solution of the above prepared ketone intermediate (322 mg, 1.85 mmol, 1 eq.) in THF (10 mL) at 0° C. is added t-BuOK (CAS #865-47-4, 622 mg, 5.54 mmol, 3 eq.). The resulting mixture is stirred 5 min at 0° C. then methyl iodide (CAS #74-88-4, 345 μL, 5.54 mmol, 3 eq.) is introduced. The reaction mixture is allowed to warm to RT and stirred for 20 min. The reaction is quenched with a 10% $Na_2S_2O_3$ solution, extracted with DCM, filtered through a phase separator, and concentrated in vacuo. The residue is purified by flash chromatography on silica gel (eluting with DCM/MeOH 99/1 to 98/2) to afford a mixture of three intermediates.

2.22. Int 81

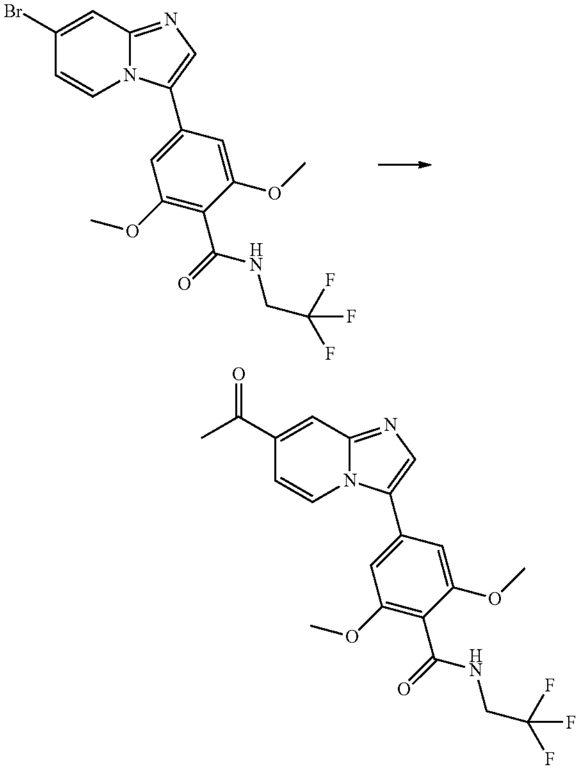

To a solution of bromide Int 36 (40 mg, 0.087 mmol, 1 eq.), n-butyl vinyl ether (CAS #111-34-2; 56 μL, 0.44 mmol, 5 eq.) and $Et_3N$ (36 μL, 0.23 mmol, 3 eq.) in degassed DMF (1 mL) are added $Pd(OAc)_2$ (CAS #3375-31-3; 0.8 mg, 0.003 mmol, 0.04 eq.) and dppp (CAS #6737-42-4; 1.5 mg, 0.004 mmol, 0.043 eq.). The resulting solution is heated to 100° C. for 18 h then more $Pd(OAc)_2$ (0.6 mg, 0.003 mmol, 0.04 eq.) and dppp (3.6 mg, 0.009 mmol, 0.1 eq.) are introduced followed by EtOH (0.4 mL). The resulting mixture is stirred at 100° C. for 8 h then cooled to RT and stirred for 72 h. Again $Pd(OAc)_2$ (0.6 mg, 0.003 mmol, 0.03 eq.), dppp (2 mg, 0.006 mmol, 0.06 eq.) and n-butyl vinyl ether (56 μL, 0.44 mmol, 5 eq.) are added and the solution is heated to 100° C. for 2 h. The reaction mixture is quenched with water and extracted with DCM. The combined organic layers are washed with brine, dried over $Na_2SO_4$, filtered, concentrated in vacuo and purified by flash chromatography on silica gel (eluting with heptane/EtOAc 100/0 to 0/100) to afford the desired intermediate.

2.23. Int 83

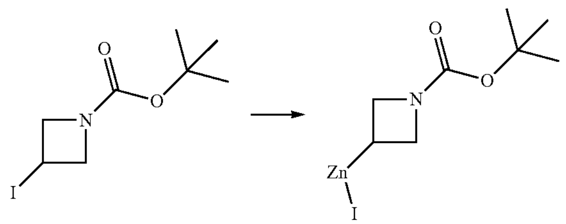

To a suspension of zinc dust (CAS #7440-66-6; 248 mg, 3.81 mmol, 1.4 eq.) in DMA (2 mL) are added 1,2-dibromoethane (CAS #106-93-4; 24 μL, 0.28 mmol, 0.1 eq.) and trimethylsilane (CAS #993-07-7; 35 μL, 0.28 mmol, 0.1 eq.). The resulting mixture is stirred at 65° C. for 1 h. After cooling to RT is added 1-Boc-3-(iodo)azetidine (CAS #254454-54-1; 790 mg, 2.79 mmol, 1 eq.). The resulting solution is stirred at 65° C. for 1 h then cooled to RT and used as such directly in the next step.

2.24. Int 100

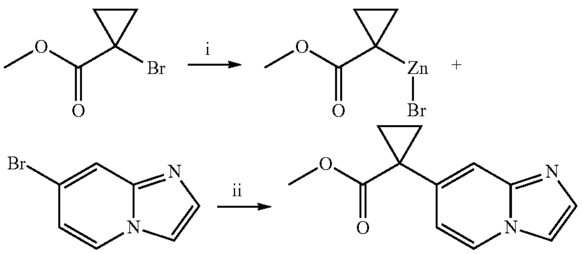

2.24.1. Step i: bromo-(1-methoxycarbonylcyclopropyl)zinc $InCl_3$ (CAS #10025-82-8; 310 mg, 1.4 mmol, 0.05 eq.) and zinc dust (CAS #7440-66-6; 9.1 g, 140 mmol, 5 eq.) are charged in a 250 mL round-bottom flask and purged with a sweep of argon for 15 min followed by anhydrous THF (40 mL). Bromine (CAS #7726-95-6; 140 μL, 2.79 mmol, 0.1 eq.) is added at RT in 3 portions. The reaction is heated to 55° C. with vigorous stirring. The heating block is removed and a solution of methyl 1-bromocyclopropanecarboxylate (CAS #96999-01-8; 5 g, 27.9 mmol, 1 eq.) in THF (10 mL) is added at 55° C. over a period of 2-3 min and stirred for 3.25 h at 55° C. then the reaction mixture is cooled to RT and stirred for 16 h. The resulting solution is titrated and used directly in the next step.

2.24.2. Step ii: Int 100

To a solution of Q-Phos (CAS #312959-24-3; 187 mg, 0.26 mmol, 0.04 eq.) and $Pd(dba)_2$ (CAS #32005-36-0; 151 mg, 0.26 mmol, 0.04 eq.) in anhydrous THF (20 mL) is added 7-bromoimidazo[1,2-a]pyridine (CAS #808744-34-5; 1.3 g, 6.60 mmol, 1 eq.). A solution of freshly prepared bromo-(1-methoxycarbonylcyclopropyl)zinc (0.43 M in THF, 21.5 mL, 9.24 mmol, 1.4 eq.) is added dropwise over 15 min. The resulting mixture is stirred at RT for 24 h, then diluted with DCM (150 mL) and quenched with a sat. $NH_4Cl$ solution (30 mL). The layers are separated, the organic layer is washed with water, brine, dried over $MgSO_4$, filtered and concentrated in vacuo. The crude is purified by flash chromatography on silica gel (eluting with DCM/MeOH 100/0 to 90/10). The expected product is then solubilized in a mixture DCM/MeOH and DCM is slowly evaporated. The solid is filtered, washed with MeOH and dried in vacuo to afford the desired compound.

2.25. Int 109

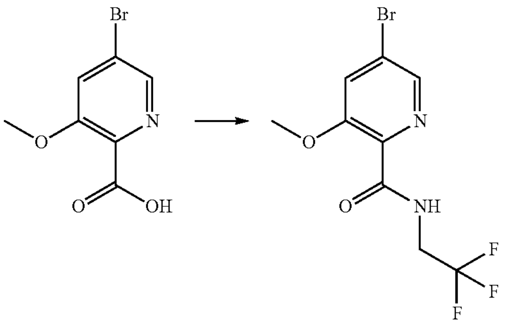 [SMILES: COc1cc(Br)cnc1C(=O)O ; COc1cc(Br)cnc1C(=O)NCC(F)(F)F]

To a solution of 5-bromo-3-methoxy-pyridine-2-carboxylic acid (CAS #1142191-66-9, 500 mg, 2.15 mmol, 1.0 eq.) in anhydrous DMF (8.3 mL) are added DIPEA (563 μL, 3.23 mmol, 1.5 eq.) and HATU (901 mg, 2.37 mmol, 1.1 eq.). The mixture is stirred at RT for 30 min and 2,2,2-trifluoroethanamine hydrochloride (CAS #373-88-6, 350 mg, 2.59 mmol, 1.2 eq.) is added. The reaction mixture is stirred at RT for 20 h and is then evaporated to dryness. The residue is diluted with DCM and a precipitate forms. The solid is filtered, the filtrate is concentrated and the residue is purified by flash chromatography on silica gel (eluting with heptane/EtOAc 10/0 to 1/1) to afford the desired compound.

2.26. Int 111

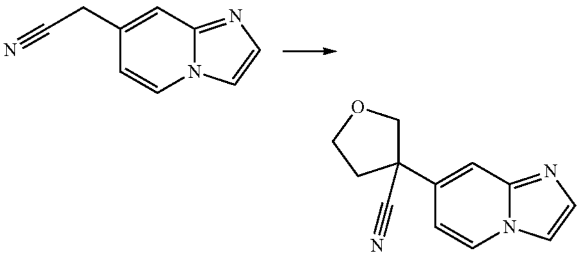

To a solution of Int 62 (50 mg, 0.32 mmol, 1.0 eq.) and 1-chloro-2-(chloromethoxy)ethane (CAS #1462-33-5, 31 μL, 0.32 mmol, 1.0 eq.) in a mixture $Et_2O$/THF (1:1, 0.4 mL) at −20° C. is added a solution of NaH (60% suspension in oil CAS #7646-69-4; 38 mg, 0.95 mmol, 3 eq.) in NMP (0.95 mL). The reaction mixture is warmed up to RT for 18 h. Ice water is added and the mixture is extracted with EtOAc (twice). The combined organic layers are washed with brine, dried over $MgSO_4$, filtered and concentrated to give the desired compound.

2.27 Int 114

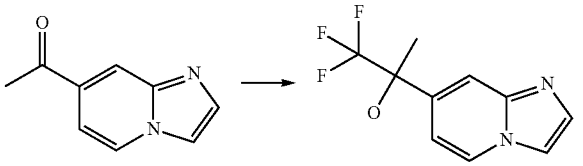 [SMILES: CC(=O)c1ccn2ccnc2c1 ; CC(O)(c1ccn2ccnc2c1)C(F)(F)F]

To a solution of 1-(imidazo[1,2-a]pyridin-7-yl)ethanone (CAS #1036991-50-0; 200 mg, 0.86 mmol, 1 eq.) in THF (6 mL) at 0° C. under inert atmosphere are added (trifluoromethyl)trimethylsilane (CAS #81290-20-2; 265 μL, 1.29 mmol, 1.2 eq.) and tetrabutylammonium fluoride (1M in THF, CAS #429-41-4; 9 μL, 0.009 mmol, 0.007 eq.). The reaction mixture is stirred at 0° C. for 2 h and more tetrabutylammonium fluoride is added (860 μL, 0.86 mmol, 1 eq.). The resulting solution is stirred at RT for 18 h then quenched with a sat. $NH_4Cl$ solution and extracted with EtOAc. The combined organic layers are washed with brine, dried over $MgSO_4$, filtered and concentrated. The residue is purified by flash chromatography on silica gel (eluting with DCM/MeOH 100/0 to 95/5) to afford the desired compound.

2.28. Int 116

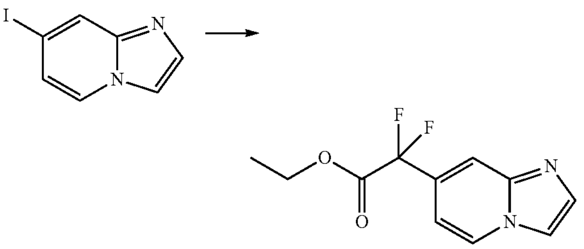

To a solution of 7-iodoimidazo[1,2-a]pyridine (CAS #908269-30-7; 500 mg, 2.05 mmol, 1 eq.) in degassed DMSO (10 mL) is added copper (CAS #7440-50-8; 470 mg, 7.37 mmol, 3.6 eq.) and ethyl-2-bromo-2,2-difluoroacetate (CAS #667-27-6; 447 μL, 3.48 mmol, 1.7 eq.). The reaction mixture is stirred at 60° C. for 18 h, then quenched with a sat. $NaHCO_3$ solution and extracted with EtOAc. The combined organic layers are washed with water, brine, dried over $Na_2SO_4$, filtered and concentrated to give the desired compound.

2.29. Int 122

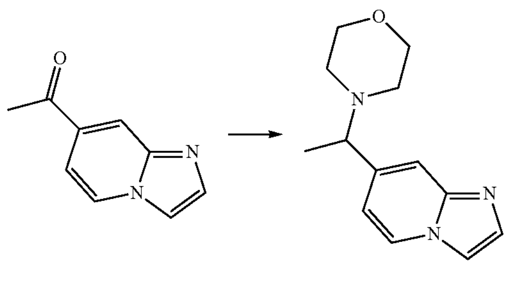 [SMILES: CC(=O)c1ccn2ccnc2c1 ; CC(c1ccn2ccnc2c1)N1CCOCC1]

To a solution of 1-(imidazo[1,2-a]pyridin-7-yl)ethanone (CAS #1036991-50-0; 30 mg, 0.19 mmol, 1 eq.) in MeOH (0.7 mL) are added morpholine (CAS #110-91-8; 49 µL, 0.56 mmol, 3 eq.), AcOH (32 µL, 0.56 mmol, 3 eq.) and $NaBH_3CN$ (CAS #25895-60-7; 35 mg, 0.56 mmol, 3 eq.). The reaction mixture is stirred at 50° C. for 21 h then quenched with a sat. $NaHCO_3$ aq. solution and extracted with DCM. The combined organic layers are passed through a phase separator and concentrated. The residue is purified by flash chromatography on silica gel (eluting with EtOAc/MeOH 100/0 to 90/10) to afford the desired compound.

2.30. Int 124

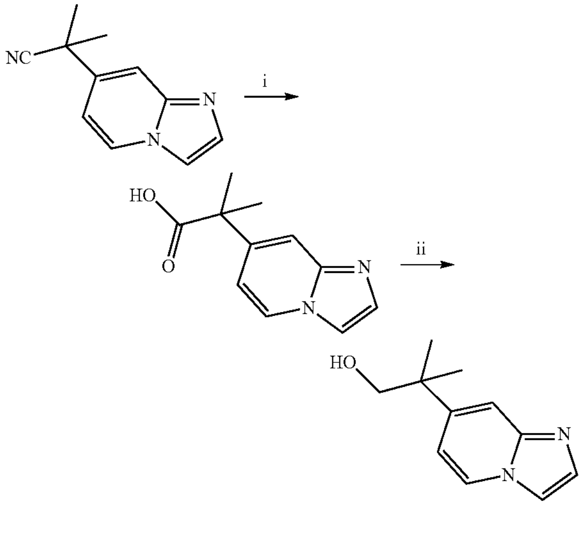

2.30.1. Step i: 2-imidazo[1,2-a]pyridin-7-yl-2-methyl-propanoic Acid

In a small vial containing Int 58 (500 mg, 2.70 mmol, 1 eq.) is added a concentrated HCl solution (37% aq. solution, CAS #7647-01-0; 1.8 mL). The vial is sealed, the resulting solution is stirred at 140° C. for 18 h then filtered. The solid is washed with $Et_2O$ and pentane to afford the desired acid. The filtrate is concentrated; the residue is triturated with pentane, filtered and dried in vacuo to afford a second batch of the desired acid.

2.30.2. Step ii: Int 124

To a solution of the previously prepared acid (250 mg, 1.22 mmol, 1 eq.) in dry THF (20 mL) at 0° C. under $N_2$ atmosphere is added $LiAlH_4$ (1M solution in THF, CAS #16853-85-3; 3.1 mL, 3.06 mmol, 2.5 eq.). The resulting solution is stirred at 0° C. for 1 h then quenched successively with a 4N NaOH solution and EtOAc. The mixture is stirred at RT for 5 min, filtered. The filtrate is washed with brine, dried over $MgSO_4$, filtered and concentrated in vacuo to afford the desired compound.

2.31. Int 144

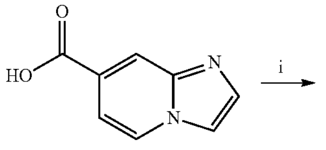

-continued

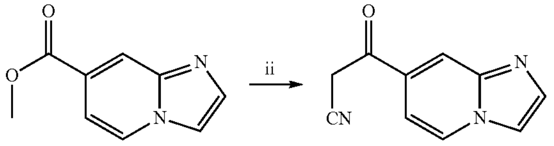

2.31.1. Step i: Methyl imidazo[1,2-a]pyridine-7-carboxylate

To a solution of imidazo[1,2-a]pyridine-7-carboxylic acid (CAS #648423-85-2; 1 g, 6.16 mmol, 1 eq.) in MeOH (40 mL) is added sulfuric acid (CAS #7664-93-9; 1 mL). The resulting solution is stirred at 75° C. for 18 h then concentrated to dryness. The residue is diluted in EtOAc and water, washed with a sat. $NaHCO_3$ solution. The organic layer is separated, dried over $MgSO_4$, filtered and concentrated in vacuo.

2.31.2. Step ii: Int 144

To a degassed solution of the above prepared ester (1.15 g, 6.53 mmol, 1 eq.) in dry toluene (6 mL) inert atmosphere is added portionwise sodium hydride (60% dispersion in mineral oil, CAS #7646-69-7; 624 mg, 13.1 mmol, 2 eq.). The reaction mixture is heated to 80° C. then dry ACN (1.6 mL, 30.7 mmol, 4.7 eq.) is added dropwise. The resulting solution is stirred at 80° C. for 18 h then cooled to 0° C. The solid formed is filtered, diluted in water and acidified to pH below 6 with a 2N HCl solution. The precipitate is filtered and dried in vacuo to afford the desired intermediate.

2.32. Int 145

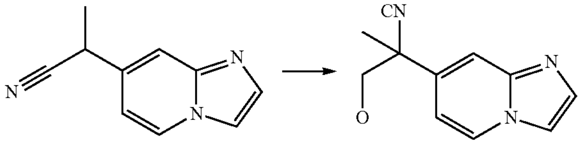

To a degassed solution of Int 64 (85 mg, 0.50 mmol, 2 eq.) in dry DMF (5 mL) under inert atmosphere is added paraformaldehyde (CAS #30525-89-4; 90 mg, 1.5 mmol, 6 eq.) then NaH (60% suspension in oil CAS #7646-69-7; 10 mg, 0.25 mmol, 1 eq.). The reaction mixture is stirred at RT for 1 h, then concentrated in vacuo, diluted in water and acidified with a 1N HCl solution. The aqueous layer is concentrated to dryness and the residue purified by flash chromatography on silica gel (eluting with DCM/MeOH 100/0 to 97/3) to give the desired compound.

2.33. Int 155

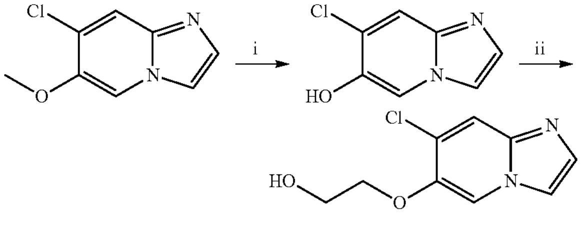

2.33.1. Step i: 7-chloroimidazo[1,2-a]pyridin-6-ol

To a solution of Int 135 (200 mg, 1.09 mmol, 1 eq.) in DCM at −78° C. is added boron tribromide (1M in DCM, CAS #10294-33-4; 5.5 mL, 5.47 mmol, 5 eq.). The resulting solution is stirred at −30° C. for 30 min, 0° C. for 1 h then at RT for 1 h. The reaction mixture is cooled to 0° C. and quenched with MeOH, stirred for 1 h, concentrated in vacuo. The residue is triturated in EtOAc, filtered and dried in vacuo to afford the desired intermediate.

2.33.2. Step ii: Int 155

To a solution of the above prepared intermediate (390 mg, 2.31 mmol, 1 eq.) in dioxane (1 mL) are added $K_2CO_3$ (CAS #584-08-7; 798 mg, 5.8 mmol, 2.5 eq.), benzyltriethylammonium chloride (CAS #56-37-1; 52 mg, 0.23 mmol, 0.1 eq.) followed by the ethylene oxide solution (2.5M in THF, CAS #75-21-8; 9.2 mL, 23.1 mmol, 10 eq.). The resulting suspension is heated to 70° C. for 3 h then 2-iodoethanol is added (CAS #624-76-0; 269 μL, 3.45 mmol, 1.5 eq.) and the mixture is stirred at RT for 18 h, concentrated in vacuo. The residue is purified by reverse phase flash chromatography (eluting with water/ACN 98/2 to 70/30) to afford the desired compound.

2.34. Int 157

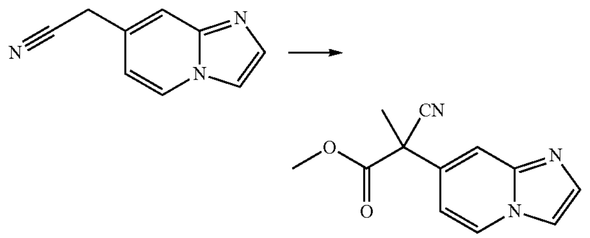

To a degassed solution of Int 62 (100 mg, 0.64 mmol, 1 eq.) in dimethyl carbonate (4 mL) under inert atmosphere is added 1-butyl-3-methylimidazolium acetate (CAS #284049-75-8; 12 mg, 0.064 mmol, 0.1 eq.). The reaction mixture is heated to 130° C. for 18 h, then diluted with EtOAc and a sat. $NH_4Cl$ solution. The combined organic layers are dried on $Na_2SO_4$, filtered and concentrated to dryness. The residue is purified by flash chromatography on silica gel (eluting with DCM/MeOH 100/0 to 98/2) to give the desired compound.

2.35. Int 161

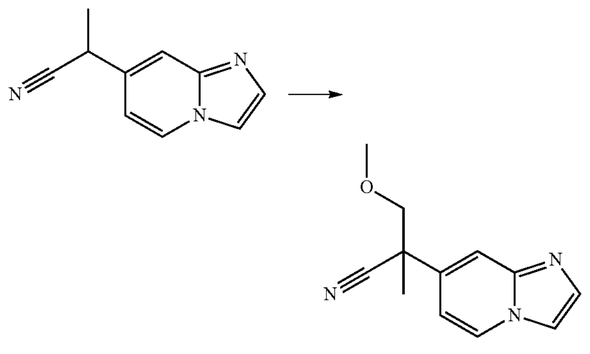

To a solution of Int 64 (300 mg, 1.75 mmol, 1 eq.) in dry THF (2 mL) at −78° C. is added dropwise LDA (2M solution in THF, 1.05 mL, 2.1 mmol, 1.2 eq.). The reaction mixture is stirred for 1 h at −78° C., then chloromethyl methyl ether (CAS #107-30-2; 160 μL, 2.1 mmol, 1.2 eq.) is added. The reaction mixture is allowed to warm up to RT, stirred for 5 min at RT, then quenched with a sat. $NH_4Cl$ solution and extracted with DCM (three times). The combined organic layers are passed through a phase separator and concentrated in vacuo. The crude residue is purified by flash chromatography on silica gel (eluting with a DCM/MeOH 90/10 to 70/30) to give the desired compound.

2.36. Int 164

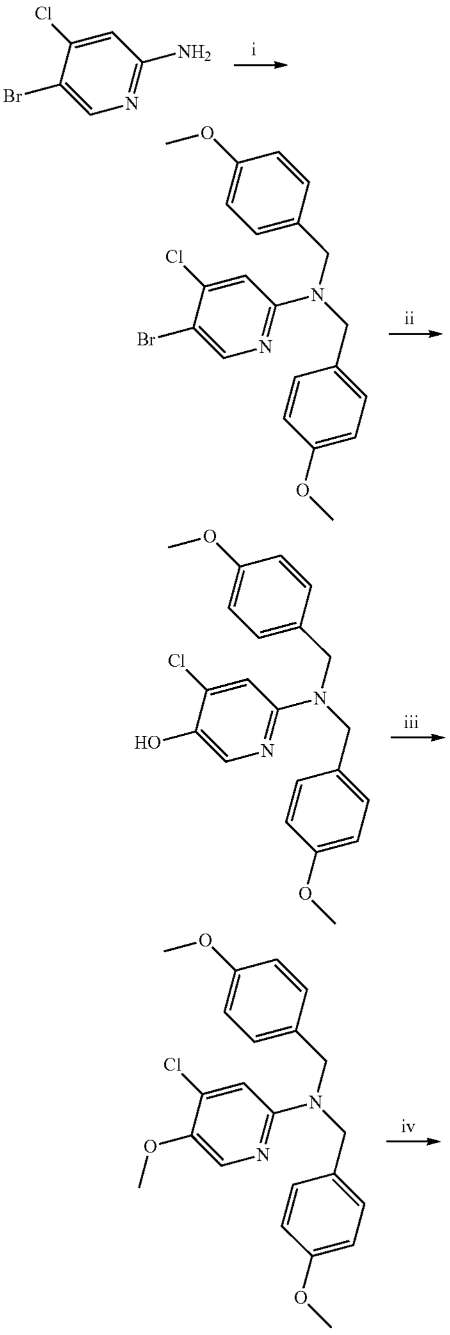

-continued

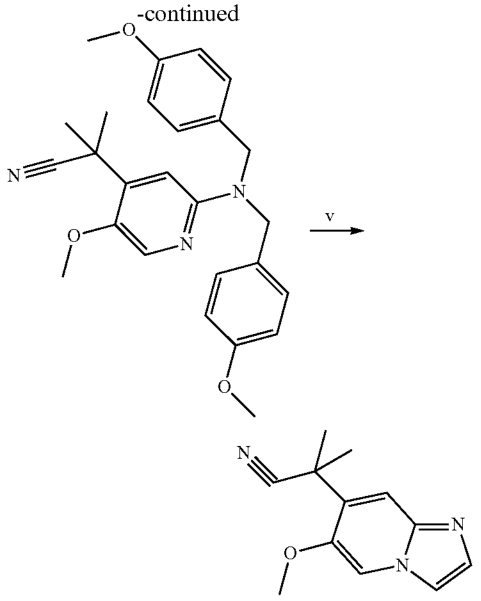

2.36.1. Step i: 5-bromo-4-chloro-N,N-bis[(4-methoxyphenyl)methyl]pyridin-2-amine To a solution of 5-bromo-4-chloro-pyridin-2-amine (CAS #942947-94-; 20 g, 93.5 mmol, 1 eq.) in dry DMF (200 mL) at 0° C. is added portionwise NaH (60% suspension in oil, CAS #7646-69-7; 9.72 g, 243 mmol, 2.6 eq.). The resulting mixture is stirred at 0° C. for 20 min. 1-(chloromethyl)-4-methoxy-benzene (CAS #824-98-6; 28.8 mL, 206 mmol, 2.2 eq.) is added dropwise and stirring is continued for 90 min at 0° C. The reaction mixture is poured into a mixture of water (2.2 L)/$Et_2O$ (500 mL)/EtOAc (500 mL). Layers are separated. Extraction is done twice with 500 mL of EtOAc. The combined organic layers are washed with water (1 L), brine (600 mL), dried over $Na_2SO_4$, filtered and concentrated. The residue is crushed and triturated with 2×300 mL of cyclohexane, filtered and dried to afford the desired intermediate.

2.36.2. Step ii: 6-[bis[(4-methoxyphenyl)methyl]amino]-4-chloro-pyridin-3-ol To a solution of 5-bromo-4-chloro-N, N-bis[(4-methoxyphenyl)methyl]pyridin-2-amine (10 g, 22.1 mmol, 1 eq.) in dry THF (200 mL) at −78° C. is added dropwise n-BuLi (2.5 M solution in hexanes (CAS #109-72-8; 11.1 mL, 27.6 mmol, 1.25 eq.). The mixture is stirred for 1 h then 2-isopropoxy-4,4,5,5-tetramethyl-1,3,2-dioxaborolane (CAS #61676-62-8; 9.3 mL, 44.2 mmol, 2 eq.) is added keeping the temperature bellow −65° C. After stirring for 45 min, the reaction mixture is allowed to warm up to −20° C. keeping it in a sodium chloride/ice mixture. Hydrogen peroxide (30% water solution (CAS #7722-84-1; 9.0 mL, 88.4 mmol, 4 eq.) is added dropwise. The mixture is allowed to warm up to RT and is stirred for 45 min, then quenched by water (800 mL) and extracted with EtOAc (2×400 mL). The combined organic layers are dried over $Na_2SO_4$, filtered and concentrated. The residue is basified with 800 mL of 1 M NaOH solution followed by addition of 14 g of NaOH. After stirring for 30 min, the resulting solution is extracted with 3×300 mL of $Et_2O$. The pH of the aqueous layer is then adjusted to 6 with a concentrated HCl solution. The precipitate formed is filtered, and washed with water, dried in vacuum oven at 40° C. for 10 h to afford the desired intermediate.

2.36.3. Step iii: 4-chloro-5-methoxy-N,N-bis[(4-methoxyphenyl)methyl]pyridin-2-amine To a solution of the above prepared intermediate (5.85 g, 13.4 mmol, 1 eq.) in dry DMF (47 mL) is added $Cs_2CO_3$ (CAS #534-17-8; 6.54 g, 20.1 mmol, 1.5 eq.). The resulting suspension is stirred for 10 min at RT then iodomethane (CAS #74-88-4; 2.3 g, 16.1 mmol, 1.2 eq.) is added. The reaction mixture is heated at 70° C. for 1.5 h, quenched with 600 mL of water/NaCl solution and extracted with 3×150 mL of EtOAc. The combined organic layers are washed with 300 mL of water, 200 mL of brine, dried over $Na_2SO_4$, filtered and concentrated in vacuo. The residue is purified by flash chromatography on silica gel (eluting with DCM/EtOAc 100/0 to 95/5) to afford the desired intermediate.

2.36.4. Step iv: 2-[2-[bis[(4-methoxyphenyl)methyl]amino]-5-methoxy-4-pyridyl]-2-methyl-propanenitrile A solution of 4-chloro-5-methoxy-N,N-bis[(4-methoxyphenyl)methyl]pyridin-2-amine (3.43 g, 8.51 mmol, 1 eq.), 2-methylpropanenitrile (CAS #78-82-0; 1.5 g, 21.3 mmol, 2.5 eq.) and LiHMDS (1.3 M THF solution, 18.3 mL, 23.8 mmol, 2.8 eq.) in dry THF (26 mL) is heated in microwave conditions at 115° C. for 12 min (the reaction is performed in 3 equal microwave tubes). The combined reaction mixtures are poured into a mixture of EtOAc (200 mL)/water (300 mL). The organic layer is separated, extracted with EtOAc, dried over Na2SO4, filtered and concentrated in vacuo. The crude residue is purified by flash chromatography on silica gel (eluting with DCM/EtOAc 100/0 to 90/10) to afford the desired intermediate.

2.36.5. Step v: Int 164

To a stirred solution of 2-[2-[bis[(4-methoxyphenyl)methyl]amino]-5-methoxy-4-pyridyl]-2-methyl-propanenitrile (2.40 g, 5.51 mmol, 1 eq.) in dry DCM (96 mL) is added TFA (CAS #76-05-1; 14.6 g, 127 mmol, 23 eq.) and the mixture is stirred at RT for 40 h. The reaction mixture is concentrated in vacuo. The residue is diluted with DCM (70 mL) and a sat. $NaHCO_3$ solution (70 mL). The organic layer is separated and extracted with DCM. The combined organic layers are dried over $Na_2SO_4$ and the solvent is evaporated. The crude is suspended in dry EtOH (48 mL). $NaHCO_3$ (CAS #144-55-8; 1.2 g, 13.8 mmol, 2.5 eq.) is added and the mixture is heated to 60° C. Upon stirring 2-chloroacetaldehyde (50% water solution, CAS #107-20-0; 1.3 mL, 9.91 mmol, 1.8 eq.) is added dropwise. The mixture is heated at 80° C. for 16 h, then concentrated. The residue is diluted with EtOAc (150 mL) and a sat. $NaHCO_3$ solution (200 mL). The organic layer is separated; the aqueous layer is extracted with EtOAc. The combined organic layers are dried over $Na_2SO_4$, filtered and concentrated in vacuo. The residue is purified by flash chromatography on silica gel (eluting with EtOAc/MeOH 100/0 to 97/3) to afford the desired intermediate.

2.37 Int 172

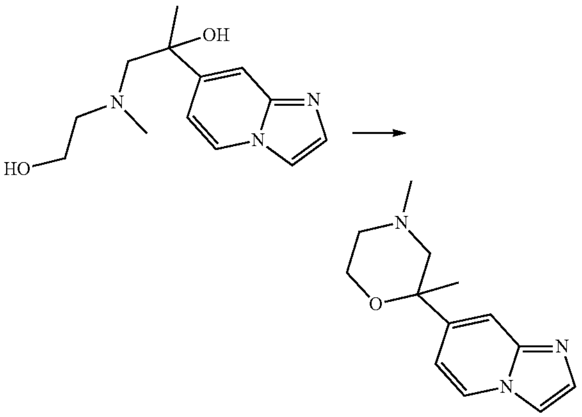

To a solution of Int 173 (50 mg, 0.20 mmol, 1 eq.) in DCM (1 mL) at 0° C. is added triphenylphosphine (CAS #603-35-0; 73 mg, 0.28 mmol, 1.4 eq.). A solution of diisopropyl azodicarboxylate (CAS #2446-83-5; 55 μL, 0.28 mmol, 1.4 eq.) in DCM (1 mL) is then introduced dropwise over 40 min and the resulting solution is stirred at RT for 18 h. The reaction mixture is concentrated in vacuo and purified by flash chromatography on silica gel (eluting with heptane/EtOAc 100/0 to 0/100). The corresponding fractions are concentrated in vacuo, diluted with a 1N HCl solution and extracted with EtOAc. The combined organic layers are dried over $Na_2SO_4$, filtered and concentrated in vacuo to afford the desired intermediate.

2.38. Int 183

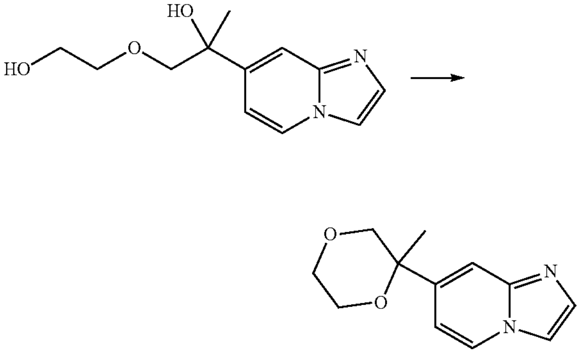

To a solution of triphenylphosphine (CAS #603-35-0; 168 mg, 0.64 mmol, 1.3 eq.) in DCM (2 mL) at 0° C. is added DIAD (CAS #2446-83-5; 127 μL, 0.64 mmol, 1.3 eq.). The reaction mixture is stirred at 0° C. for 15 min and then a solution of Int 184 (117 mg, 0.50 mmol, 1 eq.) in DCM (3 mL) is introduced. The reaction mixture is stirred at RT for 1 h then quenched with a 1N HCl solution and extracted with DCM. The layers are separated. The aqueous layer is basified with a 2N NaOH solution and extracted with EtOAc (three times). The combined organic layers are dried over $Na_2SO_4$, filtered and concentrated in vacuo. The residue is purified by flash chromatography on silica gel (eluting with DCM/MeOH 100/0 to 80/20) to give the desired intermediate.

2.39. Int 186

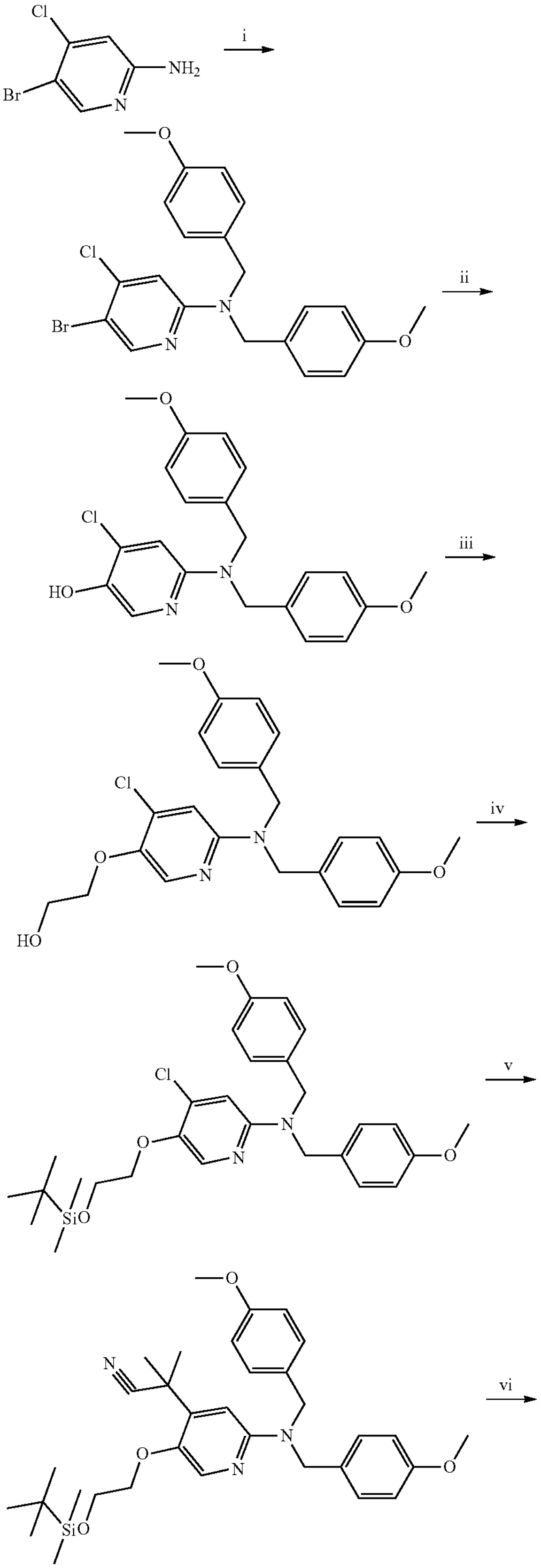

-continued

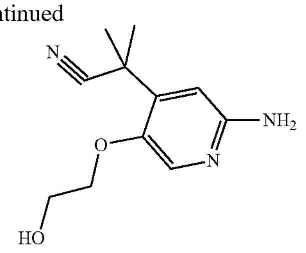

2.39.1. Step i: 5-bromo-4-chloro-N,N-bis[(4-methoxyphenyl)methyl]pyridin-2-amine To a solution of 5-bromo-4-chloro-2-pyridinamine (CAS #942947-94-6; 2 g, 9.64 mmol, 1 eq.) in DMF (20 mL) at 0° C. is added NaH (60% suspension in oil CAS #7646-69-7; 1 g, 25.1 mmol, 2.6 eq.). The reaction mixture is stirred for 20 min at 0° C. then 4-methoxybenzyl chloride (CAS #824-94-2, 2.6 mL, 19.3 mmol, 2.2 eq.) is added dropwise. The reaction mixture is stirred at 0° C. for 1.5 h. More NaH (1 g, 25.1 mmol, 2.6 eq.) is added and the reaction mixture is stirred at 0° C. for 2 h. The reaction mixture is quenched with water, extracted with a mixture $Et_2O$/EtOAc 50/50 (three times). The combined organic layers are washed with water, brine, dried over $Na_2SO_4$, filtered and concentrated. The crude is purified by flash chromatography on silica gel (eluting with heptane/EtOAc 100/0 to 70/30) to give the desired intermediate.

2.39.2. Step ii: 6-[bis[(4-methoxyphenyl)methyl]amino]-4-chloro-pyridin-3-ol

To a solution of the above prepared intermediate (1.5 g, 3.35 mmol, 1 eq.) in THF (35 mL) at −78° C. under argon is added dropwise n-BuLi (2.5M in hexanes CAS #109-72-8; 1.7 mL, 4.2 mmol, 1.25 eq.). The reaction mixture is stirred at −78° C. for 40 min, then 4,4,5,5-tetramethyl-2-(1-methylethoxy)-1,3,2-dioxaborolane (CAS #61676-62-8; 2.6 mL, 19.3 mmol, 2 eq.) is added dropwise. The resulting solution is stirred at −78° C. for 45 min, then is warmed-up to −20° C. At this temperature, $H_2O_2$(CAS #7722-84-1; 1.4 mL, 13.4 mmol, 4 eq.) is added. The reaction mixture is allowed to warm to RT and is stirred for 1 h. Water (150 mL) is added and the reaction mixture is extracted with EtOAc (2×150 mL). The combined organic layer is dried over $Na_2SO_4$, filtered and concentrated. The residue is basified with a 1N NaOH solution and NaOH (2 g) is added. The solution is stirred for 30 min at RT, washed with $Et_2O$ (3×100 mL) then acidified to pH=2 with a concentrated HCl solution. The precipitate formed is filtered, washed with water and dried under reduced pressure to give the desired intermediate.

2.39.3. Step iii: 2-[[6-[bis[(4-methoxyphenyl)methyl]amino]-4-chloro-3-pyridyl]oxy]ethanol To a solution of the previously prepared intermediate (450 mg, 1.17 mmol, 1 eq.) in DMF (4 mL) are added $Cs_2CO_3$ (CAS #534-17-8; 571 mg, 1.75 mmol, 1.5 eq.) then iodoethanol (CAS #624-76-0; 114 µL, 1.46 mmol, 1.25 eq.) The reaction mixture is stirred at 70° C. for 1.5 h, then quenched with water and extracted with EtOAc (three times). The combined organic layers are dried over $Na_2SO_4$, filtered and concentrated in vacuo. The crude is purified by flash chromatography (eluting with heptane/EtOAc 100/to 50/50) to give the desired intermediate.

2.39.4. Step iv: 5-[2-[tert-butyl(dimethyl)silyl]oxyethoxy]-4-chloro-N,N-bis[(4-methoxyphenyl)methyl]pyridin-2-amine To a solution of the previously prepared intermediate (100 mg, 0.23 mmol, 1 eq.) in $CH_3CN$ (1 mL) are added imidazole (CAS #288-32-4; 39 mg, 0.56 mmol, 2.4 eq.), DMAP (CAS #1122-58-3; 3 mg, 0.02 mmol, 0.1 eq.) and TBDMSCl (CAS #18162-48-6; 42 mg, 0.28 mmol, 1.2 eq.). The reaction mixture is stirred at RT for 3 h. Water is added, the reaction mixture is extracted with DCM. The layers are separated on a phase separator. The organic layer is concentrated and the residue is purified by flash chromatography on silica gel (eluting with heptane/EtOAc 100/0 to 85/15) to give the desired intermediate.

2.39.5. Step v: 2-[2-[bis[(4-methoxyphenyl)methyl]amino]-5-[2-[tert-butyl(dimethyl)silyl]oxyethoxy]-4-pyridyl]-2-methyl-propanenitrile To a solution of the previously prepared intermediate (198 mg, 0.36 mmol, 1 eq.) in THF (1 mL) are added isobutyronitrile (CAS #78-82-0; 327 µL, 3.65 mmol, 10 eq.) and LiHMDS (1M in THF, CAS #4039-32-1; 1.9 mL, 1.82 mmol, 5 eq.). The reaction mixture is heated under microwave irradiation at 100° C. for 30 min then at 120° C. for 20 min. More isobutyronitrile (5 eq.) is added and the reaction mixture is irradiated at 120° C. for 30 min more. Water is added, the reaction mixture is extracted with EtOAc (three times). The layers are separated, the organic layer is dried over $Na_2SO_4$, filtered and concentrated. The crude is purified by flash chromatography on silica gel (eluting with heptane/EtOAc 100/0 to 85/15) to afford the desired intermediate.

2.39.6. Step vi: Int 186

To a solution of the previously prepared intermediate (213 mg, 0.37 mmol, 1 eq.) in DCM (6 mL) is added TFA (CAS #76-05-1, 655 µL, 8.5 mmol, 23 eq.). The reaction mixture is stirred at RT for 18 h then concentrated, quenched by a sat. $NaHCO_3$ solution and extracted with EtOAc (three times). The combined organic layers are dried over $Na_2SO_4$, filtered and concentrated to give the desired intermediate.

2.40. Int 189

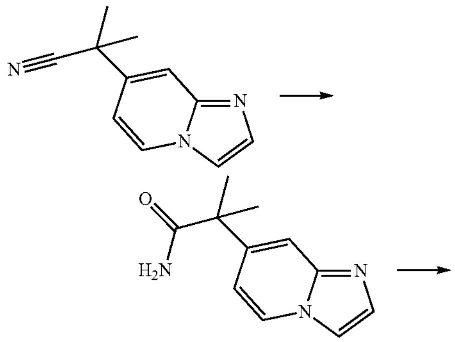

-continued

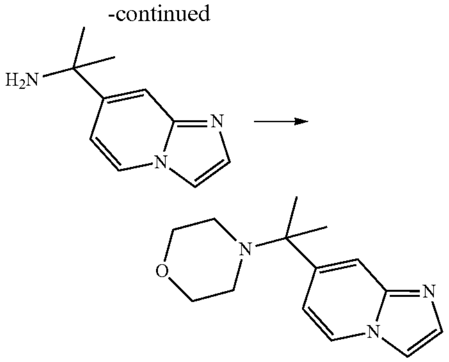

2.40.1. Step i: 2-imidazo[1,2-a]pyridin-7-yl-2-methyl-propanamide

To a solution of Int 58 (500 mg, 2.70 mmol, 1 eq.) in a mixture of $CH_3CN/H_2O$ (1:2, 12 mL) is added a sat. $K_2CO_3$ solution (13 mL). The reaction mixture is cooled to 0° C. and $H_2O_2$ (30% in water, 8.3 mL, 81 mmol, 30 eq.) is added dropwise. The reaction mixture is stirred at RT for 18 h. The volatiles are concentrated in vacuo. The aqueous layer is extracted with DCM (twice) then EtOAc (three times). The combined organic layers are dried over $Na_2SO_4$, filtered and concentrated to give the amide.

2.40.2. Step ii: 2-imidazo[1,2-a]pyridin-7-ylpropan-2-amine

To a solution of the above prepared amide (499 mg, 2.45 mmol, 1 eq.) in a mixture of $CH_3CN/H_2O$ (1/2, 12 mL) is added PIFA (CAS #2712-78-9; 1.2 g, 2.97 mmol, 1.1 eq.). The reaction mixture is stirred at RT for 18 h, then quenched with a 2N NaOH solution and extracted with EtOAc then i-PrOH (twice). The combined organic layers are dried over $MgSO_4$, filtered and concentrated. The residue is purified by flash chromatography on silica gel (eluting with DCM/MeOH 98/2 to 90/10) to give the desired amine.

2.40.3. Step iii: Int 189

To a solution of the above prepared amine (140 mg, 0.08 mmol, 1 eq.) in DMF (2 mL) at 0° C. is added NaH (60% suspension in oil CAS #7646-69-7; 96 mg, 2.40 mmol, 3 eq.). The reaction mixture is stirred at 0° C. for 10 min then bis(2-bromoethyl) ether (CAS #5414-19-7; 150 µL, 1.20 mmol, 1.5 eq.) is added. The reaction mixture is stirred at 80° C. for 4 h. EtOAc is added, the precipitate is filtered and the filtrate concentrated. The residue is concentrated and purified by flash chromatography on silica gel (eluting with DCM/MeOH 98/2 to 90/10) to give the desired intermediate.

2.41. Int 195

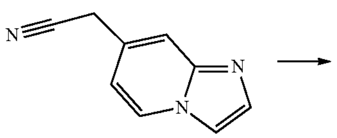

-continued

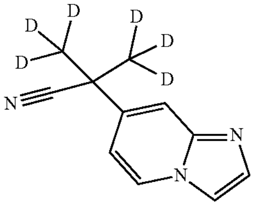

To a solution of Int 62 (50 mg, 0.32 mmol, 1.0 eq.) in THF at −40° C. under $N_2$ atmosphere is added t-BuOK (CAS #865-47-4; 107 mg, 0.95 mmol, 3.0 eq.). The reaction mixture is stirred for 5 min. Then, $CD_3I$ is added (CAS #865-50-9; 59 µL, 145 mmol, 3.0 eq.) and the resulting solution is stirred for 30 min at −40° C. then 30 min at RT. The reaction mixture is quenched with an aq. solution of $Na_2S_2O_3$ (10%) and extracted twice with EtOAc. The combined organic layers are dried over $MgSO_4$, filtered and concentrated under reduced pressure to give the desired intermediate.

2.42. Int 206

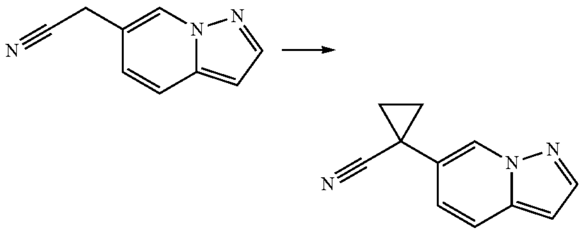

To a solution of 2-pyrazolo[1,5-a]pyridin-6-ylacetonitrile Int 207 (66 mg, 0.37 mmol, 1 eq.) in DMSO (1.65 mL) are added diphenylvinylsulfonium triflate (CAS #247129-88-0; 164 mg, 0.44 mmol, 1.2 eq.) and 1,8-diazabicyclo[5.4.0]undec-7-ene (CAS #6674-22-2; 167 µL, 1.11 mmol, 3 eq.). The reaction mixture is stirred at RT for 18 h then quenched with a sat. $NH_4Cl$ solution and extracted with EtOAc. The combined organic layers are dried over $MgSO_4$, filtered and concentrated in vacuo. The residue is purified by flash chromatography on silica gel (eluting with heptane/EtOAc 100/0 to 40/60) to afford the desired compound.

2.43. Int 210

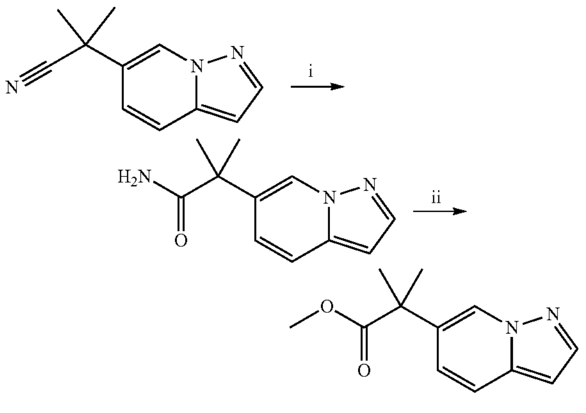

2.43.1. Step i: 2-methyl-2-pyrazolo[1,5-a]pyridin-6-yl-propanamide

To a solution of 2-methyl-2-pyrazolo[1,5-a]pyridin-6-yl-propanenitrile Int 171 (300 mg, 1.62 mmol, 1 eq.) in DMSO (8 mL) are added potassium carbonate (CAS #584-08-7; 45 mg, 0.32 mmol, 0.2 eq.) and hydrogen peroxide (8.82N aq. solution, CAS #7722-84-1; 0.367 mL, 3.24 mmol, 2 eq.). The resulting mixture is stirred at RT for 18 h then quenched by addition of water and extracted with EtOAc. The combined organic layers are dried over $MgSO_4$, filtered and concentrated in vacuo.

2.43.2. Step ii: Int 210

To a solution of the above prepared amide intermediate 2-methyl-2-pyrazolo[1,5-a]pyridin-6-yl-propanamide (330 mg, 1.6 mmol, 1 eq.) in MeOH (5.4 mL) is added N,N-dimethylformamide dimethyl acetal (CAS #4637-24-5; 2.6 mL, 19 mmol, 12 eq.). The resulting mixture is stirred at 60° C. for 18 h then concentrated. The residue is purified by flash chromatography on silica gel (eluting with heptane/EtOAc 100/0 to 0/100) to afford the desired intermediate.

2.44. Int 216

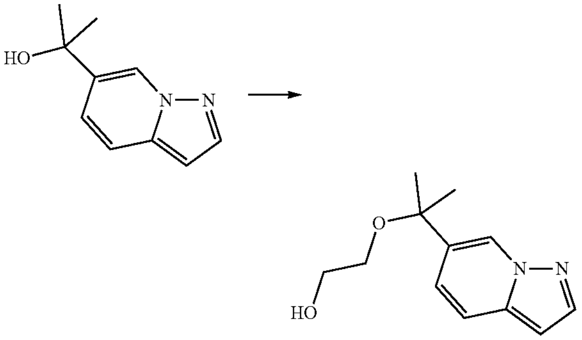

To a solution of 2-pyrazolo[1,5-a]pyridin-6-ylpropan-2-ol Int 191 (30 mg, 0.17 mmol, 1 eq.) in ethylene glycol (0.35 M, 0.5 mL) is added methanesulfonic acid (CAS #75-75-2; 56 μL, 0.85 mmol, 5 eq.). The reaction mixture is stirred at RT for 20 h, concentrated and purified by flash chromatography on silica gel (eluting with DCM/MeOH 99/1 to 97/3) to afford the desired intermediate.

2.45. Int 220

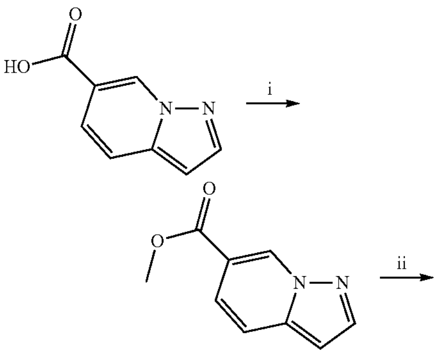

-continued

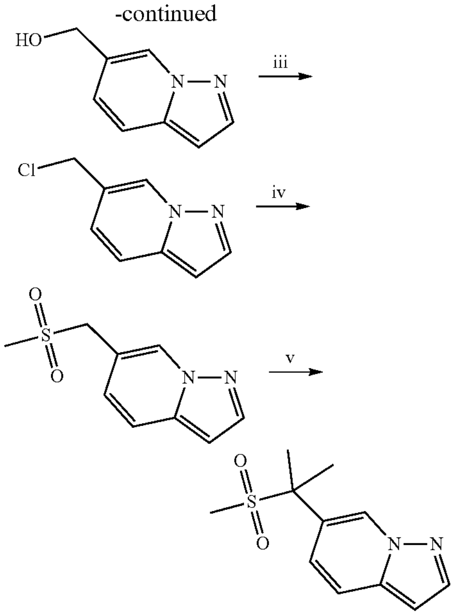

2.45.1. Step i: Methyl pyrazolo[1,5-a]pyridine-6-carboxylate

In a 3-necked round-bottom flask containing pyrazolo[1,5-a]pyridine-6-carboxylic acid (CAS #474432-61-6; 100 mg, 0.60 mmol, 1 eq.) is added HCl in MeOH (1.25M in MeOH, 4.8 mL, 6 mmol, 10 eq.). The reaction mixture is stirred at 70° C. for 18 h then concentrated. The residue is triturated with pentane, filtered and dried in vacuo.

2.45.2. Step ii: pyrazolo[1,5-a]pyridin-6-ylmethanol

To a solution of previously described methyl pyrazolo[1,5-a]pyridine-6-carboxylate (250 mg, 1.3 mmol, 1 eq.) in THF (12.5 mL) at 0° C. is added dropwise $LiAlH_4$ (1M solution in THF, CAS #16853-85-32.0 mL, 2.0 mmol, 1.5 eq.). The reaction mixture is stirred at 0° C. for 30 min then quenched with water, filtered on celite and the filter cake is washed with EtOAc. The filtrate is washed with water, the aqueous layer is separated and extracted with EtOAc (×5). The combined organic layers are dried on $MgSO_4$, filtered and concentrated in vacuo.

2.45.3. Step iii: 6-(chloromethyl)pyrazolo[1,5-a]pyridine

To a solution of previously prepared pyrazolo[1,5-a]pyridin-6-ylmethanol (173 mg, 1.13 mmol, 1 eq.) in DCM (0.8 mL) is added dropwise 1-chloro-N,N,2-trimethylpropenylamine (CAS #26189-59-3; 173 mg, 0.171 mL, 1.24 mmol, 1.1 eq.). The resulting mixture is stirred at 0° C. for 1 h, then at RT for 1 h. The reaction solution is concentrated and purified by flash chromatography on silica gel (eluting with heptane/EtOAc 100/0 to 60/40) to afford the chloride intermediate.

2.45.4. Step iv: 6-(methylsulfonylmethyl)pyrazolo[1,5-a]pyridine

To a solution of the above described 6-(chloromethyl)pyrazolo[1,5-a]pyridine (117 mg, 0.69 mmol, 1 eq.) in DMF (2.3 mL) is added sodium methanesulfinate (99 mg, 0.82 mmol, 1.2 eq.). The resulting mixture is stirred at 125° C. for 2 h, cooled to RT, filtered and the filtrate is concentrated. The residue is purified by flash chromatography on silica gel (eluting with EtOAc/MeOH 100/0 to 90/10) to afford the sulfone intermediate.

2.45.5. Step v: Int 220

To a solution of the previously prepared 6-(methylsulfonylmethyl)pyrazolo[1,5-a]pyridine (105 mg, 0.48 mmol, 1 eq.) in DMF (2.8 mL) at 0° C. are added methyl iodide (CAS #74-88-4; 60 µL, 0.97 mmol, 2.02 eq.) and sodium tert-butoxide (CAS #865-48-5; 96 mg, 0.97 mmol, 2.02 eq.). The resulting solution is allowed to warm to RT and stirred for 8 h. More methyl iodide (15 µL, 0.24 mmol, 0.5 eq.) and sodium tert-butoxide (24 mg, 0.24 mmol, 0.5 eq.) are added at 0° C. and the reaction mixture is stirred at RT for 18 h. Again methyl iodide (15 µL, 0.24 mmol, 0.5 eq.) and sodium tert-butoxide (24 mg, 0.24 mmol, 0.5 eq.) are added at 0° C. and the reaction mixture is stirred at RT for 2 days. Then DCM (10 mL) is added, the resulting solution is washed with a 2N HCl solution (20 mL) and water (2*25 mL). The organic layer is filtered on a phase separator and concentrated. The residue is purified by flash chromatography on silica gel (eluting with heptane/EtOAc 100/0 to 30/70) to afford the desired compound.

2.46. Int 222

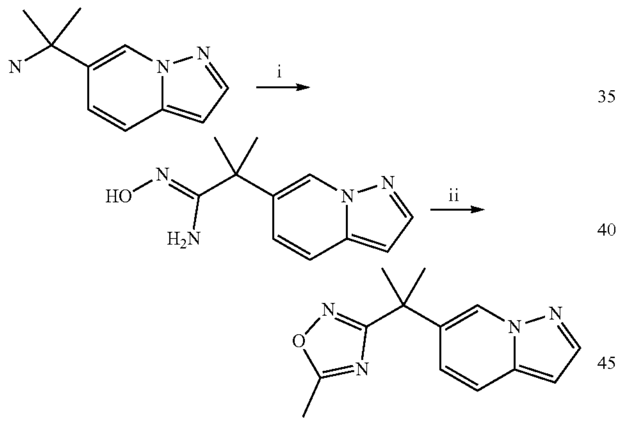

2.46.1. Step i: N'-hydroxy-2-methyl-2-pyrazolo[1,5-a]pyridin-6-yl-propanamidine

To a solution of Int 171 (200 mg, 1.08 mmol, 1 eq.) in EtOH (0.7 mL) under $N_2$ atmosphere are added hydroxylamine hydrochloride (CAS #5470-11-1; 82 mg, 1.19 mmol, 1.1 eq.) followed by $Et_3N$ (452 µL, 3.24 mmol, 3.0 eq.). The resulting solution is heated to 80° C. for 18 h. More hydroxylamine hydrochloride and $Et_3N$ are added and the mixture is stirred at 95° C. for 5 h, then concentrated in vacuo. The residue is purified by flash chromatography on silica gel (eluting with heptane/EtOAc 90/10 to 0/100).

2.46.2. Step ii: Int 222

The above prepared intermediate is diluted in acetic anhydride (CAS #108-24-7; 1 mL) and the resulting solution is heated to 100° C. for 18 h. The reaction mixture is then concentrated in vacuo and purified by flash chromatography on silica gel (eluting with DCM/MeOH 100/0 to 90/10) to afford the desired compound.

2.47 Int 224

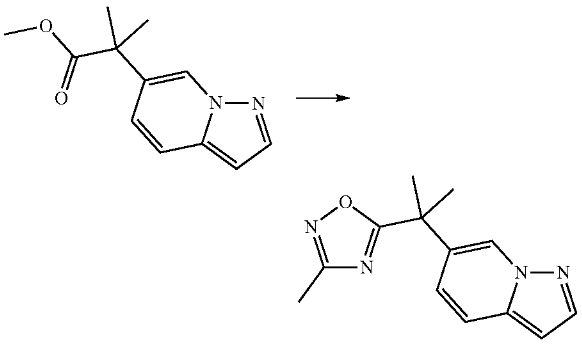

To a suspension of sodium hydride (60% dispersion in mineral oil, CAS #7646-69-7; 55 mg, 1.37 mmol, 1.2 eq.) in THF (2 mL) is added N'-hydroxyacetimidamide (CAS #22059-22-9; 107 mg, 1.37 mmol, 1.2 eq.). The resulting suspension is heated to 60° C. for 1 h. Then a solution of the ester methyl 2-methyl-2-pyrazolo[1,5-a]pyridin-6-yl-propanoate Int 210 (250 mg, 1.14 mmol, 1 eq.) in THF (1 mL) is added. The resulting mixture is stirred at 60° C. for 18 h, quenched by addition of a sat. $NH_4Cl$ solution and extracted with EtOAc. The combined organic layers are washed with water, brine, dried over $MgSO_4$, filtered and concentrated in vacuo to afford the desired compound which is used without further purification.

2.48. Int 226

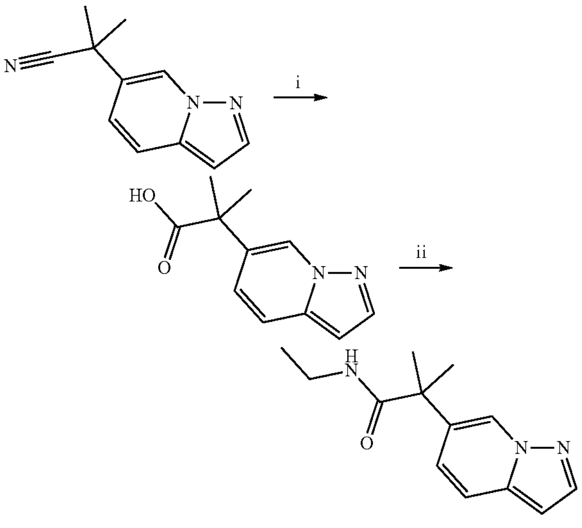

2.48.1. Step i: 2-methyl-2-pyrazolo[1,5-a]pyridin-6-yl-propanoic Acid

To a solution of 2-methyl-2-pyrazolo[1,5-a]pyridin-6-yl-propanenitrile Int 171 (500 mg, 2.7 mmol, 1 eq.) in EtOH (5 mL) is added NaOH (6N aq. solution, 4.5 mL, 27 mmol, 10 eq.). The resulting mixture is heated to 100° C. for 18 h, concentrated in vacuo. The residue is acidified with HCl 37% and extracted with EtOAc twice. The combined organic layers are dried over $MgSO_4$, filtered and concentrated in vacuo.

2.48.2. Step ii: Int 226

To a solution of the above prepared acid (260 mg, 1.27 mmol, 1 eq.) and ethylamine hydrochloride (CAS #557-66-4; 56 mg, 1.91 mmol, 1.5 eq.) in DCM are added DIPEA (CAS #7087-68-5; 0.888 mL, 5.1 mmol, 4 eq.) and HATU (CAS #148893-10-1; 593 mg, 1.53 mmol, 1.2 eq.). The reaction mixture is stirred at RT for 18 h, quenched with water and extracted with EtOAc. The combined organic layers are washed with brine, dried over $MgSO_4$, filtered and concentrated in vacuo. The residue is purified by flash chromatography on silica gel (eluting with heptane/EtOAc 90/10 to 0/100) to afford the desired intermediate.

2.49. Int 230

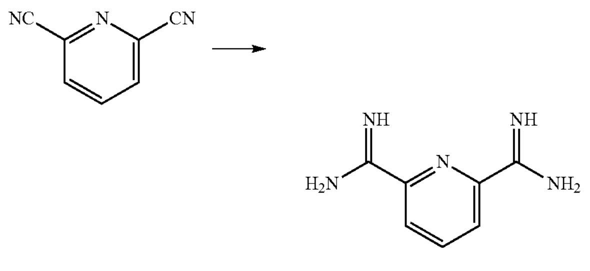

To a solution of 2,6-dicyanopyridine (CAS #2893-33-6; 1 g, 0.77 mmol, 1 eq.) in MeOH (1 mL) is added MeONa (83 mg, 1.54 mmol, 1.9 eq.). The resulting mixture is heated to 75° C. for 18 h then $NH_4Cl$ (CAS #12125-02-9; 90 mg, 1.70 mmol, 2.2 eq.) is added. The mixture is stirred at 75° C. for 20 min. The formed precipitate is filtered, washed with $Et_2O$ to afford the desired intermediate.

2.50. Int 235

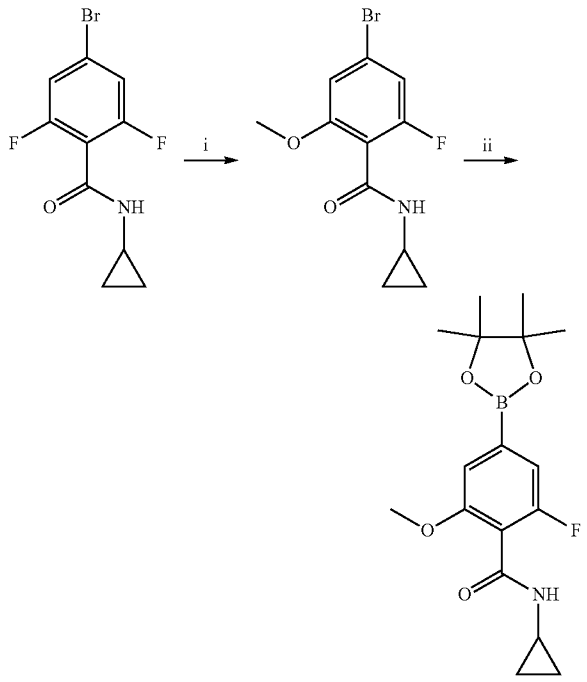

2.50.1. Step i: 4-bromo-N-cyclopropyl-2-fluoro-6-methoxy-benzamide

To a solution of Int 1 (4.0 g, 14 mmol, 1 eq.) in THF (20 mL) is added MeONa (0.97 g, 17 mmol, 1.2 eq.). The reaction mixture is stirred at 60° C. for 3 h then quenched with water and extracted with DCM (x3). The combined organic layers are filtered on a phase separator and concentrated in vacuo. The crude residue is purified by flash chromatography on silica gel (eluting with a gradient heptane/EtOAc from 100/0 to 0/100) to afford 4-bromo-N-cyclopropyl-2-fluoro-6-methoxy-benzamide.

LCMS: MW (calcd): 288.1; m/z MW (obsd): 288.1-290.1 (M+H)

250.2 Step ii: Int 235

To a degassed solution of 4-bromo-N-cyclopropyl-2-fluoro-6-methoxy-benzamide (500 mg, 1.74 mmol, 1 eq.) in dioxane (9 mL) under $N_2$ atmosphere are added $B_2pin_2$ (0.534 g, 2.08 mmol, 1.20 eq.), potassium acetate (0.510 g, 5.21 mmol, 3 eq.) and Pd(dppf)$Cl_2$·DCM (CAS #95464-05-4, 85 mg, 0.10 mmol, 0.06 eq.). The reaction mixture is stirred at 80° C. for 2 h. More Pd(dppf)$Cl_2$·DCM (CAS #95464-05-4, 1 mg, 0.0012 mmol, 0.006 eq.) is added and the reaction mixture is stirred at 80° C. for 30 minutes more. The reaction mixture is filtered on Dicalite®, washed with EtOAc and concentrated. The crude is diluted with EtOAc and washed with a sat. $NaHCO_3$ solution. The organic layer is separated, dried over $MgSO_4$, filtered and concentrated to afford the desired intermediate Int 235.

2.51. Int 236

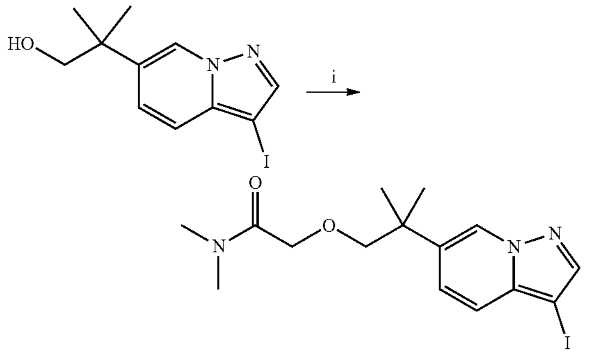

To a solution of Int 208 (0.12 g, 0.38 mmol, 1 eq.) under $N_2$ atmosphere in THF at 0° C. is added sodium hydride (60% suspension in oil, 18 mg, 0.46 mmol, 1.2 eq.). The resulting mixture is stirred at 0° C. for 1 h then 2-bromo-N,N-dimethylacetamide (CAS #5468-77-9; 52 µL, 0.46 mmol, 1.2 eq.) is introduced. After 5 min stirring at 0° C., the resulting mixture is warmed to RT and heated at 50° C. for 18 h. The reaction mixture is quenched by addition of water and then extracted with EtOAc. The combined organic layers are washed with water, brine and dried over $MgSO_4$, filtered and concentrated in vacuo. Purification by flash chromatography on silica gel (eluting with heptane/EtOAc 90/10 to 0/100) affords Int 236.

2.52 Int 237

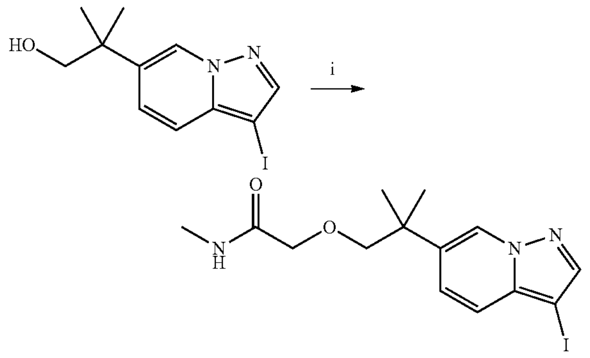

To a solution of Int 208 (0.12 g, 0.38 mmol, 1 eq.) under $N_2$ in THF at 0° C. is added NaH (60 m % suspension in oil, 18.2 mg, 0.46 mmol, 1.2 eq.). The resulting mixture is stirred at 0° C. for 1 h then 2-bromo-N-methylacetamide (CAS #34680-81-4; 99 mg, 0.63 mmol, 1.7 eq.) is introduced. The resulting mixture is heated to 50° C. for 36 h and at 75° C. for 1 h. After cooling to RT, the reaction mixture is quenched by addition of water and extracted with EtOAc. The combined organic layers are washed with water, brine and dried over $MgSO_4$, filtered and concentrated in vacuo. Purification by flash chromatography on silica gel (eluting with heptane/EtOAc 90/10 to 0/100) affords Int 237.

2.53. Int 238

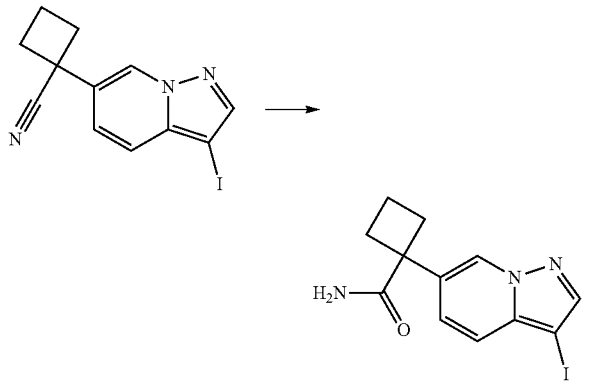

To a solution of Int 227 (710 mg, 2.2 mmol, 1 eq.) in DMSO (8 mL) are added potassium carbonate (60 mg, 0.43 mmol, 0.20 eq.) and $H_2O_2$ (10.6 M in water, 0.495 mL, 4.37 mmol, 2 eq.). The resulting white mixture is stirred at RT for 18 h then cooled to 0° C., diluted with water and EtOAc. The organic layer is separated, filtered over a hydrophobic filter and concentrated. The residue is purified by flash chromatography on silica gel (eluting with heptane/EtOAc 50/50 to 0/100) to afford Int 238.

2.54. Int 240

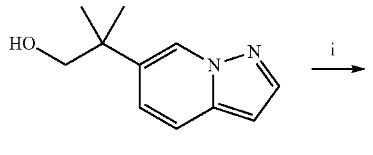

-continued

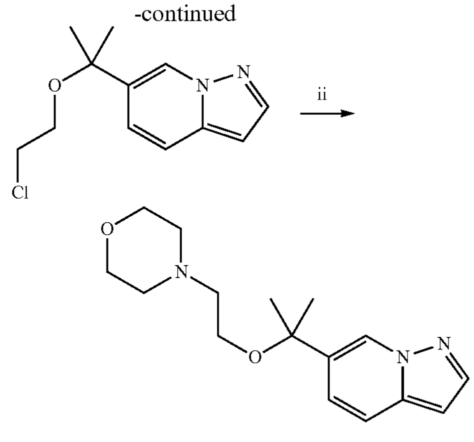

2.54.1. Step i: 6-[1-(2-chloroethoxy)-1-methyl-ethyl]pyrazolo[1,5-a]pyridine

To 2-chloroethanol (CAS #107-07-3; 0.5 mL) is added Int 191 (30 mg, 0.17 mmol, 1 eq.) and methanesulfonic acid (CAS #75-75-2; 90 μL, 1.36 mmol, 8 eq.). The mixture is stirred at RT for 18 h. The reaction mixture is then quenched with water, extracted with EtOAc (×3). The combined organic layers are dried over $Na_2SO_4$, filtered and concentrated under reduced pressure to afford 6-[1-(2-chloroethoxy)-1-methyl-ethyl]pyrazolo[1,5-a]pyridine.

2.54.2. Step ii: Int 240

To 6-[1-(2-chloroethoxy)-1-methyl-ethyl]pyrazolo[1,5-a]pyridine from in step i is added morpholine (CAS #110-91-8, 1 mL) and the reaction mixture is stirred for 2 h at 100° C. The solution is concentrated in vacuo and the crude obtained is purified by flash chromatography on silica gel (eluting with a gradient DCM/MeOH 100/0 to 98/2) to afford Int 240.

2.55. Int 241

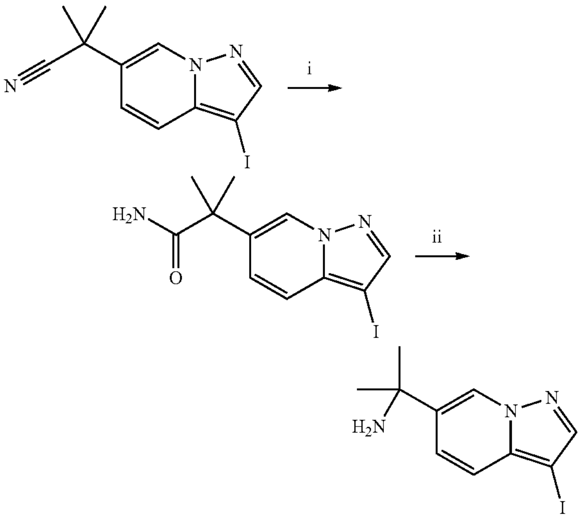

2.55.1. Step i: 2-(3-iodopyrazolo[1,5-a]pyridin-6-yl)-2-methyl-propanamide

To a solution of Int 169 (200 mg, 0.64 mmol, 1 eq.) in EtOH (3.2 mL) under $N_2$ atmosphere is added potassium carbonate (3.4 g, 28 mmol, 43 eq.) in water (3.1 mL). The mixture is cooled to 0° C. and hydrogen peroxide (35 mass % in water; 2.2 mL, 19 mmol, 30 eq.) is added by quick drip. The resulting solution is stirred at RT for 18 h then quenched with water, extracted with EtOAc (×3). The combined organic layers are dried over $Na_2SO_4$, filtered and concentrated under reduced pressure to afford crude 2-(3-iodopyrazolo[1,5-a]pyridin-6-yl)-2-methyl-propanamide.

LCMS: MW (calcd): 301.1; m/z MW (obsd): 302.1 and 303.1 (M+H+2)

255.2 Step ii: Int 241

To a solution of crude 2-(3-iodopyrazolo[1,5-a]pyridin-6-yl)-2-methyl-propanamide (step i) in ACN (1 mL) and water (1.8 mL) is added PIFA (CAS #2712-78-9; 0.31 g, 0.71 mmol, 1.1 eq.) and the mixture is stirred at RT for 18 h. More PIFA (0.31 g, 0.71 mmol, 1.1 eq.) is added and the mixture is stirred 25 h at RT. The solution is concentrated in vacuo and the residue is purified by flash chromatography on silica gel (eluting with DCM/MeOH 98/2 to 90/10) to afford Int 241.

2.56. Int 242

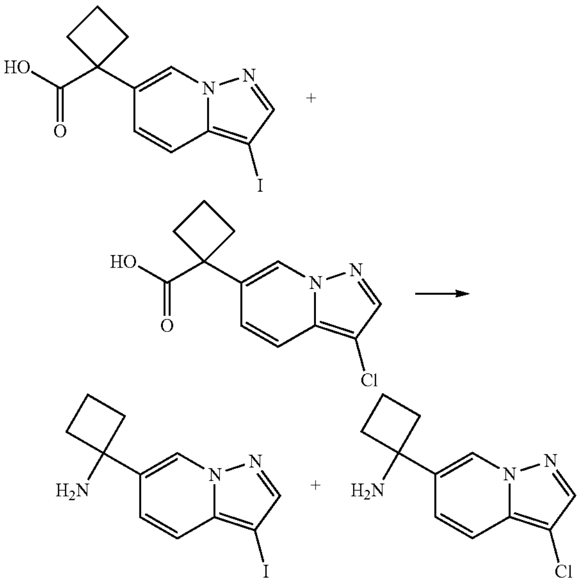

To a solution of Int 243 (325 mg, 0.95 mmol, 1 eq.) in dioxane (5 mL) under argon atmosphere are added $Et_3N$ (0.2 mL, 1.43 mmol, 1.5 eq.) and diphenyl phosphorazidate (CAS #26386-88-9; 0.308 mL, 1.43 mmol, 1.5 eq.). The resulting solution is stirred at RT for 2 h, then diluted with DCM and water. The organic layer is separated, filtered off a hydrophobic filter and concentrated. The resulting residue is suspended in HCl 2N (5 mL) and heated at 60° C. for 2 h. Then THF (5 mL) is added in order to obtain a clear solution. The resulting solution is heated at 60° C. for 18 h. The solution is then basified to pH 7-8 with NaOH 2N then extracted twice with DCM. The combined organic layer is filtered off a hydrophobic filter and concentrated. The residue is purified by flash chromatography on silica gel (eluting with DCM/MeOH 100/0 to 92/8) to afford Int 242 as a mixture of 1-(3-iodopyrazolo[1,5-a]pyridin-6-yl)cyclobutanamine and 1-(3-chloropyrazolo[1,5-a]pyridin-6-yl)cyclobutanamine.

2.57 Int 243

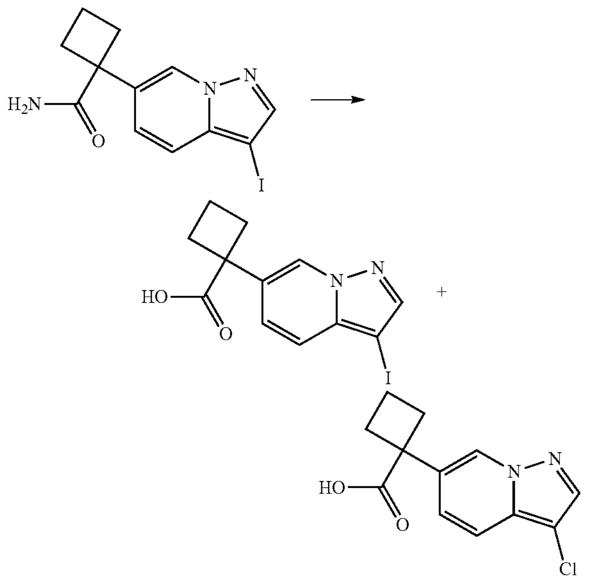

To a solution of Int 238 (510 mg, 1.5 mmol, 1 eq.) in dioxane (4 mL) is added a 2N HCl solution (4 mL, 8 mmol, 5.4 eq.). The resulting solution is heated to 100° C. for 8 h, extracted with EtOAc. The combined organic layers are filtered off a hydrophobic filter and concentrated. The residue is purified by flash chromatography on silica gel (eluting with DCM/MeOH 100/0 to 94/6) to afford Int 243 as a mixture of 1-(3-iodopyrazolo[1,5-a]pyridin-6-yl)cyclobutanecarboxylic acid and 1-(3-chloropyrazolo[1,5-a]pyridin-6-yl)cyclobutanecarboxylic acid.

2.58. Int 244 & Int 263

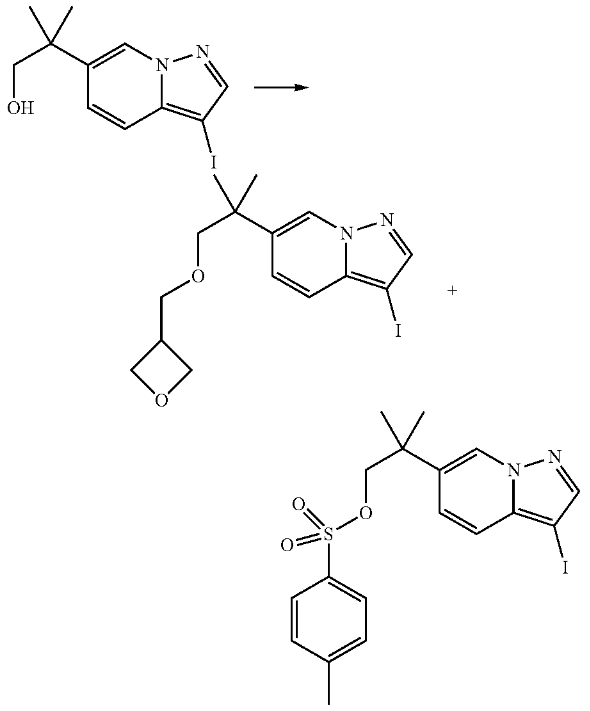

To a solution of Int 208 (100 mg, 0.32 mmol, 1 eq.) in DMF (2 mL) at 0° C. under argon atmosphere is added in one portion NaH (60% dispersion in mineral oil, CAS #7646-69-7; 17 mg, 0.42 mmol, 1.3 eq.). The resulting mixture is stirred at 0° C. for 15 min. 3-(Bromomethyl) oxetane (CAS #1374014-30-8; 75 mg, 0.47 mmol, 1.5 eq.) is added and the reaction mixture is stirred at RT for 3 h. More NaH (17 mg, 0.42 mmol, 1.3 eq.) is added in one portion and the resulting mixture is stirred at RT for 15 min. The same amount of 3-(bromomethyl)oxetane (75 mg, 0.47 mmol, 1.5 eq.) is then added. The reaction mixture is heated at 90° C. for 18 h, then cooled to 0° C., quenched with a sat. $NH_4Cl$ solution and extracted twice with EtOAc. The combined organic layers are filtered over a hydrophobic filter and concentrated. The crude residue is purified by flash chromatography on silica gel (eluting with heptane/EtOAc 100/0 to 40/60) to give a mixture of starting material Int 208 and the desired intermediate Int 244.

The mixture of Int 208 and Int 244 is dissolved in pyridine (1.5 mL) and 4-dimethylaminopyridine (3 mg, 0.02 mmol) and 4-methylbenzene-1-sulfonyl chloride (88 mg, 0.46 mmol) are added. The resulting solution is stirred at RT for 18 h, and then quenched at 0° C. with a 1N HCl solution, extracted twice with EtOAc. The combined organic layers are filtered off a hydrophobic filter and concentrated to give a mixture of intermediates Int 244, Int 263 and the corresponding deiodinated intermediates.

This mixture of compounds is dissolved in DMF (1 mL) and N-iodosuccinimide (112, mg, 0.5 mmol) is added. The resulting solution is stirred at RT for 4 h then quenched with a 10% $Na_2S_2O_3$ aq. solution and extracted with EtOAc. The combined organic layers are washed with brine, dried over $Na_2SO_4$, and concentrated in vacuo.

The crude residue is purified by flash chromatography on silica gel (eluting with heptane/EtOAc form 100/0 to 30/70) to give intermediates Int 244 (second eluting) and Int 263 (first eluting).

2.59. Int 245

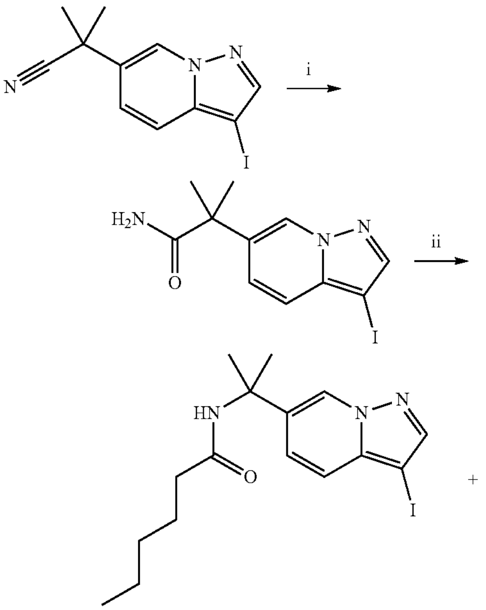

-continued

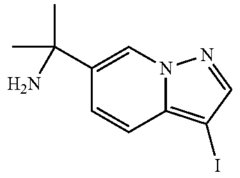

2.59.1. Step i: 2-(3-iodopyrazolo[1,5-a]pyridin-6-yl)-2-methyl-propanamide

To a solution of Int 169 (500 mg, 1.60 mmol, 1 eq.) in EtOH (8 mL) under $N_2$ atmosphere is added potassium carbonate (8.5 g, 69 mmol, 43 eq.) in water (7.7 mL). The mixture is cooled to 0° C. and hydrogen peroxide (35% in water; 5.5 mL, 48 mmol, 30 eq.) is added by quick drip. The resulting solution is stirred at RT for 18 h then quenched with water and extracted with EtOAc(×3). The combined organic layers are dried over $Na_2SO_4$, filtered and concentrated under reduced pressure to afford 2-(3-iodopyrazolo[1,5-a]pyridin-6-yl)-2-methyl-propanamide.

LCMS: MW (calcd): 401.2; m/z MW (obsd): 402.3 (M+H)

2.59.2 Step ii: Int 245

To a solution of the above prepared 2-(3-iodopyrazolo[1,5-a]pyridin-6-yl)-2-methyl-propanamide (100 mg, 0.30 mmol, 1 eq.) in n-BuOH (0.675 mL) is added sodium hypochlorite (0.42 mL, 0.76 mmol, 2.5 eq.) and sodium hydroxide (0.304 mL, 0.91 mmol, 3 eq.). The mixture is stirred at RT for 18 h then quenched with water, extracted with EtOAc (×3). The combined organic layers are dried over $Na_2SO_4$, filtered and concentrated under reduced pressure. The crude residue is purified by flash chromatography on silica gel (eluting with DCM/MeOH 98/2 to 92/8) to give the desired Int 245 as the second eluting compound.

2.60. Int 246

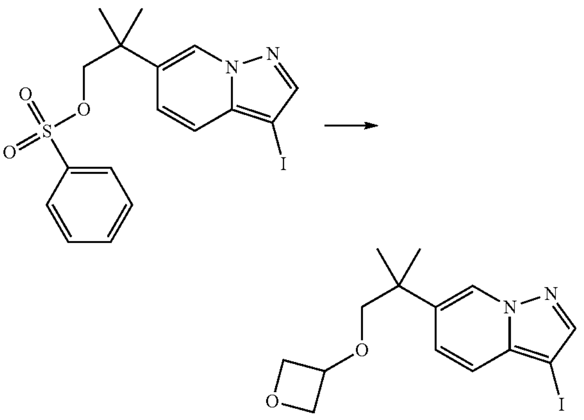

To a solution of Int 263 (120 mg, 0.26 mmol, 1 eq.) in DMF (0.5 mL) are added $Cs_2CO_3$ (333 mg, 1.02 mmol, 4 eq.) and 3-hydroxyoxetane (CAS #7748-36-9; 23 mg, 0.31 mmol, 1.2 eq.). The resulting mixture is heated at 85° C. for 72 h, then diluted with water and EtOAc. The organic layer is separated, filtered off a hydrophobic filter and concentrated. The residue is purified by flash chromatography on silica gel (eluting with heptane/EtOAc 100/0 to 40/60) to give the desired intermediate Int 246.

2.61. Int 248

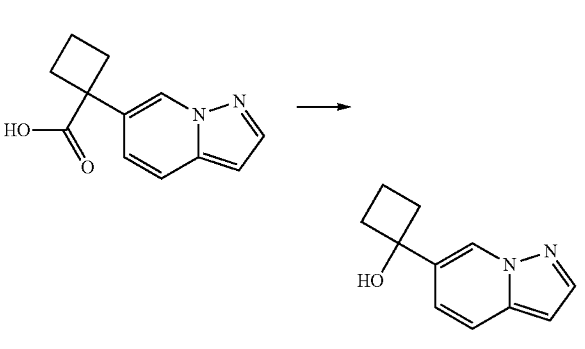

To a solution of Int 255 (100 mg, 0.46 mmol, 1 eq.) in THF (2.3 mL) and AcOH (0.6 mL) under argon atmosphere is added lead tetraacetate (CAS #546-67-8; 260 mg, 0.55 mmol, 1.2 eq.). The resulting solution is stirred at RT for 2 h then diluted with NaOH (2M in water) (10 mL, 20 mmol, 43 eq.) and the resulting mixture is heated at 60° C. for 4 h. The reaction solution is quenched by a sat. $NaHCO_3$ solution and extracted with EtOAc. The combined organic layers are filtered over an hydrophobic filter and concentrated in vacuo. The residue obtained is purified by flash chromatography on silica gel (eluting with heptane/EtOAc 100/0 to 80/20) to afford Int 248.

2.62 Int 250

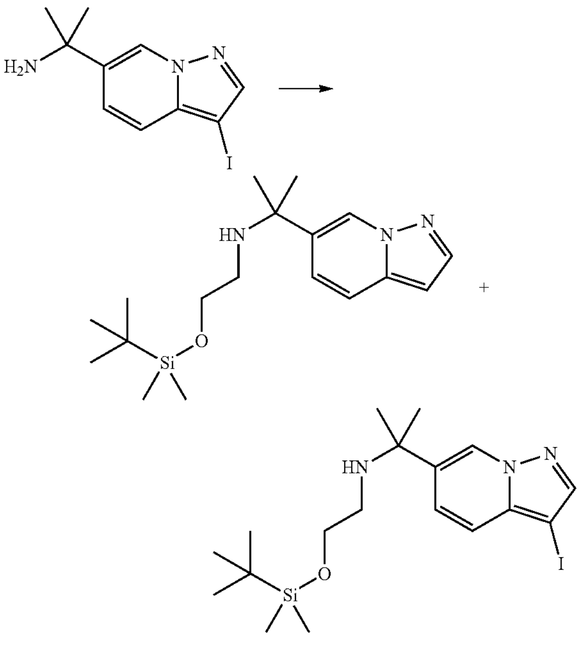

To a solution of Int 169 (30 mg, 0.098 mmol, 1 eq.) in DCM (1 mL) is added $NaBH(OAc)_3$ (CAS #56553-60-7; 32 mg, 0.15 mmol, 1.5 eq.) and AcOH (0.5 μL, 0.01 mmol, 0.1 eq.). The mixture is stirred at RT for 18 h then concentrated under $N_2$ and the crude is purified by flash chromatography on silica (eluting with heptane/EtOAc 100/0 to 70/30) to give the desired intermediate Int 250 as second eluting compound and N-[2-[tert-butyl(dimethyl)silyl]oxyethyl]-2-pyrazolo[1,5-a]pyridin-6-yl-propan-2-amine as the first eluting compound.

2.63. Int 251

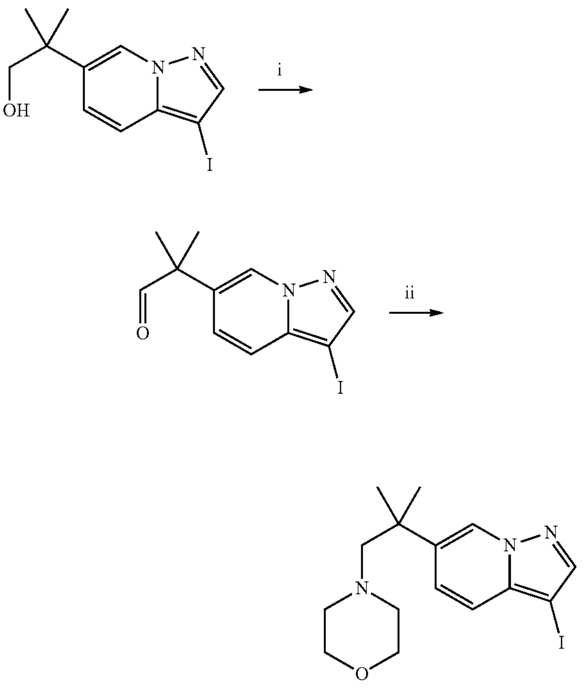

2.63.1. Step i: 2-(3-iodopyrazolo[1,5-a]pyridin-6-yl)-2-methyl-propanal

To a degassed solution of Int 208 (0.100 g, 0.32 mmol, 1 eq.) in dry DCM (16 mL) at 0° C. under $N_2$ atmosphere is added Dess-martin periodinane (CAS #87413-09-0; 0.163 g, 0.38 mmol, 1.2 eq.). The reaction mixture is stirred at RT for 45 min then quenched with a sat. $NaHCO_3$ solution and extracted with DCM (twice). The combined organic layers are filtered through a phase separator and concentrated. The residue is purified by flash chromatography on silica gel (eluting with heptane/EtOAc 100/0 to 50/50) to afford 2-(3-iodopyrazolo[1,5-a]pyridin-6-yl)-2-methyl-propanal.

LCMS: MW (calcd): 314.1; m/z MW (obsd): 315.1 (M+H)

2.63.2 Step ii: Int 251

To a solution of the previously prepared 2-(3-iodopyrazolo[1,5-a]pyridin-6-yl)-2-methyl-propanal (30 mg, 0.095 mmol, 1 eq.) in 1,2-dichloroethane (0.47 mL) are added morpholine (CAS #110-91-8; 25 μL, 0.28 mmol, 3 eq.) and titanium isopropoxide (CAS #546-68-9; 43 μL, 0.14 mmol, 1.5 eq.). The resulting mixture is stirred at 65° C. for 18 h. $NaBH(OAc)_3$ (CAS #56553-60-7; 62 mg, 0.28 mmol, 3 eq.) is added. The reaction mixture is stirred at 65° C. for 24 h, quenched with a sat. $NaHCO_3$ solution, then poured onto 10 mL of water, stirred for 1 h at RT, filtered through a Dicalite® pad and the filtrate is extracted with DCM. The combined organic layers are washed with brine, filtered on a phase separator and concentrated in vacuo. The crude is purified by flash chromatography on silica gel (eluting with DCM/MeOH 100/0 to 95/5) to afford Int 251.

2.64. Int 253

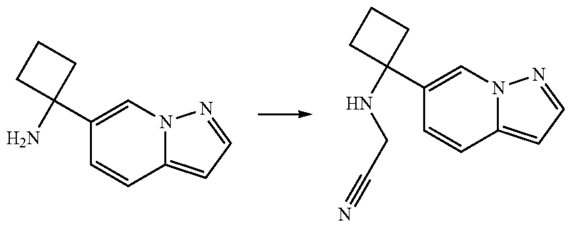 [SMILES: NC1(c2ccc3ccnn3c2)CCC1 ; N#CCNC1(c2ccc3ccnn3c2)CCC1]

To a solution of Int 254 (75 mg, 0.40 mmol, 1 eq.) in THF (2 mL) are added at 0° C. potassium carbonate (140 mg, 1.0 mmol, 2.5 eq.) and bromoacetonitrile (CAS #590-17-0; 0.084 mL, 1.21 mmol, 3 eq.). The resulting mixture is stirred at 0° C. 5 min then at RT for 18 h. More bromoacetonitrile (28 μL, 0.40 mmol, 2 eq.) is added. The reaction mixture is stirred at RT for 24 h, then diluted with water and DCM. The organic layer is separated, filtered off a hydrophobic filter. Piperidine (CAS #110-89-4; 0.237 mL, 2.4 mmol, 6.0 eq.) is added and the resulting solution is concentrated in vacuo. The residue is purified by flash chromatography on silica gel (eluting with heptane/EtOAc 100/0 to 20/80) to afford Int 253.

2.65. Int 254

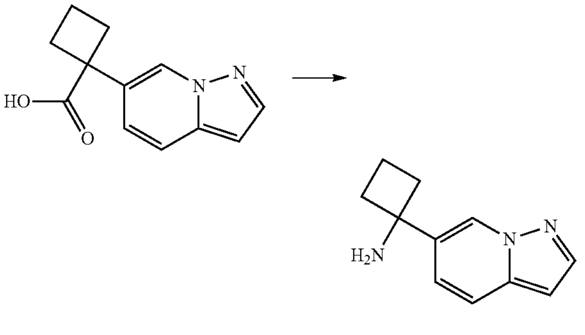

To a solution of Int 255 (100 mg, 0.46 mmol, 1 eq.) in dioxane (2.5 mL) are added $Et_3N$ (0.10 mL, 0.72 mmol, 1.6 eq.) and diphenyl phosphorazidate (CAS #26386-88-9; 0.15 mL, 0.70 mmol, 1.5 eq.). The resulting solution is stirred at RT for 2 h, then diluted with DCM and water. The organic layer is separated, filtered off a hydrophobic filter and concentrated. The residue is dissolved in THF (2.5 mL) and a 2N HCl solution (2.5 mL) is added. The resulting solution is heated at 60° C. for 18 h, then basified to pH 7-8 with a 2N NaOH solution and extracted twice with DCM. The combined organic layers are filtered off a hydrophobic filter and concentrated. The residue is purified by flash chromatography on silica gel (eluting with DCM/MeOH 100/0 to 92/8) to afford Int 254.

2.66. Int 255

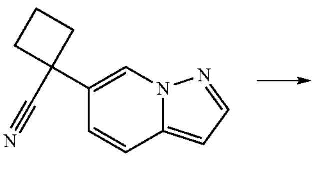

-continued

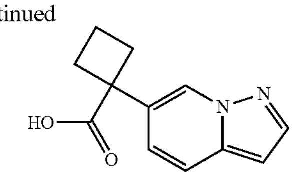

To a solution of Int 229 (700 mg, 3.5 mmol, 1 eq.) in dioxane (12 mL) is added a 1N NaOH solution (35 mL, 70 mmol, 20 eq.). The resulting solution is heated to 100° C. for 18 h. After cooling to RT, the aqueous layer is separated, washed with EtOAc, acidified with a 2N HCl solution and finally extracted twice with EtOAc. The combined organic layers are filtered off a hydrophobic filter and concentrated in vacuo. The residue is purified by flash chromatography on silica gel (eluting with DCM/MeOH 100/0 to 95/5) to afford Int 255.

2.67 Int 257

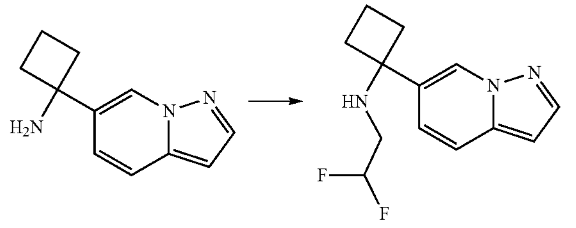 [SMILES: NC1(c2ccc3ccnn3c2)CCC1 ; FC(F)CNC1(c2ccc3ccnn3c2)CCC1]

To a solution of Int 254 (50 mg, 0.27 mmol, 1 eq.) in ACN (1.5 mL) are added at RT DIPEA (CAS #7087-68-5; 93 μL, 0.53 mmol, 2 eq.) and 2,2-difluoroethyl trifluoromethanesulfonate (CAS #74427-22-8; 37 μL, 0.28 mmol, 1 eq.). The resulting solution is heated at 80° C. for 3 h, then diluted with water and DCM. The organic layer is separated, filtered off a hydrophobic filter and concentrated. The residue is purified by flash chromatography on silica gel (eluting with heptane/EtOAc 100/0 to 50/50) to afford Int 257.

2.68. Int 259

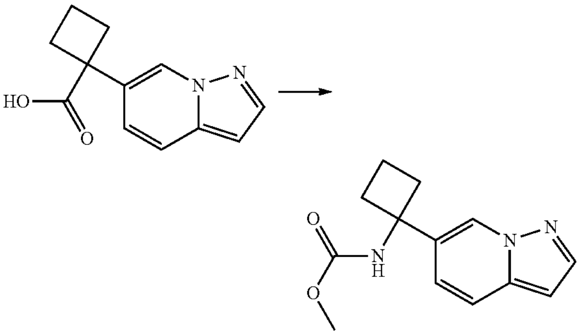 [SMILES: O=C(O)C1(c2ccc3ccnn3c2)CCC1 ; COC(=O)NC1(c2ccc3ccnn3c2)CCC1]

To a solution of Int 255 (75 mg, 0.35 mmol, 1 eq.) in dioxane (2.0 mL) under argon atmosphere are added $Et_3N$ (0.073 mL, 0.52 mmol, 1.5 eq.) and diphenyl phosphorazidate (CAS #26386-88-9; 112 μL, 0.52 mmol, 1.5 eq.). The resulting solution is stirred at RT for 2 h then diluted with water and DCM. The organic layer is separated, filtered off a hydrophobic filter and concentrated in vacuo. The residue is dissolved in a 1.25 M HCl solution in MeOH (CAS #7647-01-0; 3.0 mL, 3.8 mmol, 11 eq.) and the solution is heated at 60° C. for 18 h. After concentration in vacuo, the residue is purified by flash chromatography on silica gel (eluting with heptane/EtOAc 100/0 to 0/100) to afford Int 259.

2.69. Int 261

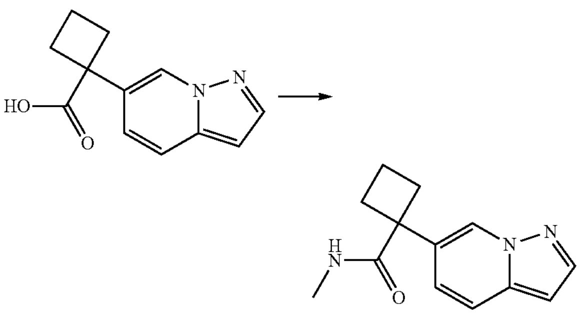 [SMILES: O=C(O)C1(c2ccc3ccnn3c2)CCC1 ; CNC(=O)C1(c2ccc3ccnn3c2)CCC1]

To a solution of Int 255 (75 mg, 0.35 mmol, 1 eq.) in DCM (2 mL) under argon atmosphere are added at 0° C. a drop of DMF and oxalyl chloride (2M solution in DCM, CAS #79-37-8; 0.263 mL, 0.5 mmol, 2 eq.) dropwise. The resulting solution is stirred at 0° C. for 1 h. Methylamine (2M solution in THF, CAS #74-89-5; 1.8 mL, 3.6 mmol, 10 eq.) is introduced dropwise at 0° C. The reaction mixture is stirred at 0° C. for 1 h then diluted with water and DCM. The organic layer is separated, filtered off a hydrophobic filter and concentrated in vacuo. The residue is purified by flash chromatography on silica gel (eluting with heptane/EtOAc 100/0 to 0/100) to afford Int 261.

2.70. Int 262

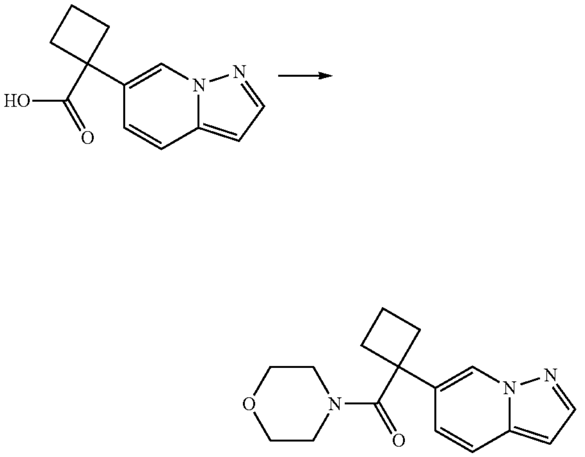

To a solution of Int 255 (75 mg, 0.35 mmol, 1 eq.) in DCM (2 mL) are added at 0° C. a drop of DMF and oxalyl chloride (2N in DCM, CAS #79-37-8; 0.26 mL, 0.5 mmol, 1 eq.) dropwise. The resulting solution is stirred at 0° C. for 1 h. Then morpholine (CAS #110-91-8; 0.183 mL, 2.09 mmol, 6 eq.) is added dropwise at 0° C. and the resulting mixture is stirred at 0° C. for 1 h. The reaction mixture is diluted with water and DCM. The organic layer is separated, filtered off with a hydrophobic filter and concentrated in vacuo. The residue is purified by flash chromatography on silica gel (eluting with heptane/EtOAc 100/0 to 0/100) to afford Int 262.

2.71. Int 266

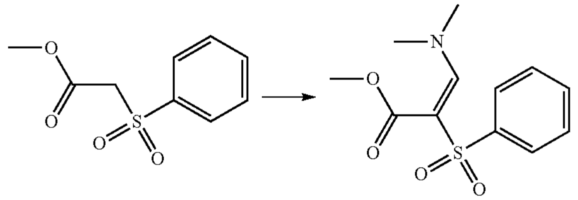 [SMILES: COC(=O)CS(=O)(=O)c1ccccc1 ; COC(=O)/C(=C\N(C)C)S(=O)(=O)c1ccccc1]

To a solution of methyl phenylsulfonylacetate (CAS #34097-60-4; 13.17 g, 59.63 mmol, 1.00 eq.) in EtOAc (60 mL, 600 mmol, 10 eq.) is added N,N-dimethylformamide dimethyl acetate (CAS #4637-24-5; 12.0 mL, 89.9 mmol, 1.51 eq.). The reaction mixture is stirred at RT for 30 min. Heptane (13 mL) is slowly added to the suspension which is then filtered. The solid is dried to afford Int 266.

2.72. Int 267

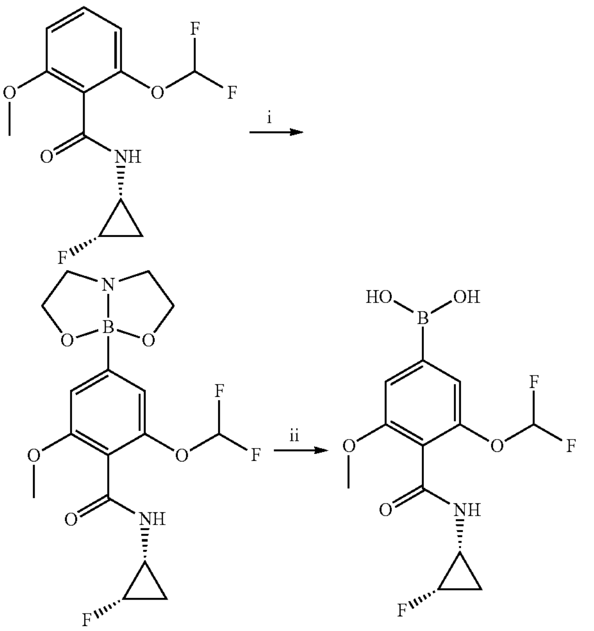

2.72.1. Step i: 2-(difluoromethoxy)-4-(2,8-dioxa-5-aza-1λ$^4$-borabicyclo[3.3.0]octan-1-yl)-N-[(1R,2S)-2-fluorocyclopropyl]-6-methoxy-benzamide To a solution of 2-(difluoromethoxy)-N-[(1R,2S)-2-fluorocyclopropyl]-6-methoxy-benzamide (cf. Ex. 2.3.2; 424 g, 1494.4 mmol, 1.00 eq) in THF (85 mL) under $N_2$ atmosphere are added $B_2pin_2$ (CAS #73183-34-3; 380 g, 1497 mmol, 1.0 eq), dtbpy (CAS #72914-19-3; 8.20 g, 29.9 mmol, 0.02 eq.) and $[Ir(OCH_3)(COD)]_2$ (CAS #12148-71-9; 10.11 g, 14.95 mmol, 0.01 eq). The reaction mixture is heated to reflux for 1 h 40 min, then cooled to 25° C. Diethanolamine (CAS #111-42-2; 288 mL, 2991 mmol, 2.0 eq.) is added. The reaction mixture is stirred at 30° C. for 1 h 20 min. The suspension is filtered. The cake is washed with THF (1200 mL) and the powder is dried to afford 2-(difluoromethoxy)-4-(2,8-dioxa-5-aza-1λ$^4$-borabicyclo[3.3.0]octan-1-yl)-N-[(1R,2S)-2-fluorocyclopropyl]-6-methoxy-benzamide.

$^{1}$H NMR (400 MHz, DMSO-$d_6$) δ 8.28 (d, 1H), 6.92 (s, 1H), 7.30-6.41 (m, 3H), 4.57 (m, 1H), 4.05-3.30 (m, 5H), 3.74 (s, 2H), 3.28-2.99 (m, 2H), 2.99-2.64 (m, 2H), 1.37-0.59 (m, 4H)

2.72.2 Step ii: Int 267

A suspension of 2-(difluoromethoxy)-4-(2,8-dioxa-5-aza-1λ$^{4}$-borabicyclo[3.3.0]octan-1-yl)-N-[(1R,2S)-2-fluorocyclopropyl]-6-methoxy-benzamide (563.9 g, 1457 mmol, 1.0 eq.) in hydrochloric acid (1 mol/L) in deionized water (2242 mL, 2242 mmol, 1.5 eq.) is stirred at 25° C. for 1 h. The suspension is filtered. The cake is washed three times with water (500 mL) and the powder is dried to afford Int 267.

2.73. Cpd 15

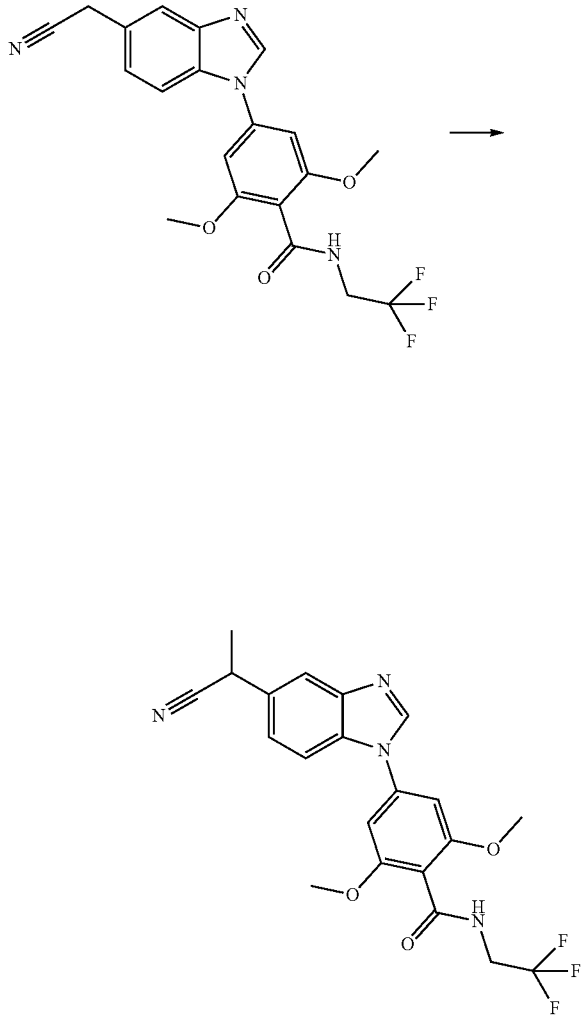

To a solution of Int 54 (47 mg, 0.11 mmol, 1 eq.) in DCM (1.5 mL) are added sodium hydride (60% dispersion in mineral oil, CAS #7646-69-7; 3.9 mg, 0.10 mmol, 0.9 eq.) and methyl iodide (CAS #74-88-4; 6.1 μL, 0.10 mmol, 0.9 eq.). The resulting solution is stirred at RT for 72 h then diluted in water and extracted with EtOAc. The combined organic layers are dried over $MgSO_4$, filtered, concentrated in vacuo and purified by prep HPLC to afford the desired compound.

2.74. Cpd 25

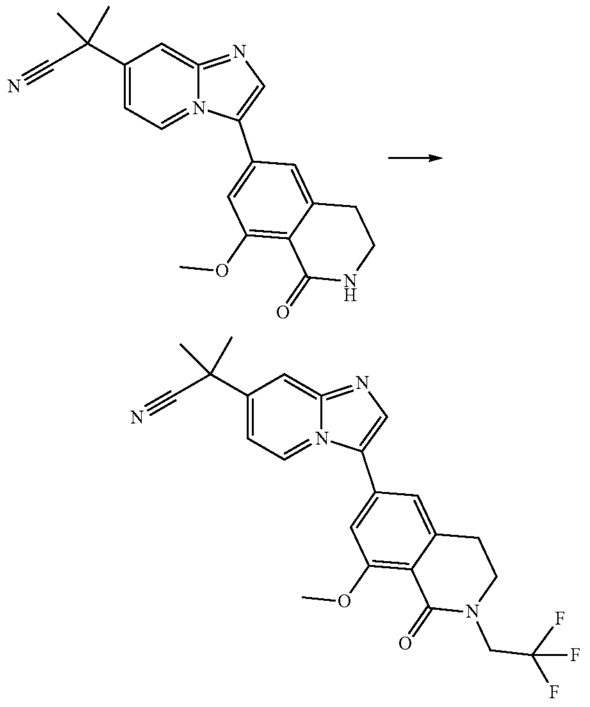

To a solution of Cpd 20 (22 mg, 0.061 mmol, 1 eq.) in THF (1.5 mL)/NMP (1 mL) at 0° C. under $N_2$ atmosphere is added LiHMDS (1M in THF, CAS #CAS #4039-32-1; 104 μL, 0.10 mmol, 1.7 eq.). After 5 min stirring at 0° C., 2,2,2-trifluoroethyl trifluoromethanesulfonate (CAS #6226-25-1; 15 μL, 0.10 mmol, 1.7 eq.) is added. The resulting solution is allowed to warm to RT then heated to 100° C. for 1 h. After 1 h stirring, the reaction mixture is cooled to 0° C. and the same amounts of LiHMDS and trifluoromethanesulfonate are added. The resulting solution is heated to 120° C. for 2 h then quenched with a sat. $NH_4Cl$ solution and brine, and extracted with EtOAc. The combined organic layers are dried over $MgSO_4$, filtered, concentrated in vacuo and purified by preparative HPLC to afford the desired compound.

2.75. Cpd 61

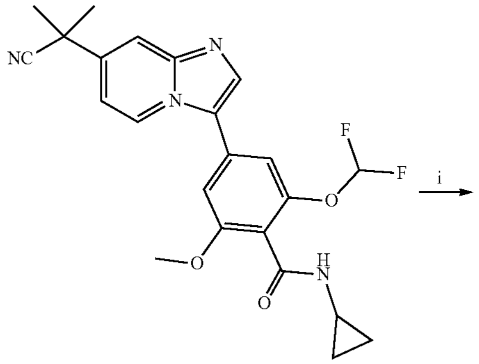

-continued

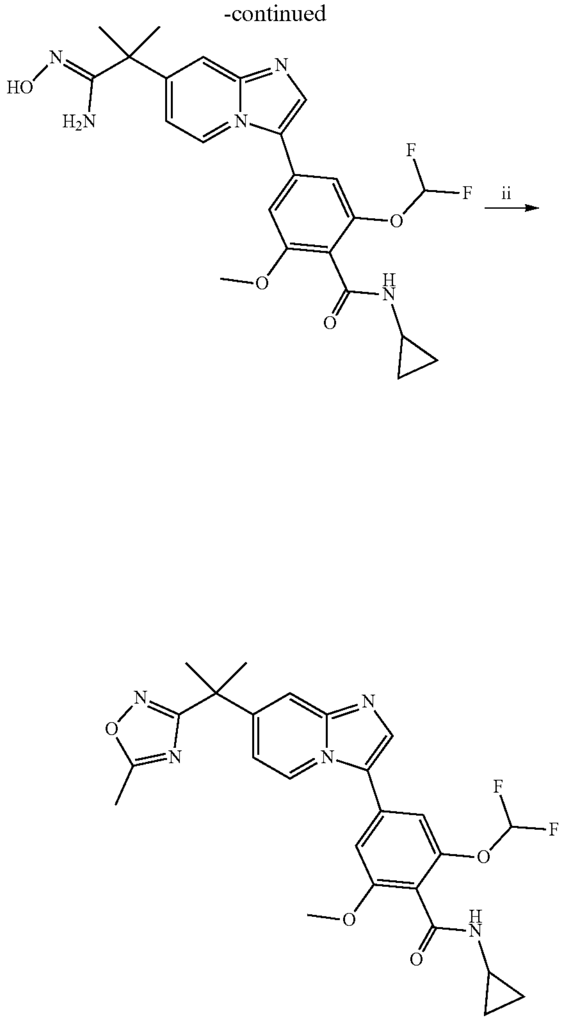

2.75.1. Step i: 4-[7-[(2Z)-2-amino-2-hydroxyimino-1,1-dimethyl-ethyl]imidazo[1,2-a]pyridin-3-yl]-N-cyclopropyl-2-(difluoromethoxy)-6-methoxy-benzamide To a solution of Cpd 19 (20 mg, 0.045 mmol, 1 eq.) in a mixture EtOH/water 3.5/1 (2 mL) are added $NaHCO_3$ (19 mg, 0.23 mmol, 5 eq.) and hydroxylamine hydrochloride (CAS #5470-11-1; 16 mg, 0.23 mmol, 5 eq.). The resulting solution is heated to 90° C. and stirred for 3 h. More hydroxylamine hydrochloride is added and the mixture is stirred at 90° C. for 18 h, then concentrated in vacuo. The residue is diluted in DCM and water, extracted with DCM, passed through a phase separator and concentrated.

2.75.2. Step ii: Cpd 61

The above prepared intermediate is transferred to a microwave reactor, diluted in pyridine (1 mL), and acetic anhydride (CAS #108-24-7; 13 μL, 0.14 mmol, 3 eq.) is added. The vial is sealed and heated to 140° C. for 30 min under microwave irradiation. The reaction mixture is then concentrated in vacuo and purified by preparative HPLC to afford the desired compound.

2.76. Cpd 63

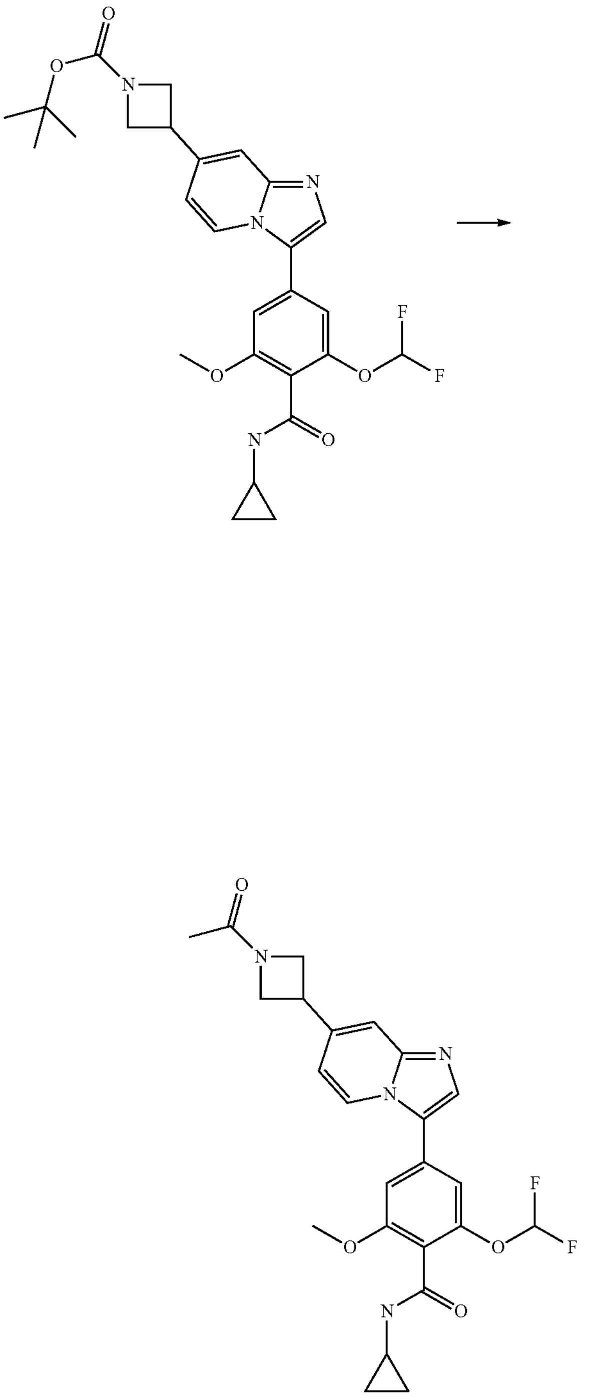

To a solution of Int 87 (110 mg, 0.21 mmol, 1 eq.) in DCM (1.5 mL) is added TFA (1.5 mL). The resulting solution is stirred at RT for 1 h then concentrated. The residue is diluted in water and EtOAc. The organic layer is separated. The aqueous layer is then basified with a 2N NaOH solution and extracted with EtOAc. The combined organic layers are dried over $Na_2SO_4$, filtered, concentrated in vacuo and purified by preparative HPLC to afford the desired compound.

2.77. Cpd 93

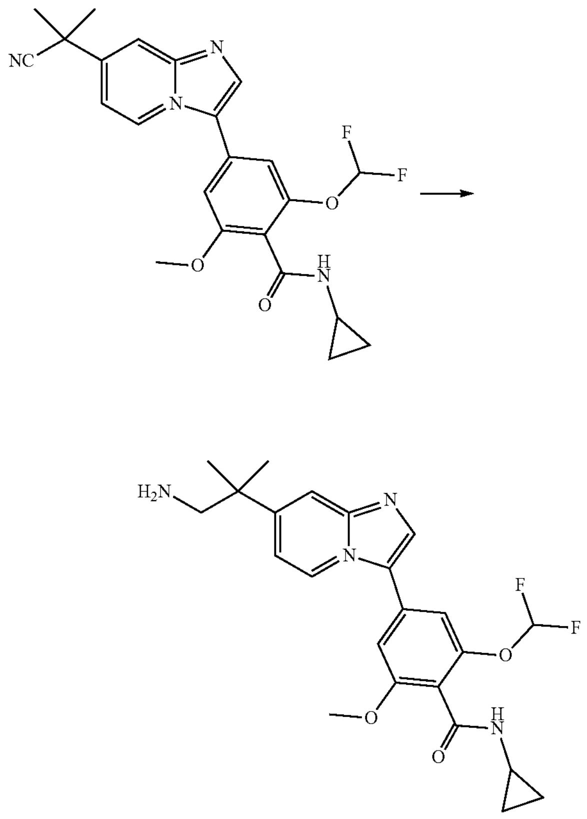

To a solution of Cpd 19 (25 mg, 0.057 mmol, 1 eq.) in dry THF (1 mL) at 0° C. under inert atmosphere is added dropwise $LiAlH_4$ (1 M solution in THF, CAS #16853-85-3; 85 μL, 0.085 mmol, 1.5 eq.). The resulting solution is stirred at RT for 18 h. The reaction mixture is quenched successively with water, a 0.1N NaOH solution and water, stirred for 10 min and then filtered. The filtrate is diluted with water and extracted with DCM. The combined organic layers are passed through a phase separator and concentrated in vacuo. The residue is purified by preparative HPLC to afford the desired compound.

2.78. Cpd 115

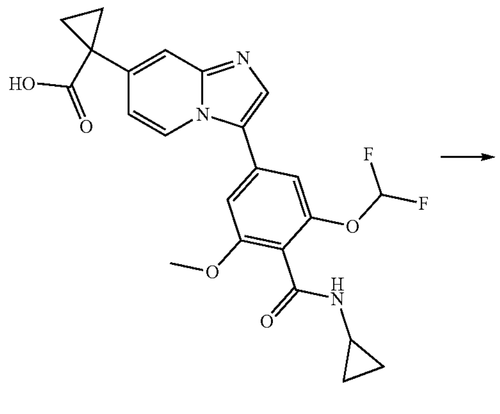

-continued

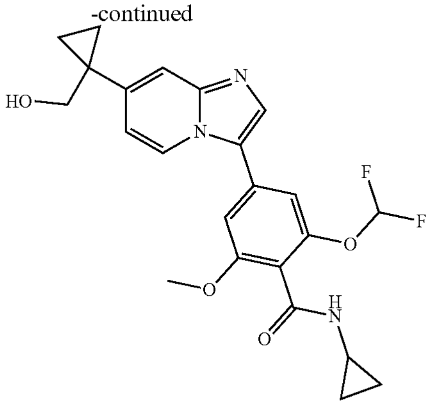

To a solution of Cpd 114 (50 mg, 0.11 mmol, 1 eq.) in dry THF (1 mL) at 0° C. under $N_2$ atmosphere is added $LiAlH_4$ (1M solution in THF, CAS #16853-85-3; 0.1 mL, 0.11 mmol, 1 eq.). The resulting solution is stirred at 0° C. for 2 h then at RT for 3 h. The reaction mixture is quenched successively with water (4 μL), a 15% NaOH solution (4 μL), and water (10 μL), filtered and concentrated in vacuo. The residue is purified by flash chromatography on silica gel (eluting with EtOAc/MeOH 100/1 to 98/2) to afford the desired compound.

2.79. Cpd 131

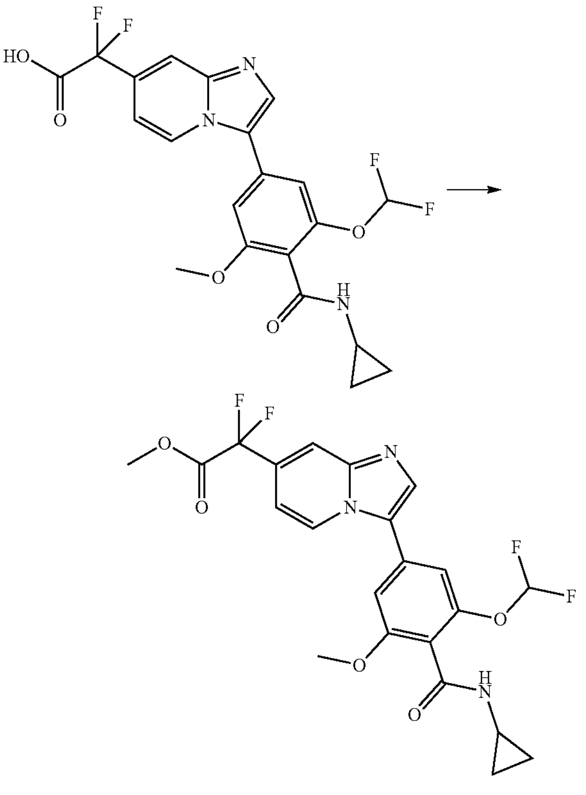

To a solution of Cpd 132 (207 mg, 0.44 mmol, 1 eq.) in MeOH (1.1 mL) at 0° C. is added thionyl chloride (CAS #7719-09-7; 110 μL, 1.52 mmol, 3.4 eq.). The resulting solution is warmed to RT and stirred for 18 h. More thionyl chloride is added at 0° C. (110 μL, 1.52 mmol, 3.4 eq.) and the reaction mixture is stirred at RT for 23 h, then concentrated in vacuo, quenched with a sat. $NaHCO_3$ solution and extracted with EtOAc. The combined organic layers are washed with brine, dried over $MgSO_4$, filtered and concentrated. The residue is purified by flash chromatography on silica gel (eluting with heptane/EtOAc 100/0 to 0/100 then DCM/MeOH 90/10). After concentration of the corresponding fractions, the residue is dissolved in ACN, concentrated in vacuo and the solid obtained triturated in $Et_2O$, filtered ad dried to afford the desired compound.

2.80. Cpd 132

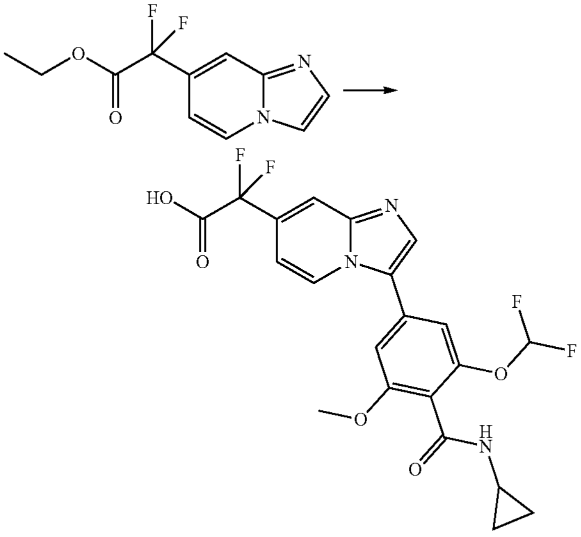

The imidazopyridine derivative Int 116 (125 mg, 0.52 mmol, 1 eq.), the bromo derivative Int 4 (175 mg, 0.52 mmol, 1 eq.), KOAc (153 mg, 1.56 mmol, 3 eq.) and Pd(dppf)$Cl_2$·DCM adduct (CAS #95464-05-4, 13 mg, 0.016 mmol, 0.03 eq.) are suspended in dry DMAC and the mixture is degassed with $N_2$. The mixture is stirred at 100° C. for 4 h. The reaction mixture is cooled to RT, concentrated in vacuo and diluted in water EtOAc and AcOH. The resulting mixture is stirred at RT for 1 h, the precipitate is filtered, washed with water and EtOAc to afford part of the desired compound. The filtrate is extracted with EtOAc. The aqueous layer is concentrated to dryness and purified by preparative HPLC. The residue is then dissolved in DCM and MeOH, concentrated, triturated in ACN and $Et_2O$, filtered and washed with EtOAc and $Et_2O$ to afford the desired compound.

2.81. Cpd 136

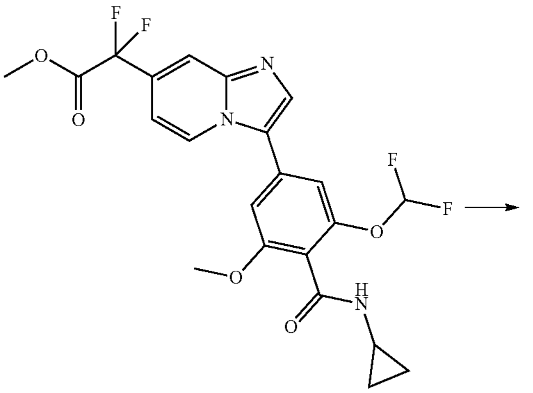

-continued

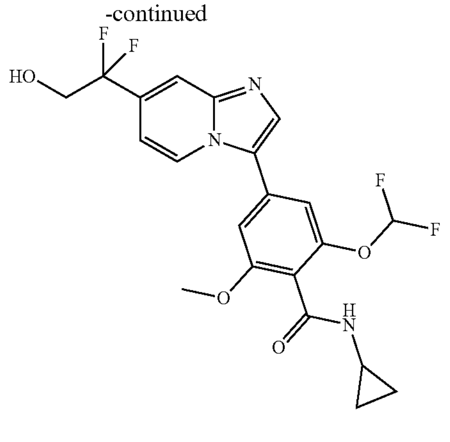

To a solution of Cpd 131 (10 mg, 0.021 mmol, 1 eq.) in dry THF (0.5 mL) at 0° C. under $N_2$ atmosphere is added $LiBH_4$ (2M solution in THF, CAS #16949-16-8; 11 μL, 0.023 mmol, 1.1 eq.). The resulting solution is stirred at 0° C. for 30 min. The reaction mixture is quenched by 10 drops of a 1N HCl solution and water, extracted with EtOAc. The aqueous layer is basified by addition of a 1N NaOH solution and extracted with EtOAc. The combined organic layers are washed with brine, dried over $MgSO_4$, filtered and concentrated in vacuo. The residue is purified by preparative HPLC to afford the desired compound.

2.82. Cpd 145

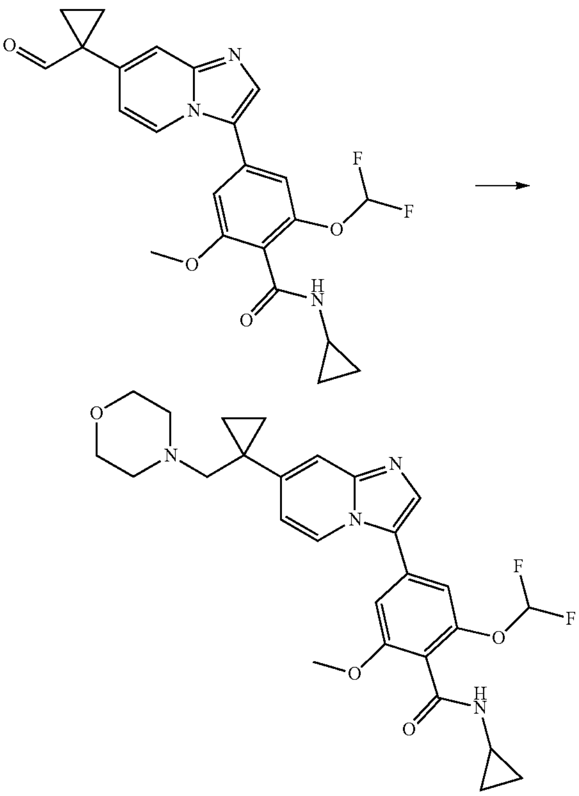

To a solution of Int 123 (20 mg, 0.04 mmol, 1 eq.) in buffer AcOH/AcONa/MeOH (96 mg/61 mg/2 mL) are added morpholine (CAS #110-91-8; 16 μL, 0.18 mmol, 4 eq.) The resulting solution is stirred at RT for 2 h before adding $NaBH_3CN$ (CAS #25895-60-7; 9 mg, 0.13 mmol, 3 eq.). The reaction mixture is stirred for 18 h then concentrated to dryness. The residue is diluted in DMSO and purified by preparative HPLC to afford the desired compound.

2.83. Cpd 162 & Cpd 163

Cpd 138 (49 mg) is diluted in MeOH (1.5 mL) and separated by chiral preparative SFC (Chiralpak® IG column, 4.6 mm ID×250 mm L, 5 μm particle size), eluting with 25% MeOH in liquid $CO_2$ to afford Cpd 162 as the first eluting and Cpd 163 as the second eluting compound.

2.84. Cpd 164 & Cpd 165

Cpd 137 (59 mg) is diluted in EtOH (1.5 mL) and separated by chiral preparative SFC (Chiralpak® IG column, 4.6 mm ID×250 mm L, 5 μm particle size), eluting with 20% EtOH in liquid $CO_2$ to afford Cpd 164 as the first eluting and Cpd 165 as the second eluting compound.

2.85. Cpd 189 & Cpd 190

Cpd 176 (20 mg) is diluted in MeOH (1.5 mL) and separated by chiral preparative SFC (LUX® Cellulose C1 column, 10 mm ID×250 mm L, 5 μm particle size), eluting with 25% MeOH in liquid $CO_2$ to afford Cpd 189 as the first eluting and Cpd 190 as the second eluting compound.

2.86. Cpd 197

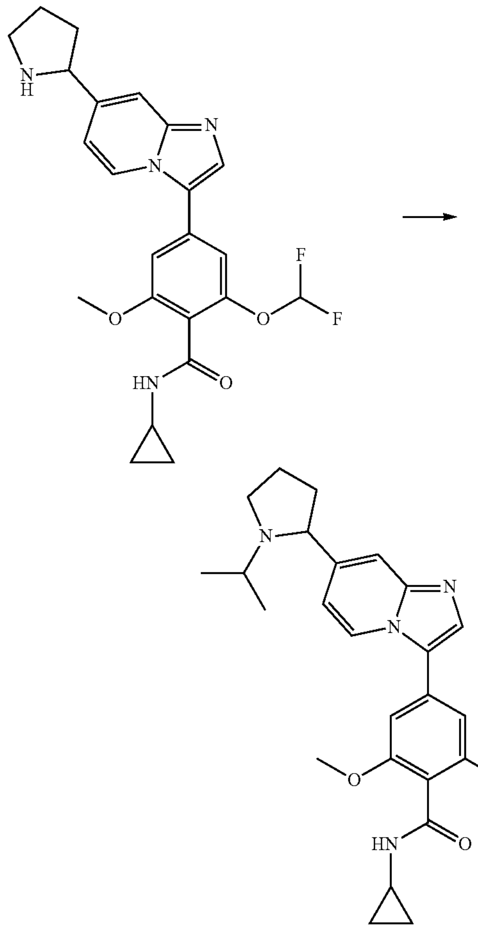

To a solution of Cpd 188 (50 mg, 0.11 mmol, 1 eq.) in DCM (1 mL) are added acetone (CAS #67-64-1; 500 μL, 6.8 mmol, 60 eq.) and one drop of AcOH. The resulting solution is stirred at RT for 1 h before adding $NaBH(OAc)_3$ (CAS #56553-60-7; 36 mg, 0.17 mmol, 1.5 eq.). The reaction mixture is stirred for 18 h then quenched with a 2N NaOH solution, extracted with EtOAc. The combined organic layers are dried over $Na_2SO_4$, filtered and concentrated in vacuo. The residue is purified by flash chromatography on silica gel (eluting with DCM/MeOH 99/1 to 98/2) to afford the desired compound.

2.87. Cpd 201 & Cpd 202

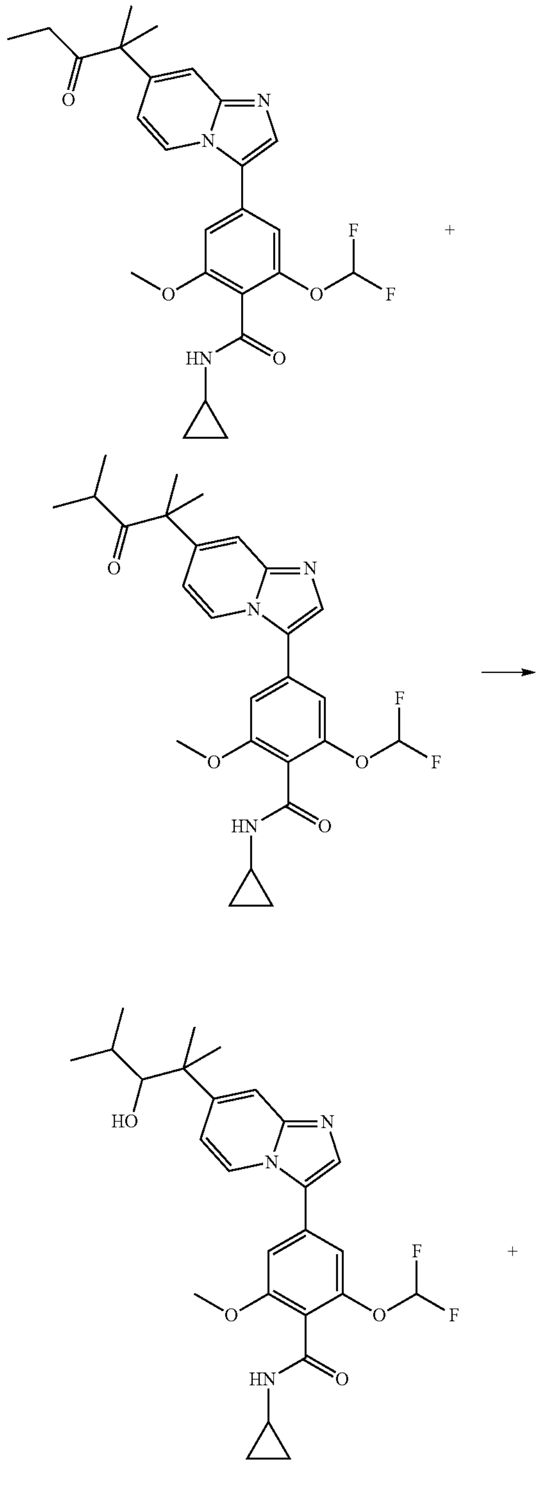

-continued

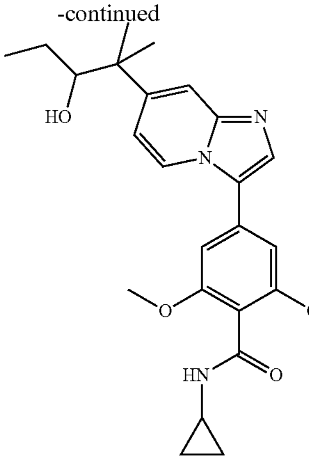

To a solution of a mixture of ketones Int 140 (150 mg, 0.312 mmol, 1 eq.) in MeOH (3 mL) at RT is added sodium borohydride (24 mg, 0.62 mmol, 2 eq.). The reaction mixture is stirred at RT for 1.5 h then concentrated in vacuo and purified by preparative HPLC to afford the desired compounds.

2.88. Cpd 217

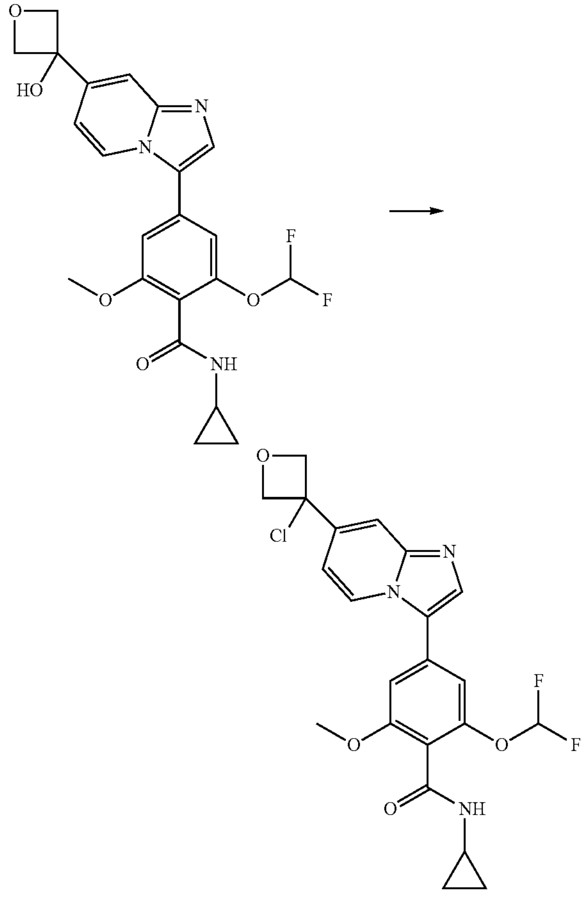

To a suspension of alcohol Cpd 177 (36 mg, 0.081 mmol, 1 eq.) in DCM (1.5 mL) are added $Et_3N$ (23 μL, 0.16 mmol, 2 eq.) followed by methanesulfonyl chloride (CAS #124-63-0; 13 μL, 0.16 mmol, 2 eq.). The resulting mixture is stirred at 45° C. for 2 h, then quenched with water and concentrated to dryness. The residue is purified by flash chromatography to afford the desired compound.

2.89. Cpd 219 (Alternative Synthesis)

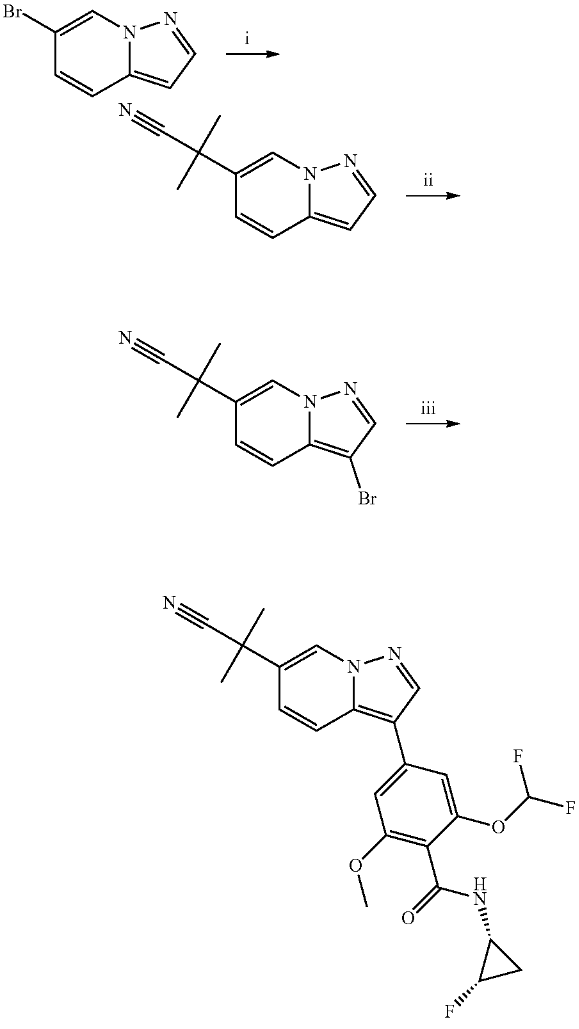

2.89.1. Step i: Int 58 (Alternative Synthesis)

In a 5 L single jacketed process reactor with baffles is added 6-bromopyrazolo[1,5-a]pyridine (CAS #1264193-11-4; 352 g, 1733 mmol, 1.0 eq.) and Int 170 (524 g, 3466 mmol, 2.0 eq.) in xylene (1760 mL). The reaction mixture is heated at 130° C. in 1 h. 4,5-Bis(diphenylphosphino)-9,9-dimethylxanthene (60 g, 103.7 mmol, 0.06 eq.) and bis(dibenzylideneacetone)palladium (40 g, 69.6 mmol, 0.04 eq.) are added at this temperature. After 30 min, the reaction mixture is cooled to 20° C. in 1 h. The crude solution is purified on a cake of silica (1200 g, 4 portions). The cake is first washed with heptane (3000 mL) to elute xylene. The cake is then washed with acetone (6000 mL) to elute the product. The filtrate is concentrated and the residue is distilled under vacuum (135-140° C. head temperature at 0.11 mbar) to afford Int 58.

LCMS: MW (calcd): 185.2; m/z MW (obsd): 186.0 (M+H)

2.89.2. Step ii: 2-(3-bromopyrazolo[1,5-a]pyridin-6-yl)-2-methyl-propanenitrile

In a 5 L single jacketed process reactor is added Int 58 (358 g, 1933 mmol, 1.0 eq.) in ACN (1790 mL). N-bromo-succinimide (CAS #128-08-5; 382 g, 2125 mmol, 1.1 eq.) is added portionwise in 30 min, maintaining the internal temperature below 30° C. The reaction mixture is warmed to 20° C. in 5 min and stirred 20 min. Water is added (1800 mL). The reaction mixture is stirred 20 min and then filtered (rinsed with 1800 mL of water) to afford 2-(3-bromopyrazolo[1,5-a]pyridin-6-yl)-2-methyl-propanenitrile as a solid.

LCMS: MW (calcd): 264.1; m/z MW (obsd): 263.9, 265.9 (M+H)

2.89.3. Step iii: Cpd 219

In a 5 L single jacketed process reactor with baffles is added 2-(3-bromopyrazolo[1,5-a]pyridin-6-yl)-2-methyl-propanenitrile (220 g, 816 mmol, 1.0 eq.) and Int 267 (307 g, 898 mmol, 1.1 eq.) in 1,4-dioxane (1760 mL) and water (440 mL), followed by sodium carbonate (260 g, 2453 mmol, 3 eq.), 2-dicyclohexylphosphino-2',6'-diiso-propoxybiphenyl (CAS #787618-22-8; 8.1 g, 16 mmol, 0.02 eq.) and $Pd_2dba_3$ (CAS #51364-51-3; 3.8 g, 4.1 mmol, 0.0051 eq.). The reaction mixture is refluxed in 40 min and stirred for 2 h. The reaction mixture is cooled to 20° C. in 1 h, filtered on a cellulose cake and rinsed with EtOAc (1000 mL). Water (1000 mL) is added and the organic phase is extracted. The organic phase is concentrated. EtOAc (1000 mL) is added and the mixture is concentrated again. The resulting solution is stirred in a 5 L single jacketed process reactor with baffles, and MTBE (1100 mL) is added under stirring over 50 min. After stirring for 30 min, the precipitate is filtered and rinsed with MTBE (600 mL) to afford the desired product as a solid.

Treatment with Pd Scavenger:

The solid (1365 g, 2978 mmol) is solubilized in acetone (10000 mL), then added in a 15 L single jacketed process reactor. SiliaMetS Thiol metal scavenger (SiliCycle Inc., Cat #R51030B) is added (500 g, 18 eq. of palladium used). The resulting mixture is heated 1 h at 60° C. The mixture is cooled down to 20° C. in 30 min, filtered, and rinsed with acetone (2000 mL). The filtrate is concentrated until 2000 mL (crystallization occurs during evaporation). The mixture is pooled into the reactor and MTBE (4000 mL) is added over 1 h. The precipitate is filtered and rinsed with MTBE (1000 mL) to afford the desired product as a powder. Rework of the filtrate: after partial evaporation, the filtrate crystallizes. The solid is filtered (rinsed with MTBE, 1000 mL) to afford a second crop of desired product as a powder.

Final Reslurry:

In a 15 L reactor, the two previous powder batches are combined (total of 1226 g), suspended in MTBE (7000 mL) and stirred at 50° C. for 2 h. The mixture is cooled to 20° C. in 30 min and filtered (rinsed with MTBE, 1000 mL) to afford Cpd 219.

2.90. Cpd 222

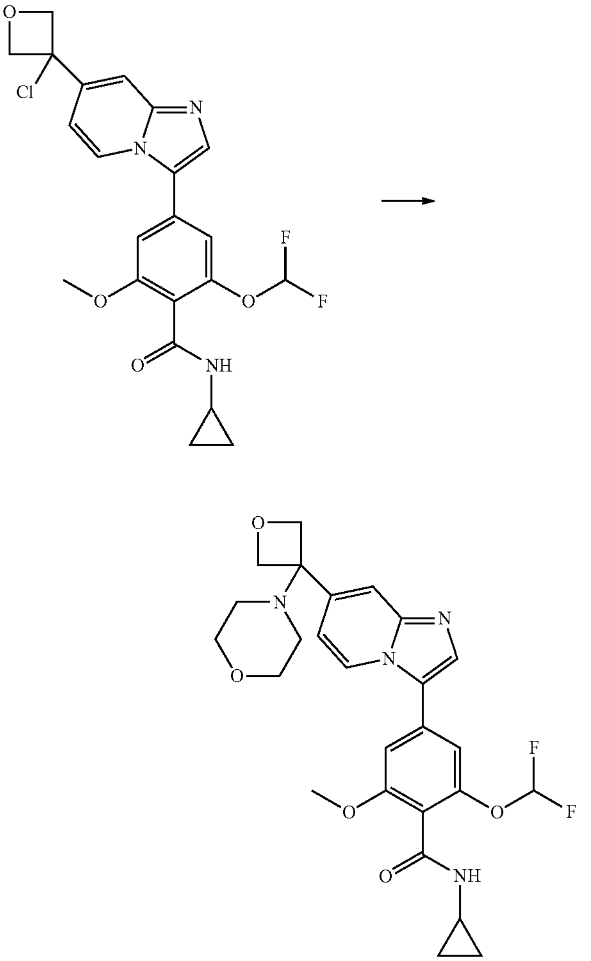 [SMILES: COc1cc(-c2cnc3cc(C4(O)COC4)ccn23)cc(OC(F)F)c1C(=O)NC1CC1 ; COc1cc(-c2cnc3cc(C4(Cl)COC4)ccn23)cc(OC(F)F)c1C(=O)NC1CC1]

A solution of Cpd 217 (46 mg, 0.10 mmol, 1 eq.) in morpholine (CAS #110-91-8; 1 mL) is stirred at 90° C. for 36 h, then concentrated. The residue is purified by preparative HPLC to afford the desired compound.

2.91. Cpd 229

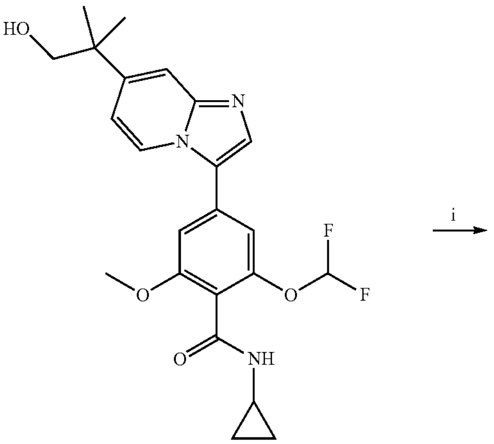

-continued

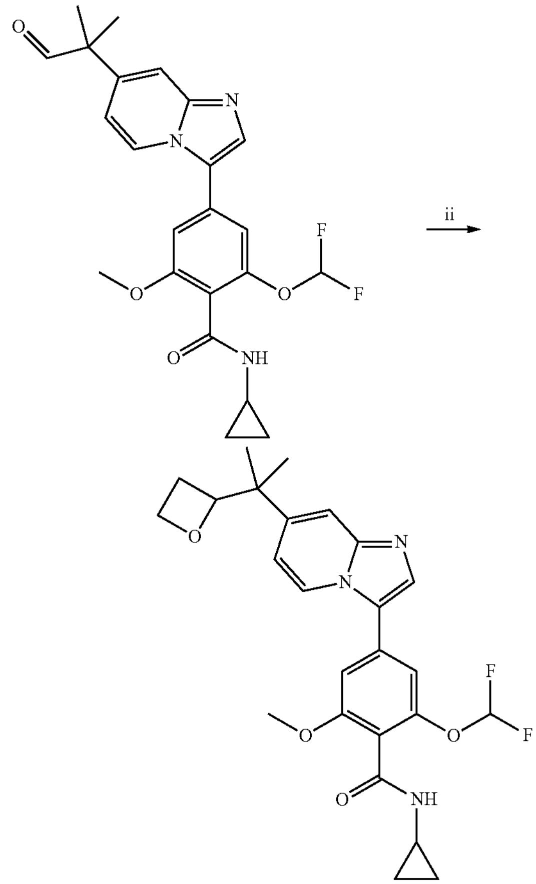

2.91.1. Step i: N-cyclopropyl-2-(difluoromethoxy)-4-[7-(1,1-dimethyl-2-oxo-ethyl)imidazo[1,2-a]pyridin-3-yl]-6-methoxy-benzamide To a solution of Cpd 150 (85 mg, 0.19 mmol, 1 eq.) in DCM (9.5 mL) is added Dess-Martin periodinane (CAS #87413-09-0; 97 mg, 0.23 mmol, 1.2 eq.). The reaction mixture is stirred at RT for 3 h, quenched with a sat. $NaHCO_3$ solution, filtered on a phase separator and concentrated. The residue is purified by flash chromatography on silica gel (eluting with DCM/MeOH 100/0 to 95/5) to afford the desired aldehyde.

2.91.2. Step ii: Cpd 229

A suspension of trimethylsulfoxonium iodide (CAS #1774-47-6; 111 mg, 0.50 mmol, 4 eq.) and t-BuOK (CAS #865-47-4; 57 mg, 0.50 mmol, 4 eq.) in t-BuOH (2.6 mL) is stirred at 50° C. for 1 h. Then a solution of the above described aldehyde in t-BuOH (1 mL) is introduced dropwise whilst stirring. The resulting mixture is stirred at 50° C. for 36 h then quenched with water and extracted with EtOAc. The combined organic layers are passed through a phase separator and concentrated in vacuo. The residue is purified by flash chromatography then by preparative HPLC to afford the desired compound.

2.92. Cpd 244

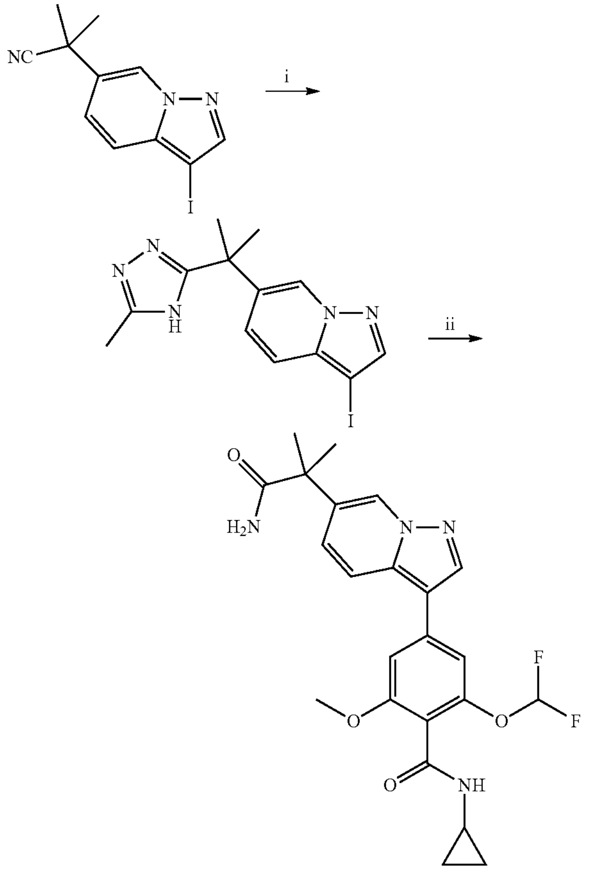

2.92.1. Step i: 3-iodo-6-[1-methyl-1-(5-methyl-4H-1,2,4-triazol-3-yl)ethyl]pyrazolo[1,5-a]pyridine To a solution of 2-(3-iodopyrazolo[1,5-a]pyridin-6-yl)-2-methyl-propanenitrile Int 169 (50 mg, 0.16 mmol, 1 eq.) in DMSO (1 mL) under $N_2$ atmosphere are added acetamidine hydrochloride (CAS #124-42-5; 23 mg, 0.24 mmol, 1.5 eq.) followed by $Cs_2CO_3$ (CAS #534-17-8; 160 mg, 0.48 mmol, 3.0 eq.) and copper bromide (CAS #7787-70-4; 1.2 mg, 0.008 mmol, 0.05 eq.). The reaction mixture is heated to 140° C. for 1 h then 125° C. for 18 h. The reaction mixture is quenched by addition of water and extracted with EtOAc. The combined organic layers are dried over $MgSO_4$, filtered and concentrated in vacuo.

2.92.2 Step ii: Cpd 244

To a degassed solution of the above prepared intermediate (59 mg, 0.16 mmol, 1 eq.) in a mixture dioxane/water under $N_2$ are added N-cyclopropyl-2-(difluoromethoxy)-6-methoxy-4-(4,4,5,5-tetramethyl-1,3,2-dioxaborolan-2-yl)benzamide Int 7 (74 mg, 0.19 mmol, 1.2 eq.) followed by $Cs_2CO_3$ (CAS #534-17-8; 160 mg, 0.49 mmol, 3.1 eq.) and $Pd(dppf)Cl_2 \cdot DCM$ (CAS #95464-05-4; 13 mg, 0.016 mmol, 0.1 eq.). The reaction mixture is heated to 90° C. for 45 min then concentrated in vacuo and purified by preparative HPLC to afford the desired compound.

2.93. Cpd 257 & Cpd 258

Cpd 241 (30 mg) is diluted in MeOH (2 mL) and separated by chiral preparative SFC (Chiralcel® OJ-H column, 10 mm ID×250 mm L, 5 μm particle size), eluting with 20% i-PrOH in liquid $CO_2$ to afford Cpd 257 as the first eluting and Cpd 258 as the second eluting compound.

2.94. Cpd 259

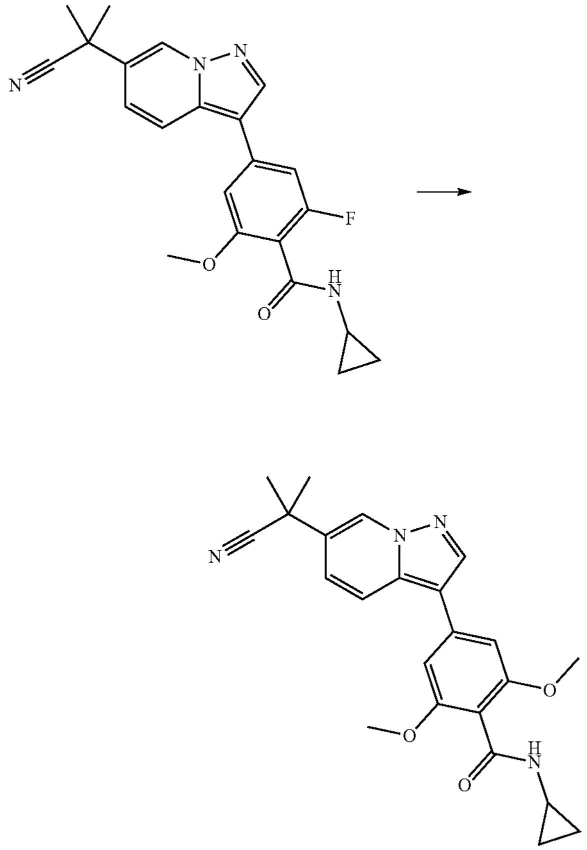

To a solution of Cpd 252 (25 mg, 0.064 mmol, 1 eq.) in DMSO (1 mL) is added MeONa (CAS #124-41-4, 11 mg, 0.19 mmol, 3 eq.). The reaction mixture is stirred at 80° C. for 18 h. MeONa (11 mg, 0.19 mmol, 3 eq.) is added and the resulting mixture is stirred at 80° C. for 4 h then concentrated in vacuo and purified by preparative HPLC to give the desired compound.

2.95. Cpd 260

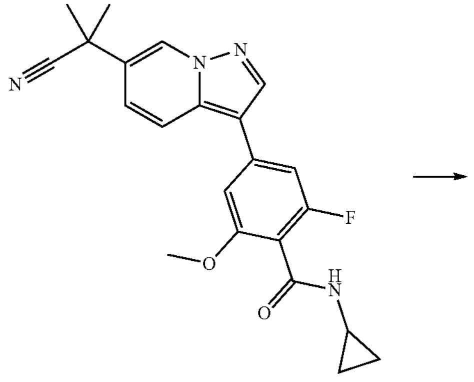

-continued

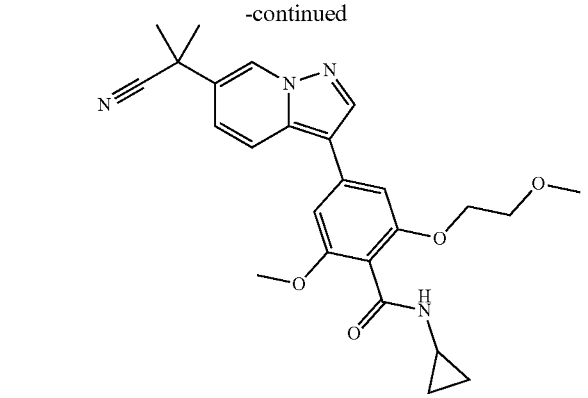

To 2-methoxyethanol (CAS #109-86-4, 0.3 mL, 4 mmol, 60 eq.) is added t-BuOK (23 mg, 0.19 mmol, 3 eq.). The resulting mixture is stirred for 5 minutes and then Cpd 252 (0.025 g, 0.064 mmol, 1.0 eq.) is introduced. The reaction mixture is stirred at 80° C. for 18 h then concentrated in vacuo and purified by preparative HPLC to give the desired Cpd 260.

2.96. Cpd 263

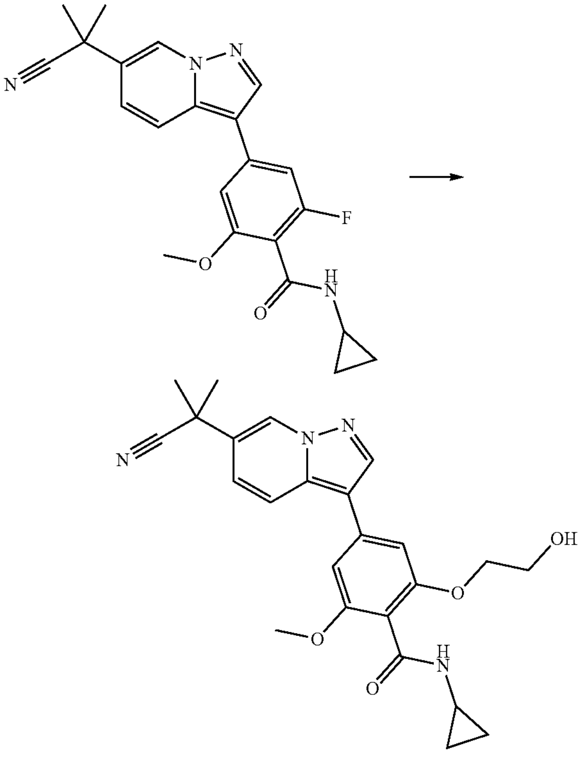

To ethylene glycol (CAS #107-21-1, 0.3 mL, 5 mmol, 80 eq.) is added t-BuOK (23 mg, 0.19 mmol, 3 eq.). The resulting solution is stirred for 5 min and then Cpd 252 (25 mg, 0.064 mmol, 1 eq.) is added. The reaction mixture is stirred at 80° C. for 18 h. More ethylene glycol (0.3 mL) and t-BuOK (23 mg, 0.19 mmol, 3 eq.) are added and the reaction mixture is stirred at 80° C. for 4 h. DMSO (1 mL) is added and the reaction mixture is stirred at 80° C. for 6 days. The reaction mixture is concentrated in vacuo and purified by preparative HPLC to afford the desired compound.

2.97. Cpd 267

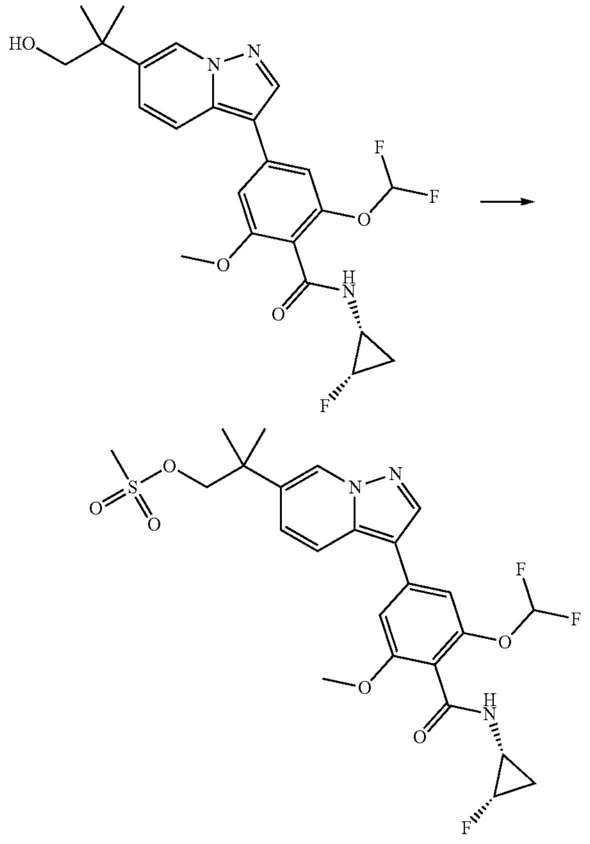

To a solution of Cpd 242 (0.253 g, 0.55 mmol, 1 eq.) in DCM (8 mL) at 0° C. under $N_2$ atmosphere are added $Et_3N$ (0.152 mL, 1.09 mmol, 2 eq.) and methanesulfonyl chloride (65 μL, 0.82 mmol, 1.5 eq.). The reaction mixture is stirred at 0° C. for 1 h, then quenched with a sat. $NaHCO_3$ solution and extracted with DCM (twice). The combined organic layers are filtered on a phase separator and concentrated in vacuo. An aliquot of the crude residue obtained is purified by flash chromatography on silica gel (eluting with a heptane/EtOAc 100/0 to 0/100) and then purified by preparative HPLC to afford Cpd 267.

2.98. Cpd 268

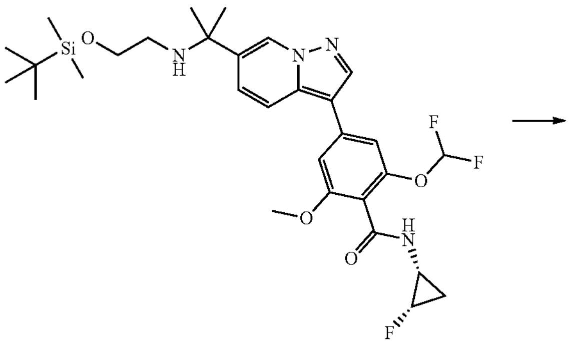

-continued

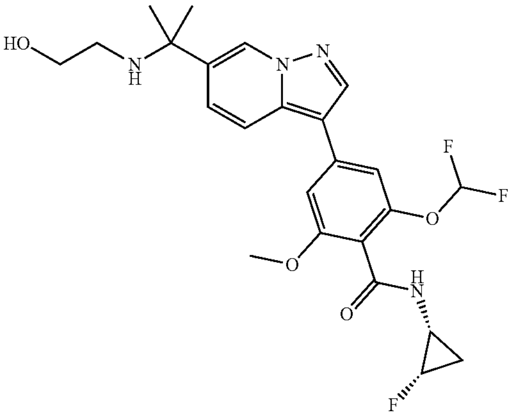

To a solution of Int 249 (24 mg, 0.026 mmol, 1 eq.) in THF (0.5 mL) is added at 0° C. tetrabutylammonium fluoride (1 M in THF, CAS #429-41-4; 51 μL, 0.05 mmol, 2 eq.). The mixture is stirred at RT for 1 h then concentrated. The crude residue is purified by flash chromatography on silica gel (eluting with heptane/EtOAc 100/0 to 0/100 then DCM/MeOH 100/0 to 98/2) to afford Cpd 268.

2.99. Cpd 275

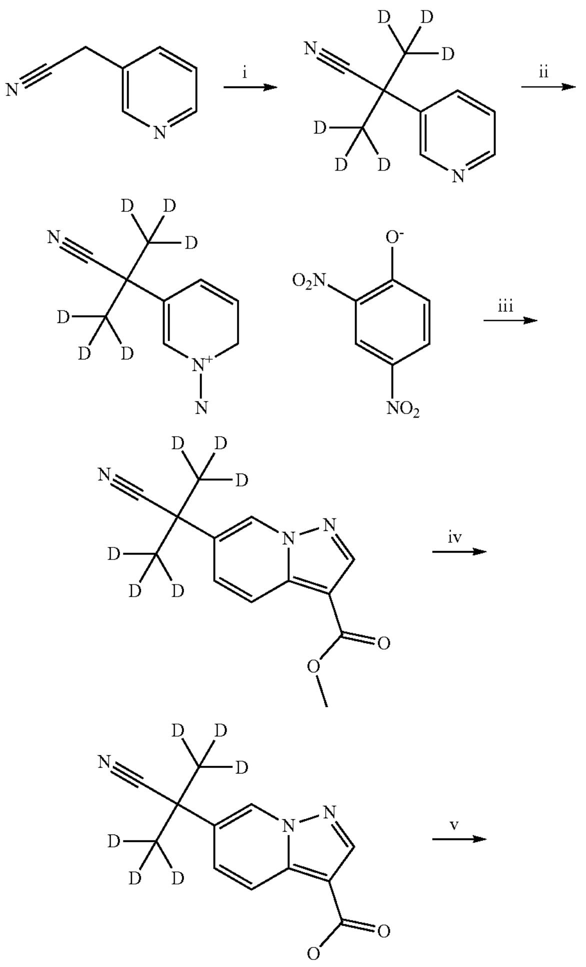

-continued

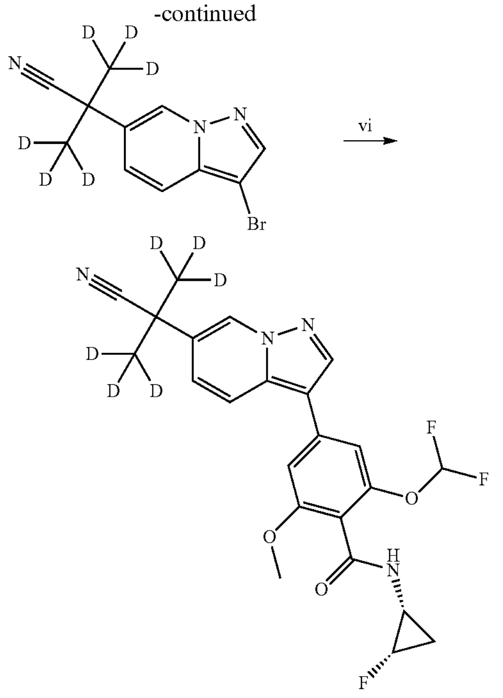

2.99.1. Step i: 3,3,3-trideuterio-2-(3-pyridyl)-2-(trideuteriomethyl)propanenitrile To a solution of 2-(3-pyridyl)acetonitrile (CAS #6443-85-2; 1.8 g, 15 mmol, 1.0 eq.) and $CD_3I$ (CAS #865-50-9; 5.1 g, 35 mmol, 2.3 eq.) in THF (10 mL) at −30° C. is added t-BuOK (3.8 g, 34 mmol, 2.2 eq.) portionwise. The reaction mixture is stirred at RT for 1 h. The suspension is filtered and the cake washed with EtOAc. The filtrate is concentrated in vacuo and the residue is purified by flash chromatography on silica gel (eluting with DCM/EtOAc 100/0 to 70/30) to afford 3,3,3-trideuterio-2-(3-pyridyl)-2-(trideuteriomethyl) propanenitrile.

LCMS: MW (calcd): 152.2; m/z MW (obsd): 153.1 (M+H)

2.99.2. Step ii: 2-(1-aminopyridin-1-ium-3-yl)-3,3,3-trideuterio-2-(trideuteriomethyl)propanenitrile; 2,4-dinitrophenolate To a solution of 3,3,3-trideuterio-2-(3-pyridyl)-2-(trideuteriomethyl)propanenitrile (1.89 g, 12.4 mmol, 1.00 eq.) in ACN (10 mL) is added in one portion N-(2,4-dinitrophenyl) hydroxylamine (CAS #17508-17-7; 2.8 g, 14 mmol, 1.1 eq.). The reaction mixture is stirred at 40° C. for 2 h. The reaction mixture is concentrated to remove half of the ACN. MTBE (10 mL) is added. The suspension is stirred at RT for 15 min and filtered. The cake is washed with MTBE and the solid is dried to afford 2-(1-aminopyridin-1-ium-3-yl)-3,3,3-trideuterio-2-(trideuteriomethyl)propanenitrile; 2,4-dinitrophenolate.

2.99.3. Step iii: methyl 6-[1-cyano-2,2,2-trideuterio-1-(trideuteriomethyl)ethyl]pyrazolo[1,5-a]pyridine-3-carboxylate To a suspension of 2-(1-aminopyridin-1-ium-3-yl)-3,3,3-trideuterio-2-(trideuteriomethyl)propanenitrile; 2,4-dinitrophenolate (3.67 g, 10.4 mmol, 1.00 eq.) in butyronitrile (18 mL) are added successively $K_2CO_3$ (2.17 g, 15.7 mmol, 1.50 eq.) and Int 266 (2.80 g, 10.4 mmol, 0.996 eq.). The reaction mixture is heated at reflux for 1 h. The reaction mixture is cooled to RT and DCM (18 mL) is added. The suspension is stirred at RT a few minutes, filtered and the cake is washed with DCM. The filtrate is washed twice with $NaHCO_3$ 5% solution, 20% NaCl solution, dried on $Na_2SO_4$, filtered and concentrated until crystallization occurs. MTBE (10 mL) is added to the suspension and the latter is left to stand at RT for 20 min before filtration. The solid is washed with MTBE, then heptane, and dried to afford methyl 6-[1-cyano-2,2,2-trideuterio-1-(trideuteriomethyl)ethyl]pyrazolo[1,5-a]pyridine-3-carboxylate.

LCMS: MW (calcd): 249.3; m/z MW (obsd): 250.4 (M+H)

2.99.4. Step iv: 6-[1-cyano-2,2,2-trideuterio-1-(trideuteriomethyl)ethyl]pyrazolo[1,5-a]pyridine-3-carboxylic acid To a solution of methyl 6-[1-cyano-2,2,2-trideuterio-1-(trideuteriomethyl)ethyl]pyrazolo[1,5-a]pyridine-3-carboxylate (1.62 g, 6.50 mmol, 1.00 eq.) in THF (3 mL), MeOH (3 mL), and water (3 mL), is added lithium hydroxide monohydrate (CAS #1310-66-3; 0.85 g, 19 mmol, 3.0 eq.). The reaction mixture is stirred at 40° C. overnight. The reaction mixture is cooled to RT and acidified with HCl 2M solution till pH<4. The suspension is filtered and the cake is washed with water. The solid is dried to afford 6-[1-cyano-2,2,2-trideuterio-1-(trideuteriomethyl)ethyl]pyrazolo[1,5-a] pyridine-3-carboxylic acid.

LCMS: MW (calcd): 235.3; m/z MW (obsd): 236.1 (M+H)

2.99.5. Step v: 2-(3-bromopyrazolo[1,5-a]pyridin-6-yl)-3,3,3-trideuterio-2-(trideuteriomethyl)propanenitrile To a suspension of 6-[1-cyano-2,2,2-trideuterio-1-(trideuteriomethyl)ethyl]pyrazolo[1,5-a]pyridine-3-carboxylic acid (1.53 g, 6.50 mmol, 1.00 eq.) in DMF (5 mL) are added sodium bicarbonate (1.6 g, 19 mmol, 2.9 eq.) and N-bromosuccinimide (CAS #128-08-5; 1.16 g, 6.52 mmol, 1.00 eq.). The reaction mixture is stirred at RT. The reaction is stopped when the gas liberation ceases. Water (5 mL) is slowly added to the reaction mixture. The suspension is filtered and the cake washed with water. The solid is dried and reslurried in water/ACN 9/1 at RT for 20 min. The suspension is filtered and the cake washed with water. The solid is dried to afford 2-(3-bromopyrazolo[1,5-a]pyridin-6-yl)-3,3,3-trideuterio-2-(trideuteriomethyl)propanenitrile.

LCMS: MW (calcd): 270.2; m/z MW (obsd): 271.9 (M+H)

2.99.6. Step vi: Cpd 275

To a suspension of 2-(3-bromopyrazolo[1,5-a]pyridin-6-yl)-3,3,3-trideuterio-2-(trideuteriomethyl)propanenitrile (1.3 g, 4.8 mmol, 1.0 eq.) in a mixture of 1,4-dioxane (5.2 mL) and water (1.3 mL) are added sodium carbonate (1.6 g, 15 mmol, 3.1 eq.), $Pd_2dba_3$ (CAS #51364-51-3; 25 mg, 0.027 mmol, 0.0057 eq.), 2-dicyclohexylphosphino-2',6'-diisopropoxybiphenyl (CAS #787618-22-8; 60 mg, 0.12 mmol, 0.025 eq.), and Int 267 (1.67 g, 4.92 mmol, 1.0 eq.). The reaction mixture is refluxed for 1.5 h. The reaction mixture is partitioned between EtOAc and water. The biphasic solution is filtered on cellulose. The organic phase is washed with a 20% NaCl solution, dried on $Na_2SO_4$, filtered and concentrated. The residue is purified by flash chromatography on a Biotage® SNAP KP-NH column (eluting with heptane/EtOAc 100/0 to 30/70) to afford the desired compound.

2.10. Cpd 276

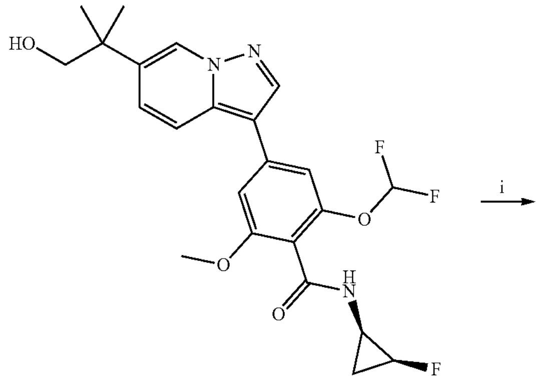

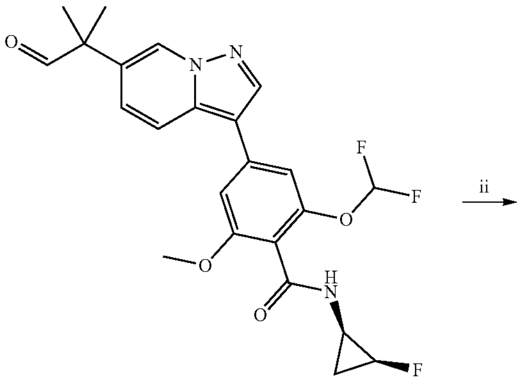

-continued

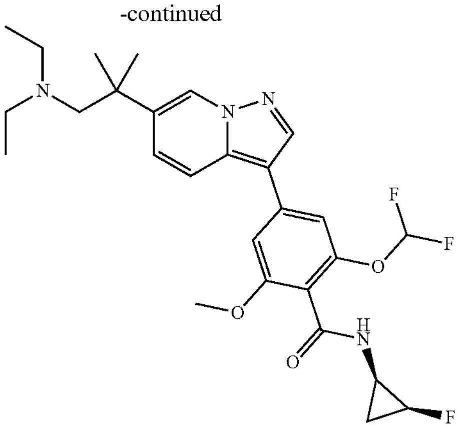

2.10.1. Step i: 2-(difluoromethoxy)-4-[6-(1,1-dimethyl-2-oxo-ethyl)pyrazolo[1,5-a]pyridin-3-yl]-N-[(1R,2S)-2-fluorocyclopropyl]-6-methoxy-benzamide To a solution of Cpd 242 (0.900 g, 1.9 mmol, 1 eq.) in dry DCM (10 mL) at 0° C. is added Dess-Martin periodinane (CAS #87413-09-0; 0.990 g, 2.3 mmol, 1.2 eq.). The reaction mixture is stirred at 0° C. for 1 h then quenched with a sat. $NaHCO_3$ solution and extracted with DCM twice. The combined organic layers are filtered through a phase separator and concentrated in vacuo. The residue is purified by flash chromatography on silica gel (eluting with DCM/MeOH 100/0 to 96/04) to afford the desired intermediate.

LCMS: MW (calcd): 461.4; m/z MW (obsd): 462.4 (M+H)

2.10.2. Step ii: Cpd 276

To a solution of 2-(difluoromethoxy)-4-[6-(1,1-dimethyl-2-oxo-ethyl)pyrazolo[1,5-a]pyridin-3-yl]-N-[(1R,2S)-2-fluorocyclopropyl]-6-methoxy-benzamide (75 mg, 0.16 mmol, 1 eq.) in 1,2-dichloroethane (1.0 mL) are added diethylamine (50 μL, 0.50 mmol, 3 eq.) and titanium isopropoxide (CAS #546-68-9; 96 μL, 0.32 mmol, 2.0 eq.). The resulting mixture is stirred at 65° C. for 18 h. $NaBH(OAc)_3$ (CAS #56553-60-7; 100 mg, 0.49 mmol, 3 eq.) is added. The reaction mixture is stirred at RT for 5 h, quenched with a sat. $NaHCO_3$ solution and extracted with EtOAc twice. The combined organic layers are washed with brine, filtered on a phase separator and concentrated in vacuo. The crude is purified by flash chromatography on a Biotage® SNAP KP-NH column (eluting with heptane/EtOAc 100/0 to 0/100) to afford the desired compound.

TABLE II

Intermediates used towards the compounds of the invention.

| Int# | Structure | Name | SM | Mtd | MW | MS Mes'd |
|---|---|---|---|---|---|---|
| 1 | 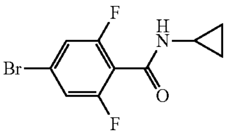 [SMILES: O=C(NC1CC1)c1c(F)cc(Br)cc1F] | 4-bromo-N-cyclopropyl-2,6-difluoro-benzamide | CAS# 183065-68-1 | Ex. 2.1 | 276.1 | 276.1 + 278.1 |

TABLE II-continued

Intermediates used towards the compounds of the invention.

| Int# | Structure | Name | SM | Mtd | MW | MS Mes'd |
|---|---|---|---|---|---|---|
| 2 | 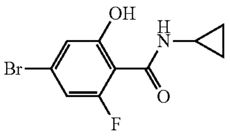 [SMILES: O=C(NC1CC1)c1c(O)cc(Br)cc1F] | 4-bromo-N-cyclopropyl-2-fluoro-6-hydroxy-benzamide | Int 1 | Ex. 2.2 | 274.1 | 273.8 + 275.8 |
| 3 | 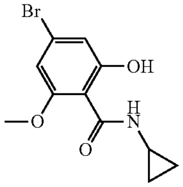 [SMILES: COc1cc(Br)cc(O)c1C(=O)NC1CC1] | 4-bromo-N-cyclopropyl-2-hydroxy-6-methoxy-benzamide | Int 2 | Q | 286.1 | 286.3 + 288.2 |
| 4 | 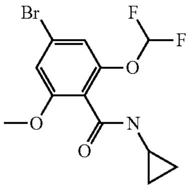 | 4-bromo-N-cyclopropyl-2-(difluoromethoxy)-6-methoxy-benzamide | Int 3 | R | 336.1 | 336.3 + 338.3 |
| 5 | 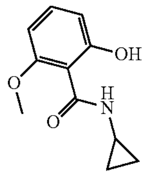 | N-cyclopropyl-2-hydroxy-6-methoxy-benzamide | CAS# 3147-64-6 + CAS# 765-30-0 | D1ii | 207.2 | 208.4 |
| 6 | 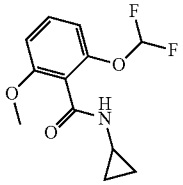 [SMILES: COc1cccc(OC(F)F)c1C(=O)NC1CC1] | N-cyclopropyl-2-(difluoromethoxy)-6-methoxy-benzamide | Int 5 | R | 257.2 | 258.4 |
| 7 | 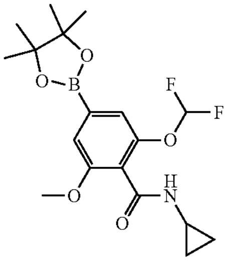 + 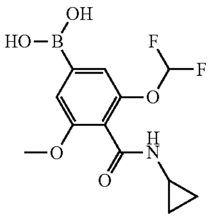 | N-cyclopropyl-2-(difluoromethoxy)-6-methoxy-4-(4,4,5,5-tetramethyl-1,3,2-dioxaborolan-2-yl)benzamide/4-(cyclopropylcarbamoyl)-3-(difluoromethoxy)-5-methoxyphenylboronic acid mixture | Int 6 | P2 | 383.2 + 301.1 | 384.4 + 302.2 |

TABLE II-continued

Intermediates used towards the compounds of the invention.

| Int# | Structure | Name | SM | Mtd | MW | MS Mes'd |
|---|---|---|---|---|---|---|
| 8 | 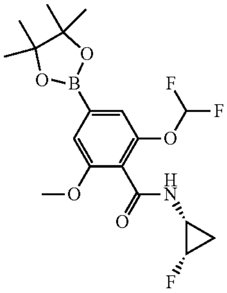 [SMILES: COc1cc(B2OC(C)(C)C(C)(C)O2)cc(OC(F)F)c1C(=O)N[C@@H]1C[C@@H]1F] | 2-(difluoromethoxy)-N-[(1R,2S)-2-fluorocyclopropyl]-6-methoxy-4-(4,4,5,5-tetramethyl-1,3,2-dioxaborolan-2-yl)benzamide | CAS# 3147-64-6 | Ex. 2.3 | 401.2 | 402.2 |
| 9 | 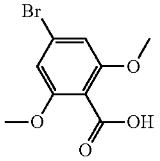 | 4-bromo-2,6-dimethoxy-benzoic acid | CAS# 81574-70-1 | D2i | 261.1 | 261. + 263.1 |
| 10 | 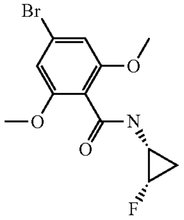 | 4-bromo-N-[(1R,2S)-2-fluorocyclopropyl]-2,6-dimethoxy-benzamide | Int 9 + CAS# 143062-84-4 | D1iii | 318.1 | 318.1 + 320.1 |
| 11 | 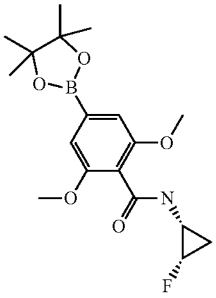 [SMILES: COc1cc(B2OC(C)(C)C(C)(C)O2)cc(OC)c1C(=O)N[C@@H]1C[C@@H]1F] | N-[(1R,2S)-2-fluorocyclopropyl]-2,6-dimethoxy-4-(4,4,5,5-tetramethyl-1,3,2-dioxaborolan-2-yl)benzamide | Int 10 | P1 | 365.2 | 366.4 |
| 12 | 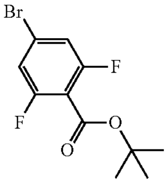 [SMILES: CC(C)(C)OC(=O)c1c(F)cc(Br)cc1F] | tert-butyl 4-bromo-2.6-difluoro-benzoate | CAS# 183065-68-1 | Ex. 2.4 | 293.1 | NA |
| 13 | 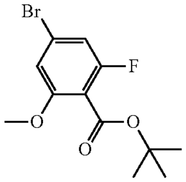 [SMILES: COc1cc(Br)cc(F)c1C(=O)OC(C)(C)C] | tert-butyl 4-bromo-2-fluoro-6-methoxy-benzoate | Int 12 | Q | 305.1 | 305.1 + 307.2 |

TABLE II-continued

Intermediates used towards the compounds of the invention.

| Int# | Structure | Name | SM | Mtd | MW | MS Mes'd |
|---|---|---|---|---|---|---|
| 14 | 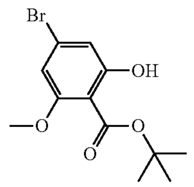 [SMILES: COc1cc(Br)cc(O)c1C(=O)OC(C)(C)C] | tert-butyl 4-bromo-2-hydroxy-6-methoxy-benzoate | Int 13 | Ex. 2.5 | 303.1 | 247.1 + 249.1 |
| 15 | 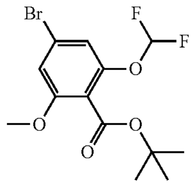 | tert-butyl 4-bromo-2-(difluoromethoxy)-6-methoxy-benzoate | Int 14 | R | 353.2 | 354.2 |
| 16 | 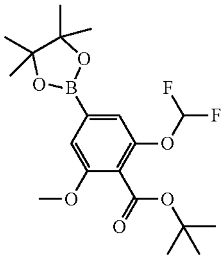 [SMILES: COc1cc(B2OC(C)(C)C(C)(C)O2)cc(OC(F)F)c1C(=O)OC(C)(C)C] | tert-butyl 2-(difluoromethoxy)-6-methoxy-4-(4,4,5,5-tetramethyl-1,3,2-dioxaborolan-2-yl)benzoate | Int 15 | P1 | 400.2 | 401.4 |
| 17 | 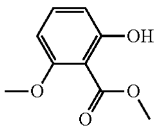 | methyl 2-hydroxy-6-methoxy-benzoate | CAS# 3147-64-6 | Ex. 2.6 | 182.2 | 183.2 |
| 18 | 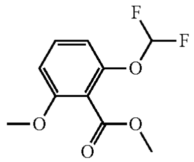 [SMILES: COC(=O)c1c(OC)cccc1OC(F)F] | methyl 2-(difluoromethoxy)-6-methoxy-benzoate | Int 17 | R | 232.2 | 233.5 |
| 19 | 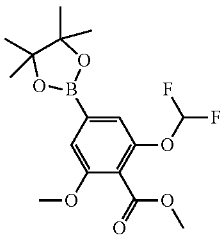 [SMILES: COC(=O)c1c(OC)cc(B2OC(C)(C)C(C)(C)O2)cc1OC(F)F] | methyl 2-(difluoromethoxy)-6-methoxy-4-(4,4,5,5-tetramethyl-1,3,2-dioxaborolan-2-yl)benzoate | Int 18 | P2 | 358.1 | 359.2 |
| 20 | 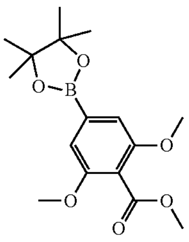 | methyl 2,6-dimethoxy-4-(4,4,5,5-tetramethyl-1,3,2-dioxaborolan-2-yl)benzoate | Int 21 | P1 | 322.1 | 323.3 |

TABLE II-continued

Intermediates used towards the compounds of the invention.

| Int# | Structure | Name | SM | Mtd | MW | MS Mes'd |
|---|---|---|---|---|---|---|
| 21 | 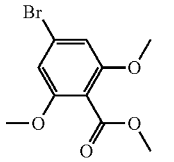 | methyl 4-bromo-2,6-dimethoxy-benzoate | CAS# 3956-34-1 | Ex. 2.7 | 275.1 | 275.1 + 277.1 |
| 22 | 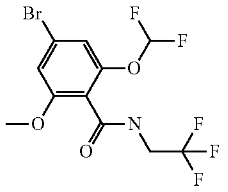 | 4-bromo-2-(difluoromethoxy)-6-methoxy-N-(2,2,2-trifluoroethyl)benzamide | Int 25 | R | 378.1 | 378.1 + 380.1 |
| 23 | 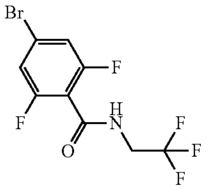 [SMILES: O=C(NCC(F)(F)F)c1c(F)cc(Br)cc1F] | 4-bromo-2,6-difluoro-N-(2,2,2-trifluoroethyl)benzamide | CAS# 183065-68-1 + CAS# 373-88-6 | Ex. 2.8 | 318.0 | 317.8 + 319.8 |
| 24 | 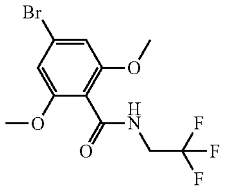 [SMILES: COc1cc(Br)cc(OC)c1C(=O)NCC(F)(F)F] | 4-bromo-2,6-dimethoxy-N-(2,2,2-trifluoroethyl)benzamide | Int 23 | Q | 342.1 | 343.8 |
| 25 | 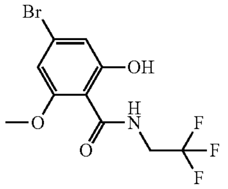 [SMILES: COc1cc(Br)cc(O)c1C(=O)NCC(F)(F)F] | 4-bromo-2-hydroxy-6-methoxy-N-(2,2,2-trifluoroethyl)benzamide | Int 24 | Ex. 2.9 | 328.1 | 328.1 + 330.1 |
| 26 | 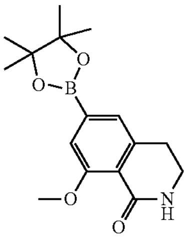 [SMILES: COc1cc(B2OC(C)(C)C(C)(C)O2)cc2c1C(=O)NCC2] | 8-methoxy-6-(4,4,5,5-tetramethyl-1,3,2-dioxaborolan-2-yl)-3,4-dihydro-2H-isoquinolin-1-one | Int 27 | P1 | 303.2 | 304.3 |
| 27 | 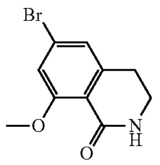 | 6-bromo-8-methoxy-3,4-dihydro-2H-isoquinolin-1-one | CAS# 1242157-15-8 | Q | 256.1 | 256. + 258.1 |

TABLE II-continued

| Int# | Structure | Name | SM | Mtd | MW | MS Mes'd |
|---|---|---|---|---|---|---|
| Intermediates used towards the compounds of the invention. | | | | | | |
| 28 | 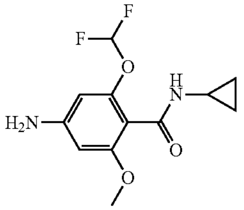 [SMILES: COc1cc(N)cc(OC(F)F)c1C(=O)NC1CC1] | 4-amino-N-cyclopropyl-2-(difluoromethoxy)-6-methoxy-benzamide | CAS# 3956-34-1 | Ex. 2.10 | 272.2 | 273.2 |
| 29 | 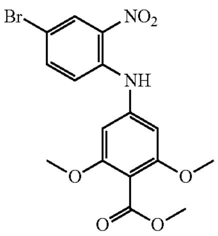 [SMILES: COC(=O)c1c(OC)cc(Nc2ccc(Br)cc2[N+](=O)[O-])cc1OC] | methyl 4-(4-bromo-2-nitro-anilino)-2,6-dimethoxy-benzoate | CAS# 3956-34-1 + CAS# 364-73-8 | F1 | 411.2 | 411.1 + 413.0 |
| 30 | 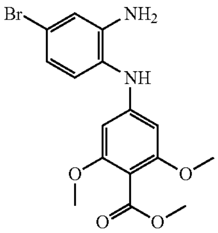 [SMILES: COC(=O)c1c(OC)cc(Nc2ccc(Br)cc2N)cc1OC] | methyl 4-(4-bromo-2-amino-anilino)-2,6-dimethoxy-benzoate | Int 29 | G1 | 380.0 | NA |
| 31 | 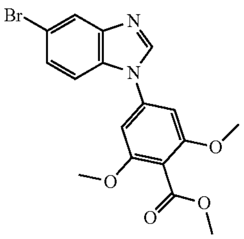 [SMILES: COC(=O)c1c(OC)cc(-n2cnc3cc(Br)ccc32)cc1OC] | methyl 4-(5-bromobenzimidazol-1-yl)-2,6-dimethoxy-benzoate | Int 30 | H | 391.2 | 391.1 + 393.1 |
| 32 | 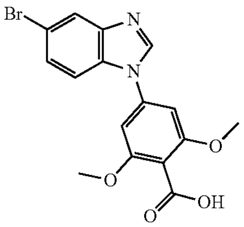 [SMILES: COc1cc(-n2cnc3cc(Br)ccc32)cc(OC)c1C(=O)O] | 4-(5-bromobenzimidazol-1-yl)-2,6-dimethoxy-benzoic acid | Int 31 | D2i | 377.2 | 378.3 |
| 33 | 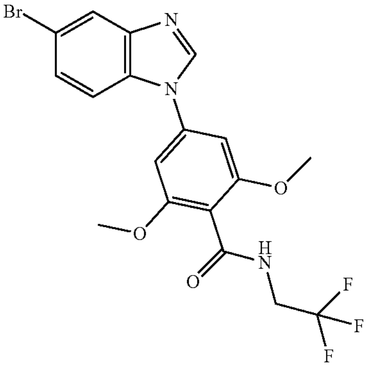 [SMILES: COc1cc(-n2cnc3cc(Br)ccc32)cc(OC)c1C(=O)NCC(F)(F)F] | 4-(5-bromobenzimidazol-1-yl)-2,6-dimethoxy-N-(2,2,2-trifluoroethyl)benzamide | Int 32 + CAS# 373-88-6 | D1ii | 458.2 | 458.3 + 460.2 |

TABLE II-continued

Intermediates used towards the compounds of the invention.

| Int# | Structure | Name | SM | Mtd | MW | MS Mes'd |
|---|---|---|---|---|---|---|
| 34 | 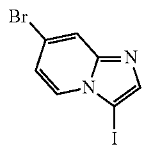 [SMILES: Brc1ccn2c(I)cnc2c1] | 7-bromo-3-iodo-imidazo[1,2-a]pyridine | CAS# 808744-34-5 | B | 322.9 | NA |
| 35 | 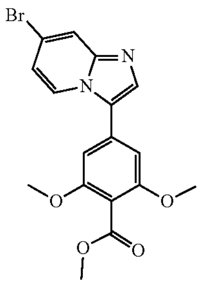 [SMILES: COC(=O)c1c(OC)cc(-c2cnc3cc(Br)ccn23)cc1OC] | methyl 4-(7-bromoimidazo[1,2-a]pyridin-3-yl)-2,6-dimethoxy-benzoate | Int 34 + Int 20 | C | 391.2 | 391.2 + 393.3 |
| 36 | 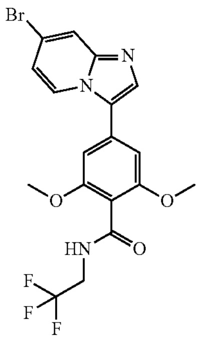 [SMILES: COc1cc(-c2cnc3cc(Br)ccn23)cc(OC)c1C(=O)NCC(F)(F)F] | 4-(7-bromoimidazo[1,2-a]pyridin-3-yl)-2,6-dimethoxy-N-(2,2,2-trifluoroethyl)benzamide | Int 35 + CAS# 753-90-2 | D2 | 458.2 | 458.4 + 460.3 |
| 37 | 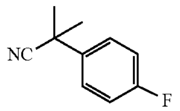 | 2-(4-fluorophenyl)-2-methyl-propanenitrile | CAS# 459-22-3 | Ex. 2.11 | 163.2 | NA |
| 38 | 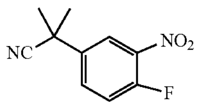 | 2-(4-fluoro-3-nitro-phenyl)-2-methyl-propanenitrile | Int 37 | S | 208.2 | NA |
| 39 | 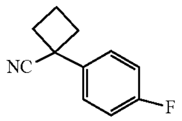 [SMILES: N#CC1(c2ccc(F)cc2)CCC1] | 1-(4-fluorophenyl) cyclobutanecarbonitrile | CAS# 459-22-3 | Ex. 2.12 | 175.2 | NA |
| 40 | 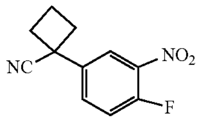 [SMILES: N#CC1(c2ccc(F)c([N+](=O)[O-])c2)CCC1] | 1-(4-fluoro-3-nitro-phenyl) cyclobutanecarbonitrile | Int 39 | S | 220.2 | NA |

TABLE II-continued

| Int# | Structure | Name | SM | Mtd | MW | MS Mes'd |
|---|---|---|---|---|---|---|
| | Intermediates used towards the compounds of the invention. | | | | | |
| 41 | 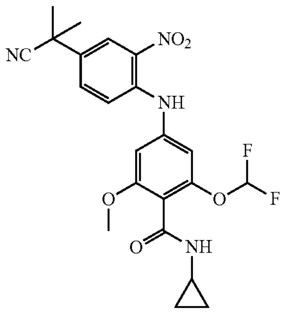 | 4-[4-(1-cyano-1-methyl-ethyl)-2-nitro-anilino]-N-cyclopropyl-2-(difluoromethoxy)-6-methoxy-benzamide | Int 38 + Int 28 | F2 | 460.4 | 461.3 |
| 42 | 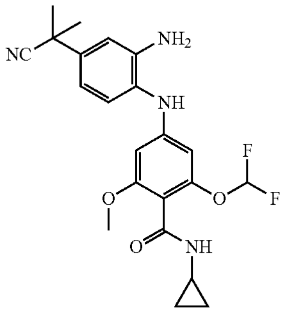 [SMILES: COc1cc(Nc2ccc(C(C)(C)C#N)cc2[N+](=O)[O-])cc(OC(F)F)c1C(=O)NC1CC1] | 4-[2-amino-4-(1-cyano-1-methyl-ethyl)anilino]-N-cyclopropyl-2-(difluoromethoxy)-6-methoxy-benzamide | Int 41 | G2 | 430.5 | 431.4 |
| 43 | 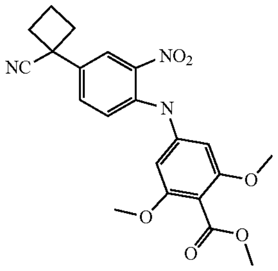 | methyl 4-[4-(1-cyanocyclobutyl)-2-nitro-anilino]-2,6-dimethoxy-benzoate | Int 40 + CAS# 3956-34-1 | F2 | 411.4 | 412.3 |
| 44 | 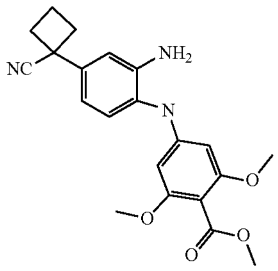 | methyl 4-[2-amino-4-(1-cyanocyclobutyl)anilino]-2,6-dimethoxy-benzoate | Int 43 | G2 | 381.4 | 382.4 |
| 45 | 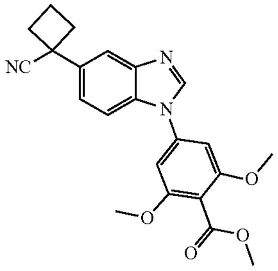 [SMILES: COC(=O)c1c(OC)cc(-n2cnc3cc(C4(C#N)CCC4)ccc32)cc1OC] | methyl 4-[5-(1-cyanocyclobutyl)benzimidazol-1-yl]-2,6-dimethoxy-benzoate | Int 44 | H | 394.4 | NA |

TABLE II-continued

| Int# | Structure | Name | SM | Mtd | MW | MS Mes'd |
|---|---|---|---|---|---|---|
| | Intermediates used towards the compounds of the invention. | | | | | |
| 46 | 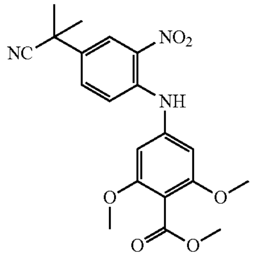 [SMILES: COC(=O)c1c(OC)cc(Nc2ccc(C(C)(C)C#N)cc2[N+](=O)[O-])cc1OC] | methyl 4-[4-(1-cyano-1-methyl-ethyl)-2-nitro-anilino]-2,6-dimethoxy-benzoate | Int 38 + CAS# 3956-34-1 | F2 | 399.4 | 400.3 |
| 47 | 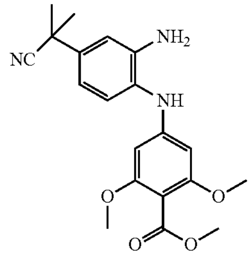 [SMILES: COC(=O)c1c(OC)cc(Nc2ccc(C(C)(C)C#N)cc2N)cc1OC] | methyl 4-[2-amino-4-(1-cyano-1-methyl-ethyl)anilino]-2,6-dimethoxy-benzoate | Int 46 | G2 | 369.4 | 370.4 |
| 48 | 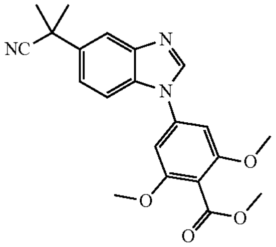 [SMILES: COC(=O)c1c(OC)cc(-n2cnc3cc(C(C)(C)C#N)ccc32)cc1OC] | methyl 4-[5-(1-cyano-1-methyl-ethyl)benzimidazol-1-yl]-2,6-dimethoxy-benzoate | Int 47 | H | 379.4 | 380.4 |
| 49 | 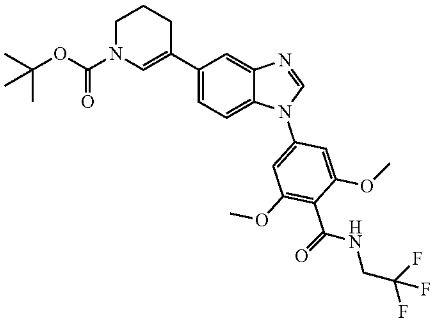 [SMILES: COc1cc(-n2cnc3cc(C4=CN(C(=O)OC(C)(C)C)CCC4)ccc32)cc(OC)c1C(=O)NCC(F)(F)F] | tert-butyl 5-[1-[3,5-dimethoxy-4-(2,2,2-trifluoroethylcarbamoyl)phenyl]benzimidazol-5-yl]-3,4-dihydro-2H-pyridine-1-carboxylate | Int 33 + CAS# 885693-20-9 | C | 560.7 | 561.7 |
| 50 | 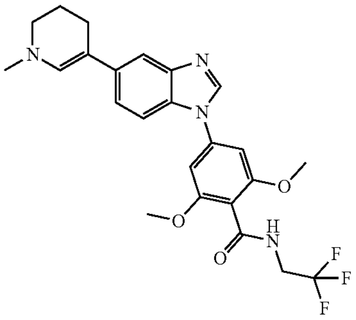 [SMILES: COc1cc(-n2cnc3cc(C4=CN(C)CCC4)ccc32)cc(OC)c1C(=O)NCC(F)(F)F] | 2,6-dimethoxy-4-[5-(1-methyl-3,4-dihydro-2H-pyridin-5-yl)benzimidazol-1-yl]-N-(2,2,2-trifluoroethyl)benzamide | Int 33 + CAS# 1254982-25-6 | C | 474.5 | 475.6 |

TABLE II-continued

| Int# | Structure | Name | SM | Mtd | MW | MS Mes'd |
|---|---|---|---|---|---|---|
| Intermediates used towards the compounds of the invention. | | | | | | |
| 51 | 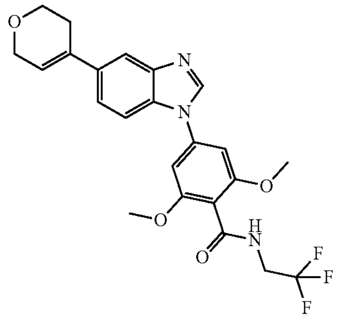 [SMILES: COc1cc(-n2cnc3cc(C4=CCOCC4)ccc32)cc(OC)c1C(=O)NCC(F)(F)F] | 4-[5-(3,6-dihydro-2H-pyran-4-yl)benzimidazol-1-yl]-2,6-dimethoxy-N-(2,2,2-trifluoroethyl) benzamide | Int 33 + CAS# 287944-16-5 | C | 461.4 | 462.5 |
| 52 | 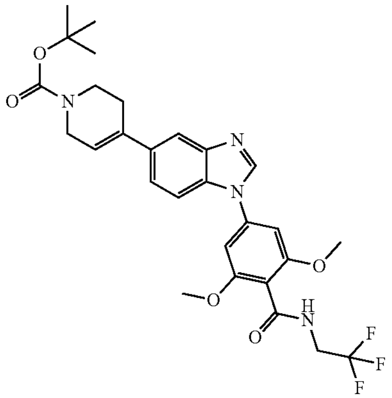 [SMILES: COc1cc(-n2cnc3cc(C4=CCN(C(=O)OC(C)(C)C)CC4)ccc32)cc(OC)c1C(=O)NCC(F)(F)F] | tert-butyl 4-[1-[3,5-dimethoxy-4-(2,2,2-trifluoroethylcarbamoyl) phenyl]benzimidazol-5-yl]-3,6-dihydro-2H-pyridine-1-carboxylate | Int 33 + CAS# 286961-14-6 | C | 560.7 | 561.7 |
| 53 | 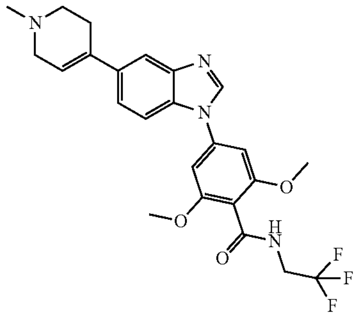 [SMILES: COc1cc(-n2cnc3cc(C4=CCN(C)CC4)ccc32)cc(OC)c1C(=O)NCC(F)(F)F] | 2,6-dimethoxy-4-[5-(1-methyl-3,6-dihydro-2H-pyridin-4-yl)benzimidazol-1-yl]-N-(2,2,2-trifluoroethyl)benzamide | Int 33 + CAS# 454482-11-2 | C | 474.4 | 475.4 |
| 54 | 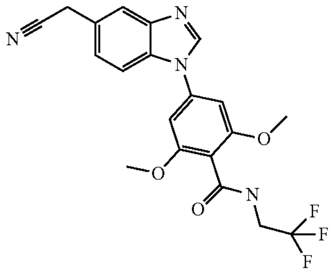 | 4-[5-(cyanomethyl) benzimidazol-1-yl]-2,6-dimethoxy-N-(2,2,2-trifluoroethyl)benzamide | Int 33 | A8 | 418.4 | 419.3 |

TABLE II-continued

Intermediates used towards the compounds of the invention.

| Int# | Structure | Name | SM | Mtd | MW | MS Mes'd |
|---|---|---|---|---|---|---|
| 55 | 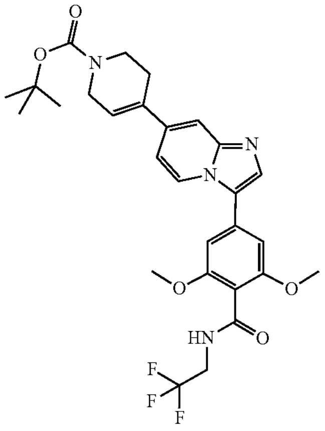 [SMILES: COc1cc(-c2cnc3cc(C4=CCN(C(=O)OC(C)(C)C)CC4)ccn23)cc(OC)c1C(=O)NCC(F)(F)F] | tert-butyl 4-[3-[3,5-dimethoxy-4-(2,2,2-trifluoroethylcarbamoyl) phenyl]imidazo[1,2-a] pyridin-7-yl]-3,6-dihydro-2H-pyridine-1-carboxylate | Int 36 + CAS# 286961-14-6 | C | 560.5 | 561.9 |
| 56 | 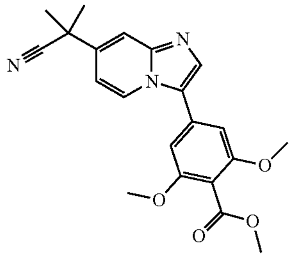 [SMILES: COC(=O)c1c(OC)cc(-c2cnc3cc(C(C)(C)C#N)ccn23)cc1OC] | methyl 4-[7-(1-cyano-1-methyl-ethyl)imidazo[1,2-a]pyridin-3-yl]-2,6-dimethoxy-benzoate | Int 57 + Int 20 | C | 379.4 | 380.3 |
| 57 | 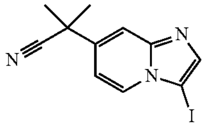 | 2-(3-iodoimidazo[1,2-a]pyridin-7-yl)-2-methyl-propanenitrile | Int 58 | B | 311.3 | 312.1 |
| 58 | 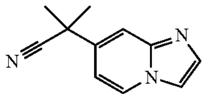 | 2-imidazo[1,2-a]pyridin-7-yl-2-methyl-propanenitrile | Int 62 | Ex. 2.13 | 185.2 | 186.6 |
| 59 | 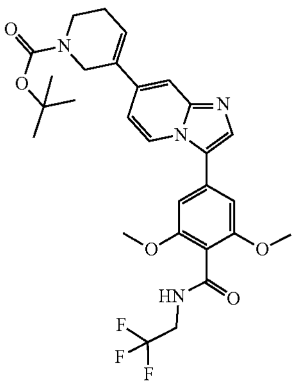 [SMILES: COc1cc(-c2cnc3cc(C4=CCCN(C(=O)OC(C)(C)C)C4)ccn23)cc(OC)c1C(=O)NCC(F)(F)F] | tert-butyl 5-[3-[3,5-dimethoxy-4-(2,2,2-trifluoroethylcarbamoyl) phenyl]imidazo[1,2-a] pyridin-7-yl]-3,6-dihydro-2H-pyridine-1-carboxylate | Int 36 + CAS# 885693-20-9 | C | 560.6 | 562.0 |

TABLE II-continued

Intermediates used towards the compounds of the invention.

| Int# | Structure | Name | SM | Mtd | MW | MS Mes'd |
|---|---|---|---|---|---|---|
| 60 | 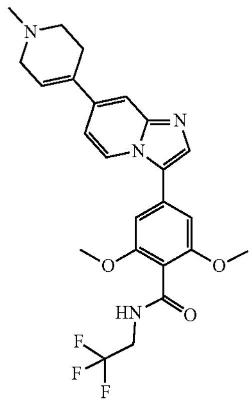 | 2,6-dimethoxy-4-[7-(1-methyl-3,6-dihydro-2H-pyridin-4-yl)imidazo[1,2-a]pyridin-3-yl]-N-(2,2,2-trifluoroethyl) benzamide | Int 61 | K1 | 474.5 | 475.6 |
| 61 | 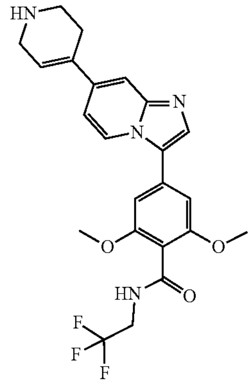 [SMILES: COc1cc(-c2cnc3cc(C4=CCNCC4)ccn23)cc(OC)c1C(=O)NCC(F)(F)F] | 2,6-dimethoxy-4-[7-(1,2,3,6-tetrahydropyridin-4-yl)imidazo[1,2-a]pyridin-3-yl]-N-(2,2,2-trifluoroethyl)benzamide | Int 55 | M1 | 460.4 | 461.6 |
| 62 | 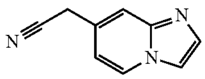 [SMILES: N#CCc1ccn2ccnc2c1] | 2-imidazo[1,2-a]pyridin-7-ylacetonitrile | CAS# 808744-34-5 | A8 | 157.1 | 158.1 |
| 63 | 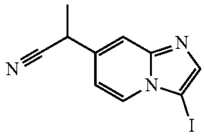 | 2-(3-ioimidazo[1,2-a]pyridin-7-yl)propanenitrile | Int 64 | B | 297.1 | 298.3 |
| 64 | 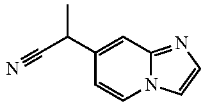 | 2-imidazo[1,2-a]pyridin-7-ylpropanenitrile | Int 62 | Ex. 2.14 | 171.2 | 172.3 |
| 65 | 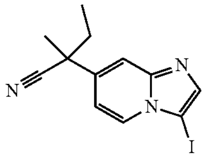 [SMILES: CCC(C)(C#N)c1ccn2c(I)cnc2c1] | 2-(3-iodoimidazo[1,2-a]pyridin-7-yl)-2-methyl-butanenitrile | Int 63 | Ex. 2.15 | 325.1 | 326.3 |

TABLE II-continued

Intermediates used towards the compounds of the invention.

| Int# | Structure | Name | SM | Mtd | MW | MS Mes'd |
|---|---|---|---|---|---|---|
| 66 | 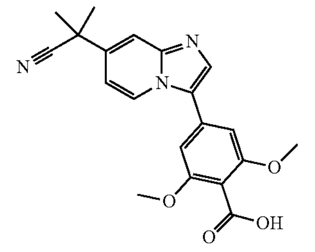<br>+<br>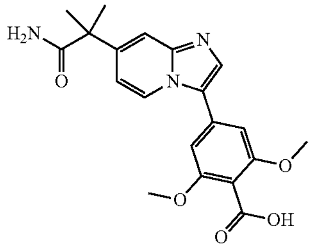 | 4-[7-(1-cyano-1-methyl-ethyl)imidazo[1,2-a]pyridin-3-yl]-2,6-dimethoxy-benzoic acid/4-[7-(2-amino-1,1-dimethyl-2-oxo-ethyl)imidazo[1,2-a]pyridin-3-yl]-2,6-dimethoxy-benzoic acid mixture | Int 56 | Ex. 2.16 | 365.4 + 383.4 | 366.5 + 384.5 |
| 67 | 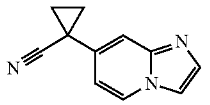 [SMILES: N#CC1(c2ccn3ccnc3c2)CC1] | 1-imidazo[1,2-a]pyridin-7-yl-cyclopropanecarbonitrile | Int 62 | Ex. 2.17 | 183.2 | 184.2 |
| 68 | 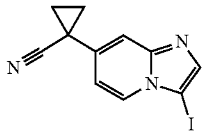 [SMILES: N#CC1(c2ccn3c(I)cnc3c2)CC1] | 1-(3-iodoimidazo[1,2-a]pyridin-7-yl) cyclopropanecarbonitrile | Int 67 | B | 309.1 | 310.3 |
| 69 | 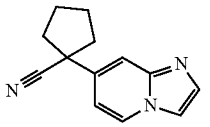 [SMILES: N#CC1(c2ccn3ccnc3c2)CCCC1] | 1-imidazo[1,2-a]pyridin-7-yl-cyclopentanecarbonitrile | Int 62 | Ex 2.18 | 211.3 | 212.6 |
| 70 | 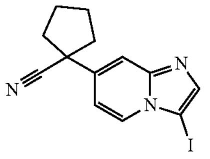 [SMILES: N#CC1(c2ccn3c(I)cnc3c2)CCCC1] | 1-(3-iodoimidazo[1,2-a]pyridin-7-yl) cyclopentanecarbonitrile | Int 69 | B | 337.2 | 338.5 |
| 71 | 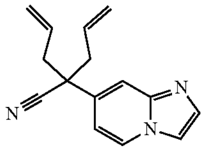 [SMILES: C=CCC(C#N)(CC=C)c1ccn2ccnc2c1] | 2-allyl-2-imidazo[1,2-a]pyridin-7-yl-pent-4-enenitrile | Int 62 | Ex. 2.19 | 237.3 | 238.2 |
| 72 | 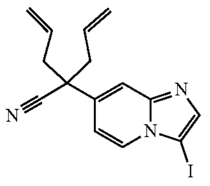 [SMILES: C=CCC(C#N)(CC=C)c1ccn2c(I)cnc2c1] | 2-allyl-2-(3-iodoimidazo[1,2-a]pyridin-7-yl)pent-4-enenitrile | Int 71 | B | 363.2 | 364.2 |

TABLE II-continued

Intermediates used towards the compounds of the invention.

| Int# | Structure | Name | SM | Mtd | MW | MS Mes'd |
|---|---|---|---|---|---|---|
| 73 | 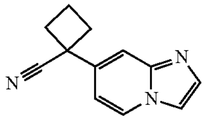 [SMILES: N#CC1(c2ccn3ccnc3c2)CCC1] | 1-imidazo[1,2-a]pyridin-7-yl-cyclobutanecarbonitrile | Int 62 | Ex. 2.19 | 197.2 | 198.1 |
| 74 | 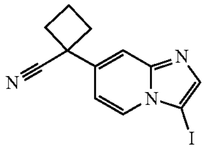 [SMILES: N#CC1(c2ccn3c(I)cnc3c2)CCC1] | 1-(3-iodoimidazo[1,2-a]pyridin-7-yl) cyclobutanecarbonitrile | Int 73 | B | 323.1 | 324.0 |
| 75 | 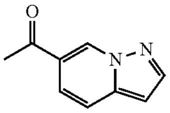 | 1-pyrazolo[1,5-a]pyridin-6-ylethanone | CAS# 1264193-11-4 | Ex. 2.20 | 160.2 | 160.9 |
| 76 | 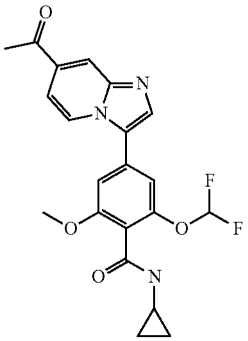 | 4-(7-acetylimidazo[1,2-a]pyridin-3-yl)-N-cyclopropyl-2-(difluoromethoxy)-6-methoxy-benzamide | Int 4 + CAS# 1036991-50-0 | E | 415.4 | 416.3 |
| 77 | 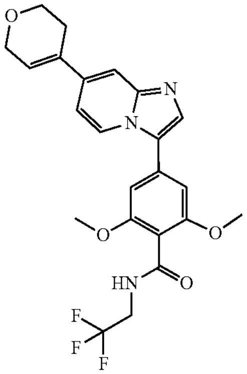 [SMILES: COc1cc(-c2cnc3cc(C4=CCOCC4)ccn23)cc(OC)c1C(=O)NCC(F)(F)F] | 4-[7-(3,6-dihydro-2H-pyran-4-yl)imidazo[1,2-a]pyridin-3-yl]-2,6-dimethoxy-N-(2,2,2-trifluoroethyl)benzamide | Int 36 + CAS# 287944-16-5 | C | 461.4 | 462.8 |
| 78 | 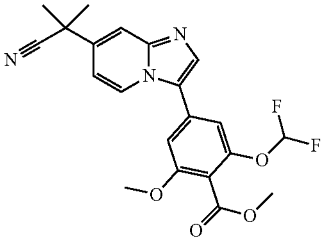 [SMILES: COC(=O)c1c(OC)cc(-c2cnc3cc(C(C)(C)C#N)ccn23)cc1OC(F)F] | methyl 4-[7-(1-cyano-1-methyl-ethyl)imidazo[1,2-a]pyridin-3-yl]-2-(difluoromethoxy)-6-methoxy-benzoate | Int 57 + Int 19 | C | 415.4 | 416.7 |
| 79 | 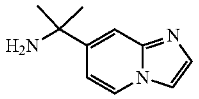 | 2-imidazo[1,2-a]pyridin-7-ylpropan-2-amine | Int 58 | V | 175.2 | 176.1 |

TABLE II-continued

Intermediates used towards the compounds of the invention.

| Int# | Structure | Name | SM | Mtd | MW | MS Mes'd |
|---|---|---|---|---|---|---|
| 80 | 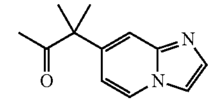 + 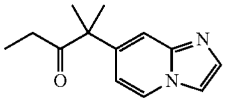 + 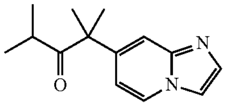 | 3-imidazo[1,2-a]pyridin-7-yl-3-methyl-butan-2-one/ 2-imidazo[1,2-a]pyridin-7-yl-2-methyl-pentan-3-one/ 2-imidazo[1,2-a]pyridin-7-yl-2,4-dimethyl-pentan-3-one mixture | CAS# 808744-34-5 | Ex. 2.21 | 202.3 | 203.2 |
| 81 | 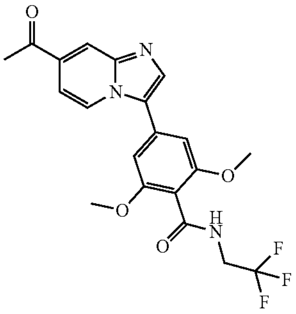 [SMILES: COc1cc(-c2cnc3cc(C(C)=O)ccn23)cc(OC)c1C(=O)NCC(F)(F)F] | 4-(7-acetylimidazo[1,2-a]pyridin-3-yl)-2,6-dimethoxy-N-(2,2,2-trifluoroethyl)benzamide | Int 36 + CAS# 111-34-2 | Ex. 2.22 | 421.4 | 422.6 |
| 82 | 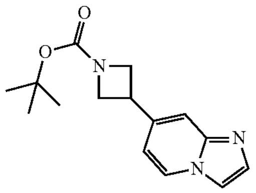 [SMILES: CC(C)(C)OC(=O)N1CC(c2ccn3ccnc3c2)C1] | tert-butyl3-imidazo[1,2-a]pyridin-7-ylazetidine-1-carboxylate | CAS# 808744-34-5 + Int 83 | A4 | 273.3 | 274.2 |
| 83 | 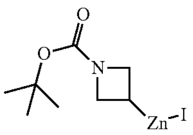 | (1-tert-butoxycarbonylazetidin-3-yl)-iodo-zinc | CAS# 254454-54-1 | Ex. 2.23 | NA | NA |
| 84 | 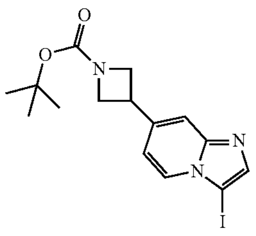 [SMILES: CC(C)(C)OC(=O)N1CC(c2ccn3c(I)cnc3c2)C1] | tert-butyl 3-(3-iodoimidazo[1,2-a]pyridin-7-yl)azetidine-1-carboxylate | Int 82 | B | 399.2 | 400.1 |

TABLE II-continued

Intermediates used towards the compounds of the invention.

| Int# | Structure | Name | SM | Mtd | MW | MS Mes'd |
|---|---|---|---|---|---|---|
| 85 | 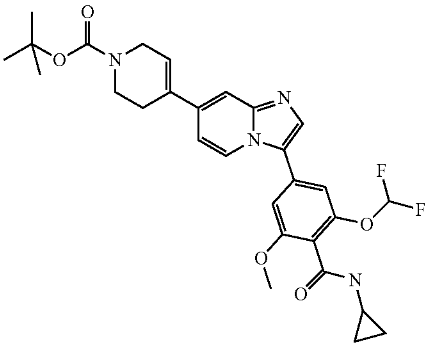 | tert-butyl 4-[3-[4-(cyclopropylcarbamoyl)-3-(difluoromethoxy)-5-methoxy-phenyl]imidazo[1,2-a]pyridin-7-yl]-3,6-dihydro-2H-pyridine-1-carboxylate | Int 86 + CAS# 286961-14-6 | C | 554.6 | 555.3 |
| 86 | 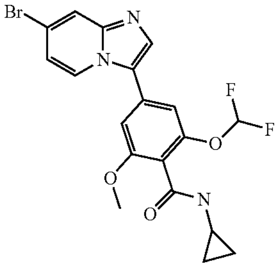 | 4-(7-bromoimidazo[1,2-a]pyridin-3-yl)-N-cyclopropyl-2-(difluoromethoxy)-6-methoxy-benzamide | Int 7 + Int 34 | C | 452.2 | 452.1 + 454.1 |
| 87 | 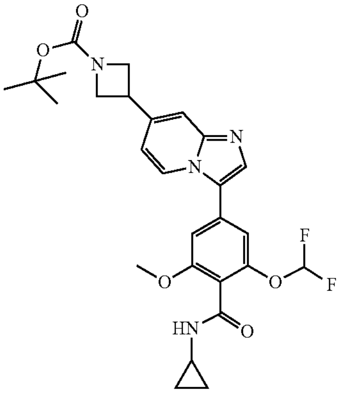 [SMILES: COc1cc(-c2cnc3cc(C4CN(C(=O)OC(C)(C)C)C4)ccn23)cc(OC(F)F)c1C(=O)NC1CC1] | tert-butyl 3-[3-[4-(cyclopropylcarbamoyl)-3-(difluoromethoxy)-5-methoxy-phenyl]imidazo[1,2-a]pyridin-7-yl]azetidine-1-carboxylate | Int 84 + Int 7 | C | 528.5 | 530.4 |
| 88 | 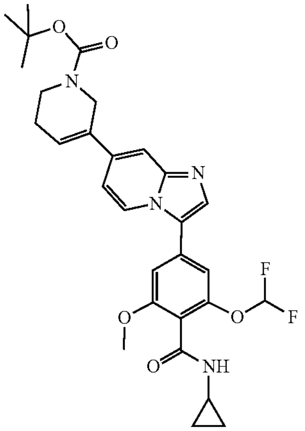 [SMILES: COc1cc(-c2cnc3cc(C4=CCCN(C(=O)OC(C)(C)C)C4)ccn23)cc(OC(F)F)c1C(=O)NC1CC1] | tert-butyl 5-[3-[4-(cyclopropylcarbamoyl)-3-(difluoromethoxy)-5-methoxy-phenyl]imidazo[1,2-a]pyridin-7-yl]-3,6-dihydro-2H-pyridine-1-carboxylate | Int 86 + CAS# 885693-20-9 | C | 554.6 | 555.3 |

TABLE II-continued

| Intermediates used towards the compounds of the invention. | | | | | | |
|---|---|---|---|---|---|---|
| Int# | Structure | Name | SM | Mtd | MW | MS Mes'd |
| 89 | 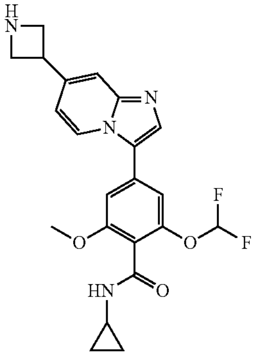 [SMILES: COc1cc(-c2cnc3cc(C4CNC4)ccn23)cc(OC(F)F)c1C(=O)NC1CC1] | 4-[7-(azetidin-3-yl)imidazo[1,2-a]pyridin-3-yl]-N-cyclopropyl-2-(difluoromethoxy)-6-methoxy-benzamide | Int 87 | M2 | 428.4 | 429.1 |
| 90 | 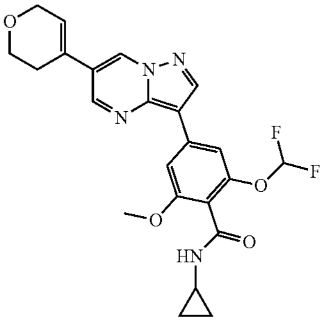 [SMILES: COc1cc(-c2cnn3cc(C4=CCOCC4)cnc23)cc(OC(F)F)c1C(=O)NC1CC1] | N-cyclopropyl-2-(difluoromethoxy)-4-[6-(3,6-dihydro-2H-pyran-4-yl)pyrazolo[1,5-a]pyrimidin-3-yl]-6-methoxy-benzamide | Int 91 + CAS# 287944-16-5 | C | 456.4 | 457.2 |
| 91 | 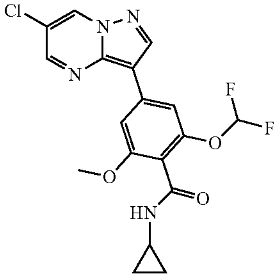 [SMILES: COc1cc(-c2cnn3cc(Cl)cnc23)cc(OC(F)F)c1C(=O)NC1CC1] | 4-(6-chloropyrazolo[1,5-a]pyrimidin-3-yl)-N-cyclopropyl-2-(difluoromethoxy)-6-methoxy-benzamide | CAS# 1314893-92-9 + Int 7 | C | 408.8 | 409.2 |
| 92 | 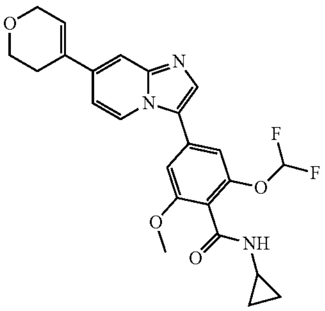 [SMILES: COc1cc(-c2cnc3cc(C4=CCOCC4)ccn23)cc(OC(F)F)c1C(=O)NC1CC1] | N-cyclopropyl-2-(difluoromethoxy)-4-[7-(3,6-dihydro-2H-pyran-4-yl)imidazo[1,2-a]pyridin-3-yl]-6-methoxy-benzamide | Int 86 + CAS# 287944-16-5 | C | 455.5 | 456.3 |
| 93 | 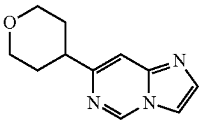 [SMILES: c1cn2cnc(C3CCOCC3)cc2n1] | 7-tetrahydropyran-4-ylimidazo[1,2-c]pyrimidine | Int 94 | L | 203.2 | NA |

TABLE II-continued

| Intermediates used towards the compounds of the invention. | | | | | | |
|---|---|---|---|---|---|---|
| Int# | Structure | Name | SM | Mtd | MW | MS Mes'd |
| 94 | 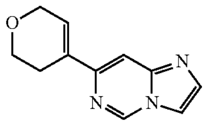 [SMILES: C1=C(c2cc3nccn3cn2)CCOC1] | 7-(3,6-dihydro-2H-pyran-4-yl)imidazo[1,2-c]pyrimidine | CAS# 1414959-21-9 + CAS# 287944-16-5 | C | 201.2 | 202.2 |
| 95 | 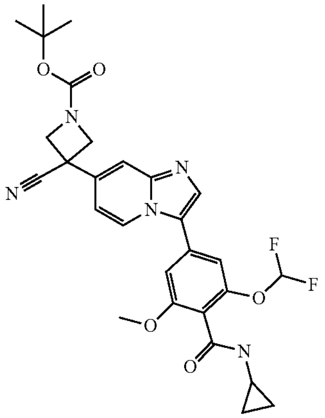 | tert-butyl 3-cyano-3-[3-[4-(cyclopropylcarbamoyl)-3-(difluoromethoxy)-5-methoxy-phenyl]imidazo[1,2-a]pyridin-7-yl]azetidine-1-carboxylate | Int 96 + Int 4 | E | 553.6 | 554.3 |
| 96 | 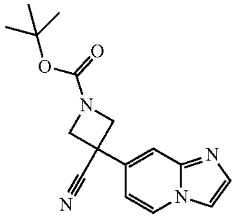 [SMILES: CC(C)(C)OC(=O)N1CC(C#N)(c2ccn3ccnc3c2)C1] | tert-butyl 3-cyano-3-imidazo[1,2-a]pyridin-7-yl-azetidine-1-carboxylate | CAS# 808744-34-5 + CAS# 142253-54-1 | A1 | 298.3 | 299.3 |
| 97 | 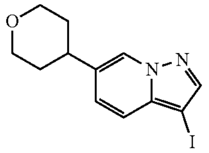 [SMILES: Ic1cnn2cc(C3CCOCC3)ccc12] | 3-iodo-6-tetrahydropyran-4-yl-pyrazolo[1,5-a]pyridine | Int 98 | B | 328.1 | 32.9 |
| 98 | 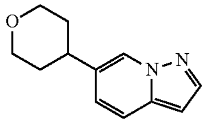 [SMILES: c1cc2ccc(C3CCOCC3)cn2n1] | 6-tetrahydropyran-4-ylpyrazolo[1,5-a]pyridine | Int 99 | L | 202.2 | 203.2 |
| 99 | 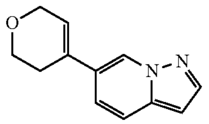 [SMILES: C1=C(c2ccc3ccnn3c2)CCOC1] | 6-(3,6-dihydro-2H-pyran-4-yl)pyrazolo[1,5-a]pyridine | CAS# 1264193-11-4 + CAS# 287944-16-5 | C | 200.2 | 201.2 |
| 100 | 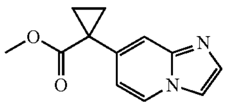 [SMILES: COC(=O)C1(c2ccn3ccnc3c2)CC1] | methyl 1-imidazo[1,2-a]pyridin-7-yl-cyclopropanecarboxylate | CAS# 808744-34-5 | Ex. 2.24 | 216.2 | 217.0 |
| 101 | 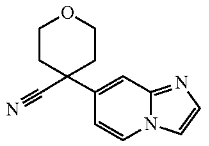 [SMILES: N#CC1(c2ccn3ccnc3c2)CCOCC1] | 4-imidazo[1,2-a]pyridin-7-yltetrahydropyran-4-carbonitrile | CAS# 1260903-17-0 + CAS# 4295-99-2 | A1 | 227.3 | 228.2 |

TABLE II-continued

Intermediates used towards the compounds of the invention.

| Int# | Structure | Name | SM | Mtd | MW | MS Mes'd |
|---|---|---|---|---|---|---|
| 102 | 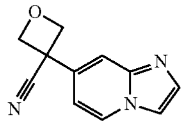 | 3-imidazo[1,2-a]pyridin-7-yloxetane-3-carbonitrile | CAS# 1260903-17-0 + CAS# 1420800-16-3 | A1 | 199.2 | 200.1 |
| 103 | 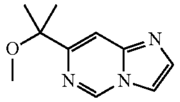 | 7-(1-methoxy-1-methyl-ethyl)imidazo[1,2-c]pyrimidine | Int 104 | I1 | 191.1 | 192.3 |
| 104 | 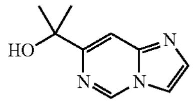 | 2-imidazo[1,2-c]pyrimidin-7-ylpropan-2-ol | CAS# 58720-90-5 + CAS# 75-16-1 | N2 | 177.1 | 178.2 |
| 105 | 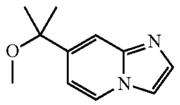 | 7-(1-methoxy-1-methyl-ethyl)imidazo[1,2-a]pyridine | Int 106 | I1 | 190.1 | 191.3 |
| 106 | 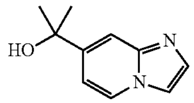 | 2-imidazo[1,2-a]pyridin-7-ylpropan-2-ol | CAS# 1036991-50-0 | N2 | 176.1 | 177.2 |
| 107 | 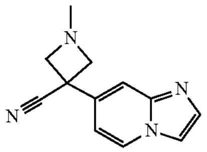 [SMILES: CN1CC(C#N)(c2ccn3ccnc3c2)C1] | 3-imidazo[1,2-a]pyridin-7-yl-1-methyl-azetidine-3-carbonitrile | CAS# 1314900-97-4 | A1 | 212.2 | 213.3 |
| 108 | 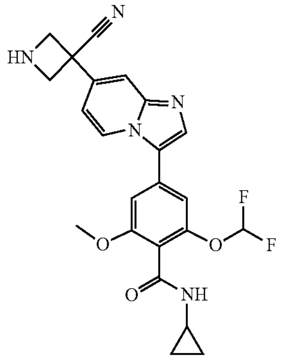 [SMILES: COc1cc(-c2cnc3cc(C4(C#N)CNC4)ccn23)cc(OC(F)F)c1C(=O)NC1CC1] | 4-[7-(3-cyanoazetidin-3-yl)imidazo[1,2-a]pyridin-3-yl]-N-cyclopropyl-2-(difluoromethoxy)-6-methoxy-benzamide | Int 95 | M1 | 453.4 | 454.4 |
| 109 | 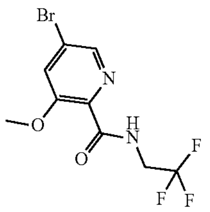 [SMILES: COc1cc(Br)cnc1C(=O)NCC(F)(F)F] | 5-bromo-3-methoxy-N-(2,2,2-trifluoroethyl)pyridine-2-carboxamide | CAS# 11421-66-9 + CAS# 373-88-6 | Ex. 2.25 | 313.1 | 313.2 + 315.2 |
| 110 | 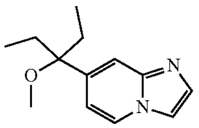 [SMILES: CCC(CC)(OC)c1ccn2ccnc2c1] | 7-(1-ethyl-1-methoxy-propyl)imidazo[1,2-a]pyridine | Int 112 | I1 | 218.3 | 219.4 |

TABLE II-continued

Intermediates used towards the compounds of the invention.

| Int# | Structure | Name | SM | Mtd | MW | MS Mes'd |
|---|---|---|---|---|---|---|
| 111 | 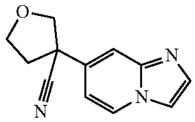 [SMILES: N#CC1(c2ccn3ccnc3c2)CCOC1] | 3-imidazo[1,2-a]pyridin-7-yltetrahydrofuran-3-carbonitrile | Int 62 | Ex. 2.26 | 213.2 | 214.2 |
| 112 | 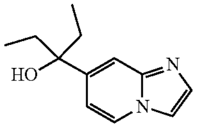 | 3-imidazo[1,2-a]pyridin-7-ylpentan-3-ol | CAS# 86718-01-6 | N2 | 204.3 | 205.2 |
| 113 | 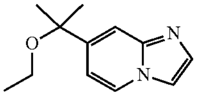 | 7-(1-ethoxy-1-methyl-ethyl)imidazo[1,2-a]pyridine | Int 106 | I1 | 204.3 | 205.3 |
| 114 | 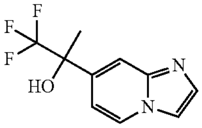 [SMILES: CC(O)(c1ccn2ccnc2c1)C(F)(F)F] | 1,1,1-trifluoro-2-imidazo[1,2-a]pyridin-7-yl-propan-2-ol | CAS# 1036991-50-0 | Ex. 2.27 | 230.2 | 231.3 |
| 115 | 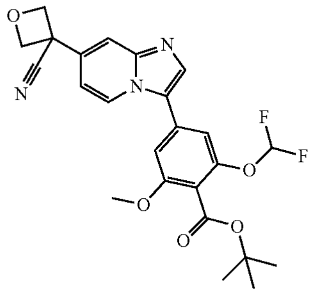 [SMILES: COc1cc(-c2cnc3cc(C4(C#N)COC4)ccn23)cc(OC(F)F)c1C(=O)OC(C)(C)C] | tert-butyl 4-[7-(3-cyanooxetan-3-yl)imidazo[1,2-a]pyridin-3-yl]-2-(difluoromethoxy)-6-methoxy-benzoate | Int 102 + Int 15 | E | 471.5 | 472.4 |
| 116 | 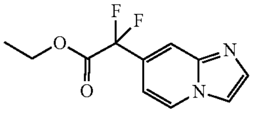 [SMILES: CCOC(=O)C(F)(F)c1ccn2ccnc2c1] | ethyl 2,2-difluoro-2-imidazo[1,2-a]pyridin-7-yl-acetate | CAS# 908269-30-7 | Ex. 2.28 | 240.2 | 241.2 |
| 117 | 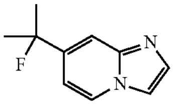 | 7-(1-fluoro-1-methyl-ethyl)imidazo[1,2-a]pyridine | Int 106 | T | 178.2 | 179.3 |
| 118 | 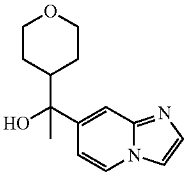 [SMILES: CC(O)(c1ccn2ccnc2c1)C1CCOCC1] | 1-imidazo[1,2-a]pyridin-7-yl-1-tetrahydropyran-4-yl-ethanol | CAS# 1036991-50-0 | N2 | 246.3 | 247.2 |
| 119 | 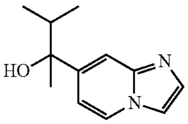 | 2-imidazo[1,2-a]pyridin-7-yl-3-inethyl-butan-2-ol | CAS# 1036991-50-0 | N2 | 204.3 | 205.5 |
| 120 | 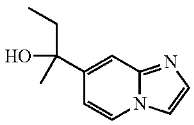 | 2-imidazo[1,2-a]pyridin-7-ylbutan-2-ol | CAS# 1036991-50-0 | N2 | 190.2 | 191.3 |

TABLE II-continued

| Int# | Structure | Name | SM | Mtd | MW | MS Mes'd |
|---|---|---|---|---|---|---|
| Intermediates used towards the compounds of the invention. | | | | | | |
| 121 | 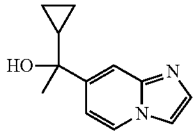 | 1-cyclopropyl-1-imidazo[1,2-a]pyridin-7-yl-ethanol | CAS# 1036991-50-0 | N2 | 202.2 | 203.3 |
| 122 | 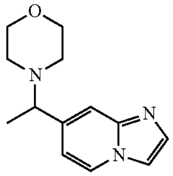 [SMILES: CC(c1ccn2ccnc2c1)N1CCOCC1] | 4-(1-imidazo[1,2-a]pyridin-7-ylethyl)morpholine | CAS# 1036991-50-0 | Ex. 2.29 | 231.3 | 232.2 |
| 123 | 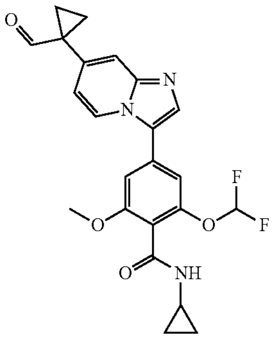 [SMILES: COc1cc(-c2cnc3cc(C4(C=O)CC4)ccn23)cc(OC(F)F)c1C(=O)NC1CC1] | N-cyclopropyl-2-(difluoromethoxy)-4-[7-(1-formylcyclopropyl) imidazo[1,2-a]pyridin-3-yl]-6-methoxy-benzamide | Cpd 115 | U | 441.4 | 442.3 |
| 124 | 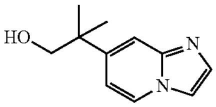 | 2-methyl-2-pyrazolo[1,5-a]pyridin-6-yl-propan-1-ol | Int 58 | Ex. 2.30 | 190.2 | 192.2 |
| 125 | 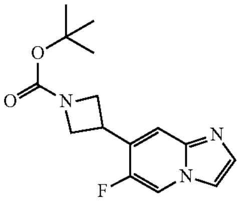 [SMILES: CC(C)(C)OC(=O)N1CC(c2cc3nccn3cc2F)C1] | tert-butyl 3-(6-fluoroimidazo[1,2-a]pyridin-7-yl)azetidine-1-carboxylate | Int 126 | A3 | 291.3 | 292.3 |
| 126 | 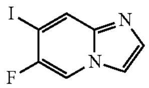 | 6-fluoro-7-iodo-imidazo[1,2-a]pyridine | CAS# 1649470-53-0 | O | 262.0 | 263.2 |
| 127 | 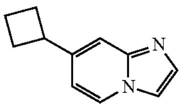 [SMILES: c1cn2ccc(C3CCC3)cc2n1] | 7-cyclobutylimidazo[1,2-a]pyridine | CAS# 4532-25-6 | A3 | 172.2 | 173.2 |
| 128 | 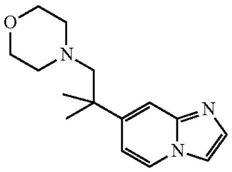 [SMILES: CC(C)(CN1CCOCC1)c1ccn2ccnc2c1] | 4-(2-imidazo[1,2-a]pyridin-7-yl-2-methyl-propyl)morpholine | Int 129 + CAS# 110-91-8 | K3 | 259.4 | 260.4 |

TABLE II-continued

Intermediates used towards the compounds of the invention.

| Int# | Structure | Name | SM | Mtd | MW | MS Mes'd |
|---|---|---|---|---|---|---|
| 129 | 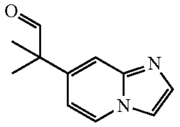 | 2-imidazo[1,2-a]pyridin-7-yl-2-methyl-propanal | Int 124 | U | 188.2 | 189.3 |
| 130 | 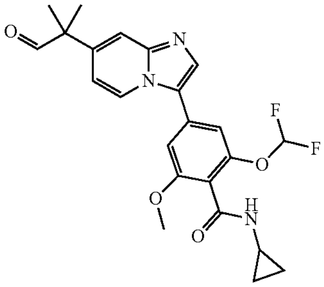 [SMILES: COc1cc(-c2cnc3cc(C(C)(C)C=O)ccn23)cc(OC(F)F)c1C(=O)NC1CC1] | N-cyclopropyl-2-(difluoromethoxy)-4-[7-(1,1-dimethyl-2-oxo-ethyl)imidazo[1,2-a]pyridin-3-yl]-6-methoxy-benzamide | Cpd 150 | U | 443.4 | 444.4 |
| 131 | 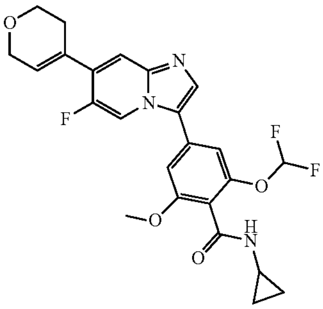 [SMILES: COc1cc(-c2cnc3cc(C4=CCOCC4)c(F)cn23)cc(OC(F)F)c1C(=O)NC1CC1] | N-cyclopropyl-2-(difluoromethoxy)-4-[7-(3,6-dihydro-2H-pyran-4-yl)-6-fluoro-imidazo[1,2-a]pyridin-3-yl]-6-methoxy-benzamide | Int 132 + Int 4 | E | 473.5 | 474.5 |
| 132 | 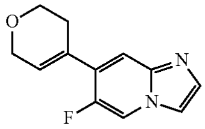 [SMILES: Fc1cn2ccnc2cc1C1=CCOCC1] | 7-(3,6-dihydro-2H-pyran-4-yl)-6-fluoro-imidazo[1,2-a]pyridine | Int 126 + CAS# 287944-16-5 | C | 218.2 | 219.5 |
| 133 | 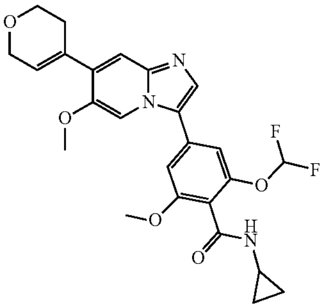 [SMILES: COc1cn2c(-c3cc(OC)c(C(=O)NC4CC4)c(OC(F)F)c3)cnc2cc1C1=CCOCC1] | N-cyclopropyl-2-(difluoromethoxy)-4-[7-(3,6-dihydro-2H-pyran-4-yl)-6-raethoxy-imidazo[1,2-a]pyridin-3-yl]-6-methoxy-benzamide | Int 134 + Int 4 | E | 485.5 | 486.3 |
| 134 | 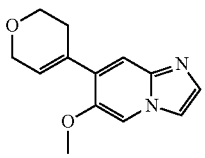 [SMILES: COc1cn2ccnc2cc1C1=CCOCC1] | 7-(3,6-dihydro-2H-pyran-4-yl)-6-methoxy-imidazo[1,2-a]pyridine | Int 135 + CAS# 287944-16-5 | C | 230.3 | 231.3 |
| 135 | 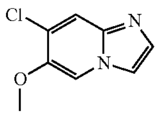 | 7-chloro-6-methoxy-imidazo[1,2-a]pyridine | CAS# 867131-26-8 | O | 182.6 | 182.7 |

TABLE II-continued

Intermediates used towards the compounds of the invention.

| Int# | Structure | Name | SM | Mtd | MW | MS Mes'd |
|---|---|---|---|---|---|---|
| 136 | 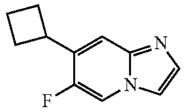 [SMILES: Fc1cn2ccnc2cc1C1CCC1] | 7-cyclobutyl-6-fluoro-imidazo[1,2-a]pyridine | Int 126 | A3 | 190.2 | 190.8 |
| 137 | 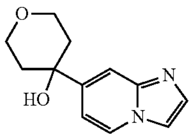 [SMILES: OC1(c2ccn3ccnc3c2)CCOCC1] | 4-imidazo[1,2-a]pyridin-7-yltetrahydropyran-4-ol | Int 138 | O | 218.3 | 219.3 |
| 138 | 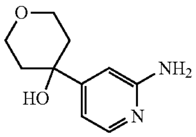 [SMILES: Nc1cc(C2(O)CCOCC2)ccn1] | 4-(2-amino-4-pyridyl)tetrahydropyran-4-ol | Int 139 | M1 | 194.2 | 195.3 |
| 139 | 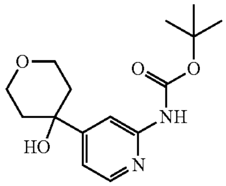 [SMILES: CC(C)(C)OC(=O)Nc1cc(C2(O)CCOCC2)ccn1] | tert-butyl N-[4-(4-hydroxytetrahydropyran-4-yl)-2-pyridyl]carbamate | CAS# 207799-10-8 + CAS# 29943-42-8 | A7 | 294.3 | 295.4 |
| 140 | 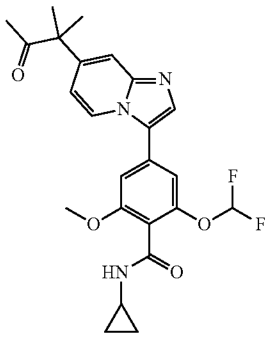 [SMILES: COc1cc(-c2cnc3cc(C(C)(C)C(C)=O)ccn23)cc(OC(F)F)c1C(=O)NC1CC1] + 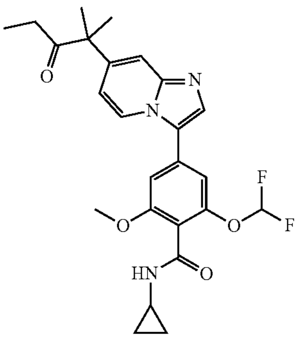 [SMILES: CCC(=O)C(C)(C)c1ccn2c(-c3cc(OC)c(C(=O)NC4CC4)c(OC(F)F)c3)cnc2c1] + | N-cyclopropyl-2-(difluoromethoxy)-4-[7-(1,1-dimethyl-2-oxo-propyl)imidazo[1,2-a]pyridin-3-yl]-6-methoxy-benzamide/N-cyclopropyl-2-(difluoromethoxy)-4-[7-(1,1-dimethyl-2-oxo-butyl)imidazo[1,2-a]pyridin-3-yl]-6-methoxy-benzamide/N-cyclopropyl-2-(difluoromethoxy)-6-methoxy-4-[7-(1,1,3-trimethyl-2-oxo-butyl)imidazo[1,2-a]pyridin-3-yl]benzamide mixture | Int 80 + Int 4 | E | 457.5 | 458.4 |

TABLE II-continued

Intermediates used towards the compounds of the invention.

| Int# | Structure | Name | SM | Mtd | MW | MS Mes'd |
|---|---|---|---|---|---|---|
| | 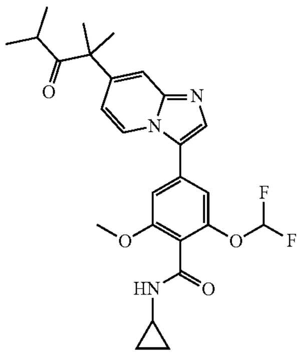 [SMILES: COc1cc(-c2cnc3cc(C(C)(C)C(=O)C(C)C)ccn23)cc(OC(F)F)c1C(=O)NC1CC1] | | | | | |
| 141 | 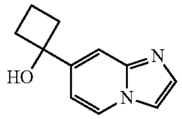 [SMILES: OC1(c2ccn3ccnc3c2)CCC1] | 1-imidazo[1,2-a]pyridin-7-ylcyclobutanol | CAS# 808744-34-5 + CAS# 1191-95-3 | A5 | 188.2 | 189.2 |
| 142 | 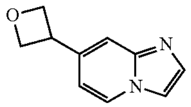 [SMILES: c1cn2ccc(C3COC3)cc2n1] | 7-(oxetan-3-yl)imidazo[1,2-a]pyridine | CAS# 808744-34-5 + CAS# 39267-79-3 | A4 | 174.2 | 175.2 |
| 143 | 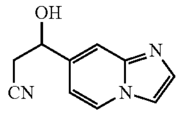 [SMILES: N#CCC(O)c1ccn2ccnc2c1] | 3-hydroxy-3-imidazo[1,2-a]pyridin-7-yl propanenitrile | Int 144 | N1 | 187.2 | 188.2 |
| 144 | 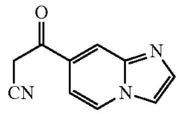 [SMILES: N#CCC(=O)c1ccn2ccnc2c1] | 3-imidazo[1,2-a]pyridin-7-yl-3-oxo-propanenitrile | CAS# 648423-85-2 | Ex. 2.31 | 185.2 | 186.3 |
| 145 | 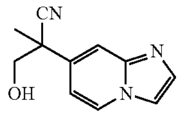 | 3-hydroxy-2-imidazo[1,2-a]pyridin-7-yl-2-methyl-propanenitrile | Int 164 | Ex. 2.32 | 201.2 | 201.9 |
| 146 | 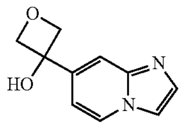 | 3-imidazo[1,2-a]pyridin-7-yloxetan-3-ol | CAS# 808744-34-5 + CAS# 6704-31-0 | A5 | 190.2 | 191.3 |
| 147 | 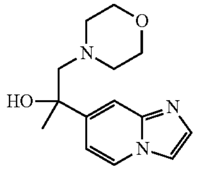 [SMILES: CC(O)(CN1CCOCC1)c1ccn2ccnc2c1] | 2-imidazo[1,2-a]pyridin-7-yl-1-morpholino-propan-2-ol | CAS# 1036991-50-0 + CAS# 110-91-8 | N3 | 261.3 | 262.4 |
| 148 | 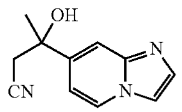 | 3-hydroxy-3-imidazo[1,2-a]pyridin-7-yl-butanenitrile | Int 144 | N2 | 201.2 | 202.4 |

TABLE II-continued

Intermediates used towards the compounds of the invention.

| Int# | Structure | Name | SM | Mtd | MW | MS Mes'd |
|---|---|---|---|---|---|---|
| 149 | 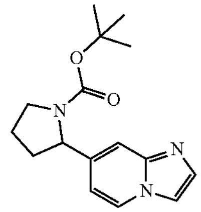 [SMILES: CC(C)(C)OC(=O)N1CCCC1c1ccn2ccnc2c1] | tert-butyl 2-imidazo[1,2-a]pyridin-7-ylpyrrolidine-1-carboxylate | Int 150 | O | 287.4 | 288.4 |
| 150 | 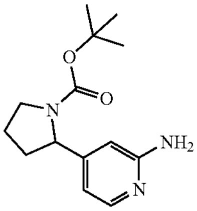 [SMILES: CC(C)(C)OC(=O)N1CCCC1c1ccnc(N)c1] | tert-butyl 2-(2-amino-4-pyridyl)pyrrolidine-1-carboxylate | CAS# 84249-14-9 | A6 | 263.3 | 264.4 |
| 151 | 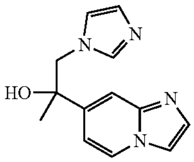 [SMILES: CC(O)(Cn1ccnc1)c1ccn2ccnc2c1] | 2-imidazo[1,2-a]pyridin-7-yl-1-imidazol-1-yl-propan-2-ol | CAS# 1036991-50-0 + CAS# 288-32-4 | N3 | 242.3 | 243.4 |
| 152 | 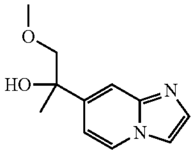 | 2-imidazo[1,2-a]pyridin-7-yl-1-methoxy-propan-2-ol | CAS# 1036991-50-0 + CAS# 151-50-8 | N3 | 206.2 | 207.4 |
| 153 | 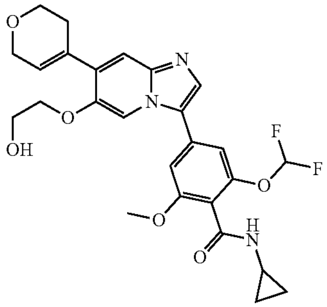 [SMILES: COc1cc(-c2cnc3cc(C4=CCOCC4)c(OCCO)cn23)cc(OC(F)F)c1C(=O)NC1CC1] | N-cyclopropyl-2-(difluoromethoxy)-4-[7-(3,6-dihydro-2H-pyran-4-yl)-6-(2-hydroxyethoxy)imidazo[1,2-a]pyridin-3-yl]-6-methoxy-benzamide | Int 154 + Int 4 | E | 515.5 | 516.4 |
| 154 | 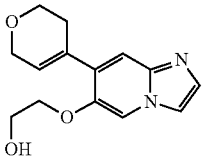 [SMILES: OCCOc1cn2ccnc2cc1C1=CCOCC1] | 2-[7-(3,6-dihydro-2H-pyran-4-yl)imidazo[1,2-a]pyridin-6-yl]oxyethanol | Int 155 + CAS# 287944-16-5 | C | 260.3 | 261.3 |
| 155 | 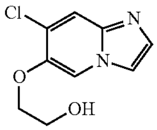 | 2-(7-chloroimidazo[1,2-a]pyridin-6-yl)oxyethanol | Int 156 | Ex. 2.33 | 212.6 | 213.2 |
| 156 | 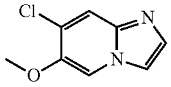 | 7-chloro-6-methoxy-imidazo[1,2-a]pyridine | CAS# 867131-26-8 | O | 182.6 | 182.8 + 185.1 |

TABLE II-continued

Intermediates used towards the compounds of the invention.

| Int# | Structure | Name | SM | Mtd | MW | MS Mes'd |
|---|---|---|---|---|---|---|
| 157 | 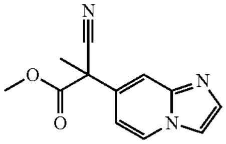 [SMILES: COC(=O)C(C)(C#N)c1ccn2ccnc2c1] | methyl 2-cyano-2-imidazo[1,2-a]pyridin-7-yl-propanoate | Int 62 | Ex. 2.34 | 229.2 | 230.2 |
| 158 | 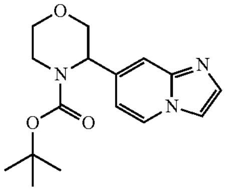 [SMILES: CC(C)(C)OC(=O)N1CCOCC1c1ccn2ccnc2c1] | tert-butyl 3-imidazo[1,2-a]pyridin-7-ylmorpholine-4-carboxylate | Int 159 | O | 303.4 | 304.3 |
| 159 | 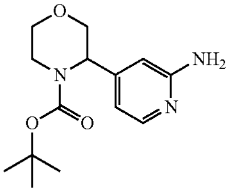 [SMILES: CC(C)(C)OC(=O)N1CCOCC1c1ccnc(N)c1] | tert-butyl 3-(2-amino-4-pyridyl)morpholine-4-carboxylate | CAS# 84249-14-9 | A6 | 279.3 | 280.3 |
| 160 | 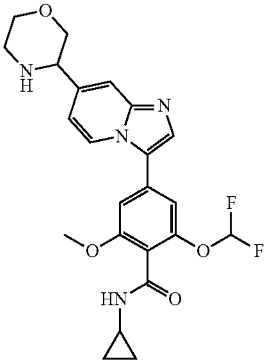 [SMILES: COc1cc(-c2cnc3cc(C4COCCN4)ccn23)cc(OC(F)F)c1C(=O)NC1CC1] | N-cyclopropyl-2-(difluoromethoxy)-6-methoxy-4-(7-morpholin-3-ylimidazo[1,2-a]pyridin-3-yl)benzamide | Cpd 186 | M1 | 458.5 | 459.4 |
| 161 | 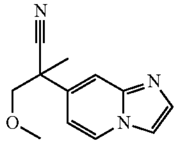 [SMILES: COCC(C)(C#N)c1ccn2ccnc2c1] | 2-imidazo[1,2-a]pyridin-7-yl-3-methoxy-2-methyl-propanenitrile | Int 64 | Ex. 2.35 | 215.3 | 216.5 |
| 162 | 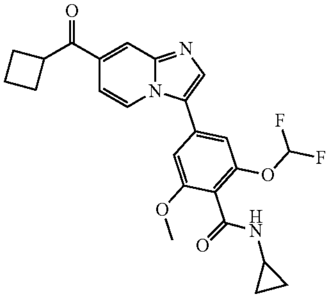 [SMILES: COc1cc(-c2cnc3cc(C(=O)C4CCC4)ccn23)cc(OC(F)F)c1C(=O)NC1CC1] | 4-[7-(cyclobutanecarbonyl)imidazo[1,2-a]pyridin-3-yl]-N-cyclopropyl-2-(difluoromethoxy)-6-methoxy-benzamide | Int 163 + Int 4 | E | 455.4 | 456.4 |
| 163 | 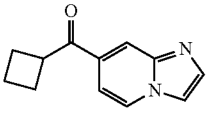 [SMILES: O=C(c1ccn2ccnc2c1)C1CCC1] | cyclobutyl(imidazo[1,2-a]pyridin-7-yl)methanone | CAS# 808744-34-5 | A5 | 200.2 | 201.3 |

TABLE II-continued

| Intermediates used towards the compounds of the invention. | | | | | | |
|---|---|---|---|---|---|---|
| Int# | Structure | Name | SM | Mtd | MW | MS Mes'd |
| 164 | 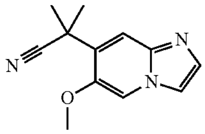 [SMILES: COc1cn2ccnc2cc1C(C)(C)C#N] | 2-(6-methoxyimidazo[1,2-a]pyridin-7-yl)-2-methyl-propanenitrile | CAS# 942947-94-6 | Ex. 2.36 | 215.1 | 216.2 |
| 165 | 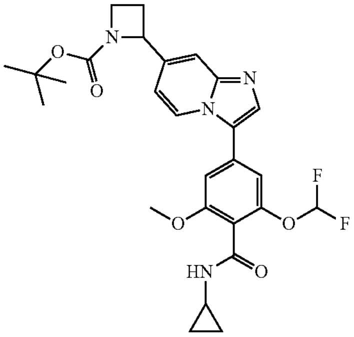 [SMILES: COc1cc(-c2cnc3cc(C4CCN4C(=O)OC(C)(C)C)ccn23)cc(OC(F)F)c1C(=O)NC1CC1] | tert-butyl 2-[3-[4-(cyclopropylcarbamoyl)-3-(difluoromethoxy)-5-methoxy-phenyl]imidazo[1,2-a]pyridin-7-yl]azetidine-1-carboxylate | Int 166 + Int 4 | E | 528.5 | 529.5 |
| 166 | 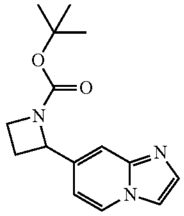 [SMILES: CC(C)(C)OC(=O)N1CCC1c1ccn2ccnc2c1] | tert-butyl 2-imidazo[1,2-a]pyridin-7-ylazetidine-1-carboxylate | CAS# 84249-14-9 | O | 273.3 | 274.4 |
| 167 | 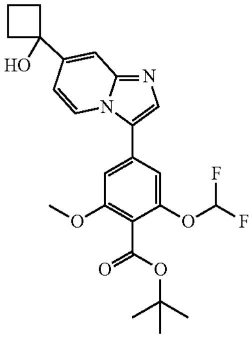 [SMILES: COc1cc(-c2cnc3cc(C4(O)CCC4)ccn23)cc(OC(F)F)c1C(=O)OC(C)(C)C] | tert-butyl 2-(difluoromethoxy)-4-[7-(1-hydroxycyclobutyl) imidazo[1,2-a]pyridin-3-yl]-6-methoxy-benzoate | Int 141 + Int 15 | E | 460.5 | 461.4 |
| 168 | 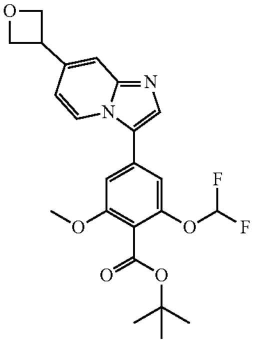 [SMILES: COc1cc(-c2cnc3cc(C4COC4)ccn23)cc(OC(F)F)c1C(=O)OC(C)(C)C] | tert-butyl 2-(difluoromethoxy)-6-methoxy-4-[7-(oxetan-3-yl)imidazo[1,2-a]pyridin-3-yl]benzoate | Int 142 + Int 15 | E | 446.4 | 447.4 |
| 169 | 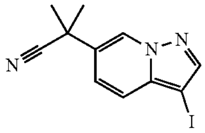 | 2-(3-iodopyrazolo[1,5-a]pyridin-6-yl)-2-methyl-propanenitrile | Int 171 | B | 311.1 | 312.1 |

TABLE II-continued

Intermediates used towards the compounds of the invention.

| Int# | Structure | Name | SM | Mtd | MW | MS Mes'd |
|---|---|---|---|---|---|---|
| 170 | 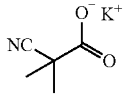 | potassium; 2-cyano-2-methyl-propanoate | CAS# 1572-98-1 | W | 151.2 | NA |
| 171 | 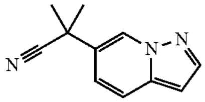 | 2-methyl-2-pyrazolo[1,5-a]pyridin-6-yl-propanenitrile | CAS# 1264193-11-4 + Int 170 | A2 | 185.2 | 186.1 |
| 172 | 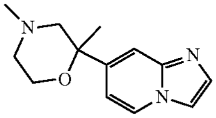 [SMILES: CN1CCOC(C)(c2ccn3ccnc3c2)C1] | 2-imidazo[1,2-a]pyridin-7-yl-2,4-dimethyl-morpholine | Int 173 | Ex. 2.37 | 231.3 | 232.4 |
| 173 | 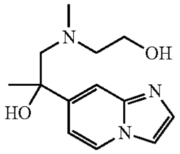 [SMILES: CN(CCO)CC(C)(O)c1ccn2ccnc2c1] | 1-[2-hydroxyethyl(methyl)amino]-2-imidazo[1,2-a]pyridin-7-yl-propan-2-ol | CAS# 1036991-50-0 + CAS# 109-83-1 | N3 | 249.3 | 250.3 |
| 174 | 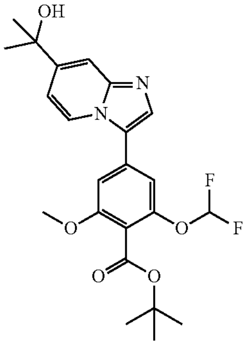 [SMILES: COc1cc(-c2cnc3cc(C(C)(C)O)ccn23)cc(OC(F)F)c1C(=O)OC(C)(C)C] | tert-butyl 2-(difluoromethoxy)-4-[7-(1-hydroxy-1-methyl-ethyl)imidazo[1,2-a]pyridin-3-yl]-6-methoxy-benzoate | Int 106 + Int 15 | E | 448.5 | 449.4 |
| 175 | 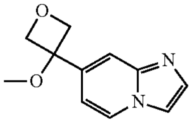 | 7-(3-methoxyoxctan-3-yl)imidazo[1,2-a]pyridine | Int 146 | I1 | 204.2 | 205.2 |
| 176 | 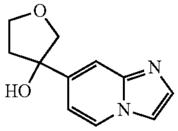 [SMILES: OC1(c2ccn3ccnc3c2)CCOC1] | 3-imidazo[1,2-a]pyridin-7-yltetrahydrofuran-3-ol | Int 177 | O | 204.2 | 205.4 |
| 177 | 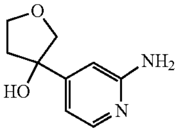 | 3-(2-amino-4-pyridyl)tetrahydrofuran-3-ol | Int 178 | M1 | 180.2 | 181.2 |
| 178 | 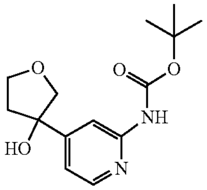 | tert-butyl N-[4-(3-hydroxytetrahydrofuran-3-yl)-2-pyridyl]carbamate | CAS# 207799-10-8 + CAS# 22929-52-8 | A7 | 280.3 | 281.4 |

TABLE II-continued

| Intermediates used towards the compounds of the invention. | | | | | | |
|---|---|---|---|---|---|---|
| Int# | Structure | Name | SM | Mtd | MW | MS Mes'd |
| 179 | 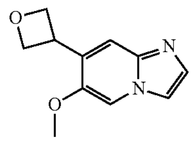 | 6-methoxy-7-(oxetan-3-yl)imidazo[1,2-a]pyridine | Int 156 | A4 | 204.2 | 205.2 |
| 180 | 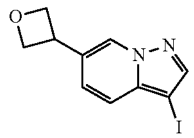 [SMILES: Ic1cnn2cc(C3COC3)ccc12] | 3-iodo-6-(oxetan-3-yl)pyrazolo[1,5-a]pyridine | Int 181 | B | 300.1 | 301.2 |
| 181 | 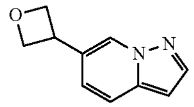 [SMILES: c1cc2ccc(C3COC3)cn2n1] | 6-(oxetan-3-yl)pyrazolo[1,5-a]pyridine | CAS# 1264193-11-4 | A4 | 174.2 | 176.2 |
| 182 | 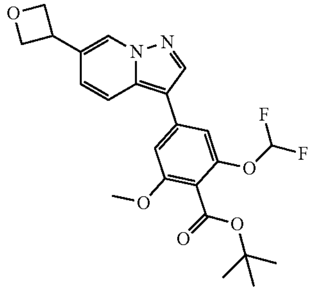 [SMILES: COc1cc(-c2cnn3cc(C4COC4)ccc23)cc(OC(F)F)c1C(=O)OC(C)(C)C] | tert-butyl 2-(difluoromethoxy)-6-methoxy-4-[6-(oxetan-3-yl)pyrazolo[1,5-a]pyridin-3-yl]benzoate | Int 181 + Int 16 | C | 446.4 | 447.4 |
| 183 | 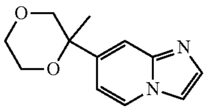 [SMILES: CC1(c2ccn3ccnc3c2)COCCO1] | 7-(2-methyl-1,4-dioxan-2-yl)imidazo[1,2-a]pyridine | Int 184 | Ex. 2.38 | 218.2 | 218.9 |
| 184 | 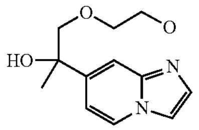 | 1-(2-hydroxyethoxy)-2-imidazo[1,2-a]pyridin-7-yl-propan-2-ol | CAS# 1036991-50-0 + CAS# 107-21-1 | N3 | 236.3 | 237.4 |
| 185 | 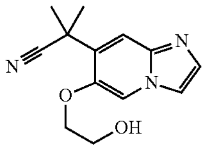 [SMILES: CC(C)(C#N)c1cc2nccn2cc1OCCO] | 2-[6-(2-hydroxyethoxy)imidazo[1,2-a]pyridin-7-yl]-2-methyl-propanenitrile | Int 186 | O | 245.1 | 246.3 |
| 186 | 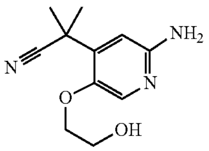 [SMILES: CC(C)(C#N)c1cc(N)ncc1OCCO] | 2-[2-amino-5-(2-hydroxyethoxy)-4-pyridyl]-2-methyl-propanenitrile | CAS# 942947-94-6 | Ex. 2.39 | 221.1 | 222.3 |

TABLE II-continued

Intermediates used towards the compounds of the invention.

| Int# | Structure | Name | SM | Mtd | MW | MS Mes'd |
|---|---|---|---|---|---|---|
| 187 | 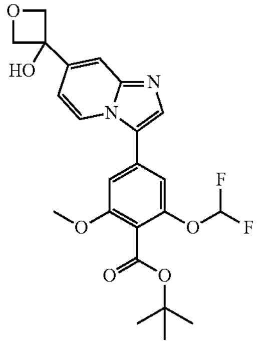 [SMILES: COc1cc(-c2cnc3cc(C4(O)COC4)ccn23)cc(OC(F)F)c1C(=O)OC(C)(C)C] | tert-butyl 2-(difluoromethoxy)-4-[7-(3-hydroxyoxetan-3-yl)imidazo[1,2-a]pyridin-3-yl]-6-methoxy-benzoate | Int 146 + Int 15 | E | 462.4 | 463.4 |
| 188 | 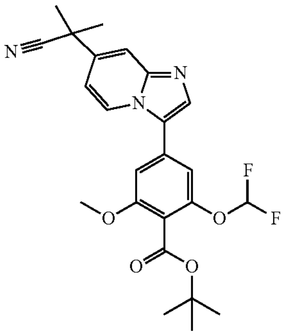 [SMILES: COc1cc(-c2cnc3cc(C(C)(C)C#N)ccn23)cc(OC(F)F)c1C(=O)OC(C)(C)C] | tert-butyl 4-[7-(1-cyano-1-methyl-ethyl)imidazo[1,2-a]pyridin-3-yl]-2-(difluoromethoxy)-6-methoxy-benzoate | Int 58 + Int 15 | E | 457.4 | 458.7 |
| 189 | 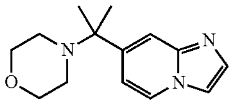 [SMILES: CC(C)(c1ccn2ccnc2c1)N1CCOCC1] | 4-(1-imidazo[1,2-a]pyridin-7-yl-1-methyl-ethyl)morpholine | Int 158 | Ex. 2.40 | 245.3 | 246.3 |
| 190 | 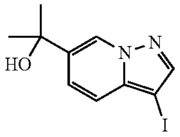 | 2-(3-iodopyrazolo[1,5-a]pyridin-6-yl)propan-2-ol | Int 191 | B | 302.1 | 303.1 |
| 191 | 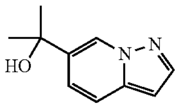 | 2-pyrazolo[1,5-a]pyridin-6-ylpropan-2-ol | Int 75 | N2 | 176.1 | 177.2 |
| 192 | 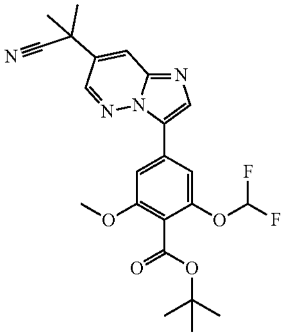 [SMILES: COc1cc(-c2cnc3cc(C(C)(C)C#N)cnn23)cc(OC(F)F)c1C(=O)OC(C)(C)C] | tert-butyl 4-[7-(1-cyano-1-methyl-ethyl)imidazo[1,2-b]pyridazin-3-yl]-2-(difluoromethoxy)-6-methoxy-benzoate | Int 193 + Int 15 | E | 458.5 | 459.4 |

TABLE II-continued

Intermediates used towards the compounds of the invention.

| Int# | Structure | Name | SM | Mtd | MW | MS Mes'd |
|---|---|---|---|---|---|---|
| 193 | 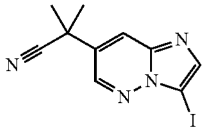 | 2-(3-iodoimidazo[1,2-b]pyridazin-7-yl)-2-methyl-propanenitrile | Int 194 | B | 312.1 | 313.1 |
| 194 | 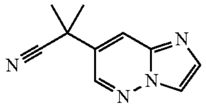 | 2-imidazo[1,2-b]pyridazin-7-yl-2-methyl-propanenitrile | CAS# 1383481-11-5 | A2 | 186.2 | 187.3 |
| 195 | 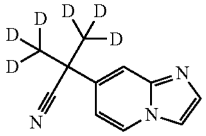 [SMILES: [2H]C([2H])([2H])C(C#N)(c1ccn2ccnc2c1)C([2H])([2H])[2H]] | 3,3,3-trideuterio-2-imidazo[1,2-a]pyridin-7-yl-2-(trideuteriomethyl) propanenitrile | Int 62 | Ex. 2.41 | 191.1 | 191.9 |
| 196 | 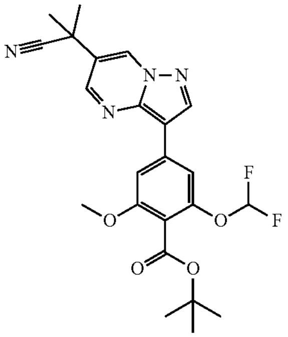 [SMILES: COc1cc(-c2cnn3cc(C(C)(C)C#N)cnc23)cc(OC(F)F)c1C(=O)OC(C)(C)C] | tert-butyl 4-[6-(1-cyano-1-methyl-ethyl)pyrazolo[1,5-a]pyrimidin-3-yl]-2-(difluoromethoxy)-6-methoxy-benzoate | Int 197 + Int 16 | C | 458.5 | 459.3 |
| 197 | 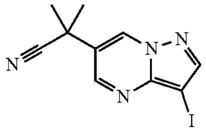 | 2-(3-iodopyrazolo[1,5-a]pyrimidin-6-yl)-2-methyl-propanenitrile | Int 198 | B | 312.1 | 312.8 |
| 198 | 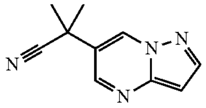 | 2-methyl-2-pyrazolo[1,5-a]pyrimidin-6-yl-propanenitrile | CAS# 705263-10-1 | A2 | 186.2 | 187.2 |
| 199 | 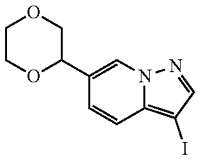 [SMILES: Ic1cnn2cc(C3COCCO3)ccc12] | 6-(1,4-dioxan-2-yl)-3-iodo-pyrazolo[1,5-a]pyridine | Int 200 | B | 330.1 | 331.1 |
| 200 | 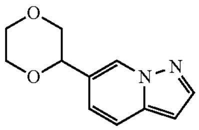 [SMILES: c1cc2ccc(C3COCCO3)cn2n1] | 6-(1,4-dioxan-2-yl)pyrazolo[1,5-a]pyridine | Int 201 | L | 204.2 | 205.2 |
| 201 | 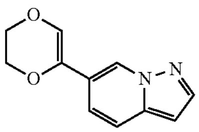 [SMILES: C1=C(c2ccc3ccnn3c2)OCCO1] | 6-(2,3-dihydro-1,4-dioxin-5-yl)pyrazolo[1,5-a]pyridine | CAS# 1264193-11-4 + CAS# 1046811-97-5 | C | 202.2 | 203.2 |

TABLE II-continued

Intermediates used towards the compounds of the invention.

| Int# | Structure | Name | SM | Mtd | MW | MS Mes'd |
|---|---|---|---|---|---|---|
| 202 | 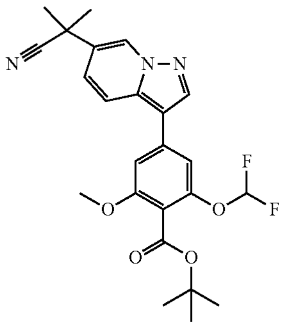 [SMILES: COc1cc(-c2cnn3cc(C(C)(C)C#N)ccc23)cc(OC(F)F)c1C(=O)OC(C)(C)C] | tert-butyl 4-[6-(1-cyano-1-methyl-ethyl)pyrazolo[1,5-a]pyridin-3-yl]-2-(difluoromethoxy)-6-methoxy-benzoate | Int 169 + Int 16 | C | 457.5 | 458.3 |
| 203 | 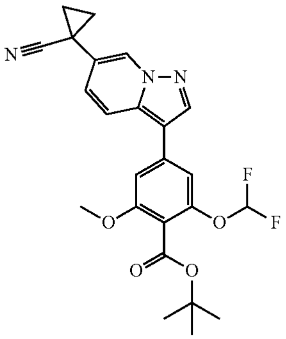 [SMILES: COc1cc(-c2cnn3cc(C4(C#N)CC4)ccc23)cc(OC(F)F)c1C(=O)OC(C)(C)C] | tert-butyl 4-[6-(1-cyanocyclopropyl) pyrazolo[1,5-a]pyridin-3-yl]-2-(difluoromethoxy)-6-methoxy-benzoate | Int 205 + Int 16 | C | 455.4 | 456.3 |
| 204 | 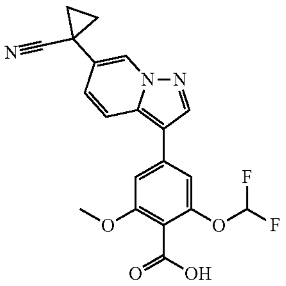 [SMILES: COc1cc(-c2cnn3cc(C4(C#N)CC4)ccc23)cc(OC(F)F)c1C(=O)O] | 4-[6-(1-cyanocyclopropyl) pyrazolo[1,5-a]pyridin-3-yl]-2-(difluoromethoxy)-6-methoxy-benzoic acid | Int 203 | D1i | 399.1 | 400.2 |
| 205 | 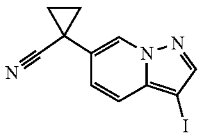 [SMILES: N#CC1(c2ccc3c(I)cnn3c2)CC1] | 1-(3-iodopyrazolo[1,5-a]pyridin-6-yl) cyclopropanecarbonitrile | Int 206 | B | 309.1 | 310.1 |
| 206 | 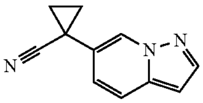 [SMILES: N#CC1(c2ccc3ccnn3c2)CC1] | 1-pyrazolo[1,5-a]pyridin-6-yl-cyclopropanecarbonitrile | Int 207 | Ex. 2.42 | 183.2 | 184.2 |
| 207 | 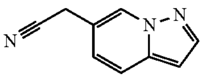 [SMILES: N#CCc1ccc2ccnn2c1] | 2-pyrazolo[1,5-a]pyridin-6-ylacetonitrile | CAS# 1264193-11-4 | A8 | 157.2 | 158.2 |
| 208 | 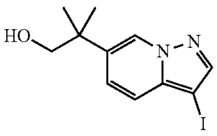 | 2-(3-iodopyrazolo[1,5-a]pyridin-6-yl)-2-methyl-propan-1-ol | Int 209 | B | 316.1 | 316.8 |

TABLE II-continued

Intermediates used towards the compounds of the invention.

| Int# | Structure | Name | SM | Mtd | MW | MS Mes'd |
|---|---|---|---|---|---|---|
| 209 | 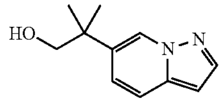 | 2-methyl-2-pyrazolo[1,5-a]pyridin-6-yl-propan-1-ol | Int 210 | N1 | 190.2 | 190.9 |
| 210 | 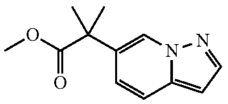 [SMILES: COC(=O)C(C)(C)c1ccc2ccnn2c1] | methyl 2-methyl-2-pyrazolo[1,5-a]pyridin-6-yl-propanoate | Int 171 | Ex. 2.43 | 218.2 | 219.3 |
| 211 | 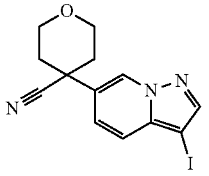 [SMILES: N#CC1(c2ccc3c(I)cnn3c2)CCOCC1] | 4-(3-iodopyrazolo[1,5-a]pyridin-6-yl)tetrahydropyran-4-carbonitrile | Int 213 | B | 353.2 | 354.1 |
| 212 | 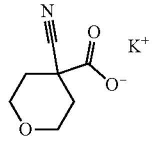 [SMILES: N#CC1(C(=O)[O-])CCOCC1 ; [K+]] | potassium; 4-cyanotetrahydropyran-4-carboxylate | CAS# 30431-99-3 | W | 193.2 | NA |
| 213 | 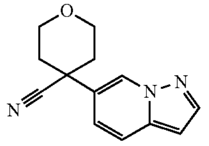 [SMILES: N#CC1(c2ccc3ccnn3c2)CCOCC1] | 4-pyrazolo[1,5-a]pyridin-6-yltetrahydropyran-4-carbonitrile | CAS# 1264193-11-4 + Int 212 | A2 | 227.3 | 228.3 |
| 214 | 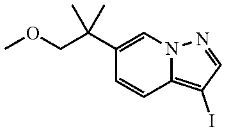 [SMILES: COCC(C)(C)c1ccc2c(I)cnn2c1] | 3-iodo-6-(2-methoxy-1,1-dimethyl-ethyl)pyrazolo[1,5-a]pyridine | Int 208 | I1 | 330.2 | 331.3 |
| 215 | 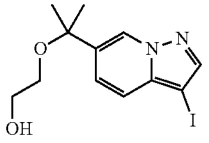 [SMILES: CC(C)(OCCO)c1ccc2c(I)cnn2c1] | 2-[1-(3-iodopyrazolo[1,5-a]pyridin-6-yl)-1-methyl-ethoxy]ethanol | Int 216 | B | 346.2 | 347.8 |
| 216 | 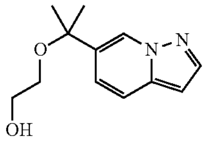 [SMILES: CC(C)(OCCO)c1ccc2ccnn2c1] | 2-(1-methyl-1-pyrazolo[1,5-a]pyridin-6-yl-ethoxy)ethanol | Int 191 | Ex. 2.44 | 220.3 | 222.3 |
| 217 | 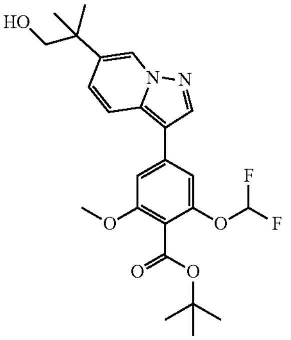 [SMILES: COc1cc(-c2cnn3cc(C(C)(C)CO)ccc23)cc(OC(F)F)c1C(=O)OC(C)(C)C] | tert-butyl 2-(difluoromethoxy)-4-[6-(2-hydroxy-1,1-dimethyl-ethyl)pyrazolo[1,5-a]pyridin-3-yl]-6-methoxy-benzoate | Int 208 + Int 16 | C | 462.5 | NA |

TABLE II-continued

Intermediates used towards the compounds of the invention.

| Int# | Structure | Name | SM | Mtd | MW | MS Mes'd |
|---|---|---|---|---|---|---|
| 218 | 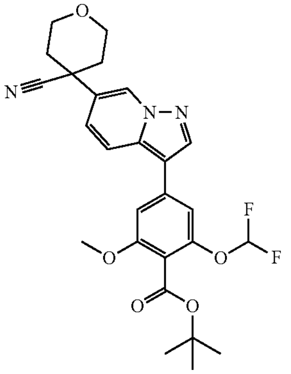 [SMILES: COc1cc(-c2cnn3cc(C4(C#N)CCOCC4)ccc23)cc(OC(F)F)c1C(=O)OC(C)(C)C] | tert-butyl 4-[6-(4-cyanotetrahydropyran-4-yl)pyrazolo[1,5-a]pyridin-3-yl]-2-(difluoromethoxy)-6-methoxy-benzoate | Int 211 + Int 16 | C | 499.5 | 500.4 |
| 219 | 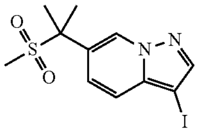 [SMILES: CC(C)(c1ccc2c(I)cnn2c1)S(C)(=O)=O] | 3-iodo-6-(1-methyl-1-methylsulfonyl-ethyl)pyrazolo[1,5-a]pyridine | Int 220 | B | 364.2 | 365.1 |
| 220 | 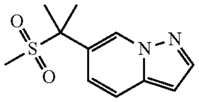 [SMILES: CC(C)(c1ccc2ccnn2c1)S(C)(=O)=O] | 6-(1-methyl-1-methylsulfonyl-ethyl)pyrazolo[1,5-a]pyridine | CAS# 47443-61-6 | Ex. 2.45 | 238.3 | 239.2 |
| 221 | 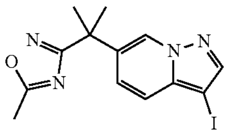 [SMILES: C/C(O)=N/C(=N)C(C)(C)c1ccc2c(I)cnn2c1] | 3-[1-(3-iodopyrazolo[1,5-a]pyridin-6-yl)-1-methyl-ethyl]-5-methyl-1,2,4-oxadiazole | Int 222 | B | 368.2 | 369.2 |
| 222 | 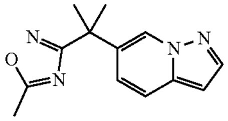 [SMILES: C/C(O)=N/C(=N)C(C)(C)c1ccc2ccnn2c1] | 5-methyl-3-(1-methyl-1-pyrazolo[1,5-a]pyridin-6-yl-ethyl)-1,2,4-oxadiazole | Int 171 | Ex. 2.46 | 242.3 | 243.6 |
| 223 | 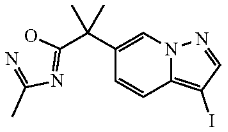 [SMILES: CC(=N)/N=C(\O)C(C)(C)c1ccc2c(I)cnn2c1] | 5-[1-(3-iodopyrazolo[1,5-a]pyridin-6-yl)-1-methyl-ethyl]-3-methyl-1,2,4-oxadiazole | Int 224 | B | 368.2 | 369.2 |
| 224 | 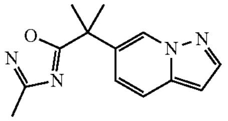 [SMILES: CC(=N)/N=C(\O)C(C)(C)c1ccc2ccnn2c1] | 3-methyl-5-(1-methyl-1-pyrazolo[1,5-a]pyridin-6-yl-ethyl)-1,2,4-oxadiazole | Int 210 | Ex. 2.47 | 242.3 | 243.3 |
| 225 | 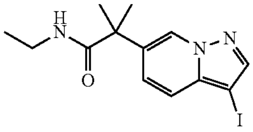 [SMILES: CCNC(=O)C(C)(C)c1ccc2c(I)cnn2c1] | N-ethyl-2-(3-iodopyrazolo[1,5-a]pyridin-6-yl)-2-methyl-propanamide | Int 226 | B | 357.2 | 358.2 |
| 226 | 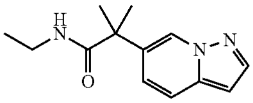 [SMILES: CCNC(=O)C(C)(C)c1ccc2ccnn2c1] | N-ethyl-2-methyl-2-pyrazolo[1,5-a]pyridin-6-yl-propanamide | Int 171 | Ex. 2.48 | 231.3 | 232.3 |

TABLE II-continued

| Int# | Structure | Name | SM | Mtd | MW | MS Mes'd |
|---|---|---|---|---|---|---|
| | Intermediates used towards the compounds of the invention. | | | | | |
| 227 | 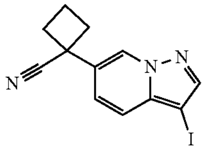 [SMILES: N#CC1(c2ccc3c(I)cnn3c2)CCC1] | 1-(3-iodopyrazolo[1,5-a]pyridin-6-yl) cyclobutanecarbonitrile | Int 229 | B | 323.1 | NA |
| 228 | 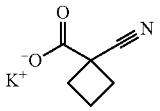 | potassium; 1-cyanocyclobutane-carboxylate | CAS# 28246-87-9 | W | 163.2 | NA |
| 229 | 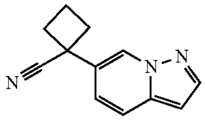 [SMILES: N#CC1(c2ccc3ccnn3c2)CCC1] | 1-pyrazolo[1,5-a]pyridin-6-yl-cyclobutanecarbonitrile | CAS# 1264193-11-4 + Int 228 | A2 | 197.2 | NA |
| 230 | 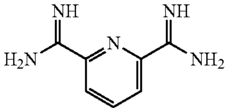 | pyridine-2,6-dicarboxamidine | CAS# 2893-33-6 | Ex. 2.49 | 163.2 | 165.2 |
| 231 | 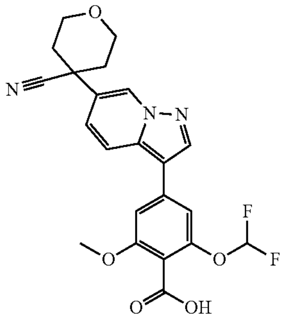 [SMILES: COc1cc(-c2cnn3cc(C4(C#N)CCOCC4)ccc23)cc(OC(F)F)c1C(=O)O] | 4-[6-(4-cyanotetrahydropyran-4-yl)pyrazolo[1,5-a]pyridin-3-yl]-2-(difluoromethoxy)-6-methoxy-benzoic acid | Int 218 | D1i | 443.4 | 444.2 |
| 232 | 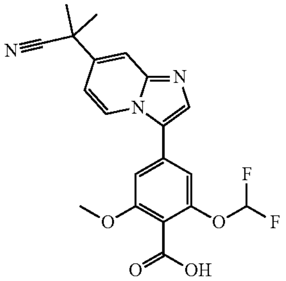 [SMILES: COc1cc(-c2cnc3cc(C(C)(C)C#N)ccn23)cc(OC(F)F)c1C(=O)O] | 4-[7-(1-cyano-1-methyl-ethyl)imidazo[1,2-a]pyridin-3-yl]-2-(difluoromethoxy)-6-methoxy-benzoic acid | Int 78 | D2i | 401.4 | 402.6 |
| 233 | 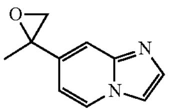 | 7-(2-methyloxiran-2-yl)imidazo[1,2-a]pyridine | CAS# 1036991-50-0 | N3i | 174.2 | 175.0 |

TABLE II-continued

| Intermediates used towards the compounds of the invention. | | | | | | |
|---|---|---|---|---|---|---|
| Int# | Structure | Name | SM | Mtd | MW | MS Mes'd |
| 234 | 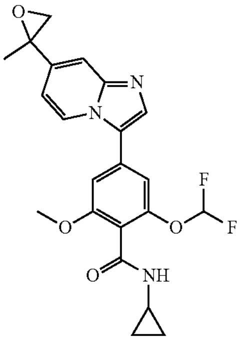 [SMILES: COc1cc(-c2cnc3cc(C4(C)CO4)ccn23)cc(OC(F)F)c1C(=O)NC1CC1] | N-cyclopropyl-2-(difluoromethoxy)-6-methoxy-4-[7-(2-methyloxiran-2-yl)imidazo[1,2-a]pyridin-3-yl]benzamide | Int 76 | N3i | 429.4 | 430.4 |
| 235 | 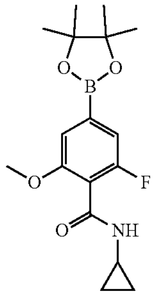 [SMILES: COc1cc(B2OC(C)(C)C(C)(C)O2)cc(F)c1C(=O)NC1CC1] | N-cyclopropyl-2-fluoro-6-methoxy-4-(4,4,5,5-tetramethyl-1,3,2-dioxaborolan-2-yl)benzamide | Int 1 | Ex. 2.50 | 335.2 | 336.5 |
| 236 | 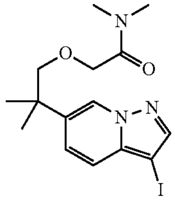 [SMILES: CN(C)C(=O)COCC(C)(C)c1ccc2c(I)cnn2c1] | 2-[2-(3-iodopyrazolo[1,5-a]pyridin-6-yl)-2-methyl-propoxy]-N,N-dimethyl-acetamide | Int 215 + CAS# 5468-77-9 | Ex. 2.51 | 402.1 | 402.2 |
| 237 | 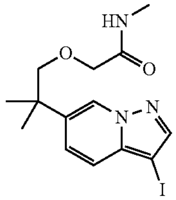 [SMILES: CNC(=O)COCC(C)(C)c1ccc2c(I)cnn2c1] | 2-[2-(3-iodopyrazolo[1,5-a]pyridin-6-yl)-2-methyl-propoxy]-N-methyl-acetamide | Int 215 + CAS# 34680-81-4 | Ex. 2.52 | 387.2 | 388.2 |
| 238 | 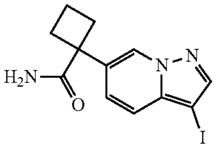 [SMILES: NC(=O)C1(c2ccc3c(I)cnn3c2)CCC1] | 1-(3-iodopyrazolo[1,5-a]pyridin-6-yl) cyclobutanecarboxamide | Int 227 | Ex. 2.53 | 341.1 | 342.5 |
| 239 | 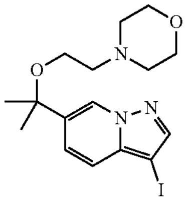 [SMILES: CC(C)(OCCN1CCOCC1)c1ccc2c(I)cnn2c1] | 4-[2-[1-(3-iodopyrazolo[1,5-a]pyridin-6-yl)-1-methyl-ethoxy]ethyl] morpholine | Int 240 | B | 415.3 | 416.2 |

TABLE II-continued

Intermediates used towards the compounds of the invention.

| Int# | Structure | Name | SM | Mtd | MW | MS Mes'd |
|---|---|---|---|---|---|---|
| 240 | 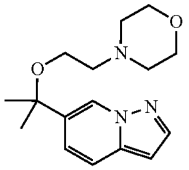 [SMILES: CC(C)(OCCN1CCOCC1)c1ccc2ccnn2c1] | 4-[2-(1-methyl-1-pyrazolo[1,5-a]pyridin-6-yl-ethoxy)ethyl] morpholine | Int 191 | Ex. 2.54 | 289.4 | 290.3 |
| 241 | 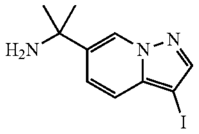 | 2-(3-iodopyrazolo[1,5-a]pyridin-6-yl)propan-2-amine | Int 169 | Ex. 2.55 | 301.1 | 302.1 |
| 242 | 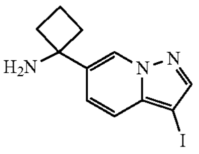 + 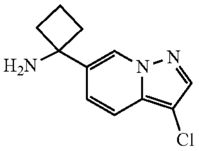 | 1-(3-iodopyrazolo[1,5-a]pyridin-6-yl) cyclobutanamine/1-(3-chloropyrazolo[1,5-a]pyridin-6-yl)cyclobutanamine mixture | Int 243 | Ex. 2.56 | 221.7 + 313.1 | 205.2 + 207.2 + 314.2 |
| 243 | 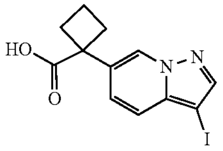 + 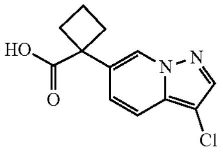 | 1-(3-iodopyrazolo[1,5-a]pyridin-6-yl) cyclobutanecarboxylic acid/1-(3-chloropyrazolo[1,5-a]pyridin-6-yl) cyclobutanecarboxylic acid mixture | Int 238 | Ex. 2.57 | 250.6 + 342.1 | 251.2 + 253.2 + 341.1 |
| 244 | 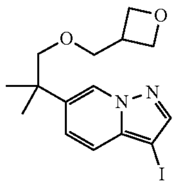 [SMILES: CC(C)(COCC1COC1)c1ccc2c(I)cnn2c1] | 6-[1,1-dimethyl-2-(oxetan-3-ylmethoxy)ethyl]-3-iodo-pyrazolo[1,5-a]pyridine | Int 208 + CAS# 1374014-30-8 | Ex. 2.58 | 386.2 | 387.2 |
| 245 | 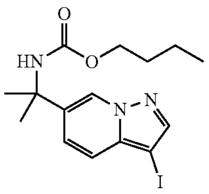 [SMILES: CCCCOC(=O)NC(C)(C)c1ccc2c(I)cnn2c1] | butyl N-[1-(3-iodopyrazolo[1,5-a]pyridin-6-yl)-1-methyl-ethyl]carbamate | Int 169 | Ex. 2.59 | 401.2 | 402.3 |

TABLE II-continued

| Int# | Structure | Name | SM | Mtd | MW | MS Mes'd |
|---|---|---|---|---|---|---|
| Intermediates used towards the compounds of the invention. | | | | | | |
| 246 | 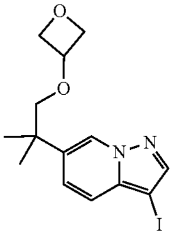 [SMILES: CC(C)(COC1COC1)c1ccc2c(I)cnn2c1] | 6-[1,1-dimethyl-2-(oxetan-3-yloxy)ethyl]-3-iodo-pyrazolo[1,5-a]pyridine | Int 263 + CAS# 7748-36-9 | Ex. 2.60 | 372.2 | 373.2 |
| 247 | 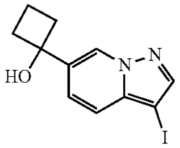 [SMILES: OC1(c2ccc3c(I)cnn3c2)CCC1] | 1-(3-iodopyrazolo[1,5-a]pyridin-6-yl)cyclobutanol | Int 248 | B | 314.1 | 315.1 |
| 248 | 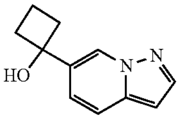 [SMILES: OC1(c2ccc3ccnn3c2)CCC1] | 1-pyrazolo[1,5-a]pyridin-6-ylcyclobutanol | Int 255 | Ex. 2.61 | 188.2 | 189.2 |
| 249 | 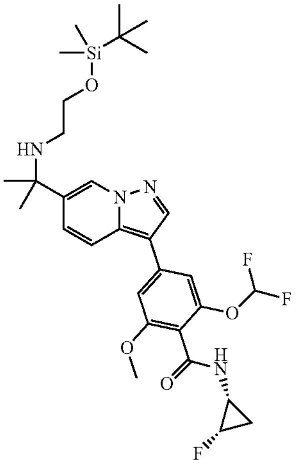 [SMILES: COc1cc(-c2cnn3cc(C(C)(C)NCCO[Si](C)(C)C(C)(C)C)ccc23)cc(OC(F)F)c1C(=O)N[C@@H]1C[C@@H]1F] | 2-(difluoromethoxy)-N-[(1R,2S)-2-fluorocyclopropyl]-4-[6-[1-(2-hydroxyethylamino)-1-methyl-ethyl]pyrazolo[1,5-a]pyridin-3-yl]-6-methoxy-benzamide | Int 250 + Int 8 | C | 492.5 | 493.4 |
| 250 | 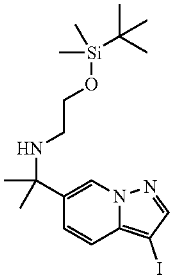 [SMILES: CC(C)(NCCO[Si](C)(C)C(C)(C)C)c1ccc2c(I)cnn2c1] | N-[2-[tert-butyl(dimethyl)silyl]oxyethyl]-2-(3-iodopyrazolo[1,5-a]pyridin-6-yl)propan-2-amine | Int 169 | Ex. 2.62 | 459.4 | 460.3 |
| 251 | 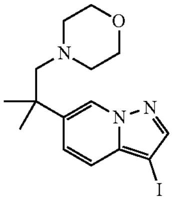 [SMILES: CC(C)(CN1CCOCC1)c1ccc2c(I)cnn2c1] | 4-[2-(3-iodopyrazolo[1,5-a]pyridin-6-yl)-2-methyl-propyl]morpholine | Int 208 | Ex. 2.63 | 385.2 | 386.2 |

TABLE II-continued

Intermediates used towards the compounds of the invention.

| Int# | Structure | Name | SM | Mtd | MW | MS Mes'd |
|---|---|---|---|---|---|---|
| 252 | 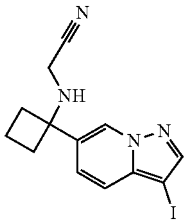 [SMILES: N#CCNC1(c2ccc3c(I)cnn3c2)CCC1] | 2-[[1-(3-iodopyrazolo[1,5-a]pyridin-6-yl)cyclobutyl]amino] acetonitrile | Int 253 | B | 352.2 | 353.3 |
| 253 | 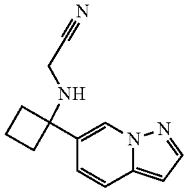 [SMILES: N#CCNC1(c2ccc3ccnn3c2)CCC1] | 2-[(1-pyrazolo[1,5-a]pyridin-6-ylcyclobutyl)amino] acetonitrile | Int 254 | Ex. 2.64 | 226.3 | 227.3 |
| 254 | 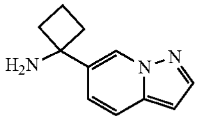 [SMILES: NC1(c2ccc3ccnn3c2)CCC1] | 1-pyrazolo[1,5-a]pyridin-6-ylcyclobutanamine | Int 255 | Ex. 2.65 | 187.2 | 188.2 |
| 255 | 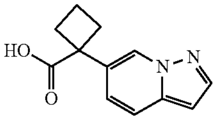 [SMILES: O=C(O)C1(c2ccc3ccnn3c2)CCC1] | 1-pyrazolo[1,5-a]pyridin-6-yl-cyclobutanecarboxylic acid | Int 229 | Ex. 2.66 | 216.2 | 217.9 |
| 256 | 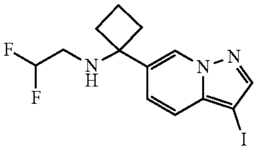 [SMILES: FC(F)CNC1(c2ccc3c(I)cnn3c2)CCC1] | N-(2,2-difluoroethyl)-1-(3-iodopyrazolo[1,5-a]pyridin-6-yl)cyclobutanamine | Int 257 | B | 377.2 | 378.3 |
| 257 | 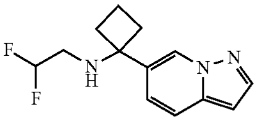 [SMILES: FC(F)CNC1(c2ccc3ccnn3c2)CCC1] | N-(2,2-difluoroethyl)-1-pyrazolo[1,5-a]pyridin-6-yl-cyclobutanamine | Int 254 | Ex. 2.67 | 251.3 | 252.4 |
| 258 | 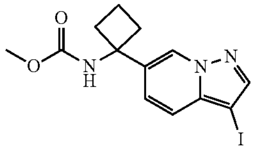 [SMILES: COC(=O)NC1(c2ccc3c(I)cnn3c2)CCC1] | methyl N-[1-(3-iodopyrazolo[1,5-a]pyridin-6-yl)cyclobutyl] carbamate | Int 259 | B | 371.2 | 372.1 |
| 259 | 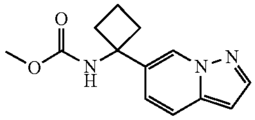 [SMILES: COC(=O)NC1(c2ccc3ccnn3c2)CCC1] | methyl N-(1-pyrazolo[1,5-a]pyridin-6-ylcyclobutyl)carbamate | Int 255 | Ex. 2.68 | 245.3 | 246.3 |
| 260 | 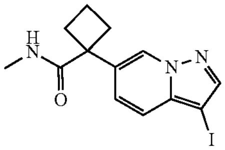 [SMILES: CNC(=O)C1(c2ccc3c(I)cnn3c2)CCC1] | 1-(3-iodopyrazolo[1,5-a]pyridin-6-yl)-N-methyl-cyclobutanecarboxamide | Int 261 | B | 355.2 | 356.1 |

TABLE II-continued

Intermediates used towards the compounds of the invention.

| Int# | Structure | Name | SM | Mtd | MW | MS Mes'd |
|---|---|---|---|---|---|---|
| 261 | 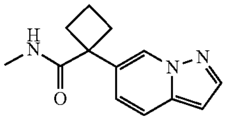 [SMILES: CNC(=O)C1(c2ccc3ccnn3c2)CCC1] | N-methyl-1-pyrazolo[1,5-a]pyridin-6-yl-cyclobutanecarboxamide | Int 255 | Ex. 2.69 | 229.3 | 230.3 |
| 262 | 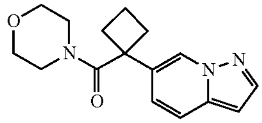 [SMILES: O=C(N1CCOCC1)C1(c2ccc3ccnn3c2)CCC1] | morpholino-(1-pyrazolo[1,5-a]pyridin-6-ylcyclobutyl) methanone | Int 255 | Ex. 2.70 | 285.3 | 286.3 |
| 263 | 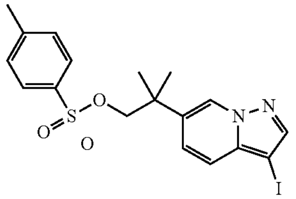 | [2-(3-iodopyrazolo[1,5-a]pyridin-6-yl)-2-methyl-propyl]4-methylbenzenesulfonate | Int 208 | Ex. 2.58 | 470.3 | 471.2 |
| 264 | 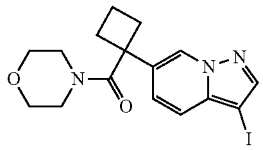 [SMILES: O=C(N1CCOCC1)C1(c2ccc3c(I)cnn3c2)CCC1] | 6-[1,1-dimethyl-2-(oxetan-3-yloxy)ethyl]-3-iodo-pyrazolo[1,5-a]pyridine | Int 262 | B | 411.2 | 412.3 |
| 265 | 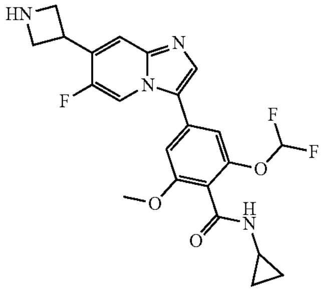 [SMILES: COc1cc(-c2cnc3cc(C4CNC4)c(F)cn23)cc(OC(F)F)c1C(=O)NC1CC1] | 4-[7-(azetidin-3-yl)-6-fluoro-imidazo[1,2-a]pyridin-3-yl]-N-cyclopropyl-2-(difluoromethoxy)-6-methoxy-benzamide | Cpd 158 | M1 | 446.4 | 447.2 |
| 266 | 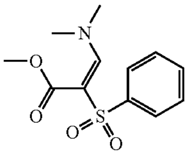 [SMILES: COC(=O)/C(=C\N(C)C)S(=O)(=O)c1ccccc1] | methyl (E)-2-(benzenesulfonyl)-3-(dimethylamino)prop-2-enoate | CAS# 34097-60-4 | Ex. 2.71 | 269.3 | 270.0 |
| 267 | 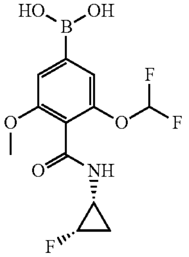 [SMILES: COc1cc(B(O)O)cc(OC(F)F)c1C(=O)N[C@@H]1C[C@@H]1F] | [3-(difluoromethoxy)-4-[[(1R,2S)-2-fluorocyclopropyl] carbamoyl]-5-methoxy-phenyl]boronic acid | 2-(difluoro-methoxy)-N-[(1R,2S)-2-fluorocyclo-propyl]-6-methoxy-benzamide (cf. Ex. 2.3.2) | Ex. 2.72 | 319.0 | 320.0 |

SM = Starting Material,
Mtd = Method,
MS Mes'd = Mesured mass,
NA = not measured

TABLE III

Illustrative compounds of the invention.

| Cpd# | Structure | Name | SM | Mtd | MW | MS Mes'd |
|---|---|---|---|---|---|---|
| 1 | 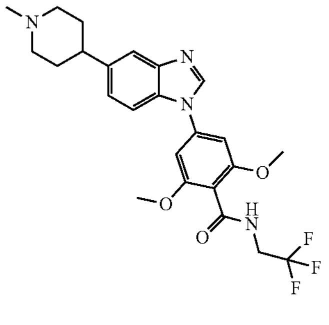 [SMILES: COc1cc(-n2cnc3cc(C4CCN(C)CC4)ccc32)cc(OC)c1C(=O)NCC(F)(F)F] | 2,6-dimethoxy-4-[5-(1-methyl-4-piperidyl)benzimidazol-1-yl]-N-(2,2,2-trifluoroethyl) benzamide | Int 53 | L | 476.5 | 477.3 |
| 2 | 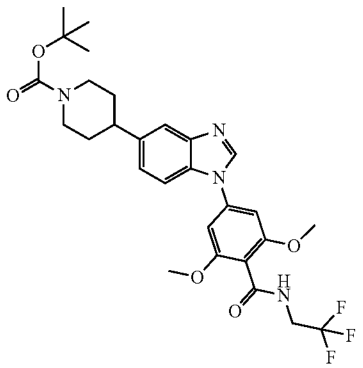 [SMILES: COc1cc(-n2cnc3cc(C4CCN(C(=O)OC(C)(C)C)CC4)ccc32)cc(OC)c1C(=O)NCC(F)(F)F] | tert-butyl 4-[1-[3,5-dimethoxy-4-(2,2,2-trifluoro ethylcarbamoyl) phenyl]benzimidazol-5-yl]piperidine-1-carboxylate | Int 52 | L | 562.6 | 563.4 |
| 3 | 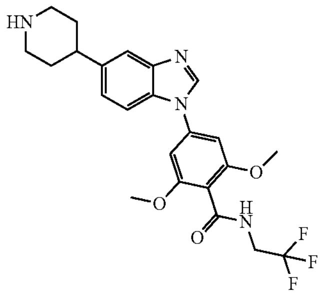 [SMILES: COc1cc(-n2cnc3cc(C4CCNCC4)ccc32)cc(OC)c1C(=O)NCC(F)(F)F] | 2,6-dimethoxy-4-[5-(4-piperidyl) benzimidazol-1-yl]-N-(2,2,2-trifluoroethyl)benzamide | Cpd 2 | M1 | 462.5 | 463.5 |
| 4 | 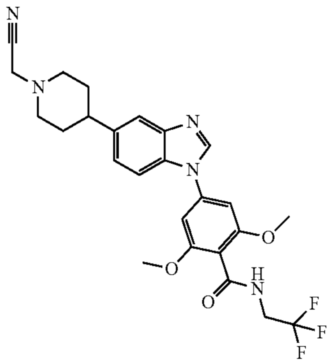 [SMILES: COc1cc(-n2cnc3cc(C4CCN(CC#N)CC4)ccc32)cc(OC)c1C(=O)NCC(F)(F)F] | 4-[5-[1-(cyano methyl)-4-piperidyl] benzimidazol-1-yl]-2,6-di methoxy-N-(2,2,2-trifluoroethyl) benzamide | Cpd 3 | 12 | 501.5 | 502.3 |

TABLE III-continued

| Illustrative compounds of the invention. | | | | | | |
|---|---|---|---|---|---|---|
| Cpd# | Structure | Name | SM | Mtd | MW | MS Mes'd |
| 5 | 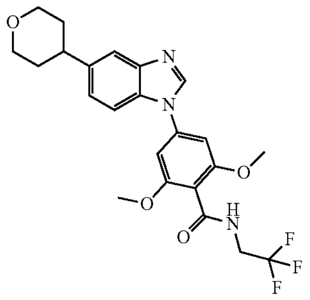 [SMILES: COc1cc(-n2cnc3cc(C4CCOCC4)ccc32)cc(OC)c1C(=O)NCC(F)(F)F] | 2,6-dimethoxy-4-(5-tetrahydropyran-4-ylbenzimidazol-1-yl)-N-(2,2,2-trifluoroethyl) benzamide | Int 51 | L | 463.4 | 464.2 |
| 6 | 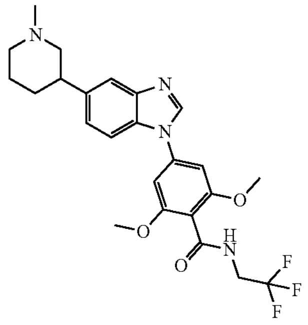 [SMILES: COc1cc(-n2cnc3cc(C4CCCN(C)C4)ccc32)cc(OC)c1C(=O)NCC(F)(F)F] | 2,6-dimethoxy-4-[5-(1-methyl-3-piperidyl)benzimidazol-1-yl]-N-(2,2,2-trifluoroethyl) benzamide | Int 50 | L | 476.5 | 477.5 |
| 7 | 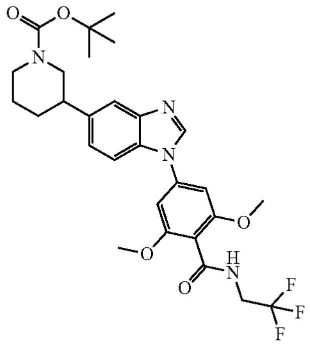 [SMILES: COc1cc(-n2cnc3cc(C4CCCN(C(=O)OC(C)(C)C)C4)ccc32)cc(OC)c1C(=O)NCC(F)(F)F] | tert-butyl 3-[1-[3,5-dimethoxy-4-(2,2,2-trifluoro ethylcarbamoyl) phenyl]benzimidazol-5-yl]piperidine-1-carboxylate | Int 49 | L | 562.6 | 563.6 |
| 8 | 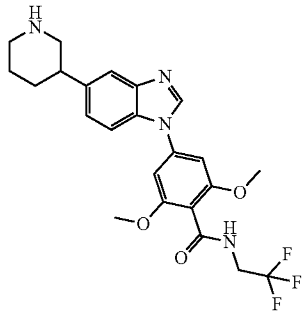 [SMILES: COc1cc(-n2cnc3cc(C4CCCNC4)ccc32)cc(OC)c1C(=O)NCC(F)(F)F] | 2,6-dimethoxy-4-[5-(3-piperidyl) benzimidazol-1-yl]-N-(2,2,2-trifluoroethyl) benzamide | Cpd 7 | M2 | 462.5 | 463.2 |

TABLE III-continued

Illustrative compounds of the invention.

| Cpd# | Structure | Name | SM | Mtd | MW | MS Mes'd |
|---|---|---|---|---|---|---|
| 9 | 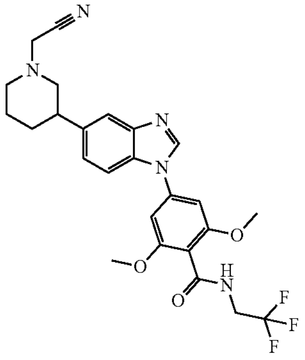 [SMILES: COc1cc(-n2cnc3cc(C4CCCN(CC#N)C4)ccc32)cc(OC)c1C(=O)NCC(F)(F)F] | 4-[5-[1-(cyano methyl)-3-piperidyl] benzimidazol-1-yl]-2,6-dimethoxy-N-(2,2,2-trifluoroethyl) benzamide | Cpd 8 | 12 | 501.5 | 502.4 |
| 10 | 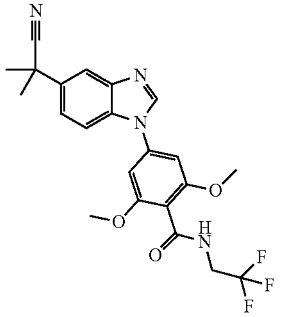 [SMILES: COc1cc(-n2cnc3cc(C(C)(C)C#N)ccc32)cc(OC)c1C(=O)NCC(F)(F)F] | 4-[5-(1-cyano-1-methyl-ethyl) benzimidazol-1-yl]-2,6-dimethoxy-N-(2,2,2-trifluoro ethyl)benzamide | Int 48 + CAS# 753-90-2 | D2 | 446.4 | 447.4 |
| 11 | 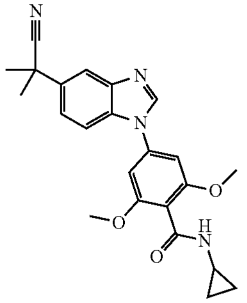 [SMILES: COc1cc(-n2cnc3cc(C(C)(C)C#N)ccc32)cc(OC)c1C(=O)NC1CC1] | 4-[5-(1-cyano-1-methyl-ethyl) benzimidazol-1-yl]-N-cyclopropyl-2,6-dimethoxy-benzamide | Int 48 + CAS# 765-30-0 | D2 | 404.5 | 405.4 |
| 12 | 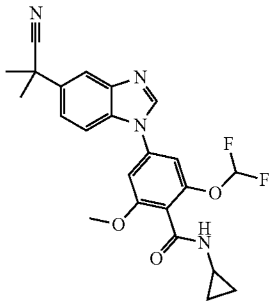 [SMILES: COc1cc(-n2cnc3cc(C(C)(C)C#N)ccc32)cc(OC(F)F)c1C(=O)NC1CC1] | 4-[5-(1-cyano-1-methyl-ethyl) benzimidazol-1-yl]-N-cyclopropyl-2-(difluoromethoxy)-6-methoxy-benzamide | Int 42 | H | 440.4 | 441.4 |

TABLE III-continued

| Illustrative compounds of the invention. | | | | | | |
|---|---|---|---|---|---|---|
| Cpd# | Structure | Name | SM | Mtd | MW | MS Mes'd |
| 13 | 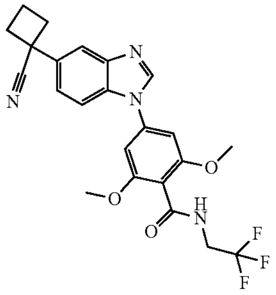 [SMILES: COc1cc(-n2cnc3cc(C4(C#N)CCC4)ccc32)cc(OC)c1C(=O)NCC(F)(F)F] | 4-[5-(1-cyano cyclobutyl) benzimidazol-1-yl]-2,6-dimethoxy-N-(2,2,2-trifluoro ethyl)benzamide | Int 45 + CAS# 753-90-2 | D2 | 458.4 | 459.4 |
| 14 | 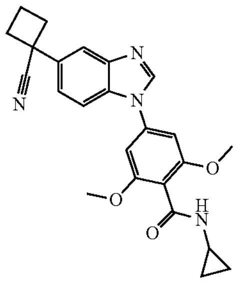 [SMILES: COc1cc(-n2cnc3cc(C4(C#N)CCC4)ccc32)cc(OC)c1C(=O)NC1CC1] | 4-[5-(1-cyano cyclobutyl) benzimidazol-1-yl]-N-cyclopropyl-2,6-dimethoxy-benzamide | Int 45 + CAS# 765-30-0 | D2 | 416.5 | 417.4 |
| 15 | 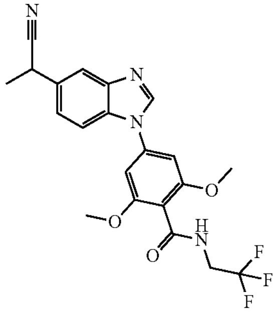 [SMILES: COc1cc(-n2cnc3cc(C(C)C#N)ccc32)cc(OC)c1C(=O)NCC(F)(F)F] | 4-[5-(1-cyano ethyl)benzimidazol-1-yl]-2,6-dimethoxy-N-(2,2,2-trifluoro ethyl)benzamide | Int 54 | Ex. 2.73 | 432.4 | 433.2 |
| 16 | 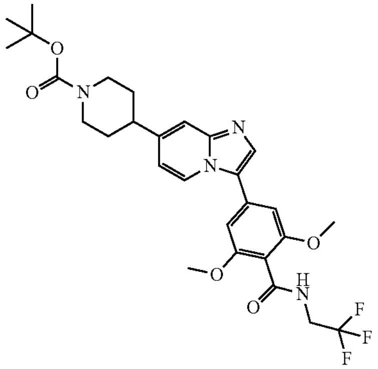 [SMILES: COc1cc(-c2cnc3cc(C4CCN(C(=O)OC(C)(C)C)CC4)ccn23)cc(OC)c1C(=O)NCC(F)(F)F] | tert-butyl 4-[3-[3,5-dimethoxy-4-(2,2,2-trifluoro ethylcarbamoyl) phenyl]imidazo[1,2-a]pyridin-7-yl]piperidine-1-carboxylate | Int 55 | L | 562.6 | 564.0 |

TABLE III-continued

Illustrative compounds of the invention.

| Cpd# | Structure | Name | SM | Mtd | MW | MS Mes'd |
|---|---|---|---|---|---|---|
| 17 | 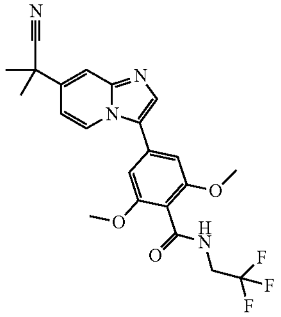 [SMILES: COc1cc(-c2cnc3cc(C(C)(C)C#N)ccn23)cc(OC)c1C(=O)NCC(F)(F)F] | 4-[7-(1-cyano-1-methyl-ethyl) imidazo[1,2-a]pyridin-3-yl]-2,6-dimethoxy-N-(2,2,2-trifluoroethyl) benzamide | Int 56 + CAS# 753-90-2 | D2 | 446.4 | 447.3 |
| 18 | 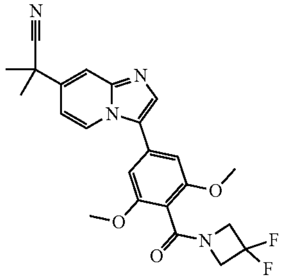 [SMILES: COc1cc(-c2cnc3cc(C(C)(C)C#N)ccn23)cc(OC)c1C(=O)N1CC(F)(F)C1] | 2-[3-[4-(3,3-difluoroazetidine-1-carbonyl)-3,5-dimethoxy-phenyl] imidazo[1,2-a] pyridin-7-yl]-2-methyl-propanenitrile | Int 56 + CAS# 679431-52-8 | D2 | 440.4 | 441.3 |
| 19 | 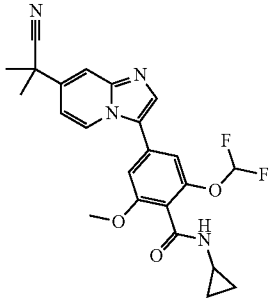 [SMILES: COc1cc(-c2cnc3cc(C(C)(C)C#N)ccn23)cc(OC(F)F)c1C(=O)NC1CC1] | 4-[7-(1-cyano-1-methyl-ethyl) imidazo[1,2-a]pyridin-3-yl]-N-cyclo propyl-2-(difluoro methoxy)-6-methoxy-benzamide | Int 57 + Int 7 | C | 440.4 | 441.8 |
| 20 | 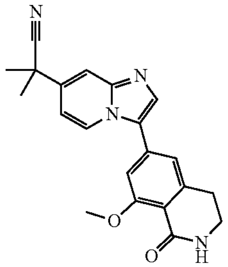 [SMILES: COc1cc(-c2cnc3cc(C(C)(C)C#N)ccn23)cc2c1C(=O)NCC2] | 2-[3-(8-methoxy-1-oxo-3,4-dihydro-2H-isoquinolin-6-yl)imidazo[1,2-a]pyridin-7-yl]-2-methyl-propanenitrile | Int 57 + Int 26 | C | 360.4 | 361.3 |
| 21 | 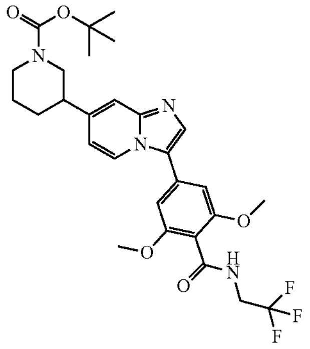 [SMILES: COc1cc(-c2cnc3cc(C4CCCN(C(=O)OC(C)(C)C)C4)ccn23)cc(OC)c1C(=O)NCC(F)(F)F] | tert-butyl 3-[3-[3,5-dimethoxy-4-(2,2,2-trifluoroethyl carbamoyl)phenyl] imidazo[1,2-a]pyridin-7-yl]piperidine-1-carboxylate | Int 59 | L | 562.6 | 564.0 |

TABLE III-continued

Illustrative compounds of the invention.

| Cpd# | Structure | Name | SM | Mtd | MW | MS Mes'd |
|---|---|---|---|---|---|---|
| 22 | 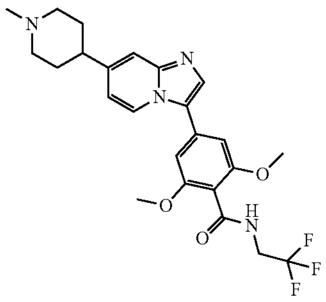 [SMILES: COc1cc(-c2cnc3cc(C4CCN(C)CC4)ccn23)cc(OC)c1C(=O)NCC(F)(F)F] | 2,6-dimethoxy-4-[7-(1-methyl-4-piperidyl)imidazo[1,2-a]pyridin-3-yl]-N-(2,2,2-trifluoroethyl)benzamide | Int 60 | L | 476.5 | 477.6 |
| 23 | 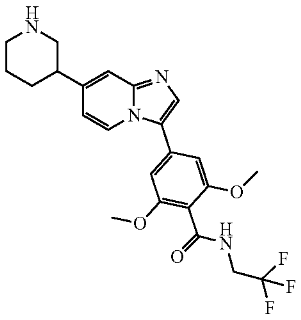 [SMILES: COc1cc(-c2cnc3cc(C4CCCNC4)ccn23)cc(OC)c1C(=O)NCC(F)(F)F] | 2,6-dimethoxy-4-[7-(3-piperidyl)imidazo[1,2-a]pyridin-3-yl]-N-(2,2,2-trifluoroethyl)benzamide | Cpd 21 | M1 | 462.5 | 463.3 |
| 24 | 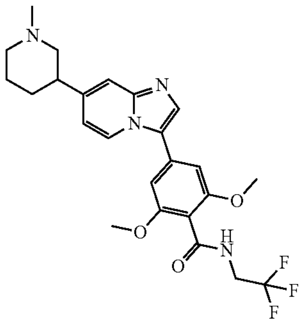 [SMILES: COc1cc(-c2cnc3cc(C4CCCN(C)C4)ccn23)cc(OC)c1C(=O)NCC(F)(F)F] | 2,6-dimethoxy-4-[7-(1-methyl-3-piperidyl)imidazo[1,2-a]pyridin-3-yl]-N-(2,2,2-trifluoroethyl)benzamide | Cpd 23 | K1 | 476.5 | 477.4 |
| 25 | 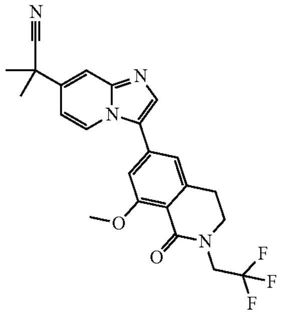 [SMILES: COc1cc(-c2cnc3cc(C(C)(C)C#N)ccn23)cc2c1C(=O)N(CC(F)(F)F)CC2] | 2-[3-[8-methoxy-1-oxo-2-(2,2,2-trifluoroethyl)-3,4-dihydroisoquinolin-6-yl]imidazo[1,2-a]pyridin-7-yl]-2-methyl-propanenitrile | Cpd 20 | Ex. 2.74 | 442.4 | 443.9 |

TABLE III-continued

| Illustrative compounds of the invention. | | | | | | |
|---|---|---|---|---|---|---|
| Cpd# | Structure | Name | SM | Mtd | MW | MS Mes'd |
| 26 | 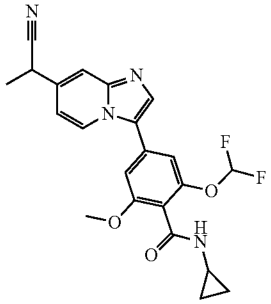 [SMILES: COc1cc(-c2cnc3cc(C(C)C#N)ccn23)cc(OC(F)F)c1C(=O)NC1CC1] | 4-[7-(1-cyanoethyl)imidazo[1,2-a]pyridin-3-yl]-N-cyclopropyl-2-(difluoromethoxy)-6-methoxy-benzamide | Int 63 + Int 7 | C | 426.4 | 427.7 |
| 27 | 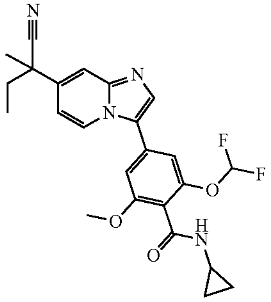 [SMILES: CCC(C)(C#N)c1ccn2c(-c3cc(OC)c(C(=O)NC4CC4)c(OC(F)F)c3)cnc2c1] | 4-[7-(1-cyano-1-methyl-propyl) imidazo[1,2-a]pyridin-3-yl]-N-cyclopropyl-2-(difluorome thoxy)-6-methoxy-benzamide | Int 65 + Int 7 | C | 454.5 | 455.9 |
| 28 | 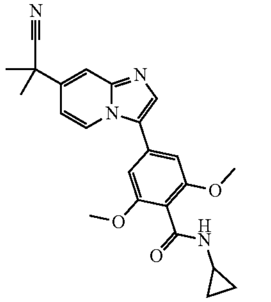 [SMILES: COc1cc(-c2cnc3cc(C(C)(C)C#N)ccn23)cc(OC)c1C(=O)NC1CC1] | 4-[7-(1-cyano-1-methyl-ethyl)imidazo[1,2-a]pyridin-3-yl]-N-cyclopropyl-2,6-dimethoxy-benzamide | Int 56 + CAS# 765-30-0 | D2 | 404.5 | 405.3 |
| 29 | 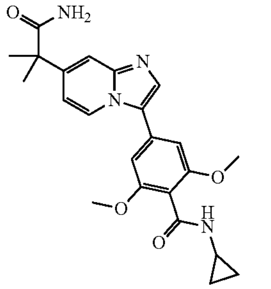 [SMILES: COc1cc(-c2cnc3cc(C(C)(C)C(N)=O)ccn23)cc(OC)c1C(=O)NC1CC1] | 4-[7-(2-amino-1,1-dimethyl-2-oxo-ethyl)imidazo[1,2-a]pyridin-3-yl]-N-cyclopropyl-2,6-dimethoxy-benzamide | Int 66 + CAS# 765-30-0 | D1ii | 422.5 | 423.6 |
| 30 | 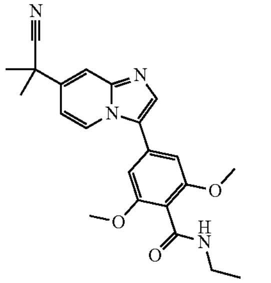 [SMILES: CCNC(=O)c1c(OC)cc(-c2cnc3cc(C(C)(C)C#N)ccn23)cc1OC] | 4-[7-(1-cyano-1-methyl-ethyl)imidazo[1,2-a]pyridin-3-yl]-N-ethyl-2,6-dimethoxy-benzamide | Int 56 + CAS# 75-04-7 | D2 | 392.5 | 393.4 |

TABLE III-continued

| Illustrative compounds of the invention. | | | | | | |
|---|---|---|---|---|---|---|
| Cpd# | Structure | Name | SM | Mtd | MW | MS Mes'd |
| 31 | 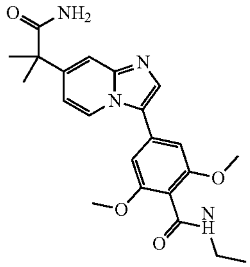 [SMILES: CCNC(=O)c1c(OC)cc(-c2cnc3cc(C(C)(C)C(N)=O)ccn23)cc1OC] | 4-[7-(2-amino-1,1-dimethyl-2-oxo-ethyl)imidazo[1,2-a]pyridin-3-yl]-N-ethyl-2,6-dimethoxy-benzamide | Int 66 + CAS# 75-04-7 | D1ii | 410.5 | 411.5 |
| 32 | 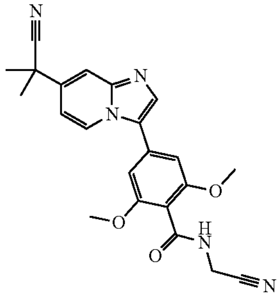 [SMILES: COc1cc(-c2cnc3cc(C(C)(C)C#N)ccn23)cc(OC)c1C(=O)NCC#N] | N-(cyanomethyl)-4-[7-(1-cyano-1-methyl-ethyl) imidazo[1,2-a]pyridin-3-yl]-2,6-dimethoxy-benzamide | Int 56 + CAS# 6011-14-9 | D2 | 403.4 | 404.3 |
| 33 | 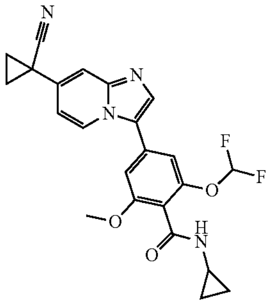 [SMILES: COc1cc(-c2cnc3cc(C4(C#N)CC4)ccn23)cc(OC(F)F)c1C(=O)NC1CC1] | 4-[7-(1-cyanocyclopropyl) imidazo[1,2-a]pyridin-3-yl]-N-cyclopropyl-2-(difluoromethoxy)-6-methoxy-benzamide | Int 68 + Int 7 | C | 438.4 | 439.2 |
| 34 | 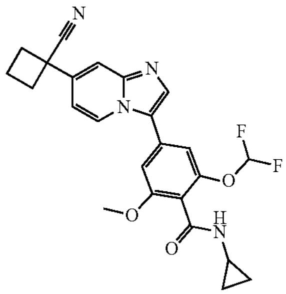 [SMILES: COc1cc(-c2cnc3cc(C4(C#N)CCC4)ccn23)cc(OC(F)F)c1C(=O)NC1CC1] | 4-[7-(1-cyanocyclobutyl) imidazo[1,2-a]pyridin-3-yl]-N-cyclopropyl-2-(difluoromethoxy)-6-methoxy-benzamide | Int 74 + Int 7 | C | 452.5 | 453.5 |
| 35 | 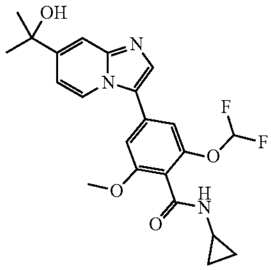 [SMILES: COc1cc(-c2cnc3cc(C(C)(C)O)ccn23)cc(OC(F)F)c1C(=O)NC1CC1] | N-cyclopropyl-2-(difluoromethoxy)-4-[7-(1-hydroxy-1-methyl-ethyl)imidazo[1,2-a]pyridin-3-yl]-6-methoxy-benzamide | Int 76 | N2 | 431.4 | 432.7 |

TABLE III-continued

| Illustrative compounds of the invention. | | | | | | |
|---|---|---|---|---|---|---|
| Cpd# | Structure | Name | SM | Mtd | MW | MS Mes'd |
| 36 | 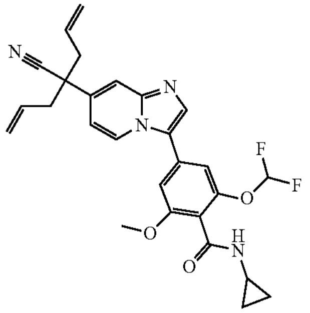 [SMILES: C=CCC(C#N)(CC=C)c1ccn2c(-c3cc(OC)c(C(=O)NC4CC4)c(OC(F)F)c3)cnc2c1] | 4-[7-(1-allyl-1-cyano-but-3-enyl)imidazo[1,2-a]pyridin-3-yl]-N-cyclopropyl-2-(difluoromethoxy)-6-methoxy-benzamide | Int 72 + Int 7 | C | 492.5 | 493.8 |
| 37 | 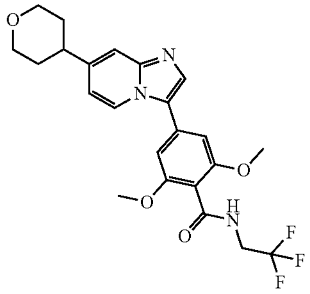 [SMILES: COc1cc(-c2cnc3cc(C4CCOCC4)ccn23)cc(OC)c1C(=O)NCC(F)(F)F] | 2,6-dimethoxy-4-(7-tetrahydropyran-4-ylimidazo[1,2-a]pyridin-3-yl)-N-(2,2,2-trifluoroethyl) benzamide | Int 77 | L | 463.4 | 464.3 |
| 38 | 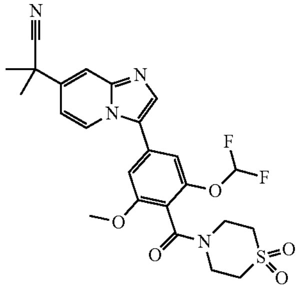 [SMILES: COc1cc(-c2cnc3cc(C(C)(C)C#N)ccn23)cc(OC(F)F)c1C(=O)N1CCS(=O)(=O)CC1] | 2-[3-[3-(difluoro methoxy)-4-(1,1-dioxo-1,4-thiazinane-4-carbonyl)-5-methoxy-phenyl] imidazo[1,2-alpyridin-7-yl]-2-methyl-propanenitrile | Int 78 + CAS# 39093-93-1 | D2 | 518.5 | 519.9 |
| 39 | 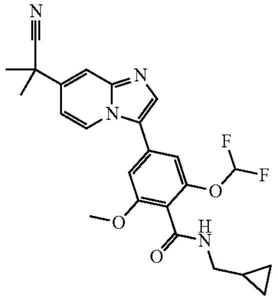 [SMILES: COc1cc(-c2cnc3cc(C(C)(C)C#N)ccn23)cc(OC(F)F)c1C(=O)NCC1CC1] | 4-[7-(1-cyano-1-methyl-ethyl)imidazo [1,2-a]pyridin-3-yl]-N-(cyclopropyl methyl)-2-(difluoro methoxy)-6-methoxy-benzamide | Int 78 + CAS# 2516-47-4 | D2 | 454.5 | 455.3 |
| 40 | 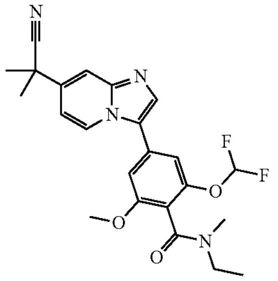 [SMILES: CCN(C)C(=O)c1c(OC)cc(-c2cnc3cc(C(C)(C)C#N)ccn23)cc1OC(F)F] | 4-[7-(1-cyano-1-methyl-ethyl) imidazo[1,2-a]pyridin-3-yl]-2-(difluoro methoxy)-N-ethyl-6-methoxy-N-methyl-benzamide | Int 78 + CAS# 624-78-2 | D2 | 442.5 | 443.3 |

TABLE III-continued

| Illustrative compounds of the invention. | | | | | | |
|---|---|---|---|---|---|---|
| Cpd# | Structure | Name | SM | Mtd | MW | MS Mes'd |
| 41 | 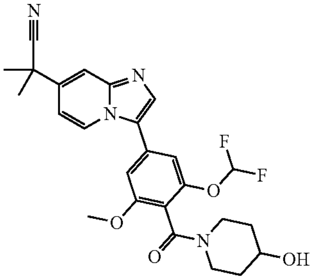 [SMILES: COc1cc(-c2cnc3cc(C(C)(C)C#N)ccn23)cc(OC(F)F)c1C(=O)N1CCC(O)CC1] | 2-[3-[3-(difluoro methoxy)-4-(4-hydroxypiperidine-1-carbonyl)-5-methoxy-phenyl] imidazo[1,2-a] pyridin-7-yl]-2-methyl-propanenitrile | Int 78 + CAS# 5382-16-1 | D2 | 484.5 | 485.3 |
| 42 | 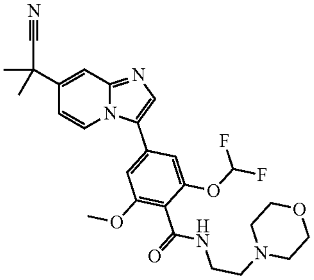 [SMILES: COc1cc(-c2cnc3cc(C(C)(C)C#N)ccn23)cc(OC(F)F)c1C(=O)NCCN1CCOCC1] | 4-[7-(1-cyano-1-methyl-ethyl)imidazo[1,2-a]pyridin-3-yl]-2-(difluoromethoxy)-6-methoxy-N-(2-morpholinoethyl) benzamide | Int 78 + CAS# 2038-03-1 | D2 | 513.5 | 514.3 |
| 43 | 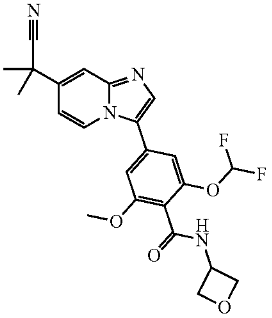 [SMILES: COc1cc(-c2cnc3cc(C(C)(C)C#N)ccn23)cc(OC(F)F)c1C(=O)NC1COC1] | 4-[7-(1-cyano-1-methyl-ethyl)imidazo[1,2-a]pyridin-3-yl]-2-(difluoromethoxy)-6-methoxy-N-(oxetan-3-yl)benzamide | Int 78 + CAS# 21635-88-1 | D2 | 456.4 | 457.2 |
| 44 | 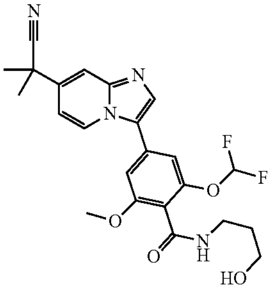 [SMILES: COc1cc(-c2cnc3cc(C(C)(C)C#N)ccn23)cc(OC(F)F)c1C(=O)NCCCO] | 4-[7-(1-cyano-1-methyl-ethyl)imidazo[1,2-a]pyridin-3-yl]-2-(difluoromethoxy)-N-(3-hydroxypropyl)-6-methoxy-benzamide | Int 78 + CAS# 156-87-6 | D2 | 458.5 | 459.3 |
| 45 | 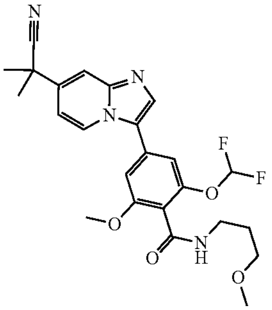 [SMILES: COCCCNC(=O)c1c(OC)cc(-c2cnc3cc(C(C)(C)C#N)ccn23)cc1OC(F)F] | 4-[7-(1-cyano-1-methyl-ethyl)imidazo[1,2-a]pyridin-3-yl]-2-(difluoromethoxy)-6-methoxy-N-(3-methoxypropyl) benzamide | Int 78 + CAS# 5332-73-0 | D2 | 472.5 | 473.3 |

TABLE III-continued

Illustrative compounds of the invention.

| Cpd# | Structure | Name | SM | Mtd | MW | MS Mes'd |
|---|---|---|---|---|---|---|
| 46 | 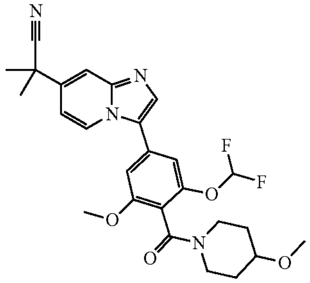 [SMILES: COc1cc(-c2cnc3cc(C(C)(C)C#N)ccn23)cc(OC(F)F)c1C(=O)N1CCC(OC)CC1] | 2-[3-[3-difluoromethoxy)-5-methoxy-4-(4-methoxypiperidine-1-carbonyl)phenyl]imidazo[1,2-a]pyridin-7-yl]-2-methyl-propanenitrile | Int 78 + CAS# 4045-24-3 | D2 | 498.5 | 499.3 |
| 47 | 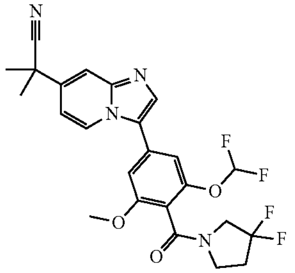 [SMILES: COc1cc(-c2cnc3cc(C(C)(C)C#N)ccn23)cc(OC(F)F)c1C(=O)N1CCC(F)(F)C1] | 2-[3-[3-(difluoromethoxy)-4-(3,3-difluoropyrrolidine-1-carbonyl)-5-methoxy-phenyl]imidazo[1,2-a]pyridin-7-yl]-2-methyl-propanenitrile | Int 78 + CAS# 163457-23-6 | D2 | 490.5 | 491.2 |
| 48 | 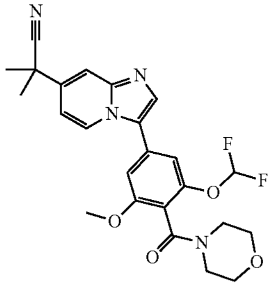 [SMILES: COc1cc(-c2cnc3cc(C(C)(C)C#N)ccn23)cc(OC(F)F)c1C(=O)N1CCOCC1] | 2-[3-[3-(difluoromethoxy)-5-methoxy-4-(morpholine-4-carbonyl)phenyl]imidazo[1,2-a]pyridin-7-yl]-2-methyl-propanenitrile | Int 78 + CAS# 110-91-8 | D2 | 470.5 | 471.2 |
| 49 | 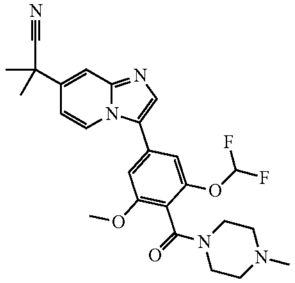 [SMILES: COc1cc(-c2cnc3cc(C(C)(C)C#N)ccn23)cc(OC(F)F)c1C(=O)N1CCN(C)CC1] | 2-[3-[3-(difluoromethoxy)-5-methoxy-4-(4-methylpiperazine-1-carbonyl)phenyl]imidazo[1,2-a]pyridin-7-yl]-2-methyl-propanenitrile | Int 78 + CAS# 109-01-3 | D2 | 483.5 | 484.3 |
| 50 | 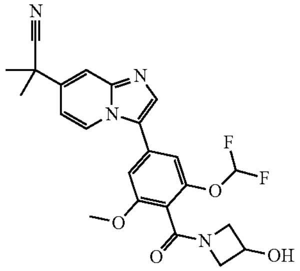 [SMILES: COc1cc(-c2cnc3cc(C(C)(C)C#N)ccn23)cc(OC(F)F)c1C(=O)N1CC(O)C1] | 2-[3-[3-(difluoromethoxy)-4-(3-hydroxyazetidine-1-carbonyl)-5-methoxy-phenyl]imidazo[1,2-a]pyridin-7-yl]-2-methyl-propanenitrile | Int 78 + CAS# 18621-18-6 | D2 | 456.4 | 457.2 |

TABLE III-continued

| Illustrative compounds of the invention. | | | | | | |
|---|---|---|---|---|---|---|
| Cpd# | Structure | Name | SM | Mtd | MW | MS Mes'd |
| 51 | 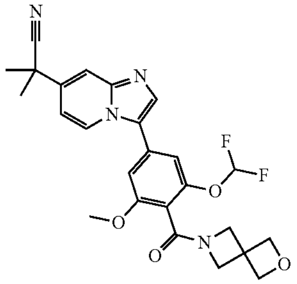 [SMILES: COc1cc(-c2cnc3cc(C(C)(C)C#N)ccn23)cc(OC(F)F)c1C(=O)N1CC2(COC2)C1] | 2-[3-[3-(difluoromethoxy)-5-methoxy-4-(2-oxa-6-azaspiro[3.3]heptane-6-carbonyl)phenyl] imidazo[1,2-a]pyridin-7-yl]-2-methyl-propanenitrile | Int 78 + CAS# 174-78-7 | D2 | 482.5 | 483.2 |
| 52 | 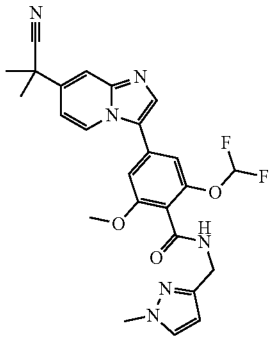 [SMILES: COc1cc(-c2cnc3cc(C(C)(C)C#N)ccn23)cc(OC(F)F)c1C(=O)NCc1ccn(C)n1] | 4-[7-(1-cyano-1-methyl-ethyl)imidazo[1,2-a]pyridin-3-yl]-2-(difluoromethoxy)-6-methoxy-N-[(1-methylpyrazol-3-yl)methyl]benzamide | Int 78 + CAS# 612511-81-6 | D2 | 494.5 | 495.2 |
| 53 | 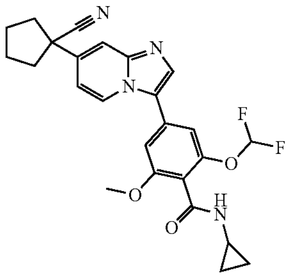 [SMILES: COc1cc(-c2cnc3cc(C4(C#N)CCCC4)ccn23)cc(OC(F)F)c1C(=O)NC1CC1] | 4-[7-(1-cyanocyclopentyl) imidazo[1,2-a]pyridin-3-yl]-N-cyclopropyl-2-(difluoromethoxy)-6-methoxy-benzamide | Int 70 + Int 7 | C | 466.5 | 467.3 |
| 54 | 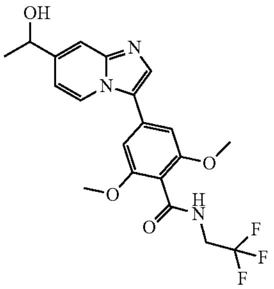 [SMILES: COc1cc(-c2cnc3cc(C(C)O)ccn23)cc(OC)c1C(=O)NCC(F)(F)F] | 4-[7-(1-hydroxyethyl) imidazo[1,2-a]pyridin-3-yl]-2,6-dimethoxy-N-(2,2,2-trifluoroethyl) benzamide | Int 81 | N1 | 423.4 | 424.2 |
| 55 | 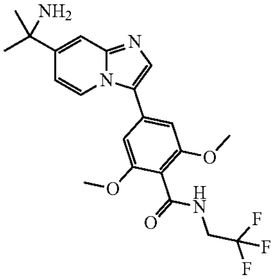 [SMILES: COc1cc(-c2cnc3cc(C(C)(C)N)ccn23)cc(OC)c1C(=O)NCC(F)(F)F] | 4-[7-(1-amino-1-methyl-ethyl)imidazo[1,2-a]pyridin-3-yl]-2,6-dimethoxy-N-(2,2,2-trifluoroethyl) benzamide | Int 79 + Int 24 | E | 436.4 | 437.8 |

TABLE III-continued

Illustrative compounds of the invention.

| Cpd# | Structure | Name | SM | Mtd | MW | MS Mes'd |
|---|---|---|---|---|---|---|
| 56 | 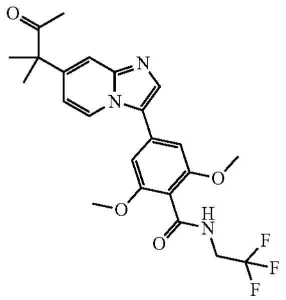 [SMILES: COc1cc(-c2cnc3cc(C(C)(C)C(C)=O)ccn23)cc(OC)c1C(=O)NCC(F)(F)F] | 4-[7-(1,1-dimethyl-2-oxo-propyl)imidazo[1,2-a]pyridin-3-yl]-2,6-dimethoxy-N-(2,2,2-trifluoroethyl) benzamide | Int 80 + Int 24 | E | 463.4 | 464.7 |
| 57 | 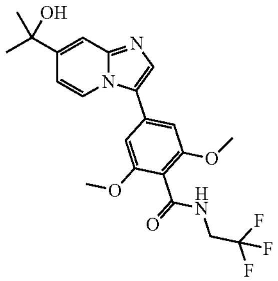 [SMILES: COc1cc(-c2cnc3cc(C(C)(C)O)ccn23)cc(OC)c1C(=O)NCC(F)(F)F] | 4-[7-(1-hydroxy-1-methyl-ethyl)imidazo[1,2-a]pyridin-3-yl]-2,6-dimethoxy-N-(2,2,2-trifluoroethyl) benzamide | Int 81 | N2 | 437.4 | 438.6 |
| 58 | 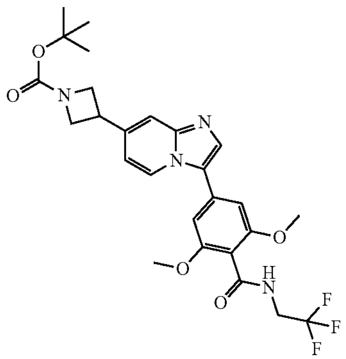 [SMILES: COc1cc(-c2cnc3cc(C4CN(C(=O)OC(C)(C)C)C4)ccn23)cc(OC)c1C(=O)NCC(F)(F)F] | tert-butyl 3-[3-[3,5-dimethoxy-4-(2,2,2-trifluoroethylcarbamoyl) phenyl]imidazo [1,2-a]pyridin-7-yl]azetidine-l-carboxylate | Int 82 + Int 24 | E | 534.5 | 534.9 |
| 59 | 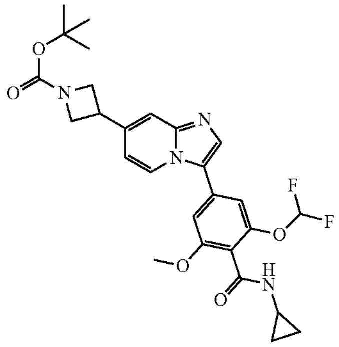 [SMILES: COc1cc(-c2cnc3cc(C4CN(C(=O)OC(C)(C)C)C4)ccn23)cc(OC(F)F)c1C(=O)NC1CC1] | tert-butyl 3-[3-[4-(cyclopropyl-carbamoyl)-3-(difluoromethoxy)-5-methoxy-phenyl]imidazo[1,2-a]pyridin-7-yl]azetidine-l-carboxylate | Int 84 + Int 7 | C | 528.5 | 529.0 |

TABLE III-continued

Illustrative compounds of the invention.

| Cpd# | Structure | Name | SM | Mtd | MW | MS Mes'd |
|---|---|---|---|---|---|---|
| 60 | 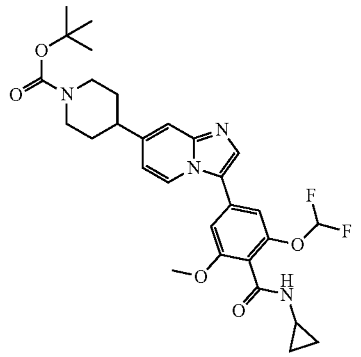 [SMILES: COc1cc(-c2cnc3cc(C4CCN(C(=O)OC(C)(C)C)CC4)ccn23)cc(OC(F)F)c1C(=O)NC1CC1] | tert-butyl 4-[3-[4-(cyclopropyl-carbamoyl)-3-(difluoromethoxy)-5-methoxy-phenyl]imidazo[1,2-a]pyridin-7-yl]piperidine-1-carboxylate | Int 85 | L | 556.6 | 557.4 |
| 61 | 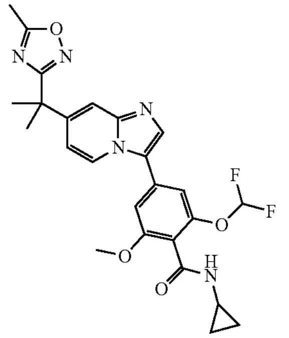 [SMILES: COc1cc(-c2cnc3cc(C(C)(C)c4noc(C)n4)ccn23)cc(OC(F)F)c1C(=O)NC1CC1] | N-cyclopropyl-2-(difluoromethoxy)-6-methoxy-4-[7-[1-methyl-1-1-(5-methyl-1,2,4-oxadiazol-3-yl)ethyl]imidazo[1,2-a]pyridin-3-yl]benzamide | Cpd 19 | Ex. 2.75 | 497.5 | 498.7 |
| 62 | 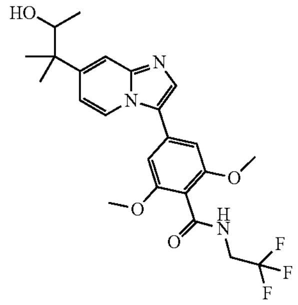 [SMILES: COc1cc(-c2cnc3cc(C(C)(C)C(C)O)ccn23)cc(OC)c1C(=O)NCC(F)(F)F] | 4-[7-(4-hydroxy-1,1-dimethyl-propyl)imidazo[1,2--a]pyridin-3-yl]-2,6-dimethoxy-N-(2,2,2-trifluoroethyl) benzamide | Cpd 56 | NI | 465.5 | 466.3 |
| 63 | 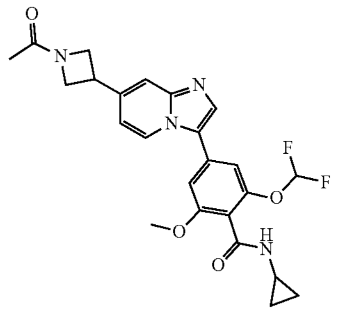 [SMILES: COc1cc(-c2cnc3cc(C4CN(C(C)=O)C4)ccn23)cc(OC(F)F)c1C(=O)NC1CC1] | 4-[7-(1-acetylazetidin-3-yl)imidazo[1,2-a]pyridin-3-yl]-N-cyclopropyl-2-(difluoromethoxy)-6-methoxy-benzamide | Int 87 | Ex. 2.76 | 470.5 | 471.3 |

TABLE III-continued

| Illustrative compounds of the invention. | | | | | | |
|---|---|---|---|---|---|---|
| Cpd# | Structure | Name | SM | Mtd | MW | MS Mes'd |
| 64 | 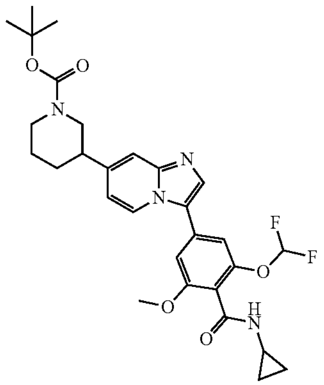 [SMILES: COc1cc(-c2cnc3cc(C4CCCN(C(=O)OC(C)(C)C)C4)ccn23)cc(OC(F)F)c1C(=O)NC1CC1] | tert-butyl 3-[3-[4-(cyclopropyl-carbamoyl)-3-(difluoromethoxy)-5-methoxy-phenyl]imidazo[1,2-a]pyridin-7-yl]piperidine-l-carboxylate | Int 88 | L | 556.6 | 557.9 |
| 65 | 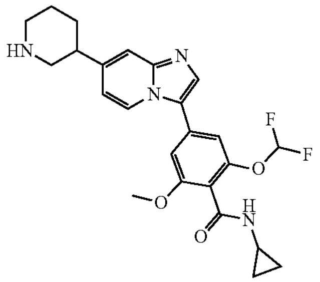 [SMILES: COc1cc(-c2cnc3cc(C4CCCNC4)ccn23)cc(OC(F)F)c1C(=O)NC1CC1] | N-cyclopropyl-2-(difluoromethoxy)-6-methoxy-4-[7-(3-piperidyl)imidazo [1,2-a]pyridin-3-yl]benzamide | Cpd 64 | M2 | 456.5 | 457.3 |
| 66 | 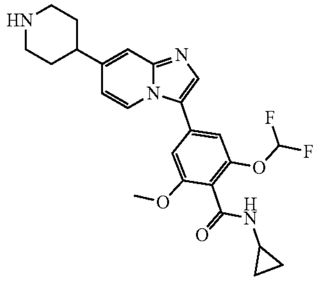 [SMILES: COc1cc(-c2cnc3cc(C4CCNCC4)ccn23)cc(OC(F)F)c1C(=O)NC1CC1] | N-cyclopropyl-2-(difluoromethoxy)-6-methoxy-4-[7-(4-piperidyl)imidazo [1,2-a]pyridin-3-yl]benzamide | Cpd 60 | M2 | 456.5 | 457.3 |
| 67 | 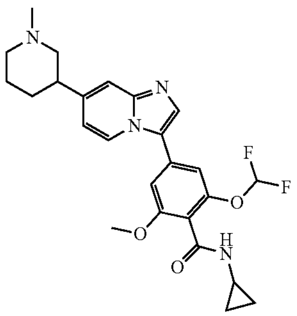 [SMILES: COc1cc(-c2cnc3cc(C4CCCN(C)C4)ccn23)cc(OC(F)F)c1C(=O)NC1CC1] | N-cyclopropyl-2-(difluoromethoxy)-6-methoxy-4-[7-(1-methyl-3-piperidyl)imidazo [1,2-a]pyridin-3-yl]benzamide | Cpd 65 | K1 | 470.5 | 471.5 |

TABLE III-continued

Illustrative compounds of the invention.

| Cpd# | Structure | Name | SM | Mtd | MW | MS Mes'd |
|---|---|---|---|---|---|---|
| 68 | 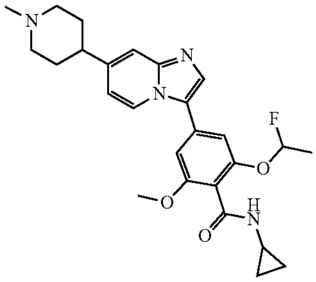 [SMILES: COc1cc(-c2cnc3cc(C4CCN(C)CC4)ccn23)cc(OC(C)F)c1C(=O)NC1CC1] | N-cyclopropyl-2-(difluoromethoxy)-6-methoxy-4-[7-(1-methyl-4-piperidyl)imidazo[1,2-a]pyridin-3-yl]benzamide | Cpd 66 | K1 | 470.5 | 471.5 |
| 69 | 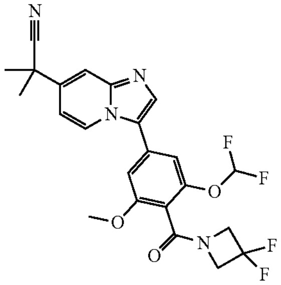 [SMILES: COc1cc(-c2cnc3cc(C(C)(C)C#N)ccn23)cc(OC(F)F)c1C(=O)N1CC(F)(F)C1] | 2-[3-[4-(3,3-difluoroazetidine-1-carbonyl)-3-(difluoromethoxy)-5-methoxy-phenyl]imidazo[1,2-a]pyridin-7-yl]-2-methyl-propanenitrile | Int 78 + CAS# 288315-03-7 | D2 | 476.4 | 477.8 |
| 70 | 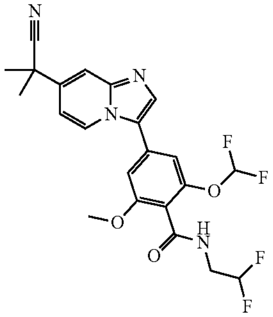 [SMILES: COc1cc(-c2cnc3cc(C(C)(C)C#N)ccn23)cc(OC(F)F)c1C(=O)NCC(F)F] | 4-[7-(1-cyano-1-methyl-ethyl)imidazo[1,2-a]pyridin-3-yl]-N-(2,2-difluoroethyl)-2-(difluoromethoxy)-6-methoxy-benzamide | Int 78 + CAS# 79667-97-7 | D2 | 464.4 | 465.8 |
| 71 | 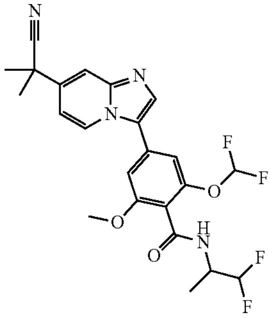 [SMILES: COc1cc(-c2cnc3cc(C(C)(C)C#N)ccn23)cc(OC(F)F)c1C(=O)NC(C)C(F)F] | 4-[7-(1-cyano-1-methyl-ethyl)imidazo[1,2-a]pyridin-3-yl]-2-(difluoromethoxy)-N-(2,2-difluoro-1-methyl-ethyl)-6-methoxy-benzamide | Int 78 + CAS# 1384427-90-+0 | D2 | 478.4 | 479.7 |
| 72 | 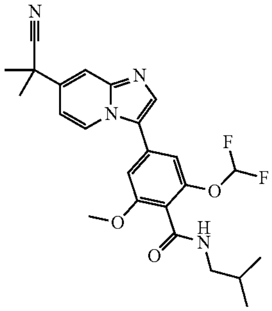 [SMILES: COc1cc(-c2cnc3cc(C(C)(C)C#N)ccn23)cc(OC(F)F)c1C(=O)NCC(C)C] | 4-[7-(1-cyano-1-methyl-ethyl)imidazo[1,2-a]pyridin-3-yl]-2-(difluoromethoxy)-N-isobutyl-6-methoxy-benzamide | Int 78 + CAS# 78-81-9 | D2 | 456.5 | 457.8 |

TABLE III-continued

Illustrative compounds of the invention.

| Cpd# | Structure | Name | SM | Mtd | MW | MS Mes'd |
|---|---|---|---|---|---|---|
| 73 | 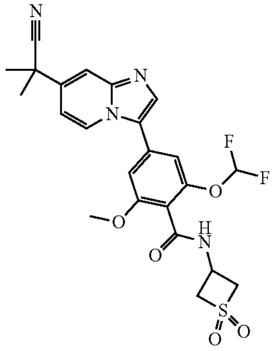 [SMILES: COc1cc(-c2cnc3cc(C(C)(C)C#N)ccn23)cc(OC(F)F)c1C(=O)NC1CS(=O)(=O)C1] | 4-[7-(1-cyano-1-methyl-ethyl)imidazo[1,2-a]pyridin-3-yl]-2-(difluoromethoxy)-N-(1,1-dioxothietan-3-yl)-6-methoxy-benzamide | Int 78 + CAS# 1422344-24-8 | D2 | 504.5 | 505.7 |
| 74 | 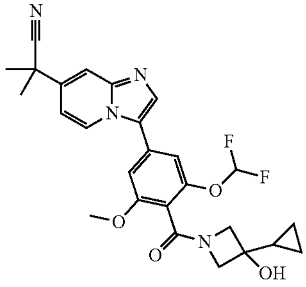 [SMILES: COc1cc(-c2cnc3cc(C(C)(C)C#N)ccn23)cc(OC(F)F)c1C(=O)N1CC(O)(C2CC2)C1] | 2-[3-[4-(3-cyclopropyl-3-hydroxy-azetidine-1-carbonyl)-3-(difluoromethoxy)-5-methoxy-phenyl]imidazo[1,2-a]pyridin-7-yl]-2-methyl-propanenitrile | Int 78 + CAS# 848192-93-8 | D2 | 496.5 | 497.8 |
| 75 | 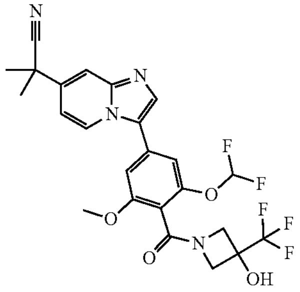 [SMILES: COc1cc(-c2cnc3cc(C(C)(C)C#N)ccn23)cc(OC(F)F)c1C(=O)N1CC(O)(C(F)(F)F)C1] | 2-[3-[3-(difluoro methoxy)-4-[3-hydroxy-3-(trifluoro-methyl)azetidine-1-carbonyl]-5-methoxy-phenyl] imidazo[1,2-a]pyridin-7-yl]-2-methyl-propanenitrile | Int 78 + CAS# 848192-96-1 | D2 | 524.4 | 526.0 |
| 76 | 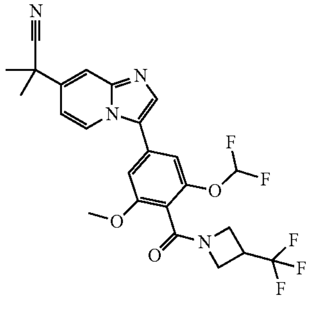 [SMILES: COc1cc(-c2cnc3cc(C(C)(C)C#N)ccn23)cc(OC(F)F)c1C(=O)N1CC(C(F)(F)F)C1] | 2-[3-[3-(difluoro methoxy)-5-methoxy-4-[3-(trifluoro methyl)azetidine-1-carbonyl]phenyl] imidazo[1,2-alpyridin-7-yl]-2-methyl-propanenitrile | Int 78 + CAS# 1221272-90-7 | D2 | 508.4 | 509.8 |

TABLE III-continued

Illustrative compounds of the invention.

| Cpd# | Structure | Name | SM | Mtd | MW | MS Mes'd |
|---|---|---|---|---|---|---|
| 77 | 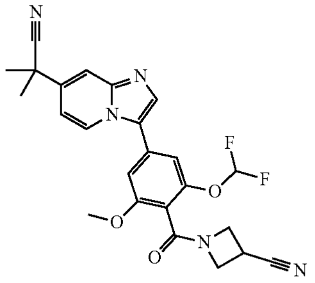 [SMILES: COc1cc(-c2cnc3cc(C(C)(C)C#N)ccn23)cc(OC(F)F)c1C(=O)N1CC(C#N)C1] | 1-[4-[7-(1-cyano-1-methyl-ethyl) imidazo[1,2-a]pyridin-3-yl]-2-(difluoro methoxy)-6-methoxy-benzoyl]azetidine-3-carbonitrile | Int 78 + CAS# 345954-83-8 | D2 | 465.5 | 466.8 |
| 78 | 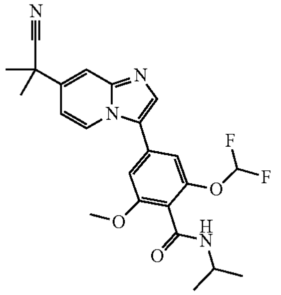 [SMILES: COc1cc(-c2cnc3cc(C(C)(C)C#N)ccn23)cc(OC(F)F)c1C(=O)NC(C)C] | 4-[7-(1-cyano-1-methyl-ethyl) imidazo[1,2-a]pyridin-3-yl]-2-(difluoro methoxy)-N-iso propyl-6-methoxy-benzamide | Int 78 + CAS# 75-31-0 | D2 | 442.5 | 443.8 |
| 79 | 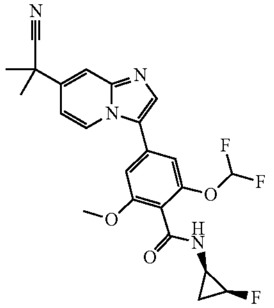 [SMILES: COc1cc(-c2cnc3cc(C(C)(C)C#N)ccn23)cc(OC(F)F)c1C(=O)N[C@@H]1C[C@@H]1F] | 4-[7-(1-cyano-1-methyl-ethyl) imidazo[1,2-a]pyridin-3-yl]-2-(difluoro methoxy)-N-[(1R,2S)-2-fluoro cyclopropyl]-6-methoxy-benzamide | Int 188 + CAS# 143062-84-4 | D1i + D1ii | 458.4 | 459.7 |
| 80 | 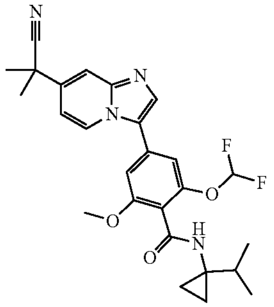 [SMILES: COc1cc(-c2cnc3cc(C(C)(C)C#N)ccn23)cc(OC(F)F)c1C(=O)NC1(C(C)C)CC1] | 4-[7-(1-cyano-1-methyl-ethyl) imidazo[1,2-a]pyridin-3-yl]-2-(difluoro methoxy)-N-(1-isopropylcyclopropyl)-yl)-6-methoxy-benzamide | Int 78 + CAS# 1215107-56-4 | D2 | 482.5 | 483.9 |
| 81 | 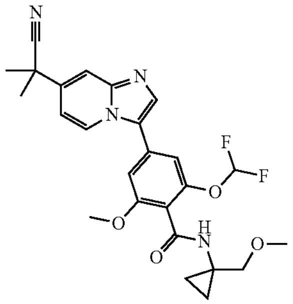 [SMILES: COCC1(NC(=O)c2c(OC)cc(-c3cnc4cc(C(C)(C)C#N)ccn34)cc2OC(F)F)CC1] | 4-[7-(1-cyano-1-methyl-ethyl) imidazo[1,2-a]pyridin-3-yl]-2-(difluoro methoxy)-6-methoxy-N-[1-(methoxy methyl)cyclopropyl] benzamide | Int 78 + CAS# 1220040-06-1 | D2 | 484.5 | 485.8 |

TABLE III-continued

Illustrative compounds of the invention.

| Cpd# | Structure | Name | SM | Mtd | MW | MS Mes'd |
|---|---|---|---|---|---|---|
| 82 | 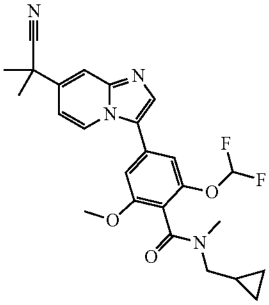 [SMILES: COc1cc(-c2cnc3cc(C(C)(C)C#N)ccn23)cc(OC(F)F)c1C(=O)N(C)CC1CC1] | 4-[7-(1-cyano-1-methyl-ethyl)imidazo[1,2-a]pyridin-3-yl]-N-(cyclopropyl methyl)-2-(difluoro methoxy)-6-methoxy-N-methyl-benzamide | Int 78 + CAS# 18977-45-2 | D2 | 468.5 | 469.7 |
| 83 | 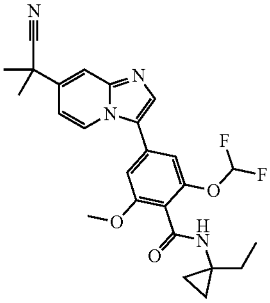 [SMILES: CCC1(NC(=O)c2c(OC)cc(-c3cnc4cc(C(C)(C)C#N)ccn34)cc2OC(F)F)CC1] | 4-[7-(1-cyano-1-methyl-ethyl)imidazo[1,2-a]pyridin-3-yl]-2-(difluorome thoxy)-N-(1-ethyl cyclopropyl)-6-methoxy-benzamide | Int 78 + CAS# 174886-06-7 | D2 | 468.5 | 469.8 |
| 84 | 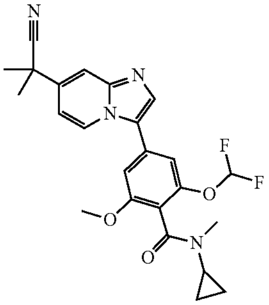 [SMILES: COc1cc(-c2cnc3cc(C(C)(C)C#N)ccn23)cc(OC(F)F)c1C(=O)N(C)C1CC1] | 4-[7-(1-cyano-1-methyl-ethyl)imidazo[1,2-a]pyridin-3-yl]-N-cyclopropyl-2-(difluoromethoxy)-6-methoxy-N-methyl-benzamide | Int 78 + CAS# 5163-20-2 | D2 | 454.5 | 455.7 |
| 85 | 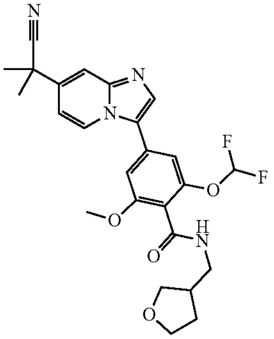 [SMILES: COc1cc(-c2cnc3cc(C(C)(C)C#N)ccn23)cc(OC(F)F)c1C(=O)NCC1CCOC1] | 4-[7-(1-cyano-1-methyl-ethyl) imidazo[1,2-a]pyridin-3-yl]-2-(difluoro methoxy)-6-methoxy-N-(tetrahydro furan-3-ylmethyl) benzamide | Int 78 + CAS# 165253-31-6 | D2 | 484.5 | 485.8 |

TABLE III-continued

Illustrative compounds of the invention.

| Cpd# | Structure | Name | SM | Mtd | MW | MS Mes'd |
|---|---|---|---|---|---|---|
| 86 | 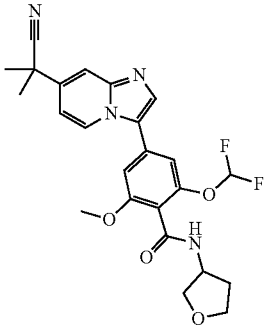 [SMILES: COc1cc(-c2cnc3cc(C(C)(C)C#N)ccn23)cc(OC(F)F)c1C(=O)NC1CCOC1] | 4-[7-(1-cyano-1-methyl-ethyl) imidazo[1,2-a]pyridin-3-yl]-2-(difluoro methoxy)-6-methoxy-N-tetrahydrofuran-3-yl-benzamide | Int 78 + CAS# 204512-94-7 | D2 | 470.5 | 471.7 |
| 87 | 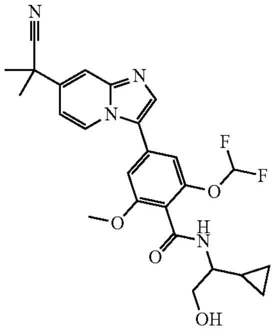 [SMILES: COc1cc(-c2cnc3cc(C(C)(C)C#N)ccn23)cc(OC(F)F)c1C(=O)NC(CO)C1CC1] | 4-[7-(1-cyano-1-methyl-ethyl) imidazo[1,2-a]pyridin-3-yl]-N-(1-cyclopropyl-2-hydroxy-ethyl)-2-(difluoro methoxy)-6-methoxy-benzamide | Int 78 + CAS# 1306603-98-4 | D2 | 484.5 | 485.7 |
| 88 | 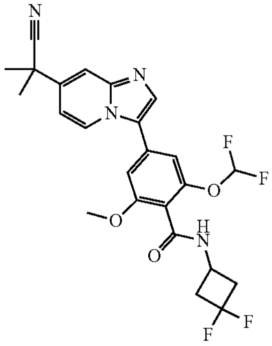 [SMILES: COc1cc(-c2cnc3cc(C(C)(C)C#N)ccn23)cc(OC(F)F)c1C(=O)NC1CC(F)(F)C1] | 4-[7-(1-cyano-1-methyl-ethyl) imidazo[1,2-a]pyridin-3-yl]-N-(3,3-difluorocyclobutyl)-2-(difluoromethoxy)-6-methoxy-benzamide | Int 78 + CAS# 791061-00-2 | D2 | 490.5 | 491.8 |
| 89 | 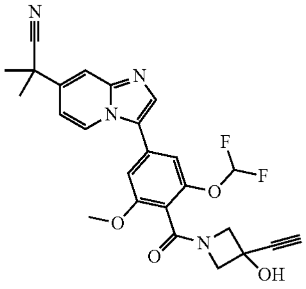 [SMILES: C#CC1(O)CN(C(=O)c2c(OC)cc(-c3cnc4cc(C(C)(C)C#N)ccn34)cc2OC(F)F)C1] | 2-[3-[3-(difluoro methoxy)-4-(3-ethynyl-3-hydroxy-azetidine-l-carbonyl)-yl)-5-methoxy-phenyl]imidazo[1,2-a] pyridin-7-yl]-2-methyl-propanenitrile | Int 78 + CAS# 1408076-23-2 | D2 | 480.5 | 481.8 |

TABLE III-continued

Illustrative compounds of the invention.

| Cpd# | Structure | Name | SM | Mtd | MW | MS Mes'd |
|---|---|---|---|---|---|---|
| 90 | 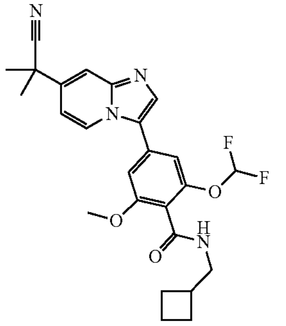 [SMILES: COc1cc(-c2cnc3cc(C(C)(C)C#N)ccn23)cc(OC(F)F)c1C(=O)NCC1CCC1] | 4-[7-(1-cyano-1-methyl-ethyl) imidazo[1,2-a]pyridin-3-yl]-N-(cyclobutyl methyl)-2-(difluoro methoxy)-6-methoxy-benzamide | Int 78 + CAS# 4415-83-2 | D2 | 468.5 | 469.8 |
| 91 | 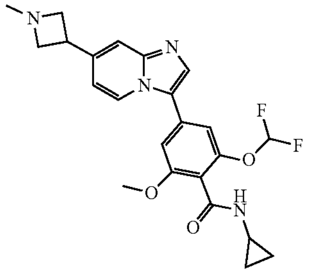 [SMILES: COc1cc(-c2cnc3cc(C4CN(C)C4)ccn23)cc(OC(F)F)c1C(=O)NC1CC1] | N-cyclopropyl-2-(difluoromethoxy)-6-methoxy-4-[7-(1-methylazetidin-3-yl)imidazo[1,2-a]pyridin-3-yl]benzamide | Int 89 | K1 | 442.5 | 443.3 |
| 92 | 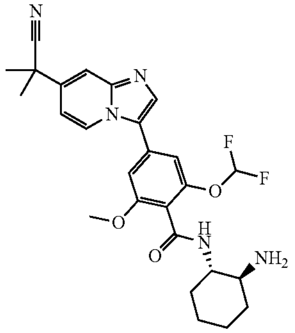 [SMILES: COc1cc(-c2cnc3cc(C(C)(C)C#N)ccn23)cc(OC(F)F)c1C(=O)N[C@H]1CCCC[C@@H]1N] | N-[(1S,2S)-2-aminocyclohexyl]-4-[7-(1-cyano-1-methyl-ethyl)imidazo [1,2-a]pyridin-3-yl]-2-(difluorome thoxy)-6-methoxy-benzamide | Int 78 + CAS# 21436-03-3 | D2 | 497.5 | 498.8 |
| 93 | 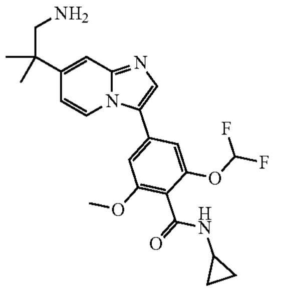 [SMILES: COc1cc(-c2cnc3cc(C(C)(C)CN)ccn23)cc(OC(F)F)c1C(=O)NC1CC1] | 4-[7-(2-amino-1,1-dimethyl-ethyl) imidazo[1,2-a]pyridin-3-yl]-N-cyclopropyl-2-(difluorome thoxy)-6-methoxy-benzamide | Cpd 19 | Ex. 2.77 | 444.5 | 445.3 |

TABLE III-continued

Illustrative compounds of the invention.

| Cpd# | Structure | Name | SM | Mtd | MW | MS Mes'd |
|---|---|---|---|---|---|---|
| 94 | 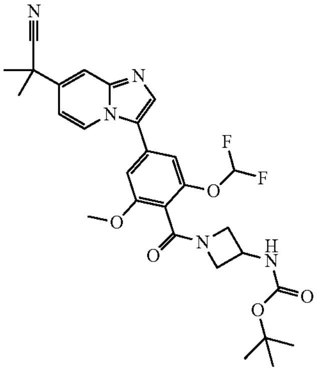 [SMILES: COc1cc(-c2cnc3cc(C(C)(C)C#N)ccn23)cc(OC(F)F)c1C(=O)N1CC(NC(=O)OC(C)(C)C)C1] | tert-butyl N-[1-[4-[7-(1-cyano-1-methyl-ethyl)imidazo[1,2-a]pyridin-3-yl]-2-(difluoromethoxy)-6-methoxy-benzoyl]azetidin-3-yl]carbamate | Int 78 + CAS# 91188-13-5 | D2 | 555.6 | 556.8 |
| 95 | 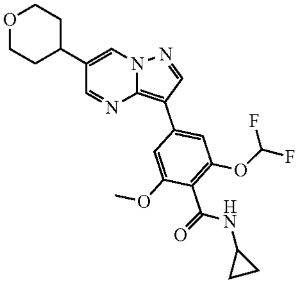 [SMILES: COc1cc(-c2cnn3cc(C4CCOCC4)cnc23)cc(OC(F)F)c1C(=O)NC1CC1] | N-cyclopropyl-2-(difluoromethoxy)-6-methoxy-4-(6-tetrahydropyran-4-ylpyrazolo[1,5-a]pyrimidin-3-yl)benzamide | Int 90 | L | 458.5 | 459.3 |
| 96 | 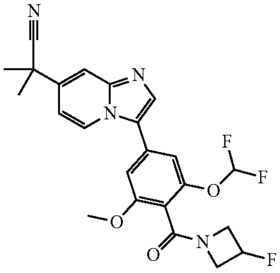 [SMILES: COc1cc(-c2cnc3cc(C(C)(C)C#N)ccn23)cc(OC(F)F)c1C(=O)N1CC(F)C1] | 2-[3-[3-(difluoromethoxy)-4-(3-fluoroazetidine-1-carbonyl)-5-methoxy-phenyl]imidazo[1,2-a]pyridin-7-yl]-2-methyl-propanenitrile | Int 78 + CAS# 617718-46-4 | D2 | 458.4 | 459.3 |
| 97 | 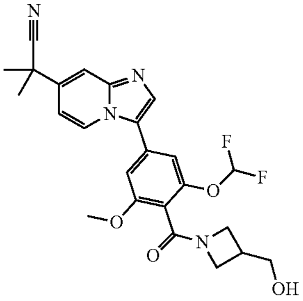 [SMILES: COc1cc(-c2cnc3cc(C(C)(C)C#N)ccn23)cc(OC(F)F)c1C(=O)N1CC(CO)C1] | 2-[3-[3-(difluoromethoxy)-4-[3-(hydroxymethyl)azetidine-1-carbonyl]-5-methoxy-phenyl]imidazo[1,2-a]pyridin-7-yl]-2-methyl-propanenitrile | Int 78 + CAS# 928038-44-2 | D2 | 470.5 | 471.3 |
| 98 | 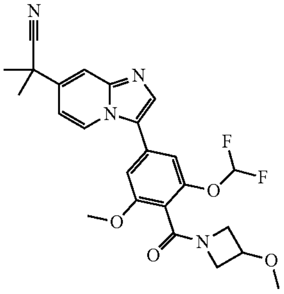 [SMILES: COc1cc(-c2cnc3cc(C(C)(C)C#N)ccn23)cc(OC(F)F)c1C(=O)N1CC(OC)C1] | 2-[3-[3-(difluoromethoxy)-5-methoxy-4-(3-methoxyazetidine-1-carbonyl)phenyl]imidazo[1,2-a]pyridin-7-yl]-2-methyl-propanenitrile | Int 78 + CAS# 148644-09-1 | D2 | 470.5 | 471.8 |

TABLE III-continued

| Illustrative compounds of the invention. | | | | | | |
|---|---|---|---|---|---|---|
| Cpd# | Structure | Name | SM | Mtd | MW | MS Mes'd |
| 99 | 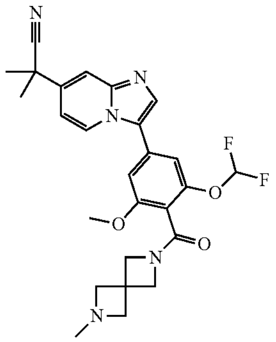 [SMILES: COc1cc(-c2cnc3cc(C(C)(C)C#N)ccn23)cc(OC(F)F)c1C(=O)N1CC2(CN(C)C2)C1] | 2-[3-[3-(difluoromethoxy)-5-methoxy-4-(6-methyl-2,6-diazaspiro[3.3]heptane-2-carbonyl)phenyl]imidazo[1,2-a]pyridin-7-yl]-2-methyl-propanenitrile | Int 78 + CAS# 1203567-11-6 | D2 | 495.5 | 496.8 |
| 100 | 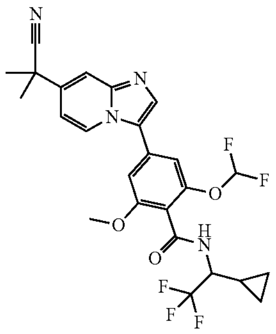 [SMILES: COc1cc(-c2cnc3cc(C(C)(C)C#N)ccn23)cc(OC(F)F)c1C(=O)NC(C1CC1)C(F)(F)F] | 4-[7-(1-cyano-1-methyl-ethyl)imidazo[1,2-a]pyridin-3-yl]-N-(1-cyclopropyl-2,2,2-trifluoro-ethyl)-2-(difluoromethoxy)-6-methoxy-benzamide | Int 78 + CAS# 75702-99-7 | D2 | 522.5 | 523.7 |
| 101 | 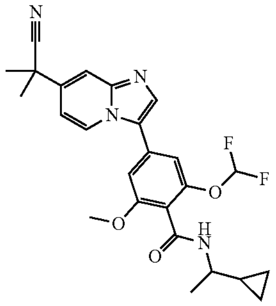 [SMILES: COc1cc(-c2cnc3cc(C(C)(C)C#N)ccn23)cc(OC(F)F)c1C(=O)NC(C)C1CC1] | 4-[7-(1-cyano-1-methyl-ethyl)imidazo[1,2-a]pyridin-3-yl]-N-(1-cyclo-propylethyl)-2-(difluoromethoxy)-6-methoxy-benzamide | Int 78 + CAS# 42390-64-7 | D2 | 468.5 | 469.8 |
| 102 | 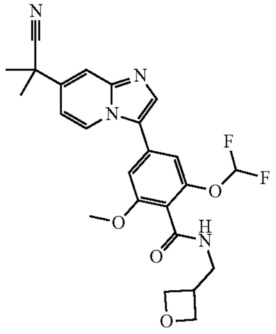 [SMILES: COc1cc(-c2cnc3cc(C(C)(C)C#N)ccn23)cc(OC(F)F)c1C(=O)NCC1COC1] | 4-[7-(1-cyano-1-methyl-ethyl) imidazo[1,2-a] pyridin-3-yl]-2-(difluoro methoxy)-6-methoxy-N-(oxetan-3-yl methyl)benzamide | Int 78 + CAS# 6246-05-5 | D2 | 470.5 | 471.7 |

TABLE III-continued

Illustrative compounds of the invention.

| Cpd# | Structure | Name | SM | Mtd | MW | MS Mes'd |
|---|---|---|---|---|---|---|
| 103 | 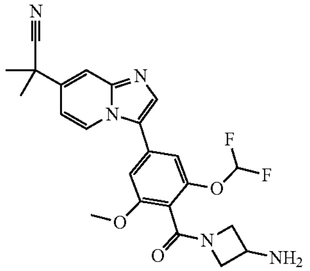 [SMILES: COc1cc(-c2cnc3cc(C(C)(C)C#N)ccn23)cc(OC(F)F)c1C(=O)N1CC(N)C1] | 2-[3-[4-(3-amino azetidine-1-carbonyl)-3-(difluoro methoxy)-5-methoxy-phenyl]imidazo [1,2-a]pyridin-7-yl]-2-methyl-propanenitrile | Cpd 94 | M1 | 455.5 | 456.3 |
| 104 | 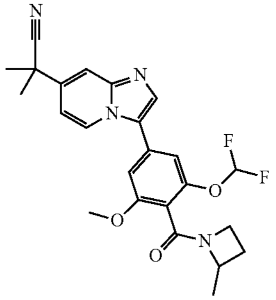 [SMILES: COc1cc(-c2cnc3cc(C(C)(C)C#N)ccn23)cc(OC(F)F)c1C(=O)N1CCC1C] | 2-[3-[3-(difluoro methoxy)-5-methoxy-4-(2-methylazetidine-1-carbonyl)phenyl] imidazo[1,2-a] pyridin-7-yl]-2-methyl-propanenitrile | Int 78 + CAS# 1152113-37-5 | D2 | 454.5 | 455.3 |
| 105 | 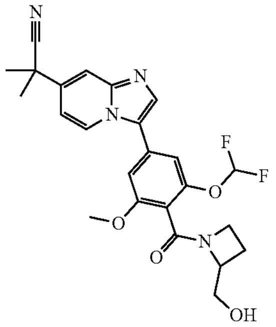 [SMILES: COc1cc(-c2cnc3cc(C(C)(C)C#N)ccn23)cc(OC(F)F)c1C(=O)N1CCC1CO] | 2-[3-[3-(difluoro methoxy)-4-[2-(hydroxymethyl) azetidine-1-carbonyl]-5-methoxy-phenyl imidazo[1,2-a] pyridin-7-yl]-2-methyl-propanenitrile | Int 78 + CAS# 250274-91-0 | D2 | 470.5 | 471.3 |
| 106 | 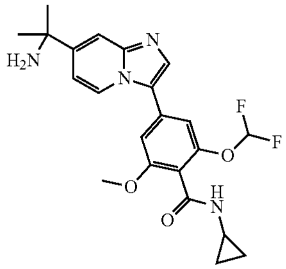 [SMILES: COc1cc(-c2cnc3cc(C(C)(C)N)ccn23)cc(OC(F)F)c1C(=O)NC1CC1] | 4-[7-(1-amino-1-methyl-ethyl)imidazo[1,2-a]pyridin-3-yl]-N-cyclopropyl-2-(difluoromethoxy)-6-methoxy-benzamide | Cpd 19 | V | 430.4 | 431.3 |
| 107 | 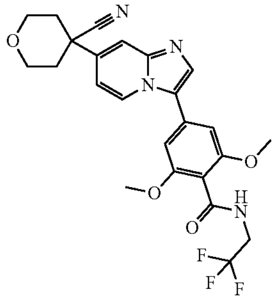 [SMILES: COc1cc(-c2cnc3cc(C4(C#N)CCOCC4)ccn23)cc(OC)c1C(=O)NCC(F)(F)F] | 4-[7-(4-cyanotetrahydro-pyran-4-yl)imidazo[1,2-a]pyridin-3-yl]-2,6-dimethoxy-N-(2,2,2-trifluoroethyl) benzamide | Int 36 + CAS# 4295-99-2 | A9 | 488.5 | 489.3 |

TABLE III-continued

Illustrative compounds of the invention.

| Cpd# | Structure | Name | SM | Mtd | MW | MS Mes'd |
|---|---|---|---|---|---|---|
| 108 | 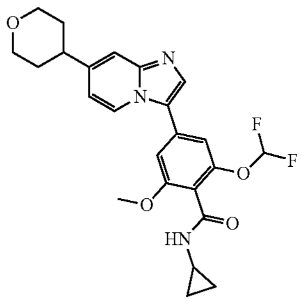 [SMILES: COc1cc(-c2cnc3cc(C4CCOCC4)ccn23)cc(OC(F)F)c1C(=O)NC1CC1] | N-cyclopropyl-2-(difluoromethoxy)-6-methoxy-4-(7-tetrahydropyran-4-ylimidazo[1,2-a]pyridin-3-yl)benzamide | Int 92 | L | 457.5 | 458.3 |
| 109 | 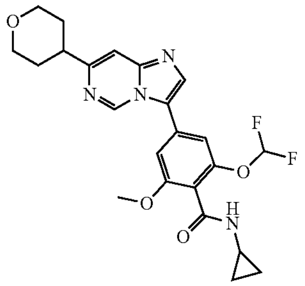 [SMILES: COc1cc(-c2cnc3cc(C4CCOCC4)ncn23)cc(OC(F)F)c1C(=O)NC1CC1] | N-cyclopropyl-2-(difluoromethoxy)-6-methoxy-4-(7-tetrahydropyran-4-ylimidazo[1,2-c]pyrimidin-3-yl)benzamide | Int 93 + Int 4 | E | 458.5 | 459.7 |
| 110 | 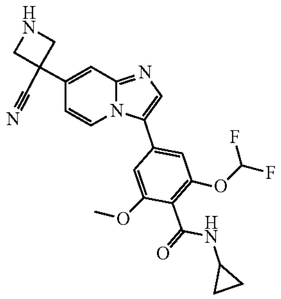 [SMILES: COc1cc(-c2cnc3cc(C4(C#N)CNC4)ccn23)cc(OC(F)F)c1C(=O)NC1CC1] | 4-[7-(3-cyanoazetidin-3-yl)imidazo[1,2-a]pyridin-3-yl]-N-cyclopropyl-2-(difluoromethoxy)-6-methoxy-benzamide | Int 95 | M1 | 453.4 | 454.3 |
| 111 | 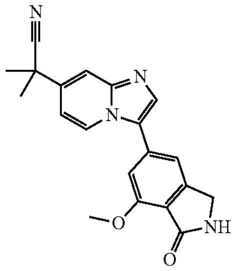 [SMILES: COc1cc(-c2cnc3cc(C(C)(C)C#N)ccn23)cc2c1C(=O)NC2] | 2-[3-(7-methoxy-1-oxo-isoindolin-5-yl)imidazo[1,2-a]pyridin-7-yl]-2-methyl-propanenitrile | Int 58 + CAS# 20870-90-0 | E | 346.4 | 347.3 |
| 112 | 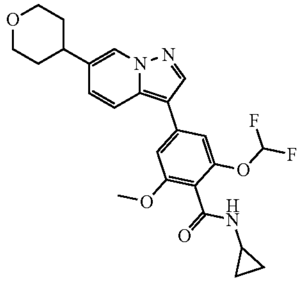 [SMILES: COc1cc(-c2cnn3cc(C4CCOCC4)ccc23)cc(OC(F)F)c1C(=O)NC1CC1] | N-cyclopropyl-2-(difluoromethoxy)-6-methoxy-4-(6-tetrahydropyran-4-ylpyrazolo[1,5-a]pyridin-3-yl)benzamide | Int 97 + Int 7 | C | 457.5 | 458.3 |

TABLE III-continued

| Cpd# | Structure | Name | SM | Mtd | MW | MS Mes'd |
|---|---|---|---|---|---|---|
| | Illustrative compounds of the invention. | | | | | |
| 113 | 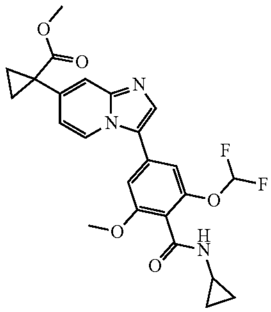 [SMILES: COC(=O)C1(c2ccn3c(-c4cc(OC)c(C(=O)NC5CC5)c(OC(F)F)c4)cnc3c2)CC1] | methyl 1-[3-[4-(cyclopropyl-carbamoyl)-3-(difluoromethoxy)-5-methoxy-phenyl]imidazo[1,2-a]pyridin-7-yl]cyclopropane-carboxylate | Int 100 + Int 4 | E | 471.5 | 472.6 |
| 114 | 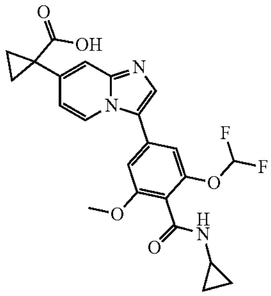 [SMILES: COc1cc(-c2cnc3cc(C4(C(=O)O)CC4)ccn23)cc(OC(F)F)c1C(=O)NC1CC1] | 1-[3-[4-(cyclopropyl-carbamoyl)-3-(difluoromethoxy)-5-methoxy-phenyl]imidazo[1,2-a]pyridin-7-yl]cyclopropane-carboxylic acid | Cpd 113 | D2i | 457.4 | 458.5 |
| 115 | 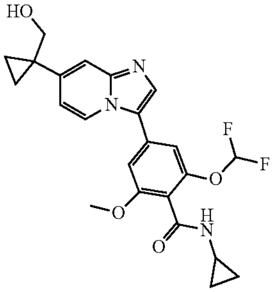 [SMILES: COc1cc(-c2cnc3cc(C4(CO)CC4)ccn23)cc(OC(F)F)c1C(=O)NC1CC1] | N-cyclopropyl-2-(difluoromethoxy)-4-[7-[1-(hydroxyl methyl)cyclopropyl] imidazo[1,2-a] pyridin-3-yl]-6-methoxy-benzamide | Cpd 114 | Ex. 2.78 | 443.4 | 444.4 |
| 116 | 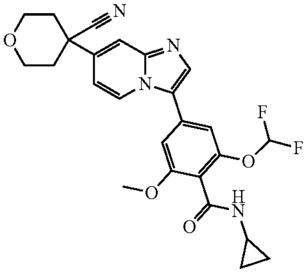 [SMILES: COc1cc(-c2cnc3cc(C4(C#N)CCOCC4)ccn23)cc(OC(F)F)c1C(=O)NC1CC1] | 4-[7-(4-cyanotetra hydropyran-4-yl) imidazo[1,2-a] pyridin-3-yl]-N-cyclo propyl-2-(difluoro methoxy)-6-methoxy-benzamide | Int 101 + Int 4 | E | 482.5 | 483.4 |
| 117 | 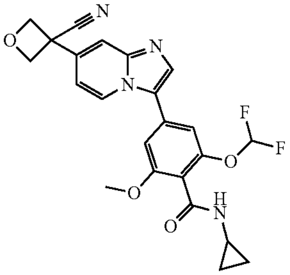 [SMILES: COc1cc(-c2cnc3cc(C4(C#N)COC4)ccn23)cc(OC(F)F)c1C(=O)NC1CC1] | 4-[7-(3-cyanooxetan-3-yl)imidazo[1,2-a]pyridin-3-yl]-N-cyclopropyl-2-(difluoromethoxy)-6-methoxy-benzamide | Int 102 + Int 4 | E | 454.4 | 455.3 |

TABLE III-continued

| Illustrative compounds of the invention. | | | | | | |
|---|---|---|---|---|---|---|
| Cpd# | Structure | Name | SM | Mtd | MW | MS Mes'd |
| 118 | 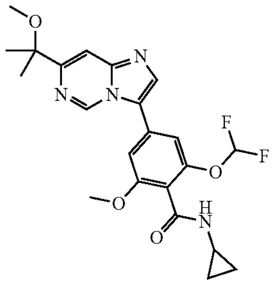 [SMILES: COc1cc(-c2cnc3cc(C(C)(C)OC)ncn23)cc(OC(F)F)c1C(=O)NC1CC1] | N-cyclopropyl-2-(difluoromethoxy)-6-methoxy-4-[7-(1-methoxy-1-methyl-ethyl)imidazo[1,2-c]pyrimidin-3-yl]benzamide | Int 103 + Int 4 | E | 446.4 | 447.6 |
| 119 | 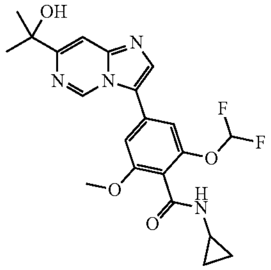 [SMILES: COc1cc(-c2cnc3cc(C(C)(C)O)ncn23)cc(OC(F)F)c1C(=O)NC1CC1] | N-cyclopropyl-2-(difluoromethoxy)-4-[7-(1-hydroxy-1-methyl-ethyl)imidazo[1,2-c]pyrimidin-3-yl]-6-methoxy-benzamide | Int 104 + Int 4 | E | 432.4 | 433.6 |
| 120 | 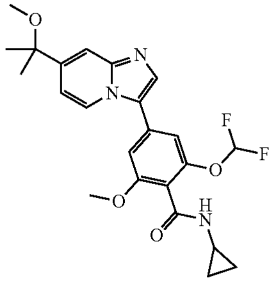 [SMILES: COc1cc(-c2cnc3cc(C(C)(C)OC)ccn23)cc(OC(F)F)c1C(=O)NC1CC1] | N-cyclopropyl-2-(difluoromethoxy)-6-methoxy-4-[7-(1-methoxy-1-methyl-ethyl)imidazo[1,2-a]pyridin-3-yl]benzamide | Int 105 + Int 4 | E | 445.5 | 446.5 |
| 121 | 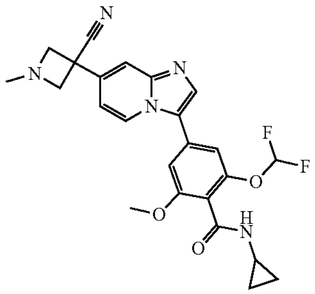 [SMILES: COc1cc(-c2cnc3cc(C4(C#N)CN(C)C4)ccn23)cc(OC(F)F)c1C(=O)NC1CC1] | 4-[7-(3-cyano-1-methyl-azetidin-3-yl)imidazo[1,2-a]pyridin-3-yl]-N-cyclopropyl-2-(difluoromethoxy)-6-methoxy-benzamide | Int 107 + Int 4 | E | 467.5 | 468.5 |
| 122 | 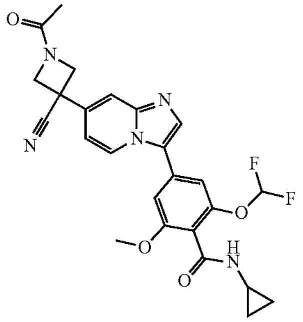 [SMILES: COc1cc(-c2cnc3cc(C4(C#N)CN(C(C)=O)C4)ccn23)cc(OC(F)F)c1C(=O)NC1CC1] | 4-[7-(1-acetyl-3-cyano-azetidin-3-yl)imidazo[1,2-a]pyridin-3-yl]-N-cyclopropyl-2-(difluoromethoxy)-6-methoxy-benzamide | Int 108 | J | 495.5 | 496.5 |

TABLE III-continued

| Illustrative compounds of the invention. | | | | | | | |
|---|---|---|---|---|---|---|---|
| Cpd# | Structure | Name | SM | Mtd | MW | MS Mes'd |
| 123 | 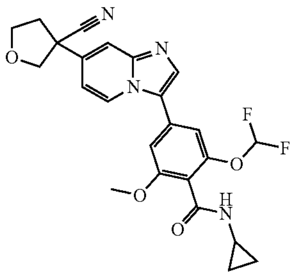 [SMILES: COc1cc(-c2cnc3cc(C4(C#N)CCOC4)ccn23)cc(OC(F)F)c1C(=O)NC1CC1] | 4-[7-(3-cyanotetrahydro-furan-3-yl)imidazo[1,2-a]pyridin-3-yl]-N-cyclopropyl-2-(difluoromethoxy)-6-methoxy-benzamide | Int 111 + Int 4 | E | 468.5 | 469.3 |
| 124 | 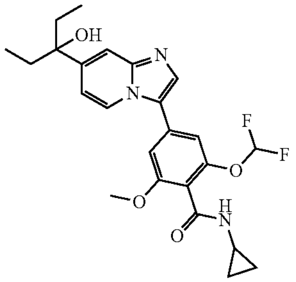 [SMILES: CCC(O)(CC)c1ccn2c(-c3cc(OC)c(C(=O)NC4CC4)c(OC(F)F)c3)cnc2c1] | N-cyclopropyl-2-(difluoromethoxy)-4-[7-(1-ethyl-1-hydroxy-propyl)imidazo[1,2-a]pyridin-3-yl]-6-methoxy-benzamide | Int 112 + Int 4 | E | 459.5 | 460.5 |
| 125 | 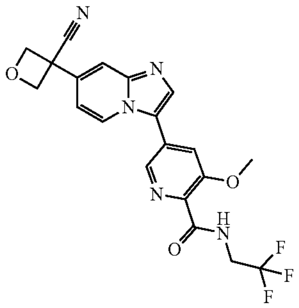 [SMILES: COc1cc(-c2cnc3cc(C4(C#N)COC4)ccn23)cnc1C(=O)NCC(F)(F)F] | 5-[7-(3-cyanooxetan-3-yl)imidazo[1,2-a]pyridin-3-yl]-3-methoxy-N-(2,2,2-trifluoroethyl)pyridine-2-carboxamide | Int 109 + Int 102 | E | 431.4 | 432.5 |
| 126 | 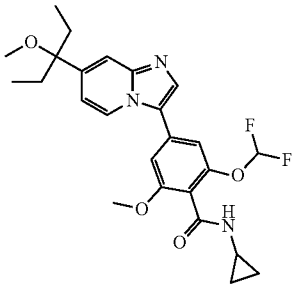 [SMILES: CCC(CC)(OC)c1ccn2c(-c3cc(OC)c(C(=O)NC4CC4)c(OC(F)F)c3)cnc2c1] | N-cyclopropyl-2-(difluoromethoxy)-4-[7-(1-ethyl-1-methoxy-propyl)imidazo[1,2-a]pyridin-3-yl]-6-methoxy-benzamide | Int 110 + Int 4 | E | 473.5 | 474.5 |
| 127 | 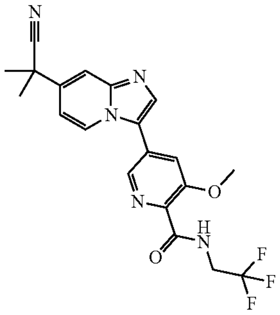 [SMILES: COc1cc(-c2cnc3cc(C(C)(C)C#N)ccn23)cnc1C(=O)NCC(F)(F)F] | 5-[7-(1-cyano-1-methyl-ethyl)imidazo[1,2-a]pyridin-3-yl]-3-methoxy-N-(2,2,2-trifluoroethyl)pyridine-2-carboxamide | Int 58 + Int 109 | E | 417.4 | 418.5 |

TABLE III-continued

Illustrative compounds of the invention.

| Cpd# | Structure | Name | SM | Mtd | MW | MS Mes'd |
|---|---|---|---|---|---|---|
| 128 | 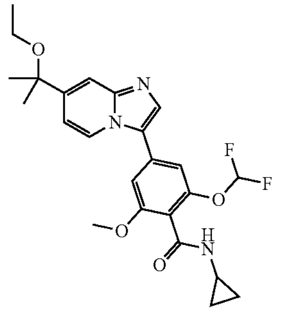 [SMILES: CCOC(C)(C)c1ccn2c(-c3cc(OC)c(C(=O)NC4CC4)c(OC(F)F)c3)cnc2c1] | N-cyclopropyl-2-(difluoromethoxy)-4-[7-(1-ethoxy-1-methyl-ethyl)imidazo[1,2-a]pyridin-3-yl]-6-methoxy benzamide | Int 113 + Int 4 | E | 459.5 | 460.5 |
| 129 | 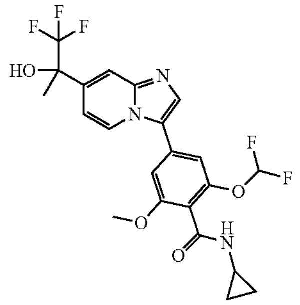 [SMILES: COc1cc(-c2cnc3cc(C(C)(O)C(F)(F)F)ccn23)cc(OC(F)F)c1C(=O)NC1CC1] | N-cyclopropyl-2-(difluoromethoxy)-6-methoxy-4-[7-(2,2,2-trifluoro-l-hydroxy-1-methyl-ethyl)imidazo[1,2-a]pyridin-3-yl]benzamide | Int 114 + Int 4 | E | 485.4 | 486.4 |
| 130 | 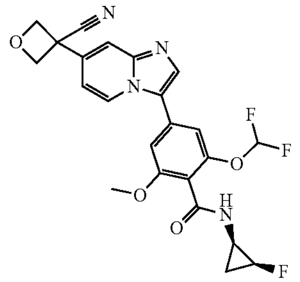 [SMILES: COc1cc(-c2cnc3cc(C4(C#N)COC4)ccn23)cc(OC(F)F)c1C(=O)N[C@@H]1C[C@@H]1F] | 4-[7-(3-cyanooxetan-3-yl)imidazo[1,2-a]pyridin-3-yl]-2-(difluoromethoxy)-N-[(1R,2S)-2-fluorocyclopropyl]-6-methoxy-benzamide | Int 115 + CAS# 143062-84-4 | D1i + D1ii | 472.4 | 473.4 |
| 131 | 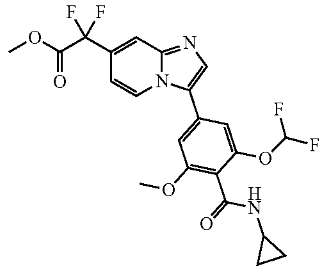 [SMILES: COC(=O)C(F)(F)c1ccn2c(-c3cc(OC)c(C(=O)NC4CC4)c(OC(F)F)c3)cnc2c1] | methyl 2-[3-[4-(cyclopropyl-carbamoyl)-3-(difluoromethoxy)-5-methoxy-phenyl]imidazo[1,2-a]pyridin-7-yl]-2,2-difluoro-acetate | Cpd 132 | Ex. 2.79 | 481.4 | 482.4 |
| 132 | 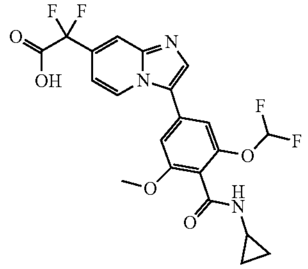 [SMILES: COc1cc(-c2cnc3cc(C(F)(F)C(=O)O)ccn23)cc(OC(F)F)c1C(=O)NC1CC1] | 2-[3-[4-(cyclopropyl-carbamoyl)-3-(difluoromethoxy)-5-methoxy-phenyl]imidazo[1,2-a]pyridin-7-yl]-2,2-difluoro-acetic acid | Int 116 + Int 4 | Ex. 2.80 | 467.4 | 468.4 |

TABLE III-continued

Illustrative compounds of the invention.

| Cpd# | Structure | Name | SM | Mtd | MW | MS Mes'd |
|---|---|---|---|---|---|---|
| 133 | 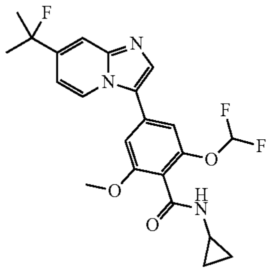 [SMILES: COc1cc(-c2cnc3cc(C(C)(C)F)ccn23)cc(OC(F)F)c1C(=O)NC1CC1] | N-cyclopropyl-2-(difluoromethoxy)-4-[7-(1-fluoro-1-methyl-ethyl)imidazo[1,2-a]pyridin-3-yl]-6-methoxy benzamide | Int 117 + Int 4 | E | 433.4 | 434.2 |
| 134 | 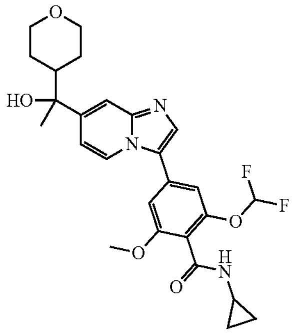 [SMILES: COc1cc(-c2cnc3cc(C(C)(O)C4CCOCC4)ccn23)cc(OC(F)F)c1C(=O)NC1CC1] | N-cyclopropyl-2-(difluoromethoxy)-4-[7-(1-hydroxy-1-tetrahydropyran-4-yl-ethyl)imidazo[1,2-a]pyridin-3-yl]-6-methoxy-benzamide | Int 118 + Int 4 | E | 501.5 | 502.5 |
| 135 | 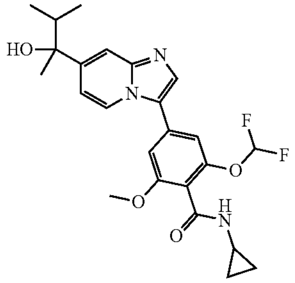 [SMILES: COc1cc(-c2cnc3cc(C(C)(O)C(C)C)ccn23)cc(OC(F)F)c1C(=O)NC1CC1] | N-cyclopropyl-2-(difluoromethoxy)-4-[7-(1-hydroxy-1,2-dimethyl-propyl)imidazo[1,2-a]pyridin-3-yl]-6-methoxy-benzamide | Int 119 + Int 4 | E | 459.5 | 460.3 |
| 136 | 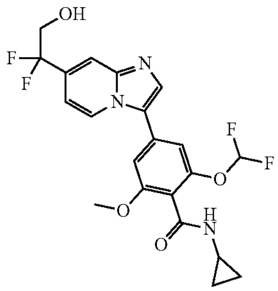 [SMILES: COc1cc(-c2cnc3cc(C(F)(F)CO)ccn23)cc(OC(F)F)c1C(=O)NC1CC1] | N-cyclopropyl-4-[7-(1,1-difluoro-2-hydroxy-ethyl)imidazo[1,2-a]pyridin-3-yl]-2-(difluoromethoxy)-6-methoxy-benzamide | Cpd 131 | Ex. 2.81 | 453.4 | 454.4 |
| 137 | 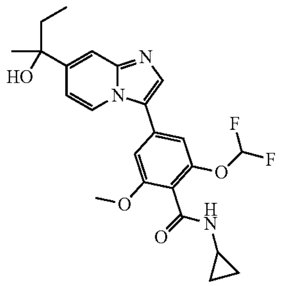 [SMILES: CCC(C)(O)c1ccn2c(-c3cc(OC)c(C(=O)NC4CC4)c(OC(F)F)c3)cnc2c1] | N-cyclopropyl-2-(difluoromethoxy)-4-[7-(1-hydroxy-1-methyl-propyl)imidazo[1,2-a]pyridin-3-yl]-6-methoxy-benzamide | Int 120 + Int 4 | E | 445.5 | 446.5 |

TABLE III-continued

| Illustrative compounds of the invention. | | | | | | |
|---|---|---|---|---|---|---|
| Cpd# | Structure | Name | SM | Mtd | MW | MS Mes'd |
| 138 | 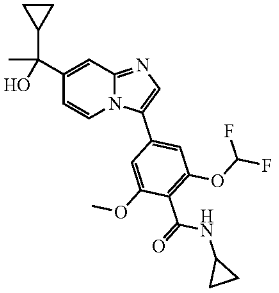 [SMILES: COc1cc(-c2cnc3cc(C(C)(O)C4CC4)ccn23)cc(OC(F)F)c1C(=O)NC1CC1] | N-cyclopropyl-4-[7-(1-cyclopropyl-1-hydroxy-ethyl)imidazo[1,2-a]pyridin-3-yl]-2-(difluoromethoxy)-6-methoxy-benzamide | Int 121 + Int 4 | E | 457.5 | 458.4 |
| 139 | 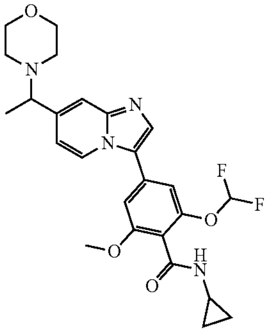 [SMILES: COc1cc(-c2cnc3cc(C(C)N4CCOCC4)ccn23)cc(OC(F)F)c1C(=O)NC1CC1] | N-cyclopropyl-2-(difluoromethoxy)-6-methoxy-4-[7-(1-morpholinoethyl) imidazo[1,2-a]pyridin-3-yl]benzamide | Int 122 + Int 4 | E | 486.5 | 487.3 |
| 140 | 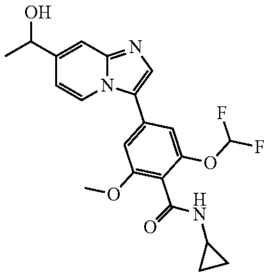 [SMILES: COc1cc(-c2cnc3cc(C(C)O)ccn23)cc(OC(F)F)c1C(=O)NC1CC1] | N-cyclopropyl-2-(difluoromethoxy)-4-[7-(1-hydroxyethyl) imidazo[1,2-a]pyridin-3-yl]-6-methoxy-benzamide | Int 76 | N1 | 417.4 | 418.3 |
| 141 | 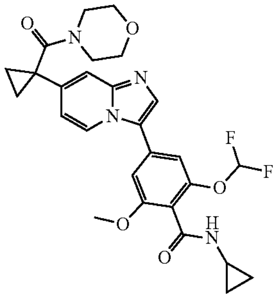 [SMILES: COc1cc(-c2cnc3cc(C4(C(=O)N5CCOCC5)CC4)ccn23)cc(OC(F)F)c1C(=O)NC1CC1] | N-cyclopropyl-2-(difluoromethoxy)-6-methoxy-4-[7-[1-(morpholine-4-carbonyl)cyclopropyl] imidazo[1,2-a]pyridin-3-yl]benzamide | Cpd 114 + CAS# 110-91-8 | D1ii | 526.5 | 527.5 |
| 142 | 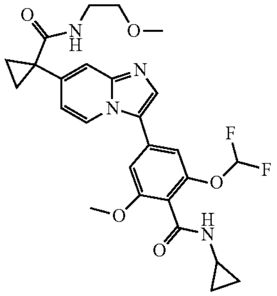 [SMILES: COCCNC(=O)C1(c2ccn3c(-c4cc(OC)c(C(=O)NC5CC5)c(OC(F)F)c4)cnc3c2)CC1] | N-cyclopropyl-2-(difluoromethoxy)-6-methoxy-4-[7-[1-(2-methoxyethyl-carbamoypcyclopropyl] imidazo[1,2-a]pyridin-3-yl]benzamide | Cpd 114 + CAS# 109-85-3 | D1ii | 514.5 | 516.4 |

TABLE III-continued

Illustrative compounds of the invention.

| Cpd# | Structure | Name | SM | Mtd | MW | MS Mes'd |
|---|---|---|---|---|---|---|
| 143 | 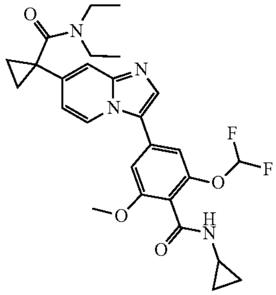 [SMILES: CCN(CC)C(=O)C1(c2ccn3c(-c4cc(OC)c(C(=O)NC5CC5)c(OC(F)F)c4)cnc3c2)CC1] | N-cyclopropyl-4-[7-[1-(diethylcarbamoyl) cyclopropyl]imidazo [1,2-a]pyridin-3-yl]-2-(difluoromethoxy)-6-methoxy-benzamide | Cpd 114 + CAS# 109-89-7 | D1ii | 512.5 | 513.3 |
| 144 | 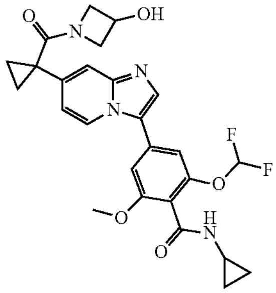 [SMILES: COc1cc(-c2cnc3cc(C4(C(=O)N5CC(O)C5)CC4)ccn23)cc(OC(F)F)c1C(=O)NC1CC1] | N-cyclopropyl-2-(difluoromethoxy)-4-[7-[1-(3-hydroxyazetidine-1-carbonyl)cyclopropyl] imidazo[1,2-a]pyridin-3-yl]-6-methoxy-benzamide | Cpd 114 + CAS# 45347-82-8 | D1ii | 512.5 | 513.6 |
| 145 | 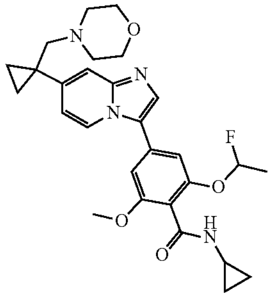 [SMILES: COc1cc(-c2cnc3cc(C4(CN5CCOCC5)CC4)ccn23)cc(OC(C)F)c1C(=O)NC1CC1] | N-cyclopropyl-2-(difluoromethoxy)-6-methoxy-4-[7-[1-(morpholinomethyl) cyclopropyl]imidazo [1,2-a]pyridin-3-yl]benzamide | Int 123 | Ex. 2.82 | 512.5 | 513.6 |
| 146 | 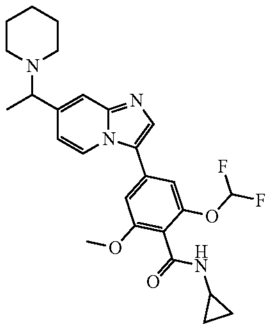 [SMILES: COc1cc(-c2cnc3cc(C(C)N4CCCCC4)ccn23)cc(OC(F)F)c1C(=O)NC1CC1] | N-cyclopropyl-2-(difluoromethoxy)-6-methoxy-4-[7-[1-piperidypethyl]imidazo [1,2-a]pyridin-3-yl]benzamide | Int 76 + CAS# 110-89-4 | K2 | 484.5 | 485.4 |
| 147 | 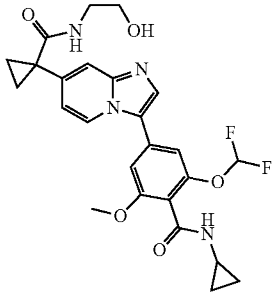 [SMILES: COc1cc(-c2cnc3cc(C4(C(=O)NCCO)CC4)ccn23)cc(OC(F)F)c1C(=O)NC1CC1] | N-cyclopropyl-2-(difluoromethoxy)-4-[7-[1-(2-hydroxyethylcarbamoyl) cyclopropyl] imidazo[1,2-a]pyridin-3-yl]-6-methoxy-benzamide | Cpd 114 + CAS# 141-43-5 | D1ii | 500.5 | 501.5 |

TABLE III-continued

Illustrative compounds of the invention.

| Cpd# | Structure | Name | SM | Mtd | MW | MS Mes'd |
|---|---|---|---|---|---|---|
| 148 | 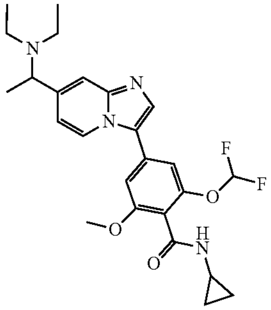 [SMILES: CCN(CC)C(C)c1ccn2c(-c3cc(OC)c(C(=O)NC4CC4)c(OC(F)F)c3)cnc2c1] | N-cyclopropyl-4-[7-[1-(diethylamino)ethyl] imidazo[1,2-a]pyridin-3-yl]-2-(difluoromethoxy)-6-methoxy-benzamide | Int 76 + CAS# 109-89-7 | K2 | 472.5 | 473.3 |
| 149 | 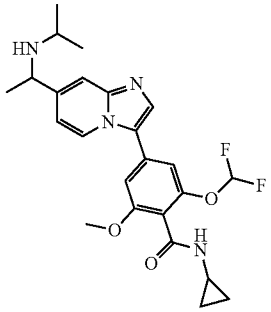 [SMILES: COc1cc(-c2cnc3cc(C(C)NC(C)C)ccn23)cc(OC(F)F)c1C(=O)NC1CC1] | N-cyclopropyl-2-(difluoromethoxy)-4-[7-[1-(isopropylamino) ethyl]imidazo[1,2-a]pyridin-3-yl]-6-methoxy-benzamide | Int 76 + CAS# 75-31-0 | K2 | 458.5 | 459.3 |
| 150 | 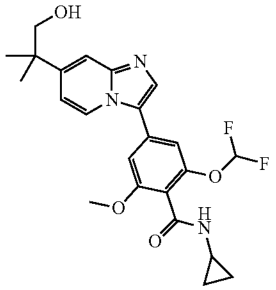 [SMILES: COc1cc(-c2cnc3cc(C(C)(C)CO)ccn23)cc(OC(F)F)c1C(=O)NC1CC1] | N-cyclopropyl-2-(difluoromethoxy)-4-[7-(2-hydroxy-1,1-dimethyl-ethyl)imidazo[1,2-a]pyridin-3-yl]-6-methoxy-benzamide | Int 124 + Int 4 | E | 445.5 | 446.5 |
| 151 | 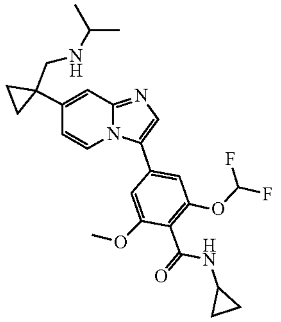 [SMILES: COc1cc(-c2cnc3cc(C4(CNC(C)C)CC4)ccn23)cc(OC(F)F)c1C(=O)NC1CC1] | N-cyclopropyl-2-(difluoromethoxy)-4-[7-[1-[(isopropylamino) methylicyclopropyl] imidazo[1,2-a]pyridin-3-yl]-6-methoxy-benzamide | Int 123 + CAS# 75-31-0 | K3 | 484.5 | 485.5 |

TABLE III-continued

| Illustrative compounds of the invention. | | | | | | |
|---|---|---|---|---|---|---|
| Cpd# | Structure | Name | SM | Mtd | MW | MS Mes'd |
| 152 | 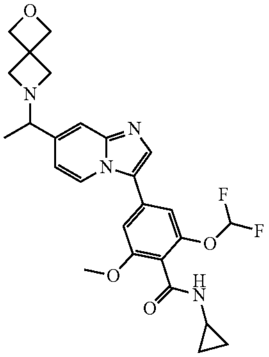 [SMILES: COc1cc(-c2cnc3cc(C(C)N4CC5(COC5)C4)ccn23)cc(OC(F)F)c1C(=O)NC1CC1] | N-cyclopropyl-2-(difluoromethoxy)-6-methoxy-4-[7-[1-(2-oxa-6-azaspiro[3.3]heptan-6-yl)ethyl]imidazo[1,2-a]pyridin-3-yl]benzamide | Int 76 + CAS# 174-78-7 | K2 | 498.5 | 499.3 |
| 153 | 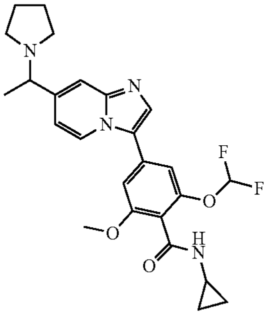 [SMILES: COc1cc(-c2cnc3cc(C(C)N4CCCC4)ccn23)cc(OC(F)F)c1C(=O)NC1CC1] | N-cyclopropyl-2-(difluoromethoxy)-6-methoxy-4-[7-(1-pyrrolidin-1-ylethyl)imidazo[1,2-a]pyridin-3-yl]benzamide | Int 76 + CAS# 123-75-1 | K2 | 470.5 | 471.3 |
| 154 | 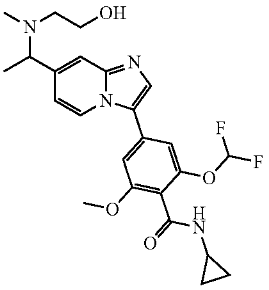 [SMILES: COc1cc(-c2cnc3cc(C(C)N(C)CCO)ccn23)cc(OC(F)F)c1C(=O)NC1CC1] | N-cyclopropyl-2-(difluoromethoxy)-4-[7-[1-[2-hydroxyethyl(methyl)amino]ethyl]imidazo[1,2-a]pyridin-3-yl]-6-methoxy-benzamide | Int 76 + CAS# 109-83-1 | K2 | 474.5 | 475.5 |
| 155 | 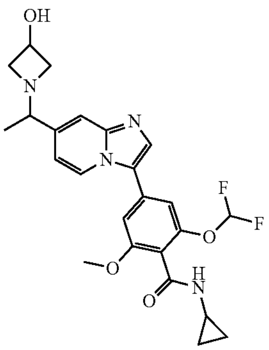 [SMILES: COc1cc(-c2cnc3cc(C(C)N4CC(O)C4)ccn23)cc(OC(F)F)c1C(=O)NC1CC1] | N-cyclopropyl-2-(difluoromethoxy)-4-[7-[1-(3-hydroxyazetidin-1-yl)ethyl]imidazo[1,2-a]pyridin-3-yl]-6-methoxy-benzamide | Int 76 + CAS# 18621-18-6 | K2 | 472.5 | 471.3 |

TABLE III-continued

Illustrative compounds of the invention.

| Cpd# | Structure | Name | SM | Mtd | MW | MS Mes'd |
|---|---|---|---|---|---|---|
| 156 | 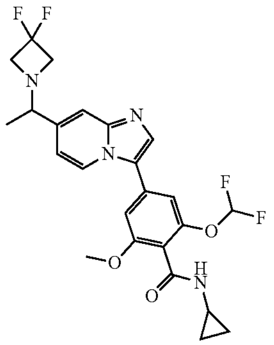 [SMILES: COc1cc(-c2cnc3cc(C(C)N4CC(F)(F)C4)ccn23)cc(OC(F)F)c1C(=O)NC1CC1] | N-cyclopropyl-4-[7-[1-(3,3-difluoro azetidin-l-yl)ethyl] imidazo[1,2-alpyridin-3-yl]-2-(difluoromethoxy)-6-methoxy-benzamide | Int 76 + CAS# 288315-03-7 | K2 | 492.5 | 499.3 |
| 157 | 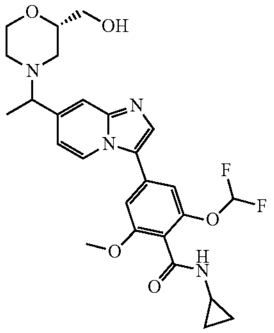 [SMILES: COc1cc(-c2cnc3cc(C(C)N4CCO[C@H](CO)C4)ccn23)cc(OC(F)F)c1C(=O)NC1CC1] | N-cyclopropyl-2-(difluoromethoxy)-4-[7-[1-[(2S)-2-(hydroxymethyl) morpholine-4-yl] ethyl]imidazo[1,2-a]pyridin-3-yl]-6-methoxy benzamide | Int 76 + CAS# 1313584-92-7 | K2 | 516.5 | 517.5 |
| 158 | 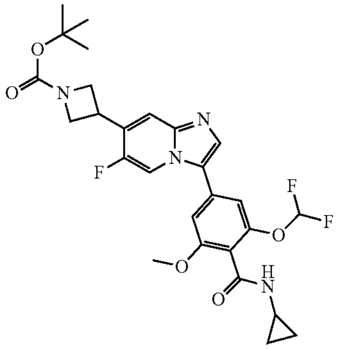 [SMILES: COc1cc(-c2cnc3cc(C4CN(C(=O)OC(C)(C)C)C4)c(F)cn23)cc(OC(F)F)c1C(=O)NC1CC1] | tert-butyl 3-[3-[4-(cyclopropylcarbamoyl)-3-(difluoro methoxy)-5-methoxy-phenyl]-6-fluoro-imidazo[1,2-a] pyridin-7-yl]azetidine-l-carboxylate | Int 125 + Int 4 | E | 546.5 | 547.5 |
| 159 | 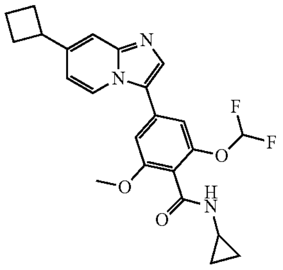 [SMILES: COc1cc(-c2cnc3cc(C4CCC4)ccn23)cc(OC(F)F)c1C(=O)NC1CC1] | 4-(7-cyclobutylimidazo] [1,2-a]pyridin-3-yl)-N-cyclopropyl-2-(difluoro methoxy)-6-methoxy-benzamide | Int 127 + Int 4 | E | 427.4 | 428.3 |

TABLE III-continued

Illustrative compounds of the invention.

| Cpd# | Structure | Name | SM | Mtd | MW | MS Mes'd |
|---|---|---|---|---|---|---|
| 160 | 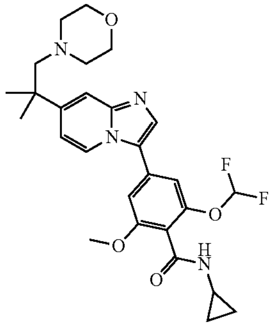 [SMILES: COc1cc(-c2cnc3cc(C(C)(C)CN4CCOCC4)ccn23)cc(OC(F)F)c1C(=O)NC1CC1] | N-cyclopropyl-2-(difluoromethoxy)-4-[7-(1,1-dimethyl-2-morpholino-ethyl)imidazo[1,2-a]pyridin-3-yl]-6-methoxy-benzamide | Int 128 + Int 4 | E | 514.6 | 515.5 |
| 161 | 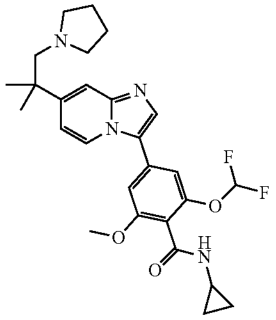 [SMILES: COc1cc(-c2cnc3cc(C(C)(C)CN4CCCC4)ccn23)cc(OC(F)F)c1C(=O)NC1CC1] | N-cyclopropyl-2-(difluoromethoxy)-4-[7-(1,1-dimethyl-2-pyrrolidin-1-yl-ethyl)imidazo[1,2-a]pyridin-3-yl]-6-methoxy-benzamide | Int 130 + CAS# 123-75-1 | K3 | 498.6 | 499.4 |
| 162 | 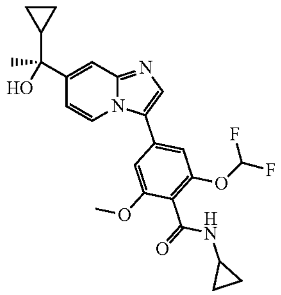 first eluting | N-cyclopropyl-4-[7-(1-cyclopropyl-1-hydroxy-ethyl)imidazo[1,2-a]pyridin-3-yl]-2-(difluoromethoxy)-6-methoxy-benzamide | Cpd 138 | Ex. 2.83 | 457.5 | 458.2 |
| 163 | 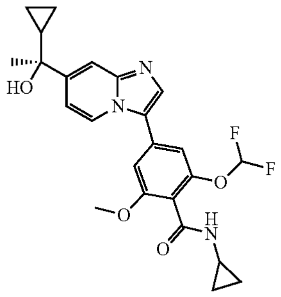 second eluting | N-cyclopropyl-4-[7-(1-cyclopropyl-1-hydroxy-ethyl)imidazo[1,2-a]pyridin-3-yl]-2-(difluoromethoxy)-6-methoxy-benzamide | Cpd 138 | Ex. 2.83 | 457.5 | 458.3 |

TABLE III-continued

| Illustrative compounds of the invention. | | | | | | |
|---|---|---|---|---|---|---|
| Cpd# | Structure | Name | SM | Mtd | MW | MS Mes'd |
| 164 | 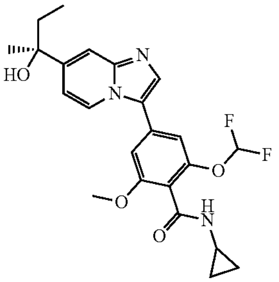 first eluting | N-cyclopropyl-2-(difluoromethoxy)-4-[7-(1-hydroxy-1-methyl-propyl)imidazo[1,2-a]pyridin-3-yl]-6-methoxy-benzamide | Cpd 137 | Ex. 2.84 | 445.5 | 446.3 |
| 165 | 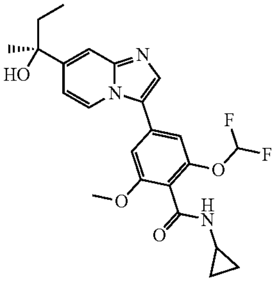 second eluting | N-cyclopropyl-2-(difluoromethoxy)-4-[7-(1-hydroxy-1-methyl-propyl)imidazo[1,2-a]pyridin-3-yl]-6-methoxy-benzamide | Cpd 137 | Ex. 2.84 | 445.5 | 446.3 |
| 166 | 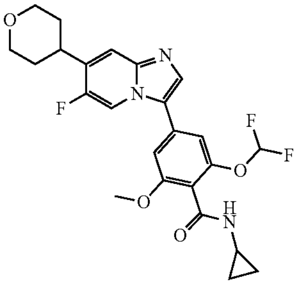 [SMILES: COc1cc(-c2cnc3cc(C4CCOCC4)c(F)cn23)cc(OC(F)F)c1C(=O)NC1CC1] | N-cyclopropyl-2-(difluoromethoxy)-(6-fluoro-7-tetrahydropyran-4-yl-imidazo[1,2-a]pyridin-3-yl)-6-methoxy-benzamide | Int 131 | L | 475.5 | 476.3 |
| 167 | 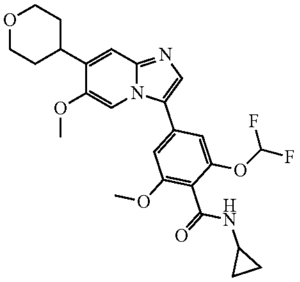 [SMILES: COc1cn2c(-c3cc(OC)c(C(=O)NC4CC4)c(OC(F)F)c3)cnc2cc1C1CCOCC1] | N-cyclopropyl-2-(difluoromethoxy)-6-methoxy-4-(6-methoxy-7-tetrahydropyran-4-yl-imidazo[1,2-a]pyridin-3-yl)benzamide | Int 133 | L | 487.5 | 488.4 |
| 168 | 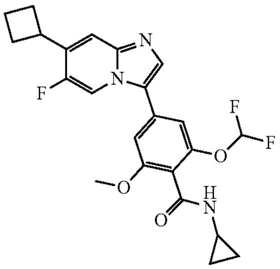 [SMILES: COc1cc(-c2cnc3cc(C4CCC4)c(F)cn23)cc(OC(F)F)c1C(=O)NC1CC1] | 4-(7-cyclobutyl-6-fluoro-imidazo[1,2-a]pyridin-3-yl)-N-cyclopropyl-2-(difluoromethoxy)-6-methoxy-benzamide | Int 136 + Int 4 | E | 445.4 | 446.3 |

TABLE III-continued

| Illustrative compounds of the invention. | | | | | | |
|---|---|---|---|---|---|---|
| Cpd# | Structure | Name | SM | Mtd | MW | MS Mes'd |
| 169 | 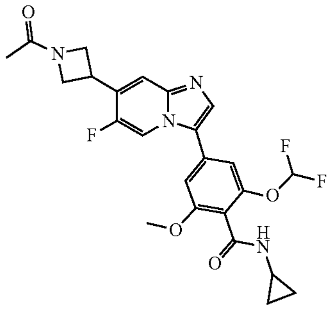 [SMILES: COc1cc(-c2cnc3cc(C4CN(C(C)=O)C4)c(F)cn23)cc(OC(F)F)c1C(=O)NC1CC1] | 4-[7-(1-acetylaze tidin-3-yl)-6-fluoro-imidazo [1,2-a]pyridin-3-yl]-N-cyclopropyl-2-(difluoromethoxy)-6-methoxy-benzamide | Int 265 | J | 488.5 | 489.3 |
| 170 | 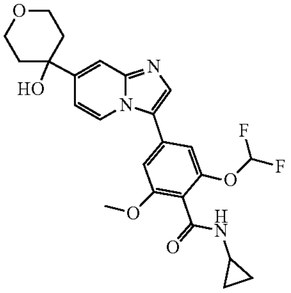 [SMILES: COc1cc(-c2cnc3cc(C4(O)CCOCC4)ccn23)cc(OC(F)F)c1C(=O)NC1CC1] | N-cyclopropyl-2-(difluoromethoxy)-4-[7-(4-hydroxy tetrahydropyran-4-yl)imidazo[1,2-a]pyridin-3-yl]-6-methoxy-benzamide | Int 137 + Int 4 | E | 473.5 | 474.4 |
| 171 | 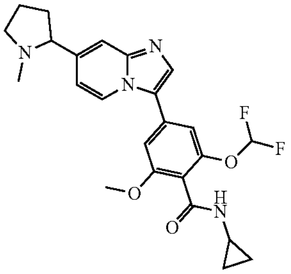 [SMILES: COc1cc(-c2cnc3cc(C4CCCN4C)ccn23)cc(OC(F)F)c1C(=O)NC1CC1] | N-cyclopropyl-2-(difluoromethoxy)-6-methoxy-4-[7-(1-methylpyrrolidin-2-yl)imidazo[1,2-a]pyridin-3-yl]benzamide | Cpd 188 | K1 | 456.5 | 457.4 |
| 172 | 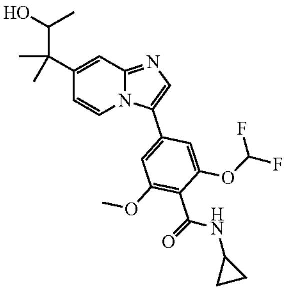 [SMILES: COc1cc(-c2cnc3cc(C(C)(C)C(C)O)ccn23)cc(OC(F)F)c1C(=O)NC1CC1] | N-cyclopropyl-2-(difluoromethoxy)-4-[7-(2-hydroxy-1,1-dimethyl-propyl)imidazo[1,2-a]pyridin-3-yl]-6-methoxy-benzamide | Int 140 | N1 | 459.5 | 460.4 |
| 173 | 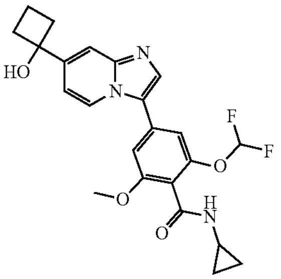 [SMILES: COc1cc(-c2cnc3cc(C4(O)CCC4)ccn23)cc(OC(F)F)c1C(=O)NC1CC1] | N-cyclopropyl-2-(difluoromethoxy)-4-[7-(1-hydroxy cyclobutyl)imidazo [1,2-a]pyridin-3-yl]-6-methoxy-benzamide | Int 141 + Int 4 | E | 443.4 | 444.3 |

TABLE III-continued

Illustrative compounds of the invention.

| Cpd# | Structure | Name | SM | Mtd | MW | MS Mes'd |
|---|---|---|---|---|---|---|
| 174 | 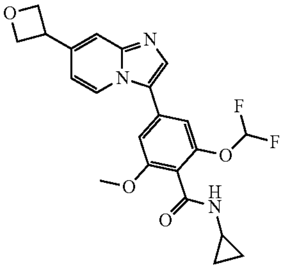 [SMILES: COc1cc(-c2cnc3cc(C4COC4)ccn23)cc(OC(F)F)c1C(=O)NC1CC1] | N-cyclopropyl-2-(difluoromethoxy)-6-methoxy-4-[7-(oxetan-3-yl)imidazo[1,2-a]pyridin-3-yl]benzamide | Int 142 + Int 4 | E | 429.4 | 430.4 |
| 175 | 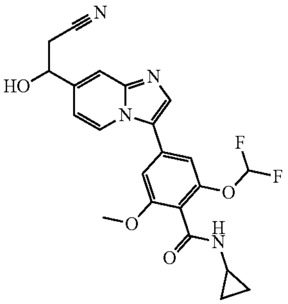 [SMILES: COc1cc(-c2cnc3cc(C(O)CC#N)ccn23)cc(OC(F)F)c1C(=O)NC1CC1] | 4-[7-(2-cyano-1-hydroxy-ethyl)imidazo[1,2-a]pyridin-3-yl]-N-cyclopropyl-2-(difluoromethoxy)-6-methoxy-benzamide | Int 143 + Int 4 | E | 442.4 | 443.4 |
| 176 | 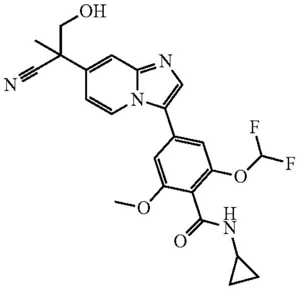 [SMILES: COc1cc(-c2cnc3cc(C(C)(C#N)CO)ccn23)cc(OC(F)F)c1C(=O)NC1CC1] | 4-[7-(1-cyano-2-hydroxy-l-methyl-ethyl)imidazo[1,2-a]pyridin-3-yl]-N-cyclopropyl-2-(difluoromethoxy)-6-methoxy-benzamide | Int 145 + Int 4 | E | 456.4 | 457.3 |
| 177 | 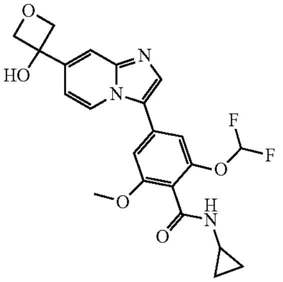 [SMILES: COc1cc(-c2cnc3cc(C4(O)COC4)ccn23)cc(OC(F)F)c1C(=O)NC1CC1] | N-cyclopropyl-2-(difluoromethoxy)-4-[7-(3-hydroxy oxetan-3-yl)imidazo[1,2-a]pyridin-3-yl-6-methoxy-benzamide | Int 146 + Int 4 | E | 445.4 | 446.4 |
| 178 | 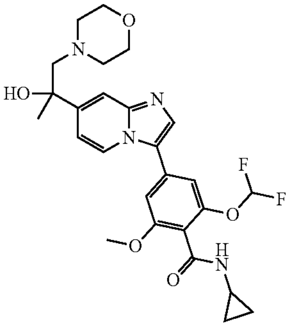 [SMILES: COc1cc(-c2cnc3cc(C(C)(O)CN4CCOCC4)ccn23)cc(OC(F)F)c1C(=O)NC1CC1] | N-cyclopropyl-2-(difluoromethoxy)-4-[7-(1-hydroxy-1-methyl-2-morpholino-ethyl) imidazo[1,2-a]pyridin-3-yl-6-methoxy-benzamide | Int 147 + Int 4 | E | 516.5 | 517.4 |

TABLE III-continued

Illustrative compounds of the invention.

| Cpd# | Structure | Name | SM | Mtd | MW | MS Mes'd |
|---|---|---|---|---|---|---|
| 179 | 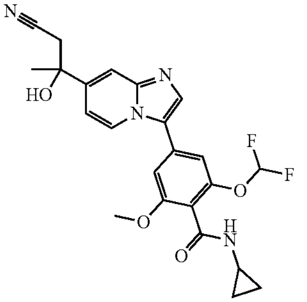 [SMILES: COc1cc(-c2cnc3cc(C(C)(O)CC#N)ccn23)cc(OC(F)F)c1C(=O)NC1CC1] | 4-[7-(2-cyano-1-hydroxy-1-methyl-ethyl)imidazo[1,2-a]pyridin-3-yl]-N-cyclopropyl-2-(difluoromethoxy)-6-methoxy-benzamide | Int 148 + Int 4 | E | 456.4 | 457.3 |
| 180 | 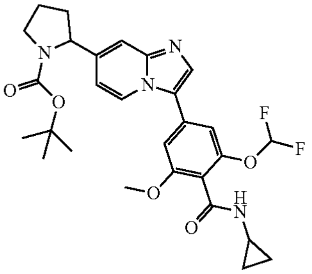 [SMILES: COc1cc(-c2cnc3cc(C4CCCN4C(=O)OC(C)(C)C)ccn23)cc(OC(F)F)c1C(=O)NC1CC1] | tert-butyl 2-[3-[4-(cyclopropylcarbamoyl)-3-(difluoromethoxy)-5-methoxy-phenyl]imidazo[1,2-a]pyridin-7-yl]pyrrolidine-1-carboxylate | Int 149 + Int 4 | E | 542.6 | 543.5 |
| 181 | 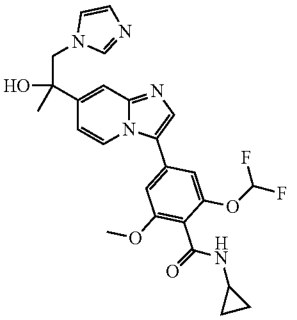 [SMILES: COc1cc(-c2cnc3cc(C(C)(O)Cn4ccnc4)ccn23)cc(OC(F)F)c1C(=O)NC1CC1] | N-cyclopropyl-2-(difluoromethoxy)-4-[7-(1-hydroxy-2-imidazol-1-yl-1-methyl-ethyl) imidazo[1,2-a]pyridin-3-yl]-6-methoxy-benzamide | Int 151 + Int 4 | E | 497.5 | 498.4 |
| 182 | 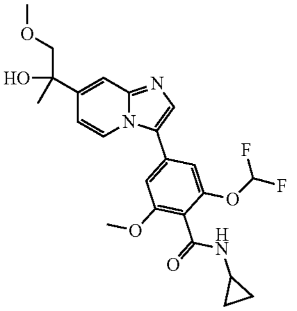 [SMILES: COCC(C)(O)c1ccn2c(-c3cc(OC)c(C(=O)NC4CC4)c(OC(F)F)c3)cnc2c1] | N-cyclopropyl-2-(difluoromethoxy)-4-[7-(1-hydroxy-2-methoxy-1-methyl-ethyl)imidazo[1,2-a]pyridin-3-yl]-6-methoxy-benzamide | Int 152 + Int 4 | E | 461.5 | 462.4 |
| 183 | 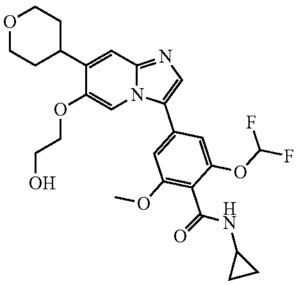 [SMILES: COc1cc(-c2cnc3cc(C4CCOCC4)c(OCCO)cn23)cc(OC(F)F)c1C(=O)NC1CC1] | N-cyclopropyl-2-(difluoromethoxy)-4-[6-(2-hydroxyethoxy)-7-tetrahydropyran-4-yl-imidazo[1,2-a]pyridin-3-yl]-6-methoxy-benzamide | Int 153 | L | 517.5 | 518.4 |

TABLE III-continued

Illustrative compounds of the invention.

| Cpd# | Structure | Name | SM | Mtd | MW | MS Mes'd |
|---|---|---|---|---|---|---|
| 184 | 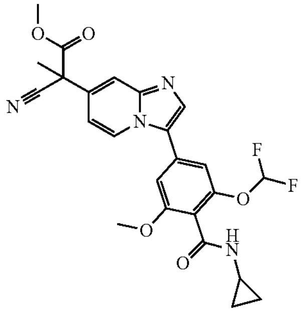 [SMILES: COC(=O)C(C)(C#N)c1ccn2c(-c3cc(OC)c(C(=O)NC4CC4)c(OC(F)F)c3)cnc2c1] | methyl 2-cyano-2-[3-[4-(cyclopropyl carbamoyl)-3-(difluoromethoxy)-5-methoxy-phenyl]imidazo[1,2-a]pyridin-7-yl]propanoate | Int 157 + Int 4 | E | 484.5 | 485.3 |
| 185 | 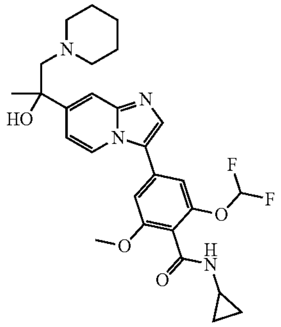 [SMILES: COc1cc(-c2cnc3cc(C(C)(O)CN4CCCCC4)ccn23)cc(OC(F)F)c1C(=O)NC1CC1] | N-cyclopropyl-2-(difluoromethoxy)-4-[7-[1-hydroxy-1-methyl-2-(1-piperidyl)ethyl] imidazo[1,2-a]pyridin-3-yl]-6-methoxy-benzamide | Int 76 + CAS# 11-89-4 | N3 | 514.6 | 515.5 |
| 186 | 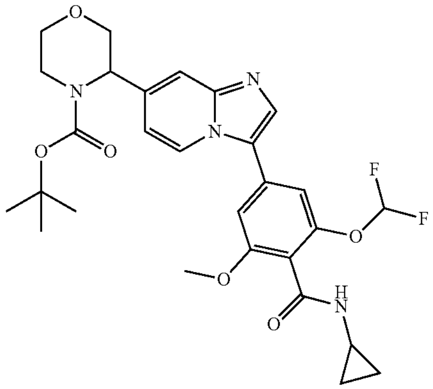 [SMILES: COc1cc(-c2cnc3cc(C4COCCN4C(=O)OC(C)(C)C)ccn23)cc(OC(F)F)c1C(=O)NC1CC1] | tert-butyl 3-[3-[4-(cyclopropylcarbamoyl)-3-(difluoromethoxy)-5-methoxy-phenyl]imidazo[1,2-a]pyridin-7-yl]morpholine-4-carboxylate | Int 158 + Int 4 | E | 558.6 | 559.4 |
| 187 | 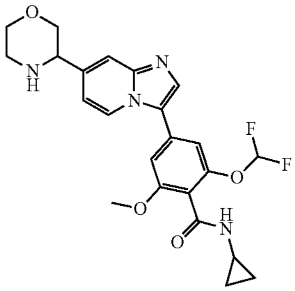 [SMILES: COc1cc(-c2cnc3cc(C4COCCN4)ccn23)cc(OC(F)F)c1C(=O)NC1CC1] | N-cyclopropyl-2-(difluoromethoxy)-6-methoxy-4-(7-morpholin-3-yl]midazo[1,2-a]pyridin-3-yl)benzamide | Cpd 186 | M1 | 458.5 | 459.4 |

TABLE III-continued

| Illustrative compounds of the invention. | | | | | | |
|---|---|---|---|---|---|---|
| Cpd# | Structure | Name | SM | Mtd | MW | MS Mes'd |
| 188 | 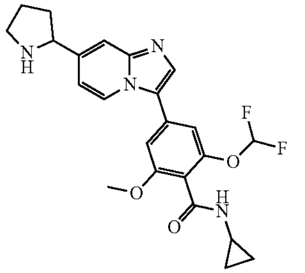 [SMILES: COc1cc(-c2cnc3cc(C4CCCN4)ccn23)cc(OC(F)F)c1C(=O)NC1CC1] | N-cyclopropyl-2-(difluoromethoxy)-6-methoxy-4-(7-pyrrolidin-2-yl]imidazo[1,2-a]pyridin-3-yl)benzamide | Cpd 180 | M1 | 442.5 | 443.4 |
| 189 | 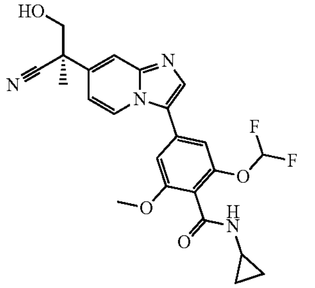 first eluting | 4-[7-(1-cyano-2-hydroxy-1-methyl-ethyl)imidazo[1,2-a]pyridin-3-yl]-N-cyclopropyl-2-(difluoromethoxy)-6-methoxy-benzamide | Cpd 176 | Ex. 2.85 | 456.4 | 457.3 |
| 190 | 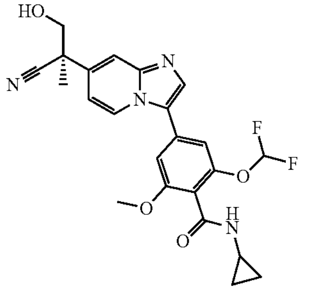 second eluting | 4-[7-(1-cyano-2-hydroxy-1-methyl-ethyl)imidazo[1,2-a]pyridin-3-yl]-N-cyclopropyl-2-(difluoromethoxy)-6-methoxy-benzamide | Cpd 176 | Ex. 2.85 | 456.4 | 457.3 |
| 191 | 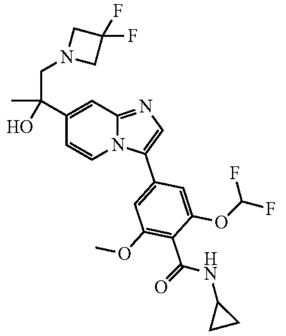 [SMILES: COc1cc(-c2cnc3cc(C(C)(O)CN4CC(F)(F)C4)ccn23)cc(OC(F)F)c1C(=O)NC1CC1] | N-cyclopropyl-4-[7-[2-(3,3-difluoroazetidin-1-yl)-1-hydroxy-1-methyl-ethyl]imidazo[1,2-a]pyridin-3-yl]-2-(difluorome thoxy)-6-methoxy-benzamide | Int 76 + CAS# 288315-03-7 | N3 | 522.5 | 523.4 |

TABLE III-continued

| Illustrative compounds of the invention. | | | | | | |
|---|---|---|---|---|---|---|
| Cpd# | Structure | Name | SM | Mtd | MW | MS Mes'd |
| 192 | 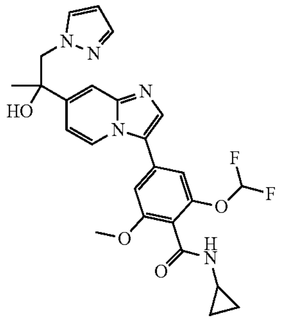 [SMILES: COc1cc(-c2cnc3cc(C(C)(O)Cn4cccn4)ccn23)cc(OC(F)F)c1C(=O)NC1CC1] | N-cyclopropyl-2-(difluoromethoxy)-4-[7-(1-hydroxy-1-methyl-2-pyrazol-1-yl-ethyl)imidazo[1,2-a]pyridin-3-yl]-6-methoxy-benzamide | Int 76 + CAS# 288-13-1 | N3 | 497.5 | 498.4 |
| 193 | 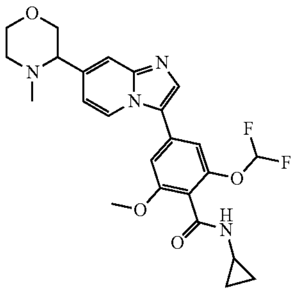 [SMILES: COc1cc(-c2cnc3cc(C4COCCN4C)ccn23)cc(OC(F)F)c1C(=O)NC1CC1] | N-cyclopropyl-2-(difluoromethoxy)-6-methoxy-4-[7-(4-methylmorpholin-3-yl)imidazo[1,2-a]pyridin-3-yl]benzamide | Int 160 | I2 | 472.5 | 473.4 |
| 194 | 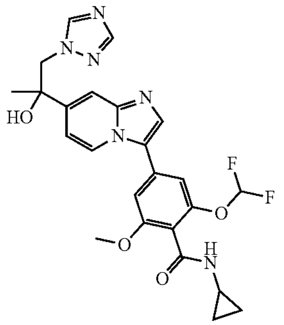 [SMILES: COc1cc(-c2cnc3cc(C(C)(O)Cn4cncn4)ccn23)cc(OC(F)F)c1C(=O)NC1CC1] | N-cyclopropyl-2-(difluoromethoxy)-4-[7-[1-hydroxy-1-methyl-2-(1,2,4-triazol-1-yl)ethyl]imidazo[1,2-a]pyridin-3-yl]-6-methoxy-benzamide | Int 76 + CAS# 288-88-0 | N3 | 498.5 | 499.4 |
| 195 | 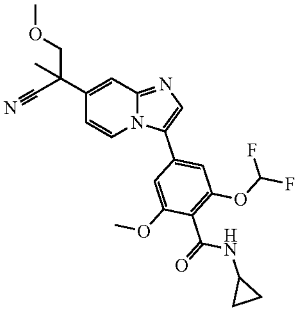 [SMILES: COCC(C)(C#N)c1ccn2c(-c3cc(OC)c(C(=O)NC4CC4)c(OC(F)F)c3)cnc2c1] | 4-[7-(1-cyano-2-methoxy-1-methyl-ethyl)imidazo[1,2-a]pyridin-3-yl]-N-cyclopropyl-2-(difluoromethoxy)-6-methoxy-benzamide | Int 161 + Int 4 | E | 470.5 | 471.4 |
| 196 | 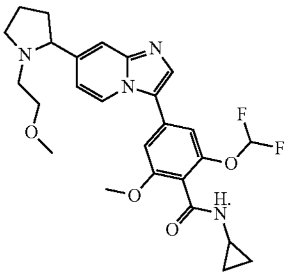 | N-cyclopropyl-2-(difluoromethoxy)-6-methoxy-4-[7-[l-(2-methoxyethyl) pyrrolidin-2-yl]imidazo[1,2-a]pyridin-3-yl]benzamide | Cpd 188 | I2 | 500.5 | 501.4 |

TABLE III-continued

Illustrative compounds of the invention.

| Cpd# | Structure | Name | SM | Mtd | MW | MS Mes'd |
|---|---|---|---|---|---|---|
| 197 | 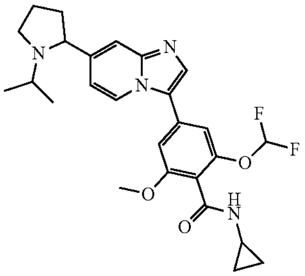 [SMILES: COc1cc(-c2cnc3cc(C4CCCN4C(C)C)ccn23)cc(OC(F)F)c1C(=O)NC1CC1] | N-cyclopropyl-2-(difluoromethoxy)-4-[7-(1-isopropyl pyrrolidin-2-yl)imidazo [1,2-a]pyridin-3-yl-6-methoxy-benzamide | Cpd 188 | Ex. 2.86 | 484.5 | 485.5 |
| 198 | 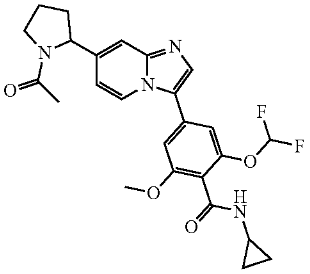 [SMILES: COc1cc(-c2cnc3cc(C4CCCN4C(C)=O)ccn23)cc(OC(F)F)c1C(=O)NC1CC1] | 4-[7-(1-acetylpyrolidin-2-yl)imidzo [1,2-a]pyridin-3-yl]-N-cyclopropyl-2-(difluoromethoxy)-6-methoxy-benzamide | Cpd 188 | J | 484.5 | 485.4 |
| 199 | 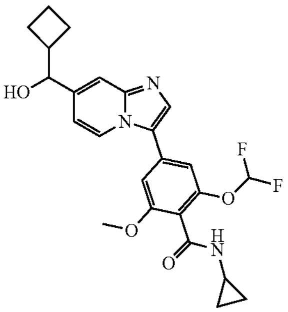 [SMILES: COc1cc(-c2cnc3cc(C(O)C4CCC4)ccn23)cc(OC(F)F)c1C(=O)NC1CC1] | 4-[7-[cyclobutyl(hydroxy) methyl]imidazo [1,2-a]pyridin-3-yl]-N-cyclopropyl-2-(difluoromethoxy)-6-methoxy-benzamide | Int 162 | N1 | 457.5 | 458.4 |
| 200 | 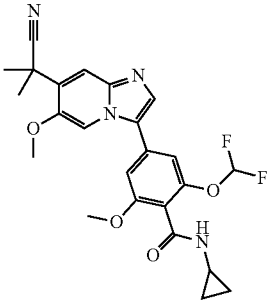 [SMILES: COc1cn2c(-c3cc(OC)c(C(=O)NC4CC4)c(OC(F)F)c3)cnc2cc1C(C)(C)C#N] | 4-[7-(1-cyano-1-methyl-ethyl)-6-methoxy-imidazo [1,2-a]pyridin-3-yl]-N-cyclopropyl-2-(difluoromethoxy)-6-methoxy-benzamide | Int 164 + Int 4 | E | 470.5 | 471.4 |
| 201 | 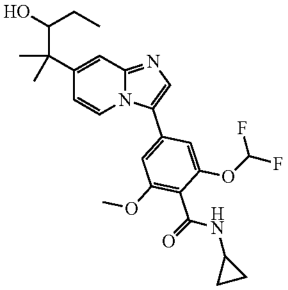 [SMILES: CCC(O)C(C)(C)c1ccn2c(-c3cc(OC)c(C(=O)NC4CC4)c(OC(F)F)c3)cnc2c1] | N-cyclopropyl-2-(difluoromethoxy)-4-[7-(2-hydroxy-1,1-dimethyl-butyl) imidazo[1,2-a]pyridin-3-yl]-6-methoxy-benzamide | Int 140 | Ex. 2.87 | 473.5 | 474.4 |

TABLE III-continued

| Illustrative compounds of the invention. | | | | | | |
|---|---|---|---|---|---|---|
| Cpd# | Structure | Name | SM | Mtd | MW | MS Mes'd |
| 202 | 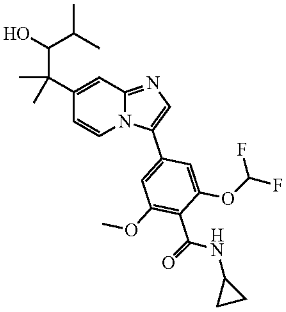 [SMILES: COc1cc(-c2cnc3cc(C(C)(C)C(O)C(C)C)ccn23)cc(OC(F)F)c1C(=O)NC1CC1] | N-cyclopropyl-2-(difluoromethoxy)-4-[7-(2-hydroxy-1,1,3-trimethyl-butyl)imidazo[1,2-a]pyridin-3-yl]-6-methoxy-benzamide | Int 140 | Ex. 2.87 | 487.5 | 488.5 |
| 203 | 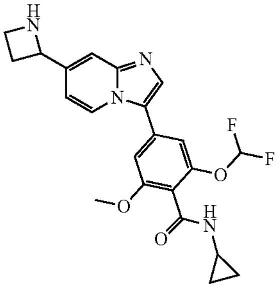 [SMILES: COc1cc(-c2cnc3cc(C4CCN4)ccn23)cc(OC(F)F)c1C(=O)NC1CC1] | 4-[7-(azetidin-2-yl)imidazo[1,2-a]pyridin-3-yl]-N-cyclopropyl-2-(difluoromethoxy)-6-methoxy-benzamide | Int 165 | M1 | 428.4 | 429.4 |
| 204 | 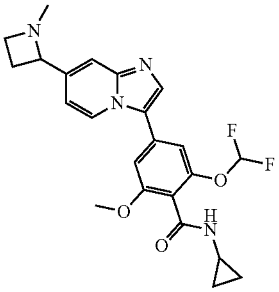 [SMILES: COc1cc(-c2cnc3cc(C4CCN4C)ccn23)cc(OC(F)F)c1C(=O)NC1CC1] | N-cyclopropyl-2-(difluoromethoxy)-6-methoxy-4-[7-(1-methylazetidin-2-yl)imidazo[1,2-a]pyridin-3-yl]benzamide | Cpd 203 | K1 | 442.5 | 443.4 |
| 205 | 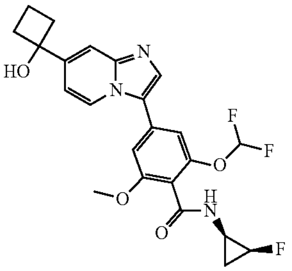 [SMILES: COc1cc(-c2cnc3cc(C4(O)CCC4)ccn23)cc(OC(F)F)c1C(=O)N[C@@H]1C[C@@H]1F] | 2-(difluoromethoxy)-N-[(1R,2S)-2-fluorocyclopropyl]-4-[7-(1-hydroxy cyclobutyl)imidazo [1,2-a]pyridin-3-yl]-6-methoxy-benzamide | Int 167 + CAS# 143062-84-4 | D1i + D1ii | 461.4 | 462.4 |
| 206 | 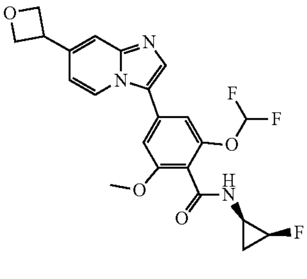 [SMILES: COc1cc(-c2cnc3cc(C4COC4)ccn23)cc(OC(F)F)c1C(=O)N[C@@H]1C[C@@H]1F] | 2-(difluoromethoxy)-N-[(1R,2S)-2-fluorocyclopropyl]-6-methoxy-4-[7-(oxetan-3-yl)imidazo [1,2-a]pyridin-3-yl]benzamide | Int 168 + CAS# 143062-84-4 | D1i + D1ii | 447.4 | 448.4 |

TABLE III-continued

| Cpd# | Structure | Name | SM | Mtd | MW | MS Mes'd |
|---|---|---|---|---|---|---|
| Illustrative compounds of the invention. | | | | | | |
| 207 | 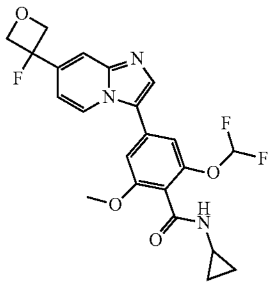 [SMILES: COc1cc(-c2cnc3cc(C4(F)COC4)ccn23)cc(OC(F)F)c1C(=O)NC1CC1] | N-cyclopropyl-2-(difluoromethoxy)-4-[7-(3-fluoro oxetan-3-yl)imidazo [1,2-a]pyridin-3-yl]-6-methoxy-benzamide | Cpd 177 | T | 447.4 | 448.4 |
| 208 | 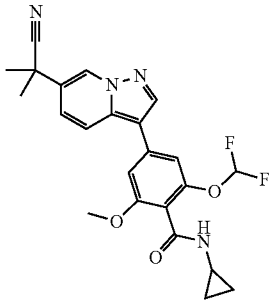 [SMILES: COc1cc(-c2cnn3cc(C(C)(C)C#N)ccc23)cc(OC(F)F)c1C(=O)NC1CC1] | 4-[6-(1-cyano-1-methyl-ethyl)pyrazolo [1,5-a]pyridin-3-yl]-N-cyclopropyl-2-(difluoro methoxy)-6-methoxy-benzamide | Int 169 + Int 7 | C | 440.4 | 441.3 |
| 209 | 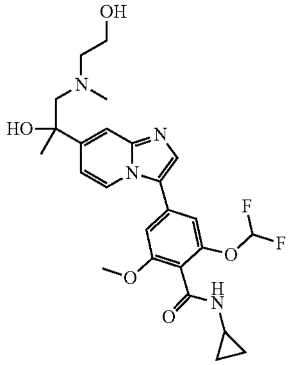 [SMILES: COc1cc(-c2cnc3cc(C(C)(O)CN(C)CCO)ccn23)cc(OC(F)F)c1C(=O)NC1CC1] | N-cyclopropyl-2-(difluoromethoxy)-4-[7-[1-hydroxy-2-[2-hydroxyethyl (methyl)amino]-1-methyl-ethyl]imidazo [1,2-a]pyridin-3-yl-6-methoxy-benzamide | Int 76 + CAS# 109-83-1 | N3 | 504.5 | 505.5 |
| 210 | 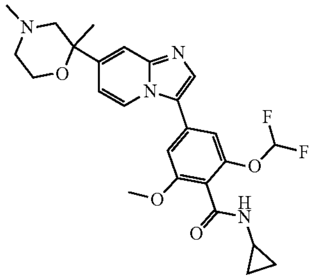 [SMILES: COc1cc(-c2cnc3cc(C4(C)CN(C)CCO4)ccn23)cc(OC(F)F)c1C(=O)NC1CC1] | N-cyclopropyl-2-(difluoromethoxy)-4-[7-(2,4-dimethyl morpholin-2-yl) imidazo[1,2-a] pyridin-3-yl]-6-methoxy-benzamide | Int 172 + Int 4 | E | 486.5 | 487.5 |
| 211 | 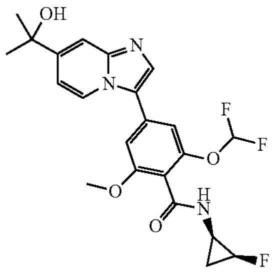 [SMILES: COc1cc(-c2cnc3cc(C(C)(C)O)ccn23)cc(OC(F)F)c1C(=O)N[C@@H]1C[C@@H]1F] | 2-(difluoromethoxy)-N-[(1R,2S)-2-fluorocyclopropyl]-4-[7-(1-hydroxy-1-methyl-ethyl)imidazo [1,2-a]pyridin-3-yl]-6-methoxy-benzamide | Int 174 + CAS# 143062-84-4 | D1i + D1ii | 449.4 | 450.4 |

TABLE III-continued

Illustrative compounds of the invention.

| Cpd# | Structure | Name | SM | Mtd | MW | MS Mes'd |
|---|---|---|---|---|---|---|
| 212 | 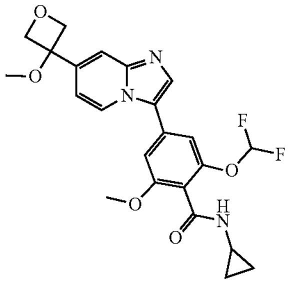 [SMILES: COc1cc(-c2cnc3cc(C4(OC)COC4)ccn23)cc(OC(F)F)c1C(=O)NC1CC1] | N-cyclopropyl-2-(difluoromethoxy)-6-methoxy-4-[7-(3-methoxyoxetan-3-yl)imidazo[1,2-a]pyridin-3-yl]benzamide | Int 175 + Int 4 | E | 459.4 | 460.4 |
| 213 | 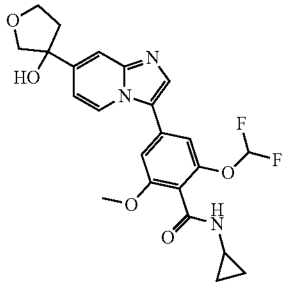 [SMILES: COc1cc(-c2cnc3cc(C4(O)CCOC4)ccn23)cc(OC(F)F)c1C(=O)NC1CC1] | N-cyclopropyl-2-(difluoromethoxy)-4-[7-(3-hydroxytetrahydrofuran-3-yl)imidazo[1,2-a] pyridin-3-yl]-6-methoxy-benzamide | Int 176 + Int 4 | E | 459.4 | 460.4 |
| 214 | 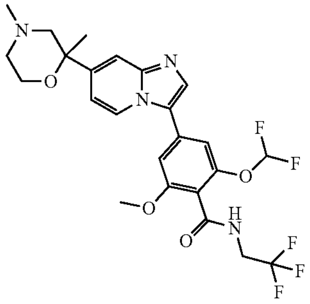 [SMILES: COc1cc(-c2cnc3cc(C4(C)CN(C)CCO4)ccn23)cc(OC(F)F)c1C(=O)NCC(F)(F)F] | 2-(difluoromethoxy)-4-[7-(2,4-dimethylmorpholin-2-yl)imidazo[1,2-a]pyridin-3-yl]-6-methoxy-N-(2,2,2-trifluoroethyl) benzamide | Int 172 + Int 22 | E | 528.5 | 529.4 |
| 215 | 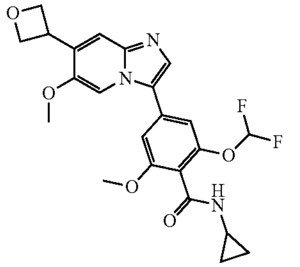 [SMILES: COc1cn2c(-c3cc(OC)c(C(=O)NC4CC4)c(OC(F)F)c3)cnc2cc1C1COC1] | N-cyclopropyl-2-(difluoromethoxy)-6-methoxy-4-[6-methoxy-7-(oxetan-3-yl)imidazo[1,2-a]pyridin-3-yl]benzamide | Int 179 + Int 4 | E | 459.4 | 460.4 |
| 216 | 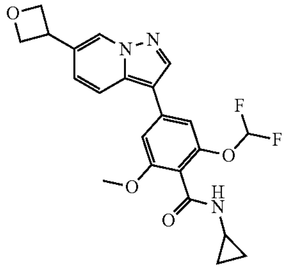 [SMILES: COc1cc(-c2cnn3cc(C4COC4)ccc23)cc(OC(F)F)c1C(=O)NC1CC1] | N-cyclopropyl-2-(difluoromethoxy)-6-methoxy-4-[6-(oxetan-3-yl)pyrazolo[1,5-a]pyridin-3-yl]benzamide | Int 180 + Int 7 | C | 429.4 | 430.4 |

TABLE III-continued

| Illustrative compounds of the invention. | | | | | | |
|---|---|---|---|---|---|---|
| Cpd# | Structure | Name | SM | Mtd | MW | MS Mes'd |
| 217 | 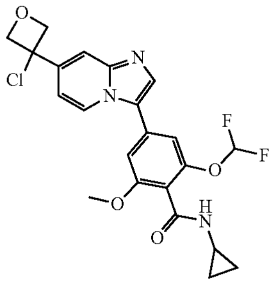 [SMILES: COc1cc(-c2cnc3cc(C4(Cl)COC4)ccn23)cc(OC(F)F)c1C(=O)NC1CC1] | 4-[7-(3-chlorooxetan-3-yl)imidazo[1,2-a]pyridin-3-yl]-N-cyclopropyl-2-(difluoromethoxy)-6-methoxy-benzamide | Cpd 177 | Ex. 2.88 | 463.9 | 464.3 |
| 218 | 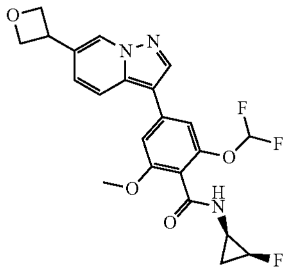 [SMILES: COc1cc(-c2cnn3cc(C4COC4)ccc23)cc(OC(F)F)c1C(=O)N[C@@H]1C[C@@H]1F] | 2-(difluoromethoxy)-N-[(1R,2S)-2-fluorocyclopropyl]-6-methoxy-4-[6-(oxetan-3-yl)pyrazolo[1,5-a]pyridin-3-yl]benzamide | Int 182 + CAS# 143062-84-4 | D1i + D1ii | 447.4 | 448.3 |
| 219 | 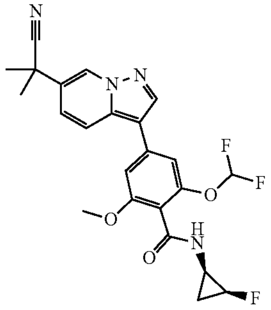 [SMILES: COc1cc(-c2cnn3cc(C(C)(C)C#N)ccc23)cc(OC(F)F)c1C(=O)N[C@@H]1C[C@@H]1F] | 4-[6-(1-cyano-1-methyl-ethyl)pyrazolo[1,5-a]pyridin-3-yl]-2-(difluoro methoxy)-N-[(1R, 2S)-2-fluorocyclopropyl]-6-methoxy-benzamide | Int 169 + Int 8 or CAS# 1264193-11-4 | C or Ex. 2.89 | 458.4 | 459.4 or 459.1 |
| 220 | 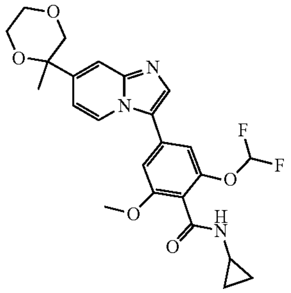 [SMILES: COc1cc(-c2cnc3cc(C4(C)COCCO4)ccn23)cc(OC(F)F)c1C(=O)NC1CC1] | N-cyclopropyl-2-(difluoromethoxy)-6-methoxy-4-[7-(2-methyl-1,4-dioxan-2-yl)imidazo[1,2-a]pyridin-3-yl]benzamide | Int 183 + Int 4 | E | 473.5 | 474.4 |
| 221 | 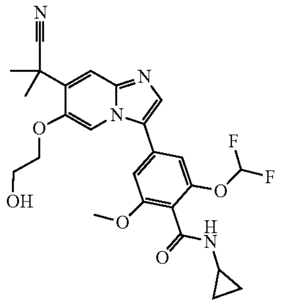 [SMILES: COc1cc(-c2cnc3cc(C(C)(C)C#N)c(OCCO)cn23)cc(OC(F)F)c1C(=O)NC1CC1] | 4-[7-(1-cyano-1-methyl-ethyl)-6-(2-hydroxyethoxy)imidazo[1,2-a]pyridin-3-yl]-N-cyclopropyl-2-(difluoro methoxy)-6-methoxy-benzamide | Int 185 + Int 4 | E | 500.5 | 501.4 |

TABLE III-continued

Illustrative compounds of the invention.

| Cpd# | Structure | Name | SM | Mtd | MW | MS Mes'd |
|---|---|---|---|---|---|---|
| 222 | 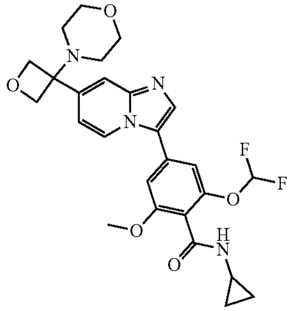 [SMILES: COc1cc(-c2cnc3cc(C4(N5CCOCC5)COC4)ccn23)cc(OC(F)F)c1C(=O)NC1CC1] | N-cyclopropyl-2-(difluoromethoxy)-6-methoxy-4-[7-(3-morpholinooxetan-3-yl)imidazo[1,2-a]pyridin-3-yl]benzamide | Cpd 217 | Ex. 2.90 | 514.5 | 515.4 |
| 223 | 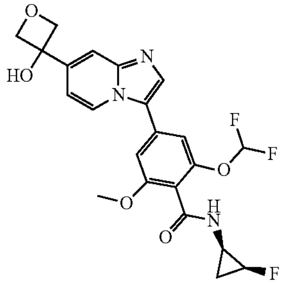 [SMILES: COc1cc(-c2cnc3cc(C4(O)COC4)ccn23)cc(OC(F)F)c1C(=O)N[C@@H]1C[C@@H]1F] | 2-(difluoromethoxy)-N-[(1R,2S)-2-fluorocyclopropyl]-4-[7-(3-hydroxyoxetan-3-yl)imidazo[1,2-a]pyridin-3-yl]-6-methoxy-benzamide | Int 187 + CAS# 143062-84-4 | D1i + D1ii | 463.4 | 464.3 |
| 224 | 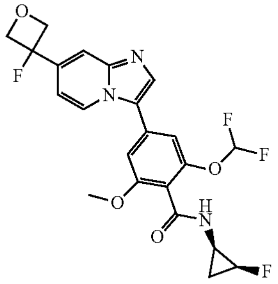 [SMILES: COc1cc(-c2cnc3cc(C4(F)COC4)ccn23)cc(OC(F)F)c1C(=O)N[C@@H]1C[C@@H]1F] | 2-(difluoromethoxy)-N-[(1R,2S)-2-fluorocyclopropyl]-4-[7-(3-fluorooxetan-3-yl)imidazo[1,2-a]pyridin-3-yl]-6-methoxy-benzamide | Cpd 223 | T | 465.4 | 466.3 |
| 225 | 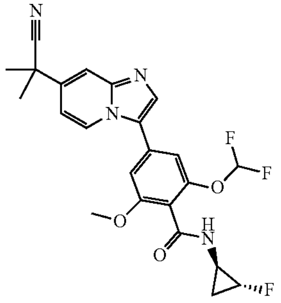 + 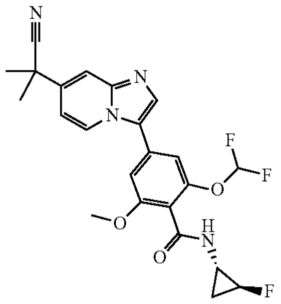 | 4-[7-(1-cyano-1-methyl-ethyl)imidazo[1,2-a]pyridin-3-yl]-2-(difluoromethoxy)-N-[(1R,2R)-2-fluorocyclopropyl]-6-methoxy-benzamide / 4-[7-(1-cyano-1-methyl-ethyl)imidazo[1,2-a]pyridin-3-yl]-2-(difluoromethoxy)-N-[(1S,2S)-2-fluorocyclopropyl]-6-methoxy-benzamide mixture | Int 188 + CAS# 1799439-05-6 | D1i + D1ii | 458.4 | 459.4 |

TABLE III-continued

| Illustrative compounds of the invention. | | | | | | |
|---|---|---|---|---|---|---|
| Cpd# | Structure | Name | SM | Mtd | MW | MS Mes'd |
| 226 | 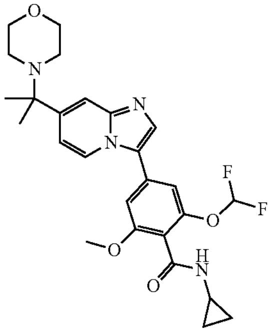 [SMILES: COc1cc(-c2cnc3cc(C(C)(C)N4CCOCC4)ccn23)cc(OC(F)F)c1C(=O)NC1CC1] | N-cyclopropyl-2-(difluoromethoxy)-6-methoxy-4-[7-(1-methyl-1-morpholino-ethyl)imidazo[1,2-a]pyridin-3-yl]benzamide | Int 189 + Int 4 | E | 500.5 | 501.4 |
| 227 | 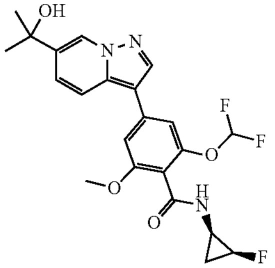 [SMILES: COc1cc(-c2cnn3cc(C(C)(C)O)ccc23)cc(OC(F)F)c1C(=O)N[C@@H]1C[C@@H]1F] | 2-(difluoromethoxy)-N-[(1R,2S)-2-fluorocyclopropyl]-4-[6-(1-hydroxy-1-methyl-ethyl)pyrazolo[1,5-a]pyridin-3-yl]-6-ethoxy-benzamide | Int 190 + Int 8 | C | 449.4 | 450.3 |
| 228 | 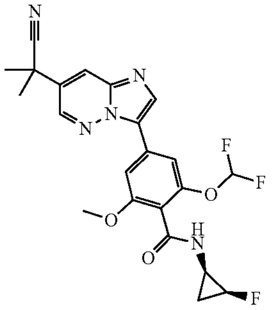 | 4-[7-(1-cyano-1-methyl-ethyl)imidazo[1,2-b]pyridazin-3-yl]-2-(difluoromethoxy)-N-[(1R,2S)-2-fluorocyclopropyl]-6-methoxy-benzamide | Int 192 + CAS# 143062-84-4 | D1i + D1ii | 459.4 | 460.7 |
| 229 | 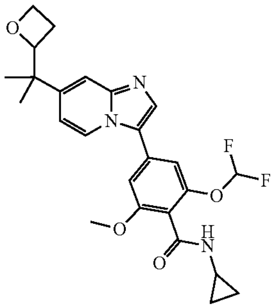 [SMILES: COc1cc(-c2cnc3cc(C(C)(C)C4CCO4)ccn23)cc(OC(F)F)c1C(=O)NC1CC1] | N-cyclopropyl-2-(difluoromethoxy)-6-methoxy-4-[7-[1-methyl-1-(oxetan-2-yl)ethyl]imidazo[1,2-a]pyridin-3-yl]benzamide | Cpd 150 | Ex. 2.91 | 471.5 | 472.4 |
| 230 | 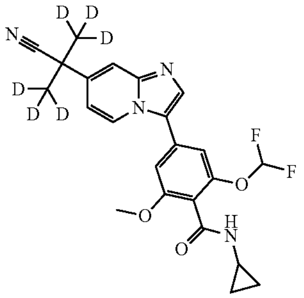 [SMILES: [2H]C([2H])([2H])C(C#N)(c1ccn2c(-c3cc(OC)c(C(=O)NC4CC4)c(OC(F)F)c3)cnc2c1)C([2H])([2H])[2H]] | 4-[7-[1-cyano-2,2,2-trideuterio-1-(trideuteriomethyl)ethyl]imidazo[1,2-a]pyridin-3-yl]-N-cyclopropyl-2-(difluoromethoxy)-6-methoxy-benzamide | Int 195 + Int 4 | E | 446.5 | 447.4 |

TABLE III-continued

Illustrative compounds of the invention.

| Cpd# | Structure | Name | SM | Mtd | MW | MS Mes'd |
|---|---|---|---|---|---|---|
| 231 | 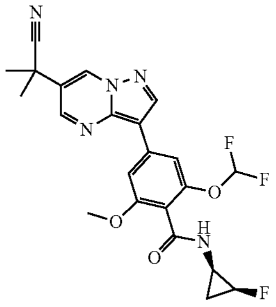 [SMILES: COc1cc(-c2cnn3cc(C(C)(C)C#N)cnc23)cc(OC(F)F)c1C(=O)N[C@@H]1C[C@@H]1F] | 4-[6-(1-cyano-1-methyl-ethyl)pyrazolo[1,5-a]pyrimidin-3-yl]-2-(difluoromethoxy)-N-[(1R,2S)-2-fluorocyclopropyl]-6-methoxy-benzamide | Int 196 + CAS# 143062-84-4 | D1i + D1ii | 459.4 | 460.4 |
| 232 | 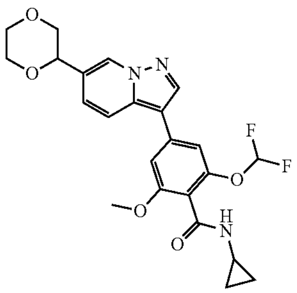 [SMILES: COc1cc(-c2cnn3cc(C4COCCO4)ccc23)cc(OC(F)F)c1C(=O)NC1CC1] | N-cyclopropyl-2-(difluoromethoxy)-4-[6-(1,4-dioxan-2-yl)pyrazolo[1,5-a]pyridin-3-yl]-6-methoxy-benzamide | Int 199 + Int 4 | C | 459.4 | 460.3 |
| 233 | 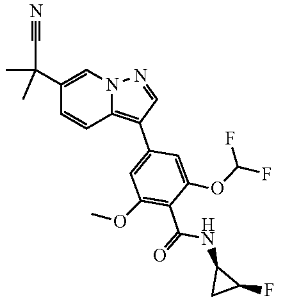 + 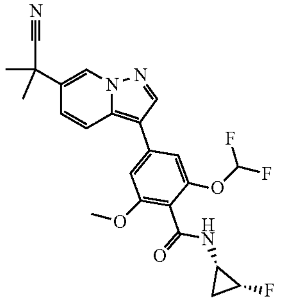 | 4-[6-(1-cyano-1-methyl-ethyl)pyrazolo[1,5-a]pyridin-3-yl]-2-(difluoromethoxy)-N-[(1R,2S)-2-fluorocyclopropyl] 6-methoxy-benzamide / 4-[6-(1-cyano-1-methyl-ethyl)pyrazolo[1,5-a]pyridin-3-yl]-2-(difluoromethoxy)-N-[(1S,2R)-2-fluorocyclopropyl]-6-methoxy-benzamide mixture | Int 202 + CAS# 143062-73-1 | D1i + D1ii | 458.4 | 459.4 |

TABLE III-continued

| Illustrative compounds of the invention. | | | | | | |
|---|---|---|---|---|---|---|
| Cpd# | Structure | Name | SM | Mtd | MW | MS Mes'd |
| 234 | 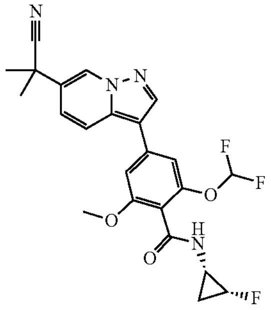 [SMILES: COc1cc(-c2cnn3cc(C(C)(C)C#N)ccc23)cc(OC(F)F)c1C(=O)N[C@H]1C[C@H]1F] | 4-[6-(1-cyano-1-methyl-ethyl)pyrazolo[1,5-a]pyridin-3-yl]-2-(difluoromethoxy)-N-[(1S,2R)-2-fluorocyclopropyl]-6-methoxy-benzamide | Int 202 + CAS# 185225-84-7 | D1i + D1ii | 458.4 | 459.4 |
| 235 | 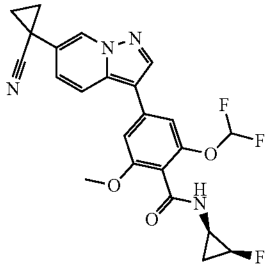 [SMILES: COc1cc(-c2cnn3cc(C4(C#N)CC4)ccc23)cc(OC(F)F)c1C(=O)N[C@@H]1C[C@@H]1F] | 4-[6-(1-cyanocyclopropyl) pyrazolo[1,5-a]pyridin-3-yl]-2-(difluoromethoxy)-N-[(1R,2S)-2-fluorocyclopropyl]-6-methoxy-benzamide | Int 204 + CAS# 143062-84-4 | D1ii | 456.4 | 457.3 |
| 236 | 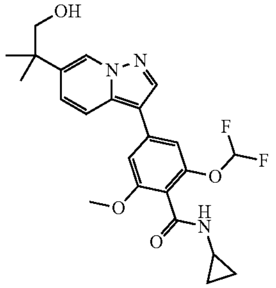 [SMILES: COc1cc(-c2cnn3cc(C(C)(C)CO)ccc23)cc(OC(F)F)c1C(=O)NC1CC1] | N-cyclopropyl-2-(difluoromethoxy)-4-[6-(2-hydroxy-1,1-dimethyl-ethyl)pyrazolo[1,5-a]pyridin-3-yl]-6-methoxy-benzamide | Int 208 + Int 7 | C | 445.5 | 447.3 |
| 237 | 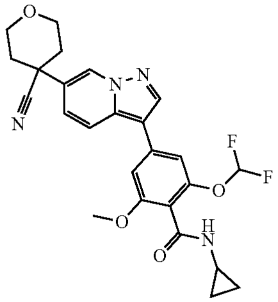 [SMILES: COc1cc(-c2cnn3cc(C4(C#N)CCOCC4)ccc23)cc(OC(F)F)c1C(=O)NC1CC1] | 4-[6-(4-cyanotetrahydropyran-4-yl)pyrazolo[1,5-a]pyridin-3-yl]-N-cyclopropyl-2-(difluoromethoxy)-6-methoxy-benzamide | Int 211 + Int 7 | C | 482.5 | 483.4 |
| 238 | 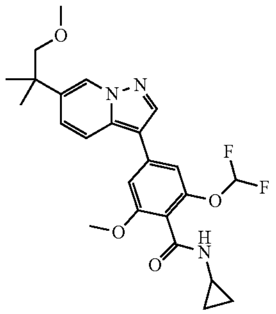 [SMILES: COCC(C)(C)c1ccc2c(-c3cc(OC)c(C(=O)NC4CC4)c(OC(F)F)c3)cnn2c1] | N-cyclopropyl-2-(difluoromethoxy)-6-methoxy-4-[6-(2-methoxy-1,1-dimethyl-ethyl)pyrazolo[1,5-a]pyridin-3-yl]benzamide | Int 214 + Int 7 | C | 459.5 | 460.7 |

TABLE III-continued

| Illustrative compounds of the invention. | | | | | | |
|---|---|---|---|---|---|---|
| Cpd# | Structure | Name | SM | Mtd | MW | MS Mes'd |
| 239 | 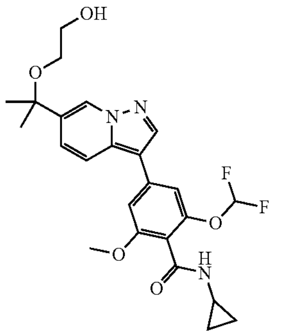 [SMILES: COc1cc(-c2cnn3cc(C(C)(C)OCCO)ccc23)cc(OC(F)F)c1C(=O)NC1CC1] | N-cyclopropyl-2-(difluoromethoxy)-4-[6-[1-(2-hydroxyethoxy)-1-methyl-ethyl]pyrazolo[1,5-a]pyridin-3-yl]-6-methoxy-benzamide | Int 215 + Int 7 | C | 475.5 | 476.3 |
| 240 | 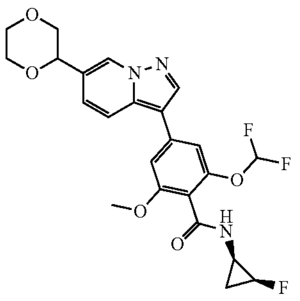 [SMILES: COc1cc(-c2cnn3cc(C4COCCO4)ccc23)cc(OC(F)F)c1C(=O)N[C@@H]1C[C@@H]1F] | 2-(difluoromethoxy)-4-[6-(1,4-dioxan-2-yl)pyrazolo[1,5-a]pyridin-3-yl]-N-[(1R,2S)-2-fluorocyclopropyl]-6-methoxy-benzamide | Int 199 + Int 8 | C | 477.4 | 478.4 |
| 241 | 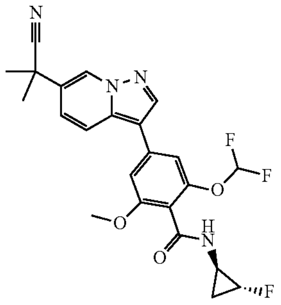 + 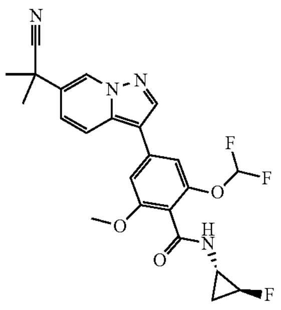 | 4-[6-(1-cyano-1-methyl-ethyl)pyrazolo[1,5-a]pyridin-3-yl]-2-(difluoromethoxy)-N-[(1R,2R)-2-fluorocyclopropyl]-6-methoxy-benzamide / 4-[6-(1-cyano-1-methyl-ethyl)pyrazolo[1,5-a]pyridin-3-yl]-2-(difluoromethoxy)-N-[(1S,2S)-2-fluorocyclopropyl]-6-methoxy-benzamide mixture | Int 202 + CAS# 1799439-05-6 | D1i + D1ii | 458.4 | 459.4 |

TABLE III-continued

Illustrative compounds of the invention.

| Cpd# | Structure | Name | SM | Mtd | MW | MS Mes'd |
|---|---|---|---|---|---|---|
| 242 | 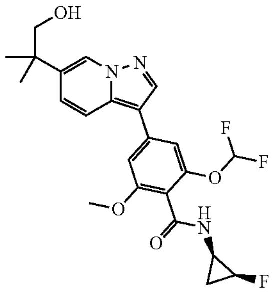 [SMILES: COc1cc(-c2cnn3cc(C(C)(C)CO)ccc23)cc(OC(F)F)c1C(=O)N[C@@H]1C[C@@H]1F] | 2-(difluoromethoxy)-N-[(1R,2S)-2-fluorocyclopropyl]-4-[6-(2-hydroxy-1,1-dimethyl-ethyl)pyrazolo[1,5-a]pyridin-3-yl]-6-methoxy-benzamide | Int 217 + CAS# 143062-84-4 | D1i + D1ii | 463.4 | 464.8 |
| 243 | 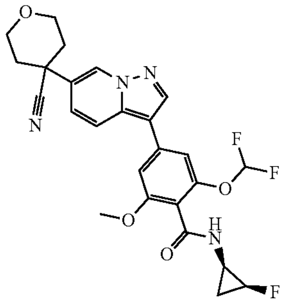 [SMILES: COc1cc(-c2cnn3cc(C4(C#N)CCOCC4)ccc23)cc(OC(F)F)c1C(=O)N[C@@H]1C[C@@H]1F] | 4-[6-(4-cyanotetrahydropyran-4-yl)pyrazolo[1,5-a]pyridin-3-yl]-2-(difluoromethoxy)-N-[(1R,2S)-2-fluorocyclopropyl]-6-methoxy-benzamide | Int 169 + Int 7 | D1i D1iii | 500.5 | 501.2 |
| 244 | 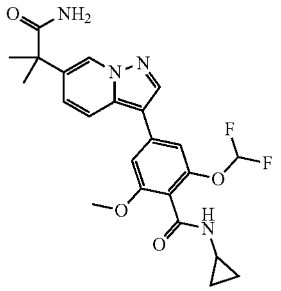 [SMILES: COc1cc(-c2cnn3cc(C(C)(C)C(N)=O)ccc23)cc(OC(F)F)c1C(=O)NC1CC1] | 4-[6-(2-amino-1,1-dimethyl-2-oxo-ethyl)pyrazolo[1,5-a]pyridin-3-yl]-N-cyclopropyl-2-(difluoromethoxy)-6-methoxy-benzamide | Int 169 + Int 7 | Ex. 2.92 | 458.5 | 459.3 |
| 245 | 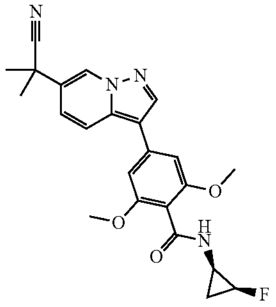 [SMILES: COc1cc(-c2cnn3cc(C(C)(C)C#N)ccc23)cc(OC)c1C(=O)N[C@@H]1C[C@@H]1F] | 4-[6-(1-cyano-1-methyl-ethyl)pyrazolo[1,5-a]pyridin-3-yl]-N-[(1R,2S)-2-fluorocyclopropyl]-2,6-dimethoxy-benzamide | Int 169 + Int 11 | C | 422.5 | 423.3 |
| 246 | 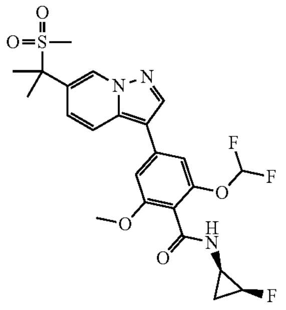 [SMILES: COc1cc(-c2cnn3cc(C(C)(C)S(C)(=O)=O)ccc23)cc(OC(F)F)c1C(=O)N[C@@H]1C[C@@H]1F] | 2-(difluoromethoxy)-N-[(1R,2S)-2-fluorocyclopropyl]-6-methoxy-4-[6-(1-methyl-1-methylsulfonyl-ethyl)pyrazolo[1,5-a]pyridin-3-yl]benzamide | Int 219 + Int 8 | C | 511.5 | 512.2 |

TABLE III-continued

Illustrative compounds of the invention.

| Cpd# | Structure | Name | SM | Mtd | MW | MS Mes'd |
|---|---|---|---|---|---|---|
| 247 | 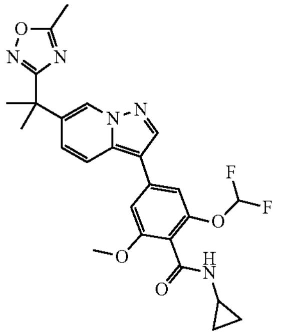 [SMILES: COc1cc(-c2cnn3cc(C(C)(C)c4noc(C)n4)ccc23)cc(OC(F)F)c1C(=O)NC1CC1] | N-cyclopropyl-2-(difluoromethoxy)-6-methoxy-4-[6-[1-methyl-1-(5-methyl-1,2,4-oxadiazol-3-yl)ethyl]pyrazolo[l,5-a]pyridin-3-yl]benzamide | Int 221 + Int 7 | C | 497.5 | 498.4 |
| 248 | 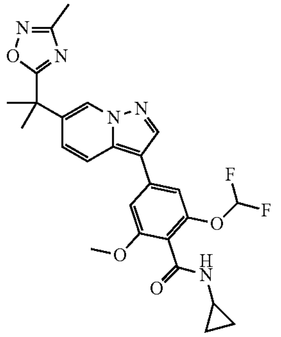 [SMILES: COc1cc(-c2cnn3cc(C(C)(C)c4nc(C)no4)ccc23)cc(OC(F)F)c1C(=O)NC1CC1] | N-cyclopropyl-2-(difluoromethoxy)-6-methoxy-4-[6-[1-methyl-1-(3-methyl-1,2,4-oxadiazol-5-yl)ethyl]pyrazolo[l,5-a]pyridin-3-yl]benzamide | Int 223 + Int 7 | C | 497.5 | 498.4 |
| 249 | 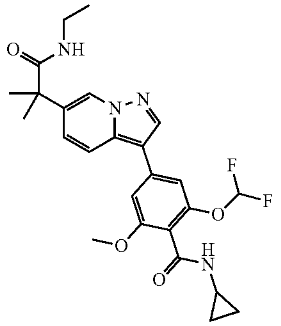 [SMILES: CCNC(=O)C(C)(C)c1ccc2c(-c3cc(OC)c(C(=O)NC4CC4)c(OC(F)F)c3)cnn2c1] | N-cyclopropyl-2-(difluoromethoxy)-4-[6-[2-(ethylamino)-1,1-dimethyl-2-oxo-ethyl]pyrazolo[1,5-a]pyridin-3-yl]-6-methoxy-benzamide | Int 225 + Int 7 | C | 486.5 | 487.3 |
| 250 | 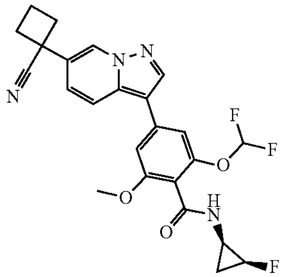 [SMILES: COc1cc(-c2cnn3cc(C4(C#N)CCC4)ccc23)cc(OC(F)F)c1C(=O)N[C@@H]1C[C@@H]1F] | 4-[6-(1-cyanocyclobutyl) pyrazolo[1,5-a]pyridin-3-yl]-2-(difluoromethoxy)-N-[(1R,2S)-2-fluorocyclopropyl]-6-methoxy-benzamide | Int 227 + Int 8 | C | 470.4 | 471.3 |

TABLE III-continued

| Illustrative compounds of the invention. | | | | | | |
|---|---|---|---|---|---|---|
| Cpd# | Structure | Name | SM | Mtd | MW | MS Mes'd |
| 251 | 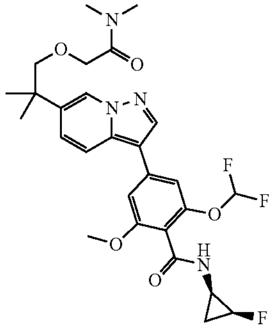 [SMILES: COc1cc(-c2cnn3cc(C(C)(C)COCC(=O)N(C)C)ccc23)cc(OC(F)F)c1C(=O)N[C@@H]1C[C@@H]1F] | 2-(difluoromethoxy)-4-[6-[2-[2-(dimethylamino)-2-oxo-ethoxy]-1,1-dimethyl-ethyl]pyrazolo[1,5-a]pyridin-3-yl]-N-[(1R,2S)-2-fluorocyclopropyl]-6-methoxy-benzamide | Int 236 + Int 8 | C | 548.6 | 549.3 |
| 252 | 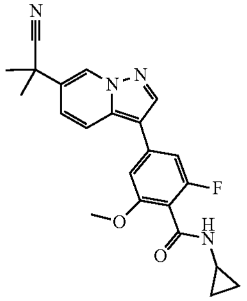 [SMILES: COc1cc(-c2cnn3cc(C(C)(C)C#N)ccc23)cc(F)c1C(=O)NC1CC1] | 4-[6-(1-cyano-1-methyl-ethyl)pyrazolo[1,5-a]pyridin-3-yl]-N-cyclopropyl-2-fluoro-6-methoxy-benzamide | Int 235 + Int 169 | C | 392.4 | 393.3 |
| 253 | 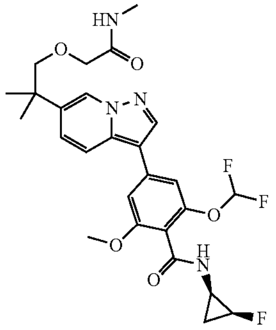 [SMILES: CNC(=O)COCC(C)(C)c1ccc2c(-c3cc(OC)c(C(=O)N[C@@H]4C[C@@H]4F)c(OC(F)F)c3)cnn2c1] | 2-(difluoromethoxy)-4-[6-[1,1-dimethyl-2-[2-(methylamino)-2-oxo-ethoxylethyl]pyrazolo[1,5-a]pyridin-3-yl]-N-[(1R,2S)-2-fluorocyclopropyl]-6-methoxy-benzamide | Int 237 + Int 8 | C | 534.5 | 535.3 |
| 254 | 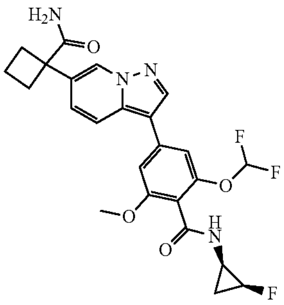 [SMILES: COc1cc(-c2cnn3cc(C4(C(N)=O)CCC4)ccc23)cc(OC(F)F)c1C(=O)N[C@@H]1C[C@@H]1F] | 4-[6-(1-carbamoylcyclobutyl)pyrazolo[1,5-a]pyridin-3-yl]-2-(difluoromethoxy)-N-[(1R,2S)-2-fluorocyclopropyl]-6-methoxy-benzamide | Int 238 + Int 8 | C | 488.5 | 489.3 |

TABLE III-continued

Illustrative compounds of the invention.

| Cpd# | Structure | Name | SM | Mtd | MW | MS Mes'd |
|---|---|---|---|---|---|---|
| 255 | 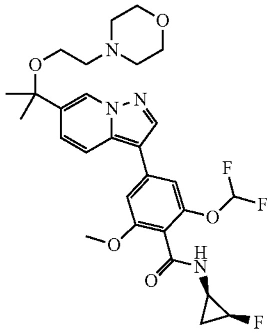 [SMILES: COc1cc(-c2cnn3cc(C(C)(C)OCCN4CCOCC4)ccc23)cc(OC(F)F)c1C(=O)N[C@@H]1C[C@@H]1F] | 2-(difluoromethoxy)-N-[(1R,2S)-2-fluorocyclopropyl]-6-methoxy-4-[6-[1-methyl-1-(2-morpholinoethoxy)ethyl]pyrazolo[1,5-a]pyridin-3-yl]benzamide | Int 239 + Int 8 | C | 562.6 | 563.3 |
| 256 | 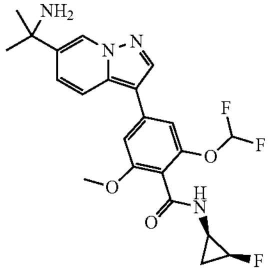 [SMILES: COc1cc(-c2cnn3cc(C(C)(C)N)ccc23)cc(OC(F)F)c1C(=O)N[C@@H]1C[C@@H]1F] | 4-[6-(1-amino-1-methyl-ethyl)pyrazolo[1,5-a]pyridin-3-yl]-2-difluoromethoxy)-N-[(1R,2S)-2-fluorocyclopropyl]-6-methoxy-benzamide | Int 241 + Int 8 | C | 448.4 | 449.3 |
| 257 | 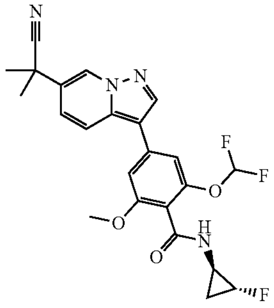 first eluting | 4-[6-(1-cyano-1-methyl-ethyl)pyrazolo[1,5-a]pyridin-3-yl]-2-(difluoromethoxy)-N-(2-fluorocyclopropyl)-6-methoxy-benzamide | Cpd 241 | Ex. 2.93 | 458.4 | 459.3 |
| 258 | 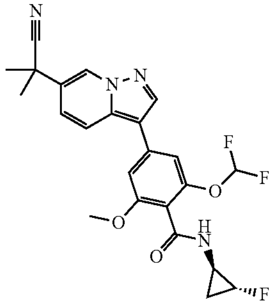 second eluting | 4-[6-(1-cyano-1-methyl-ethyl)pyrazolo[1,5-a]pyridin-3-yl]-2-(difluoromethoxy)-N-(2-fluorocyclopropyl)-6-methoxy-benzamide | Cpd 241 | Ex. 2.93 | 458.4 | 459.3 |

TABLE III-continued

Illustrative compounds of the invention.

| Cpd# | Structure | Name | SM | Mtd | MW | MS Mes'd |
|---|---|---|---|---|---|---|
| 259 | 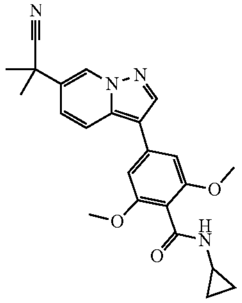 [SMILES: COc1cc(-c2cnn3cc(C(C)(C)C#N)ccc23)cc(OC)c1C(=O)NC1CC1] | 4-[6-(1-cyano-1-methyl-ethyl)pyrazolo[1,5-a]pyridin-3-yl]-N-cyclopropyl-2,6-dimethoxy-benzamide | Cpd 252 + CAS# 124-41-4 | Ex. 2.94 | 404.5 | 405.4 |
| 260 | 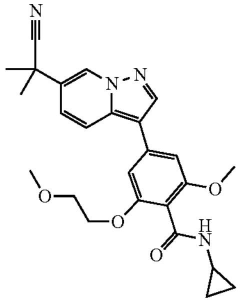 [SMILES: COCCOc1cc(-c2cnn3cc(C(C)(C)C#N)ccc23)cc(OC)c1C(=O)NC1CC1] | 4-[6-(1-cyano-1-methyl-ethyl)pyrazolo[1,5-a]pyridin-3-yl]-N-cyclopropyl-2-methoxy-6-(2-methoxyethoxy) benzamide | Cpd 252 + CAS# 109-86-4 | Ex. 2.95 | 448.5 | 449.4 |
| 261 | 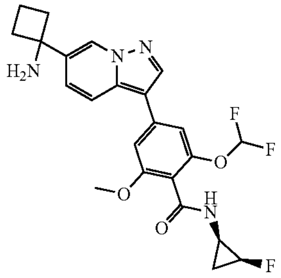 [SMILES: COc1cc(-c2cnn3cc(C4(N)CCC4)ccc23)cc(OC(F)F)c1C(=O)N[C@@H]1C[C@@H]1F] | 4-[6-(1-aminocyclobutyl) pyrazolo[1,5-a]pyridin-3-yl]-2-(difluoromethoxy)-N-[(1R,2S)-2-fluorocyclopropyl]-6-methoxy-benzamide | Int 242 + Int 8 | C | 460.4 | 461.3 |
| 262 | 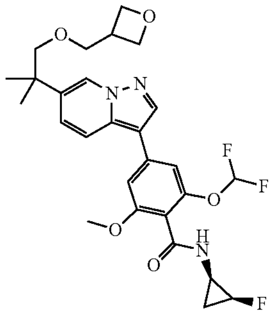 [SMILES: COc1cc(-c2cnn3cc(C(C)(C)COCC4COC4)ccc23)cc(OC(F)F)c1C(=O)N[C@@H]1C[C@@H]1F] | 2-(difluoromethoxy)-4-[6-[1,1-dimethyl-2-(oxetan-3-ylmethoxy)ethyl] pyrazolo[1,5-a]pyridin-3-yl]-N-[(1R,2S)-2-fluorocyclopropyl]-6-methoxy-benzamide | Int 244 + Int 8 | C | 533.5 | 534.5 |
| 263 | 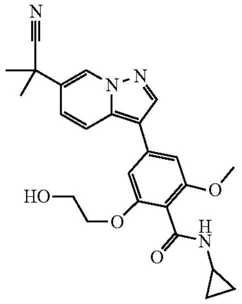 [SMILES: COc1cc(-c2cnn3cc(C(C)(C)C#N)ccc23)cc(OCCO)c1C(=O)NC1CC1] | 4-[6-(1-cyano-1-methyl-ethyl)pyrazolo[1,5-a]pyridin-3-yl]-N-cyclopropyl-2-(2-hydroxyethoxy)-6-methoxy-benzamide | Cpd 252 + CAS# 107-21-1 | Ex. 2.96 | 434.5 | 435.4 |

TABLE III-continued

Illustrative compounds of the invention.

| Cpd# | Structure | Name | SM | Mtd | MW | MS Mes'd |
|---|---|---|---|---|---|---|
| 264 | 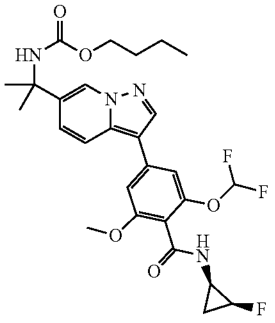 [SMILES: CCCCOC(=O)NC(C)(C)c1ccc2c(-c3cc(OC)c(C(=O)N[C@@H]4C[C@@H]4F)c(OC(F)F)c3)cnn2c1] | butyl N-[1-[3-[3-(difluoromethoxy)-4-[[(1R,2S)-2-fluorocyclopropyl]carbamoyl]-5-methoxy-phenyl]pyrazolo[1,5-a]pyridin-6-yl]-1-methyl-ethylicarbamate | Int 245 + Int 8 | C | 548.6 | 549.5 |
| 265 | 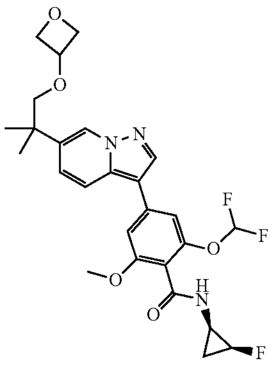 [SMILES: COc1cc(-c2cnn3cc(C(C)(C)COC4COC4)ccc23)cc(OC(F)F)c1C(=O)N[C@@H]1C[C@@H]1F] | 2-(difluoromethoxy)-4-[6-[1,1-dimethyl-2-(oxetan-3-yloxy)ethyl]pyrazolo[1,5-a]pyridin-3-yl]-N-[(1R,2S)-2-fluorocyclopropyl]-6-methoxy-benzamide | Int 246 + Int 8 | C | 519.5 | 520.3 |
| 266 | 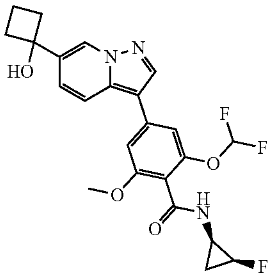 [SMILES: COc1cc(-c2cnn3cc(C4(O)CCC4)ccc23)cc(OC(F)F)c1C(=O)N[C@@H]1C[C@@H]1F] | 2-(difluoromethoxy)-N-[(1R,2S)-2-fluorocyclopropyl]-4-[6-(1-hydroxycyclobutyl)pyrazolo[1,5-a]pyridin-3-yl]-6-methoxy-benzamide | Int 247 + Int 8 | C | 461.4 | 462.3 |
| 267 | 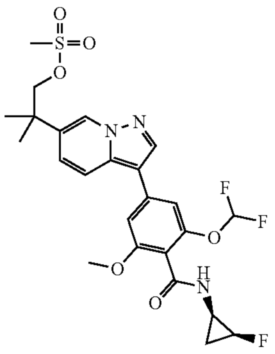 [SMILES: COc1cc(-c2cnn3cc(C(C)(C)COS(C)(=O)=O)ccc23)cc(OC(F)F)c1C(=O)N[C@@H]1C[C@@H]1F] | [2-[3-[3-(difluoromethoxy)-4-[[(1R,2S)-2-fluorocyclopropyl]carbamoyl]-5-methoxy-phenyl]pyrazolo[1,5-a]pyridin-6-yl]-2-methyl-propyl] methanesulfonate | Cpd 242 | Ex. 2.97 | 541.5 | 542.2 |

TABLE III-continued

Illustrative compounds of the invention.

| Cpd# | Structure | Name | SM | Mtd | MW | MS Mes'd |
|---|---|---|---|---|---|---|
| 268 | 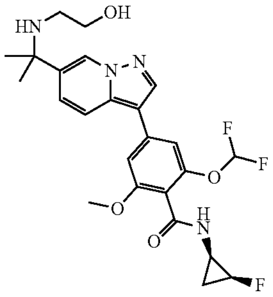 [SMILES: COc1cc(-c2cnn3cc(C(C)(C)NCCO)ccc23)cc(OC(F)F)c1C(=O)N[C@@H]1C[C@@H]1F] | 2-(difluoromethoxy)-N-[(1R,2S)-2-fluorocyclopropyl]-4-[6-[1-(2-hydroxyethylamino)-1-methyl-ethyl]pyrazolo[1,5-a]pyridin-3-yl]-6-methoxy-benzamide | Int 249 | Ex. 2.98 | 492.5 | 493.4 |
| 269 | 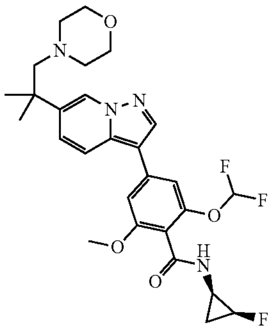 [SMILES: COc1cc(-c2cnn3cc(C(C)(C)CN4CCOCC4)ccc23)cc(OC(F)F)c1C(=O)N[C@@H]1C[C@@H]1F] | 2-(difluoromethoxy)-4-[6-(1,1-dimethyl-2-morpholino-ethyl)pyrazolo[1,5-a]pyridin-3-yl]-N-[(1R,2S)-2-fluorocyclopropyl]-6-methoxy-benzamide | Int 251 + Int 8 | C | 532.6 | 533.3 |
| 270 | 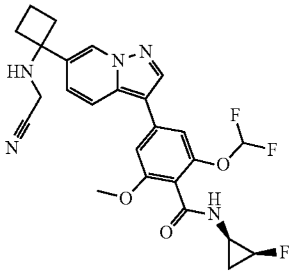 [SMILES: COc1cc(-c2cnn3cc(C4(NCC#N)CCC4)ccc23)cc(OC(F)F)c1C(=O)N[C@@H]1C[C@@H]1F] | 4-[6-[1-(cyanomethylamino) cyclobutyl]pyrazolo [1,5-a]pyridin-3-yl]-2-(difluoromethoxy)-N-[(1R,2S)-2-fluorocyclopropyl]-6-methoxy-benzamide | Int 252 + Int 8 | C | 499.5 | 500.3 |
| 271 | 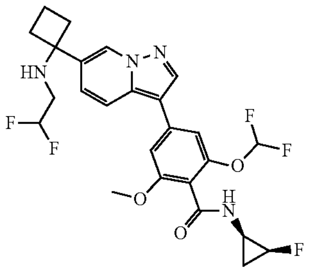 [SMILES: COc1cc(-c2cnn3cc(C4(NCC(F)F)CCC4)ccc23)cc(OC(F)F)c1C(=O)N[C@@H]1C[C@@H]1F] | 4-[6-[1-(2,2-difluoroethylamino) cyclobutyl]pyrazolo [1,5-a]pyridin-3-yl]-2-(difluoromethoxy)-N-[(1R,2S)-2-fluorocyclopropyl]-6-methoxy-benzamide | Int 256 + Int 8 | C | 524.5 | 525.3 |
| 272 | 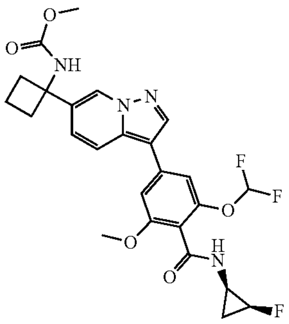 [SMILES: COC(=O)NC1(c2ccc3c(-c4cc(OC)c(C(=O)N[C@@H]5C[C@@H]5F)c(OC(F)F)c4)cnn3c2)CCC1] | methyl N-[1-[3-[3-(difluoromethoxy)-4-[[(1R,2S)-2-fluorocyclopropyl] carbamoyl-5-methoxy-phenyl]pyrazolo[1,5-a]pyridin-6-yl]cyclobutyl] carbamate | Int 258 + Int 8 | C | 518.5 | 519.3 |

TABLE III-continued

| Illustrative compounds of the invention. | | | | | | |
|---|---|---|---|---|---|---|
| Cpd# | Structure | Name | SM | Mtd | MW | MS Mes'd |
| 273 | 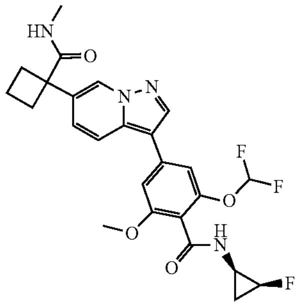 [SMILES: CNC(=O)C1(c2ccc3c(-c4cc(OC)c(C(=O)N[C@@H]5C[C@@H]5F)c(OC(F)F)c4)cnn3c2)CCC1] | 2-(difluoromethoxy)-N-[(1R,2S)-2-fluorocyclopropyl]-6-methoxy-4-[6-[1-(methylcarbamoyl)(cyclobutyl]pyrazolo[1,5-a]pyridin-3-yl]benzamide | Int 260 + Int 8 | C | 502.5 | 503.3 |
| 274 | 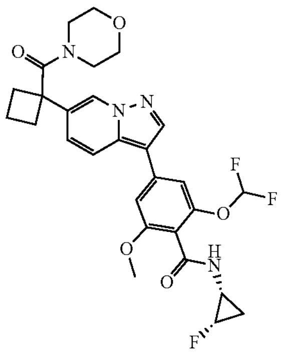 [SMILES: COc1cc(-c2cnn3cc(C4(C(=O)N5CCOCC5)CCC4)ccc23)cc(OC(F)F)c1C(=O)N[C@@H]1C[C@@H]1F] | 2-(difluoromethoxy)-N-[(1R,2S)-2-fluorocyclopropyl] 6-methoxy-4-[6-[1-(morpholine-4-carbonyl)cyclobutyl] pyrazolo[1,5-a]pyridin-3-yl]benzamide | Int 264 + Int 8 | C | 558.5 | 559.3 |
| 275 | 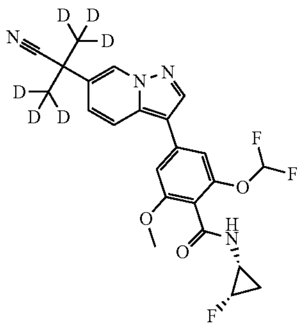 [SMILES: [2H]C([2H])([2H])C(C#N)(c1ccc2c(-c3cc(OC)c(C(=O)N[C@@H]4C[C@@H]4F)c(OC(F)F)c3)cnn2c1)C([2H])([2H])[2H]] | 4-[6-[1-cyano-2,2,2-trideuterio-1-(trideuteriomethyl) ethyl]pyrazolo[1,5-a]pyridin-3-yl]-2-(difluoromethoxy)-N-[(1R,2S)-2-fluorocyclopropyl]-6-methoxy-benzamide | CAS# 6443-85-2 | Ex. 2.99 | 464.5 | 465.2 |
| 276 | 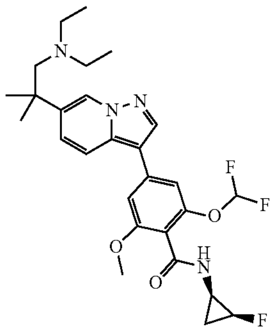 [SMILES: CCN(CC)CC(C)(C)c1ccc2c(-c3cc(OC)c(C(=O)N[C@@H]4C[C@@H]4F)c(OC(F)F)c3)cnn2c1] | 4-[6-[2-(diethylamino)-1,1-dimethyl-ethyl]pyrazolo[1,5-a]pyridin-3-yl]-2-(difluoromethoxy)-N-[(1R,2S)-2-fluorocyclopropyl]-6-methoxy-benzamide | Cpd 242 | Ex. 2.100 | 518.6 | 519.8 |

SM = Starting Material,

Mtd = Method,

MS Mes'd = Mesured mass

TABLE IV

| Cpd# | NMR data of illustrative compounds of the invention.<br>NMR data |
|---|---|
| 19 | $^1$H NMR (400 MHz, DMSO-$d_6$) δ 8.67 (dd, 1H), 8.37 (d, 1H), 7.92 (s, 1H), 7.74-7.73 (m, 1H), 7.42-7.06 (m, 1H), 7.23-7.22 (m, 1H), 7.19 (dd, 1H), 7.08-7.07 (m, 1H), 3.88 (s, 3H), 2.82-2.75 (m, 1H), 1.77 (s, 6H), 0.70-0.66 (m, 2H), 0.48-0.44 (m, 2H) |
| 116 | $^1$H NMR (400 MHz, DMSO-$d_6$) δ 8.69 (dd, 1H), 8.36 (d, 1H), 7.93 (s, 1H), 7.78-7.77 (m, 1H), 7.42-7.05 (m, 1H), 7.24-7.21 (m, 2H), 7.08-7.07 (m, 1H), 4.10-4.01 (m, 2H), 3.88 (s, 3H), 3.72-3.66 (m, 2H), 2.85-2.74 (m, 1H), 2.28-2.20 (m, 2H), 2.20-2.07 (m, 2H), 0.75-0.62 (m, 2H), 0.51-0.45 (m, 2H) |
| 117 | $^1$H NMR (400 MHz, DMSO-$d_6$) δ 8.75 (dd, 1H), 8.37 (d, 1H), 7.96 (s, 1H), 7.89-7.88 (m, 1H), 7.42-7.05 (m, 1H), 7.24-7.23 (m, 2H), 7.08-7.07 (m, 1H), 5.22 (d, 2H), 4.98 (d, 2H), 3.89 (s, 3H), 2.83-2.76 (m, 1H), 0.73-0.62 (m, 2H), 0.51-0.39 (m, 2H) |
| 150 | $^1$H NMR (400 MHz, $CD_3OD$) δ 8.50 (dd, 1H), 7.74 (s, 1H), 7.58 (dd, 1H), 7.21-7.15 (m, 2H), 7.08-7.03 (m, 1H), 6.92 (t, 1H), 3.94 (s, 3H), 3.67 (s, 2H), 2.91-2.83 (m, 1H), 1.39 (s, 6H), 0.88-0.76 (m, 2H), 0.67-0.55 (m, 2H) |
| 173 | $^1$H NMR (400 MHz, DMSO-$d_6$) δ 8.60 (dd, 1H), 8.36 (d, 1H), 7.84 (s, 1H), 7.64-7.63 (m, 1H), 7.42-7.04 (m, 1H), 7.20-7.19 (m, 1H), 7.14 (dd, 1H), 7.05-7.04 (m, 1H), 5.78 (s, 1H), 3.89 (s, 3H), 2.82-2.76 (m, 1H), 2.47-2.42 (m, 2H), 2.36-2.27 (m, 2H), 1.99-1.90 (m, 1H), 1.76-1.65 (m, 1H), 0.71-0.65 (m, 2H), 0.51-0.42 (m, 2H) |
| 174 | $^1$H NMR (400 MHz, DMSO-$d_6$) δ 8.65 (dd, 1H), 8.36 (d, 1H), 7.85 (s, 1H), 7.63-7.59 (m, 1H), 7.44-7.04 (m, 1H), 7.20-7.19 (m, 1H), 7.14 (dd, 1H), 7.05-7.04 (m, 1H), 4.99 (dd, 2H), 4.68 (t, 2H), 4.42-4.30 (m, 1H), 3.88 (s, 3H), 2.85-2.74 (m, IH), 0.73-0.62 (m, 2H), 0.51-0.38 (m, 2H) |
| 219 | $^1$H NMR (400 MHz, DMSO-$d_6$) δ 8.81 (dd, 1H), 8.55 (s, 1H), 8.46 (d, 1H), 8.08 (dd, 1H), 7.59 (dd, 1H), 7.25-7.18 (m, 2H), 7.15-7.01 (m, 1H), 4.84-4.61 (m, 1H), 3.90 (s, 3H), 2.90-2.79 (m, 1H), 1.80 (s, 6H), 1.18-1.03 (m, 1H), 1.02-0.86 (m, 1H) |
| 227 | $^1$H NMR (400 MHz, $CD_3OD$) δ 8.67 (dd, 1H), 8.29 (s, 1H), 7.90 (d, 1H), 7.52 (dd, 1H), 7.18 (d, 1H), 7.10-7.04 (m, 1H), 6.88 (t, 1H), 4.84-4.61 (m, 1H), 3.94 (s, 3H), 2.96-2.87 (m, 1H), 1.62 (s, 6H), 1.28-1.14 (m, 1H), 1.10-0.96 (m, 1H) |
| 228 | $^1$H NMR (400 MHz, $CD_3OD$) δ 8.89 (d, 1H), 8.34 (s, 1H), 8.19 (d, 1H), 7.79 (d, 1H), 7.76-7.72 (m, 1H), 6.87 (t, 1H), 4.82-4.66 (m, 1H), 3.98 (s, 3H), 2.97-2.87 (m, 1H), 1.89 (s, 6H), 1.28-1.14 (m, 1H), 1.11-0.96 (m, 1H) |
| 231 | $^1$H NMR (400 MHz, DMSO-$d_6$) δ 9.02 (d, 1H), 8.92 (d, 1H), 8.72 (s, 1H), 7.80 (d, 1H), 7.66 (d, 1H), 6.85 (t, 1H), 4.84-4.61 (m, 1H), 3.97 (s, 3H), 2.95-2.85 (m, 1H), 1.85 (s, 6H), 1.27-1.12 (m, 2H), 1.10-0.97 (m, 2H) |

Biological Examples

Example 3. In Vitro Assays 3.1. Biochemical Assays 3.1.1. $^{33}$P Radioactive Kinase Assay 3.1.1.1. Overview The principle of the $^{33}$P radioactive kinase assay consists in measuring the incorporated $^{33}$P into the substrate AMARA peptide when phosphorylated by SIK1, SIK2 or SIK3 using [$^{33}$P]-g-ATP, which correlates with kinase activity.

3.1.1.2. Protocol

The test compounds are prepared as a serial dilution of 10 point dose responses with 1/5 dilution steps in 100% DMSO starting from 2 mM highest concentration, diluted 1/20 in water and 5 μL is transferred to the assay plates (Greiner, Cat #651201).

1% DMSO and 10 μM staurosporine final concentrations are used as negative and positive controls.

11 μL of enzyme-substrate mixture is added on the assay plates. The reactions are started by adding 9 μL ATP mixture, consisting of non-labeled and $^{33}$P-labeled ATP, on the assay plates. Plates are incubated at 30° C. for the time intervals indicated in Table V.

TABLE V

Conditions for human SIK kinase $^{33}$P radioactive assays

| Kinase, [Kinase] | Substrate, [Substrate] | ATP | Assay buffer | Incubation time |
|---|---|---|---|---|
| SIK1 (Carna Biosciences, Cat# 02-131), 0.4 ng/mL | AMARA (SignalChem, Cat# A11-58), 7 μM | 10 μM ATP + 0.25 μCi/25 μL [γ-$^{33}$P]ATP | 25 mM Tris pH 7.5<br>0.01% Triton X-100<br>0.5 mM EGTA<br>2.5 mM DTT<br>10 mM MgCl | 120 min |
| SIK2 (ThermoFisher Scientific, Cat# PV4792), 0.0532 ng/mL | AMARA (SignalChem, Cat# A11-58), 5 μM | 10 μM ATP + 0.25 μCi/25 μL [γ-$^{33}$P]ATP | 25 mM Tris pH 7.5<br>0.01% Triton X-100<br>0.5 mM EGTA<br>5 mM $MgCl_2$<br>2.5 mM DTT | 120 min |
| SIK3 (SignalChem, Cat# S12-11G-100), 0.4 ng/mL | AMARA (SignalChem, Cat# A11-58), 7 μM | 15 μM ATP + 0.50 μCi/25 μL [γ-$^{33}$P]ATP | 25 mM MOPS pH 7.5<br>0.01% Triton X-100<br>0.5 mM EGTA<br>5 mM MgCl | 80 min |

The reactions are stopped by adding 25 μL phosphoric acid (150 mM) to the reactions.

The completely terminated kinase reactions are transferred using a harvester on pre-wetted UniFilter-96 plates (UniFilter-96 GF/B, PerkinElmer Inc., Cat #6005177).

After harvesting the kinase reactions, the filter plates are washed 6 times with phosphoric acid (75 mM). The back of the UniFilter-96 plates are sealed and 40 μL MicroScint-20 (PerkinElmer Inc., Cat #6013621) is added to each well. The top of the plates are sealed with TopSeal-A. Read-out is performed with a TopCount instrument (PerkinElmer Inc.).

3.1.1.3. Data Analysis and Results

Raw data are generated following the read-out performed on the TopCount, plotted to generate dose response curves to calculate percentage inhibition (PIN) and average $IC_{50}$ for each SIK homologue which are reported in the table below.

TABLE VI $^{33}$P radioactive SIK kinase assay $IC_{50}$ of illustrative compounds of the invention

| Cpd# | SIK1 $IC_{50}$ | SIK2 $IC_{50}$ | SIK3 $IC_{50}$ |
|---|---|---|---|
| 1 | * | * | * |
| 2 | * | ** | ** |
| 3 | * | ** | ** |
| 4 | * | * | ** |
| 5 | * | * | ** |
| 6 | * | * | ** |
| 7 | * | * | * |
| 8 | * | * | ** |
| 9 | * | * | ** |
| 10 | * | * | ** |
| 11 | * | * | * |
| 12 | * | * | ** |
| 13 | * | * | * |
| 14 | * | * | * |
| 15 | * | * | * |
| 16 | * | ** | *** |
| 17 | * | * | *** |
| 18 | * | * | *** |
| 19 | * | * | **** |

TABLE VI-continued

| $^{33}P$ radioactive SIK kinase assay $IC_{50}$ of illustrative compounds of the invention | | | |
|---|---|---|---|
| Cpd# | SIK1 $IC_{50}$ | SIK2 $IC_{50}$ | SIK3 $IC_{50}$ |
| 20 | * | * | *** |
| 21 | * | ** | *** |
| 22 | * | ** | *** |
| 23 | * | ** | *** |
| 24 | * | ** | *** |
| 25 | * | * | *** |
| 26 | * | ** | *** |
| 27 | * | * | *** |
| 28 | * | * | *** |
| 29 | * | * | *** |
| 30 | * | * | ** |
| 31 | * | * | ** |
| 32 | * | * | *** |
| 33 | ** | *** | **** |
| 34 | * | * | *** |

* >500 nM
** >100-500 nM
*** >10-100 nM
**** 0.01-10 nM
NA not measured 3.1.2. ADP-Glo™ Kinase Assay 3.1.2.1. Overview The ADP-Glo™ kinase assay is a luminescent technology assay which measures the ADP formed from a kinase reaction. In this specific study, the kinase reactions consisted of the phosphorylation of the AMARA peptide substrate (SignalChem, Cat #A11-58) by SIK1 (Carna Biosciences, Cat #02-131), SIK2 (ThermoFisher Scientific, Cat #PV4792) or SIK3 (SignalChem, Cat #512-11G-100). In a second step the kinase reactions are terminated and all the remaining ATP is depleted. In a final step the ADP is converted into ATP and this newly synthesized ATP is measured by using a luciferase/luciferin reaction. The generated light is measured using an Envision plate reader, wherein the luminescent signal obtained positively correlates with the kinase activity.

3.1.2.2. Protocol

The test compounds are prepared as a serial dilution of 10 point dose responses with 1/5 dilution steps in 100% DMSO starting from 2 mM highest concentration, diluted 1/20 in water and 1 µL is transferred to the assay plates (PerkinElmer Inc., Cat #6007290).

1% DMSO and 10 µM staurosporine final concentrations are used as negative and positive controls.

2 µL enzyme-substrate mixture is added to the assay plates.

The reaction is started by adding 2 µL diluted ATP on the assay plates. Plates are centrifuged for a few seconds at 1000 rpm and gently shaken for 2 mM followed by an incubation at RT for 120 min.

The reactions are stopped and the unconsumed ATP is depleted by adding 5 µL ADP-Glo Reagent (Promega, Cat #V9120) to the reaction. The plates are centrifuged for a few seconds at 1000 rpm and incubated at RT for 40 min (ATP depletion).

The ADP is converted to ATP and luciferase and luciferin is introduced to detect ATP by adding 10 µL Kinase Detection Reagent (Promega, Cat #V913B+V914r) to the reaction. The plates are centrifuged for a few seconds at 1000 rpm and incubated at RT for 30 min (ADP detection).

Luminescence is measured on an Envision plate reader (PerkinElmer Inc.).

TABLE VII

| Conditions for human SIK kinase ADP-Glo ™ assays | | | | |
|---|---|---|---|---|
| Kinase, [Kinase] | Substrate, [Substrate] | ATP | Assay buffer | Incubation time |
| SIK1 (Carna Biosciences, Cat# 02-131), 0.25 ng/µL | AMARA (SignalChem, Cat# A11-58), 45 µM | 5 µM ATP (Promega, Cat# V915B) | 25 mM Tris pH 7.5 0.01% Triton X-100 0.5 mM EGTA 2.5 mM DTT 5 mM $MgCl_2$ | 120 min |
| SIK2 (ThermoFisher Scientific, Cat# PV4792), 0.0625 ng/µL | AMARA (SignalChem, Cat# A11-58), 45 µM | 5 µM ATP (Promega, Cat# V915B) | 25 mM Tris pH 7.5 0.01% Triton X-100 0.5 mM EGTA 5 mM $MgCl_2$ 2.5 mM DTT | 120 min |
| SIK3 (SignalChem, Cat# S12-11G-100), 0.5 ng/µL | AMARA (SignalChem, Cat# A11-58), 45 µM | 5 µM ATP (Promega, Cat# V915B) | 25 mM Tris pH 7.5 0.01% Triton X-100 0.5 mM EGTA 5 mM $MgCl_2$ 2.5 mM DTT | 120 min |

3.1.2.3. Data Analysis and Results

Raw data are generated following the read-out performed on the TopCount, plotted to generate dose response curves to calculate percentage inhibition (PIN) and average $IC_{50}$ for each SIK homologue which are reported in the table below.

TABLE VIII

| ADP-Glo ™ SIK kinase assay $IC_{50}$ of illustrative compounds of the invention. | | | |
|---|---|---|---|
| Cpd# | SIK1 $IC_{50}$ | SIK2 $IC_{50}$ | SIK3 $IC_{50}$ |
| 10 | * | * | ** |
| 11 | * | * | ** |
| 17 | * | * | *** |
| 18 | * | * | *** |
| 19 | * | * | **** |
| 20 | * | * | *** |
| 22 | * | ** | *** |
| 23 | * | ** | *** |
| 24 | * | ** | *** |
| 25 | * | * | *** |
| 26 | * | ** | **** |
| 27 | * | * | *** |
| 28 | * | * | *** |
| 30 | * | * | *** |
| 32 | * | * | *** |
| 33 | ** | *** | **** |
| 34 | * | ** | **** |
| 35 | * | * | *** |
| 36 | * | * | *** |
| 37 | * | ** | *** |
| 38 | * | * | * |
| 39 | * | * | **** |
| 40 | * | * | * |
| 41 | * | * | * |
| 42 | * | * | ** |
| 43 | * | * | *** |
| 44 | * | * | *** |
| 45 | * | * | ** |
| 46 | * | * | * |
| 47 | * | * | *** |
| 48 | * | * | * |
| 49 | * | * | * |
| 50 | * | * | ** |
| 51 | * | * | *** |
| 52 | * | * | * |
| 53 | * | * | **** |

TABLE VIII-continued

ADP-Glo ™ SIK kinase assay $IC_{50}$ of illustrative compounds of the invention.

| Cpd# | SIK1 $IC_{50}$ | SIK2 $IC_{50}$ | SIK3 $IC_{50}$ |
|---|---|---|---|
| 54 | * | * | *** |
| 55 | * | * | *** |
| 56 | * | * | *** |
| 57 | * | * | *** |
| 58 | ** | ** | *** |
| 59 | *** | *** | **** |
| 60 | ** | *** | **** |
| 61 | * | * | *** |
| 62 | * | * | *** |
| 63 | ** | *** | **** |
| 64 | * | ** | **** |
| 65 | * | *** | **** |
| 66 | * | *** | *** |
| 67 | * | *** | **** |
| 68 | * | *** | **** |
| 69 | * | * | **** |
| 70 | * | * | **** |
| 71 | * | * | *** |
| 72 | * | * | *** |
| 73 | * | * | *** |
| 74 | * | * | *** |
| 75 | * | ** | **** |
| 76 | * | ** | **** |
| 77 | * | * | **** |
| 78 | * | * | *** |
| 79 | * | ** | **** |
| 80 | * | * | * |
| 81 | * | * | * |
| 82 | * | * | * |
| 83 | * | * | * |
| 84 | * | * | ** |
| 85 | * | * | ** |
| 86 | * | * | *** |
| 87 | * | * | * |
| 88 | * | * | *** |
| 89 | * | * | *** |
| 90 | * | * | *** |
| 91 | * | ** | *** |
| 92 | * | * | *** |
| 93 | * | * | *** |
| 94 | * | * | * |
| 95 | * | ** | **** |
| 96 | * | * | **** |
| 97 | * | * | *** |
| 98 | * | * | *** |
| 99 | * | * | ** |
| 100 | * | * | * |
| 101 | * | * | ** |
| 102 | * | * | *** |
| 103 | * | * | *** |
| 104 | * | * | * |
| 105 | * | * | ** |
| 106 | * | * | **** |
| 107 | * | * | **** |
| 108 | ** | *** | **** |
| 109 | * | * | * |
| 110 | * | * | *** |
| 111 | * | * | *** |
| 112 | * | *** | **** |
| 113 | * | * | **** |
| 114 | * | * | *** |
| 115 | ** | *** | **** |
| 116 | * | * | **** |
| 117 | * | * | **** |
| 118 | * | * | *** |
| 119 | * | * | ** |
| 120 | * | * | **** |
| 121 | * | * | *** |
| 122 | * | * | *** |
| 123 | * | * | *** |
| 124 | * | * | ** |
| 125 | * | * | * |
| 126 | * | * | *** |
| 127 | * | * | ** |

TABLE VIII-continued

ADP-Glo ™ SIK kinase assay $IC_{50}$ of illustrative compounds of the invention.

| Cpd# | SIK1 $IC_{50}$ | SIK2 $IC_{50}$ | SIK3 $IC_{50}$ |
|---|---|---|---|
| 128 | * | * | *** |
| 129 | * | * | *** |
| 130 | * | * | **** |
| 131 | * | * | **** |
| 132 | ** | ** | **** |
| 133 | ** | ** | *** |
| 134 | * | * | *** |
| 135 | * | * | *** |
| 136 | * | ** | **** |
| 137 | * | * | *** |
| 138 | * | * | *** |
| 139 | * | * | *** |
| 140 | ** | ** | *** |
| 141 | * | * | ** |
| 142 | * | * | *** |
| 143 | * | * | ** |
| 144 | * | * | *** |
| 145 | * | * | ** |
| 146 | * | * | *** |
| 147 | * | * | *** |
| 148 | * | * | *** |
| 149 | * | * | *** |
| 150 | * | * | **** |
| 151 | * | * | ** |
| 152 | * | * | *** |
| 153 | * | * | *** |
| 154 | * | * | *** |
| 155 | * | * | *** |
| 156 | * | * | *** |
| 157 | * | * | *** |
| 158 | ** | ** | *** |
| 159 | *** | *** | **** |
| 160 | * | * | *** |
| 161 | * | * | *** |
| 162 | * | * | *** |
| 163 | * | * | *** |
| 164 | * | * | *** |
| 165 | * | * | *** |
| 166 | * | ** | **** |
| 167 | * | ** | *** |
| 168 | ** | *** | **** |
| 169 | * | ** | *** |
| 170 | * | * | *** |
| 171 | * | * | *** |
| 172 | * | * | *** |
| 173 | * | ** | *** |
| 174 | ** | *** | **** |
| 175 | * | ** | *** |
| 176 | * | * | *** |
| 177 | * | * | *** |
| 178 | * | * | *** |
| 179 | **** | **** | **** |
| 180 | ** | ** | *** |
| 181 | * | * | *** |
| 182 | * | * | *** |
| 183 | * | ** | *** |
| 184 | * | * | * |
| 185 | * | * | *** |
| 186 | * | * | * |
| 187 | * | * | *** |
| 188 | * | ** | *** |
| 189 | * | * | *** |
| 190 | * | * | *** |
| 191 | * | * | *** |
| 192 | * | * | *** |
| 193 | * | * | *** |
| 194 | * | * | ** |
| 195 | * | * | *** |
| 196 | ** | *** | *** |
| 197 | ** | *** | *** |
| 198 | * | * | *** |
| 199 | * | * | *** |
| 200 | * | ** | *** |
| 201 | * | * | *** |

TABLE VIII-continued

ADP-Glo ™ SIK kinase assay $IC_{50}$ of illustrative compounds of the invention.

| Cpd# | SIK1 $IC_{50}$ | SIK2 $IC_{50}$ | SIK3 $IC_{50}$ |
|---|---|---|---|
| 202 | * | * | *** |
| 203 | * | ** | *** |
| 204 | * | * | *** |
| 205 | * | ** | **** |
| 206 | ** | *** | **** |
| 207 | * | ** | **** |
| 208 | * | * | *** |
| 209 | * | * | *** |
| 210 | * | * | *** |
| 211 | * | ** | **** |
| 212 | * | * | *** |
| 213 | * | * | *** |
| 214 | * | * | ** |
| 215 | ** | ** | *** |
| 216 | ** | ** | *** |
| 217 | * | ** | *** |
| 218 | ** | *** | **** |
| 219 | * | * | **** |
| 220 | * | * | *** |
| 221 | * | * | *** |
| 222 | * | * | ** |
| 223 | * | ** | *** |
| 224 | ** | *** | **** |
| 225 | * | * | **** |
| 226 | * | * | *** |
| 227 | * | ** | **** |
| 228 | * | ** | **** |
| 229 | * | * | *** |
| 230 | * | ** | **** |
| 231 | * | * | **** |
| 232 | * | ** | **** |
| 233 | * | * | **** |
| 234 | * | * | *** |
| 235 | ** | *** | **** |
| 236 | * | * | *** |
| 237 | * | * | **** |
| 238 | * | * | *** |
| 239 | * | * | *** |
| 240 | ** | *** | **** |
| 241 | * | * | **** |
| 242 | * | * | **** |
| 243 | * | * | **** |
| 244 | * | * | *** |
| 245 | * | * | *** |
| 246 | * | * | *** |
| 247 | * | * | *** |
| 248 | * | * | *** |
| 249 | * | * | *** |
| 250 | * | ** | **** |
| 251 | * | * | **** |
| 252 | * | * | ** |
| 253 | * | * | **** |
| 254 | * | * | **** |
| 255 | * | * | *** |
| 256 | * | * | **** |
| 257 | * | * | *** |
| 258 | * | * | **** |
| 259 | * | * | *** |
| 260 | * | * | ** |
| 261 | * | * | **** |
| 262 | * | * | **** |
| 263 | * | * | ** |
| 264 | * | * | *** |
| 265 | * | * | *** |
| 266 | * | ** | **** |
| 267 | * | * | **** |
| 268 | * | * | *** |
| 269 | * | * | **** |
| 270 | * | * | *** |
| 271 | * | * | *** |
| 272 | * | * | *** |
| 273 | * | * | *** |
| 274 | * | * | ** |
| 275 | * | * | **** |
| 276 | * | * | *** |

* >500 nM
** >100-500 nM
*** >10-100 nM
**** 0.01-10 nM
NA not measured

3.2. Cellular Assays

3.2.1. MdM Assay: LPS-Triggered TNFα/IL-10 (ELISA)

3.2.1.1. Overview

SIK inhibition inhibits TNFα and increases IL-10 release in LPS triggered monocyte-derived macrophages (MdM) and dendritic cells (MdDCs) (Clark et al. 2012; Sundberg et al. 2014; Ozanne et al. 2015). This assay evaluates illustrative compounds of the invention for their inhibition of LPS-induced TNFα and LPS triggered IL-10 secretion in monocyte-derived macrophages.

3.2.1.2. Protocols

PBMCs are isolated from human blood samples (buffy-coats). The buffy coat is aseptically transferred into a 50 mL Falcon tube, and diluted 1/2 in PBS. Falcon tubes are filled with 20 mL Lymphoprep™, on top of which 25 mL of the buffy coat is carefully added, tubes are centrifuged for 35 min at 400 g in temperature controlled centrifuge, without brake, at 25° C. PBMCs are aspirated from the white interface layer between sample and Lymphoprep™. PBMCs are washed five times in PBS. Cells are resuspended in RPMI 1640 complete medium supplemented with 10% FBS, 1% P/S, and cell density is determined using a hematologic analyzer (Sysmex XS-500i).

PBMCs are centrifuged at 300×g for 10 min and resuspended at a density of $1.0*10^7$ cells/80 μL Miltenyi buffer (PBS, pH 7.4, 1% FBS, 2 mM EDTA).

3.2.1.2.1 Positive Labelling of CD14+ Monocytes.

Starting from this point of the protocol all steps are performed on ice. 20 μL of CD14+ micro-beads are added per $1.0*10^7$ cells, the tube is mixed and incubated for 15 min in the fridge at 4° C. Cell suspension volume is adjusted to total volume of 100 mL using Miltenyi buffer, mixed gently and subsequently centrifuged for 10 min at 300×g. Supernatant is discarded and cell pellet is resuspended in 12 mL of Miltenyi buffer.

3.2.1.2.2 Magnetic Cell Sorting

Four LS columns are placed in the MACS Separator (magnet) from Miltenyi Biotec, and are prewet by rinsing with 3 mL of MACS buffer per column. Three mL of cell suspension is added onto the column (max $1*10^8$ of labelled cells/column), and columns are subsequently washed 3 times with 3 mL of Miltenyi buffer.

The columns are removed from the magnets, and 5 mL of Miltenyi buffer are added to the column to flush out the CD14+ fraction by pushing the plunger into the column. The flushed fractions are collected in a fresh 50 mL Falcon and volume is adjusted to 30 mL using Miltenyi buffer, cells are centrifuged for 10 min at 300×g. The obtained cell pellet is resuspended in 10 mL RPMI w/o FBS, and cell density is determined using a hematologic analyser (Sysmex XS-500i). 100 000 cells are seeded per well of a 96-well plate for differentiation to MdM in RPMI 1640 medium supplemented with 10% FBS, 1% P/S and 100 ng/mL rhM-CSF. On day 5 the medium is refreshed with 100 μL RPMI 1640 medium supplemented with 10% FBS, 1% P/S and 100 ng/mL rhM-CSF.

On day 10, MdMs are triggered and compound is added.

A compound dilution plate is made in 100% DMSO by 3-fold dilution of 10 mM stock solution. An intermediate dilution plate (10× final concentration) is made by diluting the compound dilution plate 50-fold in RPMI medium.

Medium is carefully removed from cell plates using multichannel pipette, and replaced by 80 μL fresh medium. 10 μL of the 10× final concentration compound is added to the cells and incubated for 1 hour at 37° C. before addition of trigger. No trigger conditions/trigger conditions are spiked with equal final DMSO concentrations of 0.2% DMSO. 10 μL of 10×LPS (final conc. 200 ng/mL) solution are added to all wells except for the 'no trigger wells' where 10 μL medium is added. Supernatant is collected after 2 h (IL-10 determination) and after 20 h (TNFα determination) of LPS triggering.

3.2.1.2.3 TNFα ELISA

A Lumitrac 600 Greiner 384-well plate is coated with 40 μL of capture antibody (BD Pharmingen, Cat #551220) reaching a final concentration of 1 μg/mL in 1×PBS and stored overnight at 4° C.

The plate is then washed once with PBST (PBS+0.05% Tween20) and once with PBS followed by the addition of 100 μL of blocking buffer (1% Bovine Serum Albumin (BSA) −5% Sucrose) and plates are sealed and incubated for at least 4 h at RT. After washing the plate once with PBST and once with PBS, 40 μL of standard or sample are added (TNFα standard curve is prepared using a 1/2 serial dilution starting from 16000 pg/mL; dilutions are made in dilution buffer (PBS+1% BSA)). Plates are washed twice with PBST, and once with PBS, after which 35 μL of the detection antibody is added (final concentration 0.25 μg/mL diluted in dilution buffer) and plates are incubated for at least 2 h at RT. Plates are washed twice with PBST, and once with PBS, where after 35 μL of Strep-HRP conjugate (0.5 μg/mL final concentration diluted in dilution buffer) is added. Plates are incubated in the dark, at RT for at least 45 min but no longer than 1 hour. Plates are washed twice with PBST, and once with PBS. Thereafter, 50 μL of luminol substrate is added to each well (prepared according to manufacturer's instructions), and incubated for 5 min at RT protected from light. Chemiluminescence is measured on the Envision 2104.

3.2.1.2.1 IL-10 ELISA

An Immulon 2HB 96-well plate (Thermo Electron Co., Cat #3455) is coated with 40 μL of capture antibody (final concentration of 2 μg/mL diluted in Tris buffer (50 mM Tris; 150 mM NaCl; pH 9 (adjusted with HCl)) and stored overnight at 4° C. The next day the plate is washed three times with PBST, and subsequently 200 μL blocking buffer (1% BSA+5% sucrose in PBS-T) is added. After an incubation of 30 min at 37° C., the plate is washed three times with PBST, and 100 μL of standard or sample are added (IL-10 standard curve samples are prepared using a 1/2 serial dilution starting from 1000 pg/mL; dilutions are made in dilution buffer: PBS+1% BSA). After 1 hour incubation at 37° C., plates are washed three times with PBST, after which 100 μL of the detection antibody (BD Pharmingen, Cat #554499) is added (final concentration 0.25 μg/mL diluted in Tris buffer) and plates are incubated for at least 2 h at RT. Plates are washed three times with PBST, where after 100 μL of Strep-HRP conjugate (0.5 μg/mL final concentration diluted in dilution buffer) is added. Plates are incubated in the dark, at 37° C. for 30 min. Plates are washed three times with PBST. A substrate solution is made, for a total volume of 20 mL, 18 mL $H_2O$; 2 mL citrate acetate buffer; 200 μL TMB mix (tetramethil benzidine (TMB) 101 mg, DMSO 10 mL stored at 4° C.); 2.5 μL 30% $H_2O_2$ are mixed. 100 μL of substrate solution is added to each well and incubated until brilliant blue color develops. The reaction is stopped by adding 50 μL of 1 M $H_2SO_4$, after which absorbance is measured at 450 nm on the SpectraMax i3, Molecular Devices.

3.2.1.3. Data Analysis and Results 3.2.1.3.1 TNFα Inhibition Calculation

To measure the inhibition of LPS induced TNFα, percentage inhibition (PIN) values are calculated for all concentrations tested, compared to controls. Unstimulated samples (no trigger/vehicle (0.2% DMSO)) are used as negative control (100% inhibition). As a positive control (0% inhibition), the stimulated samples (trigger/vehicle)) are used.

$$PIN = \frac{(RLUp - RLUtest\ \text{compound})}{RLU - RLUn} \times 100$$

Wherein RLU=Relative Chemiluminescent Light Units (background subtracted) and p and n subscripts refer to the average of positive and negative controls, respectively.

PIN values are plotted in concentration-response and $EC_{50}$ values are derived using GraphPad Prism Software, applying 4-parameter nonlinear regression (sigmoidal) curve fitting. Because no clear bottom plateau is obtained, bottom of the curve is constrained to be equal to 0.

3.2.1.3.2 IL-10 Induction Calculation

IL-10 is induced upon SIK inhibition. To quantify these inductions fold changes (FC) compared to 'LPS only' are calculated for each concentration tested and the maximal FC is calculated (IL-10FCmax):

$$IL - 10FC\max = \frac{\max ABStest\ \text{compound}}{ABStrigger}$$

wherein ABS=Absorbance measured at 450 nm.

The median maximal FC for test compounds across two or more assays is reported (IL-10FCmax median).

3.2.1.3.3 Results & Outcome

The data obtained when subjecting illustrative compounds of the invention are described in the table below.

TABLE IX

MdM TNFα inhibition and IL-10 induction of illustrative compounds of the invention.

| Cpd# | TNFα $EC_{50}$ (nM) | IL-10 FCmax median |
|---|---|---|
| 16 | * | NA |
| 17 | *** | NA |
| 19 | *** | + |
| 20 | ** | NA |
| 24 | ** | NA |
| 25 | ** | NA |
| 26 | *** | NA |
| 27 | *** | NA |
| 28 | *** | NA |
| 33 | *** | NA |
| 34 | *** | NA |
| 35 | *** | NA |

TABLE IX-continued

MdM TNFα inhibition and IL-10 induction of illustrative compounds of the invention.

| Cpd# | TNFα $EC_{50}$ (nM) | IL-10 FCmax median |
|---|---|---|
| 39 | *** | NA |
| 53 | *** | NA |
| 63 | ** | NA |
| 64 | *** | NA |
| 67 | *** | NA |
| 68 | ** | NA |
| 69 | *** | NA |
| 70 | *** | NA |
| 77 | *** | NA |
| 79 | *** | NA |
| 93 | ** | NA |
| 95 | ** | NA |
| 96 | *** | NA |
| 106 | *** | NA |
| 107 | ** | NA |
| 113 | *** | NA |
| 116 | ** | NA |
| 117 | *** | NA |
| 120 | *** | NA |
| 123 | ** | NA |
| 128 | *** | NA |
| 129 | *** | NA |
| 130 | *** | NA |
| 135 | *** | NA |
| 136 | *** | NA |
| 137 | *** | NA |
| 138 | *** | NA |
| 140 | ** | NA |
| 146 | ** | NA |
| 150 | *** | NA |
| 160 | *** | NA |
| 162 | *** | NA |
| 163 | *** | NA |
| 164 | *** | NA |
| 165 | *** | NA |
| 166 | *** | NA |
| 168 | *** | NA |
| 170 | ** | NA |
| 171 | ** | NA |
| 172 | *** | NA |
| 173 | *** | NA |
| 174 | *** | NA |
| 175 | ** | NA |
| 176 | ** | NA |
| 189 | ** | NA |
| 190 | ** | NA |
| 193 | ** | NA |
| 195 | *** | NA |
| 205 | *** | NA |
| 206 | *** | NA |
| 207 | *** | NA |
| 208 | *** | + |
| 211 | *** | NA |
| 216 | *** | NA |
| 218 | *** | NA |
| 219 | *** | + |
| 224 | *** | NA |
| 227 | *** | ++ |
| 228 | *** | + |
| 231 | *** | ++ |
| 232 | *** | NA |
| 235 | *** | NA |
| 236 | *** | NA |
| 237 | ** | NA |
| 242 | *** | + |
| 243 | *** | + |
| 245 | *** | + |
| 254 | ** | + |
| 256 | ** | ++ |
| 257 | *** | NA |
| 258 | *** | NA |
| 261 | ** | + |
| 266 | *** | NA |

TABLE IX-continued

MdM TNFα inhibition and IL-10 induction of illustrative compounds of the invention.

| Cpd# | TNFα $EC_{50}$ (nM) | IL-10 FCmax median |
|---|---|---|
| 267 | *** | NA |
| 269 | *** | NA |
| 275 | *** | + |

* >5000 nM
** >1000-5000 nM
*** >100-1000 nM
**** 0.1-100 nM
+ ≤1.5
++ >1.5-4.5
+++ >4.5
NA not measured 3.2.2. Monocytes Assay: LPS-Triggered TNFα/IL-10 (ELISA)

3.2.2.1. Overview

SIK inhibition inhibits TNFα and increases IL-10 release in LPS triggered monocyte-derived macrophages (MdM) and dendritic cells (MdDCs) (Clark et al. 2012; Sundberg et al. 2014; Ozanne et al. 2015). This assay evaluates illustrative compounds of the invention for their inhibition of LPS-induced TNFα and LPS triggered IL-10 secretion in monocytes.

3.2.2.2. Protocols

PBMCs are isolated from human blood samples (buffy-coats). The buffy coat is aseptically transferred into a 50 mL Falcon tube, and diluted 1/2 in PBS. Falcon tubes are filled with 20 mL Lymphoprep™, on top of which 25 mL of the buffy coat is carefully added, tubes are centrifuged for 35 min at 400 g in temperature controlled centrifuge, without brake, at 25° C. PBMCs are aspirated from the white interface layer between sample and Lymphoprep™. PBMCs are washed five times in PBS. Cells are resuspended in RPMI 1640 complete medium supplemented with 10% FBS, 1% P/S, and cell density is determined using a hematologic analyzer (Sysmex XS-500i).

PBMCs are centrifuged at 300×g for 10 min and resuspended at a density of $1.0*10^7$ cells/80 μL Miltenyi buffer (PBS, pH 7.4, 1% FBS, 2 mM EDTA).

3.2.2.2.1 Positive Labelling of CD14+ Monocytes.

Starting from this point of the protocol all steps are performed on ice. 20 μL of CD14+ micro-beads are added per $1.0*10^7$ cells, the tube is mixed and incubated for 15 min in the fridge at 4° C. Cell suspension volume is adjusted to total volume of 100 mL using Miltenyi buffer, mixed gently and subsequently centrifuged for 10 min at 300×g. Supernatant is discarded and cell pellet is resuspended in 12 mL of Miltenyi buffer.

3.2.2.2.2 Magnetic Cell Sorting

Four LS columns are placed in the MACS Separator (magnet) from Miltenyi Biotec, and are prewet by rinsing with 3 mL of MACS buffer per column. Three mL of cell suspension is added onto the column (max $1*10^8$ of labelled cells/column), and columns are subsequently washed 3 times with 3 mL of Miltenyi buffer.

The columns are removed from the magnets, and 5 mL of Miltenyi buffer are added to the column to flush out the CD14+ fraction by pushing the plunger into the column. The flushed fractions are collected in a fresh 50 mL Falcon and volume is adjusted to 30 mL using Miltenyi buffer, cells are centrifuged for 10 min at 300×g. The obtained cell pellet is resuspended in 10 mL RPMI w/o FBS, and cell density is determined using a hematologic analyser (Sysmex XS-500i). 100 000 cells are seeded in 80 μL per well of a 96-well plate in RPMI 1640 medium supplemented with 10% FBS, 1% P/S.

A compound dilution plate is made in 100% DMSO by 3-fold dilution of 10 mM stock solution. An intermediate dilution plate (10× final concentration) is made by diluting the compound dilution plate 50-fold in RPMI medium.

10 μL of the 10× final concentration compound is added to the cells and incubated for 1 h at 37° C. before addition of trigger. No trigger conditions/trigger conditions are spiked with equal final DMSO concentrations of 0.2% DMSO. 10 μL of 10×LPS (final conc. 200 ng/mL) solution are added to all wells except for the 'no trigger wells' where 10 μL medium is added. Supernatant is collected after 4 h of LPS triggering.

3.2.2.2.3 TNFα ELISA

A Lumitrac 600 Greiner 384-well plate is coated with 40 μL of capture antibody (BD Pharmingen, Cat #551220) reaching a final concentration of 1 μg/mL in 1×PBS and stored overnight at 4° C.

The plate is then washed once with PBST (PBS+0.05% Tween20) and once with PBS followed by the addition of 100 μL of blocking buffer (1% Bovine Serum Albumin (BSA)-5% Sucrose) and plates are sealed and incubated for at least 4 h at RT. After washing the plate once with PBST and once with PBS, 100 μL of blocking buffer (1% BSA-5% Sucrose) is added and plates are sealed and incubated for at least 4 h at RT. Plates are washed twice with PBST, and once with PBS, after which 35 μL of the detection antibody is added (final concentration 0.25 μg/mL diluted in dilution buffer) and plates are incubated for at least 2 h at RT. Plates are washed twice with PBST, and once with PBS, whereafter 35 μL of Strep-HRP conjugate (0.5 μg/mL final concentration diluted in dilution buffer) is added. Plates are incubated in the dark, at RT for at least 45 min but no longer than 1 h. Plates are washed twice with PBST, and once with PBS. Thereafter, 50 μL of luminol substrate is added to each well (prepared according to manufacturer's instructions), and incubated for 5 min at RT protected from light. Chemiluminescence is measured on the Envision 2104.

3.2.2.2.4 IL-10 ELISA

A Lumitrac 600 Greiner 384-well plate is coated with 40 μL of capture antibody (final concentration of 1 μg/mL in 1×PBS) and stored overnight at 4° C. The next day the plate is washed three times with PBST (PBS+0.05% Tween20) and once with PBS followed by the addition of 100 μL of blocking buffer (1% BSA-5% Sucrose) and plates are sealed and incubated for at least 4 h at RT. After washing the plate once with PBST and once with PBS, 40 μL of standard or sample are added (IL-10 standard curve is prepared using a 1/2 serial dilution starting from 2000 pg/mL; dilutions are made in dilution buffer (PBS+1% BSA)). Plates are washed twice with PBST, and once with PBS, after which 35 μL of the detection antibody is added (final concentration 0.143 μg/mL diluted in dilution buffer) and plates are incubated for at least 2 h at RT. Plates are washed twice with PBST, and once with PBS, whereafter 35 μL of Strep-HRP conjugate (0.5 μg/mL final concentration diluted in dilution buffer) is added. Plates are incubated in the dark, at RT for at least 45 min but no longer than 1 h. Plates are washed twice with PBST, and once with PBS. Thereafter, 50 μL of luminol substrate is added to each well (prepared according to manufacturer's instructions), and incubated for 5 min at RT protected from light. Chemiluminescence is measured on the Envision 2104.

3.2.2.3. Data Analysis and Results 3.2.2.3.1 TNFα Inhibition Calculation

To measure the inhibition of LPS induced TNFα, percentage inhibition (PIN) values are calculated for all concentrations tested, compared to controls. Unstimulated samples (no trigger/vehicle (0.2% DMSO)) are used as negative control (100% inhibition). As a positive control (0% inhibition), the stimulated samples (trigger/vehicle)) are used.

$$PIN = \frac{(RLUp - RLUtest\text{ compound})}{RLU - RLUn} \times 100$$

Wherein RLU=Relative Chemiluminescent Light Units (background subtracted) and p and n subscripts refer to the average of positive and negative controls, respectively.

PIN values are plotted in concentration-response and $EC_{50}$ values are derived using GraphPad Prism Software, applying 4-parameter nonlinear regression (sigmoidal) curve fitting. When no clear bottom plateau is obtained, bottom of the curve is constrained to be equal to 0.

3.2.2.3.2 IL-10 Induction Calculation

LPS-induced IL-10 is increased upon SIK inhibition. To quantify these increases, fold changes (FC) compared to 'LPS only' are calculated for each concentration tested and the maximal FC is calculated (IL-10 FCmax):

$$IL - 10FC\text{max} = \text{max}\frac{(RLUtest\text{ compound})}{RLUtrigger}$$

The median maximal FC for test compounds across two or more runs is reported (IL-10FCmax median).

3.2.2.3.3 Results & Outcome

The data obtained when subjecting illustrative compounds of the invention are described in the table below.

TABLE X

Monocytes TNFα inhibition and IL-10 induction of illustrative compounds of the invention.

| Cpd# | TNFα $EC_{50}$ (nM) | IL-10 FCmax median |
|---|---|---|
| 19 | *** | + |
| 27 | *** | + |
| 28 | *** | NA |
| 33 | **** | NA |
| 35 | *** | ++ |
| 39 | *** | ++ |
| 62 | ** | NA |
| 63 | *** | NA |
| 64 | *** | NA |
| 69 | *** | NA |
| 70 | *** | NA |
| 77 | *** | ++ |
| 79 | **** | ++ |
| 93 | *** | NA |
| 95 | *** | NA |
| 96 | *** | NA |
| 106 | *** | NA |
| 107 | *** | ++ |
| 113 | *** | NA |
| 116 | *** | ++ |
| 117 | *** | ++ |
| 121 | ** | NA |
| 123 | *** | ++ |
| 128 | *** | NA |
| 129 | *** | ++ |

TABLE X-continued

Monocytes TNFα inhibition and IL-10 induction of illustrative compounds of the invention.

| Cpd# | TNFα $EC_{50}$ (nM) | IL-10 FCmax median |
|---|---|---|
| 130 | *** | ++ |
| 133 | *** | ++ |
| 136 | *** | ++ |
| 137 | *** | + |
| 138 | *** | NA |
| 139 | ** | NA |
| 140 | *** | NA |
| 146 | ** | NA |
| 150 | *** | + |
| 160 | *** | NA |
| 162 | *** | NA |
| 163 | *** | NA |
| 164 | *** | NA |
| 165 | *** | NA |
| 166 | *** | NA |
| 167 | ** | NA |
| 168 | *** | ++ |
| 169 | ** | NA |
| 170 | ** | ++ |
| 171 | ** | ++ |
| 172 | *** | + |
| 173 | *** | ++ |
| 174 | *** | ++ |
| 175 | ** | ++ |
| 176 | *** | ++ |
| 177 | *** | + |
| 178 | *** | NA |
| 179 | **** | NA |
| 181 | ** | + |
| 182 | *** | + |
| 183 | ** | + |
| 185 | *** | NA |
| 188 | *** | NA |
| 189 | *** | + |
| 190 | ** | + |
| 191 | ** | + |
| 192 | *** | NA |
| 193 | *** | NA |
| 195 | *** | + |
| 200 | *** | + |
| 205 | *** | ++ |
| 206 | *** | ++ |
| 207 | *** | + |
| 208 | **** | + |
| 211 | *** | ++ |
| 212 | *** | NA |
| 213 | *** | NA |
| 216 | *** | + |
| 218 | **** | ++ |
| 219 | **** | + |
| 221 | *** | NA |
| 223 | *** | NA |
| 224 | *** | ++ |
| 225 | *** | + |
| 227 | *** | + |
| 228 | *** | + |
| 229 | *** | NA |
| 230 | *** | + |
| 231 | *** | + |
| 232 | *** | + |
| 233 | *** | + |
| 234 | *** | + |
| 235 | **** | NA |
| 236 | *** | + |
| 237 | *** | + |
| 238 | *** | + |
| 240 | *** | ++ |
| 241 | *** | + |
| 242 | **** | + |
| 243 | *** | + |
| 245 | *** | + |
| 248 | *** | NA |
| 250 | *** | NA |

TABLE X-continued

Monocytes TNFα inhibition and IL-10 induction of illustrative compounds of the invention.

| Cpd# | TNFα $EC_{50}$ (nM) | IL-10 FCmax median |
|---|---|---|
| 251 | *** | NA |
| 253 | *** | NA |
| 254 | *** | + |
| 255 | *** | NA |
| 256 | *** | + |
| 257 | *** | ++ |
| 258 | *** | + |
| 261 | *** | + |
| 262 | *** | NA |
| 265 | *** | NA |
| 266 | *** | + |
| 267 | **** | NA |
| 268 | *** | NA |
| 269 | *** | ++ |
| 272 | *** | NA |
| 273 | *** | NA |
| 275 | *** | ++ |

* >5000 nM
** >1000-5000 nM
*** >100-1000 nM
**** 0.1-100 nM
+ ≤1.5
++ >1.5-4.5
+++ >4.5
NA not measured

Example 4. In Vivo Assays 4.1. Inflammatory Bowel Disease: DSS Model (Mice)

The mouse chronic DSS-induced inflammatory bowel disease model (IBD) is a well validated disease model for inflammatory bowel disease (Wirtz et al. 2007; Sina et al. 2009).

To induce a chronic colitis, female BALB/c mice are fed with drinking water containing 4% dextran sodium sulfate (DSS) for 4 days, followed by 3 days of regular drinking water. This cycle is repeated until sacrifice on day 12 or 18. Animals are divided into several groups:

a. intact water; vehicle alone, n=10),
b. diseased (DSS; vehicle alone, n=10),
c. sulfasalazine used as reference (DSS; 20 mg/kg/day, p.o., n=10) and
d. the tested compound (DSS; e.g., 1, 3, 10, 30 mg/kg/day, p.o., n=10).

Clinical parameters are measured every other day. The disease activity index (DAI) is a composite measure combining the individual scores for weight loss, stool consistency and blood presence in stools. Mice are sacrificed according to the protocol introduced by Sina et al. (2009) (Sina et al. 2009). At sacrifice time, the complete colon is removed and rinsed with sterile PBS. Segments of the distal colon are dissected for histological analysis, gene expression and protein level measurement.

4.2. CIA Model 4.2.1. Materials

Completed Freund's adjuvant (CFA) and incomplete Freund's adjuvant (IFA) were purchased from Difco. Bovine collagen type II (CII), lipopolysaccharide (LPS), and Enbrel® (etanercept) were obtained from Chondrex (L'Isle d'Abeau, France); Sigma (P4252, L'Isle d'Abeau, France), Wyeth (25 mg injectable syringe, France), respectively. All other reagents used were of reagent grade and all solvents were of analytical grade.

4.2.2. Animals

DBA1/J mice (male, 7-8 weeks old) were obtained from Charles River Laboratories (Écully, France). Mice were kept on a 12 h light/dark cycle. Temperature was maintained at 22° C., and food and water were provided ad libitum.

4.2.3. Collagen Induced Arthritis (CIA)

One day before the experiment, CII solution (2 mg/mL) was prepared with 0.05 M AcOH and stored at 4° C. Just before the immunization, equal volumes of adjuvant (IFA) and CII were mixed by a homogenizer in a pre-cooled glass bottle in an ice water bath. Extra adjuvant and prolonged homogenization may be required if an emulsion is not formed. 0.2 mL of the emulsion was injected intradermally at the base of the tail of each mouse on day 1, a second booster intradermal injection (CII solution at 2 mg/mL in CFA 0.1 mL saline) was performed on day 9. This immunization method was modified from published methods (Jou et al. 2005; Sims et al. 2004).

4.2.4. Study Design

The therapeutic effects of the compounds were tested in the mouse CIA model. Mice were randomly divided into equal groups and each group contained 10 mice. All mice were immunized on day 1 and boosted on day 21. The negative control group was treated with vehicle (MC 0.5%) and the positive control group with Enbrel® (10 mg/kg, 3× week, sc). A compound of interest was typically tested at 3 doses per os (p.o.). At day 32, randomization between groups was performed with respect with clinical score and animals were therapeutically treated regarding their group until day 47. Body weight and clinical score, were recorded at least twice a week.

4.25. Clinical Assessment of Arthritis

Arthritis is scored according to the method of Khachigian 2006, Lin et al 2007 and Nishida et al. 2004 (Khachigian 2006; Lin et al. 2007; Nishida et al. 2004). The swelling of each of the four paws is ranked with the arthritic score as follows: 0—no symptoms; 1—mild, but definite redness and swelling of one type of joint such as the ankle or wrist, or apparent redness and swelling limited to individual digits, regardless of the number of affected digits; 2—moderate redness and swelling of two or more types of joints; 3—severe redness and swelling of the entire paw including digits; 4—maximally inflamed limb with involvement of multiple joints (maximum cumulative clinical arthritis score 16 per animal) (Nishida et al. 2004).

4.2.5.1. Change in Body Weight (%) after Onset of Arthritis

Clinically, body weight loss is associated with arthritis (Argilés & López-Soriano 1998; Rall & Roubenoff 2004; Shelton et al. 2005; Walsmith et al. 2004). Hence, changes in body weight after onset of arthritis can be used as a non-specific endpoint to evaluate the effect of therapeutics in the mouse model. The change in body weight (%) after onset of arthritis was calculated as follows:

Mice:

$$\frac{\text{Body } Weight_{(week6)} - \text{Body } Weight_{(week5)}}{\text{Body } Weight_{(week6)}} \times 100\%$$

4.2.5.2. Radiology

X-ray photos were taken of the hind paws of each individual animal. A random blind identity number was assigned to each of the photos, and the severity of bone erosion was ranked by two independent scorers with the radiological Larsen's score system as follows: 0—normal with intact bony outlines and normal joint space; 1—slight abnormality with any one or two of the exterior metatarsal bones showing slight bone erosion; 2—definite early abnormality with any three to five of the exterior metatarsal bones showing bone erosion; 3—medium destructive abnormality with all the exterior metatarsal bones as well as any one or two of the interior metatarsal bones showing definite bone erosions; 4—severe destructive abnormality with all the metatarsal bones showing definite bone erosion and at least one of the inner metatarsal joints completely eroded leaving some bony joint outlines partly preserved; 5-mutilating abnormality without bony outlines. This scoring system is a modification from Salvemini et al., 2001; Bush et al., 2002; Sims et al., 2004; Jou et al., 2005 (Bush et al. 2002; Jou et al. 2005; Salvemini et al. 2001; Sims et al. 2004).

4.2.5.3. Steady State PK

At day 7, blood samples were collected at the retro-orbital sinus with lithium heparin as anticoagulant at the following time points: predose, 1, 3 and 6 hrs. Whole blood samples were centrifuged and the resulting plasma samples were stored at −20° C. pending analysis. Plasma concentrations of each test compound were determined by an LC-MS/MS method in which the mass spectrometer was operated in positive electrospray mode.

4.26. Results

When subjected to this protocol, Cpd 174 dosed at 60 mg/kg p.o. b.i.d., Cpd 261 dosed at 30 mg/kg p.o. b.i.d., and Cpd 219 dosed at 3 mg/kg p.o. b.i.d. showed a statistically significant decrease of the clinical score compared to the vehicle group.

4.3. Murine Model of Psoriatic-Like Epidermal Hyperplasia Induced by Topical Applications of Imiquimod, a TLR7/8 Agonist.

4.3.1. Materials

Aldara® 5% imiquimod cream is obtained from MEDA.

Anti mouse IL 12/IL 23 p40purified antibody (C17.8) (Cat #16 7123 85) is obtained from eBioscience (Frankfurt, Germany).

4.3.2. Animals

Balb/cJ mice (female, 18-20 g body weight) are obtained from Janvier Labs (Le Genest-Saint-Isle, France). Mice are kept on a 12 h light/dark cycle. Temperature is maintained at 22±2° C., food and water are provided ad libitum.

4.3.3. Study Design

The design of the study is adapted from Van der Fits L. et al. (van der Fits et al. 2009).

On the first day, the mice are shaved around the two ears under light anaesthesia.

30 mg of commercially available imiquimod cream (Aldara® 5% cream) are applied on both internal and external surfaces of each ear for 4 consecutive days, corresponding to a daily dose of 1.5 mg of the active compound. Control animals received the same quantity of vaseline.

From day 1 to day 5, mice are dosed with test compound, 10 or 30 mg/kg, p.o., b.i.d. in methyl cellulose 0.5%, before application of imiquimod (on day 5, the mice are dosed only once, 2 h before euthanasia).

In a positive reference group, the animals receive two intraperitoneal injections of anti mouse IL-12/IL-23 p40 antibody, 10 mg/kg, on day 1 and 3 days before day 1.

4.3.4. Assessment of Disease

The thickness of both ears is measured daily with a thickness gage (Mitutoyo, Absolute Digimatic, 547 321). Body weight is assessed at initiation of the experiment and at sacrifice. At day 5, 2 h after the last dosing, the mice are sacrificed. The pinnae of the ear are cut, excluding cartilage.

The pinnae are weighed and then immersed in a vial containing 1 mL of RNAlater® solution to assess gene expression.

The results are expressed as mean±SEM and statistical analysis is performed using one way ANOVA followed by Dunnett's post hoc test versus imiquimod vehicle group.

4.3.5. Gene Expression Analysis

Ears are removed from the RNAlater® solution and put in Trizol® after disruption with 1.4 mm ceramic beads in a Precellys® device. Total RNA is then purified using NucleoSpin® RNA kit. cDNA is prepared and quantitative PCR is performed with gene-specific primers from Qiagen using SYBR Green technology in a ViiA7 real-time PCR system (Applied Biosystems). Expression levels of each gene (are calculated relative to the cyclophilin A housekeeping gene expression level. Data are expressed as mean±SEM of the relative quantity. The statistical test used is ANOVA analysis of variance with Dunnett's post-hoc test versus imiquimod vehicle group.

4.4. Murine Model of Psoriatic-Like Epidermal Hyperplasia Induced by Intradermal Injections of IL-23

4.4.1. Materials

Mouse recombinant IL-23, carrier free (Cat #14-8231) is provided by e-Bioscience (Frankfurt, Germany).

4.4.2. Animals

Balb/c mice (female, 18-20 g body weight) were obtained from Janvier Labs (Le Genest-Saint-Isle, France). Mice are kept on a 12 h light/dark cycle. Temperature was maintained at 22° C., food and water are provided ad libitum.

4.4.3. Study Design

The design of the study was adapted from Rizzo H L. et al. (Rizzo et al. 2011).

On the first day (D1), the mice were shaved around the two ears. For 4 consecutive days (D1 to D4), the mice received a daily intradermal dose of mouse recombinant IL-23 (1 μg/20 μL in PBS/0.1% BSA) in the right pinna ear and 20 μL of PBS/0.1% BSA in the left pinna ear under anesthesia.

From D1 to D5, mice were dosed with test-compound or with vehicle, 1 h prior IL-23 injection.

4.4.4. Assessment of Disease

The thickness of both ears was measured daily with an automatic caliper. Body weight was assessed at initiation and at sacrifice. On fifth day, 2 h after the last dosing, the mice were sacrificed. The pinnae of the ear were cut, excluding cartilage. The pinnae, placed in a vial containing 1 mL of RNAlater® solution.

At D4, blood samples were also collected from the retro-orbital sinus for PK profiling just before dosing (T0) and 1 h, 3 h, 6 h post-dosing.

There were 8 mice per group. The results were expressed as mean±SEM and statistical analysis was performed using one-way ANOVA followed by Dunnett's post-hoc test versus IL-23 vehicle groups.

4.4.5. Gene Expression Analysis

Half ears were removed from RNAlater® solution and put in Trizol® after disruption with 1.4 mm ceramic beads in a Precellys® device. Total RNA was then purified using NucleoSpin® RNA kit. cDNA was prepared and quantitative PCR was performed with gene-specific primers from Qiagen using SYBR Green technology in a ViiA7 real-time PCR system (Applied Biosystems). Expression levels of each gene were calculated relative to the cyclophilin A housekeeping gene expression level. Data were expressed as mean±SEM of the relative quantity. The statistical test used was ANOVA analysis of variance with Dunnett's post-hoc test versus the IL-23 vehicle group.

4.4.6. Results

When subjected to this protocol, Cpd 174 dosed at 3 mg/kg p.o. b.i.d., Cpd 19 dosed at 10 mg/kg p.o. b.i.d., and Cpd 117 dosed at 30 mg/kg p.o. b.i.d. showed a statistically significant decrease of the ear thickness compared to IL-23 vehicle group.

4.5. Murine Model of Systemic Lupus Erythematosus Induced by Epicutaneous Applications of Imiquimod 4.5.1. Materials Aldara® 5% imiquimod cream is obtained from MEDA.

Mouse anti-double-stranded DNA antibodies ELISA kits are obtained from Alpha Diagnostic International (Cat #5120). Mouse urinary albumin ELISA kits are obtained from Abcam (Cat #ab108792). Urine creatinine assay kits are obtained from Abnova (Cat #KA4344).

4.5.2. Animals

BALB/cJ mice (female, 18-20 g body weight) are obtained from Janvier Labs (Le Genest-Saint-Isle, France). Mice are kept on a 12 h light/dark cycle. Temperature is maintained at 22±2° C., food and water are provided ad libitum.

4.5.3. Study Design

The design of the study is adapted from Yokogawa M. et al. (Yokogawa et al. 2014).

On the first day (D1), the mice are shaved around the right ears.

The mice receive an epicutaneous application of 1.25 mg of imiquimod 3 times per week on the right pinna ear for 12 consecutive weeks (D1 to D86). The control group receives the same quantity of vaseline.

From D1 to D86, mice are dosed with test compound (30 mg/kg, p.o., q.d. in methylcellulose 0.5%) or with vehicle (10 mL/kg).

4.5.4. Assessment of Disease

The thickness of the ears is measured once a week with an automatic gage (Mitutoyo, Absolute Digimatic, 547-321).

Body weight is assessed at initiation and once a week until sacrifice. At necropsy, the spleen weight is also measured. The mice are sacrificed 2 h after the last dosing.

At different time points (e.g., on days D28, D56 and D84), the mice are individually placed in a metabolic cage to perform urinalysis and assess proteinuria (albumin to creatinine ratio).

Serums are collected at different time points (e.g., on D28, D56 and D86) to assess anti-double stranded-DNA IgG levels.

At D13, blood samples are also collected from the retro-orbital sinus for PK profiling just before dosing (T0) and 1 h, 3 h, and 6 h post-dosing.

There are 8-19 mice per group. The results are expressed as mean±SEM and statistical analysis is performed using one-way ANOVA followed by Dunnett's post-hoc test versus imiquimod vehicle groups.

4.5.5. Quantification of Compound Levels in Plasma

Plasma concentrations of each test compound are determined by an LC-MS/MS method in which the mass spectrometer is operated in positive or negative electrospray mode.

4.5.5.1. Histopathology

In each glomerulus, 4 different readouts including mesangioproliferation, endocapillary proliferation, mesangial matrix expansion and segmental sclerosis are graded on a scale of 0 to 2 and then summed. For each kidney, about 50 glomeruli are scored and then averaged giving one glomerular lesion score (Yokogawa et al. 2014). Data are expressed as mean±SEM and statistical analysis is performed using the Kruskal-Wallis test followed by Dunn's post-hoc test versus imiquimod vehicle group.

4.5.5.2. Cellular Quantifications

For each cell type, immunohistochemical analysis is performed using image analysis (CaloPix software, TRIBVN Healthcare) on the whole tissue section at a magnification of ×20. Data are expressed as mean±SEM and statistical analysis is performed using one-way ANOVA followed by Dunnett's post-hoc test versus imiquimod vehicle group.

4.5.5.3. Gene Expression Analysis

At sacrifice, the second part of the left kidneys is placed in tubes containing 1.4 mm ceramic beads and disrupted in 1% DTT RLT lysis buffer (Qiagen, Cat #79216) with a Bertin Instruments Precellys® homogenizer. Total RNA is then purified with a QIAcube using an RNeasy® 96 QIAcube® HT Kit (Qiagen, Cat #74171). cDNA is prepared and quantitative PCR performed with gene-specific primers from Qiagen using SYBR Green technology in a ViiA 7 real-time PCR system (Applied Biosystems). Expression levels of each gene of interest (GOI=CD3, CD68, CD20, OAS1, Mx1, IFIT1, CXCL11 and Usp18) are calculated relative to the cyclophilin, GAPDH and β-actin housekeeping gene expression levels.

At sacrifice, one-third of the spleen is placed into tubes containing 1.4 mm ceramic beads and disrupted in Trizol® with a Bertin Instruments Precellys® homogenizer. Total RNA is extracted using a phenol/chloroform process and then purified with a QIAcube using an RNeasy® 96 QIAcube® HT Kit (Qiagen, Cat #74171). cDNA is prepared and quantitative PCR performed with gene-specific primers from Qiagen using SYBR Green technology in a ViiA 7 real-time PCR system (Applied Biosystems). Expression levels of each gene of interest are calculated relative to the cyclophilin, GAPDH and $3-actin housekeeping gene expression levels.

4.6. Systemic Lupus Erythematosus Model in NZB/WF1/J Mice

The purpose of this study is to evaluate the activity of test compounds of the invention in the treatment of systemic lupus erythematosus (SLE). The NZB/W F1 model is the first murine model described for lupus nephritis, which consists of the F1 hybrid between New Zealand Black and New Zealand White (NZB/W) mice. They can develop lymphadenopathy, splenomegaly, and elevated serum antinuclear autoantibodies (ANA). Particularly, they develop renal lesions that are remarkably similar to the pathology described in human lupus (Tejon et al. 2019; Zampeli et al. 2017).

4.6.1. Materials

The test compounds are stored as dry matters in the dark and formulated weekly as suspensions using magnetic stirring in the vehicle solution (aqueous methyl cellulose 5%). The resulting suspensions are kept under magnetic stirring protected from light.

Dexamethasone (DEX; VetOne, Cat #501012) is prepared in 1% carboxymethylcellulose for PO dosing at 10 mL/kg.

4.6.2. Animals

NZBW/F1/J mice (female, 20-week old) and NZW mice (female, 8-week old) are obtained from the Jackson laboratory (USA). The mice are 28 weeks old at the time of first treatment.

4.6.3. Study Design

At 27 weeks old (study day 0), the mice with developing disease are randomized by animal body weight into each group.

Treatment is initiated after randomization when the animals are 28 weeks old and continued until the animals are sacrificed at 39 weeks of age.

The animals are observed daily for significant clinical signs, morbidity and mortality.

The activity of test compounds of the invention is evaluated based on weight, proteinuria levels, tissue weights at necropsy (kidney, spleen, and lymph nodes); anti-dsDNA Ab, Igs, cytokine/chemokine and gene expression levels; and histopathology and immunohistochemistry.

The study is carried out on the following groups (15 mice/group):

| Group (n = 15) | Treatment | Dose Level (mg/kg) | Dose Route | Regimen | Dose Vol (mL/kg)[3] | Dose Conc (mg/mL) |
|---|---|---|---|---|---|---|
| 1 | Non-Diseased Vehicle Control | N/A | PO | BID* | 5 | N/A |
| 2 | Diseased Vehicle Control | N/A | PO | BID* | 5 | N/A |
| 3 | DEX Positive Control | 1 | PO | QD* | 10 | 0.1 |
| 4 | Test compound | 10 | PO | BID* | 5 | 2.0 |

*BID dosing to occur at approximately 10-12 h intervals-QD dosing at approximately 24 h intervals The test compound doses to be administered are calculated daily in mg/kg based on the latest body weight of the animal 4.6.4. Endpoints Proteinuria score is recorded for all animals once a week starting on week 28 until week 39, from fresh urine samples using colorimetric Albustix® test strips (Siemens, Cat #2872A).

The resulting score is obtained matching the color to the code scale within 1 to 2 min from sampling, giving the following endpoints:

0=none

1=1 to 30 mg/dL

2=31 to 99 mg/dL

3=100 to 299 mg/dL

4=300 to 1999 mg/dL

5=>2000 mg/dL

Body weight is recorded once a week for all animals from week 28 to week 39.

Blood is collected under anesthesia on week 27, 33 and 38 for all animals for blood dsDNA Ab and Igs.

Blood is collected for PK analysis in the test compound treated animal group on week 29 at the following time points: pre-dose, and 0.25 h, 1 h, 3 h, and 6 h post dosing.

At sacrifice, spleen, kidneys and lymph nodes are weighed and kept for anti-dsDNA Ab, Igs, cytokine/chemokine and gene expression levels; and histopathology and immunohistochemistry analysis.

4.6.5. Statistical Analysis

Based on individual animal raw data, the means for each group are determined and percent change from disease controls is calculated. Treatment groups are compared to disease controls using a one-way analysis of variance (1-way ANOVA) with a Dunnett's post-hoc analysis for measured (parametric) data or a Kruskal-Wallis test with a Dunn's post-hoc analysis for scored (non-parametric) data.

Data is reported as 1) all animals including those that died interim and 2) only animals that survived to study termination (surviving animals). Statistical analysis is performed using Prism 6.0d software (GraphPad).

Significance for all tests is set at $p<0.05$, and p values are rounded to the third decimal place. Percent inhibition is calculated using the following formula:

$$\text{perectage change} = \frac{\text{mean [treated]} - \text{mean [disease control]}}{0 - \text{mean [disease control]}} * 100$$

4.7 Murine Model of Psoriatic Arthritis Induced by Over-expression of IL-23

4.7.1. Materials

Mouse IL-23 enhanced episomal expression vector (EEV) was obtained from System Biosciences (Cat #EEV651A-1). Mouse IL-23 Quantikine ELISA Kits were obtained from R&D Systems (Cat #M2300). ProSense® 680 and Osteo-Sense® 750EX were obtained from PerkinElmer (Cat #NEV10003 and NEV10053EX). RNAlater® was obtained from Ambion (Cat #AM7021). Imalgene® 1000 (Merial) and Rompun® 2% (Bayer) were obtained from Centravet (Cat #IMA004-6827812 and ROM001-6835444).

4.7.2. Animals

B10.RIII mice (male, 8-week old) were obtained from Charles River (Écully, France). Mice were kept on a 12 h light/dark cycle. Temperature was maintained at 22±2° C., food and water were provided ad libitum.

4.7.3. Study Design

The design of the study is adapted from Sherlock J P. et al. (Sherlock et al. 2012).

On the first day (D1), the mice underwent a hydrodynamic injection of Ringer or IL-23 EEV in Ringer into the tail vein.

As of D5, twice a week, the mice were scored for clinical symptoms until the end of the experiment.

On D5, blood was collected by puncture in the submandibular vein to assess the serum IL-23 concentration.

On D9, mice from all groups received ProSense® 680 probe (0.8 nmol/10 g, i.p.). On D10, the mice were anesthetized. Granulocyte infiltration was then measured using in vivo molecular imaging (Bruker In-Vivo Xtreme imaging system).

On D11, randomization was performed according to ProSense® 680 molecular imaging and scoring.

As of D12, mice were dosed with test compound or with vehicle.

On D19, blood was sampled at time T0, T1h, T3h and T6h after last dosing. Plasma was separated and kept at 20° C. until bioanalysis.

On D36, mice from all groups were sacrificed 2 h after last administration of compound.

Total blood was collected in a serum blood tube and mixed by gentle inversion 8-10 times. After clotting, blood samples were centrifuged 10 min at 1800×g. After centrifugation, serum was stored at −80° C.

4.7.4. Assessment of Disease

Body weight was assessed at initiation of the study, then twice a week and at sacrifice.

Twice weekly, clinical signs of inflammation were scored: 0 for normal paw; 1 if swelling of one digit; 2 if swelling of two or more digits; 3 if swelling of the entire paw. The scores of all limbs were summed up to produce a global score.

On D32, mice from all groups received ProSense® 680 probe (0.8 nmol/10 g, i.p.) and OsteoSense®750EX probe (0.8 nmol/10 g, i.p.). On D33, the mice were anesthetized and granulocyte infiltration and bone remodelling were measured using in vivo molecular imaging (Bruker In-Vivo Xtreme imaging system).

There were 10 mice per group. The results are expressed as mean±SEM and statistical analysis is performed using one-way ANOVA followed by Dunnett's post-hoc test versus diseased vehicle group for scoring and imaging analysis, versus sham vehicle group for body weight.

4.7.5. Results

When subjected to this protocol, Cpd 19 dosed at 10 mg/kg p.o. b.i.d., Cpd 219 dosed at 3 mg/kg p.o. b.i.d., Cpd 261 dosed at 50 mg/kg p.o. b.i.d., and Cpd 174 dosed at 30 mg/kg p.o. b.i.d. showed a statistically significant decrease of the clinical score compared to diseased vehicle group.

4.8. Murine Collagen-Antibody Induced Arthritis Model (CAIA)

4.8.1. Materials

ArthritoMab™ antibody cocktail for inducing arthritis and lipopolysaccharide (LPS) from *Escherichia Coli* serotype O55:B5 are purchased from MD Biosciences (Oakdale, MN, USA, Cat #CIA-MAB-50); PBS 1× (GIBCO, Cat #140190-086) is obtained from ThermoFisher Scientific, and Enbrel® (etanercept) is purchased from Chondrex (L'Isle d'Abeau, France, Cat #3771910).

4.8.2. Animals

Five to seven week old BALBc female mice are obtained from Janvier Labs (Le Genest-Saint-Isle, France). Mice are kept on a 12 h light/dark cycle. Temperature is maintained at 22° C., food and water are provided ad libitum.

4.8.3. Study Design

The therapeutic effects of the compounds of the invention are tested in the mouse CAIA model (MD Biosciences 2008; Nandakumar et al. 2003). At day 1 (D1), mice are randomly divided into equal groups containing 10 mice. All mice including vehicle, except the non-treated group, are immunized with ArthritoMab™ cocktail (100 mg/kg, i.v., 200 μL/mouse) and treatment with compound or vehicle starts. Bodyweight and clinical score of each mouse is assessed every day except the weekend until the end of the study. At D4, all mice, except the non-treated group, receive a challenge of LPS (2.5 mg/kg, i.p.). At D11, all mice are sacrificed and blood is sampled on serum tube. After centrifugation, serum is collected and frozen at −80° C. pending analysis (e.g., cytokine levels, gene expression, compound levels). For histology readouts, right and left hind paws are individually collected in vials (25 mL minimum) filled with 4% buffered formaldehyde for a minimum of 24 h to a maximum of 4 days at RT.

4.8.4. Clinical Assessment of Arthritis

Arthritis is scored according to the method of Khachigian 2006; Lin et al 2007 and Nishida et al. 2004 (Khachigian 2006; Lin et al. 2007; Nishida et al. 2004). The swelling of each of the four paws is ranked with the arthritic score as follows:

| Score | Definition |
|---|---|
| 0 | no symptoms |
| 1 | mild, but definite redness and swelling of one type of joint such as the ankle or wrist, or apparent redness and swelling limited to individual digits, regardless of the number of affected digits |
| 2 | moderate redness and swelling of two or more types of joints |
| 3 | severe redness and swelling of the entire paw including digits |
| 4 | maximally inflamed limb with involvement of multiple joints |

The final clinical score is the cumulative score of the four paws (maximum cumulative clinical arthritis score 16 per animal)(Nishida et al. 2004). A curve of cumulative clinical score is drawn for each group, and the area under the curve is calculated. The results are expressed as mean±SEM and statistical analysis is performed using one-way ANOVA followed by Dunnett's post-hoc test versus vehicle groups.

4.9. Murine Therapeutic Model of Atopic Dermatitis Induced by Topical Application of MC903

4.9.1. Materials

Methylcellulose 0.5% (Cat #AX021233) is obtained from VWR. MC903 (calcipotriol, Cat #2700/50) is obtained from Tocris Bioscience (Bristol, UK). ProSense® 680 (Cat #NEV10003) is obtained from PerkinElmer (Massachusetts, USA). RNAlater® (Cat #AM7021) is obtained from Ambion (California, USA).

4.9.2. Animals

BALB/cN mice (female, 18-20 g body weight) or CD1/Swiss mice (female, 24-26 g body weight) are obtained from Janvier Labs (Le Genest-Saint-Isle, France). Mice are kept on a 12 h light/dark cycle. Temperature is maintained at 22±2° C., food and water are provided ad libitum.

4.9.3. Study Design

The design of the study is adapted from Li M. et al. (Li et al. 2006). On the first day (D1), the mice are anesthetized and shaved around the two ears. As of D1, either 20 μL EtOH or 2 nmol of MC903 (in 20 μL EtOH) are topically applied on each ear of the mice up to D9, D11 or D15 (except during the weekend).

From D5, the mice are dosed with test compound (15 or 30 mg/kg, p.o., b.i.d. in methylcellulose 0.5%) or dexamethasone (5 mg/kg, p.o., q.d. in methylcellulose 0.5%), or with vehicle, until D10, D12, or D16.

4.9.4. Quantification of Compound Levels in Plasma

Plasma concentrations of each test compound are determined by an LC-MS/MS method in which the mass spectrometer is operated in positive or negative electrospray mode.

4.9.5. Determination of Pharmacokinetic Parameters

Pharmacokinetic parameters are calculated using Phoenix® WinNonlin® (Pharsight®, USA).

4.9.6. Assessment of Disease

The thickness of each ear is measured immediately before first application of MC903 (baseline), three times a week, and at sacrifice using a thickness gauge (Mitutoyo, Absolute Digimatic, Cat #547-321).

Body weight is assessed at immediately before first application of EtOH (baseline), three times a week and at sacrifice.

On D8, D10 or D11, mice from all groups receive ProSense® 680 probe (0.8 nmol/10 g, i.p.). On the next day (D9, D11 or D12), the mice are anesthetized. Granulocyte infiltration is then measured using in vivo molecular imaging (Bruker In-Vivo Xtreme imaging system, excitation wavelength: 630 nm, emission wavelength: 700 nm, acquisition time: 5 seconds).

On D10, D12, or D16, 2 h after the last dosing, the mice are sacrificed, total blood is collected in EDTA-coated tubes and plasma is frozen for further measurements (including circulating compound).

The pinnae of the ears are collected. One ear is cut longitudinally into 2 halves. One half is fixed in formaldehyde buffer 3.7% for histology; the other one is immersed in RNAlater® to assess gene expression.

There are 8 mice per group. The results are expressed as mean±SEM and statistical analysis is performed using one-way ANOVA followed by Dunnett's post-hoc test versus MC903 vehicle groups (MC903 treated mice dosed with vehicle alone) for ear thickness and weight, and/or versus EtOH vehicle group (EtOH treated mice dosed with vehicle alone) for body weight.

4.9.7. Histology

After sacrifice, half ears are collected and fixed in 3.7% formaldehyde before embedding in paraffin. 4 μm thick sections are immunostained by immunohistochemistry with anti-CD3 antibody. The immunostained cell areas from a whole section per mouse are measured by image analysis (CaloPix software, TRIBVN Healthcare, France). Data are expressed as mean±SEM and statistical analysis is performed using one-way ANOVA followed by Dunnett's post-hoc test versus MC903 vehicle group.

4.9.8. Gene Expression Analysis

Ears are removed from RNAlater® solution and placed in Trizol® after disruption with 1.4 mm ceramic beads in a Bertin Instruments Precellys® homogenizer. Total RNA is then extracted using a phenol/chloroform protocol and purified with a QIAcube using an RNeasy® 96 QIAcube® HT Kit (Qiagen, Cat #74171). cDNA is prepared and quantitative PCR performed with gene-specific primers from Qiagen using SYBR Green technology in a ViiA 7 real-time PCR system (Applied Biosystems). Expression levels of each gene of interest (GOI=IL4, IL5, IL13, TSLP, IL33, ST2, IL25, IL31, IFNγ, IL6, IL10, LCN2, S100A8, and S100A9) are calculated relative to the housekeeping gene expression levels (HPRT, GAPDH and β-actin).

All qPCR data are expressed as mean±SEM of the normalized relative quantity (NRQ) calculated according to the following steps:

1—Calculate the geometric mean of NRQ for each group of animals $$NRQ_{sample} = \frac{2^{-CqGOI}}{\text{Geometric mean}\left(2^{-CqhPRT}, 2^{-CqGADPH}, 2^{-Cq\beta\text{-}actin}\right)}$$

2—Calculate NRQ-scaled compared to the MC903 vehicle group $$NRQscaled = \frac{NRQ_{sample}}{\text{Geometric mean}\left(NRQ_{samples\ MC903\ vehicle\ group}\right)}$$

The statistical test used is ANOVA analysis of variance with Dunnett's post-hoc test versus the EtOH vehicle group and/or MC903 vehicle group.

4.10. Mouse LPS-Induced Endotoxic Shock

Injection of lipopolysaccharide (LPS) induces a rapid release of soluble tumour necrosis factor (TNFα) into the periphery. This model is used to assess prospective blockers of TNFα release in vivo.

4.10.1. Materials

Lipopolysaccharide (LPS) from *Escherichia Coli* serotype O111:B4 is obtained from Sigma Aldrich (Cat #L2630).

4.102. Animals

BALB/cAnNCrl mice (female, 18-20 g body weight) are obtained from Charles River (Calco, Italy). Mice are kept on a 12 h light/dark cycle. Temperature was maintained at 22±2° C., food and water are provided ad libitum.

4.10.3. Study Design

Mice are dosed once by oral (p.o.) or subcutaneous (sc) route with the tested compound in the appropriate vehicle.

At the Tmax of compound, 100 μg of LPS (in $H_2O$) is injected intraperitoneally to mice. A control group is included which comprises administering the vehicle without an LPS challenge.

Mice are sacrificed 90 min after LPS challenge and blood is collected in heparinised tubes. Plasma is obtained by centrifugation for 15 min, 2000×g at +4° C. and frozen at −80° C. before cytokine analysis.

4.10.4. Assessment of Disease

TNFα and IL-10 are quantified in plasma by AlphaLISA detection kits obtained from PerkinElmer (Massachusetts, USA), Cat #AL505C and AL502C, respectively.

Statistics are performed with Prism 5.03 software (GraphPad).

Active compounds are defined as showing a statistically significant decrease in TNFα with or without a statistically significant induction of IL-10.

4.11. MultiDrug Resistance-1a-Ablated (MDRa1) Model (Mice)

4.11.1. Principle of Assay

Mice deficient in Abcb1a (MDRa1) develop spontaneous colitis that can be accelerated by infection with *Helicobacter bilis*. This model is used to evaluate the ability of a compound to treat or prevent colitis (Maxwell et al. 2015).

4.11.2. Materials

Sterile PBS (Gibco, Cat #20012027) is obtained from ThermoFisher Scientific (Massachusetts, USA); *Brucella agar* (Cat #211086) is obtained from Becton Dickinson (New Jersey, USA); *Brucella* Broth Base (Cat #B3051-500 g) is obtained from Sigma Aldrich (Missouri, USA). Defibrinated sheep blood (Cat #SR0051) and Campygen (Cat #CN0025) are obtained from ThermoFisher Scientific (Massachusetts, USA). *H. bilis* ATCC 51360 is obtained from LGC Standards (Molsheim, France) and Combur testE (Cat #11896857) is obtained from Roche Diagnostics (Basel, Switzerland).

4.11.3. Animals

Seven to nine week old MDR1a (FVB.129P2-Abcb1atm1B or N7) female mice are obtained from Taconic (Rensselaer, NY, USA) and seven to nine week old FVB female mice are obtained from Janvier Labs (Le Genest-Saint-Isle, France). Mice are kept on a 12 h light/dark cycle. Temperature is maintained at 22° C., food and water are provided ad libitum.

4.11.4. *H. bilis* Inoculum Preparation

Frozen vial of *H. bilis* is thawed, put in *Brucella* Broth and incubated in *Brucella agar* slant containing 5% of defibrinated sheep blood under microaerophily at 37° C. for 4 to 5 days. At D1, just before administration, a part of *H. bilis* culture is diluted in PBS in order to obtain $10^7$ cfu/mouse and a second part is put in fresh *Brucella* Broth and incubated as previously for 7 days. At D8, just before administration, *H. bilis* culture is diluted in PBS in order to obtain $10^7$ cfu/mouse.

4.11.5. Study Design

After a 10 days acclimatization period, the disease activity index of each MDR1a mouse is determined in order to constitute homogene groups regarding the DAI score between groups. All mice (10 mice per group), except for the sham group (n=10), are then administered by oral route with an inoculum of *H. bilis* ($10^7$ cfu/mouse) and treatment starts accordingly to the protocol for six weeks. Seven days after the start of treatment, a second administration of *H. bilis* is performed. During the whole treatment period, disease activity index is determined twice a week. Six weeks after the start of treatment, mice are sacrificed, blood is sampled and the complete colon is collected and rinsed with sterile PBS. Collected colons are measured and weighed in order to determine colon weight/length ratio, and histological analysis, gene expression, protein level measurement and/or FACs immunophenotyping analysis are performed on the samples. The results are expressed as mean±SEM and statistical analysis is performed using one-way ANOVA followed by Dunnett's post-hoc test versus vehicle groups.

4.11.6. Disease Activity Index (DAI) Determination

The DAI score of each mouse (sum of scores for weight loss, stool consistency and rectal bleeding) is monitored during the entire treatment period and a DAI score progression curve is obtained.

| DAI | Weight evolution | Stool consistency | Rectal bleeding* |
|---|---|---|---|
| 0 Point | No weight loss (vs D1) | Well molded stools | |
| 1 point | 1 to 5% | Semi-soft stools | |
| 2 points | 5 to 10% | Soft stools that do not stick to the anus | |
| 3 points | 10 to 20% | Semi-liquid stools not sticking to the anus | |
| 4 Points | >20% | Liquid stools remaining stuck to the anus | |

*A little piece of stool is deposited on a vial containing 1 mL of D-PBS and homogeneized, deposited on a test strip (Combur TestE), a color appears according to the blood intensity in the stool, a score is given according to this intensity, from 0 to 4 points.

4.12. Radiation Induced Fibrosis Mouse Model 4.12.1. Study Overview

Pneumonitis and lung fibrosis are the major radiation-induced complications following thoracic radiotherapy, which is one of the major treatment of lung and breast cancers, lymphomas and hematopoietic transplant conditioning. The objective of this model is to evaluate the effect of a compound of the invention in lung fibrosis induced by radiation in mice (Favaudon et al. 2014), in particular on lung functionality (FlexiVent®) and fibrosis marker (Collagen I).

4.12.2. Animals 7 weeks old (18-22 g) female C57BL/6J mice from Charles River (Écully, France), batch number S1672) are maintained on 12 h light/dark cycle at 22° C. with ad libitum access to tap water and food.

4.12.3. Materials

The test compounds are dissolved/suspended in appropriate vehicle prior to using and kept light-free, under agitation at RT.

An aliquot of the formulation (~200 μL) is frozen at T0 (day of preparation) and all the formulations are checked (daily) for any change in aspect.

The dose volume administered is 10 mL/kg and the volume is adapted following mean (body weight (BW) of the group as follows: 200 μL if mean BW<22.5 g, 250 μL if mean BW≥22.5 g; 300 μL if mean BW>27.5 g.

4.12.4. In Vivo Experimental Procedure

On day 1 of week 1, the animals are exposed at the thorax to a 17 Gray irradiation dose, under isoflurane anesthesia.

At the beginning of week 18 post radiation (D1), animals are randomized into 6 study groups (15 subjects per group): 1) sham (vehicle: methylcellulose (MC) 0.5%), 2) diseased (vehicle: methylcellulose (MC) 0.5%), 3) positive control (nintedanib dosed 60 mg/kg in 0.1% Natrosol™), and 4) 3 groups test compound (60 mg/kg in 0.5% Methylcellulose (MC)), and dosed p.o. b.i.d. until D23 (week 21).

Body weight is recorded once a week, and on D23, lung function measurement under anesthesia is realized by FlexiVent® (Devos et al. 2017) for all groups (6 successful measurements per group) before sacrifice.

Lungs are collected and fixed in 4% formaldehyde for 24 h before embedding in paraffin. 4 μm thick sections are immunostained with anti-collagen I antibody (LSBio, 2401 Fourth Avenue Suite 900, Seattle WA 98121, USA, Cat

#LS-343921). The sections are deparaffinized and processed by heat antigen retrieval before incubation for one hour with the primary antibody. The anti-collagen I antibody is detected and amplified by ImmPress kit (Vector Laboratories, 3, Accent Park, Bakewell Road, Orton Southgate, Peterborough, PE2 6XS, United Kingdom, Cat #MP-7401). The immunostained sections are then scanned (Nanozoomer, Hamamatsu) before quantification by image analysis (CaloPix software, TRIBVN Healthcare). Data are expressed as percentage collagen I area per area of lung tissue.

Values of all mice from the same group are averaged. Data are expressed as mean±sem and are compared with a one-way ANOVA on Log-transformed data and Dunnett's post-hoc test. Significance levels are defined as * ($p<0.05$),  ($p<0.01$), or * ($p<0.001$) versus irradiated control group.

4.13. Bleomycin Induced Pulmonary Fibrosis in Mice 4.13.1. Study Overview

The aim of the study is to test the efficacy of a test compound at three different doses in a 14-day model of bleomycin induced pulmonary fibrosis in mice.

4.13.2. Animals

This study is carried out on C527BL/6N male mice, supplied by Charles River (Calco, Italy), which are acclimatized for at least 5 days in an environment maintained at 22° C., at 55% relative humidity, with 15-20 air changes per h under light cycles of 12 h. Mice pelleted food and water are provided ad libitum.

At least one day prior to start of experiment, all animals are allocated randomly into groups as indicated in the table below.

TABLE XI

Study groups

| Groups | Purpose | n | Dose | Treatment schedule Days (Frequency) | Route | Vehicle |
|---|---|---|---|---|---|---|
| 1<br>PBS + vehicle | control | 15 | — | D0-D14 (b.i.d.) | NA | NA |
| 2<br>BLM + vehicle | control | 15 | — | D0-D14<br>(b.i.d.) | p.o. | PEG400/MC 0.5%<br>20/80 (v/v) |
| 3<br>BLM + pirfenidone | control | 15 | 50<br>mg/kg | D0-D14 (b.i.d.) | p.o. | 0.1% Natrosol ™ |
| 4<br>BLM + test compound | active | 15 | 1<br>mg/kg | D0-D14 (b.i.d.) | p.o. | PEG400/MC 0.5%<br>20/80 (v/v) |
| 5<br>BLM + test compound | active | 15 | 3<br>mg/kg | D0-D14 (b.i.d.) | p.o. | PEG400/MC 0.5%<br>20/80 (v/v) |
| 6<br>BLM + test compound | active | 15 | 10<br>mg/kg | D0-D14 (b.i.d.) | p.o. | PEG400/MC 0.5%<br>20/80 (v/v) |
| 7<br>BLM + test compound<br>satellite for PK | active | 10 | 10<br>mg/kg | D0-D7 (b.i.d.) | p.o. | PEG400/MC 0.5%<br>20/80 (v/v) |

4.13.3. Materials

The solvent for the test solutions is prepared by adding 0.5 g of hydroxyethylcellulose (Natrosol™) into 500 mL aqua distillate (0.1%) under continuous stirring without heating for 5 h on a magnetic stirrer.

To prepare a solution for intranasal (i.n.) challenge, 0.8 mg/mL stock solutions of bleomycin (Cat #BML-AP302-0010, Enzo Life Sciences, Inc., USA) are thawed and diluted in 330 μL of saline.

Prior to i.n. administration, mice are anesthetized i.p.

Fresh pirfenidone formulation is prepared daily in 0.1% Natrosol™ formulations to a final concentration of 5 mg/mL. Before dosing, animals are weighed and the pirfenidone amount administered is adjusted accordingly to individual weights corresponding to 10 mL/kg body weight, twice daily p.o., with 7.5 h intervals between two administrations.

Finally, test compound solutions are prepared by dissolving the suitable amount of said test compound in PEG 400 (20% of the final volume) then MC 0.5% (80% of the final volume) to reach final concentrations of 1 mg/mL, 0.3 mg/mL and 0.1 mg/mL, thus yielding compound for a doses of 10 mg/kg, 3 mg/kg and 1 mg/kg. Prior to dosing, animals are weighed and the amount administered adjusted accordingly to individual weights.

The application volume of the test doses corresponds to 10 mL/kg body weight, and the test compounds are administered p.o. twice daily, with 7.5 h interval between two administrations.

4.13.4. Study

Animals are examined clinically twice daily, and clinical signs and parameters are recorded. Animals are weighed daily starting from D0.

On day 14, 2 h post dosing with vehicle, pirfenidone or test compound, mice are sacrificed.

The lungs are excised and weighed individually. For all groups: the whole superior right lung lobe is placed into a Precellys® tube containing silica beads and immediately snap frozen in liquid nitrogen and subjected to gene expression analysis.

All remaining lungs are placed into marked bottles containing 10% buffered formalin for further histopathological evaluation.

4.14. Therapeutic Bleomycin Induced Pulmonary Fibrosis 21-Day Mice Model

The aim of the study is to test the efficacy of a test compound at three different doses in a 21-day model of bleomycin induced pulmonary fibrosis in mice.

4.14.1. Animals

This study is carried out on C57BL/6N male mice, supplied by Charles River (Calco, Italy), which are acclimatized for at least 5 days in an environment maintained at 22° C., at 55% relative humidity, with 15-20 air changes per hour under light cycles of 12 h. Mice pelleted food and water are provided ad libitum.

At least one day prior to start of experiment, all animals are allocated randomly into groups as indicated in the table below.

TABLE XII

| Study groups | | | | | | |
|---|---|---|---|---|---|---|
| Groups | Purpose | n | Dose | Treatment schedule Days (Frequency) | Route | Vehicle |
| 1 PBS + Vehicle | control | 15 or 6 | — | D7-D21 (b.i.d.) | NA | NA |
| 2 BLM + Vehicle | control | 15 | — | D7-D21 (b.i.d.) | p.o. | PEG400 or PEG200/MC 0.5% 20/80 (v/v) |
| 3 BLM + Nintedanib | control | 15 | 60 mg/kg | D7-D21 (q.d. or b.i.d.) | p.o. | 0.1% Natrosol ™ |
| 4 BLM + test compound | active | 15 | 1 mg/kg | D7-D21 (b.i.d.) | p.o. | PEG400 or PEG200/MC 0.5% 20/80 (v/v) |
| 5 BLM + test compound | active | 15 | 3 mg/kg | D7-D21 (b.i.d.) | p.o. | PEG400 or PEG200/MC 0.5% 20/80 (v/v) |
| 6 BLM + test compound | active | 15 | 10 mg/kg | D7-D21 (b.i.d.) | p.o. | PEG400 or PEG200/MC 0.5% 20/80 (v/v) |
| 7 BLM + test compound satellite for PK | active | 10 | 10 mg/kg | D7-D14 (b.i.d.) | p.o. | PEG400 or PEG200/MC 0.5% 20/80 (v/v) |

4.14.2. Materials

The solvent for the test solutions is prepared by adding 0.5 g of hydroxyethylcellulose (Natrosol™) into 500 mL aqua distillate (0.1%) under continuous stirring without heating for 5 h on a magnetic stirrer.

To prepare a solution for intranasal (i.n.) challenge, 0.8 mg/mL stock solutions of bleomycin (Cat #BML-AP302-0010, Enzo Life Sciences, Inc., USA) are thawed and diluted in 330 μL of saline. Prior to i.n. administration, mice are anesthetized i.p.

Fresh nintedanib formulation is prepared daily in 0.1% Natrosol™ formulations to a final concentration of 5 mg/mL. Before dosing, animals are weighed and the nintedanib amount administered is adjusted accordingly to individual weights corresponding to 10 mL/kg body weight, once daily p.o.

Finally, test compound solutions are prepared by dissolving the suitable amount of said test compound in PEG 400 or PEG 200 (20% of the final volume) then MC 0.5% (80% of the final volume) to reach final concentrations of 1 mg/mL, 0.3 mg/mL and 0.1 mg/mL, thus yielding compound for a doses of 10 mg/kg, 3 mg/kg and 1 mg/kg. Prior to dosing, animals are weighed and the amount administered adjusted accordingly to individual weights.

The application volume of the test doses corresponds to 10 mL/kg body weight, and is the test compounds are administered p.o. twice daily, with 7.5 h interval between two administrations.

4.14.3. Study

Animals are examined clinically twice daily. List of clinical signs and parameters are indicated in human endpoints table. Animals are weighed daily starting from D0.

On day 21, 2 h post dosing with vehicle, nintedanib or test compound, mice are sacrificed.

The lungs are excised and weighed individually. For all groups: the whole superior right lung lobe is placed into a Precellys® tube containing silica beads and immediately snap frozen in liquid nitrogen and subjected to gene expression analysis.

All remaining lungs are placed into marked bottles containing 10% buffered formalin for further histopathological evaluation.

4.14.4. Sample Analysis, Data Processing and Statistical Evaluation

Body weight data and lung weight data are processed using MS Excel. Statistical analysis and graphical presentation are performed using GraphPad Prism software. One-way ANOVA or Mann-Whitney test are employed for lung weights. Two-way ANOVA are employed for body weight changes.

Differences between groups are considered statistically significant when $p<0.05$.

For histopathological evaluation, whole lungs (except sampled superior right lung) are embedded in paraffin and stained with Mallory's trichrome.

Pulmonary histological changes are assessed using Matsuse modification of Ashcroft score (Ashcroft et al. 1988; Matsuse et al. 1999). Statistical analysis and graphical presentation is performed using GraphPad Prism software. A Mann-Whitney test is employed.

Differences between groups are considered statistically significant when $p<0.05$.

| Ashcroft Score | Definition |
|---|---|
| 1 | Normal lungs (no fibrosis) |
| 2 | Minimal fibrotic thickening of alveolar or bronchial walls (network of fine collagen fibrils) |
| 3 | Moderate fibrotic thickening of walls without obvious damage to lung architecture |
| 4 | Fibrosis with damage of pulmonary structure (coarse fibrous bands or small fibrous masses, intra-alveolar collagen fibrils) |
| 5 | Large fibrous area with severe distortion of lung structure |

4.14.5. PK Analysis—Group 7

4.14.5.1. Protocol

Animals in group 7 (n=10) are included for PK study only and are not subjected to clinical sign scoring.

These animals are induced with the disease at the start of treatment at day 0 (D0) and are sequentially sacrificed on D7 at 1 h, 3 h, 6 h, 8 h, 24 h after the first administration of test compound.

A blood sample (50 μL) is collected from the tail vein into Li-heparin anticoagulant tubes for each time point and kept on ice until separation. Within maximum 30 min after collection, blood samples are centrifuged at 2000×g for 10 min at 4° C. and the resulting plasma samples are aliquoted into polypropylene tubes (1×25 μL). The samples are stored frozen at −20° C. until analysis.

The lung tissue is collected at sacrifice after blood sampling for each animal, then weighed and placed into polypropylene tubes prior to freezing. The samples are stored frozen at −80° C. until analysis.

4.14.5.2. Plasma Concentration and Pharmacokinetic Analysis

Plasma and lung concentrations are measured via LC-MS/MS. Samples are prepared for LC-MS/MS analysis via protein precipitation. The plasma concentrations measured below the lower limit of quantification (LLOQ) are reported as below the limit of quantification (BLQ). The test compound concentrations in plasma are expressed in ng/mL. Mean plasma concentrations are calculated. For mean calculation, the concentrations below the LLOQ are set to zero. Therefore, mean values may be BLQ. Standard deviation (SD), standard error of the mean (SE) and coefficient of variation (CV, %) are tabulated when at least three plasma concentration values are above the LLOQ.

Non-compartmental analysis on individual plasma concentrations is performed using Phoenix™ WinNonlin® 6.3 (Pharsight Corporation) to determine at least, the following pharmacokinetic parameters:

- Maximum plasma concentration, Cmax (μg/mL) with the corresponding time, tmax (h),
- Area under the plasma concentration versus time curve up to the last quantifiable concentration $AUC_{0-t}$ or up to 24 h $AUC_{0-24h}$ (μg·h/mL) (if compound is quantifiable up to 24 h postdose), and/or up to infinity $AUC_{0-\infty}$, (μg·h/mL) is calculated according to the linear up/log down trapezoidal rule. Partial AUC may be calculated if deemed necessary. Concentrations below the limit of quantification (BLQ) are set to zero. No AUC is calculated if there are less than three quantifiable time points. AUC0-∞ is considered if % AUCextra <20%,
- Apparent terminal elimination half-life, t1/2 (h) is only reported if three or more time points, excluding tmax is used for linear regression, and if the adjusted $R^2$>0.80.
- Normalized AUC and Cmax dose.
- Mean pharmacokinetic parameters are calculated. Standard deviation (SD) and coefficient of variation (CV, %) are tabulated if at least three values are available.

4.14.6. Results

When subjected to this protocol, Cpd 219 dosed at 10 mg/kg p.o. b.i.d. in PEG200/MC 0.5% 20/80 (v/v) vehicle showed a statistically significant decrease of the Ashcroft score compared to the vehicle group (meta-analysis of two pooled identical study runs).

4.15. T Cell Transfer Model (Mice)

4.15.1. Materials

DynaMag (Cat #12321D and 123203D) is obtained from Life Technologies Invitrogen (California, USA); DynabeadsFlowComp Mouse CD4+CD25-treg cells (Cat #11463D) are obtained from Life Technologies Invitrogen (California, USA), Fetal Bovine Serum (GIBCO), Cat #10270-106; RPMI (Gibco) Cat #32404-014 and D-PBS 1× without $CaCl_2$ without $MgCl_2$ (GIBCO), Cat #14190-086 are obtained from ThermoFisher Scientific (Massachusetts, USA). Red Blood Cell (RBC) lysis buffer 10×, Cat #BLE420301 obtained from Ozyme (Montigny-le-Bretonneux, France). Cell strainer (70 μm grid), Cat #352350, obtained from Corning (New York, USA). Bovine Serum Albumin (BSA), Cat #A9647-50 g and EDTA, Cat #EDS-100 g obtained from Sigma Aldrich (Missouri, USA) and Combur testE, Cat #11896857, obtained from Roche Diagnostics (Basel, Switzerland).

4.152. Animals

Five to seven week old BALBc/N female mice and five to seven week old SCID female mice are obtained from Janvier Labs (Le Genest-Saint-Isle, France). Mice are kept on a 12 h light/dark cycle. Temperature is maintained at 22° C., food and water are provided ad libitum.

4.15.3. Study Design

The therapeutic effects of the compounds are tested in the mouse T cell transfer model (Lindebo Holm et al. 2012). After a 7-day acclimatization period, BALBc/N mice are sacrificed, spleens are removed, homogenized, rinsed with D-PBS and centrifuged. Cell pellets are resuspended in RBC lysis isolation buffer (D-PBS, EDTA, BSA, 1/1/1) and centrifuged, then resuspended in isolation buffer and processed following DynabeadsFlowComp Mouse CD4+CD25-treg cells Dynabeads kit protocol. The obtained cells are resuspended in RPMI and 0.2 mL are injected to SCID mice by intra-peritoneal injection. Sham group mice receive RPMI alone.

Fourteen days after cell injection, 100 μL of blood is sampled on each mouse under anesthetic conditions in order to determine CD4 level. Treatment starts on the next day, with groups homogenized by level of disease activity index (DAI). Disease activity index is determined twice a week. Four to six weeks after the start of treatment, mice are sacrificed, blood is sampled and the complete colon is removed and rinsed with sterile PBS, it is measured and weighed in order to determine colon weight/length ratio. Segments of colon are dissected for histological analysis, gene expression, protein level measurement and/or totally sampled for immunophenotyping by FACs.

There are 12 mice per group. The results are expressed as mean±SEM and statistical analysis is performed using non parametric test Kruskal-Wallis with Dunn's multiple comparison test versus vehicle groups.

4.15.4. Disease Activity Index (DAI) Determination

The DAI score of each mouse (sum of scores for weight loss, stool consistency and rectal bleeding) is monitored during the entire treatment period and a DAI score progression curve is obtained.

| DAI | Weight evolution | Stool consistency | Rectal bleeding* |
|---|---|---|---|
| 0 Point | No weight loss (vs D1) | Well molded stools | |
| 1 point | 1 to 5% | Semi-soft stools | |
| 2 points | 5 to 10% | Soft stools that do not stick to the anus | |
| 3 points | 10 to 20% | Semi-liquid stools not sticking to the anus | |
| 4 Points | >20% | Liquid stools remaining stuck to the anus | |

*A little piece of stool is deposited on a vial containing 1 mL of D-PBS and homogeneized, deposited on a test strip (Combur TestE), a color appears according to the blood intensity in the stool, a score is given according to this intensity, from 0 to 4 points.

4.16. Surgical Destabilization of the Medial Meniscus (DMM) Mouse Model of Osteoarthritis The experiment assesses disease-modifying osteoarthritis drug (DMOAD) effect by prophylactic treatment of compounds that inhibits the structural disease progression of OA and ideally also improves symptoms and/or function.

DMM surgery is performed in the right knees of 10-week old male C57BL/6 mice. For the prophylactic study, systemic (p.o.) treatment starts at the time of surgery. Mice are sacrificed 8 weeks after surgery, and another group are sacrificed 12 weeks after surgery. Knees are harvested for detailed histopathological assessment (Glasson et al. 2007). Thus, the DMM model uniquely captures the chronic progressive nature of OA and associated sensitization and pain-related behaviours. Knees are collected for histology, following standard methods (Miller et al. 2016).

4.17 Ovariectomized (OVX) Mouse Model

The OVX model is used widely for investigating problems related to postmenopausal bone loss, a primary risk factor for osteoporosis A cohort of C57B16 female mice of 12 weeks of age are subjected to sham surgery, or to OVX. Animals are kept for a period of 8 weeks, during which time hypogonadal bone loss is established. Then, at 20 weeks of age (8 weeks after sham or OVX surgery), the OVX mice are treated once daily over the course of 4 weeks (Dempster et al. 2013).

The following skeletal-directed endpoints are used at the completion of the 4 weeks treatment period: μ-CT of the femur and L5 vertebrae to assess bone mass and micro-architecture.

4.18. Murine Sclerodermatous Chronic Graft-Versus Host Disease (cGvHD)

4.18.1. General Overview

In this cGvHD model, fibrosis is induced in BALB/c ($H2^d$) mice by allogeneic transplantation of bone marrow cells and splenocytes from B10.D2 ($H2^d$) donor mice (minor HLA mismatch). The recipient mice develop inflammation-driven dermal and pulmonary fibrosis resembling patients with rapidly progressive diffuse cutaneous systemic sclerosis (Zerr et al. 2012).

The treatment is provided only after the onset of first clinical symptoms of sclerodermatous cGvHD.

4.18.2. Study Groups

The following groups with each eight mice are used in this study

Syngeneically Transplanted, Placebo-Treated Control Group:

Syngeneic bone marrow and splenocyte transplantation (BALB/c ($H2^d$)→BALB/c ($H2^d$)). Application of methyl cellulose 0.5% from day 21 to day 56 post transplantation.

Vehicle-Treated Fibrosis Group:

Allogeneic bone marrow and splenocyte transplantation (B10.D2 ($H2^d$)→BALB/c ($H2^d$)). Application of methyl cellulose 0.5% from day 21 to day 56 post transplantation Control Group to Assess Pretreatment Levels of Fibrosis Induced by Allogeneic Transplantation:

Allogeneic bone marrow and splenocyte transplantation (B10.D2 ($H2^d$)→BALB/c ($H2^d$)). Sacrifice at day 21, before treatment is initiated in the other groups.

Treatment Group:

Allogeneic bone marrow and splenocyte transplantation (B10.D2 ($H2^d$)→BALB/c ($H2^d$)).

Application of a test compound of the invention at 10 mg/kg po bid in 0.5% methyl cellulose from day 21 to day 56 post transplantation.

Positive Control Group:

Allogeneic bone marrow and splenocyte transplantation (B10.D2 ($H2^d$)→BALB/c (H2)). Application of 50 mg/kg qd nintedanib from day 21 to day 56 post transplantation.

4.18.3. Steady State PK

On D20, for the groups receiving test compounds, blood is collected from the tail vein from 2 animals per timepoint, at the following timepoints: pre-dose, 1, 3 and 6 h with anticoagulant Li-heparin.

The blood samples are kept on ice and centrifuged at approx. 3500×g, for 10 min at +4° C., within 1 h after blood sampling; plasma is transferred in labelled polypropylene tubes and stored at −20° C.

4.18.4. Sampling and Analysis

Animals are sacrificed 2 h post last dose, and samples of skin (3 mm punch biopsies), lung, spleen and blood are collected for histology and gene expression analysis.

4.18.5. Main Readouts

The anti-fibrotic effects on skin are analysed by determination of dermal thickness, quantification of lesional collagen and staining for myofibroblasts.

In case of positive effects on skin fibrosis, effects on pulmonary fibrosis are analysed by Ashcroft scoring, hydroxyproline content, and quantification of the collagen covered area using SirCol staining.

4.18.6. Analysis

Based on individual animal raw data, the means for each group are determined and percent change from disease controls is calculated. Treatment groups are compared to disease controls using a one-way analysis of variance (1-way ANOVA) with a Dunnett's post-hoc analysis for measured (parametric) data or a Kruskal-Wallis test with a Dunn's post-hoc analysis for scored (non-parametric) data.

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by OpenEye Scientific Software, Inc. and the Autonom Software tool sold by MDL, Inc. In the instance where the indicated chemical name and the depicted structure differ, the depicted structure will control.

REFERENCES

Argiles J M, López-Soriano F J. 1998. Catabolic proinflammatory cytokines. *Curr. Opin. Clin. Nutr. Metab. Care* 1, 245-251.

Ashcroft T, Simpson J M, Timbrell V. 1988. Simple method of estimating severity of pulmonary fibrosis on a numerical scale. *J Clin. Pathol.* 41, 467-470.

Ashour Ahmed A et al. 2010. SIK2 is a centrosome kinase required for bipolar mitotic spindle formation that provides a potential target for therapy in ovarian cancer. *Cancer Cell* 18, 109-121.

Bundgaard H. 1985. *Design of prodrugs*, Elsevier.

Bush K A et al. 2002. Reduction of joint inflammation and bone erosion in rat adjuvant arthritis by treatment with interleukin-17 receptor IgG1 Fc fusion protein. *Arthritis Rheum.* 46, 802-805.

Charoenfuprasert S et al. 2011. Identification of salt-inducible kinase 3 as a novel tumor antigen associated with tumorigenesis of ovarian cancer. *Oncogene* 30, 3570-3584.

Clark K et al. 2012. Phosphorylation of CRTC3 by the salt-inducible kinases controls the interconversion of classically activated and regulatory macrophages. *Proc. Natl. Acad. Sci. U.S.A* 109, 16986-16991.

Darling N J et al. 2017. Inhibition of SIK2 and SIK3 during differentiation enhances the anti-inflammatory phenotype of macrophages. *Biochem. J* 474, 521-537.

Dempster D W et al. 2013. Standardized nomenclature, symbols, and units for bone histomorphometry: a 2012 update of the report of the ASBMR Histomorphometry Nomenclature Committee. *J Bone Miner. Res. Off. J. Am. Soc. Bone Miner. Res.* 28, 2-17.

Devos F C et al. 2017. Forced expiration measurements in mouse models of obstructive and restrictive lung diseases. *Respir. Res.* 18, 123.

Favaudon V et al. 2014. Ultrahigh dose-rate FLASH irradiation increases the differential response between normal and tumor tissue in mice. *Sci. Transl. Med.* 6, 245ra93.

van der Fits L et al. 2009. Imiquimod-induced psoriasis-like skin inflammation in mice is mediated via the IL-23/IL-17 axis. *J Immunol.* 182, 5836-5845.

Glasson S S, Blanchet T J, Morris E A. 2007. The surgical destabilization of the medial meniscus (DMM) model of osteoarthritis in the 129/SvEv mouse. *Osteoarthritis Cartilage* 15, 1061-1069.

Jou I-M et al. 2005. Thrombospondin 1 as an effective gene therapeutic strategy in collagen-induced arthritis. *Arthritis Rheum.* 52, 339-344.

Katoh Y et al. 2004. Salt-inducible kinase (SIK) isoforms: their involvement in steroidogenesis and adipogenesis. *Mol. Cell. Endocrinol.* 217, 109-112.

Khachigian L M. 2006. Collagen antibody-induced arthritis. *Nat. Protoc.* 1, 2512-2516.

Kumagai A et al. 2011. A Potent Inhibitor of SIK2,3,3',7-Trihydroxy-4'-Methoxyflavon (4'-O-Methylfisetin), Promotes Melanogenesis in B16F10 Melanoma Cells. *PLoS ONE* 6.

Li M et al. 2006. Topical vitamin D3 and low-calcemic analogs induce thymic stromal lymphopoietin in mouse keratinocytes and trigger an atopic dermatitis. *Proc. Natl. Acad. Sci. U.S.A* 103, 11736-11741.

Lin H-S et al. 2007. Anti-rheumatic activities of histone deacetylase (HDAC) inhibitors in vivo in collagen-induced arthritis in rodents. *Br. J. Pharmacol.* 150, 862-872.

Lindebo Holm T et al. 2012. Pharmacological Evaluation of the SCID T Cell Transfer Model of Colitis: As a Model of Crohn's Disease. *Int. J Inflamm.* 2012, 412178.

Liu J Z et al. 2013. Dense genotyping of immune-related disease regions identifies nine new risk loci for primary sclerosing cholangitis. *Nat. Genet.* 45, 670-675.

Matsuse T et al. 1999. ICAM-1 mediates lung leukocyte recruitment but not pulmonary fibrosis in a murine model of bleomycin-induced lung injury. *Eur. Respir. J.* 13, 71-77.

Maxwell J R et al. 2015. Differential Roles for Interleukin-23 and Interleukin-17 in Intestinal Immunoregulation. *Immunity* 43, 739-750.

M D Biosciences Inc. 2008. Monoclonal Antibody Induced Arthritis: a shorter, more synchronized alternative to the classic CIA model. *BioTechniques* 44, 279-280.

Miller R E et al. 2016. Therapeutic effects of an anti-ADAMTS-5 antibody on joint damage and mechanical allodynia in a murine model of osteoarthritis. *Osteoarthritis Cartilage* 24, 299-306.

Nandakumar K S, Svensson L, Holmdahl R. 2003. Collagen Type II-Specific Monoclonal Antibody-Induced Arthritis in Mice. *Am. J Pathol.* 163, 1827-1837.

Nishida K et al. 2004. Histone deacetylase inhibitor suppression of autoantibody-mediated arthritis in mice via regulation of p16INK4a and p21WAF1/Cip1 expression. *Arthritis Rheum.* 50, 3365-3376.

Nixon M et al. 2016. Skeletal muscle salt inducible kinase 1 promotes insulin resistance in obesity. *Mol. Metab.* 5, 34-46.

Ozanne J, Prescott A R, Clark K. 2015. The clinically approved drugs dasatinib and bosutinib induce anti-inflammatory macrophages by inhibiting the salt-inducible kinases. *Biochem. J.* 465, 271-279.

Rall L C, Roubenoff R. 2004. Rheumatoid cachexia: metabolic abnormalities, mechanisms and interventions. *Rheumatology* 43, 1219-1223.

Remington J P. 1985. Pharmaceutical Preparations and Their Manufacture. in Gennaro A R, (Ed.) *Remington's Pharmaceutical Sciences*. Mack Pub. Co., Easton, PA 18042.

Rizzo H L et al. 2011. IL-23-Mediated Psoriasis-Like Epidermal Hyperplasia Is Dependent on IL-17A. *J Immunol.* 186, 1495-1502.

Salvemini D et al. 2001. Amelioration of joint disease in a rat model of collagen-induced arthritis by M40403, a superoxide dismutase mimetic. *Arthritis Rheum.* 44, 2909-2921.

Sasaki T et al. 2011. SIK2 Is a Key Regulator for Neuronal Survival after Ischemia via TORC1-CREB. *Neuron* 69, 106-119.

Shelton D L et al. 2005. Nerve growth factor mediates hyperalgesia and cachexia in auto-immune arthritis. *Pain* 116, 8-16.

Sherlock J P et al. 2012. IL-23 induces spondyloarthropathy by acting on ROR-γt+CD3+CD4−CD8− entheseal resident T cells. *Nat. Med.* 18, 1069-1076.

Sims N A et al. 2004. Targeting osteoclasts with zoledronic acid prevents bone destruction in collagen-induced arthritis. *Arthritis Rheum.* 50, 2338-2346.

Sina C et al. 2009. G Protein-Coupled Receptor 43 Is Essential for Neutrophil Recruitment during Intestinal Inflammation. *J Immunol.* 183, 7514-7522.

Sundberg T B et al. 2014. Small-molecule screening identifies inhibition of salt-inducible kinases as a therapeutic strategy to enhance immunoregulatory functions of dendritic cells. *Proc. Natl. Acad. Sci. U.S.A* 111, 12468-12473.

Tejon G et al. 2019. A Spontaneous Mouse Model of Lupus: Physiology and Therapy. *Lupus—New Adv. Chall.*

Walsmith J et al. 2004. Tumor necrosis factor-alpha production is associated with less body cell mass in women with rheumatoid arthritis. *J. Rheumatol.* 31, 23-29.

Wein M N et al. 2016. SIKs control osteocyte responses to parathyroid hormone. *Nat. Commun.* 7, 13176.

Wirtz S et al. 2007. Chemically induced mouse models of intestinal inflammation. *Nat. Protoc.* 2, 541-546.

Wuts P G M, Greene T W. 2006. *Greene's Protective Groups in Organic Synthesis* 4th ed., Wiley-Interscience.

Yao C et al. 2013. Prostaglandin $E_2$ promotes Th1 differentiation via synergistic amplification of IL-12 signalling by cAMP and PI3-kinase. *Nat. Commun.* 4, 1685.

Yokogawa M et al. 2014. Epicutaneous Application of Toll-like Receptor 7 Agonists Leads to Systemic Autoimmunity in Wild-Type Mice: A New Model of Systemic Lupus Erythematosus. *Arthritis Rheumatol.* 66, 694-706.

Yu J et al. 2013. Salt-inducible kinase 1 is involved in high glucose-induced mesangial cell proliferation mediated by the ALK5 signaling pathway. *Int. J. Mol. Med.* 32, 151-157.

Zampeli E et al. 2017. A comprehensive evaluation for the treatment of lupus nephritis. *J. Autoimmun.* 78, 1-10.

Zerr P et al. 2012. Combined Inhibition of c-Abl and PDGF Receptors for Prevention and Treatment of Murine Sclerodermatous Chronic Graft-versus-Host Disease. *Am. J Pathol.* 181, 1672-1680.

The invention claimed is:

1. A compound according to Formula I:

I

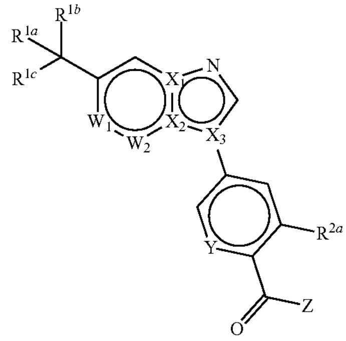

wherein, $W_1$ is N or $CR^3$ and $W_2$ is N or CH, with the proviso that $W_1$ and $W_2$ cannot both be N;

one of $X_1$, $X_2$ and $X_3$ is N and the other two are C;

Y is N or $CR^{2b}$;

Z is

—$NR^{4a}R^{4b}$,

—$R^{4c}$—, wherein the N atom and $R^{2a}$ together with the atoms onto which they are attached form a fused 5-6 membered heterocycloalkenyl comprising one double bond, or N-linked 4-7 membered monocyclic or spirocyclic heterocycloalkyl further comprising zero, one, or two additional heteroatoms independently selected from N, O, and S, optionally substituted with one or more independently selected $R^5$ groups;

$R^{1a}$ is selected from

H, halo,

—OH,

—CN, $C_{1-6}$ alkyl optionally substituted with one or more independently selected $R^6$, $C_{1-4}$ alkoxy optionally substituted with one or more —OH or 5-6 membered monocyclic heterocycloalkyl comprising one, two or three heteroatoms independently selected from N, O, and S,

—C(O)—$R^7$,

—$NR^{8a}R^{8b}$,

—$S(=O)_2$—$C_{1-4}$ alkyl, 5-6 membered monocyclic heteroaryl comprising one, two or three heteroatoms independently selected from N, O, and S, which heteroaryl is optionally substituted with one or more independently selected $C_{1-4}$ alkyl, and 4-6 membered monocyclic heterocycloalkyl comprising one, two or three heteroatoms independently selected from N, O, and S;

$R^{1b}$ and $R^{1c}$ are independently selected from halo,

—OH,

—CN, $C_{1-4}$ alkyl optionally substituted with one or more independently selected —OH, —CN, or $C_{2-4}$ alkenyl, $C_{3-7}$ cycloalkyl, 4-8 membered monocyclic or spirocyclic heterocycloalkyl comprising one, two or three heteroatoms independently selected from N, O, and S, which heterocycloalkyl is optionally substituted with one or more independently selected $R^9$ groups, and —$NR^{10a}R^{10b}$, or $R^{1b}$ and $R^{1c}$ together with the atom onto which they are attached form a $C_{3-6}$ cycloalkyl, or $R^{1b}$ and $R^{1c}$ together with the atom onto which they are attached form a 4-6 membered monocyclic heterocycloalkyl comprising one, two, or three heteroatoms independently selected from N, O, and S, which heterocycloalkyl is optionally substituted with one or more independently selected $R^{11}$ groups;

$R^{2a}$ and $R^{2b}$ are independently selected from halo, $C_{1-4}$ alkyl, $C_{1-4}$ alkoxy optionally substituted with one or more independently selected halo, —OH, or $C_{1-4}$ alkoxy, —$NR^{12a}R^{12b}$, and

—OH;

$R^3$ is H, halo, or $C_{1-4}$ alkoxy optionally substituted with one or more independently selected —OH or $C_{1-4}$ alkoxy;

$R^{4a}$ is H or $C_{1-4}$ alkyl;

$R^{4b}$ is selected from $C_{1-6}$ alkyl optionally substituted with one or more independently selected $R^{13}$, $C_{3-7}$ cycloalkyl optionally substituted with one or more independently selected $R^{14a}$, 4-7 membered monocyclic heterocycloalkyl comprising one, two or three heteroatoms independently selected from N, O, and S, which heterocycloalkyl is optionally substituted with one or more independently selected $R^{14b}$, and 5-6 membered monocyclic heteroaryl comprising one, two or three heteroatoms independently selected from N, O, and S, which heteroaryl is optionally substituted with one or more independently selected $C_{1-4}$ alkyl;

$R^{4c}$ is H, $C_{3-7}$ cycloalkyl, or $C_{1-6}$ alkyl optionally substituted with one or more independently selected halo or —CN;

each $R^5$ is independently selected from oxo, halo,

—CN,

—OH,

—$NR^{15a}R^{15b}$,
phenyl,
$C_{3-7}$ cycloalkyl,
$C_{2-4}$ alkynyl,
—C(=O)—$C_{1-4}$ alkoxy,
$C_{1-4}$ alkoxy optionally substituted with one or more independently selected halo or phenyl,
$C_{1-4}$ alkyl optionally substituted with one or more independently selected halo, —OH, or $C_{1-4}$ alkoxy, and
4-7 membered monocyclic heterocycloalkyl comprising one, two or three heteroatoms independently selected from N, O, and S;

each $R^6$ is independently selected from
halo,
—O—$R^{16}$,
—$NR^{17a}R^{17b}$,
5-6 membered monocyclic heteroaryl comprising one, two or three heteroatoms independently selected from N, O, and S, and
4-6 membered monocyclic heterocycloalkyl comprising one, two or three heteroatoms independently selected from N, O, and S, which heterocycloalkyl is optionally substituted with one or more independently selected halo;

$R^7$ is —OH, $C_{1-4}$ alkyl, $C_{1-4}$ alkoxy, —$NR^{18a}R^{18b}$, or 4-6 membered monocyclic heterocycloalkyl comprising one, two or three heteroatoms independently selected from N, O, and S, which heterocycloalkyl is optionally substituted with one or more —OH;

$R^{8a}$ and $R^{8b}$ are independently H, —C(=O)—$C_{1-4}$ alkoxy, or $C_{1-4}$ alkyl optionally substituted with one or more independently selected halo, —CN or —OH;

each $R^9$ is independently halo, —OH, or $C_{1-4}$ alkyl optionally substituted with one or more —OH;

each $R^{10a}$ and $R^{10b}$ is independently H or $C_{1-4}$ alkyl optionally substituted with one or more —OH;

each $R^{11}$ is independently selected from
$C_{1-4}$ alkyl optionally substituted with one or more independently selected-CN or $C_{1-4}$ alkoxy,
—C(=O)—$C_{1-6}$ alkyl, and
—C(=O)—$C_{1-6}$ alkoxy;

each $R^{12a}$ and $R^{12b}$ is independently H or $C_{1-4}$ alkyl optionally substituted with one —OH or $C_{1-4}$ alkoxy;

each $R^{13}$ is independently selected from
halo,
—CN,
—$NR^{19a}R^{19b}$,
—OH,
$C_{1-4}$ alkoxy,
$C_{3-7}$ cycloalkyl,
—$S(=O)_2$—$C_{1-4}$ alkyl,
4-7 membered monocyclic heterocycloalkyl comprising one, two or three heteroatoms independently selected from N, O, and S, and
5-6 membered monocyclic heteroaryl comprising one, two or three heteroatoms independently selected from N, O, and S, which heteroaryl is optionally substituted with one or more independently selected $C_{1-4}$ alkyl;

each $R^{14a}$ and $R^{14b}$ is independently selected from
halo,
oxo,
$C_{1-4}$ alkyl optionally substituted with one or more independently selected halo, —OH, or $C_{1-4}$ alkoxy,
—OH,
$C_{1-4}$ alkoxy, and
—$NR^{20a}R^{20b}$;

each $R^{15a}$ and $R^{15b}$ is independently H, $C_{1-4}$ alkyl, or —C(=O)—$C_{1-4}$ alkoxy;

each $R^{16}$ is independently selected from
H,
—$S(=O)_2$—$C_{1-4}$ alkyl,
$C_{1-4}$ alkyl optionally substituted with one or more —C(=O)—$NR^{21a}R^{21b}$ or 4-6 membered monocyclic heterocycloalkyl comprising one, two or three heteroatoms independently selected from N, O, and S, and
4-6 membered monocyclic heterocycloalkyl comprising one, two or three heteroatoms independently selected from N, O, and S;

each $R^{17a}$ and $R^{17b}$ is independently H or $C_{1-4}$ alkyl optionally substituted with one or more independently selected-OH or $C_{1-4}$ alkoxy;

$R^{18a}$ and $R^{18b}$ are independently H or $C_{1-4}$ alkyl optionally substituted with one or more independently selected —OH or $C_{1-4}$ alkoxy;

each $R^{19a}$, $R^{19b}$, $R^{20a}$, $R^{20b}$, $R^{21a}$, and $R^{21b}$ is independently H or $C_{1-4}$ alkyl;

or a pharmaceutically acceptable salt thereof.

2. A compound or pharmaceutically acceptable salt thereof, according to claim 1, wherein $W_1$ is $CR^3$, and $R^3$ is H.

3. A compound or pharmaceutically acceptable salt thereof, according to claim 1, wherein Y is $CR^{2b}$ and $R^{2b}$ is $C_{1-4}$ alkoxy.

4. A compound or pharmaceutically acceptable salt thereof, according to claim 1, wherein $R^{2a}$ is —O—$CH_3$, substituted with one, two, or three independently selected halo.

5. A compound or pharmaceutically acceptable salt thereof, according to claim 1, wherein Z is —$NR^{4a}R^{4b}$, and $R^{4a}$ is H.

6. A compound or pharmaceutically acceptable salt thereof, according to claim 1, wherein the compound is according to Formula IIIa, IIIb, IIIc, or IIId:

IIIa

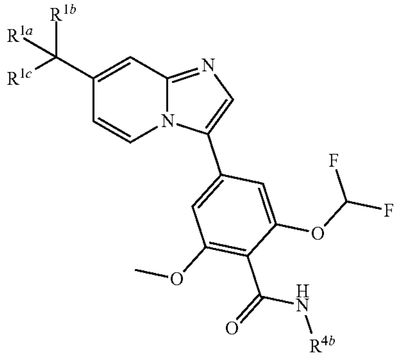

-continued

IIIb

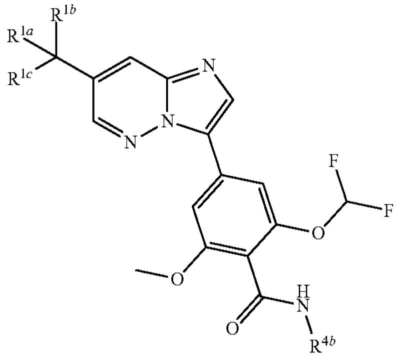

IIIc

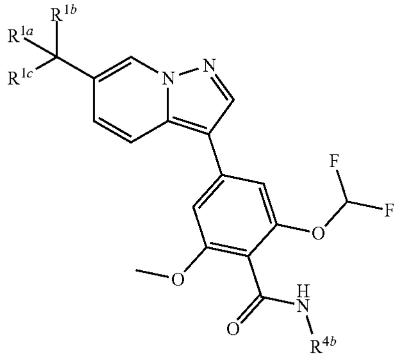

IIId

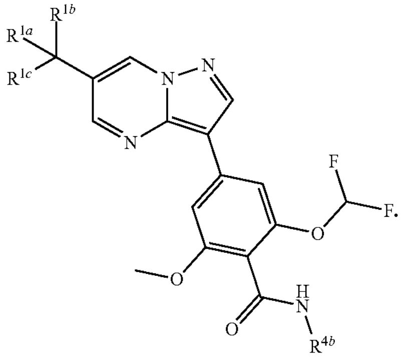

7. A compound or pharmaceutically acceptable salt thereof, according to claim 1, wherein $R^{1b}$ and $R^{1c}$ together with the atom onto which they are attached form a cyclobutyl.

8. A compound or pharmaceutically acceptable salt thereof, according to claim 1, wherein $R^{1b}$ and $R^{1c}$ together with the atom onto which they are attached form an oxetanyl or tetrahydropyranyl.

9. A compound or pharmaceutically acceptable salt thereof, according to claim 1, wherein the compound is according to Formula IVe, IVf, IVg, or IVh:

IVe

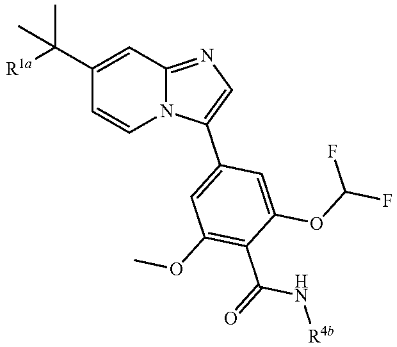

IVf

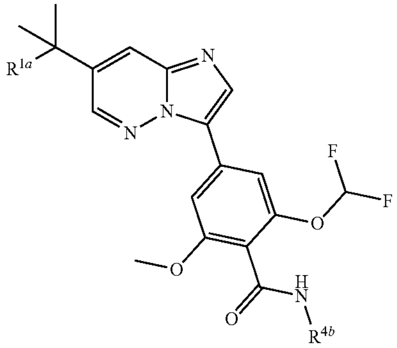

IVg

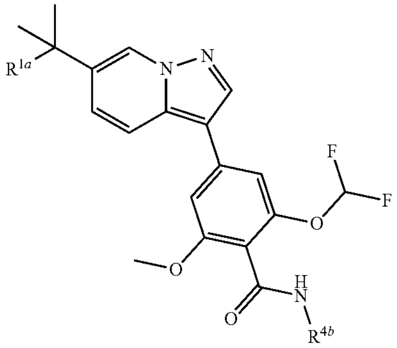

IVh

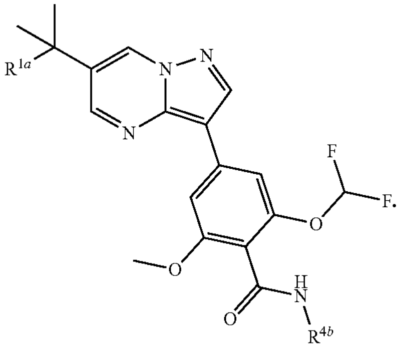

10. A compound or pharmaceutically acceptable salt thereof, according to claim 1, wherein $R^{4b}$ is cyclopropyl or 2-fluorocyclopropyl.

11. A compound or pharmaceutically acceptable salt thereof, according to claim 1, wherein $R^{1a}$ is H, —OH, or —CN.

12. A compound or pharmaceutically acceptable salt thereof, according to claim 1, wherein $R^{1a}$ is $C_{1-6}$ alkyl substituted with one —OH.

13. A pharmaceutical composition comprising a pharmaceutically acceptable carrier and a pharmaceutically effective amount of a compound or pharmaceutically acceptable salt thereof according to claim 1.

14. A method for prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases, comprising administering a compound or pharmaceutically acceptable salt thereof, according to claim 1, to a human in need thereof.

15. A method for prophylaxis and/or treatment of inflammatory diseases, autoinflammatory diseases, autoimmune diseases, proliferative diseases, fibrotic diseases, transplantation rejection, diseases involving impairment of cartilage turnover, congenital cartilage malformation, diseases involving impairment of bone turnover, diseases associated with hypersecretion of IL-6, diseases associated with hypersecretion of TNFα, interferons, IL-12 and/or IL-23, respiratory diseases, endocrine and/or metabolic diseases, cardiovascular diseases, dermatological diseases, and/or abnormal angiogenesis associated diseases, comprising administering a pharmaceutical composition of claim 13 to a human in need thereof.

* * * * *